(12) United States Patent
Dyckman et al.

(10) Patent No.: US 11,878,975 B2
(45) Date of Patent: Jan. 23, 2024

(54) SUBSTITUTED INDOLE COMPOUNDS USEFUL AS TLR INHIBITORS

(71) Applicant: BRISTOL-MYERS SQUIBB COMPANY, Princeton, NJ (US)

(72) Inventors: Alaric J. Dyckman, Lawrenceville, NJ (US); Dharmpal S. Dodd, Monmouth Junction, NJ (US); Christopher P. Mussari, Princeton, NJ (US); John L. Gilmore, Yardley, PA (US); Tasir Shamsul Haque, Yardley, PA (US); Trevor C. Sherwood, West Windsor, NJ (US); Brian K. Whiteley, Lebanon, NJ (US); Shoshana L. Posy, Highland Park, NJ (US); Sreekantha Ratna Kumar, Bangalore (IN); Laxman Pasunoori, Waranagal (IN); Srinivasan Kunchithapatham Duraisamy, Hosur (IN); Subramanya Hegde, Bangalore (IN); Rushith Kumar Anumula, Secunderabad (IN); Pitani Veera Venkata Srinivas, West Godawri (IN)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 16/955,097

(22) PCT Filed: Dec. 18, 2018

(86) PCT No.: PCT/US2018/066149
§ 371 (c)(1),
(2) Date: Jun. 18, 2020

(87) PCT Pub. No.: WO2019/126113
PCT Pub. Date: Jun. 27, 2019

(65) Prior Publication Data
US 2020/0308172 A1 Oct. 1, 2020

Related U.S. Application Data

(60) Provisional application No. 62/607,472, filed on Dec. 19, 2017.

(51) Int. Cl.
| | | |
|---|---|---|
| *C07D 471/08* | (2006.01) | |
| *C07D 487/08* | (2006.01) | |
| *C07D 519/00* | (2006.01) | |
| *C07D 471/04* | (2006.01) | |
| *C07D 401/04* | (2006.01) | |
| *C07D 401/10* | (2006.01) | |
| *C07D 401/14* | (2006.01) | |
| *C07D 405/14* | (2006.01) | |
| *C07D 413/14* | (2006.01) | |

(Continued)

(52) U.S. Cl.
CPC ......... *C07D 471/04* (2013.01); *C07D 401/04* (2013.01); *C07D 401/10* (2013.01); *C07D 401/14* (2013.01); *C07D 405/14* (2013.01); *C07D 413/14* (2013.01); *C07D 417/14* (2013.01); *C07D 453/02* (2013.01); *C07D 487/04* (2013.01); *C07D 491/08* (2013.01)

(58) Field of Classification Search
CPC .. C07D 471/04; C07D 401/04; C07D 401/10; C07D 401/14; C07D 405/14; C07D 413/14; C07D 417/14; C07D 453/02; C07D 487/04; C07D 491/08; C07D 471/08; C07D 487/08; C07D 519/00; A61K 31/437; A61K 31/4439; A61P 19/02; A61P 29/00; A61P 37/00
USPC ......................................................... 514/210
See application file for complete search history.

(56) References Cited

U.S. PATENT DOCUMENTS

| | | | |
|---|---|---|---|
| 6,187,777 B1 | 2/2001 | Norman et al. | |
| 6,306,874 B1 | 10/2001 | Fraley et al. | |

(Continued)

FOREIGN PATENT DOCUMENTS

| | | |
|---|---|---|
| EP | 2738172 A1 | 6/2014 |
| WO | 03057696 A1 | 7/2003 |

(Continued)

OTHER PUBLICATIONS

Bobko, M. et al., "Synthesis of 2,5-disubstituted-3-cyanoindoles", Tetrahedron Letters, 53 (2012) 200-202.

(Continued)

*Primary Examiner* — Jared Barsky
*Assistant Examiner* — Liyuan Mou
(74) *Attorney, Agent, or Firm* — Gary Greenblatt

(57) ABSTRACT

Disclosed are compounds of Formula (I) N-oxides, or salts thereof, wherein G, A, $R_1$, $R_5$, and n are defined herein. Also disclosed are methods of using such compounds as inhibitors of signaling through Toll-like receptor 7, or 8, or 9, and pharmaceutical compositions comprising such compounds. These compounds are useful in treating inflammatory and autoimmune diseases.

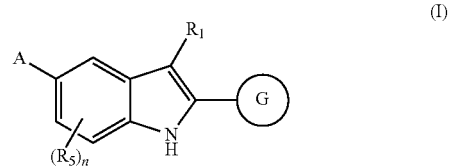

(I)

14 Claims, No Drawings

(51) Int. Cl.
*C07D 417/14* (2006.01)
*C07D 453/02* (2006.01)
*C07D 487/04* (2006.01)
*C07D 491/08* (2006.01)

(56) References Cited

U.S. PATENT DOCUMENTS

| | | | |
|---|---|---|---|
| 6,867,200 | B1 | 3/2005 | Allen et al. |
| 7,008,958 | B2 * | 3/2006 | Watterson ............ C07D 417/14 549/49 |
| 7,410,975 | B2 | 8/2008 | Lipford et al. |
| 8,138,187 | B2 | 3/2012 | Zemolka et al. |
| 8,354,400 | B2 | 1/2013 | Zheng et al. |
| 9,126,996 | B2 | 9/2015 | Lipford et al. |
| 9,126,999 | B2 | 9/2015 | Bolvin et al. |
| 9,241,991 | B2 | 1/2016 | Ji et al. |
| 9,353,115 | B2 | 5/2016 | Lipford et al. |
| 9,376,398 | B2 | 6/2016 | Hori et al. |
| 9,428,495 | B2 | 8/2016 | Carlson et al. |
| 9,643,967 | B2 | 5/2017 | Koul et al. |
| 2006/0235037 | A1 * | 10/2006 | Purandare ............ C07D 401/14 514/304 |
| 2009/0247504 | A1 * | 10/2009 | Churcher ............ C07D 487/10 548/362.5 |
| 2010/0160314 | A1 | 6/2010 | Lipford et al. |
| 2010/0197657 | A1 * | 8/2010 | Chang .................. C07D 209/08 514/211.09 |
| 2011/0015219 | A1 | 1/2011 | Trawick et al. |
| 2011/0071150 | A1 | 3/2011 | Alam et al. |
| 2011/0105427 | A1 | 5/2011 | Daun et al. |
| 2011/0183967 | A1 | 7/2011 | Zheng et al. |
| 2011/0275631 | A1 | 11/2011 | Abeywardane et al. |
| 2013/0045986 | A1 | 2/2013 | Nagarathnam et al. |
| 2013/0324547 | A1 | 12/2013 | Boivin et al. |
| 2014/0066432 | A1 | 3/2014 | Howbert et al. |
| 2014/0088085 | A1 | 3/2014 | Burgess et al. |
| 2014/0242121 | A1 | 8/2014 | Lipford et al. |
| 2015/0231142 | A1 | 8/2015 | van Goor et al. |
| 2017/0008885 | A1 | 1/2017 | Koul et al. |
| 2017/0273983 | A1 | 9/2017 | Ding et al. |
| 2018/0000790 | A1 | 1/2018 | Dyckman et al. |

FOREIGN PATENT DOCUMENTS

| | | |
|---|---|---|
| WO | 2005000804 A2 | 1/2005 |
| WO | 2006113458 A1 | 10/2006 |
| WO | 2007084135 A2 | 7/2007 |
| WO | 2007115306 A2 | 10/2007 |
| WO | 2008065198 A1 | 6/2008 |
| WO | 2008152471 A1 | 12/2008 |
| WO | 2009030996 A1 | 3/2009 |
| WO | 2010149769 A1 | 12/2010 |
| WO | 2013010904 A1 | 1/2013 |
| WO | 2013181579 A2 | 12/2013 |
| WO | 2015088045 A1 | 6/2015 |
| WO | 2016029077 A1 | 2/2016 |
| WO | 2016151085 A1 | 9/2016 |
| WO | 2018005586 A1 | 1/2018 |
| WO | 2018026620 A1 | 2/2018 |
| WO | 2018049089 A1 | 3/2018 |
| WO | 2019028301 A1 | 2/2019 |
| WO | 2019028302 A1 | 2/2019 |
| WO | 2019099336 A1 | 5/2019 |

OTHER PUBLICATIONS

International Preliminary Report on Patentability for No. PCT/US2018/066149, dated Jun. 23, 2020.

International Search Report for PCT/US2018/066149—Filed: Dec. 18, 2018.

Kawai, T., et al., "The Role of Pattern-Recognition Receptors in Innate Immunity: Update on Toll-like Receptors", Nature Immunol., 2011, 11, 373-384.

Lamphier, M. et al., "Novel Small Molecule Inhibitors of TLR7 and TLR9: Mechanism of Action and Efficacy in Vivo", Mol Pharmacol, 2014, 85:429-440.

Patra, Mahesh Chandra, et al., "Recent Progress in the Development of Toll-like Receptor (TLR) antagonists", Exp. Opin. On Therapeutic Patents, 2016, vol. 26, No. 6, 719-730.

Roy, et al., "Design and developmen of benzoxazole derivatives with toll-like receptor 9 antagonism", Eur J Med Chem, 2017, vol. 134, 334-347.

Sims, et al., "The IL-1 Family: Regulators of Immunity", Nature Rev. Immunol., 2010, 10, 89-102.

Huang, et al., Development of 6-substituted indolylquinolinonesbras potent Chek1 kinase inhibitors, Bioorganic & Medicinal Chemistry Letters 16 (2006) 5907-5912.

Zarrin, Ali A., et al., "Kinase inhibition in autoimmunity and inflammation", Nature Reviews Drug Discovery, Jan. 2021, vol. 20, pp. 39-63.

* cited by examiner

SUBSTITUTED INDOLE COMPOUNDS USEFUL AS TLR INHIBITORS

CROSS REFERENCE

This application is a national phase application under 35 U.S.C. § 371 of International Patent Application No. PCT/US2018/066149, filed Dec. 18, 2018, which claims priority to U.S. Provisional Application Ser. No. 62/607,472, filed Dec. 19, 2017, the contents of which are specifically incorporated fully herein by reference.

DESCRIPTION

The present invention generally relates to substituted indole compounds useful as inhibitors of signaling through Toll-like receptor 7, 8, or 9 (TLR7, TLR8, TLR9) or combinations thereof provided herein are substituted indole compounds, compositions comprising such compounds, and methods of their use. The invention further pertains to pharmaceutical compositions containing at least one compound according to the invention that are useful for the treatment of conditions related to TLR modulation, such as inflammatory and autoimmune diseases, and methods of inhibiting the activity of TLRs in a mammal.

Toll/IL-1 receptor family members are important regulators of inflammation and host resistance. The Toll-like receptor family recognizes molecular patterns derived from infectious organisms including bacteria, fungi, parasites, and viruses (reviewed in Kawai, T. et al., Nature Immunol., 11:373-384 (2010)). Ligand binding to the receptor induces dimerization and recruitment of adaptor molecules to a conserved cytoplasmic motif in the receptor termed the Toll/IL-1 receptor (TIR) domain with the exception of TLR3, all TLRs recruit the adaptor molecule MyD88. The IL-1 receptor family also contains a cytoplasmic TIR motif and recruits MyD88 upon ligand binding (reviewed in Sims, J. E. et al., Nature Rev. Immunol., 10:89-102 (2010)).

Toll-like receptors (TLRs) are a family of evolutionarily conserved, transmembrane innate immune receptors that participate in the first-line defense. As pattern recognition receptors, the TLRs protect against foreign molecules, activated by pathogen associated molecular patterns (PAMPs), or from damaged tissue, activated by danger associated molecular patterns (DAMPs). A total of 13 TLR family members have been identified, 10 in human, that span either the cell surface or the endosomal compartment. TLR7/8/9 are among the set that are endosomally located and respond to single-stranded RNA (TLR7 and TLR8) or unmethylated single-stranded DNA containing cytosine-phosphate-guanine (CpG) motifs (TLR9).

Activation of TLR7/8/9 can initiate a variety of inflammatory responses (cytokine production, B cell activation and IgG production, Type I interferon response). In the case of autoimmune disorders, the aberrant sustained activation of TLR7/8/9 leads to worsening of disease states. Whereas overexpression of TLR7 in mice has been shown to exacerbate autoimmune disease, knockout of TLR7 in mice was found to be protective against disease in lupus-prone MRL/lpr mice. Dual knockout of TLR7 and 9 showed further enhanced protection.

As numerous conditions may benefit by treatment involving modulation of cytokines, IFN production and B cell activity, it is immediately apparent that new compounds capable of modulating TLR7 and/or TLR8 and/or TLR9 and methods of using these compounds could provide substantial therapeutic benefits to a wide variety of patients.

The present invention relates to a new class of substituted indole compounds found to be effective inhibitors of signaling through TLR7/8/9. These compounds are provided to be useful as pharmaceuticals with desirable stability, bioavailability, therapeutic index, and toxicity values that are important to their druggability.

SUMMARY OF THE INVENTION

The present invention provides compounds of Formula (I) that are useful as inhibitors of signaling through Toll-like receptor 7, 8, or 9 and are useful for the treatment of proliferative diseases, allergic diseases, autoimmune diseases and inflammatory diseases, or stereoisomers, tautomers, pharmaceutically acceptable salts, solvates or prodrugs thereof.

The present invention also provides pharmaceutical compositions comprising a pharmaceutically acceptable carrier and at least one of the compounds of the present invention or stereoisomers, tautomers, pharmaceutically acceptable salts, solvates, or prodrugs thereof.

The present invention also provides a method for inhibition of Toll-like receptor 7, 8, or 9 comprising administering to a host in need of such treatment a therapeutically effective amount of at least one of the compounds of the present invention or stereoisomers, tautomers, pharmaceutically acceptable salts, solvates, or prodrugs thereof.

The present invention also provides a method for treating proliferative, metabolic, allergic, autoimmune and inflammatory diseases, comprising administering to a host in need of such treatment a therapeutically effective amount of at least one of the compounds of the present invention or stereoisomers, tautomers, pharmaceutically acceptable salts, solvates, or prodrugs thereof.

The present invention also provides a method of treating a disease or disorder associated with Toll-like receptor 7, 8, or 9 activity, the method comprising administering to a mammal in need thereof, at least one of the compounds of Formula (I) or salts, solvates, and prodrugs thereof.

The present invention also provides processes and intermediates for making the compounds of Formula (I) including salts, solvates, and prodrugs thereof.

The present invention also provides at least one of the compounds of Formula (I) or salts, solvates, and prodrugs thereof, for use in therapy.

The present invention also provides the use of at least one of the compounds of Formula (I) or salts, solvates, and prodrugs thereof, for the manufacture of a medicament for the treatment of prophylaxis of Toll-like receptor 7, 8, or 9 related conditions, such as allergic disease, autoimmune diseases, inflammatory diseases, and proliferative diseases.

The compound of Formula (I) and compositions comprising the compounds of Formula (I) may be used in treating, preventing, or curing various Toll-like receptor 7, 8, or 9 related conditions. Pharmaceutical compositions comprising these compounds are useful for treating, preventing, or slowing the progression of diseases or disorders in a variety of therapeutic areas, such as allergic disease, autoimmune diseases, inflammatory diseases, and proliferative diseases.

These and other features of the invention will be set forth in expanded form as the disclosure continues.

DETAILED DESCRIPTION

The first aspect of the present invention provides at least one compound of Formula (I):

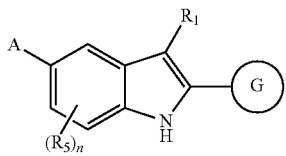
N-oxide, or a salt thereof, wherein:
G is:
(i)
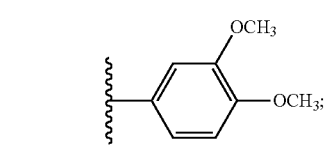
(ii)
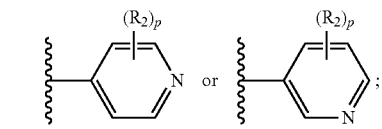
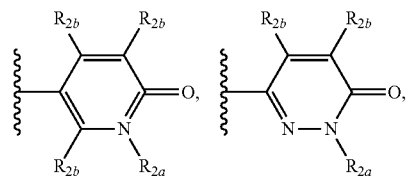
(iii)
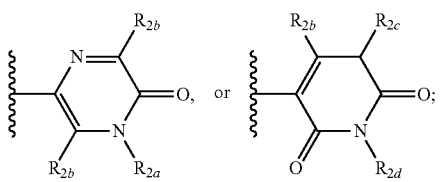
(iv) a 9-membered heterocyclic ring selected from:
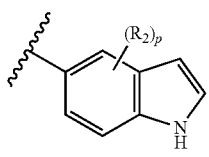 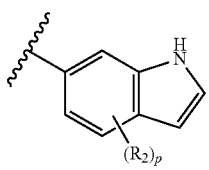
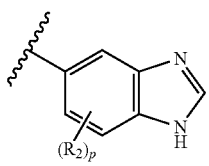 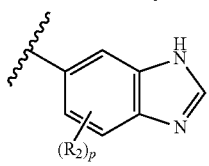
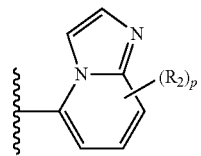 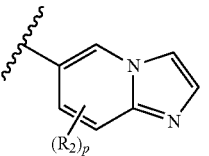
-continued
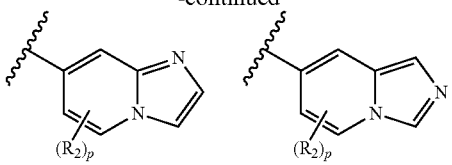
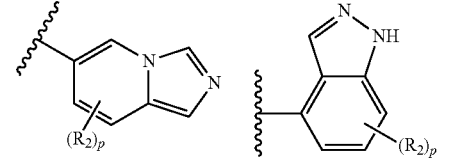
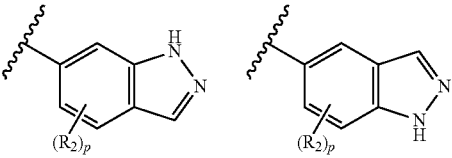
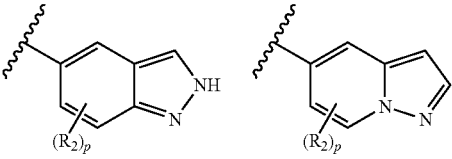
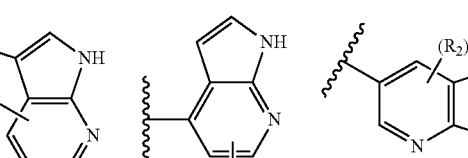
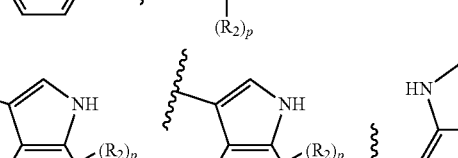
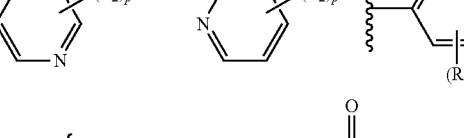
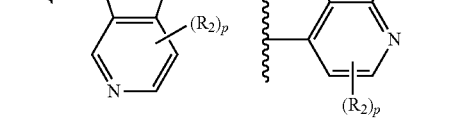
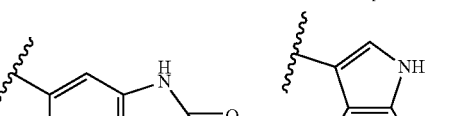
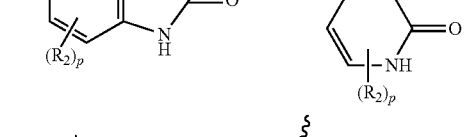
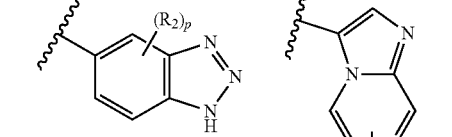
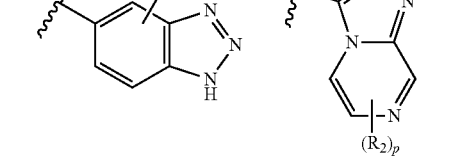

-continued
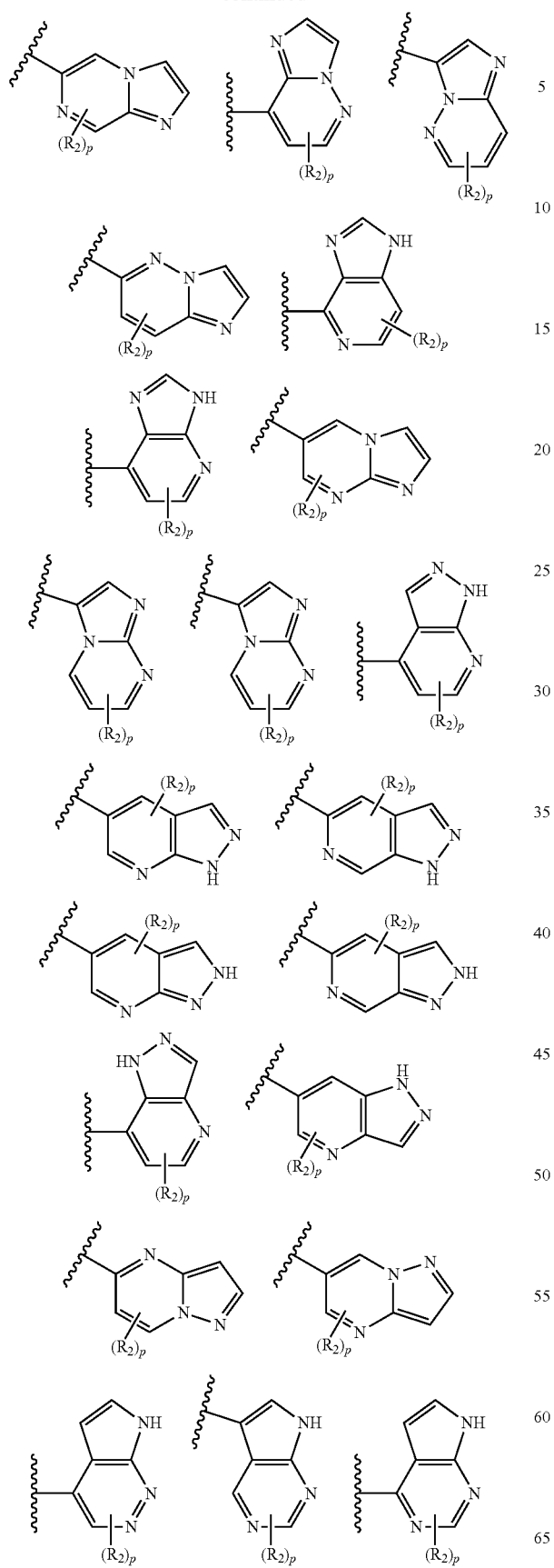
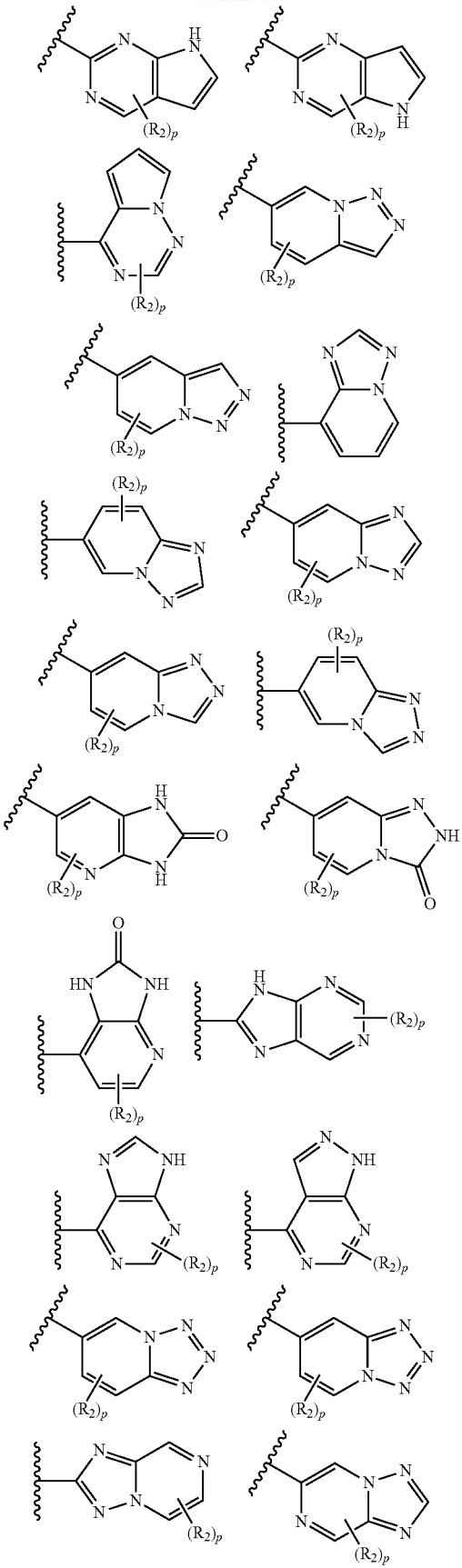

-continued
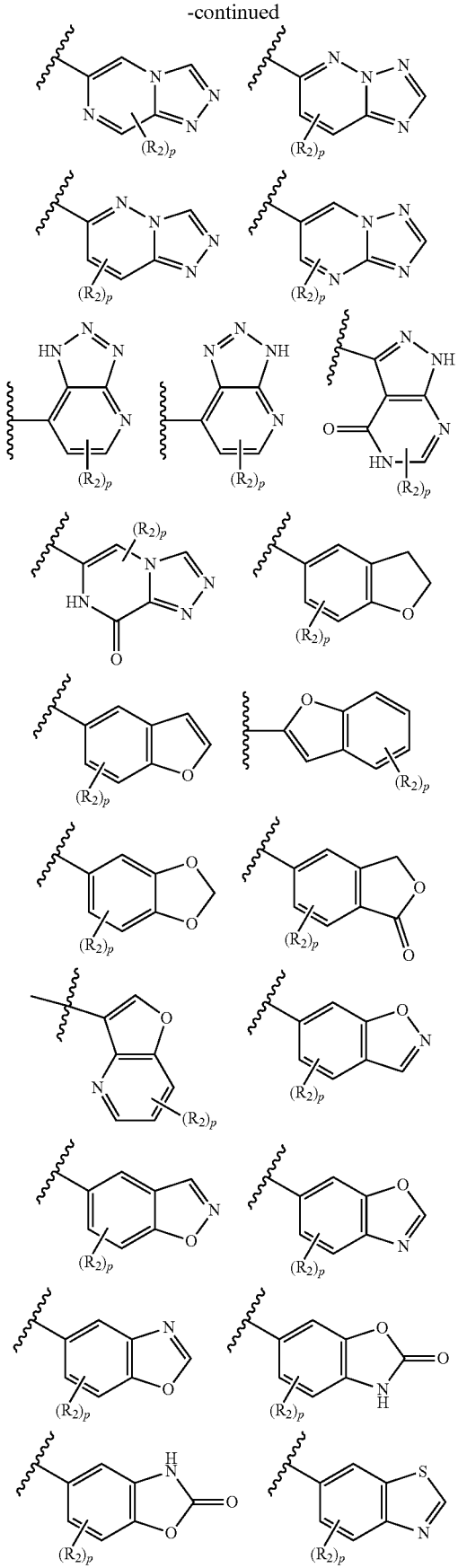
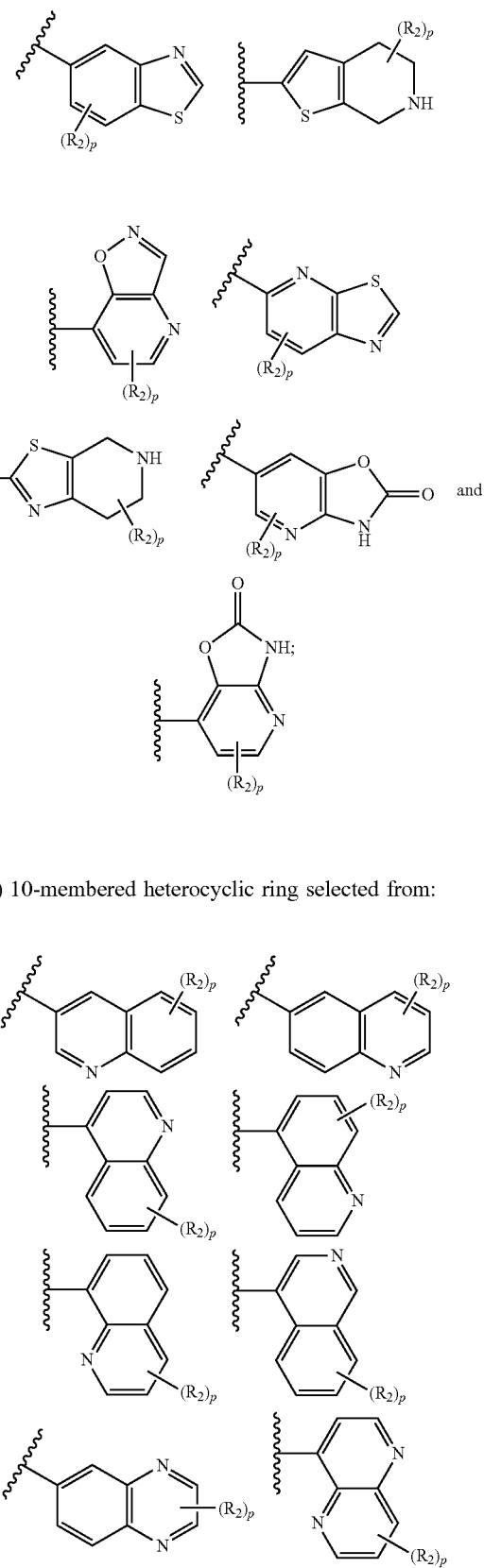
or
(v) 10-membered heterocyclic ring selected from:

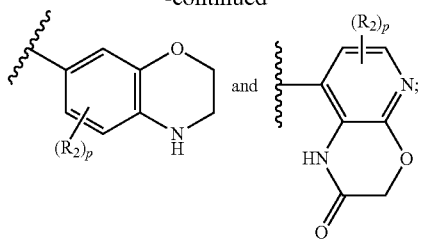

A is:
(i) —(CR$_x$R$_x$)$_{1-3}$R$_{11}$, C$_{1-3}$ aminoalkyl, —(CR$_x$R$_x$)$_{1-3}$NR$_x$C(O)R$_{11}$,
—(CR$_x$R$_x$)$_{1-2}$NR$_x$C(O)(CH$_2$)$_{1-2}$(piperidinyl),
—(CR$_x$R$_x$)$_{1-2}$NR$_x$C(O)O(CH$_2$)$_{1-2}$(piperidinyl), or
—(CR$_x$R$_x$)$_{1-2}$NR$_x$C(O)(CH$_2$)$_{1-2}$NR$_x$R$_x$;
(ii) —CR$_x$R$_{12}$R$_{13}$, wherein R$_{12}$ and RB together with the carbon atom to which they are attached form a cyclic group selected from azabicyclo[4.1.1]octanyl, azepanyl, azetidinyl, C$_{3-7}$ cycloalkyl, diazepanyl, diazaspiro[4.5]decanonyl, morpholinyl, octahydrocyclopenta[c]pyrrolyl, piperazinyl, piperidinyl, pyrrolidinyl, and quinuclidinyl, each substituted with zero to 4 R$_{12a}$; or
(iii) —CR$_x$=CR$_x$(piperidinyl); or R$_1$ is H, Cl, —CN, C$_{1-4}$ alkyl, C$_{1-3}$ fluoroalkyl, C$_{1-3}$ hydroxyalkyl, C$_{1-3}$ hydroxy-fluoroalkyl, —CR$_y$=CH$_2$, C$_{3-6}$ cycloalkyl, —CH$_2$(C$_{3-6}$ cycloalkyl), —C(O)O(C$_{1-3}$ alkyl), or tetrahydropyranyl;

each R$_2$ is independently halo, —CN, —OH, —NO$_2$, C$_{1-4}$ alkyl, C$_{1-2}$ fluoroalkyl, C$_{1-2}$ cyanoalkyl, C$_{1-3}$ hydroxyalkyl, C$_{1-3}$ aminoalkyl, —O(CH$_2$)$_{1-2}$OH, —(CH$_2$)$_{0-4}$(C$_{1-4}$ alkyl), C$_{1-3}$ fluoroalkoxy, —(CH$_2$)$_{1-40}$(C$_{1-3}$ alkyl), —O(CH$_2$)$_{1-2}$OC(O)(C$_{1-3}$ alkyl), —O(CH$_2$)$_{1-2}$NR$_x$R$_x$, —C(O)O(C$_{1-3}$ alkyl), —(CH$_2$)$_{0-2}$C(O)NR$_y$R$_y$, —C(O)NR$_x$(C$_{1-5}$ hydroxyalkyl), —C(O)NR$_x$(C$_{2-6}$ alkoxyalkyl), —C(O)NR$_x$(C$_{3-6}$ cycloalkyl), —NR$_y$R$_y$, —NR$_y$(C$_{1-3}$ fluoroalkyl), —NR$_y$(C$_{1-4}$ hydroxyalkyl), —NR$_x$CH$_2$(phenyl), —NR$_x$S(O)$_2$(C$_{3-6}$ cycloalkyl), —NR$_x$C(O)(C$_{1-3}$ alkyl), —NR$_x$CH$_2$(cyclopropyl), —S(O)$_2$(C$_{1-3}$ alkyl), —(CH$_2$)$_{0-2}$(C$_{3-6}$ cycloalkyl), —(CH$_2$)$_{0-2}$(phenyl), morpholinyl, dioxothiomorpholinyl, dimethyl pyrazolyl, methylpiperidinyl, methylpiperazinyl, amino-oxadiazolyl, imidazolyl, triazolyl, or —C(O)(thiazolyl);

R$_{2a}$ is C$_{1-6}$ alkyl, C$_{1-3}$ fluoroalkyl, C$_{1-6}$ hydroxyalkyl, C$_{1-3}$ aminoalkyl, —(CH$_2$)$_{0-4}$O(C$_{1-3}$ alkyl), C$_{3-6}$ cycloalkyl, —(CH$_2$)$_{0-3}$C(O)NR$_x$R$_x$, —CH$_2$(C$_{3-6}$ cycloalkyl), —CH$_2$(phenyl), tetrahydrofuranyl, tetrahydropyranyl, or phenyl;

each R$_{2b}$ is independently H, halo, —CN, —NR$_x$R$_x$, C$_{1-6}$ alkyl, C$_{1-3}$ fluoroalkyl, C$_{1-3}$ hydroxyalkyl, C$_{1-3}$ fluoroalkoxy, —(CH$_2$)$_{0-2}$O(C$_{1-3}$ alkyl), —(CH$_2$)$_{0-3}$C(O)NR$_x$R$_x$, —(CH$_2$)$_{1-3}$(C$_{3-6}$ cycloalkyl), —C(O)O(C$_{1-3}$ alkyl), —C(O)NR$_x$(C$_{1-3}$ alkyl), —CR$_x$=CR$_x$R$_x$, or —CR$_x$=CH(C$_{3-6}$ cycloalkyl);

R$_{2c}$ is R$_{2a}$ or R$_{2b}$;

R$_{2d}$ is R$_{2a}$ or R$_{2b}$; provided that one of R$_{2c}$ and R$_{2d}$ is R$_{2a}$, and the other of R$_{2c}$ and R$_{2d}$ is R$_{2b}$;

each R$_5$ is independently F, Cl, —CN, C$_{1-3}$ alkyl, C$_{1-2}$ fluoroalkyl, or —OCH$_3$;

R$_{11}$ is azetidinyl, azaspiro[3.5]nonanyl, dioxidothiomorpholinyl, hexahydropyrrolo[3,4-c]pyrrolyl, morpholinyl, piperazinyl, piperidinyl, pyridinyl, or pyrrolidinyl, each substituted with zero to 3 substituents independently selected from halo, —CN, C$_{1-4}$ alkyl, C$_{1-3}$ aminoalkyl, —(CH$_2$)$_{1-2}$(phenyl), —C(O)CH$_2$NR$_x$R$_x$, C$_{1-5}$ hydroxyalkyl, —(CH$_2$)$_{1-2}$C(O)NR$_x$R$_x$, —(CH$_2$)$_{1-2}$S(O)$_2$(C$_{1-3}$ alkyl), —(CH$_2$)$_{1-2}$S(O)(C$_{1-3}$ alkyl), oxetanyl, tetrahydrofuranyl, and tetrahydropyranyl;

each R$_{12a}$ is independently F, Cl, —OH, C$_{1-6}$ alkyl, C$_{1-4}$ fluoroalkyl, C$_{1-5}$ cyanoalkyl, C$_{1-6}$ hydroxyalkyl, —(CH$_2$)$_{1-2}$O(C$_{1-3}$ alkyl), —(CH$_2$)$_{1-2}$C(O)NR$_x$R$_x$, —(CH$_2$)$_{1-2}$S(O)$_2$(C$_{1-2}$ alkyl), —(CH$_2$)$_{1-2}$NR$_x$HS(O)$_2$(C$_{1-2}$ alkyl), —(CH$_2$)$_{1-2}$NR$_x$R$_x$, C$_{1-3}$ alkoxy, —NR$_y$R$_y$, —NR$_x$(C$_{1-3}$ fluoroalkyl), —NR$_x$(CH$_2$CH$_2$O(C$_{1-3}$ alkyl)), —NR$_x$(C$_{1-2}$ cyanoalkyl), —NR$_x$CH$_2$NR$_x$R$_x$, —NR$_x$(C$_{1-4}$ hydroxyalkyl), —NR$_x$(CH$_2$C(O)NR$_x$R$_x$), —NR$_x$(C$_{1-3}$ alkoxy), —NR$_x$CH$_2$CH$_2$S(O)$_2$(C$_{1-2}$ alkyl), —NR$_x$C(O)CH$_3$, —NR$_x$C(O)(C$_{1-2}$ fluoroalkyl), —NR$_x$C(O)CR$_x$R$_x$NR$_x$R$_x$, —NR$_x$C(O)CH$_2$NR$_y$R$_y$, —NR$_x$C(O)CH$_2$NR$_x$(C$_{1-4}$ hydroxyalkyl), —NR$_x$(CH$_2$)$_{1-2}$C(O)NR$_x$R$_x$, —NR$_x$S(O)$_2$(C$_{1-2}$ alkyl), —C(O)(C$_{1-5}$ alkyl), —C(O)(CH$_2$)$_{1-3}$O(C$_{1-2}$ alkyl), —C(O)CR$_x$R$_x$NR$_y$R$_y$, R$_{12b}$, —CR$_x$R$_x$R$_{12b}$, —C(O)R$_{12b}$, —CR$_x$R$_x$R$_{12b}$, —C(O)CR$_x$R$_x$NR$_x$R$_{12b}$, —C(O)NR$_x$R$_{12b}$, —NR$_x$C(O)CR$_x$R$_x$R$_{12b}$, —NR$_x$R$_{12b}$, —NR$_x$CR$_x$R$_x$R$_{12b}$, —NR$_x$C(O)CR$_x$R$_x$NR$_x$R$_{12b}$, —NR$_x$C(O)CR$_x$R$_x$NR$_x$CH$_2$R$_{12b}$, —NR$_x$CR$_x$R$_x$C(O)NR$_x$R$_{12b}$, or —OR$_{12b}$;

R$_{12b}$ is azetidinyl, C$_{3-6}$ cycloalkyl, diazabicyclo[2.2.1]heptanyl, dioxolanyl, dioxidotetrahydrothiopyranyl, dioxidothiomorpholinyl, imidazolyl, morpholinyl, octahydrocyclopenta[c]pyrrolyl, octahydropyrrolo[3,4-c]pyrrolyl, oxaazaspiro[3.3]heptanyl, oxetanyl, phenyl, piperazinyl, piperazinonyl, piperidinyl, pyridinyl, pyrrolidinyl, quinuclidinyl, tetrahydrofuranyl, tetrahydropyranyl, or triazolyl, each substituted with zero to 4 substituents independently selected from F, Cl, —OH, C$_{1-4}$ alkyl, C$_{1-3}$ fluoroalkyl, C$_{1-3}$ hydroxyalkyl, C$_{1-3}$ aminoalkyl, C$_{1-4}$ alkoxy, —(CH$_2$)$_{1-2}$O(C$_{1-3}$ alkyl), —NR$_x$R$_x$, and —C(O)NR$_x$R$_x$;

R$_v$ is H, C$_{1-2}$ alkyl, or C$_{1-2}$ fluoroalkyl;

each R$_x$ is independently H or —CH$_3$;

each R$_y$ is independently F, Cl, —CN, C$_{1-3}$ alkyl, C$_{1-3}$ fluoroalkyl, C$_{1-3}$ alkoxy, —NR$_x$C(O)(C$_{1-3}$ alkyl), —C(O)NR$_x$R$_x$, C$_{3-6}$ cycloalkyl, piperidinyl, or morpholinyl;

n is zero, 1, or 2; and p is zero, 1, 2, 3, or 4.

The compounds of Formula (I) or salts thereof in which A is —CHR$_{12}$R$_{13}$; and R$_{12}$ and R$_{13}$ together with the carbon atom to which they are attached form a cyclic group and the cyclic group has one or more heteroatoms, the cyclic group is bonded to the indole ring by a carbon atom in the cyclic group.

One embodiment provides a compound of Formula (I) or a salt thereof wherein G is:

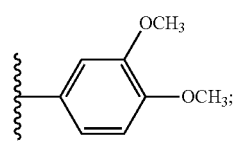 [SMILES: *c1ccc(OC)c(OC)c1]

and A, R$_1$, R$_5$, and n are defined in the first aspect.

One embodiment provides a compound of Formula (I), N-oxide, or a salt thereof wherein G is:

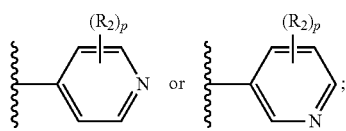

and A, R₁, R₂, R₅, n, and p are defined in the first aspect.

One embodiment provides a compound of Formula (I) or a salt thereof wherein G is

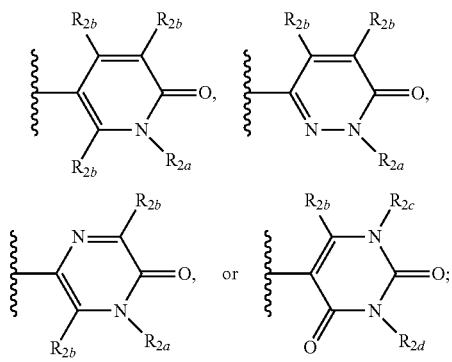

and A, $R_1$, $R_{2a}$, $R_{2b}$, $R_{2c}$, $R_{2d}$, $R_5$, n, and p are defined in the first aspect. Included in this embodiment are compounds in which $R_{2a}$ is $C_{1-4}$ alkyl, $C_{1-2}$ fluoroalkyl, $C_{1-4}$ hydroxyalkyl, —(CH₂)$_{1-3}$OCH₃, $C_{3-6}$ cycloalkyl, —CH₂C(O)NR$_x$R$_x$, —CH₂($C_{3-6}$ cycloalkyl), —CH₂(phenyl), tetrahydrofuranyl, or phenyl; and each $R_{2b}$ is independently H, F, Cl, —CN, —NR$_x$R$_x$, $C_{1-6}$ alkyl, $C_{1-2}$ fluoroalkyl, $C_{1-3}$ hydroxyalkyl, —(CH₂)$_{0-2}$O($C_{1-2}$ alkyl), —(CH₂)$_{0-2}$C(O)NR$_x$R$_x$, —(CH₂)$_{1-3}$(cyclopropropyl), —C(O)O($C_{1-2}$ alkyl), —C(O)NR$_x$($C_{1-3}$ alkyl), —CR$_x$=CH₂, or —CH=CH($C_{3-6}$ cycloalkyl). Also included in this embodiment are compounds in which $R_{2a}$ is —CH₃; and each $R_{2b}$ is independently H, Cl, or —CH₃.

One embodiment provides a compound of Formula (I) or a salt thereof wherein G is a 9-membered heterocyclic ring selected from:

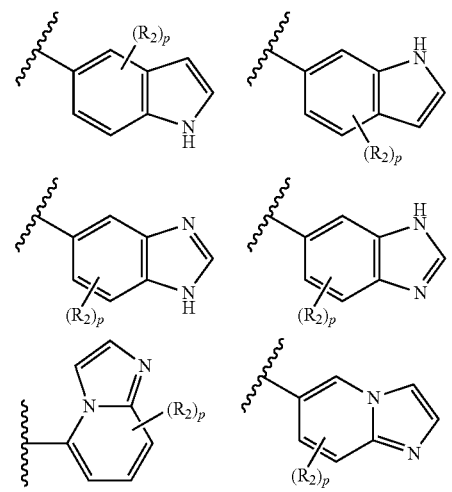

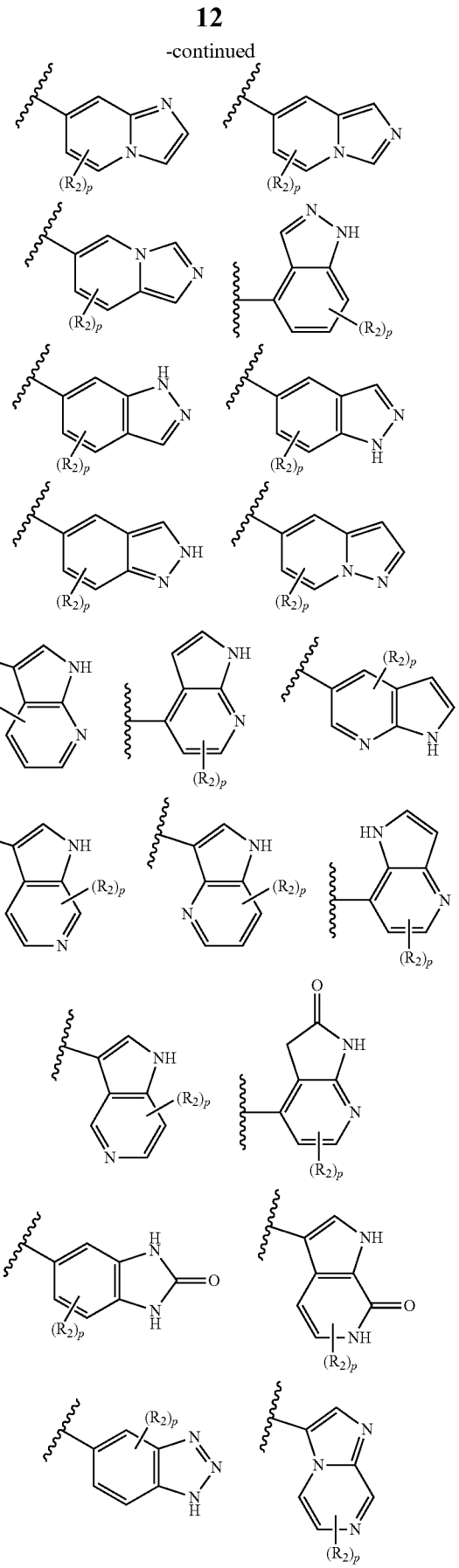

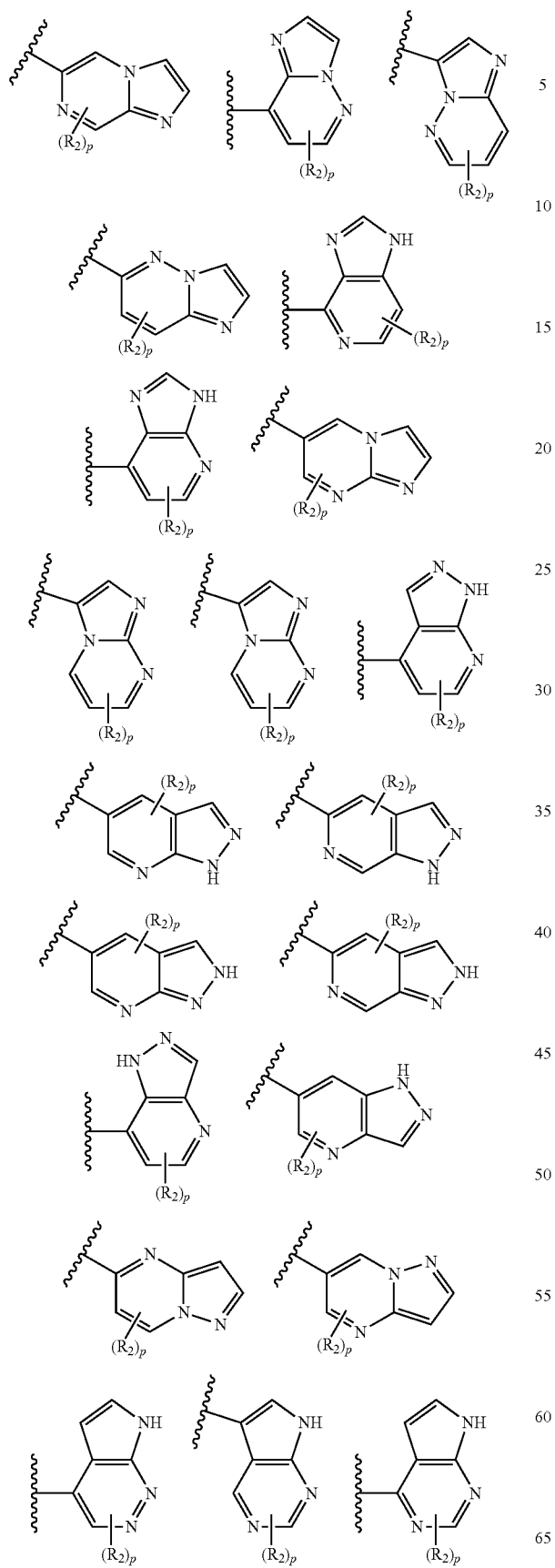
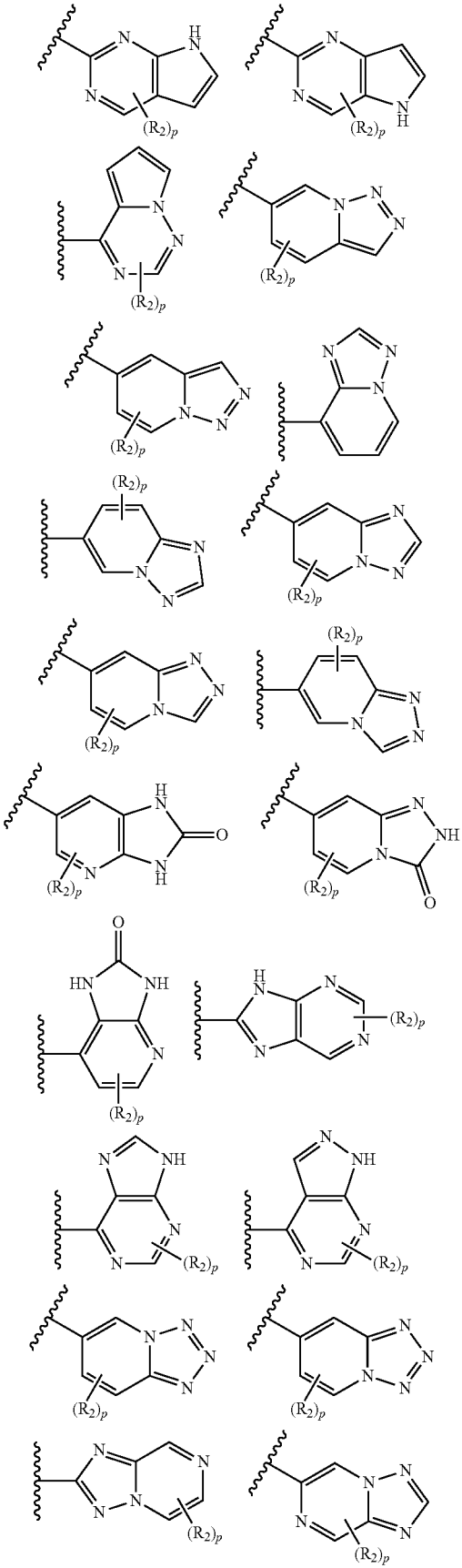

-continued
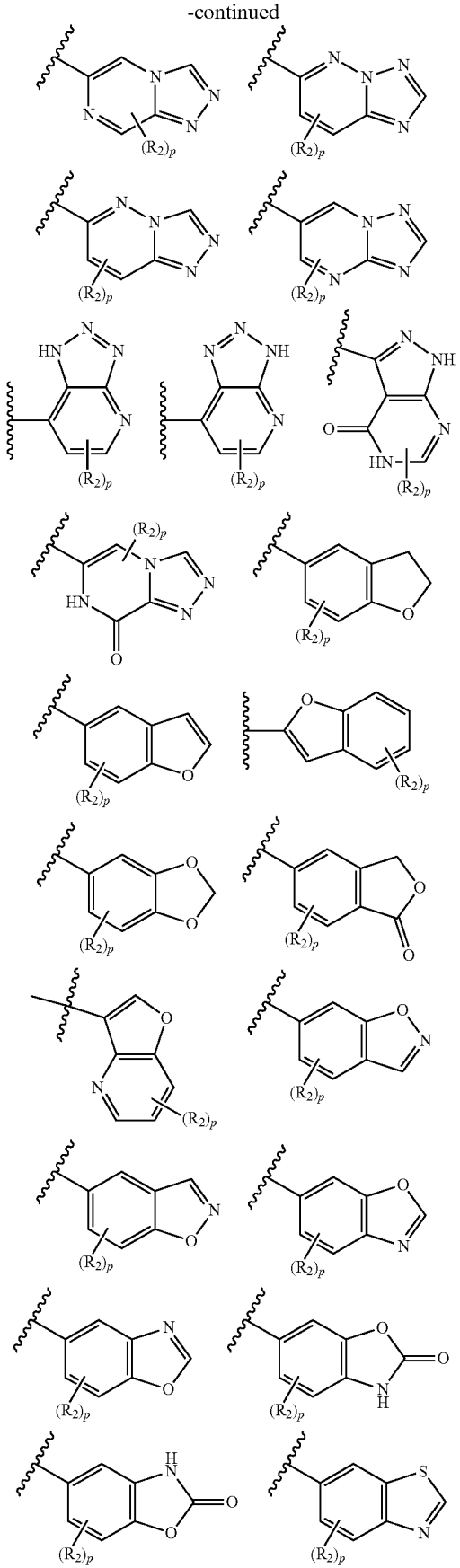
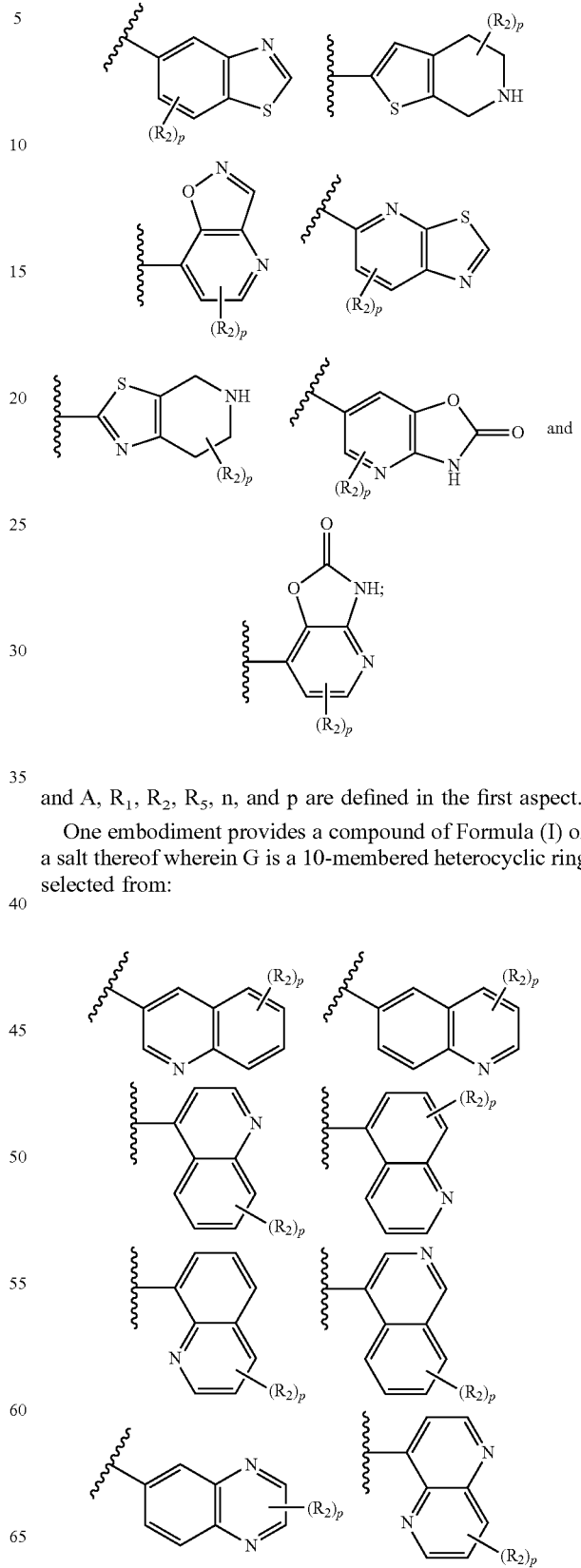
and A, $R_1$, $R_2$, $R_5$, n, and p are defined in the first aspect.
One embodiment provides a compound of Formula (I) or a salt thereof wherein G is a 10-membered heterocyclic ring selected from:

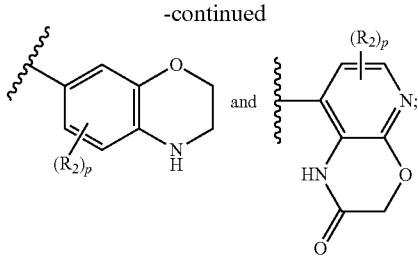

and A, R₁, R₂, R₅, n, and p are defined in the first aspect.

One embodiment provides a compound of Formula (I), N-oxide, or a salt thereof wherein $R_1$ is H, Cl, —CN, $C_{1-4}$ alkyl, $C_{1-2}$ fluoroalkyl, $C_{1-2}$ hydroxyalkyl, or —C(O)O($C_{1-2}$ alkyl); each $R_2$ is independently F, Cl, —CN, —OH, $C_{1-3}$ alkyl, $C_{1-2}$ fluoroalkyl, $C_{1-2}$ cyanoalkyl, $C_{1-3}$ hydroxyalkyl, $C_{1-2}$ aminoalkyl, —(CH₂)₀₋₂O($C_{1-3}$ alkyl), $C_{3-6}$ cycloalkyl, —NR$_x$R$_x$, —(CH₂)₀₋₂C(O)NR$_x$R$_x$, —CH₂($C_{3-6}$ cycloalkyl), —CH₂(phenyl), or phenyl, $R_{2a}$ is $C_{1-4}$ alkyl, $C_{1-2}$ fluoroalkyl, $C_{1-4}$ hydroxyalkyl, —(CH₂)₁₋₃OCH₃, $C_{3-6}$ cycloalkyl, —CH₂C(O)NR$_x$R$_x$, —CH₂($C_{3-6}$ cycloalkyl), —CH₂(phenyl), tetrahydrofuranyl, or phenyl; each $R_{2b}$ is independently H, F, Cl, —CN, —NR$_x$R$_x$, $C_{1-6}$ alkyl, $C_{1-2}$ fluoroalkyl, $C_{1-3}$ hydroxyalkyl, —(CH₂)₀₋₂O($C_{1-2}$ alkyl), —(CH₂)₀₋₂C(O)NR$_x$R$_x$, —(CH₂)₁₋₃(cyclopropyl), —C(O)O($C_{1-2}$ alkyl), —C(O)NR$_x$($C_{1-3}$ alkyl), —CR$_x$=CH₂, or —CH=CH($C_{3-6}$ cycloalkyl); A is: (i) —(CR$_x$R$_x$)₁₋₂R₁₁, $C_{1-2}$ aminoalkyl, (CR$_x$R$_x$)₁₋₂NR$_x$C(O)R₁₁, —CH₂NR$_x$C(O)(CH₂)₁₋₂(piperidinyl), —CH₂NR$_x$C(O)OCH₂(piperidinyl), or —CH₂NR$_x$C(O)(CH₂)₁₋₂NR$_x$R$_x$; (ii) —CR$_x$R₁₂R₁₃, wherein R₁₂ and R₁₃ together with the carbon atom to which they are attached form a cyclic group selected from azabicyclo[4.1.1]octanyl, azepanyl, azetidinyl, $C_{3-7}$ cycloalkyl, diazepanyl, diazaspiro[4.5]decanonyl, morpholinyl, octahydrocyclopenta[c]pyrrolyl, piperazinyl, piperidinyl, pyrrolidinyl, or quinuclidinyl, each substituted with zero to 3 R₁₂$_a$; or (iii) —CR$_x$=CR$_x$(piperidinyl); R₁₁ is azetidinyl, azaspiro[3.5]nonanyl, dioxidothiomorpholinyl, hexahydropyrrolo[3,4-c]pyrrolyl, morpholinyl, piperazinyl, piperidinyl, pyridinyl, or pyrrolidinyl, each substituted with zero to 3 substituents independently selected from F, Cl, —CN, $C_{1-3}$ alkyl, $C_{1-2}$ aminoalkyl, —CH₂(phenyl), —C(O)CH₂NR$_x$R$_x$, —CH₂CR$_x$R$_x$OH, —CH₂C(O)NR$_x$R$_x$, —CH₂CH₂S(O)₂($C_{1-3}$ alkyl), —CH₂CH₂S(O)($C_{1-3}$ alkyl), oxetanyl, tetrahydrofuranyl, and tetrahydropyranyl; each R₁₂$_a$ is independently —OH, $C_{1-4}$ alkyl, $C_{1-3}$ fluoroalkyl, $C_{1-2}$ cyanoalkyl, $C_{1-4}$ hydroxyalkyl, —(CH₂)₁₋₂O($C_{1-2}$ alkyl), —CH₂C(O)NR$_x$R$_x$, —(CH₂)₁₋₂S(O)₂($C_{1-2}$ alkyl), —(CH₂)₁₋₂NHS(O)₂($C_{1-2}$ alkyl), —(CH₂)₁₋₂NR$_x$R$_x$$C_{1-2}$ alkoxy, —NR$_y$R$_y$, —NR$_x$($C_{1-3}$ fluoroalkyl), —NR$_x$(CH₂CH₂O($C_{1-2}$ alkyl)), —NR$_x$($C_{1-2}$ cyanoalkyl), —NR$_x$CH₂NR$_x$R$_x$, —NR$_x$($C_{1-4}$ hydroxyalkyl), —NR$_x$(CH₂C(O)NH₂), —NR$_x$(OCH₃), —NR$_x$CH₂CH₂S(O)₂($C_{1-2}$ alkyl), —NR$_x$C(O)CH₃, —NR$_x$C(O)($C_{1-2}$ fluoroalkyl), —NR$_x$C(O)CR$_x$R$_x$NR$_x$R$_x$, —NR$_x$C(O)CH₂NR$_y$R$_y$, —NR$_x$C(O)CH₂NR$_x$($C_{1-4}$ hydroxyalkyl), —NR$_x$CH₂C(O)NR$_x$R$_x$, —NR$_x$S(O)₂CH₃, —C(O)($C_{1-5}$ alkyl), —C(O)CH₂O($C_{1-2}$ alkyl), —C(O)CH₂CH₂O($C_{1-2}$ alkyl), —C(O)CH₂NR$_x$R$_x$, —C(O)CHR$_x$NR$_y$R$_y$, R₁₂$_b$, —CR$_x$R$_x$R₁₂$_b$, —C(O)R₁₂$_b$, —CR$_x$R$_x$R₁₂$_b$, —C(O)CH₂NR$_x$R₁₂$_b$, —C(O)NR$_x$R₁₂$_b$, —NR$_x$C(O)CR$_x$R$_x$R₁₂$_b$, —NR$_x$R₁₂$_b$, —NR$_x$CR$_x$R$_x$R₁₂$_b$, —NR$_x$C(O)CH₂NR$_x$R₁₂$_b$, —NR$_x$C(O)CH₂NR$_x$CH₂R₁₂$_b$, —NR$_x$CH₂C(O)NR$_x$R₁₂$_b$, or —OR₁₂$_b$; R₁₂$_b$ is azetidinyl, $C_{3-6}$ cycloalkyl, diazabicyclo[2.2.1]heptanyl, dioxolanyl, dioxidotetrahydrothiopyranyl, dioxidothiomorpholinyl, imidazolyl, morpholinyl, octahydrocyclopenta[c]pyrrolyl, octahydropyrrolo[3,4-c]pyrrolyl, oxaazaspiro[3.3]heptanyl, oxetanyl, phenyl, piperazinyl, piperazinonyl, piperidinyl, pyridinyl, pyrrolidinyl, quinuclidinyl, tetrahydrofuranyl, tetrahydropyranyl, or triazolyl, each substituted with zero to 4 substituents independently selected from F, Cl, —OH, $C_{1-3}$ alkyl, $C_{1-2}$ hydroxyalkyl, $C_{1-2}$ alkoxy, —(CH₂)₁₋₂O($C_{1-2}$ alkyl), —NR$_x$R$_x$, and —C(O)NR$_x$R$_x$; each $R_5$ is independently F, Cl, —CN, $C_{1-2}$ alkyl, or —OCH₃; n is zero or 1; p is zero, 1, 2, or 3; and G is defined in the first aspect.

One embodiment provides a compound of Formula (I), N-oxide, or a salt thereof wherein G is:

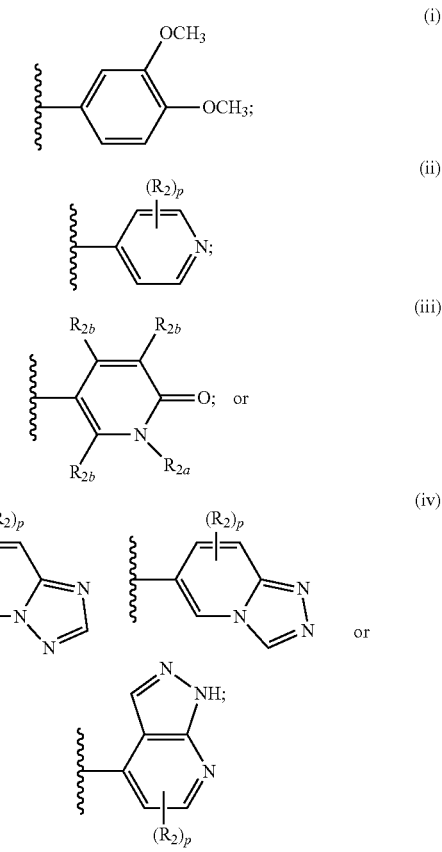

and A, R₁, R₂, R₁₂$_a$, R₁₂$_b$, R₅, n, and p are defined in the first aspect. Included in this embodiment are compounds in which $R_1$ is H, Cl, —CN, $C_{1-4}$ alkyl, $C_{1-2}$ fluoroalkyl, $C_{1-2}$ hydroxyalkyl, or —C(O)O($C_{1-2}$ alkyl); each $R_2$ is independently F, Cl, —CN, —OH, $C_{1-3}$ alkyl, $C_{1-2}$ fluoroalkyl, $C_{1-2}$ cyanoalkyl, $C_{1-3}$ hydroxyalkyl, $C_{1-2}$ aminoalkyl, —(CH₂)₀₋₂O($C_{1-3}$ alkyl), $C_{1-6}$ cycloalkyl, —NR$_x$R$_x$, —(CH₂)₁₋₂C(O)NR$_x$R$_x$, —CH₂($C_{3-6}$ cycloalkyl), —CH₂(phenyl), or phenyl; $R_{2a}$ is $C_{1-4}$ alkyl, $C_{1-2}$ fluoroalkyl, $C_{1-4}$ hydroxyalkyl, —(CH₂)₁₋₃OCH₃, $C_{3-6}$ cycloalkyl, —CH₂C(O)NR$_x$R$_x$, —CH₂($C_{3-6}$ cycloalkyl), —CH₂(phenyl), tetrahydrofuranyl, or phenyl; each $R_{2b}$ is independently H, F, Cl, —CN, —NR$_x$R$_x$, $C_{1-6}$ alkyl, $C_{1-2}$ fluoroalkyl, $C_{1-3}$ hydroxyalkyl, —(CH₂)₀₋₂O($C_{1-2}$ alkyl), —(CH₂)₀₋₂C(O)NR$_x$R$_x$, —(CH₂)₁₋₃(cyclopropyl), —C(O)O($C_{1-2}$ alkyl), —C(O)NR$_x$($C_{1-3}$ alkyl), —CR$_x$=CH₂, or —CH=CH($C_{3-6}$ cycloalkyl); A is: (i) —(CR$_x$R$_x$)₁₋₂R₁₁, $C_{1-2}$ aminoalkyl, —(CR$_x$R$_x$)₁₋₂NR$_x$C(O)R₁₁, —CH₂NR$_x$C(O)(CH₂)₁₋₂(piperidinyl), —CH₂NR$_x$C(O)OCH₂(piperidinyl), or —CH$_2$NR$_x$C(O)(CH$_2$)$_{1-2}$NR$_x$R$_x$; (ii) —CR$_x$R$_{12}$R$_{13}$, wherein R$_{12}$ and R$_{13}$ together with the carbon atom to which they are attached form a cyclic group selected from azabicyclo[4.1.1] octanyl, azepanyl, azetidinyl, C$_{3-7}$ cycloalkyl, diazepanyl, diazaspiro[4.5]decanonyl, morpholinyl, octahydrocyclopenta[c]pyrrolyl, piperazinyl, piperidinyl, pyrrolidinyl, or quinuclidinyl, each substituted with zero to 3 R$_{12a}$; or (iii) —CR$_x$=CR$_x$(piperidinyl); R$_{11}$ is azetidinyl, azaspiro[3.5]nonanyl, dioxidothiomorpholinyl, hexahydropyrrolo[3,4-c]pyrrolyl, morpholinyl, piperazinyl, piperidinyl, pyridinyl, or pyrrolidinyl, each substituted with zero to 3 substituents independently selected from F, Cl, —CN, C$_{1-3}$ alkyl, C$_{1-2}$ aminoalkyl, —CH$_2$(phenyl), —C(O)CH$_2$NR$_x$R$_x$, —CH$_2$CR$_x$R$_x$OH, —CH$_2$C(O)NR$_x$R$_x$, —CH$_2$CH$_2$S(O)$_2$(C$_{1-3}$ alkyl), —CH$_2$CH$_2$S(O)(C$_{1-3}$ alkyl), oxetanyl, tetrahydrofuranyl, and tetrahydropyranyl; each R$_{12a}$ is independently —OH, C$_{1-5}$ alkyl, C$_{1-3}$ fluoroalkyl, C$_{1-2}$ cyanoalkyl, C$_{1-4}$ hydroxyalkyl, —(CH$_2$)$_{1-2}$O(C$_{1-2}$ alkyl), —CH$_2$C(O)NR$_x$R$_x$, —(CH$_2$)$_{1-2}$S(O)$_2$(C$_{1-2}$ alkyl), —(CH$_2$)$_{1-2}$NHS(O)$_2$(C$_{1-2}$ alkyl), —(CH$_2$)$_{1-2}$NR$_x$R$_x$, C$_{1-2}$ alkoxy, —NR$_y$R$_y$, —NR$_x$(C$_{1-3}$ fluoroalkyl), —NR$_x$(CH$_2$CH$_2$O(C$_{1-2}$ alkyl)), —NR$_x$(C$_{1-2}$ cyanoalkyl), —NR$_x$CH$_2$NR$_x$R$_x$, —NR$_x$(C$_{1-5}$ hydroxyalkyl), —NR$_x$(CH$_2$C(O)NH$_2$), —NR$_x$(OCH$_3$), —NR$_x$CH$_2$CH$_2$S(O)$_2$(C$_{1-2}$ alkyl), —NR$_x$C(O)CH$_3$, —NR$_x$C(O)(C$_{1-2}$ fluoroalkyl), —NR$_x$C(O)CR$_x$R$_x$NR$_x$R$_x$, —NR$_x$C(O)CH$_2$NR$_x$R$_y$, —NR$_x$C(O)CH$_2$NR$_x$(C$_{1-4}$ hydroxyalkyl), —NR$_x$CH$_2$C(O)NR$_x$R$_x$, —NR$_x$S(O)$_2$CH$_3$, —C(O)(C$_{1-5}$ alkyl), —C(O)CH$_2$O(C$_{1-2}$ alkyl), —C(O)CH$_2$CH$_2$O(C$_{1-2}$ alkyl), —C(O)CH$_2$NR$_x$, —C(O)CHR$_x$NR$_y$R$_y$, R$_{12b}$, —CR$_x$R$_R$R$_{12b}$, —C(O)R$_{12b}$, —CR$_x$R$_x$R$_{12b}$, —C(O)CH$_2$NR$_x$R$_{12b}$, —C(O)NR$_x$R$_{12b}$, —NR$_x$C(O)CR$_x$R$_{12b}$, —NR$_x$R$_{12b}$, —NR$_x$CR$_x$R$_x$R$_{12b}$, —NR$_x$C(O)CH$_2$NR$_x$R$_{12b}$, —NR$_x$C(O)CH$_2$NR$_x$CH$_2$R$_{12b}$, —NR$_x$CH$_2$C(O)NR$_x$R$_{12b}$, or —OR$_{12b}$; R$_{12b}$ is azetidinyl, C$_{3-6}$ cycloalkyl, diazabicyclo[2.2.1]heptanyl, dioxolanyl, dioxidotetrahydrothiopyranyl, dioxidothiomorpholinyl, imidazolyl, morpholinyl, octahydrocyclopenta[c]pyrrolyl, octahydropyrrolo[3,4-c]pyrrolyl, oxaazaspiro[3.3]heptanyl, oxetanyl, phenyl, piperazinyl, piperazinonyl, piperidinyl, pyridinyl, pyrrolidinyl, quinuclidinyl, tetrahydrofuranyl, tetrahydropyranyl, or triazolyl, each substituted with zero to 4 substituents independently selected from F, Cl, —OH, C$_{1-3}$ alkyl, C$_{1-2}$ hydroxyalkyl, C$_{1-2}$ alkoxy, —(CH$_2$)$_{1-2}$O(C$_{1-2}$ alkyl), —NR$_x$R$_x$, and —C(O)NR$_x$R$_x$; each R$_1$ is independently F, Cl, —CN, C$_{1-2}$ alkyl, or —OCH$_3$; n is zero or 1; p is zero, 1, 2, or 3; and R$_x$ and R$_y$ are defined in the first aspect. Also included in this embodiment are compounds in which R$_1$ is —CH$_2$CH$_3$ or —CH(CH$_3$)$_2$; each R$_2$ is independently —CH$_3$ or —OCH$_3$; R$_{2a}$ is —CH$_3$; each Rb is independently H or —CH$_3$; A is: (i) —CHR$_x$R$_{11}$, —CH$_2$CH$_2$R$_{11}$, —CH$_2$NH$_2$, —CH$_2$NHC(O)R$_{11}$, —CH$_2$NHC(O)CH$_2$CH$_2$(piperidinyl), —CH$_2$NHC(O)OCH$_2$(piperidinyl), or —CH$_2$NHC(O)CH$_2$CH$_2$N(CH$_3$)$_2$; (ii) —CHR$_{12}$R$_{13}$, wherein R$_{12}$ and R$_{13}$ together with the carbon atom to which they are attached form a cyclic group selected from azabicyclo[4.1.1]octanyl, azepanyl, azetidinyl, C$_{3-6}$ cycloalkyl, diazaspiro[4.5]decanonyl, morpholinyl, octahydrocyclopenta[c]pyrrolyl, piperidinyl, pyrrolidinyl, or quinuclidinyl, each substituted with zero to 3 R$_{12a}$; or (iii) —CH=CH(piperidinyl); R$_{11}$ is azetidinyl, azaspiro[3.5]nonanyl, dioxidothiomorpholinyl, hexahydropyrrolo[3,4-c]pyrrolyl, morpholinyl, piperazinyl, piperidinyl, or pyrrolidinyl, each substituted with zero to 2 substituents independently selected from F, —CH$_3$, —CH(CH$_3$)$_2$, —CH$_2$CN, —CH$_2$(phenyl), —C(O)CH$_2$N(CH$_3$)$_2$, —CH$_2$C(CH$_3$)$_2$OH, —CH$_2$C(O)N(CH$_3$)$_2$, —CH$_2$CH$_2$S(O)$_2$CH$_3$, —CH$_2$CH$_2$S(O)CH$_3$, oxetanyl, and tetrahydropyranyl; each R$_{12a}$ is independently —OH, —CH$_3$, —CH$_2$CH$_2$CH$_3$, —CH(CH$_3$)$_2$, —CH$_2$CH(CH$_3$)$_2$, —CF$_3$, —CH$_2$CH$_2$CH$_2$CF$_3$, —CH$_2$CN, —CH$_2$C(CH$_3$)$_2$OH, —CH$_2$CH$_2$OCH$_3$, —CH$_2$C(O)NH(CH$_3$), —CH$_2$C(O)N(CH$_3$)$_2$, —CH$_2$CH$_2$S(O)$_2$CH$_3$, —CH$_2$CH$_2$NHS(O)$_2$CH$_3$, —CH$_2$NR$_x$R$_x$, —CH$_2$CH$_2$NH(CH$_3$), —OCH$_3$, —NR$_x$R$_x$, —N(CH$_3$)(CH$_2$CH$_3$), —N(CH$_3$)(CH(CH$_3$)$_2$), —NR$_x$(CH$_2$CHF$_2$) —NH(CH$_2$CF$_3$), —N(CH$_3$)(CH$_2$CH$_2$CF$_3$), —N(CH$_3$)(CH$_2$CH$_2$OCH$_3$), —NH(CH$_2$CN), —N(CH$_3$)CH$_2$N(CH$_3$)$_2$, —NH(CH$_2$C(CH$_3$)$_2$OH), —NH(CH$_2$C(O)NH$_2$), —N(CH$_3$)OCH$_3$), —NR$_x$CH$_2$CH$_2$S(O)$_2$CH$_3$, —NHC(O)CH$_3$, —NHC(O)CH$_2$CF$_3$, —NHC(O)CHR$_x$NH(CH$_3$), —NR$_x$C(O)CH$_2$N(CH)$_2$, —NHC(O)CH$_2$N(CH$_3$)(CH$_2$CH$_3$), —NHC(O)CH$_2$N(CH$_2$CH$_3$)$_2$, —NHC(O)CH$_2$NH(CH$_2$C(CH$_3$)$_2$OH), —NHCH$_2$C(O)NR$_x$(CH$_3$), —NHS(O)$_2$CH$_3$, —C(O)C(CH$_3$)$_3$, —C(O)CH(CH$_2$CH$_3$)$_2$, —C(O)CH$_2$OCH$_3$, —C(O)CH$_2$CH$_2$OCH$_3$, —C(O)CH$_2$NH(CH$_3$), —C(O)CH$_2$N(CH$_3$)$_2$, —C(O)CH(CH$_3$)NH(CH$_3$), —C(O)CH$_2$N(CH$_3$)(CH$_2$CH$_3$), —C(O)CH$_2$N(CH$_2$CH$_3$)$_2$, R$_{12b}$, —CH$_2$R$_{12b}$, —C(O)R$_{12b}$, —C(O)CH$_2$R$_{12b}$, —C(O)CH$_2$NHR$_{12b}$, —C(O)NR$_x$R$_{12b}$, —NR$_x$C(O)CH$_2$R$_{12b}$, —NR$_x$R$_{12b}$, —NR$_x$CH$_2$R$_{12b}$, —NHC(O)CH$_2$NR$_x$R$_{12b}$, —NHC(O)CH$_2$NR$_x$CH$_2$R$_{12b}$, —NHCH$_2$C(O)NHR$_{12b}$, or —OR$_{12b}$; R$_{12b}$ is azetidinyl, cyclopropyl, diazabicyclo[2.2.1]heptanyl, dioxolanyl, dioxidotetrahydrothiopyranyl, dioxidothiomorpholinyl, imidazolyl, morpholinyl, octahydrocyclopenta[c]pyrrolyl, octahydropyrrolo[3,4-c]pyrrolyl, oxaazaspiro[3.3]heptanyl, oxetanyl, phenyl, piperazinyl, piperazinonyl, piperidinyl, pyridinyl, pyrrolidinyl, quinuclidinyl, tetrahydrofuranyl, tetrahydropyranyl, or triazolyl, each substituted with zero to 4 substituents independently selected from F, —OH, —CH$_3$, —CH(CH$_3$)$_2$, —CH$_2$OH, —OCH$_3$, —CH$_2$CH$_2$OCH$_3$, —NR$_x$R$_x$, and —C(O)NH$_2$; n is zero; and p is zero, 1, 2, or 3.

One embodiment provides a compound of Formula (I), N-oxide, or a salt thereof, wherein R$_1$ is —CH$_2$CH$_3$ or —CH(CH$_3$)$_2$; each R$_2$ is independently —CH$_3$ or —OCH$_3$; R$_{2a}$ is —CH$_3$; each R$_{2b}$ is independently H or —CH$_3$; A is: (i) —CHR$_x$R$_{11}$, —CH$_2$CH$_2$R$_{11}$. —CH$_2$NH$_2$, —CH$_2$NHC(O)R$_{11}$, —CH$_2$NHC(O)CH$_2$CH$_2$(piperidinyl), —CH$_2$NHC(O)OCH$_2$(piperidinyl), or —CH$_2$NHC(O)CH$_2$CH$_2$N(CH$_3$)$_2$; (ii) —CHR$_{12}$R$_{13}$, wherein R$_{12}$ and R$_{13}$ together with the carbon atom to which they are attached form a cyclic group selected from azabicyclo[4.1.1]octanyl, azepanyl, azetidinyl, C$_{3-6}$ cycloalkyl, diazaspiro[4.5]decanonyl, morpholinyl, octahydrocyclopenta[c]pyrrolyl, piperidinyl, pyrrolidinyl, or quinuclidinyl, each substituted with zero to 3 R$_{12a}$; or (iii) —CH=CH(piperidinyl); R$_{11}$ is azetidinyl, azaspiro[3.5]nonanyl, dioxidothiomorpholinyl, hexahydropyrrolo[3,4-c]pyrrolyl, morpholinyl, piperazinyl, piperidinyl, or pyrrolidinyl, each substituted with zero to 2 substituents independently selected from F, —CH$_3$, —CH(CH$_3$)$_2$, —CH$_2$CN, —CH$_2$(phenyl), —C(O)CH$_2$N(CH$_3$)$_2$, —CH$_2$C(CH$_3$)$_2$OH, —CH$_2$C(O)N(CH$_3$)$_2$, —CH$_2$CH$_2$S(O)$_2$CH$_3$, —CH$_2$CH$_2$S(O)CH$_3$, oxetanyl, and tetrahydropyranyl; each R$_{12a}$ is independently —OH, —CH$_3$, —CH$_2$CH$_2$CH$_3$, (CH$_3$), —NR$_x$C(O)CH$_2$N(CH$_3$)$_2$, —NHC(O)CH$_2$N(CH$_3$)(CH$_2$CH$_3$), —NHC(O)CH$_2$N(CH$_2$CH$_3$)$_2$, —NHC(O)CH$_2$NH(CH$_2$C(CH$_3$)$_2$OH), —NHCH$_2$C(O)NR$_x$(CH$_3$), —NHS(O)$_2$CH$_3$, —C(O)C(CH$_3$)$_3$, —C(O)CH$_2$N(CH$_3$)$_2$, —C(O)CH$_2$OCH$_3$, —C(O)CH$_2$CH$_2$OCH$_3$, —C(O)CH$_2$NH(CH$_3$), —C(O)CH$_2$N(CH$_3$)$_2$, —C(O)CH(CH$_3$)NH(CH$_3$), —C(O)CH$_2$N(CH$_3$)(CH$_2$CH$_3$), —C(O)CH$_2$N(CH$_2$CH$_3$)$_2$, R$_{12b}$, —CH$_2$R$_{12b}$, —C(O)R$_{12b}$, —C(O)CH$_2$R$_{12b}$, —C(O)CH$_2$NHR$_{12b}$, —C(O)NR$_x$R$_{12b}$, —NR$_x$C(O)CH$_2$R$_{12b}$, —NR$_x$R$_{12b}$, —NR$_x$CH$_2$R$_{12b}$, —NHC(O)CH$_2$NR$_x$R$_{12b}$, —NHC(O)CH$_2$NR$_x$CH$_2$R$_{12a}$, —NHCH$_2$C(O)NHR$_{12b}$, or —OR$_{12b}$; R$_{12b}$ is azetidinyl, cyclopropyl, diazabicyclo[2.2.1]heptanyl, dioxolanyl, dioxidotetrahydrothiopyranyl, dioxidothiomorpholinyl, imidazolyl, morpholinyl, octahydrocyclopenta[c]pyrrolyl, octahydropyrrolo[3,4-c]pyrrolyl, oxaazaspiro[3.3]heptanyl, oxetanyl, phenyl, piperazinyl, piperazinonyl, piperidinyl, pyridinyl, pyrrolidinyl, quinuclidinyl, tetrahydrofuranyl, tetrahydropyranyl, or triazolyl, each substituted with zero to 4 substituents independently selected from F, —OH, —CH$_3$, —CH(CH$_3$)$_2$, —CH$_2$OH, —OCH$_3$, —CH$_2$OCH$_3$, —NR$_y$R$_x$, and —C(O)NH$_2$; n is zero; p is zero, 1, 2, or 3; and G and R$_x$ are defined in the first aspect.

One embodiment provides a compound of Formula (I), N-oxide, or a salt thereof, wherein R$_1$ is H, Cl, —CN, C$_{1-4}$ alkyl, C$_{1-3}$ fluoroalkyl, C$_{1-3}$ hydroxyalkyl, C$_{1-3}$ hydroxyfluoroalkyl, C$_{3-6}$ cycloalkyl, —CH$_2$(C$_{3-6}$ cycloalkyl), or —C(O)O(CJ-3 alkyl); and G, A, R$_5$, and n are defined in the first aspect. Included in this embodiment are compounds in which R$_1$ is H, Cl, —CN, C$_{1-4}$ alkyl, C$_{1-2}$ fluoroalkyl, C$_{1-2}$ hydroxyalkyl, or —C(O)O(C$_{1-2}$ alkyl). Also included in this embodiment are compounds in which R$_1$ is —CH$_2$CH$_3$ or —CH(CH$_3$)$_2$.

One embodiment provides a compound of Formula (I), N-oxide, or a salt thereof, wherein each R$_2$ is independently F, Cl, Br, —CN, —OH, —NO$_2$, C$_{1-4}$ alkyl, C$_{1-2}$ fluoroalkyl, C$_{1-2}$ cyanoalkyl, C$_{1-3}$ hydroxyalkyl, C$_{1-3}$ aminoalkyl, —OCH$_2$OH, —(CH$_2$)$_{0-2}$O(C$_{1-4}$ alkyl), C$_{1-2}$ fluoroalkoxy, —(CH$_2$)$_{1-2}$O(C$_{1-3}$ alkyl), —O(CH$_2$)$_{1-2}$OC(O)(C$_{1-2}$ alkyl), —O(CH$_2$)$_{1-2}$NR$_x$R$_x$, —C(O)O(C$_{1-2}$ alkyl), —C(O)NR$_y$R$_y$, —C(O)NR$_x$C$_{1-5}$ hydroxyalkyl), —C(O)NR$_x$(C$_{2-6}$ alkoxyalkyl), —C(O)NR$_x$(C$_{3-6}$ cycloalkyl), —NR$_R$R$_y$, —NR$_y$(C$_{1-3}$ fluoroalkyl), —NR(C$_{1-4}$ hydroxyalkyl), —NR$_x$C(O)(C$_{1-3}$ alkyl), —S(O)$_2$(C$_{1-3}$ alkyl), C$_{3-6}$ cycloalkyl, phenyl, morpholinyl, dioxothiomorpholinyl, dimethyl pyrazolyl, methylpiperidinyl, methylpiperazinyl, amino-oxadiazolyl, imidazolyl, or triazolyl; and G, A, R$_1$, R$_5$, R$_x$, R$_y$, n, and p are defined in the first aspect. Included in this embodiment are compounds in which each R$_2$ is independently F, Cl, —CN, —OH, C$_{1-3}$ alkyl, C$_{1-2}$ fluoroalkyl, C$_{1-2}$ cyanoalkyl, C$_{1-3}$ hydroxyalkyl, C$_{1-2}$ aminoalkyl, —(CH$_2$)$_{0-2}$O(C$_{1-3}$ alkyl), C$_{3-6}$ cycloalkyl, —NR$_x$R$_x$, —(CH$_2$)$_{0-2}$C(O)NR$_x$R$_x$, —CH$_2$(C$_{3-6}$cycloalkyl), —CH$_2$(phenyl), or phenyl. Also included in this embodiment are compounds in which each R$_2$ is independently —CH$_3$ or —OCH$_3$.

One embodiment provides a compound of Formula (I), N-oxide, or a salt thereof wherein A is (i) —(CR$_x$R$_x$)$_{1-2}$R$_{11}$, C$_{1-2}$ aminoalkyl, —(CR$_x$R$_x$)$_{1-2}$NR$_x$C(O)R$_{11}$, —CH$_2$NR$_x$C(O)(CH$_2$)$_{1-2}$(piperidinyl), —CH$_2$NR$_x$C(O)OCH$_2$(piperidinyl), or —CH$_2$NR$_x$C(O)(CH$_2$)$_{1-2}$NR$_x$R$_x$; (ii) —CR$_x$R$_{12}$R$_{13}$, wherein R$_{12}$ and R$_{13}$ together with the carbon atom to which they are attached form a cyclic group selected from azabicyclo[4.1.1]octanyl, azepanyl, azetidinyl, C$_{3-7}$ cycloalkyl, diazepanyl, diazaspiro[4.5]decanonyl, morpholinyl, octahydrocyclopenta[c]pyrrolyl, piperazinyl, piperidinyl, pyrrolidinyl, or quinuclidinyl, each substituted with zero to 3 R$_{12a}$; or (iii) —CR$_x$=CR$_x$(piperidinyl); and G, R$_1$, R$_5$, R$_{11}$, R$_{12}$, R$_{12a}$, R$_{13}$, R$_x$, and n are defined in the first aspect. Included in this embodiment are compounds in which A is: (i) —CHR$_x$R$_{11}$, —CH$_2$CH$_2$R$_{11}$, —CH$_2$NH$_2$, —CH$_2$NHC(O)R$_{11}$, —CH$_2$NHC(O)CH$_2$CH$_2$(piperidinyl), —CH$_2$NHC(O)OCH$_2$(piperidinyl), or —CH$_2$NHC(O)CH$_2$CH$_2$N(CH$_3$)$_2$; (ii) —CHR$_{12}$R$_{13}$, wherein R$_{12}$ and R$_{13}$ together with the carbon atom to which they are attached form a cyclic group selected from azabicyclo[4.1.1]octanyl, azepanyl, azetidinyl, C$_{3-6}$ cycloalkyl, diazaspiro[4.5]decanonyl, morpholinyl, octahydrocyclopenta[c]pyrrolyl, piperidinyl, pyrrolidinyl, or quinuclidinyl, each substituted with zero to 3 R$_{12a}$; or (iii) —CH=CH(piperidinyl).

One embodiment provides a compound of Formula (I), N-oxide, or a salt thereof wherein A is (i) —(CR$_x$R$_x$)$_{1-3}$R$_{11}$, C$_{1-3}$ aminoalkyl, —(CR$_x$R$_x$)$_{1-3}$NR$_x$C(O)R$_{11}$, —(CR$_x$R$_x$)$_{1-2}$NR$_x$C(O)(CH$_2$)$_{1-2}$(piperidinyl), —(CR$_x$R$_x$)$_{1-2}$NR$_x$C(O)O(CH$_2$)$_{1-2}$(piperidinyl), or —(CR$_x$R$_x$)$_{1-2}$NR$_x$C(O)(CH$_2$)$_{1-2}$NR$_x$R$_x$; or (ii) —CR$_x$R$_{12}$R$_{13}$, wherein R$_{12}$ and R$_{13}$ together with the carbon atom to which they are attached form a cyclic group selected from azabicyclo[4.1.1]octanyl, azepanyl, azetidinyl, C$_{3-7}$ cycloalkyl, diazepanyl, diazaspiro[4.5]decanonyl, morpholinyl, octahydrocyclopenta[c]pyrrolyl, piperazinyl, piperidinyl, pyrrolidinyl, or quinuclidinyl, each substituted with zero to 4 R$_{12a}$, and G, R$_1$, R$_5$, R$_{11}$, R$_{12}$, R$_{12a}$, R$_{13}$, R$_x$, and n are defined in the first aspect. Included in this embodiment are compounds in which (i) —(CR$_x$R$_x$)$_{1-2}$R$_{11}$, C$_{1-2}$ aminoalkyl, —(CR$_x$R$_x$)$_{1-2}$NR$_x$C(O)R$_{11}$, —CH$_2$NR$_x$C(O)(CH$_2$)$_{1-2}$(piperidinyl), —CH$_2$NR$_x$C(O)OCH$_2$(piperidinyl), or —CH$_2$NR$_x$C(O)(CH$_2$)$_{1-2}$NR$_x$R$_x$; or (ii) —CR$_x$R$_{12}$R$_{13}$, wherein R$_{12}$ and R$_{13}$ together with the carbon atom to which they are attached form a cyclic group selected from azabicyclo[4.1.1]octanyl, azepanyl, azetidinyl, C$_{3-7}$ cycloalkyl, diazepanyl, diazaspiro[4.5]decanonyl, morpholinyl, octahydrocyclopenta[c]pyrrolyl, piperazinyl, piperidinyl, pyrrolidinyl, or quinuclidinyl, each substituted with zero to 3 R$_{12a}$. Also included in this embodiment are compounds in which A is (i) —CHR$_x$R$_{11}$, —CH$_2$CH$_2$R$_{11}$, —CH$_2$NH$_2$, —CH$_2$NHC(O)R$_{11}$, —CH$_2$NHC(O)CH$_2$CH$_2$(piperidinyl), —CH$_2$NHC(O)OCH$_2$(piperidinyl), or —CH$_2$NHC(O)CH$_2$CH$_2$N(CH$_3$)$_2$; or (ii) —CHR$_{12}$R$_{13}$, wherein R$_{12}$ and R$_{13}$ together with the carbon atom to which they are attached form a cyclic group selected from azabicyclo[4.1.1]octanyl, azepanyl, azetidinyl, C$_{3-6}$ cycloalkyl, diazaspiro[4.5]decanonyl, morpholinyl, octahydrocyclopenta[c]pyrrolyl, piperidinyl, pyrrolidinyl, or quinuclidinyl, each substituted with zero to 3 R$_{12a}$.

One embodiment provides a compound of Formula (I), N-oxide, or a salt thereof wherein A is —(CR$_x$R$_x$)$_{1-3}$R$_{11}$, C$_{1-3}$ aminoalkyl, —(CR$_x$R$_x$)$_{1-3}$NR$_x$C(O)R$_{11}$, —(CR$_x$R$_x$)$_{1-2}$NR$_x$C(O)(CH$_2$)$_{1-2}$(piperidinyl), —(CR$_x$R$_x$)$_{1-2}$NR$_x$C(O)O(CH$_2$)$_{1-2}$(piperidinyl), or —(CR$_x$R$_x$)$_{1-2}$NR$_x$C(O)(CH$_2$)$_{1-2}$NR$_x$R$_x$; and G, R$_1$, R$_5$, R$_{11}$, R$_x$, and n are defined in the first aspect. Included in this embodiment are compounds in which —(CR$_x$R$_x$)$_{1-2}$R$_{11}$, C$_{1-2}$ aminoalkyl, —(CR$_x$R$_x$)$_{1-2}$NR$_x$C(O)R$_{11}$, —CH$_2$NR$_x$C(O)(CH$_2$)$_{1-2}$(piperidinyl), —CH$_2$NR$_x$C(O)OCH$_2$(piperidinyl), or —CH$_2$NR$_x$C(O)(CH$_2$)$_{1-2}$NR$_x$R$_x$. Also included in this embodiment are compounds in which A is —CHR$_x$R$_{11}$, —CH$_2$CH$_2$R$_{11}$, —CH$_2$NH$_2$, —CH$_2$NHC(O)R$_{11}$, —CH$_2$NHC(O)CH$_2$CH$_2$(piperidinyl), —CH$_2$NHC(O)OCH$_2$(piperidinyl), or —CH$_2$NHC(O)CH$_2$CH$_2$N(CH$_3$)$_2$. Additionally, included in this embodiment are compounds in which R$_{11}$ is azetidinyl, azaspiro[3.5]nonanyl, dioxidothiomorpholinyl, hexahydropyrrolo[3,4-c]pyrrolyl, morpholinyl, piperazinyl, piperidinyl, or pyrrolidinyl, each substituted with zero to 2 substituents independently selected from F, —CH$_3$, —CH(CH$_3$)$_2$, —CH$_2$CN, —CH$_2$(phenyl), —C(O)CH$_2$N(CH$_3$)$_2$, —CH$_2$C (CH₃)₂OH, —CH₂C(O)N(CH₃)₂, —CH₂CH₂S(O)₂CH₃, —CH₂CH₂S(O)CH₃, oxetanyl, and tetrahydropyranyl.

One embodiment provides a compound of Formula (I), N-oxide, or a salt thereof wherein A is —CR$_x$R$_{12}$R$_{13}$, wherein R$_{12}$ and R$_{13}$ together with the carbon atom to which they are attached form a cyclic group selected from azabicyclo[4.1.1]octanyl, azepanyl, azetidinyl, C$_{3-7}$ cycloalkyl, diazepanyl, diazaspiro[4.5]decanonyl, morpholinyl, octahydrocyclopenta[c]pyrrolyl, piperazinyl, piperidinyl, pyrrolidinyl, or quinuclidinyl, each substituted with zero to 4 R$_{12a}$; and G, R$_1$, R$_5$, R$_{12}$, R$_{12a}$, R$_{13}$, R$_x$, and n are defined in the first aspect. Included in this embodiment are compounds in which —CR$_x$R$_{12}$R$_{13}$, wherein R$_{12}$ and R$_{13}$ together with the carbon atom to which they are attached form a cyclic group selected from azabicyclo[4.1.1]octanyl, azepanyl, azetidinyl, C$_{3-7}$ cycloalkyl, diazepanyl, diazaspiro[4.5]decanonyl, morpholinyl, octahydrocyclopenta[c]pyrrolyl, piperazinyl, piperidinyl, pyrrolidinyl, or quinuclidinyl, each substituted with zero to 3 R$_{12a}$. Also included in this embodiment are compounds in which A is —CHR$_{12}$R$_{13}$, wherein R$_{12}$ and R$_{13}$ together with the carbon atom to which they are attached form a cyclic group selected from azabicyclo[4.1.1]octanyl, azepanyl, azetidinyl, C$_{3-6}$ cycloalkyl, diazaspiro[4.5]decanonyl, morpholinyl, octahydrocyclopenta[c]pyrrolyl, piperidinyl, pyrrolidinyl, or quinuclidinyl, each substituted with zero to 3 R$_{12a}$. Additionally, included in this embodiment are compounds in which each R$_{12a}$ is independently —OH, —CH₃, —CH₂CH₃, —CH(CH₃)₂, —CH₂CH(CH₃)₂, —CF₃, —CH₂CH₂CH₂CF₃, —CH₂CN, —CH₂C(CH₃)₂OH, —CH₂CH₂OCH₃, —CH₂C(O)NH(CH₃), —CH₂C(O)N(CH₃)₂, —CH₂C(O)NH₂, —CH₂CH₂S(O)₂CH₃, —CH₂CH₂NHS(O)₂CH₃, —CH₂NR$_x$R$_x$, —CH₂CH₂NH(CH₃), —OCH₃, —NR$_x$R$_x$, —N(CH₃)(CH₂CH₃), —N(CH₃)(CH(CH₃)₂), —NR$_x$(CH₂CHF₂)—NH(CH₂CF₃), —N(CH₃)(CH₂CH₂CF₃), —N(CH₃)(CH₂CH₂OCH₃), —NH(CH₂CN), —N(CH₃)CH₂N(CH₃)₂. —NH(CH₂C(CH₃)₂OH), —NH(CH₂C(O)NH₂), —N(CH₃)(OCH₃), —NR$_x$CH₂CH₂S(O)₂CH₃, —NHC(O)CH₃, —NHC(O)CH₂CF₃, —NHC(O)CHR$_x$NH(CH₃), —NR$_x$C(O)CH₂N(CH₃)₂, —NHC(O)CH₂N(CH₃)(CH₂CH₃), —NHC(O)CH₂N(CH₂CH₃)₂, —NHC(O)CH₂NH(CH₂C(CH₃)₂OH), —NHCH₂C(O)NR$_x$(CH₃), —NHS(O)₂CH₃, —C(O)C(CH₃)₃, —C(O)CH(CH₂CH₃)₂, —C(O)CH₂OCH₃, —C(O)CH₂CH₂OCH₃, —C(O)CH₂NH(CH₃), —C(O)CH₂N(CH₃)₂, —C(O)CH(CH₃)NH(CH₃), —C(O)CH₂N(CH₃)(CH₂CH₃), —C(O)CH₂N(CH₂CH₃)₂, R$_{12b}$, —CH₂R$_{12b}$, —C(O)R$_{12b}$, —C(O)CH₂R$_{12b}$, —C(O)CH₂NHR$_{12b}$, —C(O)NR$_x$R$_{12b}$, —NR$_x$C(O)CH₂R$_{12b}$, —NR$_x$R$_{12b}$, —NR$_x$CH₂R$_{12b}$, —NHC(O)CH₂NR$_x$R$_{12b}$, —NHC(O)CH₂NR$_x$CH₂R$_{12b}$, —NHCH₂C(O)NHR$_{12b}$, or —OR$_{12b}$; and R$_{12b}$ is azetidinyl, cyclopropyl, diazabicyclo[2.2.1]heptanyl, dioxolanyl, dioxidotetrahydrothiopyranyl, dioxidothiomorpholinyl, imidazolyl, morpholinyl, octahydrocyclopenta[c]pyrrolyl, octahydropyrrolo[3,4-c]pyrrolyl, oxaazaspiro[3.3]heptanyl, oxetanyl, phenyl, piperazinyl, piperazinonyl, piperidinyl, pyridinyl, pyrrolidinyl, quinuclidinyl, tetrahydrofuranyl, tetrahydropyranyl, or triazolyl, each substituted with zero to 4 substituents independently selected from F, —OH, —CH₃, —CH(CH₃)₂, —CH₂OH, —OCH₃, —CH₂CH₂OCH₃, —NR$_x$R$_x$, and —C(O)NH₂.

One embodiment provides a compound of Formula (I), N-oxide, or a salt thereof wherein each R$_5$ is independently F, Cl, —CN, C$_{1-3}$ alkyl, —CF₃, or —OCH₃; n is zero, 1, or 2; and G, A, R$_1$, and n are defined in the first aspect. Included in this embodiment are compounds in which each R$_5$ is independently F, Cl, —CN, C$_{1-2}$ alkyl, or —OCH₃. Also included in this embodiment are compounds in which each R$_5$ is independently —CH₃ or —CH(CH₃)₂. This embodiment also includes compounds in which n is zero or 1.

One embodiment provides a compound of Formula (I), N-oxide, or a salt thereof wherein A is —CHR$_{12}$R$_{13}$; and R$_{12}$ and R$_{13}$ together with the carbon atom to which they are attached form a cyclic group selected from azetidinyl, pyrrolidinyl, piperidinyl, and azepanyl, each substituted with zero to 3 R$_{12a}$; and G, R$_1$, R$_5$, R$_{12a}$, and n are defined in the first aspect. Included in this embodiment are compounds in which A is azetidinyl or piperidinyl, each substituted with zero to 3 R$_{12a}$.

One embodiment provides compounds of Formula (I) or salts thereof wherein A is azetidinyl substituted with zero to 3 R$_{12a}$; G is

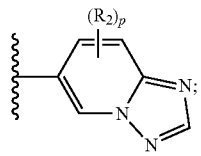

and R$_2$, R$_5$, R$_{12a}$, n, and p are defined in the first aspect. The compounds of this embodiment have the structure of Formula (Ia):

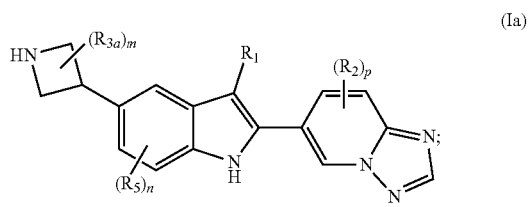

(Ia)

wherein m is zero, 1, 2, or 3.

One embodiment provides compounds of Formula (I) or salts thereof wherein A is azetidinyl substituted with zero to 3 R$_{12a}$; G is

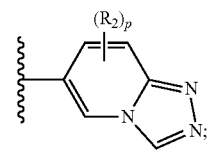

and R$_2$, R$_5$, R$_{12a}$, n, and p are defined in the first aspect. The compounds of this embodiment have the structure of Formula (Ib):

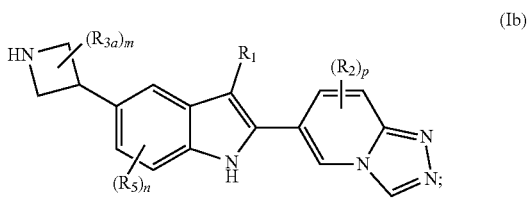

(Ib)

wherein m is zero, 1, 2, or 3.

One embodiment provides compounds of Formula (I) or salts thereof wherein A is azetidinyl substituted with zero to 3 R$_{12a}$; G is

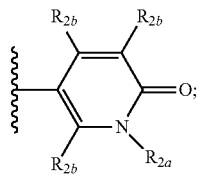

and $R_{2a}$, $R_{2b}$, $R_5$, $R_{12a}$, and n are defined in the first aspect. Included in this embodiment are compounds having the structure of Formula (Ic):

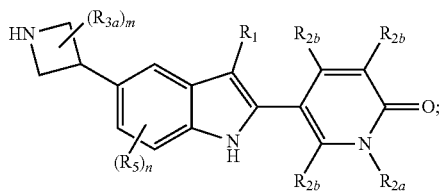

wherein m is zero, 1, 2, or 3.

One embodiment provides compounds of Formula (I) or salts thereof wherein A is piperidinyl substituted with zero to 3 $R_{12a}$; G is

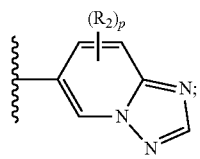

and $R_2$, $R_5$, $R_{12a}$, n, and p are defined in the first aspect. Included in this embodiment are compounds having the structure of Formula (Id):

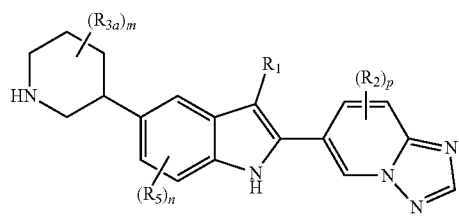

wherein m is zero, 1, 2, or 3.

One embodiment provides compounds of Formula (I), N-oxide, or salts thereof wherein A is piperidinyl substituted with zero to 3 $R_{12a}$; G is

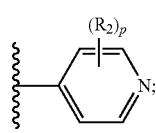

and $R_2$, $R_5$, $R_{12a}$, and n are defined in the first aspect. Included in this embodiment are compounds having the structure of Formula (If) and compounds having the structure of Formula (Ie):

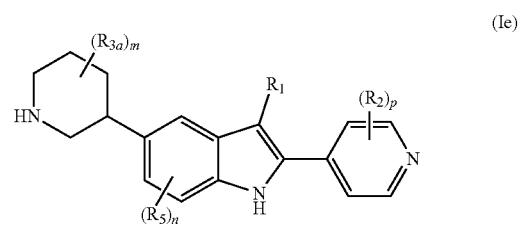

wherein m is zero, 1, 2, or 3.

One embodiment provides compounds of Formula (I) or salts thereof wherein A is morpholinyl substituted with zero to 3 $R_{12a}$; G is

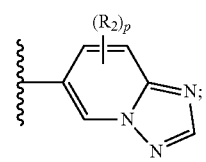

and $R_2$, $R_5$, $R_{12a}$, n, and p are defined in the first aspect. Included in this embodiment are compounds having the structure of Formula (If):

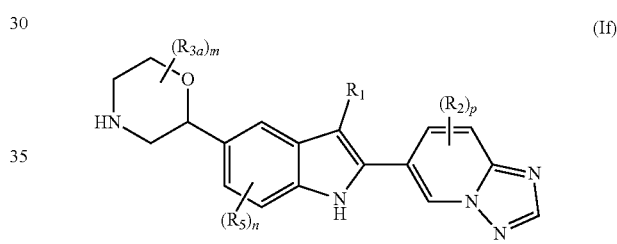

wherein m is zero, 1, 2, or 3. Also included in this embodiment are compounds having the structure of Formula (Ig):

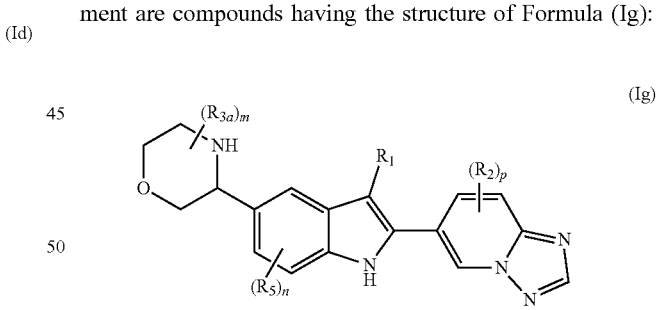

wherein m is zero, 1, 2, or 3.

One embodiment provides compounds of Formula (I) or salts thereof wherein A is octahydrocyclopenta[c]pyrrolyl substituted with zero to 3 $R_{12a}$; G is

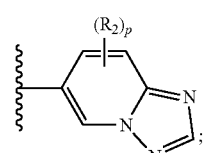

and $R_2$, $R_5$, $R_{12a}$, n, and p are defined in the first aspect. Included in this embodiment are compounds having the structure of Formula (Ih):

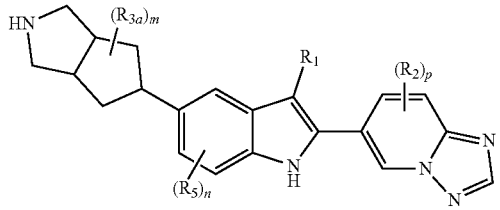

wherein m is zero, 1, 2, or 3.

One embodiment provides compounds of Formula (I) or salts thereof wherein A is octahydrocyclopenta[c]pyrrolyl substituted with zero to 3 $R_{12a}$; G is

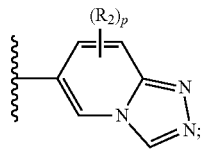

and $R_2$, $R_5$, $R_{12a}$, n, and p are defined in the first aspect. Included in this embodiment are compounds having the structure of Formula (Ij):

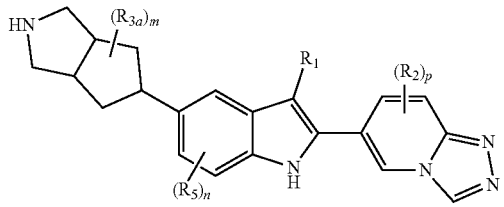

wherein m is zero, 1, 2, or 3.

One embodiment provides compound of Formula (I) or salts thereof wherein A is cyclobutyl substituted with zero to 3 $R_{12a}$; G is

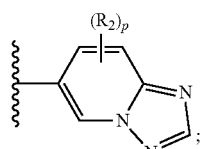

and $R_2$, $R_5$, $R_{12a}$, n, and p are defined in the first aspect. Included in this embodiment are compounds having the structure of Formula (Ij):

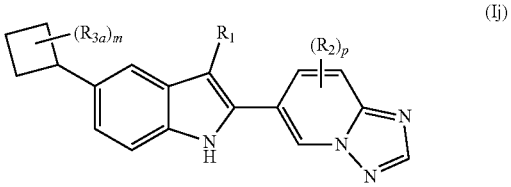

wherein m is zero, 1, 2, or 3.

One embodiment provides compounds of Formula (I) or salts thereof wherein A is cyclobutyl substituted with zero to 3 $R_{12a}$; G is

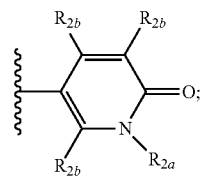

and $R_{2a}$, $R_{2b}$, $R_5$, $R_{12a}$, and n are defined in the first aspect. Included in this embodiment are compounds having the structure of Formula (Im):

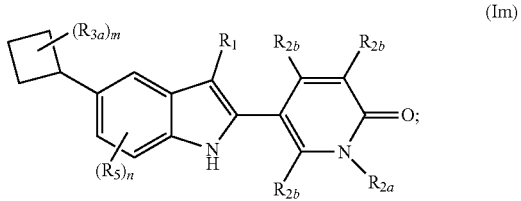

wherein m is zero, 1, 2, or 3.

One embodiment provides compounds of Formula (I) or salts thereof wherein A is cyclohexyl substituted with zero to 3 $R_{12a}$; G is

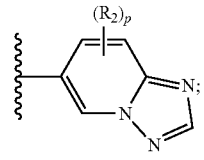

and $R_2$, $R_5$, $R_{12a}$, n, and p are defined in the first aspect. Included in this embodiment are compounds having the structure of Formula (In):

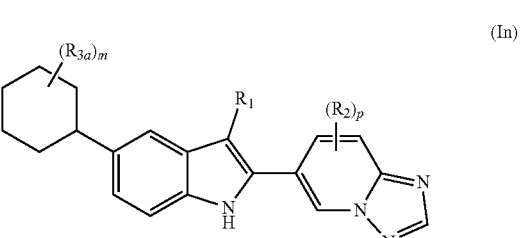

wherein m is zero, 1, 2, or 3.

One embodiment provides compounds of Formula (I) or salts thereof wherein A is cyclohexyl substituted with zero to 3 $R_{12a}$; G is

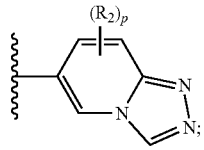

$R_2$, $R_5$, $R_{12a}$, n, and p are defined in the first aspect. Included in this embodiment are compounds having the structure of Formula (Ip):

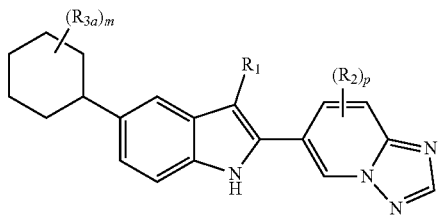

(Ip)

wherein m is zero, 1, 2, or 3.

One embodiment provides compounds of Formula (I), N-oxide, or salts thereof wherein A is cyclohexyl substituted with zero to 3 $R_{12a}$; G is

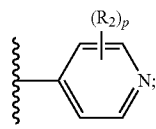

and $R_2$, $R_5$, $R_{12a}$, and n are defined in the first aspect. Included in this embodiment are compounds having the structure of Formula (Iq):

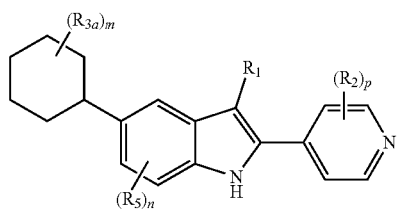

(Iq)

wherein m is zero, 1, 2, or 3.

One embodiment provides compounds of Formula (I) or salts thereof wherein A is cyclohexyl substituted with zero to 3 $R_{12a}$; G is

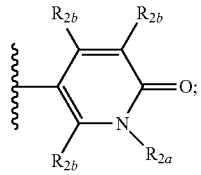

and $R_{2a}$, $R_{2b}$, $R_5$, $R_{12a}$, and n are defined in the first aspect. Included in this embodiment are compounds having the structure of Formula (Ir):

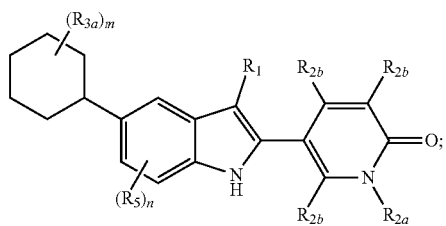

(Ir)

wherein m is zero, 1, 2, or 3.

One embodiment provides compounds of Formula (I), N-oxide, or salts thereof wherein A is cyclopropyl substituted with zero to 3 $R_{12a}$; G is

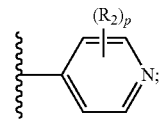

and $R_2$, $R_5$, $R_{12a}$, n, and p are defined in the first aspect. Included in this embodiment are compounds having the structure of Formula (Is):

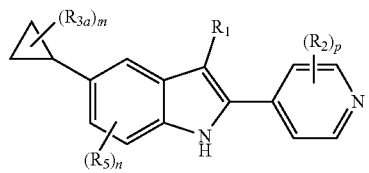

(Is)

wherein m is zero, 1, 2, or 3.

One embodiment provides a compound of Formula (I), N-oxide, or salt thereof, wherein said compound is selected from Examples 1 to 82, 85-93, 95-%, and 99 to 592.

The present invention may be embodied in other specific forms without departing from the spirit or essential attributes thereof. The invention encompasses all combinations of the aspects and/or embodiments of the invention noted herein. It is understood that any and all embodiments of the present invention may be taken in conjunction with any other embodiment or embodiments to describe additional embodiments. It is also to be understood that each individual element of the embodiments is meant to be combined with any and all other elements from any embodiment to describe an additional embodiment.

Definitions

The features and advantages of the invention may be more readily understood by those of ordinary skill in the art upon reading the following detailed description. It is to be appreciated that certain features of the invention that are, for clarity reasons, described above and below in the context of separate embodiments, may also be combined to form a single embodiment. Conversely, various features of the invention that are, for brevity reasons, described in the context of a single embodiment, may also be combined so as to form sub-combinations thereof. Embodiments identified herein as exemplary or preferred are intended to be illustrative and not limiting.

Unless specifically stated otherwise herein, references made in the singular may also include the plural. For example, "a" and "an" may refer to either one, or one or more.

As used herein, the phrase "compounds" refers to at least one compound. For example, a compound of Formula (I) includes a compound of Formula (I) and two or more compounds of Formula (I).

Unless otherwise indicated, any heteroatom with unsatisfied valences is assumed to have hydrogen atoms sufficient to satisfy the valences.

The definitions set forth herein take precedence over definitions set forth in any patent, patent application, and/or patent application publication incorporated herein by reference.

Listed below are definitions of various terms used to describe the present invention. These definitions apply to the terms as they are used throughout the specification (unless they are otherwise limited in specific instances) either individually or as part of a larger group.

Throughout the specification, groups and substituents thereof may be chosen by one skilled in the field to provide stable moieties and compounds.

In accordance with a convention used in the art,

is used in structural formulas herein to depict the bond that is the point of attachment of the moiety or substituent to the core or backbone structure.

The terms "halo" and "halogen," as used herein, refer to F, Cl, Br, and I.

The term "cyano" refers to the group —CN.
The term "amino" refers to the group —NH$_2$.
The term "oxo" refers to the group =O.
The term "alkyl" as used herein, refers to both branched and straight-chain saturated aliphatic hydrocarbon groups containing, for example, from 1 to 12 carbon atoms, from 1 to 6 carbon atoms, and from 1 to 4 carbon atoms. Examples of alkyl groups include, but are not limited to, methyl (Me), ethyl (Et), propyl (e.g., n-propyl and i-propyl), butyl (e.g., n-butyl, i-butyl, sec-butyl, and t-butyl), and pentyl (e.g., n-pentyl, isopentyl, neopentyl), n-hexyl, 2-methylpentyl, 2-ethylbutyl, 3-methylpentyl, and 4-methylpentyl. When numbers appear in a subscript after the symbol "C", the subscript defines with more specificity the number of carbon atoms that a particular group may contain. For example, "$C_{1-6}$ alkyl" denotes straight and branched chain alkyl groups with one to six carbon atoms.

The term "fluoroalkyl" as used herein is intended to include both branched and straight-chain saturated aliphatic hydrocarbon groups substituted with one or more fluorine atoms. For example, "CM fluoroalkyl" is intended to include $C_1$, $C_2$, $C_3$, and $C_4$ alkyl groups substituted with one or more fluorine atoms. Representative examples of fluoroalkyl groups include, but are not limited to, —CF$_3$ and —CH$_2$CF$_3$.

The term "cyanoalkyl" includes both branched and straight-chain saturated alkyl groups substituted with one or more cyano groups. For example, "cyanoalkyl" includes —CH$_2$CN, —CH$_2$CH$_2$CN, and CM cyanoalkyl.

The term "aminoalkyl" includes both branched and straight-chain saturated alkyl groups substituted with one or more amine groups. For example, "aminoalkyl" includes —CH$_2$NH$_2$, —CH$_2$CH$_2$NH$_2$, and C M aminoalkyl.

The term "hydroxyalkyl" includes both branched and straight-chain saturated allyl groups substituted with one or more hydroxy 1 groups. For example, "hydroxyalkyl" includes —CH$_2$OH, —CH$_2$CH$_2$OH, and CM hydroxyalkyl.

The term "hydroxy-fluoroalkyl" includes both branched and straight-chain saturated alkyl groups substituted with one or more hydroxyl groups and one or more fluorine atoms. For example, "hydroxy-fluoroalkyl" includes —CHFCH$_2$OH, —CH$_2$CHFC(CH$_3$)$_2$OH, and CM hydroxy-fluoroalkyl.

The term "cycloalkyl," as used herein, refers to a group derived from a non-aromatic monocyclic or polycyclic hydrocarbon molecule by removal of one hydrogen atom from a saturated ring carbon atom. Representative examples of cycloalkyl groups include, but are not limited to, cyclopropyl, cyclopentyl, and cyclohexyl. When numbers appear in a subscript after the symbol "C", the subscript defines with more specificity the number of carbon atoms that a particular cycloalkyl group may contain. For example, "$C_3$-$C_6$ cycloalkyl" denotes cycloalkyl groups with three to six carbon atoms.

The term "alkoxy," as used herein, refers to an alkyl group attached to the parent molecular moiety through an oxygen atom, for example, methoxy group (—OCH$_3$). For example. "$C_{1-3}$ alkoxy" denotes alkoxy groups with one to three carbon atoms.

The term "alkoxy alkyl," as used herein, refers to an alkoxy group attached through its oxygen atom to an alkyl group, which is attached to the parent molecular moiety, for example, methoxymethyl group (—CH$_2$OCH$_3$). For example, "CM alkoxy alkyl" denotes alkoxyalkyl groups with two to four carbon atoms, such as —CH$_2$OCH$_3$, —CH$_2$CH$_2$OCH$_3$, —CH$_2$OCH$_2$CH$_3$, and —CH$_2$CH$_2$OCH$_2$CH$_3$.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The compounds of Formula (I) can be provided as amorphous solids or crystalline solids. Lyophilization can be employed to provide the compounds of Formula (I) as amorphous solids.

It should further be understood that solvates (e.g., hydrates) of the compounds of Formula (I) are also within the scope of the present invention. The term "solvate" means a physical association of a compound of Formula (I) with one or more solvent molecules, whether organic or inorganic. This physical association includes hydrogen bonding. In certain instances the solvate will be capable of isolation, for example when one or more solvent molecules are incorporated in the crystal lattice of the crystalline solid. "Solvate" encompasses both solution-phase and isolable solvates. Exemplary solvates include hydrates, ethanolates, methanolates, isopropanolates, acetonitrile solvates, and ethyl acetate solvates. Methods of solvation are known in the art.

Various forms of prodrugs are well known in the art and are described in:

a) *The Practice of Medicinal Chemistry*, Camille G. Wermuth et al., Ch 31, (Academic Press, 1996);

b) *Design of Prodrugs*, edited by H. Bundgaard, (Elsevier, 1985);

c) *A Textbook of Drug Design and Development*, P. Krogsgaard-Larson and H. Bundgaard, eds. Ch 5, pgs 113-191 (Harwood Academic Publishers, 1991); and d) *Hydrolysis in Drug and Prodrug Metabolism*, Bernard Testa and Joachim M. Mayer, (Wiley-VCH, 2003).

In addition, compounds of Formula (I), subsequent to their preparation, can be isolated and purified to obtain a composition containing an amount by weight equal to or greater than 99% of a compound of Formula (I) ("substantially pure"), which is then used or formulated as described herein. Such "substantially pure" compounds of Formula (I) are also contemplated herein as part of die present invention.

"Stable compound" and "stable structure" are meant to indicate a compound that is sufficiently robust to survive isolation to a useful degree of purity from a reaction mixture, and formulation into an efficacious therapeutic agent. The present invention is intended to embody stable compounds.

"Therapeutically effective amount" is intended to include an amount of a compound of the present invention alone or an amount of the combination of compounds claimed or an amount of a compound of the present invention in combination with other active ingredients effective to act as an inhibitor to TLR7/8/9, or effective to treat or prevent autoimmune and/or inflammatory disease states, such as SLE, IBD, multiple sclerosis (MS), and Sjögren's syndrome, and rheumatoid arthritis.

As used herein, "treating" or "treatment" cover the treatment of a disease-state in a mammal, particularly in a human, and include, (a) preventing the disease-state from occurring in a mammal, in particular, when such mammal is predisposed to the disease-state but has not yet been diagnosed as having it; (b) inhibiting the disease-state, i.e., arresting its development; and/or (c) relieving the disease-state, i.e., causing regression of the disease state.

The compounds of the present invention are intended to include all isotopes of atoms occurring in the present compounds. Isotopes include those atoms having the same atomic number but different mass numbers. By way of general example and without limitation, isotopes of hydrogen include deuterium (D) and tritium (T). Isotopes of carbon include $^{13}C$ and $^{14}C$. Isotopically-labeled compounds of the invention can generally be prepared by conventional techniques known to those skilled in the art or by processes analogous to those described herein, using an appropriate isotopically-labeled reagent in place of the non-labeled reagent otherwise employed. For example, methyl (—$CH_3$) also includes deuterated methyl groups such as —$CD_3$.

Utility

The human immune system has evolved to defend the body from micro-organisms, viruses, and parasites that can cause infection, disease or death. Complex regulatory mechanisms ensure that the various cellular components of the immune system target the foreign substances or organisms, while not causing permanent or significant damage to the individual. While the initiating events are not well understood at this time, in autoimmune disease states the immune system directs its inflammatory response to target organs in the afflicted individual. Different autoimmune diseases are typically characterized by the predominate or initial target organ or tissues affected; such as the joint in the case of rheumatoid arthritis, the thyroid gland in the case of Hashimoto s thyroiditis, the central nervous system in the case of multiple sclerosis, the pancreas in the case of type I diabetes, and the bowel in the case of inflammatory bowel disease.

The compounds of the invention inhibit signaling through Toll-like receptor 7, or 8, or 9 (TLR7, TLR8, TLR9) or combinations thereof. Accordingly, compounds of Formula (I) have utility in treating conditions associated with the inhibition of signaling through one or more of TLR7, TLR8, or TLR9. Such conditions include TLR7, TLR8, or TLR9 receptor associated diseases in which cytokine levels are modulated as a consequence of intracellular signaling.

As used herein, the terms "treating" or "treatment" encompass the treatment of a disease state in a mammal, particularly in a human, and include: (a) preventing or delaying the occurrence of the disease state in a mammal, in particular, when such mammal is predisposed to the disease state but has not yet been diagnosed as having it; (b) inhibiting the disease state, i.e., arresting its development; and/or (c) achieving a full or partial reduction of the symptoms or disease state, and/or alleviating, ameliorating, lessening, or curing the disease or disorder and/or its symptoms.

In view of their activity as selective inhibitors of TLR7, TLR8, or TLR9, compounds of Formula (I) are useful in treating TLR7, TLR8, or TLR9 family receptor associated diseases, but not limited to, inflammatory diseases such as Crohn's disease, ulcerative colitis, asthma, graft versus host disease, allograft rejection, chronic obstructive pulmonary disease; autoimmune diseases such as Graves' disease, rheumatoid arthritis, systemic lupus erythematosus, lupus nephritis, cutaneous lupus, psoriasis; auto-inflammatory diseases including Cryopyrin-Associated Periodic Syndromes (CAPS), TNF Receptor Associated Periodic Syndrome (TRAPS), Familial Mediterranean Fever (FMF), adult onset stills, systemic onset juvenile idiopathic arthritis, gout, gouty arthritis; metabolic diseases including type 2 diabetes, atherosclerosis, myocardial infarction; destructive bone disorders such as bone resorption disease, osteoarthritis, osteoporosis, multiple myeloma-related bone disorder; proliferative disorders such as acute myelogenous leukemia, chronic myelogenous leukemia; angiogenic disorders such as angiogenic disorders including solid tumors, ocular neovascularization, and infantile haemangiomas; infectious diseases such as sepsis, septic shock, and Shigellosis: neurodegenerative diseases such as Alzheimer's disease, Parkinson's disease, cerebral ischemias or neurodegenerative disease caused by traumatic injury, oncologic and viral diseases such as metastatic melanoma, Kaposi's sarcoma, multiple myeloma, and HIV infection and CMV retinitis, AIDS, respectively.

More particularly, the specific conditions or diseases that may be treated with the inventive compounds include, without limitation, pancreatitis (acute or chronic), asthma, allergies, adult respiratory distress syndrome, chronic obstructive pulmonary disease, glomerulonephritis, rheumatoid arthritis, systemic lupus erythematosus, scleroderma, chronic thyroiditis, Graves' disease, autoimmune gastritis, diabetes, autoimmune hemolytic anemia, autoimmune neutropenia, thrombocytopenia, atopic dermatitis, chronic active hepatitis, my asthenia gravis, multiple sclerosis, inflammatory bowel disease, ulcerative colitis, Crohn's disease, psoriasis, graft vs. host disease, inflammatory reaction induced by endotoxin, tuberculosis, atherosclerosis, muscle degeneration, cachexia, psoriatic arthritis, Reiter's syndrome, gout, traumatic arthritis, rubella arthritis, acute synovitis, pancreatic β-cell disease; diseases characterized by massive neutrophil infiltration; rheumatoid spondylitis, gouty arthritis and other arthritic conditions, cerebral malaria, chronic pulmonary inflammatory disease, silicosis, pulmonary sarcoidosis, bone resorption disease, allograft rejections, fever and myalgias due to infection, cachexia secondary to infection, keloid formation, scar tissue formation, ulcerative colitis, pyresis, influenza, osteoporosis, osteoarthritis, acute myelogenous leukemia, chronic myelogenous leukemia, metastatic melanoma, Kaposi's sarcoma, multiple myeloma, sepsis, septic shock, and Shigellosis; Alzheimer's disease, Parkinson's disease, cerebral ischemias or neurodegenerative disease caused by traumatic injury; angiogenic disorders including solid tumors, ocular neovascularization, and infantile haemangiomas; viral diseases including acute hepatitis infection (including hepatitis A, hepatitis B and hepatitis C), HIV infection and CMV retinitis, AIDS, ARC or malignancy, and herpes; stroke, myocardial ischemia, ischemia in stroke heart attacks, organ hypoxia, vascular hyperplasia, cardiac and renal reperfusion injury, thrombosis, cardiac hypertrophy, thrombin-induced platelet aggregation, endotoxemia and/or toxic shock syndrome, conditions associated with prostaglandin endoperoxidase syndase-2, and pemphigus vulgaris. Included in this embodiment are methods of treatment in which the condition is selected from lupus including lupus nephritis and systemic lupus erythematosus (SLE), Crohn's disease, ulcerative colitis, allograft rejection, rheumatoid arthritis, psoriasis, ankylosing spondylitis, psoriatic arthritis, and pemphigus vulgaris. Also included are methods of treatment in which the condition is selected from ischemia reperfusion injury, including cerebral ischemia reperfusions injury arising from stroke and cardiac ischemia reperfusion injury arising from myocardial infarction. Another method of treatment is one in which the condition is multiple myeloma.

In one embodiment, the compounds of Formula (I) are useful in treating cancer, including Waldenstrom's Macroglobulinemia (WM), diffuse large B cell lymphoma (DLBCL), chronic lymphocytic leukemia (CLL), cutaneous diffuse large B cell lymphoma, and primary CNS lymphoma.

In addition, the TLR7, TLR8, or TLR9 inhibitors of the present invention inhibit the expression of inducible pro-inflammatory proteins such as prostaglandin endoperoxide synthase-2 (PGHS-2), also referred to as cyclooxygenase-2 (COX-2), IL-1, IL-6, IL-18, chemokines. Accordingly, additional TLR7/8/9 associated conditions include edema, analgesia, fever and pain, such as neuromuscular pain, headache, pain caused by cancer, dental pain and arthritis pain. The inventive compounds also may be used to treat veterinary viral infections, such as lentivirus infections, including, but not limited to equine infectious anemia virus; or retrovirus infections, including feline immunodeficiency virus, bovine immunodeficiency virus, and canine immunodeficiency virus.

The present invention thus provides methods for treating such conditions, comprising administering to a subject in need thereof a therapeutically-effective amount of at least one compound of Formula (I) or a salt thereof. "Therapeutically effective amount" is intended to include an amount of a compound of the present invention that is effective when administered alone or in combination to inhibit autoimmune disease or chronic inflammatory disease.

The methods of treating TLR7, TLR8, or TLR9 associated conditions may comprise administering compounds of Formula (I) alone or in combination with each other and/or other suitable therapeutic agents useful in treating such conditions. Accordingly, "therapeutically effective amount" is also intended to include an amount of the combination of compounds claimed that is effective to inhibit TLR7, TLR8, or TLR9 and/or treat diseases associated with TLR7, TLR8, or TLR9.

Exemplary of such other therapeutic agents include corticosteroids, rolipram, calphostin, cytokine-suppressive anti-inflammatory drugs (CSAIDs), Interleukin-10, glucocorticoids, salicylates, nitric oxide, and other immunosuppressants; nuclear translocation inhibitors, such as deoxyspergualin (DSG); non-steroidal anti-inflammatory drugs (NSAIDs) such as ibuprofen, celecoxib and rofecoxib; steroids such as prednisone or dexamethasone; antiviral agents such as abacavir; antiproliferative agents such as methotrexate, leflunomide, FK506 (tacrolimus, PROGRAF®); anti-malarials such as hydroxychloroquine; cytotoxic drugs such as azathiprine and cyclophosphamide; TNF-α inhibitors such as tenidap, anti-TNF antibodies or soluble TNF receptor, and rapamycin (sirolimus or RAPAMUNE®) or derivatives thereof.

The above other therapeutic agents, when employed in combination with the compounds of the present invention, may be used, for example, in those amounts indicated in the *Physicians' Desk Reference* (PDR) or as otherwise determined by one of ordinary skill in the art. In the methods of the present invention, such other therapeutic agent(s) may be administered prior to, simultaneously with, or following the administration of the inventive compounds. The present invention also provides pharmaceutical compositions capable of treating TLR7/8/9 receptor-associated conditions, including IL-1 family receptor-mediated diseases as described above.

The inventive compositions may contain other therapeutic agents as described above and may be formulated, for example, by employing conventional solid or liquid vehicles or diluents, as well as pharmaceutical additives of a type appropriate to the mode of desired administration (e.g., excipients, binders, preservatives, stabilizers, flavors, etc.) according to techniques such as those well known in the art of pharmaceutical formulation.

Accordingly, the present invention further includes compositions comprising one or more compounds of Formula (I) and a pharmaceutically acceptable carrier.

A "pharmaceutically acceptable carrier" refers to media generally accepted in the art for the delivery of biologically active agents to animals, in particular, mammals. Pharmaceutically acceptable carriers are formulated according to a number of factors well within the purview of those of ordinary skill in the art. These include without limitation the type and nature of the active agent being formulated; the subject to which the agent-containing composition is to be administered; the intended route of administration of the composition; and, the therapeutic indication being targeted. Pharmaceutically acceptable carriers include both aqueous and non-aqueous liquid media, as well as a variety of solid and semi-solid dosage forms. Such carriers can include a number of different ingredients and additives in addition to the active agent, such additional ingredients being included in the formulation for a variety of reasons, e.g., stabilization of the active agent, binders, etc., well known to those of ordinary skill in the art. Descriptions of suitable pharmaceutically acceptable carriers, and factors involved in their selection, are found in a variety of readily available sources such as, for example, *Remington's Pharmaceutical Sciences,* 17th Edition (1985), which is incorporated herein by reference in its entirety.

Compounds in accordance with Formula (I) can be administered by any means suitable for the condition to be treated, which can depend on the need for site-specific treatment or quantity of Formula (I) compound to be delivered.

Also embraced within this invention is a class of pharmaceutical compositions comprising a compound of Formula (I) and one or more non-toxic, pharmaceutically-acceptable carriers and/or diluents and/or adjuvants (collectively referred to herein as 'carrier' materials) and, if desired, other active ingredients. The compounds of Formula (I) may be administered by any suitable route, preferably in the form of a pharmaceutical composition adapted to such a route, and in a dose effective for the treatment intended. The compounds and compositions of the present invention may, for example, be administered orally, mucosally, or parenterally including intravascularly, intravenously, intraperitoneally, subcutaneously, intramuscularly, and intrasternally in dosage unit formulations containing conventional pharmaceutically acceptable carriers, adjuvants, and vehicles. For example, the pharmaceutical carrier may contain a mixture of mannitol or lactose and microcrystalline cellulose. The mixture may contain additional components such as a lubricating agent, e.g. magnesium stearate and a disintegrating agent such as crospovidone. The carrier mixture may be filled into a gelatin capsule or compressed as a tablet. The pharmaceutical composition may be administered as an oral dosage form or an infusion, for example.

For oral administration, the pharmaceutical composition may be in the form of, for example, a tablet, capsule, liquid capsule, suspension, or liquid. The pharmaceutical composition is preferably made in the form of a dosage unit containing a particular amount of the active ingredient. For example, the pharmaceutical composition may be provided as a tablet or capsule comprising an amount of active ingredient in the range of from about 0.1 to 1000 mg, preferably from about 0.25 to 250 mg, and more preferably from about 0.5 to 100 mg. A suitable daily dose for a human or other mammal may vary widely depending on the condition of the patient and other factors, but, can be determined using routine methods.

Any pharmaceutical composition contemplated herein can, for example, be delivered orally via any acceptable and suitable oral preparations. Exemplary oral preparations, include, but are not limited to, for example, tablets, troches, lozenges, aqueous and oily suspensions, dispersible powders or granules, emulsions, hard and soft capsules, liquid capsules, syrups, and elixirs. Pharmaceutical compositions intended for oral administration can be prepared according to any methods known in the art for manufacturing pharmaceutical compositions intended for oral administration. In order to provide pharmaceutically palatable preparations, a pharmaceutical composition in accordance with the invention can contain at least one agent selected from sweetening agents, flavoring agents, coloring agents, demulcents, antioxidants, and preserving agents.

A tablet can, for example, be prepared by admixing at least one compound of Formula (I) with at least one non-toxic pharmaceutically acceptable excipient suitable for the manufacture of tablets. Exemplary excipients include, but are not limited to, for example, inert diluents, such as, for example, calcium carbonate, sodium carbonate, lactose, calcium phosphate, and sodium phosphate; granulating and disintegrating agents, such as, for example, microcrystalline cellulose, sodium crosscarmellose, corn starch, and alginic acid; binding agents, such as, for example, starch, gelatin, polyvinyl-pyrrolidone, and acacia; and lubricating agents, such as, for example, magnesium stearate, stearic acid, and talc. Additionally, a tablet can either be uncoated, or coated by known techniques to either mask the bad taste of an unpleasant tasting drug, or delay disintegration and absorption of the active ingredient in the gastrointestinal tract thereby sustaining the effects of the active ingredient for a longer period. Exemplary water soluble taste masking materials, include, but are not limited to, hydroxypropyl-methylcellulose and hydroxypropyl-cellulose. Exemplary time delay materials, include, but are not limited to, ethyl cellulose and cellulose acetate butyrate.

Hard gelatin capsules can, for example, be prepared by mixing at least one compound of Formula (I) with at least one inert solid diluent, such as, for example, calcium carbonate; calcium phosphate; and kaolin.

Soft gelatin capsules can, for example, be prepared by mixing at least one compound of Formula (I) with at least one water soluble carrier, such as, for example, polyethylene glycol; and at least one oil medium, such as, for example, peanut oil, liquid paraffin, and olive oil.

An aqueous suspension can be prepared, for example, by admixing at least one compound of Formula (I) with at least one excipient suitable for the manufacture of an aqueous suspension. Exemplary excipients suitable for the manufacture of an aqueous suspension, include, but are not limited to, for example, suspending agents, such as, for example, sodium carboxymethylcellulose, methylcellulose, hydroxypropylmethyl-cellulose, sodium alginate, alginic acid, polyvinyl-pyrrolidone, gum tragacanth, and gum acacia; dispersing or wetting agents, such as, for example, a naturally-occurring phosphatide, e.g., lecithin; condensation products of alkylene oxide with fatty acids, such as, for example, polyoxyethylene stearate; condensation products of ethylene oxide with long chain aliphatic alcohols, such as, for example heptadecaethylene-oxycetanol; condensation products of ethylene oxide with partial esters derived from fatty acids and hexitol, such as, for example, polyoxyethylene sorbitol monooleate; and condensation products of ethylene oxide with partial esters derived from fatty acids and hexitol anhydrides, such as, for example, polyethylene sorbitan monooleate. An aqueous suspension can also contain at least one preservative, such as, for example, ethyl and n-propyl p-hydroxybenzoate; at least one coloring agent; at least one flavoring agent; and/or at least one sweetening agent, including but not limited to, for example, sucrose, saccharin, and aspartame.

Oily suspensions can, for example, be prepared by suspending at least one compound of Formula (I) in either a vegetable oil, such as, for example, arachis oil; olive oil; sesame oil; and coconut oil; or in mineral oil, such as, for example, liquid paraffin. An oily suspension can also contain at least one thickening agent, such as, for example, beeswax; hard paraffin; and cetyl alcohol. In order to provide a palatable oily suspension, at least one of the sweetening agents already described hereinabove, and/or at least one flavoring agent can be added to the oily suspension. An oily suspension can further contain at least one preservative, including, but not limited to, for example, an antioxidant, such as, for example, butylated hydroxyanisol, and alpha-tocopherol.

Dispersible powders and granules can, for example, be prepared by admixing at least one compound of Formula (I) with at least one dispersing and/or wetting agent; at least one suspending agent; and/or at least one preservative. Suitable dispersing agents, wetting agents, and suspending agents are as already described above. Exemplary preservatives include, but are not limited to, for example, anti-oxidants, e.g., ascorbic acid. In addition, dispersible powders and granules can also contain at least one excipient, including, but not limited to, for example, sweetening agents; flavoring agents; and coloring agents.

An emulsion of at least one compound of Formula (I) thereof can, for example, be prepared as an oil-in-water emulsion. The oily phase of the emulsions comprising compounds of Formula (I) may be constituted from known ingredients in a known manner. The oil phase can be provided by, but is not limited to, for example, a vegetable oil, such as, for example, olive oil and arachis oil; a mineral oil, such as, for example, liquid paraffin; and mixtures thereof. While the phase may comprise merely an emulsifier, it may comprise a mixture of at least one emulsifier with a fat or an oil or with both a fat and an oil. Suitable emulsifying agents include, but are not limited to, for example, naturally-occurring phosphatides, e.g., soy bean lecithin; esters or partial esters derived from fatty acids and hexitol anhydrides, such as, for example, sorbitan monooleate; and condensation products of partial esters with ethylene oxide, such as, for example, polyoxyethylene sorbitan monooleate. Preferably, a hydrophilic emulsifier is included together with a lipophilic emulsifier which acts as a stabilizer. It is also preferred to include both an oil and a fat. Together, the emulsifiers) with or without stabilizers) make-up the so-called emulsifying w ax, and the wax together with the oil and fat make up the so-called emulsifying ointment base which forms the oily dispersed phase of the cream formulations. An emulsion can also contain a sweetening agent, a flavoring agent, a preservative, and/or an antioxidant. Emulsifiers and emulsion stabilizers suitable for use in the formulation of the present invention include Tween 60, Span 80, cetostearyl alcohol, myristyl alcohol, glyceryl monostearate, sodium lauryl sulfate, glyceryl distearate alone or with a wax, or other materials w ell known in the art.

The compounds of Formula (I) can, for example, also be delivered intravenously, subcutaneously, and/or intramuscularly via any pharmaceutically acceptable and suitable injectable form. Exemplary injectable forms include, but are not limited to, for example, sterile aqueous solutions comprising acceptable vehicles and solvents, such as, for example, water. Ringer's solution, and isotonic sodium chloride solution; sterile oil-in-water microemulsions; and aqueous or oleaginous suspensions.

Formulations for parenteral administration may be in the form of aqueous or non-aqueous isotonic sterile injection solutions or suspensions. These solutions and suspensions may be prepared from sterile powders or granules using one or more of the carriers or diluents mentioned for use in the formulations for oral administration or by using other suitable dispersing or wetting agents and suspending agents. The compounds may be dissolved in water, polyethylene glycol, propylene glycol, ethanol, corn oil, cottonseed oil, peanut oil, sesame oil, benzyl alcohol, sodium chloride solution, tragacanth gum, and/or various buffers. Other adjuvants and modes of administration are well and widely known in the pharmaceutical art. The active ingredient may also be administered by injection as a composition with suitable carriers including saline, dextrose, or water, or with cyclodextrin (i.e. Captisol), cosolvent solubilization (i.e. propylene glycol) or micellar solubilization (i.e. Tween 80).

The sterile injectable preparation max also be a sterile injectable solution or suspension in a non-toxic parenterally acceptable diluent or solvent, for example as a solution in 1,3-butanediol. Among the acceptable vehicles and solvents that may be employed are water. Ringer's solution, and isotonic sodium chloride solution. In addition, sterile, fixed oils are conventionally employed as a solvent or suspending medium. For this purpose any bland fixed oil may be employed, including synthetic mono- or diglycerides. In addition, fatty acids such as oleic acid find use in the preparation of injectables.

A sterile injectable oil-in-water microemulsion can, for example, be prepared by 1) dissolving at least one compound of Formula (I) in an oily phase, such as, for example, a mixture of soybean oil and lecithin; 2) combining the Formula (I) containing oil phase with a water and glycerol mixture; and 3) processing the combination to form a microemulsion.

A sterile aqueous or oleaginous suspension can be prepared in accordance with methods already known in the art. For example, a sterile aqueous solution or suspension can be prepared with a non-toxic parenterally-acceptable diluent or solvent such as, for example, 1,3-butane diol; and a sterile oleaginous suspension can be prepared with a sterile non-toxic acceptable solvent or suspending medium, such as, for example, sterile fixed oils, e.g., synthetic mono- or diglycerides; and fatty acids, such as, for example, oleic acid.

Pharmaceutically acceptable carriers, adjuvants, and vehicles that max be used in the pharmaceutical compositions of this invention include, but are not limited to, ion exchangers, alumina, aluminum stearate, lecithin, self-emulsifying drug delivery systems (SEDDS) such as d-alpha-tocopherol polyethyleneglycol 1000 succinate, surfactants used in pharmaceutical dosage forms such as Tweens, polyethoxylated castor oil such as CREMOPHOR surfactant (BASF), or other similar polymeric delivery matrices, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxy methylcellulose, polyacrylates, waxes, polyethylene-polyoxypropylene-block polymers, polyethylene glycol and wool fat Cyclodextrins such as alpha-, beta-, and gamma-cyclodextrin, or chemically modified derivatives such as hydroxyalkylcyclodextrins, including 2- and 3-hydroxypropyl-cyclodextrins, or other solubilized derivatives may also be advantageously used to enhance delivery of compounds of the formulae described herein.

The pharmaceutically active compounds of this invention can be processed in accordance with conventional methods of pharmacy to produce medicinal agents for administration to patients, including humans and other mammals. The pharmaceutical compositions may be subjected to conventional pharmaceutical operations such as sterilization and/or may contain conventional adjuvants, such as preservatives, stabilizers, wetting agents, emulsifiers, buffers etc. Tablets and pills can additionally be prepared with enteric coatings. Such compositions may also comprise adjuvants, such as wetting, sweetening, flavoring, and perfuming agents.

The amounts of compounds that are administered and the dosage regimen for treating a disease condition with the compounds and/or compositions of this invention depends on a variety of factors, including the age, weight, sex, the medical condition of the subject, the type of disease, the severity of the disease, the route and frequency of administration, and the particular compound employ ed. Thus, the dosage regimen may vary widely, but can be determined routinely using standard methods. A daily dose of about 0.001 to 100 mg/kg body weight, preferably between about 0.0025 and about 50 mg/kg body w eight and most preferably between about 0.005 to 10 mg/kg body weight, may be appropriate. The daily dose can be administered in one to four doses per day. Other dosing schedules include one dose per week and one dose per two day cycle.

For therapeutic purposes, the active compounds of this invention are ordinarily combined with one or more adjuvants appropriate to the indicated route of administration. If administered orally, the compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or poly vinyl alcohol, and then tableted or encapsulated for convenient administration. Such capsules or tablets may contain a controlled-release formulation as may be provided in a dispersion of active compound in hydroxypropylmethyl cellulose.

Pharmaceutical compositions of this invention comprise at least one compound of Formula (I) and optionally an additional agent selected from any pharmaceutically acceptable carrier, adjuvant, and vehicle. Alternate compositions of this invention comprise a compound of the Formula (I) described herein, or a prodrug thereof, and a pharmaceutically acceptable carrier, adjuvant, or vehicle.

The present invention also encompasses an article of manufacture. As used herein, article of manufacture is intended to include, but not be limited to, kits and packages. The article of manufacture of the present invention, comprises: (a) a first container; (b) a pharmaceutical composition located within the first container, w herein the composition, comprises: a first therapeutic agent, comprising, a compound of the present invention or a pharmaceutically acceptable salt form thereof; and (c) a package insert stating that the pharmaceutical composition can be used for the treatment of an inflammatory disorder and/or an autoimmune disease (as defined previously). In another embodiment, the package insert states that the pharmaceutical composition can be used in combination (as defined previously) with a second therapeutic agent to treat an inflammatory disorder and/or an autoimmune disease. The article of manufacture can further comprise: (d) a second container, wherein components (a) and (b) are located within the second container and component (c) is located within or outside of the second container. Located within the first and second containers means that the respective container holds the item within its boundaries.

The first container is a receptacle used to hold a pharmaceutical composition. This container can be for manufacturing, storing, shipping, and/or individual/bulk selling. First container is intended to cover a bottle, jar, vial, flask, syringe, tube (e.g., for a cream preparation), or any other container used to manufacture, hold, store, or distribute a pharmaceutical product.

The second container is one used to hold the first container and, optionally, the package insert. Examples of the second container include, but are not limited to, boxes (e.g., cardboard or plastic), crates, cartons, bags (e.g., paper or plastic bags), pouches, and sacks. The package insert can be physically attached to the outside of the first container via tape, glue, staple, or another method of attachment, or it can rest inside the second container without any physical means of attachment to the first container. Alternatively, the package insert is located on the outside of the second container. When located on the outside of the second container, it is preferable that the package insert is physically attached via tape, glue, staple, or another method of attachment. Alternatively, it can be adjacent to or touching the outside of the second container without being physically attached.

The package insert is a label, tag, marker, etc. that recites information relating to the pharmaceutical composition located within the first container. The information recited will usually be determined by the regulator) agency governing the area in which the article of manufacture is to be sold (e.g., the United States Food and Drug Administration). In one embodiment, the package insert specifically recites the indications for which the pharmaceutical composition has been approved. The package insert may be made of any material on which a person can read information contained therein or thereon. For example, the package insert is a printable material (e.g., paper, plastic, cardboard, foil, adhesive-backed paper or plastic, etc.) on which the desired information has been formed (e.g., printed or applied).

Methods of Preparation

The compounds of the present invention can be prepared in a number of ways well known to one skilled in the art of organic synthesis. The compounds of the present invention can be synthesized using the methods described below, together with synthetic methods known in the art of synthetic organic chemistry, or variations thereon as appreciated by those skilled in the art. Preferred methods include, but are not limited to, those described below. All references cited herein are hereby incorporated in their entirety by reference.

The compounds of this invention may be prepared using the reactions and techniques described in this section. The reactions are performed in solvents appropriate to the reagents and materials employed and are suitable for the transformations being effected. Also, in the description of the synthetic methods described below, it is to be understood that all proposed reaction conditions, including choice of solvent, reaction atmosphere, reaction temperature, duration of the experiment and work up procedures, are chosen to be the conditions standard for that reaction, which should be readily recognized by one skilled in the art. It is understood by one skilled in the art of organic synthesis that the functionality present on various portions of the molecule must be compatible with the reagents and reactions proposed. Such restrictions to die substituents that are compatible with the reaction conditions will be readily apparent to one skilled in the art and alternate methods must then be used. This will sometimes require a judgment to modify the order of the synthetic steps or to select one particular process scheme over another in order to obtain a desired compound of the invention. It will also be recognized that another major consideration in the planning of any synthetic route in this field is the judicious choice of the protecting group used for protection of the reactive functional groups present in the compounds described in this invention. An authoritative account describing the many alternatives to the trained practitioner is Greene and Wuts (*Protective Groups In Organic Synthesis*, Third Edition, Wiley and Sons, 1999).

EXAMPLES

Preparation of compounds of Formula (I), and intermediates used in the preparation of compounds of Formula (I), can be prepared using procedures shown in the following Examples and related procedures. The methods and conditions used in these examples, and the actual compounds prepared in these Examples, are not meant to be limiting, but are meant to demonstrate how the compounds of Formula (I) can be prepared. Starting materials and reagents used in these examples, when not prepared by a procedure described herein, are generally either commercially available, or are reported in the chemical literature, or may be prepared by using procedures described in the chemical literature.

ABBREVIATIONS

Ac acetyl
ACN acetonitrile
AcOH acetic acid
anhyd. anhydrous
aq. aqueous
Bn benzyl
Bu butyl
Boc tert-butoxy carbonyl
CV Column Volumes
DCE dichloroethane
DCM dichloromethane
DMAP dimethylaminopyridine
DMF dimethylformamide
DMSO dimethylsulfoxide
EDC 1-(3-dimethylaminopropyl)-3-ethylcarbodiimide hydrochloride
EtOAc ethyl acetate
Et ethyl
EtOH ethanol
H or $H_2$ hydrogen
h, hr or hrs hour(s)
HCTU O-(6-Chlorobenzotriazol-1-yl)-N,N,N',N'-tetramethyluronium hexafluorophosphate
hex hexane
i iso
IPA isopropyl alcohol
HOAc acetic acid
HCl hydrochloric acid
HPLC high pressure liquid chromatography
LC liquid chromatography
M molar
mM millimolar
Me methyl
MeOH methanol
MHz megahertz
min. minute(s)
mins minute(s)
$M^{+1}$ $(M+H)^+$
MS mass spectrometry
n or N normal
NBS n-bromosuccinimide
nm nanometer
nM nanomolar
NMP N-methylpyrrolidine
Pd/C palladium on carbon
$PdCl_2(dppf)_2$ [1,1'-bis(diphenylphosphino)ferrocene]dichloropalladium(II)
$Pd(PPh_3)_4$ tetrakis(triphenylphosphine)palladium
Ph phenyl
$PPh_3$ triphenylphosphine
Pr propyl
PSI pounds per square inch
PyBOP bromotripyrrolidinophosphonium hexafluorophosphate Ret Time retention time
sat. saturated
SFC supercritical fluid chromatography
TEA triethylamine
TFA trifluoroacetic acid
THF tetrahydrofuran Analytical and Preparative HPLC Conditions.

QC-ACN-AA-XB: Column: Waters Acquity UPLC BEH C18, 2.1×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.0 mL/min; Detection: UV at 220 nm.

QC-ACN-TFA-XB: Column: Waters Acquity UPLC BEH C18, 2.1×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 3 minutes, then a 0.75-minute hold at 100% B; Flow: 1.0 mL/min; Detection: UV at 220 nm.

Method A1: L3 Acquity: Column: (LCMS) UPLC BEH C18, 2.1×50 mm, 1.7 μm particles; Mobile Phase: (A) water; (B) acetonitrile; Buffer: 0.05% TFA; Gradient Range: 2%-98% B (0 to 1 min) 98% B (to 1.5 min) 98%-2% B (to 1.6 min); Gradient Time: 1.6 min; Flow Rate: 0.8 mL/min; Analysis Time: 2.2 min; Detection: Detector 1: UV at 220 nm; Detector 2: MS (ESI$^+$).

Method B1: L2 Acquity: Column: (LCMS) UPLC BEH C18, 2.1×50 mm, 1.7 μm particles; Mobile Phase. (A) water; (B) acetonitrile; Buffer: 0.05% TFA; Gradient Range: 2%-98% B (0 to 1 min), 98%-2% B (to 1.5 min); Gradient Time: 1.8 min; Flow Rate: 0.8 mL/min; Analysis Time: 2.2 min; Detection: Detector 1: UV at 220 nm; Detector 2: MS (ESI$^+$)

Method C1 SCP: Column: Waters Acquity UPLC BEH C18, 2.1×50 mm, 1.7 μm particles; Mobile Phase A: 5:95 acetonitrile:water with 10 mM ammonium acetate; Mobile Phase B: 95:5 acetonitrile:water with 10 mM ammonium acetate. Temperature: 50° C.; Gradient: 0-100% B over 3 minutes, then a 0.75 minute hold at 100% B; Flow: 1.11 mL/min; Detection: UV at 220 nm.

Method D1 SCP: Column: Waters Acquity UPLC BEH C18, 2.1×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 3 minutes, then a 0.75 minute hold at 100% B; Flow: 1.11 mL/min; Detection: UV al 220 nm.

Method D2 SCP: Column: XBridge C18, 19×200 mm, 5 μm particles; Mobile Phase A: 5:95 acetonitrile: water with 10 mM ammonium acetate; Mobile Phase B: 95:5 acetonitrile: water with 10 mM ammonium acetate; Gradient: 10-50% B over 20 minutes, then a 5 minute hold at 100% B; Flow: 20 mL/min. Detection: UV at 220 nm.

Method D3 SCP: Column: XBridge C18, 19×200 mm, 5 μm particles; Mobile Phase A: 5:95 acetonitrile: water with 0.1% trifluoroacetic acid; Mobile Phase B: 95:5 acetonitrile: water with 0.1% trifluoroacetic acid; Gradient: 6-46% B over 20 minutes, then a 4-minute hold at 100% B; Flow: 20 mL/min. Detection: UV at 220 nm.

Method E1 iPAC: Column: Waters Xbridge C18 4.6×50 mm 5 μm particles; Mobile Phase A: 5:95 acetonitrile:

water with 10 mM ammonium acetate; Mobile Phase B: 95:5 acetonitrile:water with 10 mM ammonium acetate. Temperature: 50° C.; Gradient: 0-100% B over 1 minute; Flow: 4 mL/min; Detection: UV at 220 nm.

Method F1 iPAC: Column: Waters Acquit) BEH C18 2.1×50 mm 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 2.20 minutes; Flow: 0.800 mL/min; Detection: UV at 220 nm (A): Column-Ascentis Express C18 (50×2.1 mm-2.7 μm) Mphase A: 10 mM $NH_4COOH$ in water: ACN (98:02); Mphase B: 10 mM $NH_4COOH$ in water: ACN (02:98), Gradient: 0-100% B over 3 minutes, Flow=1 mL/min.

(B): Waters Acquity BEH C18 (2.1×50 mm) 1.7 micron; Buffer: 5 mM ammonium acetate pH 5 adjusted with HCOOH, Solvent A: Buffer:ACN (95:5), Solvent B. Buffer:ACN (5:95), Method: % B: 0 min-5%: 1.1 min-95%: 1.7 min-95%, Flow: 0.8 mL/min.

(C): Column-Ascentis Express C18 (50×2.1 mm-2.7 μm) Mobile phase A: 0.1% HCOOH in water; Mobile phase B: ACN. Temperature: 50° C.; Gradient: 0-100% B over 3 minutes; Flow rate: 1.0 mL/min.

(D): Kinetex XB-C18 (75×3 mm) 2.6 micron; Solvent A: 10 mM ammonium formate in water: acetonitrile (98:02); Mobile Phase B: 10 mM ammonium formate in water: acetonitrile (02:98); Temperature: 50° C.; Gradient: 0-100% B over 3 minutes; Flow rate: 1.1 mL/min; Detection: UV at 220 nm.

(E): Column: Ascentis Express C18 (50×2.1) mm, 2.7 μm; Mobile Phase A: 5:95 acetonitrile: water with 10 mM $NH_4OAc$; Mobile Phase B: 95:5 acetonitrile: water with 10 mM $NH_4OAc$; Temperature: 50° C.; Gradient: 0-100% B over 3 minutes; Flow: 1.1 mL/min.

(F): Column: Ascentis Express C18 (50×2.1) mm, 2.7 μm; Mobile Phase A: 5:95 acetonitrile: water with 0.1% TFA; Mobile Phase B: 95:5 acetonitrile: water with 0.1% TFA; Temperature: 50° C.; Gradient: 0-100% B over 3 minutes; Flow: 1.1 mL/min.

(G): Column: Waters Acquity UPLC BEH C18 (2.1×50 mm), 1.7 micron; Solvent A=100% water with 0.05% TFA; Solvent B=100% acetonitrile with 0.05% TFA; gradient=2-98% B over 1 minute, then a 0.5 minute hold at 98% B; Flow rate: 0.8 mL/min; Detection: UV at 220 nm.

(H): Column: Acentis Express C18 (50×2.1 mm) 1.7 μm, Acentis C8 $NH_4COOH$ 5 min. M, Mobile Phase A: 10 mM ammonium formate: ACN (98:2), Mobile Phase B: 10 mM ammonium formate: ACN (2:98), gradient: 20%-100% B (0-4 min); 100% B (4-4.6 min); Flow: 1 mL/min.

(I) Column: Sunfire C18 (4.6×150) mm, 3.5 μm; Mobile Phase A: 5:95 acetonitrile: water with 0.05% TFA; Mobile Phase B: 95:5 acetonitrile: water with 0.05% TFA; Temperature: 50° C.; Gradient: 10-100% B over 12 minutes; Flow: 1 mL/min.

(J) Column: Sunfire C18 (4.6×150) mm, 3.5 μm; Mobile Phase A: 5:95 acetonitrile: water with 0.05% TFA; Mobile Phase B: 95:5 acetonitrile: water with 0.05% TFA;

(K) Waters Acquity SDS.

Mobile Phase: A: water B: ACN; 5%-95% B in 1 min; Gradient Range: 50%-98% B (0-0.5 min); 98% B (0.5 min-1 min); 98%-2% B (1-1.1 min); Run time: 1.2 min;

Flow Rate: 0.7 mL/min; Analysis Time: 1.7 min; Detection: Detector 1: UV at 220 nm; Detector 2: MS (ES+).

(L) Acquity UPLC BEH C18 (3.0×50 mm) 1.7 μm. Buffer: 5 mM ammonium acetate Mobile phase A: Buffer: ACN (95:5); Mobile phase B: Buffer: ACN (5:95) Method: % B: 0 min-20%: 1.1 min-90%: 1.7 min-90%. Run time: 2.25 min; Flow Rate: 0.7 mL/min; Detection: Detector 1: UV at 220 nm; Detector 2: MS (ES+).

(M): Kinetex SBC 18 (4.6×50 mm) 5 micron; Solvent A: 10 mM ammonium formate in water: acetonitrile (98:02); Mobile Phase B: 10 mM ammonium formate in water: acetonitrile (02:98); Temperature: 50° C.; Gradient: 30-100% B (0-4 min), 100% B (4-4.6 min), 100-30% B (4.6-4.7 min), 30% B (4.7-5.0 min); Flow rate: 1.5 mL/min; Detection: UV at 220 nm.

(N): Column-Ascends Express C18 (50×2.1 mm-2.7 μm) Mphase A: 10 mM $NH_4COOH$ in water: ACN (98:02); Mphase B: 10 mM $NH_4COOH$ in water: ACN (02:98), Gradient: 0-100% B (0-1.7 minutes); 100% B (1.7-3.4 minutes). Flow=1 mL/min.

(O) Waters Acquity SDS Column BEH C18 (2.1×50 mm) 1.7 μm. Phase A: buffer in water; Mphase B: buffer in ACN, Gradient: 20-98% B (0-1.25 minutes); 98% B (1.25-1.70 minutes); 98%-2% B (1.70-1.75 minutes); Flow=0.8 mL/min.

(P): Column: Xbridge BEH XP C18 (50×2.1) mm, 2.5 μm; Mobile Phase A: 5:95 acetonitrile: water with 10 mM $NH_4OAc$; Mobile Phase B: 95:5 acetonitrile: water with 10 mM $NH_4OAc$; Temperature: 50° C.; Gradient: 0-100% B over 3 minutes; Flow: 1.1 mL/min.

(Q): Column: Xbridge BEH XP C18 (50×2.1) mm, 2.5 μm; Mobile Phase A: 5:95 acetonitrile: water with 0.1% TFA; Mobile Phase B: 95:5 acetonitrile: water with 0.1% TFA; Temperature: 50° C.; Gradient: 0-100% B over 3 minutes; Flow: 1.1 mL/min. (TS1): Column: Waters Acquity UPLC BEH C18 (2.1×50 mm), 1.7 micron; Solvent A=100% water with 0.05% TFA; Solvent B=100% acetonitrile with 0.05% TFA; gradient=2-98% B over 1 minute, then a 0.5 minute hold at 98% B; Flow rate: 0.8 mL/min; Detection: UV at 254 nm.

Examples 1 and 2

4-(3-isopropyl-2-(8-methoxy-[1,2,4]triazolo[1,5-a] pyridin-6-yl)-1H-indol-5-yl) cyclohexanamine

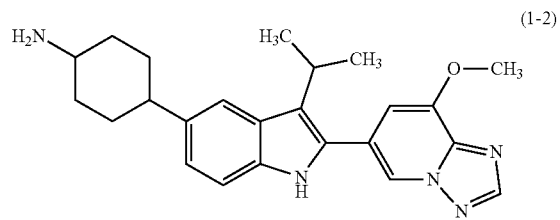 [SMILES: COc1cc(-c2[nH]c3ccc(C4CCC(N)CC4)cc3c2C(C)C)cn2ncnc12]

(1-2)

Intermediate 1A: 1,4-dioxaspiro[4.5]dec-7-en-8-yl trifluoromethanesulfonate

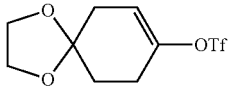

(1A)

To a solution of 1,4-dioxaspiro[4.5]decan-8-one (10.0 g, 64.0 mmol) and N-phenyl-bis(trifluoromethanesulfonimide) (29.7 g, 83 mmol) in THF (1000 mL) at −78° C., was added KHMDS (16.60 g, 83 mmol), the resulting reaction mixture was slowly brought to room temperature, stirred at same temperature for 16 h. The reaction mixture was quenched with cold water (300 mL), and extracted with ethyl acetate (2×500 mL), combined organic layer was washed with water, brine, dried over sodium sulphate and concentrated to afford crude compound. The crude material was purified by silica gel chromatography on an ISCO instrument using 120 g silica column, compound w as eluted with 15% ethyl acetate in petroleum ether, die fraction was collected and concentrated to afford 1,4-dioxaspiro[4.5]dec-7-en-8-yltrifluoromethanesulfonate (12.0 g, 41.6 mmol, 65% yield) as a colorless liquid. $^1$H NMR (400 MHz, CDCl$_3$) δ ppm 5.67-5.65 (m, 1H), 4.02-3.95 (m, 4H), 2.55-2.52 (m, 2H), 2.51-2.40 (T, 2H), 1.92-1.89 (m, 2H).

Intermediate 1B: 5-bromo-3-isopropyl-1H-indole

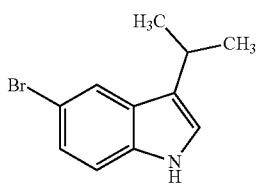

(1B)

To a solution of trichloroacetic acid (43.8 g, 268 mmol) and triethylsilane (86 mL, 536 mmol) in toluene (500 mL) at 70° C. was added a solution of 5-bromo-1H-indole (35.0 g, 179 mmol) in toluene (150 mL) and acetone (65.5 mL, 893 mmol) for 35 min, the mixture was further heated to 90° C., continued stirring for 14 h. The reaction mixture was slowly quenched with cold water, brought to basic with 10% aqueous NaHCO$_3$ solution and extracted with ethyl acetate (3×500 mL), the combined organic layers were washed with water (500 mL) followed by brine solution (50 mL), dried over Na$_2$SO$_4$ and concentrated to afford crude compound. The crude material was purified by silica gel chromatography on an ISCO instrument using 240 g silica column, compound was eluted with 15% ethyl acetate in hexane, the fractions were collected and concentrated to afford 5-bromo-3-isopropyl-1H-indole (32.0 g, 134 mmol, 75% yield) as light brown liquid. LCMS retention time 3.10 min [G], MS (E$^+$) m z: 238.0 (M).

Intermediate 1C: 3-isopropyl-5-(4,4,5,5-tetramethyl-1,3,2-dioxaborolan-2-yl)-1H-indole

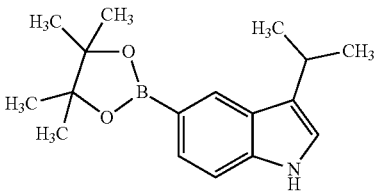

(1C)

To a degassed solution of 5-bromo-3-isopropyl-1H-indole (32.0 g, 134 mmol) and bis(pinacolato)diboron (BISPIN) (44.4 g, 175 mmol) in dioxane (800 mL) was added PdCl$_2$(dppf)-CH$_2$Ch adduct (8.78 g, 10.75 mmol) and potassium acetate (39.6 g, 403 mmol), the resulting mixture w as stirred at 95° C. for 14 h in a sealed tube. The reaction mixture was diluted with ethyl acetate, filtered and washed with excess ethyl acetate, combined organic layer was dried over sodium sulphate and evaporated to afford crude compound. The crude material was purified by silica gel chromatography on an ISCO instrument using 240 g silica column, compound was eluted with 15% ethyl acetate in petroleum ether to afford 3-isopropyl-5-(4,4,5,5-tetramethyl-1,3,2-dioxaborolan-2-yl)-1H-indole (26.0 g, 91 mmol, 68% yield) as a white solid. LCMS retention time 3.98 min, (D) MS m/z: 286.1 (M+H).

Intermediate 1D: 3-isopropyl-5-(1,4-dioxaspiro[4.5]dec-7-en-8-yl)-1H-indole

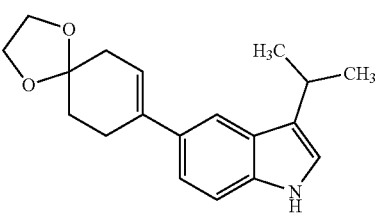

(1D)

To a degassed solution of 3-isopropyl-5-(4,4,5,5-tetramethyl-1,3,2-dioxaborolan-2-yl)-1H-indole (90.0 g, 316 mmol) and 1,4-dioxaspiro[4.5]dec-7-en-8-yl trifluoromethanesulfonate (109 g, 379 mmol) in mixture of dioxane (2000 mL), water (300 mL), were added PdCl$_2$(dppf)-CH$_2$Cl$_2$ adduct (15.46 g, 18.93 mmol) and potassium phosphate dibasic (165 g, 947 mmol), the resulting mixture was stirred at 95° C. for 16 h. The reaction mixture was diluted with ethyl acetate, filtered and washed with excess ethyl acetate, combined organic layer were washed with water, brine, dried over sodium sulphate and evaporated to afford crude compound. The crude material was purified by silica gel chromatography on an ISCO instrument using 240 g silica column, compound was eluted with 40% ethyl acetate in petroleum ether, the fractions were collected and concentrated to afford 3-isopropyl-5-(1,4-dioxaspiro[4.5]dec-7-en-8-yl)-1H-indole (70.0 g, 235 mmol, 75% yield) as a light yellow solid. LCMS retention time 1.44 min (L) MS m z: 298.4 (M+H).

Intermediate 1E: 3-isopropyl-5-(1,4-dioxaspiro[4.5]decan-8-yl)-1H-indole

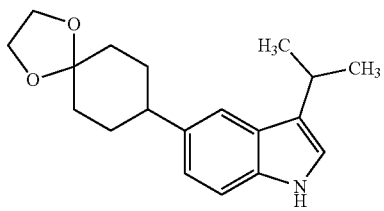

To a degassed mixture of 3-isopropyl-5-(1,4-dioxaspiro[4.5]dec-7-en-8-yl)-1H-indole (70.0 g, 235 mmol) in methanol (200 mL), was added Pd/C (25.05 g, 235 mmol), the resulting mixture was stirred at room temperature for 6 h under hydrogen gas bladder pressure. The reaction mixture was filtered and washed with excess methanol and THF, combined organic layer was evaporated to afford 3-isopropyl-5-(1,4-dioxaspiro[4.5]decan-8-yl)-1H-indole (60.0 g, 200 mmol, 85% yield) as a light brown solid compound. LCMS retention time 2.84 min [G] MS m/z: 300.2 (M+H).

Intermediate 1F: 2-bromo-3-isopropyl-5-(1,4-dioxaspiro[4.5]decan-8-yl)-1H-indole

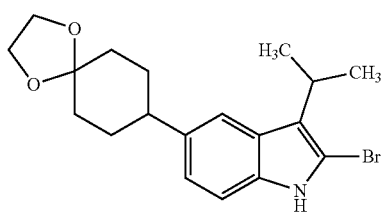

To a solution of 3-isopropyl-5-(1,4-dioxaspiro[4.5]decan-8-yl)-1H-indole (30.0 g, 100 mmol) in DCE (2000 mL) at 0° C. was added slowly NBS (17.83 g, 100 mmol) in DCE (800 mL), stirred at same temperature for 2 h. The reaction was quenched with cold water. The reaction mixture was stirred for 15 min, the organic layer was separated, dried over sodium sulphate and concentrated to afford crude compound. The crude material was purified by silica gel chromatography on an ISCO instrument using 240 g silica column, compound was eluted with 15% ethyl acetate in petroleum ether, the product fractions were collected and concentrated to afford 2-bromo-3-isopropyl-5-(1,4-dioxaspiro[4.5]decan-8-yl)-1H-indole (17.0 g, 44.9 mmol, 45% yield) as a light brown solid. LCMS Retention time 1.61 min (L) MS m/z: 380.3 (M+2H).

Intermediate 1G: 6-(3-isopropyl-5-(1,4-dioxaspiro[4.5]decan-8-yl)-1H-indol-2-yl)-8-methoxy-[1,2,4]triazolo[1,5-a]pyridine

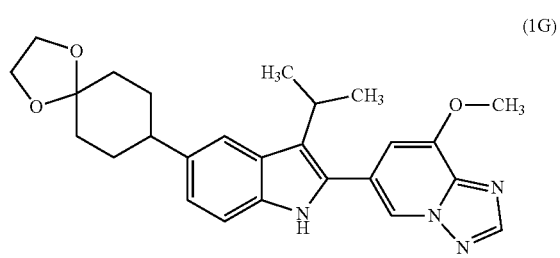 [SMILES: COc1cc(-c2[nH]c3ccc(C4CCC5(CC4)OCCO5)cc3c2C(C)C)cn2ncnc12]

To a degassed solution of 2-bromo-3-isopropyl-5-(1,4-dioxaspiro[4.5]decan-8-yl)-1H-indole (5.0 g, 13.22 mmol) and 8-methoxy-6-(4,4,5,5-tetramethyl-1,3,2-dioxaborolan-2-yl)-[1,2,4]triazolo[1,5-a]pyridine (5.82 g, 21.15 mmol) in dioxane (200 mL) and water (35.0 mL) were added PdCl$_2$(dppf)-CH$_2$Cl$_2$ adduct (1.079 g, 1.322 mmol) and potassium phosphate dibasic (6.91 g, 39.7 mmol) at room temperature, the resulting mixture was stirred at 95° C. for 4 h in a sealed tube. The reaction mixture was diluted with ethyl acetate, filtered and washed with excess ethyl acetate, combined organic layer was washed with water, brine, dried over sodium sulphate and evaporated to afford crude. The crude material was purified by silica gel chromatography on an ISCO instrument using 120 g silica column, compound was eluted with 80%-100% ethyl acetate in petroleum ether to afford 6-(3-isopropyl-5-(1,4-dioxaspiro [4.5]decan-8-yl)-1H-indol-2-yl)-8-methoxy-[1,2,4]triazolo[1,5-a]pyridine (5.0 g, 11.20 mmol, 85% yield) as an off-white solid. LCMS retention time 1.38 min [L]. MS m/z: 447.6 (M+H).

The following Intermediates were prepared according to the general procedure used to prepare Intermediate 1G.

TABLE 1

| Intermediate | Structure | Mol Wt. | LCMS MH+ | Ret Time (min) | HPLC Method |
| --- | --- | --- | --- | --- | --- |
| INT-1G-2 | 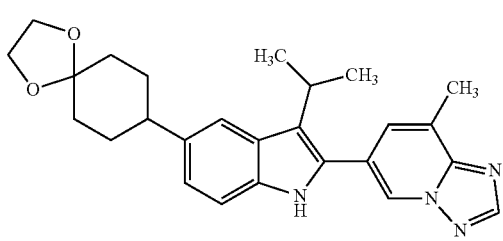 [SMILES: Cc1cc(-c2[nH]c3ccc(C4CCC5(CC4)OCCO5)cc3c2C(C)C)cn2ncnc12] | 430.5 | 431.6 | 1.48 | L |

TABLE 1-continued

| Inter-mediate | Structure | Mol Wt. | LCMS MH+ | Ret Time (min) | HPLC Method |
|---|---|---|---|---|---|
| INT-1G-3 | 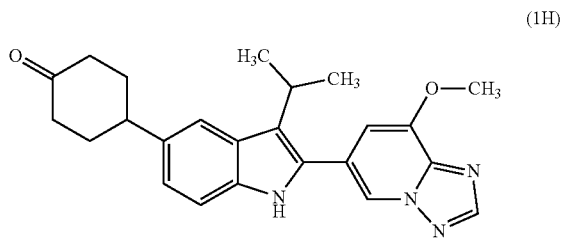 [SMILES: COc1cc(-c2[nH]c3ccc(C4CCC(=O)CC4)cc3c2C(C)C)cn2ncnc12] | 444.56 | 445.6 | 1.51 | L |

Intermediate 1H: 4-(3-isopropyl-2-(8-methoxy-[1,2,4]triazolo[1,5-a]pyridin-6-yl)-1H-indol-5-yl)cyclohexanone (1H)

To a solution of 6-(3-isopropyl-5-(1,4-dioxaspiro[4.5]decan-8-yl)-1H-indol-2-yl)-8-methoxy-[1,2,4]triazolo[1,5-a]pyridine (5.0 g, 11.20 mmol) in DCM (100 mL) at 0° C. was added TFA (21.57 mL, 280 mmol) then stirred at room temperature for 12 h. The volatiles were evaporated and dried under vacuum, then brought to basic with saturated NaHCO₃ solution and extracted with CHCl₃ (2×200 mL), washed with water, brine, the organic layer was dried over sodium sulphate and concentrated to afford 4-(3-isopropyl-2-(8-methoxy-[1,2,4]triazolo[1,5-a]pyridin-6-yl)-1H-indol-5-yl)cyclohexanone (4.0 g, 9.94 mmol, 89% yield) as a brown solid. LCMS retention time 1.24 min [L], MS m/z: 403.6 (M+H).

Examples 1 and 2

A solution of 4-(3-isopropyl-2-(8-methoxy-[1,2,4]triazolo[1,5-a]pyridin-6-yl)-1H-indol-5-yl) cyclohexanone (0.150 g, 0.373 mmol), ammonium acetate (0.287 g, 3.73 mmol), ammonium chloride (0.199 g, 3.73 mmol) and acetic acid (2.133 µl, 0.037 mmol) in DMF (3.0 mL), and THF (3.0 mL) solvent mixture was stirred at room temperature for 8 h. Then was added sodium cyanoborohydride (0.035 g, 0.559 mmol) at 0° C., the resulting reaction mixture was stirred at room temperature for 16 h. Concentrated the reaction mass, the residue was dissolved with excess DCM, washed with water, brine, organic layer was dried over sodium sulphate and concentrated to afford crude. The crude material was purified by preparative HPLC, using method D2 to separate both cis and trans isomers, the fractions containing the desired compounds w as collected and dried using a Genevac centrifugal evaporator.

Example 1 (Isomer 1): (0.044 g, 29% yield) as a white solid. LCMS retention time 1.57 min. (E) MS m/z: 404.1 (M+H); $^1$H NMR (400 MHz. METHANOL-d₄) δ ppm 8.56-8.39 (m, 2H), 7.68-7.59 (m, 1H), 7.41-7.32 (m, 1H), 7.28-7.20 (m, 1H), 7.15-7.02 (m, 1H), 4.18 (s, 3H), 3.47-3.21 (m, 1H), 2.73-2.60 (m, 1H), 2.26-2.17 (m, 2H), 2.15-2.03 (m, 2H), 1.81-1.60 (m, 4H), 1.56 (d, J=7.1 Hz, 6H), 1.39-1.24 (m, 1H).

Example 2 (Isomer 2): (0.001 g, 0.892 mmol, 1% yield) as a white solid. LCMS retention time 1.42 min (E) MS m/z: 404.1 (M+H); $^1$H NMR (400 MHz, METHANOL-d₄) δ ppm 8.52-8.37 (m, 2H), 7.64 (s, 1H), 7.37 (d, J=8.6 Hz, 1H), 7.23 (s, 1H), 7.09 (d, J=8.6 Hz, 1H), 4.23-4.09 (m, 3H), 3.75 (s, 1H), 3.46-3.37 (m, 3H), 2.96-2.85 (m, 2H), 2.73 (br. s., 3H), 2.32-2.09 (m, 5H), 1.86-1.70 (m, 6H), 1.54 (d, J=7.1 Hz, TH), 1.33 (t, J=7.3 Hz, 8H).

The following Examples were prepared according to the general procedure used to prepare Examples 1 and 2.

TABLE 2

| Ex. No. | Structure | Mol Wt. | LCMS MH+ | Ret Time (min) | HPLC Method |
|---|---|---|---|---|---|
| 3 | 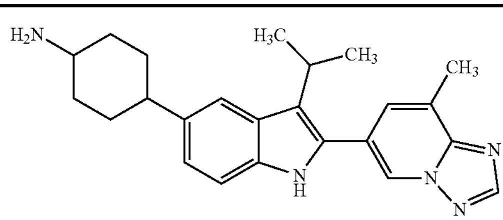 | 387.5 | 388.2 | 1.47 | E |

TABLE 2-continued

| Ex. No. | Structure | Mol Wt. | LCMS MH+ | Ret Time (min) | HPLC Method |
|---|---|---|---|---|---|
| 4 | H₂N-cyclohexyl-indole(iPr)-8-methyltriazolopyridine | 387.5 | 388.3 | 1.22 | E |
| 5 | H₂N-cyclohexyl-indole(iPr)-2,6-dimethylpyridine | 361.2 | 362.2 | 1.41 | E |

Examples 6 and 7

N-isopropyl-4-(3-isopropyl-2-(8-methoxy-[1,2,4]triazolo[1,5-a]pyridin-6-yl)-1H-indol-5-yl)-N-methylcyclohexanamine

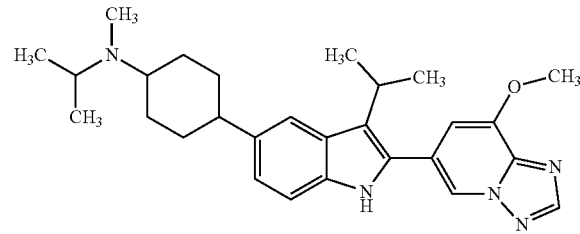

(6-7)

A solution of 4-(3-isopropyl-2-(8-methoxy-[1,2,4]triazolo[1,5-a]pyridin-6-yl)-1H-indol-5-yl)cyclohexanone (0.150 g, 0.373 mmol), N-methylpropan-2-amine (0.136 g, 1.863 mmol) and acetic acid (2.133 µl, 0.037 mmol) in DMF (3.0 mL) and THF (3.0 mL) solvent mixture was stirred at room temperature for 8 h, then was added sodium cyanoborohydride (0.035 g, 0.559 mmol) at 0° C., the resulting reaction mixture was stirred at room temperature for 16 h. The volatiles were evaporated, the residue w as dissolved with excess DCM, washed with water, brine, organic layer was dried over sodium sulphate and concentrated to afford crude. The crude material was purified via preparative LC/MS to afford both the isomers using method D2, the fractions containing the desired product were combined and dried via centrifugal evaporation.

Example 6 (Isomer 1)): (3.0 mg, 2% yield) as a pale solid. LCMS retention time 1.63 min. MS m/z: 460.1 (M+H); ¹H NMR (400 MHz, METHANOL-$d_4$) δ ppm 8.42 (d, J=18.34 Hz, 2H) 7.60 (br. s., 1H) 7.32 (d, J=8.80 Hz, 1H) 7.21 (s, 1H) 7.06 (d, J=8.31 Hz, 1H) 4.13 (s, 3H) 3.36-3.50 (m, 2H) 2.94 (br. s., 1H) 2.61 (d, J=12.23 Hz, 1H) 2.43 (br. s., 3H) 2.01-2.24 (m, 5H) 1.89 (br. s, 1H) 1.58-1.76 (m, 4H) 1.52 (d, J=6.60 Hz, 6H) 1.29 (br. s., 1H) 1.21 (d, J=5.87 Hz, 6H).

Example 7 (Isomer 2): (2.0 mg, 1% yield) as a pale solid. LCMS retention time 1.73 min. MS m/z: 460.1 (M+H); ¹H NMR (400 MHz, METHANOL-$d_4$) δ ppm 8.37-8.49 (m, 2H) 7.72 (s, 1H) 7.29-7.38 (m, 1H) 7.08-7.22 (m, 2H) 4.13 (s, 3H) 3.79 (s, 1H) 3.34-3.51 (m, 2H) 2.80-3.00 (m, 3H) 2.14-2.39 (m, 5H) 2.03 (s, 1H) 1.68-1.97 (m, 6H) 1.53 (d, J=6.85 Hz, 6H) 1.29 (br. s, 1H) 1.03-1.17 (m, 6H).

The examples in Table 3 were prepared according to the general procedure used to prepare Examples 6 and 7.

TABLE 3

| Ex. No. | Structure | Mol Wt. | LCMS MH+ | Ret Time (min) | HPLC Method |
|---|---|---|---|---|---|
| 8 | N-cyclopropyl-N-methyl-cyclohexyl-indole(iPr)-8-methyltriazolopyridine | 441.6 | 442.4 | 1.47 | E |

TABLE 3-continued
| Ex. No. | Structure | Mol Wt. | LCMS MH+ | Ret Time (min) | HPLC Method |
|---|---|---|---|---|---|
| 9 | 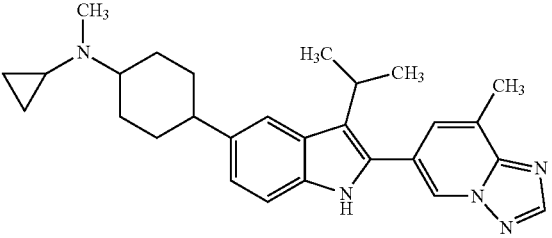 [SMILES: Cc1cc(-c2[nH]c3ccc(C4CCC(N(C)C5CC5)CC4)cc3c2C(C)C)cn2ncnc12] | 441.6 | 442.4 | 1.35 | E |
| 10 | 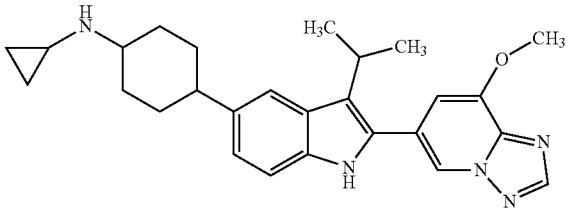 [SMILES: COc1cc(-c2[nH]c3ccc(C4CCC(NC5CC5)CC4)cc3c2C(C)C)cn2ncnc12] | 443.6 | 444.3 | 1.249 | F |
| 11 | 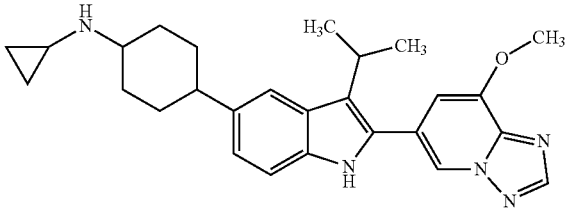 [SMILES: COc1cc(-c2[nH]c3ccc(C4CCC(NC5CC5)CC4)cc3c2C(C)C)cn2ncnc12] | 443.6 | 444.1 | 1.907 | E |
| 12 | 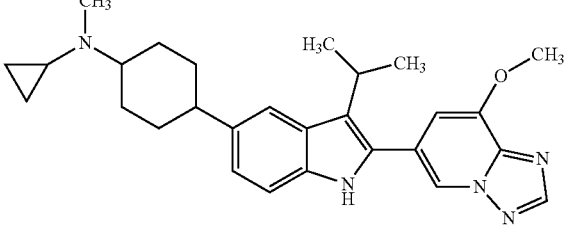 | 457.6 | 458.1 | 2.138 | P |
| 13 | 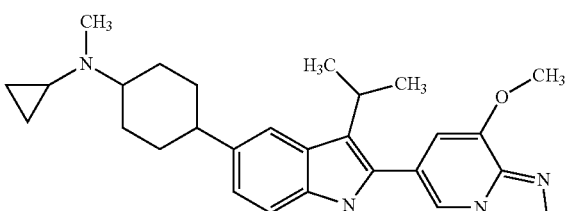 | 457.6 | 458.1 | 2.365 | P |
| 14 | 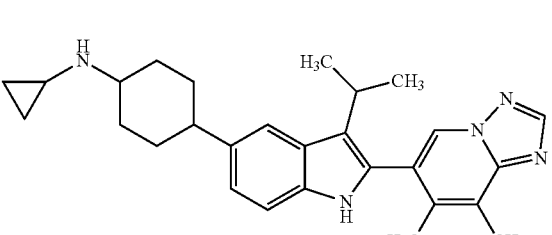 | 441.6 | 442.3 | 1.78 | P |

TABLE 3-continued
| Ex. No. | Structure | Mol Wt. | LCMS MH+ | Ret Time (min) | HPLC Method |
|---|---|---|---|---|---|
| 15 | 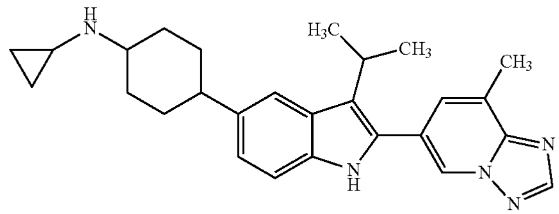 [SMILES: Cc1cc(-c2[nH]c3ccc(C4CCC(NC5CC5)CC4)cc3c2C(C)C)cn2ncnc12] | 427.6 | 428.3 | 1.72 | P |
| 16 | 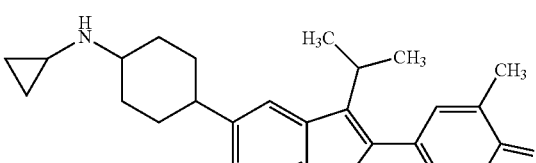 | 427.6 | 428.3 | 1.5 | P |
| 17 | 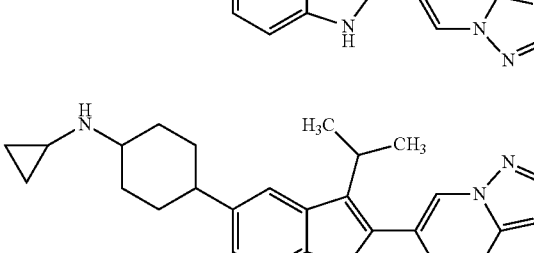 | 441.6 | 442.3 | 1.54 | P |
| 18 | 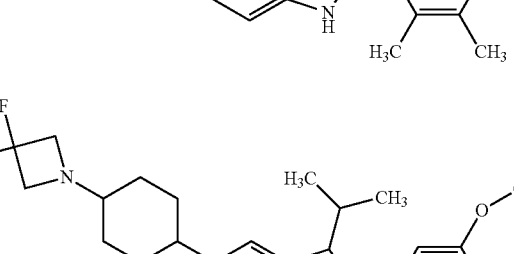 | 479.6 | 480.3 | 1.216 | F |
| 19 | 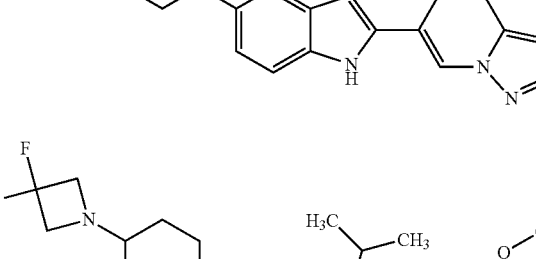 | 479.6 | 480.3 | 2.395 | E |
| 20 | 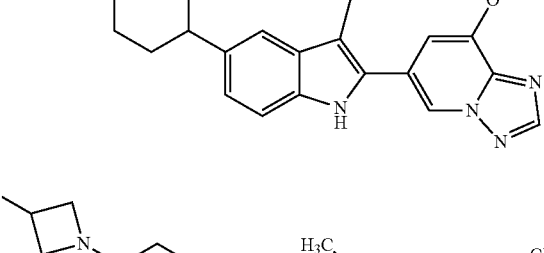 | 459.6 | 460.1 | 1.425 | P |

TABLE 3-continued
| Ex. No. | Structure | Mol Wt. | LCMS MH+ | Ret Time (min) | HPLC Method |
|---|---|---|---|---|---|
| 21 | 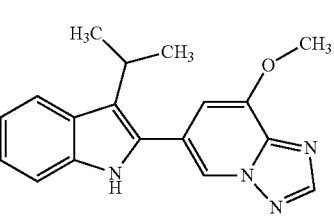 | 461.6 | 462.1 | 2.063 | P |
| 22 | 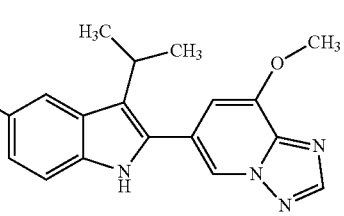 | 459.6 | 460.1 | 1.608 | P |
| 23 | 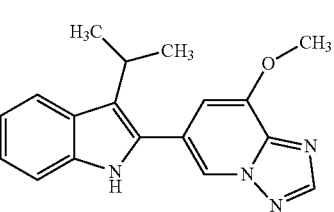 | 461.6 | 462.1 | 2.438 | P |
| 24 | 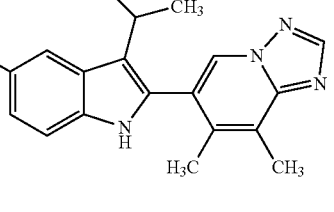 | 477.6 | 478.2 | 2.48 | E |
| 25 | 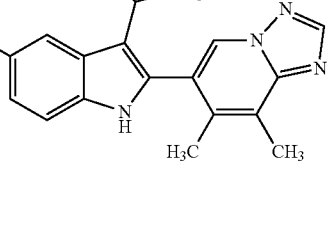 | 477.6 | 478.2 | 2.77 | E |

TABLE 3-continued
| Ex. No. | Structure | Mol Wt. | LCMS MH+ | Ret Time (min) | HPLC Method |
|---|---|---|---|---|---|
| 26 | 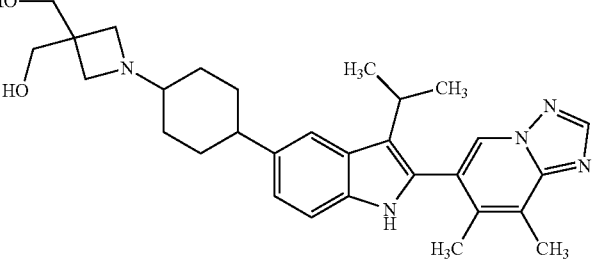 | 501.7 | 502.2 | 1.48 | E |
| 27 | 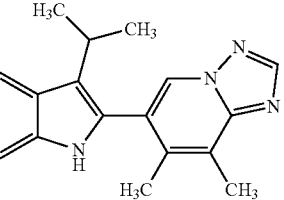 | 501.7 | 502.2 | 1.59 | E |
| 28 | 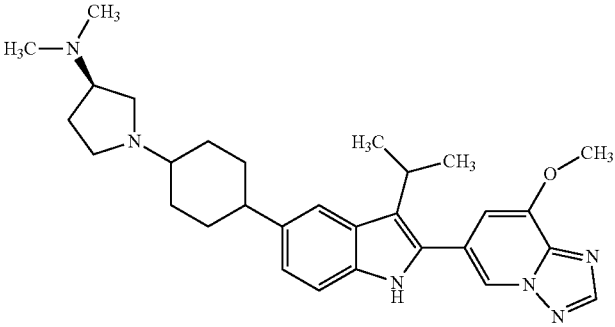 [SMILES: COc1cc(-c2[nH]c3ccc(C4CCC(N5CC[C@@H](N(C)C)C5)CC4)cc3c2C(C)C)cn2ncnc12] | 500.7 | 501.3 | 1.211 | F |
| 29 | 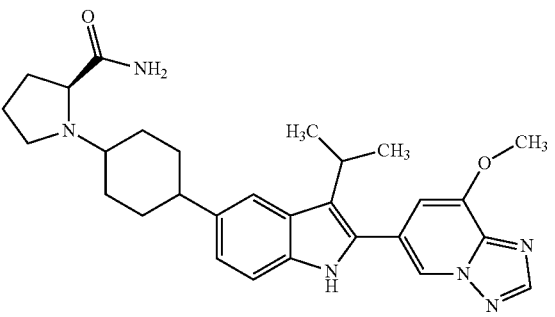 [SMILES: COc1cc(-c2[nH]c3ccc(C4CCC(N5CCC[C@H]5C(N)=O)CC4)cc3c2C(C)C)cn2ncnc12] | 500.6 | 501.3 | 1.62 | E |
| 30 | 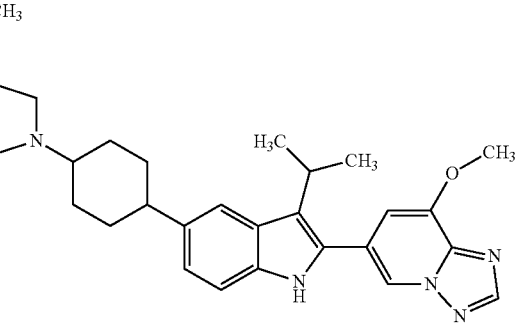 | 500.7 | 501.3 | 1.051 | F |

TABLE 3-continued

| Ex. No. | Structure | Mol Wt. | LCMS MH+ | Ret Time (min) | HPLC Method |
|---|---|---|---|---|---|
| 31 | 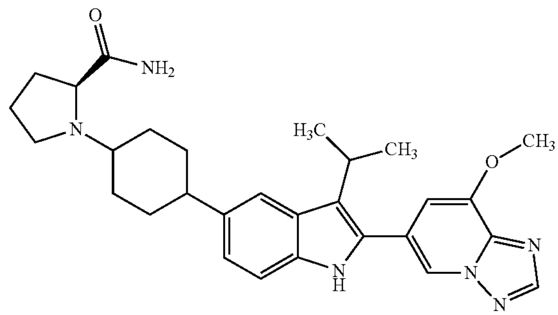 [SMILES: COc1cc(-c2[nH]c3ccc(C4CCC(N5CCC[C@H]5C(N)=O)CC4)cc3c2C(C)C)cn2ncnc12] | 500.6 | 501.2 | 1.423 | F |
| 32 | 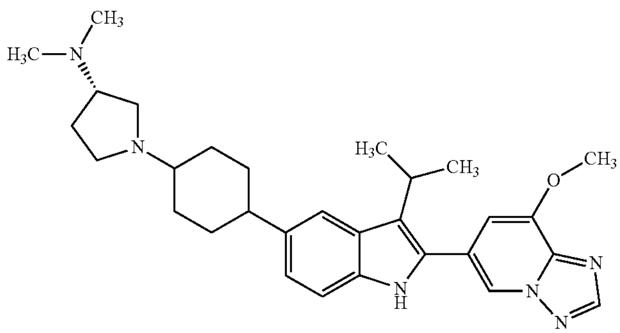 [SMILES: COc1cc(-c2[nH]c3ccc(C4CCC(N5CC[C@H](N(C)C)C5)CC4)cc3c2C(C)C)cn2ncnc12] | 500.7 | 501.3 | 1.371 | E |
| 33 | 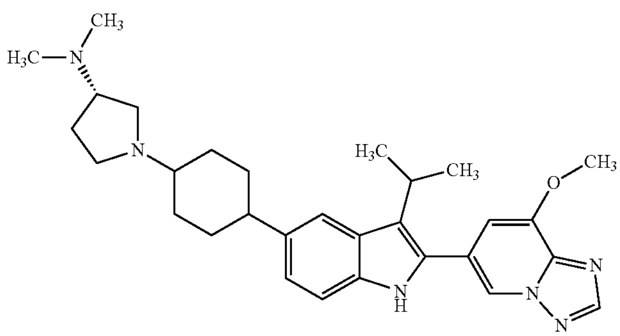 [SMILES: COc1cc(-c2[nH]c3ccc(C4CCC(N5CC[C@H](N(C)C)C5)CC4)cc3c2C(C)C)cn2ncnc12] | 500.7 | 501.2 | 1.802 | E |
| 34 | 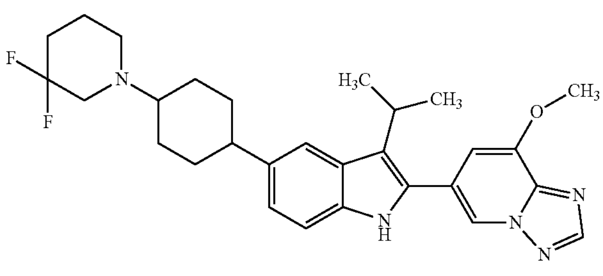 [SMILES: COc1cc(-c2[nH]c3ccc(C4CCC(N5CCCC(F)(F)C5)CC4)cc3c2C(C)C)cn2ncnc12] | 507.6 | 508.3 | 2.35 | E |
| 35 | 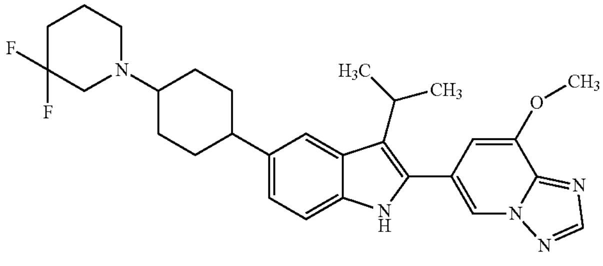 [SMILES: COc1cc(-c2[nH]c3ccc(C4CCC(N5CCCC(F)(F)C5)CC4)cc3c2C(C)C)cn2ncnc12] | 507.6 | 508.3 | 1.328 | F |

TABLE 3-continued

| Ex. No. | Structure | Mol Wt. | LCMS MH+ | Ret Time (min) | HPLC Method |
|---|---|---|---|---|---|
| 36 | 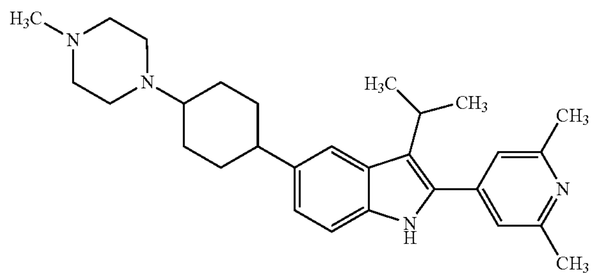 | 444.7 | 445.3 | 1.74 | E |
| 37 | 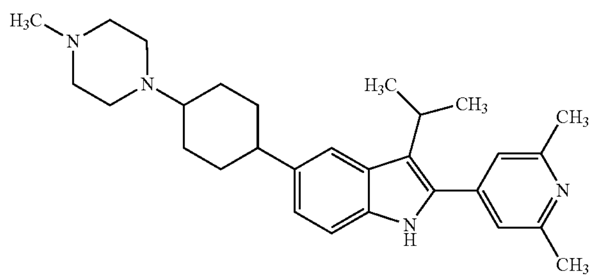 | 444.7 | 445.3 | 1.97 | E |
| 38 | 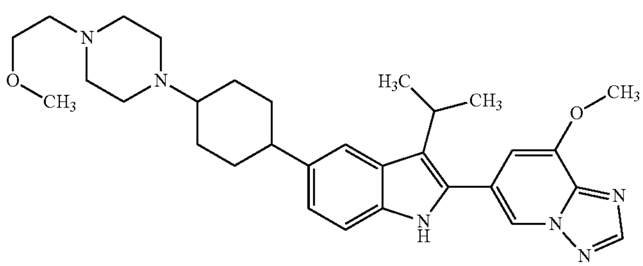 [SMILES: COCCN1CCN(C2CCC(c3ccc4[nH]c(-c5cc(OC)c6ncnn6c5)c(C(C)C)c4c3)CC2)CC1] | 530.7 | 531.3 | 1.336 | Q |
| 39 | 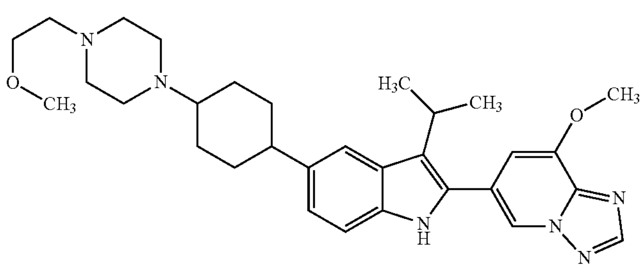 [SMILES: COCCN1CCN(C2CCC(c3ccc4[nH]c(-c5cc(OC)c6ncnn6c5)c(C(C)C)c4c3)CC2)CC1] | 530.7 | 531.3 | 1.438 | Q |
| 40 | 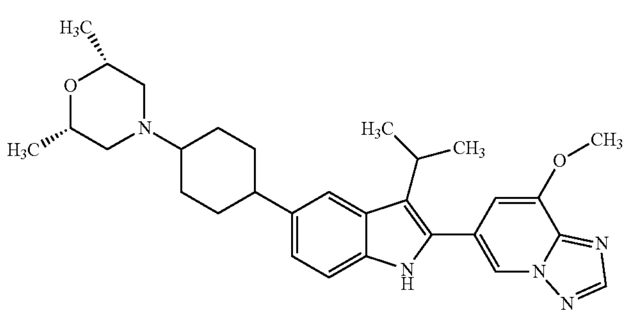 [SMILES: COc1cc(-c2[nH]c3ccc(C4CCC(N5C[C@@H](C)O[C@@H](C)C5)CC4)cc3c2C(C)C)cn2ncnc12] | 501.7 | 502.2 | 1.670 | Q |

TABLE 3-continued

| Ex. No. | Structure | Mol Wt. | LCMS MH+ | Ret Time (min) | HPLC Method |
|---|---|---|---|---|---|
| 41 | 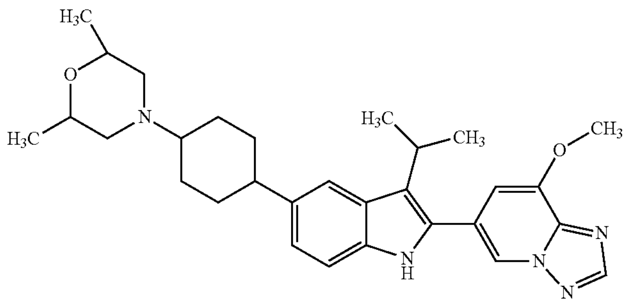 [SMILES: COc1cc(-c2[nH]c3ccc(C4CCC(N5CC(C)OC(C)C5)CC4)cc3c2C(C)C)cn2ncnc12] | 501.7 | 502.2 | 2.566 | Q |
| 42 | 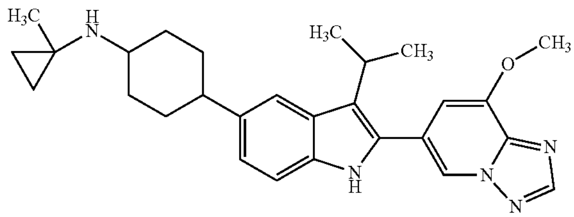 [SMILES: COc1cc(-c2[nH]c3ccc(C4CCC(NC5(C)CC5)CC4)cc3c2C(C)C)cn2ncnc12] | 457.6 | 458.2 | 1.809 | P |
| 43 | 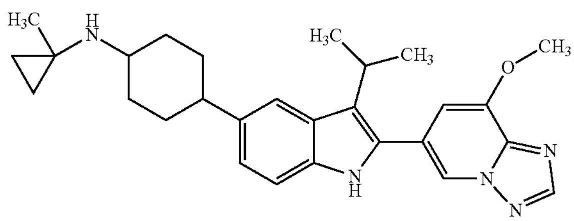 [SMILES: COc1cc(-c2[nH]c3ccc(C4CCC(NC5(C)CC5)CC4)cc3c2C(C)C)cn2ncnc12] | 457.6 | 458.3 | 1.748 | Q |
| 44 | 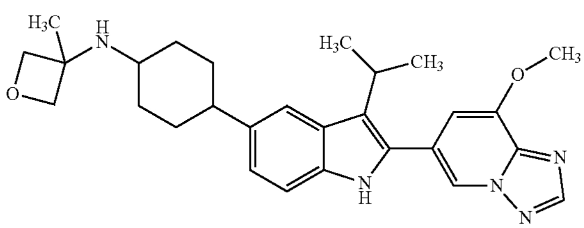 [SMILES: COc1cc(-c2[nH]c3ccc(C4CCC(NC5(C)COC5)CC4)cc3c2C(C)C)cn2ncnc12] | 473.6 | 474.2 | 1.78 | E |
| 45 | 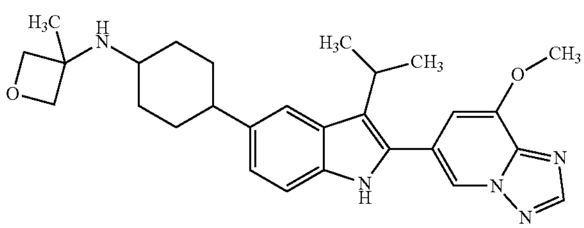 [SMILES: COc1cc(-c2[nH]c3ccc(C4CCC(NC5(C)COC5)CC4)cc3c2C(C)C)cn2ncnc12] | 473.6 | 474.2 | 2.04 | E |
| 46 | 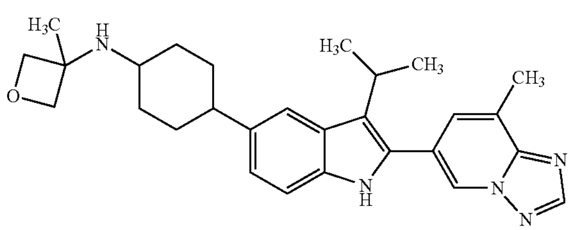 [SMILES: Cc1cc(-c2[nH]c3ccc(C4CCC(NC5(C)COC5)CC4)cc3c2C(C)C)cn2ncnc12] | 457.6 | 458.3 | 1.2 | Q |

TABLE 3-continued

| Ex. No. | Structure | Mol Wt. | LCMS MH+ | Ret Time (min) | HPLC Method |
|---|---|---|---|---|---|
| 47 | 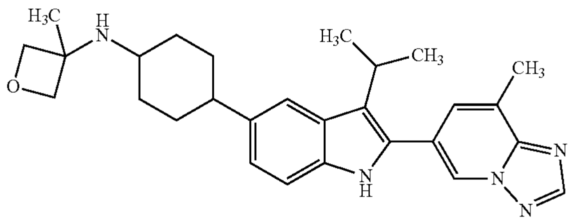 [SMILES: Cc1cc(-c2[nH]c3ccc(C4CCC(NC5(C)COC5)CC4)cc3c2C(C)C)cn2ncnc12] | 457.6 | 458.3 | 1.29 | Q |
| 48 | 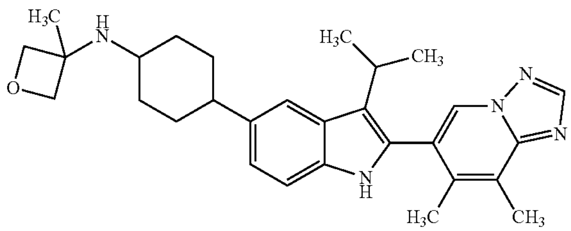 [SMILES: Cc1c(-c2[nH]c3ccc(C4CCC(NC5(C)COC5)CC4)cc3c2C(C)C)cn2ncnc2c1C] | 471.6 | 472.2 | 1.94 | P |
| 49 | 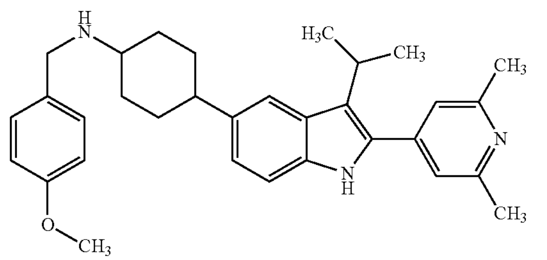 [SMILES: COc1ccc(CNC2CCC(c3ccc4[nH]c(-c5cc(C)nc(C)c5)c(C(C)C)c4c3)CC2)cc1] | 481.7 | 482.3 | 1.93 | E |
| 50 | 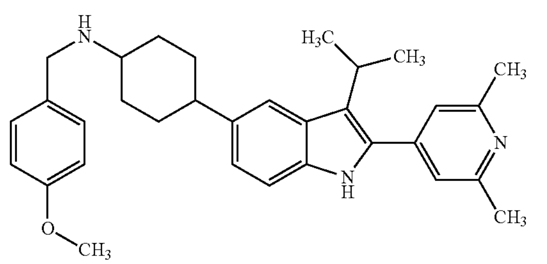 [SMILES: COc1ccc(CNC2CCC(c3ccc4[nH]c(-c5cc(C)nc(C)c5)c(C(C)C)c4c3)CC2)cc1] | 481.7 | 482.3 | 2.22 | E |
| 51 | 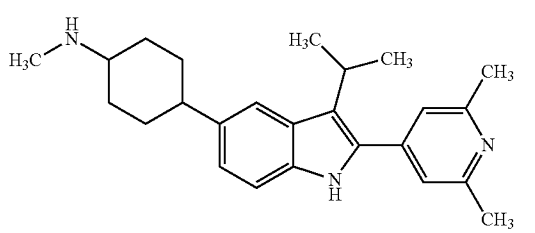 | 375.6 | 376.0 | 1.49 | E |
| 52 | 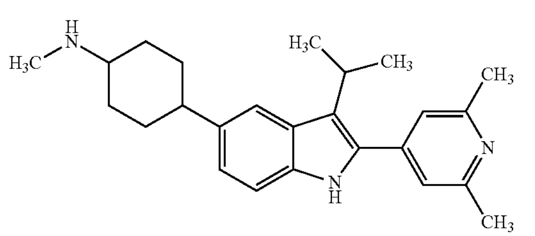 | 375.6 | 376.3 | 1.46 | E |

TABLE 3-continued

| Ex. No. | Structure | Mol Wt. | LCMS MH+ | Ret Time (min) | HPLC Method |
|---|---|---|---|---|---|
| 53 | 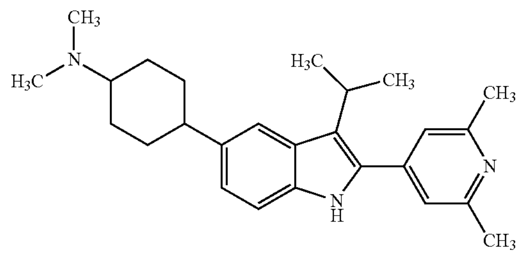 | 389.6 | 390.3 | 1.57 | F |
| 54 | 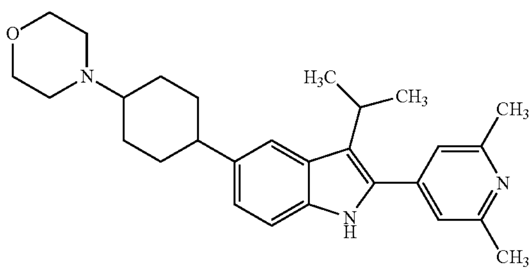 [SMILES: Cc1cc(-c2[nH]c3ccc(C4CCC(N5CCOCC5)CC4)cc3c2C(C)C)cc(C)n1] | 431.6 | 432.3 | 2.16 | E |
| 55 | 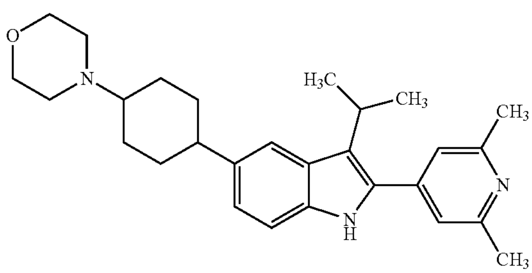 [SMILES: Cc1cc(-c2[nH]c3ccc(C4CCC(N5CCOCC5)CC4)cc3c2C(C)C)cc(C)n1] | 431.6 | 432.3 | 2.49 | E |
| 56 | 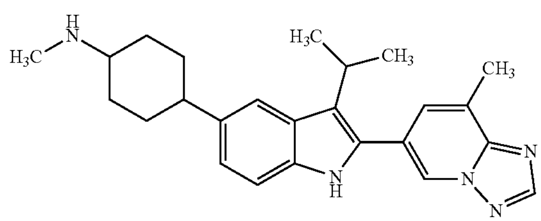 [SMILES: CNC1CCC(c2ccc3[nH]c(-c4cc(C)c5ncnn5c4)c(C(C)C)c3c2)CC1] | 401.6 | 402.3 | 1.39 | E |
| 57 | 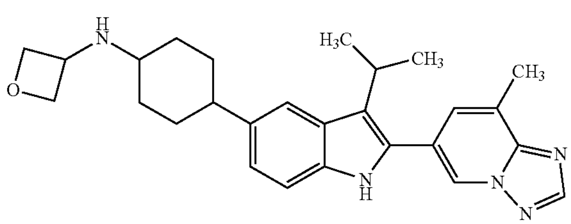 [SMILES: Cc1cc(-c2[nH]c3ccc(C4CCC(NC5COC5)CC4)cc3c2C(C)C)cn2ncnc12] | 443.6 | 444.3 | 1.98 | E |
| 58 | 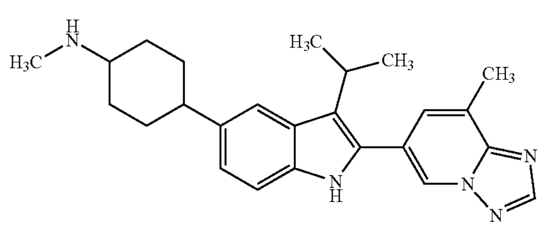 [SMILES: CNC1CCC(c2ccc3[nH]c(-c4cc(C)c5ncnn5c4)c(C(C)C)c3c2)CC1] | 401.6 | 402.3 | 1.48 | E |

TABLE 3-continued

| Ex. No. | Structure | Mol Wt. | LCMS MH+ | Ret Time (min) | HPLC Method |
|---|---|---|---|---|---|
| 59 | 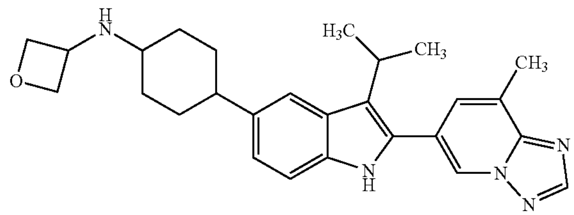 [SMILES: Cc1cc(-c2[nH]c3ccc(C4CCC(NC5COC5)CC4)cc3c2C(C)C)cn2ncnc12] | 443.59 | 444.3 | 1.78 | E |
| 60 | 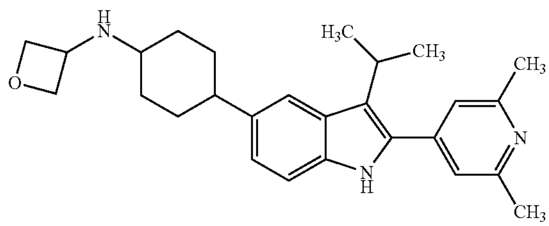 [SMILES: Cc1cc(-c2[nH]c3ccc(C4CCC(NC5COC5)CC4)cc3c2C(C)C)cc(C)n1] | 417.6 | 418.3 | 1.9 | E |
| 61 | 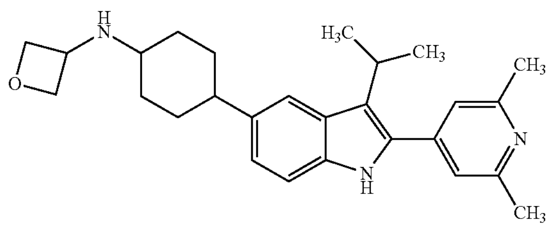 [SMILES: Cc1cc(-c2[nH]c3ccc(C4CCC(NC5COC5)CC4)cc3c2C(C)C)cc(C)n1] | 417.6 | 418.3 | 2.08 | E |
| 62 | 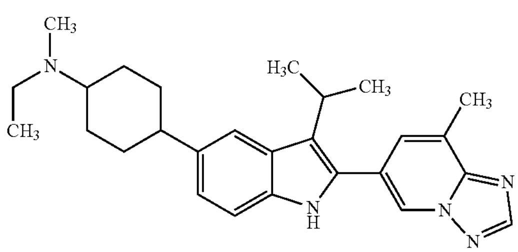 [SMILES: CCN(C)C1CCC(c2ccc3[nH]c(-c4cc(C)c5ncnn5c4)c(C(C)C)c3c2)CC1] | 429.6 | 430.1 | 1.64 | E |
| 63 | 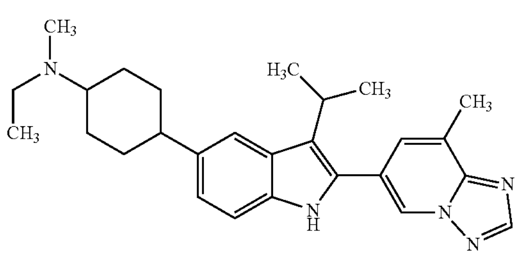 [SMILES: CCN(C)C1CCC(c2ccc3[nH]c(-c4cc(C)c5ncnn5c4)c(C(C)C)c3c2)CC1] | 429.6 | 430.2 | 1.58 | E |
| 64 | 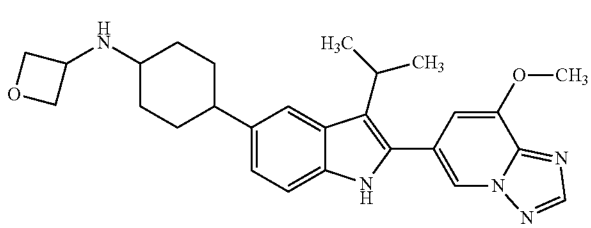 [SMILES: COc1cc(-c2[nH]c3ccc(C4CCC(NC5COC5)CC4)cc3c2C(C)C)cn2ncnc12] | 459.6 | 460.2 | 1.69 | E |

TABLE 3-continued

| Ex. No. | Structure | Mol Wt. | LCMS MH+ | Ret Time (min) | HPLC Method |
|---|---|---|---|---|---|
| 65 | 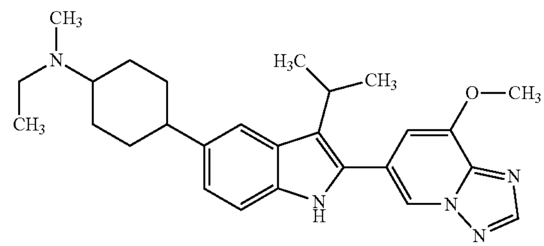 [SMILES: CCN(C)C1CCC(c2ccc3[nH]c(-c4cc(OC)c5ncnn5c4)c(C(C)C)c3c2)CC1] | 445.6 | 446.3 | 1.44 | E |
| 66 | 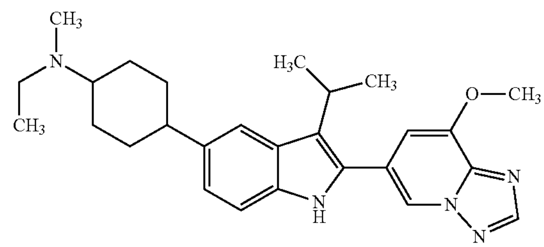 | 445.6 | 446.3 | 1.525 | E |
| 67 | 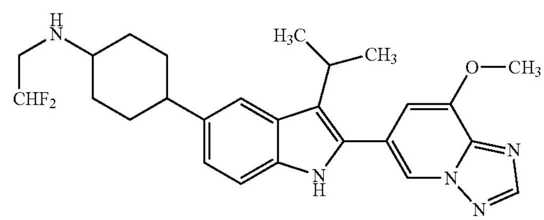 [SMILES: COc1cc(-c2[nH]c3ccc(C4CCC(NCC(F)F)CC4)cc3c2C(C)C)cn2ncnc12] | 467.6 | 468.1 | 2.14 | E |
| 68 | 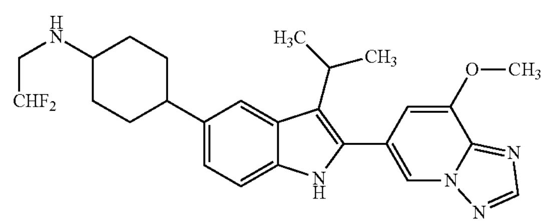 | 467.6 | 468.1 | 2.38 | E |
| 69 | 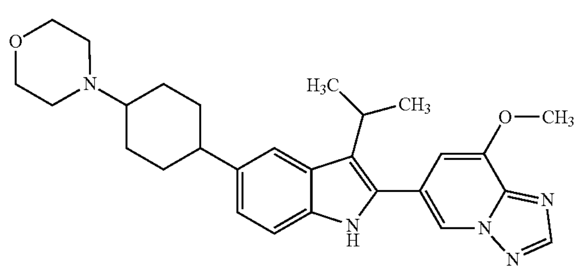 [SMILES: COc1cc(-c2[nH]c3ccc(C4CCC(N5CCOCC5)CC4)cc3c2C(C)C)cn2ncnc12] | 473.6 | 474.2 | 1.382 | F |
| 70 | 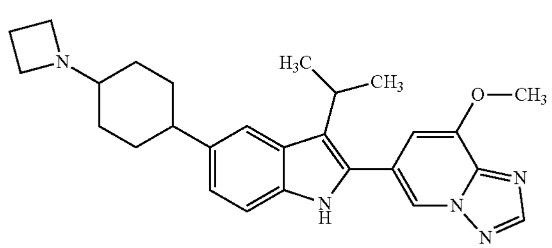 [SMILES: COc1cc(-c2[nH]c3ccc(C4CCC(N5CCC5)CC4)cc3c2C(C)C)cn2ncnc12] | 443.6 | 444.2 | 1.396 | F |

TABLE 3-continued

| Ex. No. | Structure | Mol Wt. | LCMS MH+ | Ret Time (min) | HPLC Method |
|---|---|---|---|---|---|
| 71 | 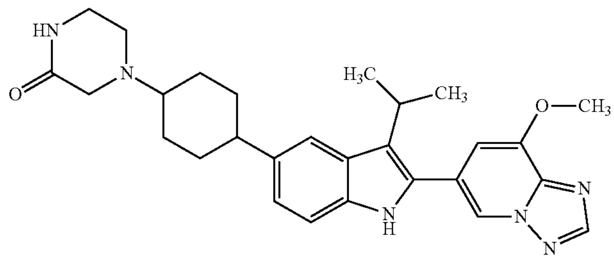 [SMILES: COc1cc(-c2[nH]c3ccc(C4CCC(N5CCNC(=O)C5)CC4)cc3c2C(C)C)cn2ncnc12] | 486.6 | 487.3 | 1.068 | F |
| 72 | 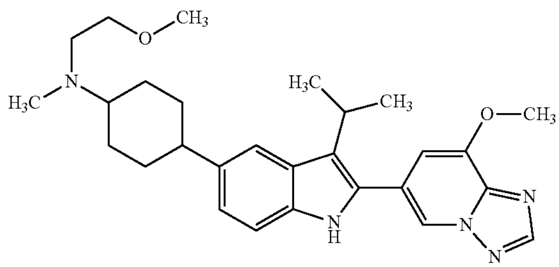 [SMILES: COCCN(C)C1CCC(c2ccc3[nH]c(-c4cc(OC)c5ncnn5c4)c(C(C)C)c3c2)CC1] | 475.6 | 476.3 | 1.346 | E |
| 73 | 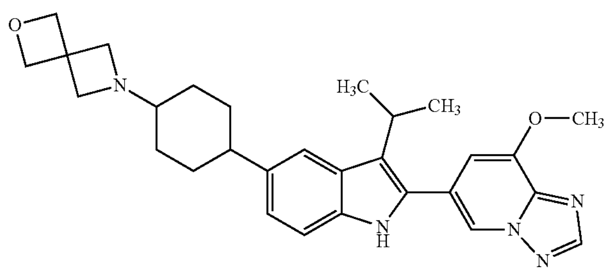 [SMILES: COc1cc(-c2[nH]c3ccc(C4CCC(N5CC6(COC6)C5)CC4)cc3c2C(C)C)cn2ncnc12] | 485.6 | 486.3 | 1.34 | E |
| 74 | 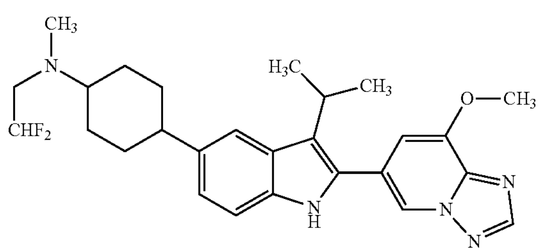 [SMILES: COc1cc(-c2[nH]c3ccc(C4CCC(N(C)CC(F)F)CC4)cc3c2C(C)C)cn2ncnc12] | 481.6 | 482.3 | 2.253 | E |
| 75 | 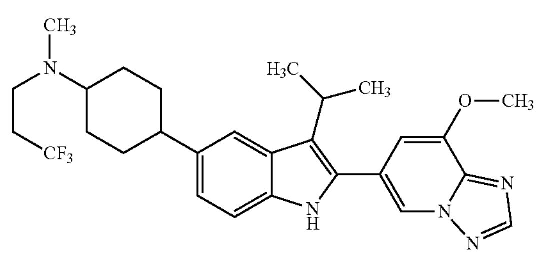 [SMILES: COc1cc(-c2[nH]c3ccc(C4CCC(N(C)CCC(F)(F)F)CC4)cc3c2C(C)C)cn2ncnc12] | 513.6 | 514.3 | 1.391 | F |
| 76 | 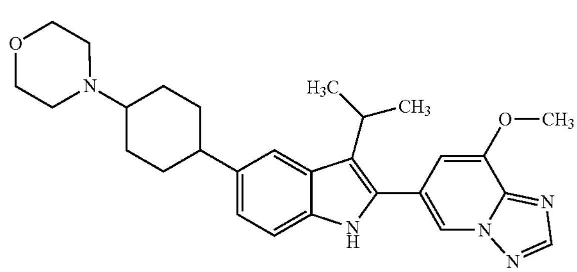 [SMILES: COc1cc(-c2[nH]c3ccc(C4CCC(N5CCOCC5)CC4)cc3c2C(C)C)cn2ncnc12] | 473.6 | 474.2 | 1.433 | F |

TABLE 3-continued

| Ex. No. | Structure | Mol Wt. | LCMS MH+ | Ret Time (min) | HPLC Method |
|---|---|---|---|---|---|
| 77 | 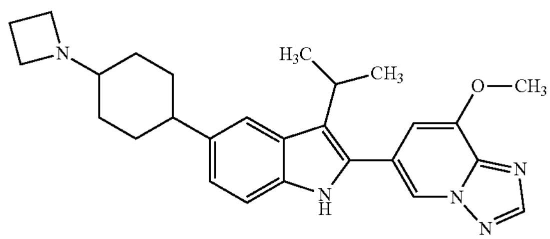 [SMILES: COc1cc(-c2[nH]c3ccc(C4CCC(N5CCC5)CC4)cc3c2C(C)C)cn2ncnc12] | 443.6 | 444.3 | 1.309 | E |
| 78 | 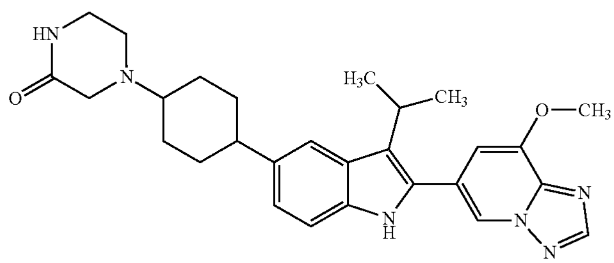 [SMILES: COc1cc(-c2[nH]c3ccc(C4CCC(N5CCNC(=O)C5)CC4)cc3c2C(C)C)cn2ncnc12] | 486.6 | 487.3 | 1.686 | F |
| 79 | 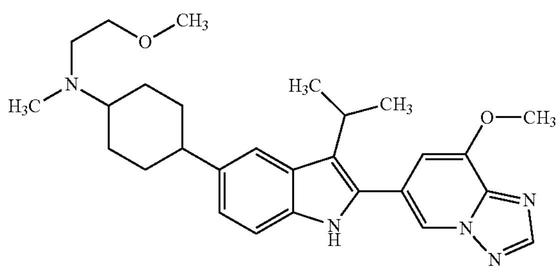 [SMILES: COCCN(C)C1CCC(c2ccc3[nH]c(-c4cc(OC)c5ncnn5c4)c(C(C)C)c3c2)CC1] | 475.6 | 476.1 | 1.736 | E |
| 80 | 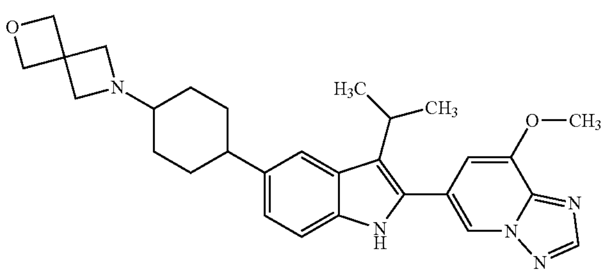 [SMILES: COc1cc(-c2[nH]c3ccc(C4CCC(N5CC6(COC6)C5)CC4)cc3c2C(C)C)cn2ncnc12] | 485.6 | 486.3 | 1.213 | F |
| 81 | 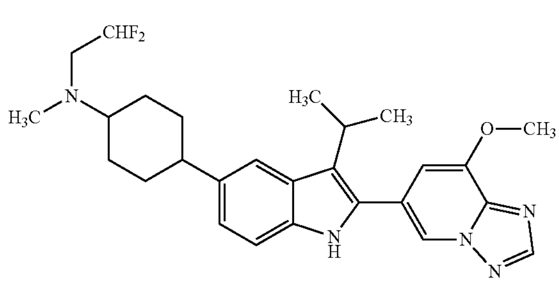 [SMILES: COc1cc(-c2[nH]c3ccc(C4CCC(N(C)CC(F)F)CC4)cc3c2C(C)C)cn2ncnc12] | 481.6 | 482.3 | 1.284 | F |

TABLE 3-continued

| Ex. No. | Structure | Mol Wt. | LCMS MH+ | Ret Time (min) | HPLC Method |
|---|---|---|---|---|---|
| 82 | 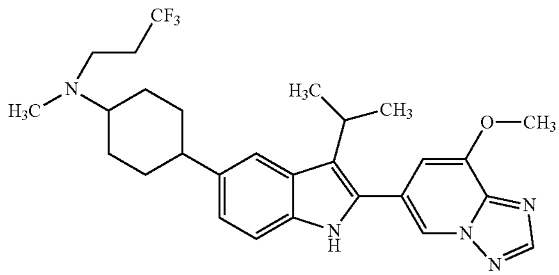 [SMILES: COc1cc(-c2[nH]c3ccc(C4CCC(N(C)CCC(F)(F)F)CC4)cc3c2C(C)C)cn2ncnc12] | 513.6 | 514.3 | 1.417 | F |
| 85 | 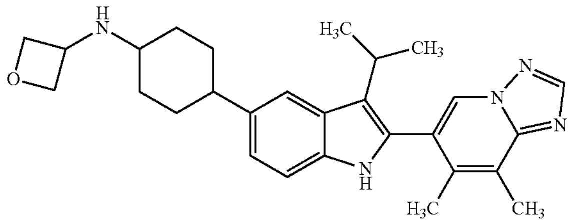 [SMILES: Cc1c(-c2[nH]c3ccc(C4CCC(NC5COC5)CC4)cc3c2C(C)C)cn2ncnc2c1C] | 457.6 | 458.2 | 1.79 | E |
| 86 | 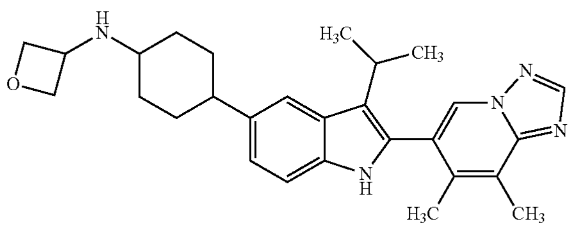 [SMILES: Cc1c(-c2[nH]c3ccc(C4CCC(NC5COC5)CC4)cc3c2C(C)C)cn2ncnc2c1C] | 457.6 | 458.3 | 2.02 | E |
| 87 | 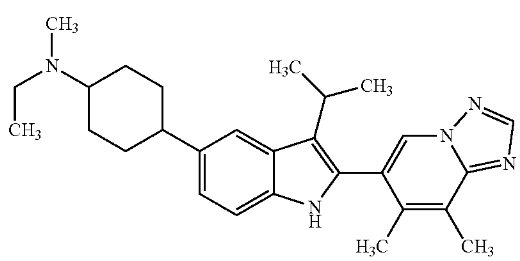 [SMILES: CCN(C)C1CCC(c2ccc3[nH]c(-c4cn5ncnc5c(C)c4C)c(C(C)C)c3c2)CC1] | 443.6 | 444.2 | 1.57 | E |
| 88 | 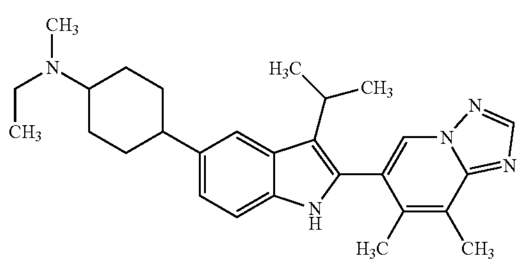 [SMILES: CCN(C)C1CCC(c2ccc3[nH]c(-c4cn5ncnc5c(C)c4C)c(C(C)C)c3c2)CC1] | 443.6 | 444.2 | 1.64 | E |
| 89 | 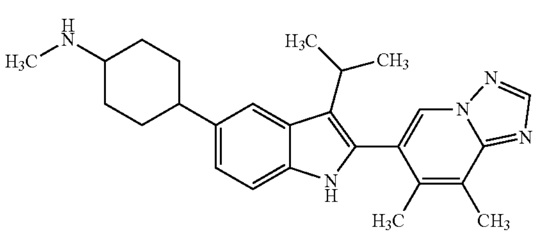 [SMILES: CNC1CCC(c2ccc3[nH]c(-c4cn5ncnc5c(C)c4C)c(C(C)C)c3c2)CC1] | 415.6 | 416.0 | 1.44 | E |

TABLE 3-continued

| Ex. No. | Structure | Mol Wt. | LCMS MH+ | Ret Time (min) | HPLC Method |
|---|---|---|---|---|---|
| 90 | 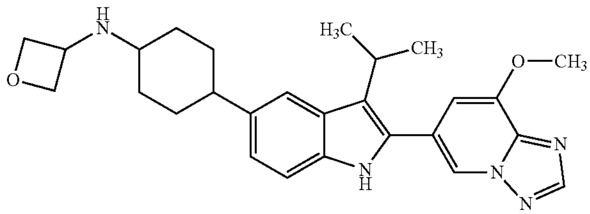 [SMILES: COc1cc(-c2[nH]c3ccc(C4CCC(NC5COC5)CC4)cc3c2C(C)C)cn2ncnc12] | 459.6 | 460.2 | 1.713 | E |
| 91 | 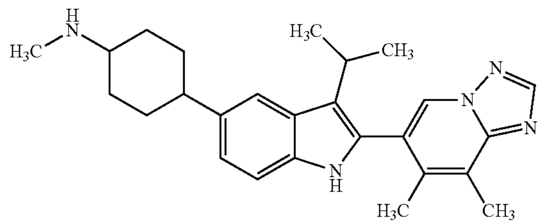 [SMILES: CNC1CCC(c2ccc3[nH]c(-c4cn5ncnc5c(C)c4C)c(C(C)C)c3c2)CC1] | 415.6 | 416.2 | 1.54 | E |
| 92 | 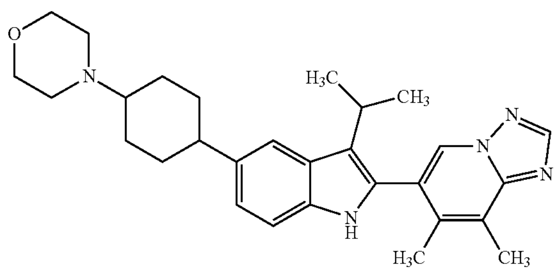 [SMILES: Cc1c(-c2[nH]c3ccc(C4CCC(N5CCOCC5)CC4)cc3c2C(C)C)cn2ncnc2c1C] | 471.6 | 472.3 | 1.72 | P |
| 93 | 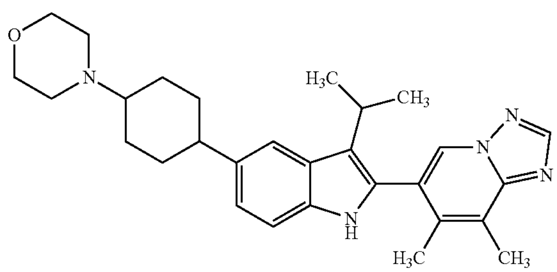 [SMILES: Cc1c(-c2[nH]c3ccc(C4CCC(N5CCOCC5)CC4)cc3c2C(C)C)cn2ncnc2c1C] | 471.6 | 472.3 | 2.13 | P |
| 94 | 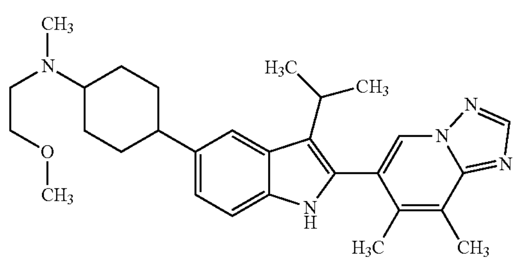 [SMILES: COCCN(C)C1CCC(c2ccc3[nH]c(-c4cn5ncnc5c(C)c4C)c(C(C)C)c3c2)CC1] | 473.7 | 474.3 | 1.45 | P |
| 95 | 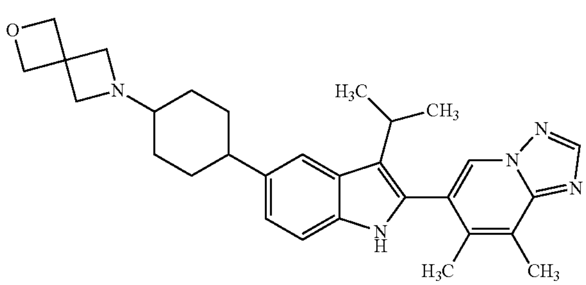 [SMILES: Cc1c(-c2[nH]c3ccc(C4CCC(N5CC6(COC6)C5)CC4)cc3c2C(C)C)cn2ncnc2c1C] | 483.7 | 484.1 | 1.93 | E |

TABLE 3-continued

| Ex. No. | Structure | Mol Wt. | LCMS MH+ | Ret Time (min) | HPLC Method |
|---|---|---|---|---|---|
| 96 | 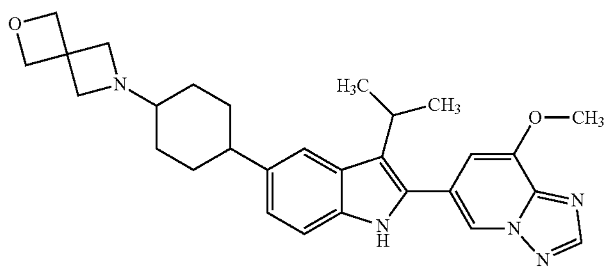 [SMILES: COc1cc(-c2[nH]c3ccc(C4CCC(N5CC6(COC6)C5)CC4)cc3c2C(C)C)cn2ncnc12] | 485.6 | 486.2 | 1.82 | P |
| 99 | 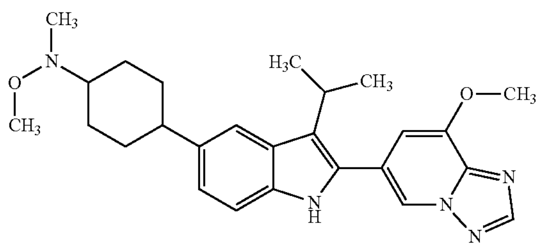 [SMILES: COc1cc(-c2[nH]c3ccc(C4CCC(N(C)OC)CC4)cc3c2C(C)C)cn2ncnc12] | 447.6 | 448.3 | 1.790 | P |
| 100 | 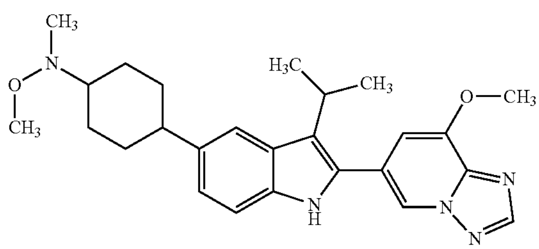 | 447.6 | 448.2 | 2.044 | Q |
| 101 | 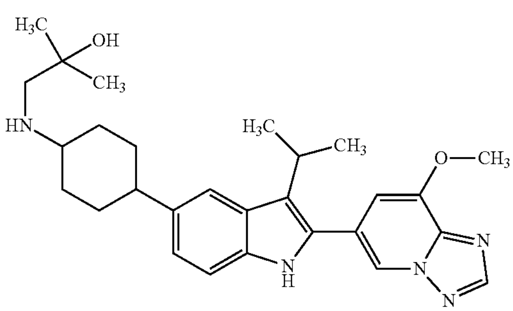 [SMILES: COc1cc(-c2[nH]c3ccc(C4CCC(NCC(C)(C)O)CC4)cc3c2C(C)C)cn2ncnc12] | 459.6 | 460.3 | 1.28 | P |
| 102 | 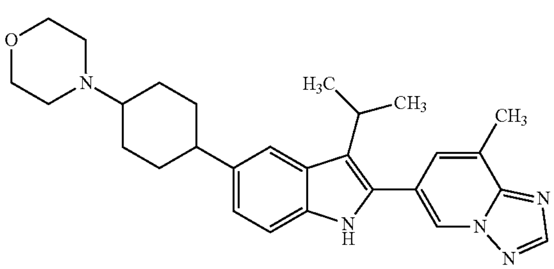 [SMILES: Cc1cc(-c2[nH]c3ccc(C4CCC(N5CCOCC5)CC4)cc3c2C(C)C)cn2ncnc12] | 457.6 | 458.3 | 1.67 | P |

TABLE 3-continued

| Ex. No. | Structure | Mol Wt. | LCMS MH+ | Ret Time (min) | HPLC Method |
|---|---|---|---|---|---|
| 103 | 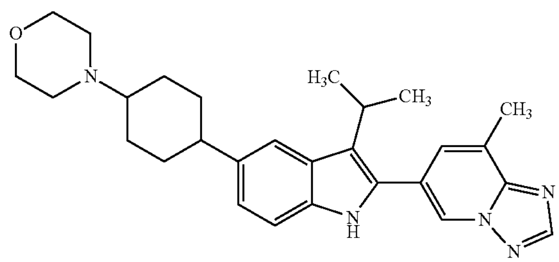 [SMILES: Cc1cc(-c2[nH]c3ccc(C4CCC(N5CCOCC5)CC4)cc3c2C(C)C)cn2ncnc12] | 457.6 | 458.3 | 2.06 | P |
| 104 | 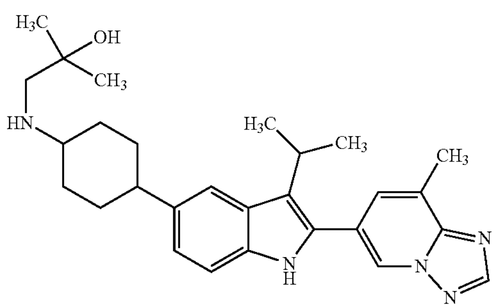 [SMILES: Cc1cc(-c2[nH]c3ccc(C4CCC(NCC(C)(C)O)CC4)cc3c2C(C)C)cn2ncnc12] | 459.6 | 460.3 | 1.45 | P |
| 105 | 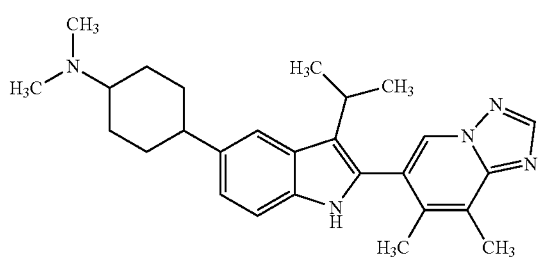 [SMILES: Cc1c(-c2[nH]c3ccc(C4CCC(N(C)C)CC4)cc3c2C(C)C)cn2ncnc2c1C] | 429.6 | 430.2 | 1.59 | P |
| 106 | 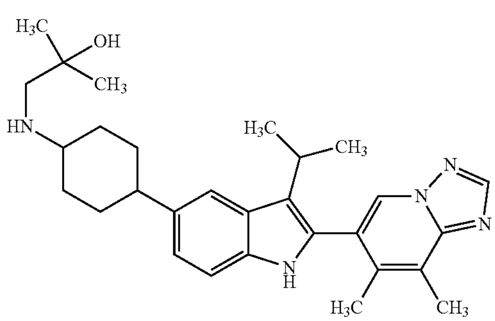 [SMILES: Cc1c(-c2[nH]c3ccc(C4CCC(NCC(C)(C)O)CC4)cc3c2C(C)C)cn2ncnc2c1C] | 473.7 | 474.2 | 1.61 | P |
| 107 | 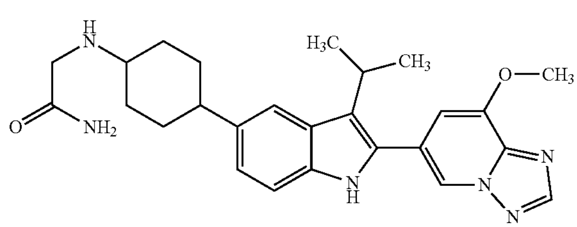 [SMILES: COc1cc(-c2[nH]c3ccc(C4CCC(NCC(N)=O)CC4)cc3c2C(C)C)cn2ncnc12] | 460.6 | 461.3 | 1.392 | Q |

TABLE 3-continued

| Ex. No. | Structure | Mol Wt. | LCMS MH+ | Ret Time (min) | HPLC Method |
|---|---|---|---|---|---|
| 108 | 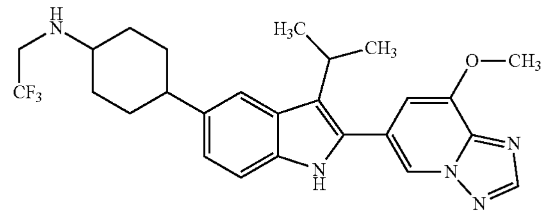 [SMILES: COc1cc(-c2[nH]c3ccc(C4CCC(NCC(F)(F)F)CC4)cc3c2C(C)C)cn2ncnc12] | 485.6 | 486.2 | 2.202 | P |
| 109 | 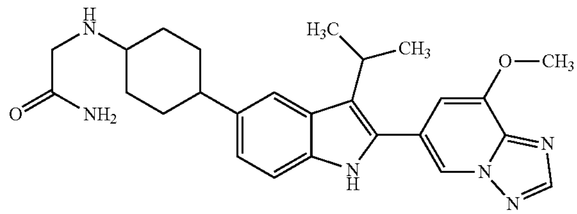 [SMILES: COc1cc(-c2[nH]c3ccc(C4CCC(NCC(N)=O)CC4)cc3c2C(C)C)cn2ncnc12] | 460.6 | 461.2 | 1.764 | P |
| 110 | 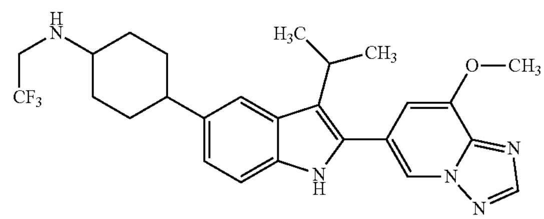 [SMILES: COc1cc(-c2[nH]c3ccc(C4CCC(NCC(F)(F)F)CC4)cc3c2C(C)C)cn2ncnc12] | 485.6 | 486.2 | 1.733 | Q |
| 111 | 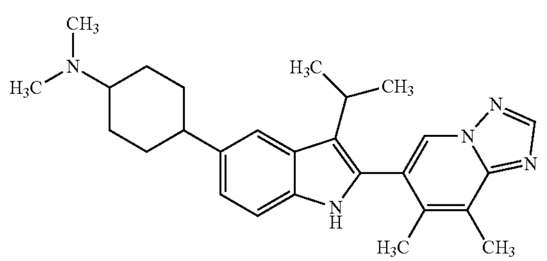 [SMILES: Cc1c(-c2[nH]c3ccc(C4CCC(N(C)C)CC4)cc3c2C(C)C)cn2ncnc2c1C] | 429.6 | 430.2 | 1.67 | P |
| 112 | 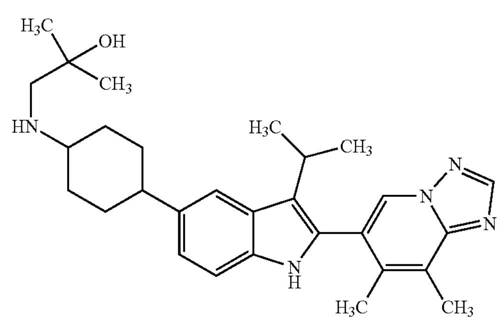 [SMILES: Cc1c(-c2[nH]c3ccc(C4CCC(NCC(C)(C)O)CC4)cc3c2C(C)C)cn2ncnc2c1C] | 473.7 | 474.2 | 1.8 | P |
| 113 | 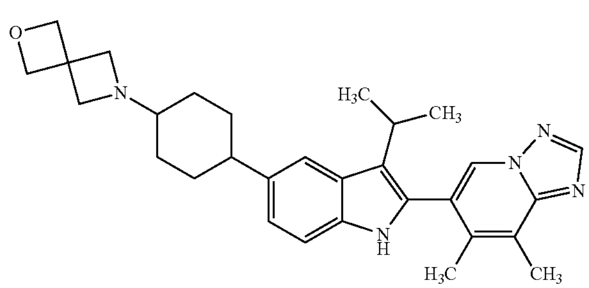 [SMILES: Cc1c(-c2[nH]c3ccc(C4CCC(N5CC6(COC6)C5)CC4)cc3c2C(C)C)cn2ncnc2c1C] | 483.7 | 484.1 | 1.72 | E |

| Ex. No. | Structure | Mol Wt. | LCMS MH+ | Ret Time (min) | HPLC Method |
|---|---|---|---|---|---|
| 114 | 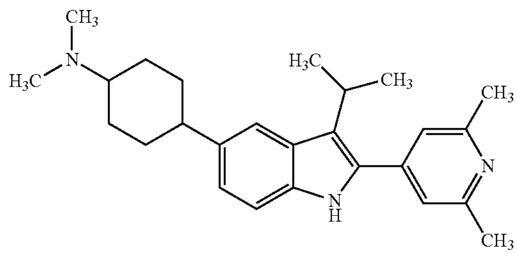 | 389.5 | 390.3 | 1.67 | E |

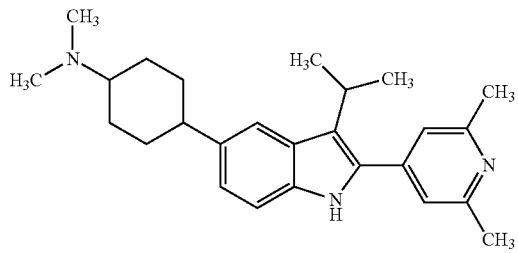

Examples 115 and 116

N-(4-(3-isopropyl-2-(8-methoxy-[1,2,4]triazolo[1,5-a]pyridin-6-yl)-1H-indol-5-yl)cyclohexyl)acetamide Example 117

N-(4-(3-isopropyl-2-(8-methoxy-[1,2,4]triazolo[1,5-a]pyridin-6-yl)-1H-indol-5-yl)cyclohexyl)methanesulfonamide (115-116)

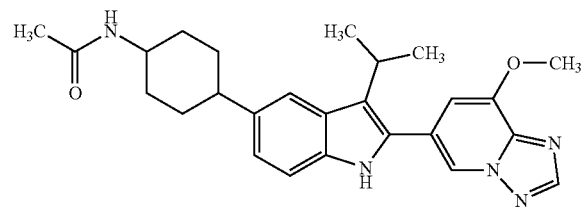

To a solution of 4-(3-isopropyl-2-(8-methoxy-[1,2,4]triazolo[1,5-a]pyridin-6-yl)-1H-indol-5-yl)cyclohexanamine (0.100 g, 0.248 mmol) and TEA (0.173 mL, 1.239 mmol) in DCM (10.0 mL), was added acetyl chloride (0.035 mL, 0.496 mmol) at 0° C., the resulting mixture was stirred at room temperature for 6 h. Concentrated the reaction mass, the residue was dissolved with excess DCM, washed with water, brine, organic layer was dried over sodium sulphate and concentrated to afford crude. The crude material was purified via preparative LC/MS using method D2 to separate both the isomers, the fractions containing the desired product were combined and dried via centrifugal evaporation:

Example 115 (Isomer 1): (13.0 mg, 12% yield) as a pale solid. LCMS retention time 1.74 min. (E) MS m/z: 446.1 (M+H); $^1$H NMR (400 MHz, METHANOL-d$_4$) δ ppm 8.44 (d, J=18.8 Hz, 2H), 7.61 (s, 1H), 7.34 (d, J=8.3 Hz, 1H), 7.22 (s, 1H), 7.07 (d, J=8.6 Hz, 1H), 4.14 (s, 3H), 3.80 (s, 2H), 3.42-3.35 (m, 1H), 2.71-2.54 (m, 1H), 2.11-2.00 (m, 7H), 1.70 (d, J=14.7 Hz, 2H), 1.53 (d, J=7.1 Hz, 62H), 1.45 (d, J=12.7 Hz, 2H), 1.28-1.25 (m, 1H).

Example 116 (Isomer 2): (3.0 mg, 3% yield) as a pale solid. LCMS retention time 1.80 min. (E) MS m/z: 446.1 (M+H); $^1$H NMR (400 MHz, METHANOL-d$_4$) δ ppm 8.44 (d, J=18.8 Hz, 2H), 7.67 (s, 1H), 7.35 (d, J=8.6 Hz, 1H), 7.23 (s, 1H), 7.13 (d, J=8.6 Hz, 1H), 4.18-4.04 (m, 4H), 3.80 (s, 1H), 3.43-3.36 (m, 2H), 2.69 (br. s., 1H), 2.05-2.02 (m, 3H), 1.98-1.88 (m, 4H), 1.86-1.74 (m, 4H), 1.54 (d, J=6.8 Hz, 6H), 1.34-1.23 (m, 2H).

(117)

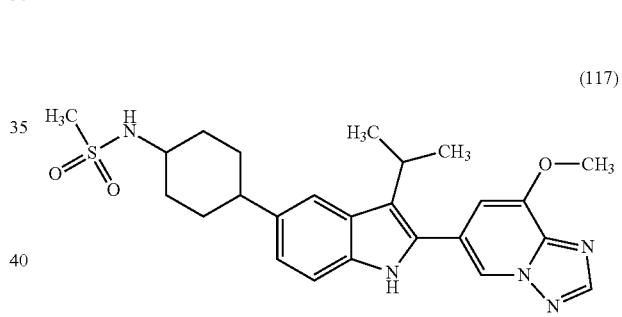

To a solution of 4-(3-isopropyl-2-(8-methoxy-[1,2,4]triazolo[1,5-a]pyridin-6-yl)-1H-indol-5-yl)cyclohexanamine (0.100 g, 0.248 mmol), TEA (0.173 mL, 1.239 mmol) in DCM (10.0 mL), was added methanesulfonyl chloride (0.039 mL, 0.496 mmol) at 0° C., then stirred at room temperature for 6 h. Concentrated the reaction mass, the residue was dissolved with excess DCM, washed with water, brine, organic layer was dried over sodium sulphate and concentrated to afford crude. The crude material was purified via preparative LC/MS using method D2, the fractions containing the desired product were combined and dried via centrifugal evaporation to afford N-(4-(3-isopropyl-2-(8-methoxy-[1,2,4]triazolo[1,5-a]pyridin-6-yl)-1H-indol-5-yl)cyclohexyl) methanesulfonamide (16.0 mg, 14% yield). LCMS retention time 1.83 min. (E) MS m/z: 482.1 (M+H); $^1$H NMR (400 MHz, METHANOL-d$_4$) δ ppm 8.47 (d, J=18.6 Hz, 1H), 7.64 (s, 1H), 7.36 (d, J=8.3 Hz, 2H), 7.25 (s, 1H), 7.10 (d, J=8.6 Hz, 1H), 4.20-4.09 (m, 3H), 3.83 (s, 2H), 3.46-3.37 (m, 2H), 3.08-2.98 (m, 3H), 2.64 (t, J=12.1 Hz, 2H), 2.21 (d, J=10.3 Hz, 2H), 2.10-1.96 (m, 2H), 1.80-1.66 (m, 2H), 1.60-1.48 (m, 8H), 1.33 (s, 2H).

Example 118

3,3,3-trifluoro-N-(4-(3-isopropyl-2-(8-methoxy-[1,2,4]triazolo[1,5-a]pyridin-6-yl)-1H-indol-5-yl)cyclohexyl)propanamide

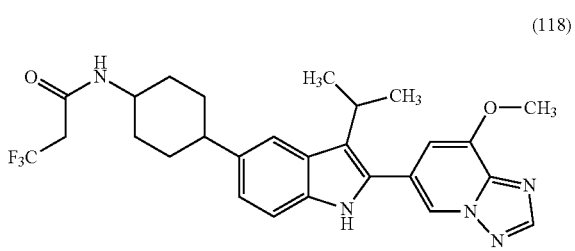 [SMILES: COc1cc(-c2[nH]c3ccc(C4CCC(NC(=O)CC(F)(F)F)CC4)cc3c2C(C)C)cn2ncnc12]

(118)

To a solution of 4-(3-isopropyl-2-(8-methoxy-[1,2,4]triazolo[1,5-a]pyridin-6-yl)-1H-indol-5-yl)cyclohexanamine (0.100 g, 0.248 mmol), 3,3,3-trifluoropropanoic acid (0.048 g, 0.372 mmol) and TEA (0.173 mL, 1.239 mmol) in DMF (5.0 mL), was added HATU (0.094 g, 0.248 mmol) at 0° C., the resulting mixture was stirred at room temperature for 16 h. The reaction mass was purified via preparative LC/MS using method D2, the fractions containing the desired product were combined and dried via centrifugal evaporation to afford 3,3,3-trifluoro-N-(4-(3-isopropyl-2-(8-methoxy-[1,2,4]triazolo[1,5-a]pyridin-6-yl)-1H-indol-5-yl)cyclohexyl)propanamide (15.0 mg, 13% yield) as a pale solid. LCMS retention time 2.04 min. (E) MS m/z: 514.1 (M+H); $^1$H NMR (400 MHz, METHANOL-$d_4$) δ ppm 9.46-9.27 (m, 1H), 8.59-8.31 (m, 2H), 7.82 (d, J=4.9 Hz, 1H), 7.61 (s, 1H), 7.45 (s, 1H), 7.33 (d, J=8.6 Hz, 1H), 7.22 (s, 1H), 7.12-6.99 (m, 1H), 4.26-4.04 (m, 4H), 3.89-3.68 (m, 2H), 3.44-3.35 (m, 1H), 3.16 (q, J=10.7 Hz, 2H), 2.84-2.59 (m, 1H), 2.41-2.35 (m, 1H), 2.10-1.93 (m, 5H), 1.77-1.65 (m, 1H), 1.57-1.41 (m, 6H), 1.33-1.23 (m, 2H), 1.05-0.77 (m, 2H), 0.56-0.30 (m, 1H).

The examples in Table 4 were prepared according to the general procedure used to prepare Example 118.

TABLE 4

| Ex. No. | Structure | Mol Wt. | LCMS MH+ | Ret Time (min) | HPLC Method |
|---|---|---|---|---|---|
| 119 | 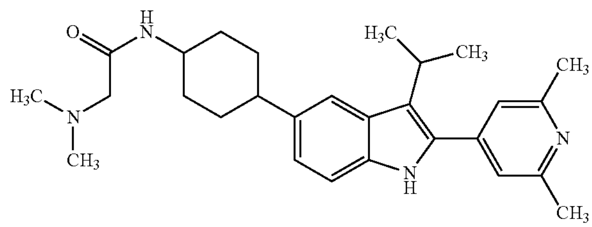 | 446.6 | 447.3 | 2.02 | E |
| 120 | 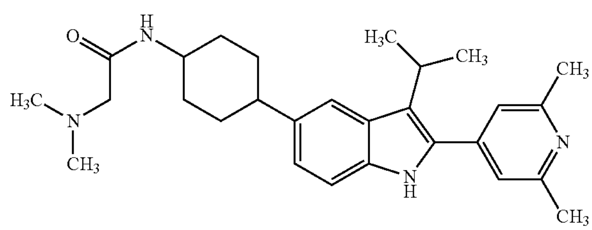 | 446.6 | 447.3 | 2.01 | E |
| 121 | 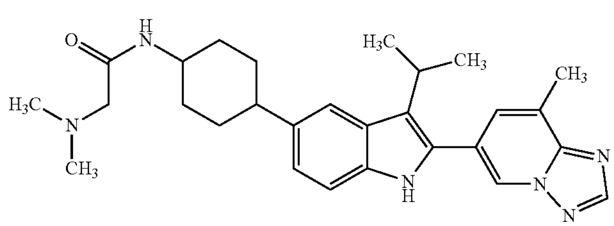 [SMILES: Cc1cc(-c2[nH]c3ccc(C4CCC(NC(=O)CN(C)C)CC4)cc3c2C(C)C)cn2ncnc12] | 472.6 | 473.3 | 1.93 | E |
| 122 | 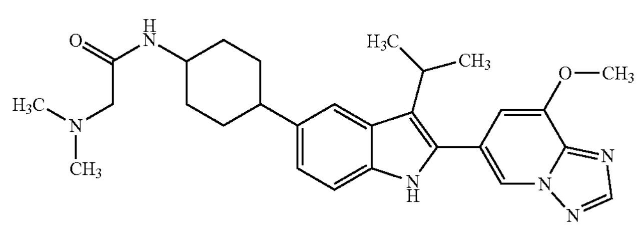 [SMILES: COc1cc(-c2[nH]c3ccc(C4CCC(NC(=O)CN(C)C)CC4)cc3c2C(C)C)cn2ncnc12] | 488.6 | | 6.041 | I |

TABLE 4-continued
| Ex. No. | Structure | Mol Wt. | LCMS MH+ | Ret Time (min) | HPLC Method |
|---|---|---|---|---|---|
| 123 | 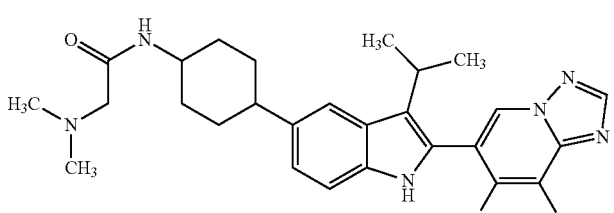 | 486.7 | 487.2 | 2.06 | P |
| 124 | 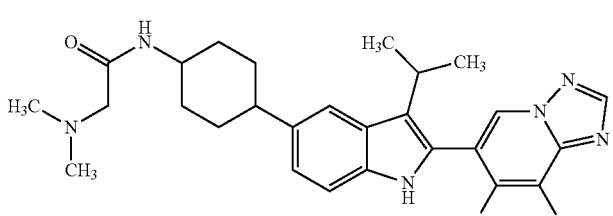 | 486.7 | 487.2 | 2.04 | P |
| 125 | 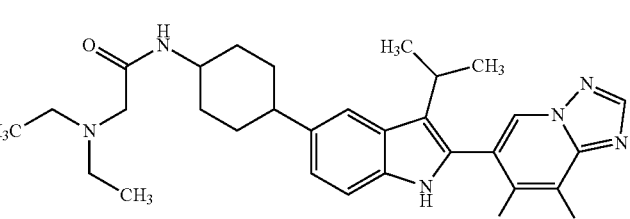 | 514.7 | 515.2 | 2.29 | P |
| 126 | 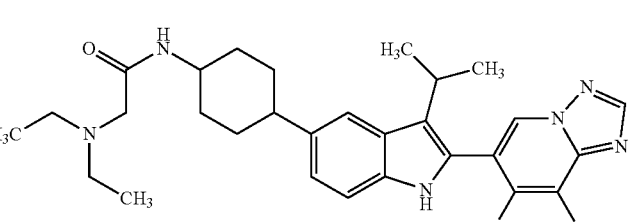 | 514.7 | 515.2 | 2.37 | P |
| 127 | 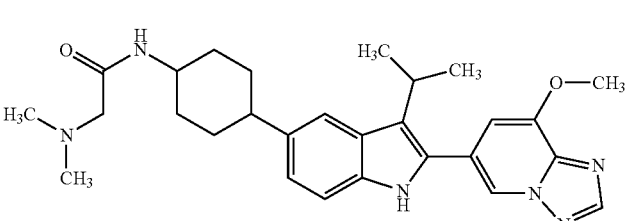 | 488.6 | 489.3 | 6.36 | I |

Example 128

N-(4-(2-(7,8-dimethyl-[1,2,4]triazolo[1,5-a]pyridin-6-yl)-3-isopropyl-1H-indol-5-yl) cyclohexyl)-2-(methylamino)acetamide

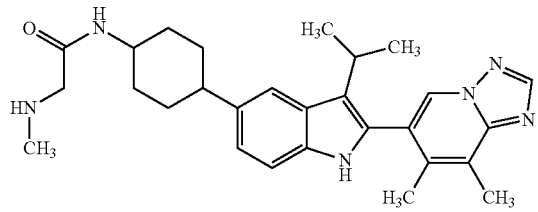

(128)

Intermediate 128A: tert-butyl (2-((4-(2-(7,8-dimethyl-[1,2,4]triazolo[1,5-a]pyridin-6-yl)-3-isopropyl-1H-indol-5-yl)cyclohexyl)amino)-2-oxoethyl)(methyl)carbamate

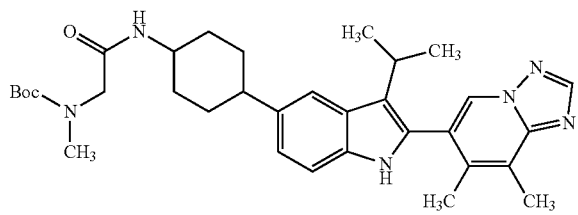 [SMILES: Cc1c(-c2[nH]c3ccc(C4CCC(NC(=O)CN(C)C)CC4)cc3c2C(C)C)cn2ncnc2c1C]

(128A)

tert-Butyl (2-((4-(2-(7,8-dimethyl-[1,2,4]triazolo[1,5-a]pyridin-6-yl)-3-isopropyl-1H-indol-5-yl)cyclohexyl)amino)-2-oxoethyl)(methyl)carbamate (0.190 g, 0.332 mmol, 89% yield) was prepared according to the general procedure described in Example 118 using 4-(2-(7,8-dimethyl-[1,2,4]triazolo[1,5-a]pyridin-6-yl)-3-isopropyl-1H-indol-5-yl)cyclohexanamine (0.150 g, 0.374 mmol) as the starting intermediate. LCMS retention time 1.35 min (L) MS m/z: 573.9 (M+H).

Example 128

To a solution of tert-butyl (2-((4-(2-(7,8-di methyl-[1,2,4]triazolo[1,5-a]pyridin-6-yl)-3-isopropyl-1H-indol-5-yl)cyclohexyl)amino)-2-oxoethyl)(methyl)carbamate (0.120 g, 0.210 mmol) in dioxane (2.0 mL) at 0° C., was added 4 M HCl in dioxane (1.048 mL, 4.19 mmol), then stirred at room temperature for 2 h. The reaction mass was concentrated and dried under vacuum to afford crude material. The crude material was purified via preparative LC/MS using method D2, fractions containing the product were combined and dried via centrifugal evaporation to afford N-(4-(2-(7,8-dimethyl-[1,2,4]triazolo[1,5-a]pyridin-6-yl)-3-isopropyl-1H-indol-5-yl)cyclohexyl)-2-(methylamino)acetamide (6.0 mg, 6%) as a pale solid. LCMS retention time 1.69 min. MS m/z: 473.1 (M+H); $^1$H NMR (400 MHz, METHANOL-$d_4$) δ ppm 8.57 (s, 1H) 8.39 (s, 1H) 7.57 (s, 1H) 7.28 (d, J=8.56 Hz, 1H) 7.06 (d, J=8.07 Hz, 1H) 3.74-3.89 (m, 1H) 3.61 (s, 2H) 3.43-3.50 (m, 1H) 3.11-3.16 (m, 1H) 2.88-3.02 (m, 1H) 2.57-2.72 (m, 1H) 2.25 (s, 3H) 1.93-2.16 (m, 6H) 1.66-1.80 (m, 2H) 1.44-1.57 (m, 2H) 1.35-1.42 (m, 6H).

The following Examples were prepared according to the general procedure used to prepare Example 128.

TABLE 5

| Ex. No. | Structure | Mol Wt. | LCMS MH+ | Ret Time (min) | HPLC Method |
|---|---|---|---|---|---|
| 129 | 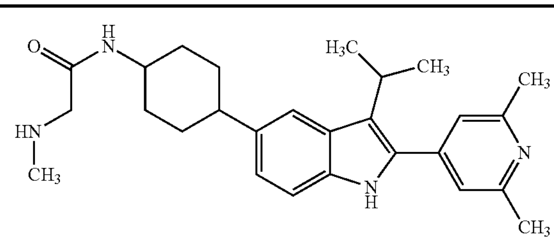 | 432.6 | 433.3 | 1.62 | E |
| 130 | 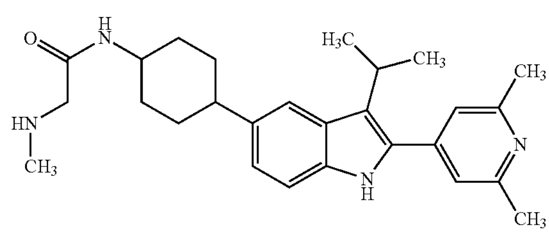 [SMILES: CNCC(=O)NC1CCC(c2ccc3[nH]c(-c4cc(C)nc(C)c4)c(C(C)C)c3c2)CC1] | 432.6 | 433.3 | 1.7 | E |

TABLE 5-continued

| Ex. No. | Structure | Mol Wt. | LCMS MH+ | Ret Time (min) | HPLC Method |
|---|---|---|---|---|---|
| 131 | 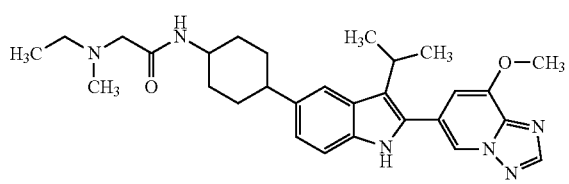 | 486.7 | 487.2 | 1.76 | P |

Example 132

2-(ethyl(methyl)amino)-N-(4-(3-isopropyl-2-(8-methoxy-[1,2,4]triazole [1,5-a]pyridin-6-yl)-1H-indol-5-yl)cyclohexyl)acetamide (132)

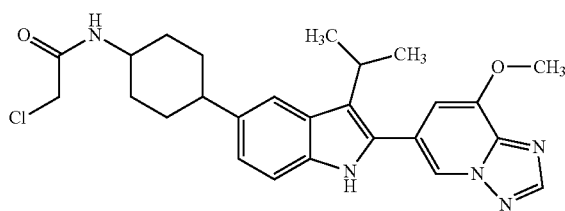

Intermediate 132A: 2-chloro-N-(4-(3-isopropyl-2-(8-methoxy-[1,2,4]triazolo[1,5-a]pyridin-6-yl)-1H-indol-5-yl)cyclohexyl)acetamide (132A)

To a solution of 4-(3-isopropyl-2-(8-methoxy-[1,2,4]triazolo[1,5-a]pyridin-6-yl)-1H-indol-5-yl)cyclohexanamine in DCM (100 mL) (1.7 g, 4.21 mmol) were added TEA (2.94 mL, 21.06 mmol) and 2-chloroacetyl chloride (0.495 mL, 5.48 mmol) at 0° C., then the mixture was stirred at room temperature for 6 h. Concentrated the reaction mass, the residue was dissolved with excess DCM, washed with water, brine, organic layer was dried over sodium sulphate and concentrated to afford 2-chloro-N-(4-(3-isopropyl-2-(8-methoxy-[1,2,4]triazolo[1,5-a]pyridin-6-yl)-1H-indol-5-yl) cyclohexyl)acetamide (1.9 g, 3.96 mmol, 94% yield) as a light brown semi solid compound. LCMS retention time 1.27 min. (L) MS m/z: 480.6 (M).

Example 132

To a solution of 2-chloro-N-(4-(3-isopropyl-2-(8-methoxy-[1,2,4]triazolo[1,5-a]pyridin-6-yl)-1H-indol-5-yl) cyclohexyl)acetamide (0.120 g, 0.250 mmol) in DMF (2.0 mL) and THF (2.0 mL) solvent mixture were added TEA (0.174 mL, 1.250 mmol) and N-methylethanamine (0.074 g, 1.250 mmol) at 0° C., then the mixture was stirred at room temperature for 16 h. Volatiles was evaporated, residue was dissolved with excess DCM, washed with water, brine, organic layer was dried over sodium sulphate and concentrated to afford crude product. The crude material was purified by prep LCMS using method D2, the fractions containing the desired product were combined and dried via centrifugal evaporation to afford 2-(ethyl(methyl)amino)-N-(4-(3-isopropyl-2-(8-methoxy-[1,2,4]triazolo[1,5-a]pyridin-6-yl)-1H-indol-5-yl)cyclohexyl) acetamide (19 mg, 14%) as a pale yellow solid. LCMS retention time 2.07 min, [G] MS m/z: 503.2 (M+H); $^1$H NMR (400 MHz, METHANOL-$d_4$) δ ppm 8.42-8.52 (m, 2H) 7.64 (s, 1H) 7.36 (d, J=8.53 Hz, 1H) 7.25 (d, J=1.51 Hz, 1H) 7.10 (dd, J=8.53, 1.51 Hz, 1H) 4.90-4.99 (m, 1H) 4.12-4.22 (m, 3H) 3.99 (br. s, 1H) 3.90 (dd, J=11.80, 3.76 Hz, 2H) 3.82 (s, 1H) 3.39-3.48 (m, 1H) 3.16-3.20 (m, 1H) 2.90-3.01 (m, 3H) 2.60-2.74 (m, 3H) 2.14 (d, J=10.04 Hz, 2H) 2.06 (d, J=11.55 Hz, 2H) 1.69-1.81 (m, 2H) 1.49-1.59 (m, 8H) 1.33-1.43 (m, 3H).

The following Examples were prepared according to the general procedure used to prepare Example 132.

TABLE 6

| Ex. No. | Structure | Mol Wt. | LCMS MH+ | Ret Time (min) | HPLC Method |
|---|---|---|---|---|---|
| 133 | 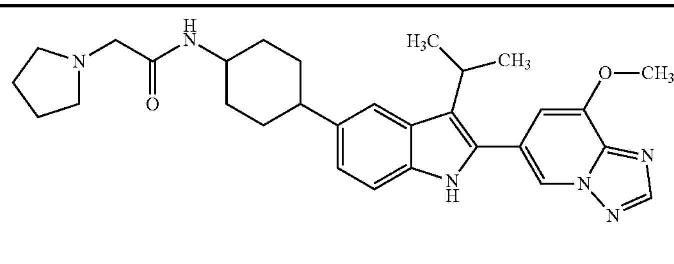 | 514.7 | 515.2 | 1.92 | P |

TABLE 6-continued
| Ex. No. | Structure | Mol Wt. | LCMS MH+ | Ret Time (min) | HPLC Method |
|---|---|---|---|---|---|
| 134 | 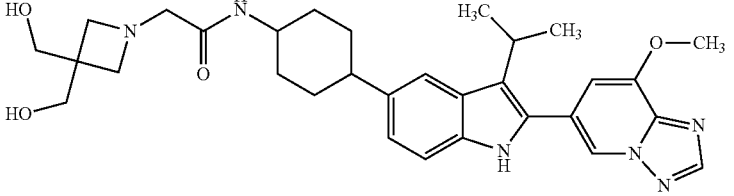 | 560.7 | 561.2 | 1.52 | P |
| 135 | 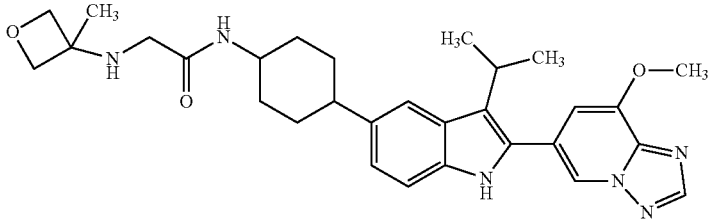 [SMILES: COc1cc(-c2[nH]c3ccc(C4CCC(NC(=O)CNC5(C)COC5)CC4)cc3c2C(C)C)cn2ncnc12] | 530.7 | 531.2 | 1.83 | P |
| 136 | 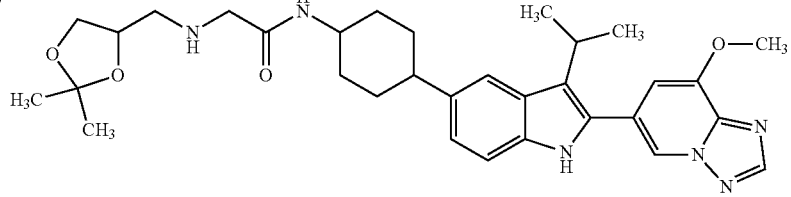 | 574.7 | 575.2 | 2.01 | P |
| 137 | 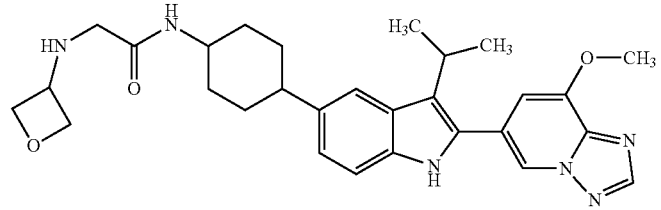 [SMILES: COc1cc(-c2[nH]c3ccc(C4CCC(NC(=O)CNC5COC5)CC4)cc3c2C(C)C)cn2ncnc12] | 516.6 | 517.1 | 1.71 | P |
| 138 | 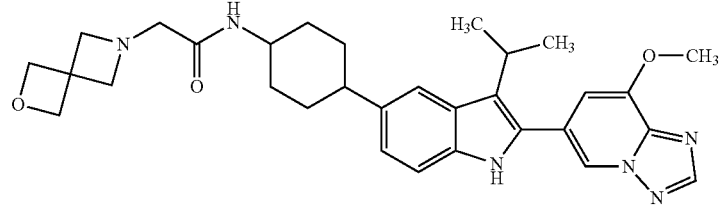 [SMILES: COc1cc(-c2[nH]c3ccc(C4CCC(NC(=O)CN5CC6(COC6)C5)CC4)cc3c2C(C)C)cn2ncnc12] | 542.7 | 543.1 | 1.78 | P |
| 139 | 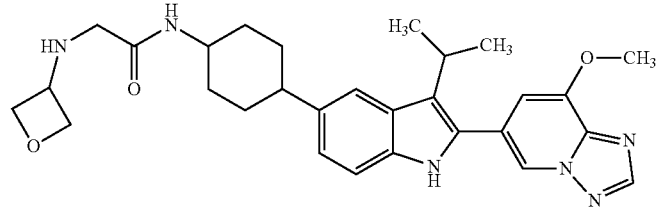 [SMILES: COc1cc(-c2[nH]c3ccc(C4CCC(NC(=O)CNC5COC5)CC4)cc3c2C(C)C)cn2ncnc12] | 516.6 | 517.2 | 1.79 | P |
| 140 | 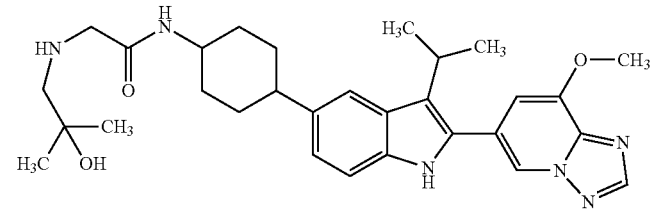 [SMILES: COc1cc(-c2[nH]c3ccc(C4CCC(NC(=O)CNCC(C)(C)O)CC4)cc3c2C(C)C)cn2ncnc12] | 532.7 | 533.3 | 1.8 | P |

TABLE 6-continued

| Ex. No. | Structure | Mol Wt. | LCMS MH+ | Ret Time (min) | HPLC Method |
|---|---|---|---|---|---|
| 141 | 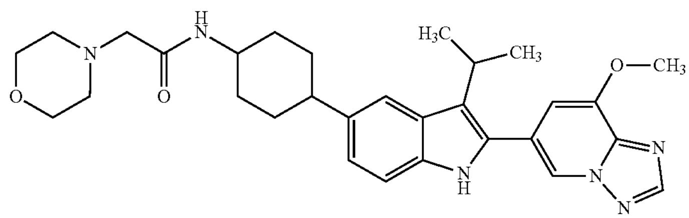 [SMILES: COc1cc(-c2[nH]c3ccc(C4CCC(NC(=O)CN5CCOCC5)CC4)cc3c2C(C)C)cn2ncnc12] | 530.7 | 531.1 | 1.38 | P |
| 142 | 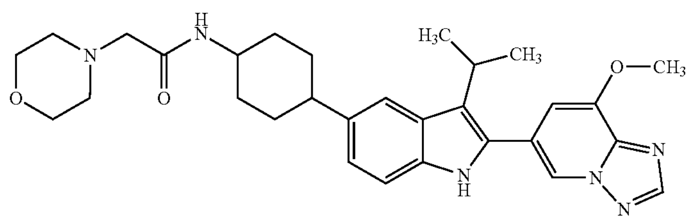 [SMILES: COc1cc(-c2[nH]c3ccc(C4CCC(NC(=O)CN5CCOCC5)CC4)cc3c2C(C)C)cn2ncnc12] | 530.7 | 531.1 | 1.68 | P |
| 143 | 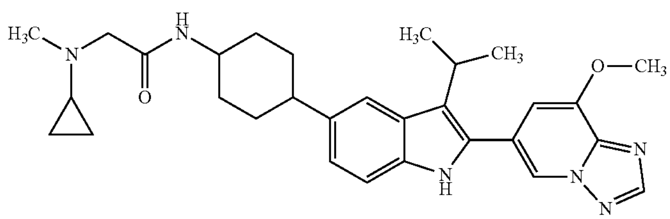 [SMILES: COc1cc(-c2[nH]c3ccc(C4CCC(NC(=O)CN(C)C5CC5)CC4)cc3c2C(C)C)cn2ncnc12] | 514.7 | 515.2 | 2.31 | P |
| 144 | 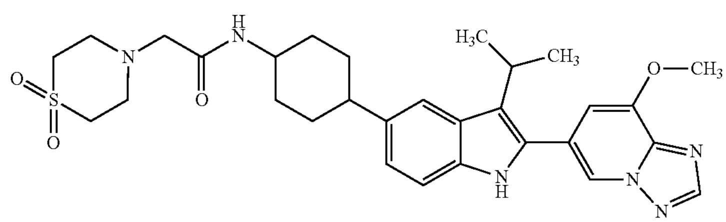 [SMILES: COc1cc(-c2[nH]c3ccc(C4CCC(NC(=O)CN5CCS(=O)(=O)CC5)CC4)cc3c2C(C)C)cn2ncnc12] | 578.7 | 579.1 | 1.77 | P |

Examples 145 and 146

4-(3-isopropyl-2-(8-methoxy-[1,2,4]triazolo[1,5-a]pyridin-6-yl)-1H-indol-5-yl)-N-methylcyclohexanamine

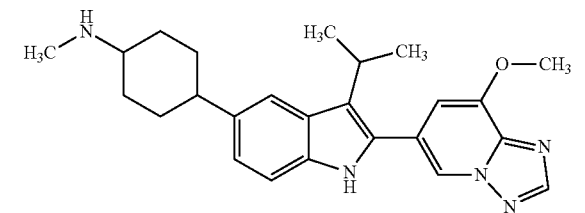

(145-146)

A solution of 4-(3-isopropyl-2-(8-methoxy-[1,2,4]triazolo[1,5-a]pyridin-6-yl)-1H-indol-5-yl) cyclohexanone (0.150 g, 0.373 mmol), methylamine (1.491 mL, 3.73 mmol) 2.5M in THF and acetic acid (2.133 µl, 0.037 mmol) in DMF (2.0 mL) THF (3.0 mL) solvent mixture was stirred at room temperature for 8 h, then was added sodium cyanoborohydride (0.035 g, 0.559 mmol) at 0° C., the resulting mixture was stirred at room temperature for 16 h. Volatiles were evaporated, the residue was dissolved with excess DCM, washed with water, brine, the organic layer was dried over sodium sulphate and concentrated to afford crude compound. The crude material was purified via preparative LC/MS using method D2, to separate both the isomers, the fractions containing the product were combined and dried via centrifugal evaporation.

Example 145 (Isomer 1): (31.0 mg, 19% yield) as a pale solid. LCMS retention time 1.63 min (E) MS m/z: 418.1 (M+H); $^1$H NMR (400 MHz, METHANOL-$d_4$) δ ppm 8.47 (d, J=16.9 Hz, 2H), 7.66 (s, 1H), 7.39 (d, J=8.3 Hz, 1H), 7.25 (s, 1H), 7.11 (d, J=8.1 Hz, 1H), 4.18 (s, 4H), 3.49-3.38 (m, 2H), 3.20 (d, J=11.0 Hz, 1H), 2.87-2.62 (m, 4H), 2.32 (br. s, 2H), 2.16 (d, J=11.7 Hz, 2H), 1.88-1.70 (m, 2H), 1.65 (br. s., 1H), 1.56 (d, J=7.1 Hz, 6H).

Example 146 (Isomer 2): (15.0 mg, 9% yield), LCMS retention time 1.73 min. (E) MS m/z: 418.1 (M+H); $^1$H NMR (400 MHz, METHANOL-$d_4$) δ pm 8.53-8.38 (m, 2H), 7.76-7.69 (m, 1H), 7.43-7.33 (m, 1H), 7.26-7.11 (m, 2H), 4.20-4.05 (m, 3H), 3.91-3.73 (m, 1H), 3.51-3.38 (m, 2H), 3.00-2.85 (m, 2H), 2.81-2.73 (m, 3H), 2.22-1.87 (m, 8H), 1.61-1.50 (m, 6H).

Example 147

2-(dimethylamino)-N-(4-(3-isopropyl-2-(8-methoxy-[1,2,4]triazolo[1,5-a]pyridin-6-yl)-1H-indol-5-yl)cyclohexyl)-N-methylacetamide

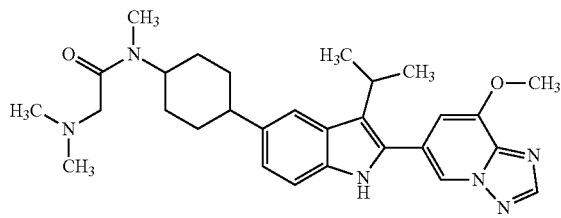

(147)

To a solution of 4-(3-isopropyl-2-(8-methoxy-[1,2,4]triazolo[1,5-a]pyridin-6-yl)-1H-indol-5-yl)-N-methylcyclohexan amine (0.150 g, 0.359 mmol) in DMF (3.0 mL) were added TEA (0.250 mL, 1.796 mmol), 2-(dimethylamino) acetic acid (0.056 g, 0.539 mmol) and HATU (0.137 g, 0.359 mmol at room temperature, then the mixture was stirred at same temperature for 16 h. The reaction mass was purified via preparative LC/MS using method D2 to separate both the isomers. The fractions containing the desired product were combined and dried via centrifugal evaporation to afford 1,2-(dimethylamino)-N-(4-(3-isopropyl-2-(8-methoxy-[1,2,4]triazolo[1,5-a]pyridin-6-yl)-1H-indol-5-yl)cyclohexyl)-N-methylacetamide (21 mg, 11% yield) as a pale solid. LCMS retention time 1.76 min. MS m/z: 503.2 (M+H); $^1$H NMR (400 MHz, METHANOL-$d_4$) δ ppm 8.38-8.53 (m, 2H) 7.82 (s, 1H) 7.63 (d, J=7.09 Hz, 1H) 7.30-7.43 (m, 1H) 7.22 (s, 2H) 7.08 (d, J=8.31 Hz, 1H) 4.52 (d, J=10.76 Hz, 1H) 4.32-4.39 (m, 1H) 4.24 (s, 1H) 4.09-4.19 (m, 4H) 3.58 (d, J=4.40 Hz, 1H) 3.34-3.47 (m, 2H) 3.11-3.26 (m, 1H) 2.91-3.03 (m, 9H) 2.72-2.80 (m, 1H) 2.65 (d, J=14.18 Hz, 1H) 2.41-2.54 (m, 1H) 2.05 (d, J=12.96 Hz, 3H) 1.91 (br. s., 2H) 1.74-1.84 (m, 3H) 1.47-1.59 (m, 7H).

The following Examples were prepared according to the general procedure used to prepare Example 147.

TABLE 7

| Ex. No. | Structure | Mol Wt. | LCMS MH+ | Ret Time (min) | HPLC Method |
|---|---|---|---|---|---|
| 148 | 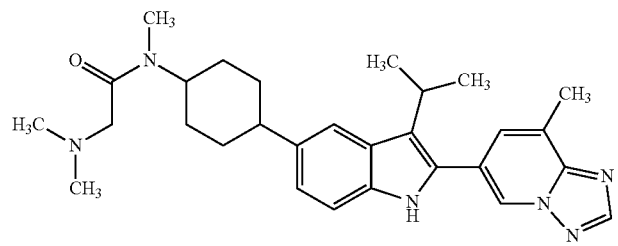 [SMILES: Cc1cc(-c2[nH]c3ccc(C4CCC(N(C)C(=O)CN(C)C)CC4)cc3c2C(C)C)cn2ncnc12] | 486.7 | 487.4 | 1.48 | P |
| 149 | 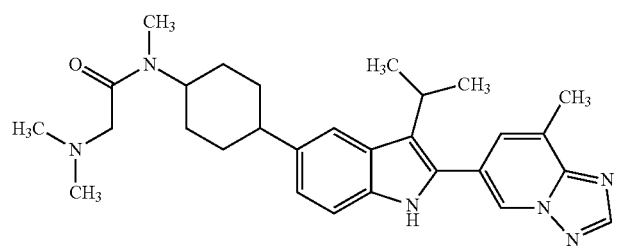 [SMILES: Cc1cc(-c2[nH]c3ccc(C4CCC(N(C)C(=O)CN(C)C)CC4)cc3c2C(C)C)cn2ncnc12] | 486.7 | 487.4 | 1.49 | P |

Example 150

4-(3-isopropyl-2-(8-methoxy-[1,2,4]triazolo[1,5-a]pyridin-6-yl)-1H-indol-5-yl)-N-methyl-N-(2-(methylsulfonyl)ethyl)cyclohexanamine (150)

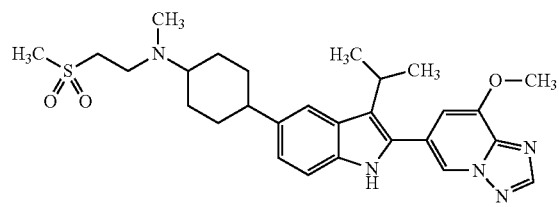

To a solution of 4-(3-isopropyl-2-(8-methoxy-[1,2,4]triazolo[1,5-a]pyridin-6-yl)-1H-indol-5-yl)-N-methylcyclohexanamine (0.180 g, 0.431 mmol) in DMF (2.0 mL) and THF (2.0 mL) were added DIPEA (0.376 mL, 2.155 mmol) and 1-chloro-2-(methylsulfonyl)ethane (0.123 g, 0.862 mmol) at room temperature, dien the mixture was stirred at 80° C. for 16 h. The reaction mass was purified via preparative LC/MS using method D2, the fractions containing the desired product were combined and dried via centrifugal evaporation to afford 4-(3-isopropyl-2-(8-methoxy-[1,2,4]triazolo[1,5-a]pyridin-6-yl)-1H-indol-5-yl)-N-methyl-N-(2-(methylsulfonyl)ethyl) cyclohexanamine (0.012 g, 5% yield) as an off white solid. LCMS retention time 1.98 min [G] MS m/z: 524.2 [M+H]$^+$; $^1$H NMR (400 MHz, METHANOL-d$_4$) δ ppm 8.36-8.47 (m, 2H) 7.59 (s, 1H) 7.30 (d, J=8.53 Hz, 1H) 7.20 (d, J=1.00 Hz, 1H) 7.04 (dd, J=8.53, 1.51 Hz, 1H) 4.12 (s, 3H) 3.78 (s, 2H) 3.33-3.45 (m, 2H) 3.03-3.09 (m, 5H) 2.85-2.89 (m, 1H) 2.54-2.69 (m, 2H) 2.37 (s, 3H) 1.93-2.09 (m, 4H) 1.56-1.73 (m, 3H) 1.51 (d, J=7.53 Hz, 7H).

The following Examples were prepared according to the general procedure used to prepare Example 150

Examples 152 and 153

4-(2-(7,8-dimethyl-[1,2,4]triazolo[1,5-a]pyridin-6-yl)-3-isopropyl-1H-indol-5-yl)-N-(2-methoxyethyl)-N-methylcyclohexanamine (152-153)

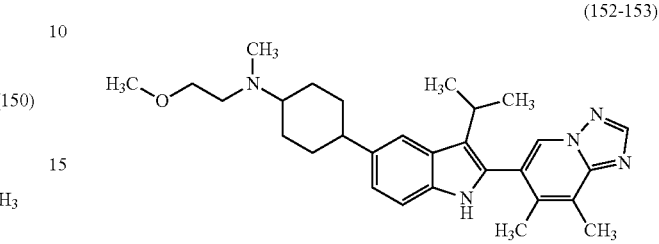

To a solution of 4-(2-(7,8-dimethyl-[1,2,4]triazolo[1,5-a]pyridin-6-yl)-3-isopropyl-1H-indol-5-yl)-N-methylcyclohexanamine (0.150 g, 0.361 mmol) in DMF (2.0 mL) and THF (2.0 mL) were added DIPEA (0.315 mL, 1.805 mmol) and 1-bromo-2-methoxyethane (0.100 g, 0.722 mmol) at 0° C., then the mixture was stirred at 80° C. for 16 h. The reaction mass was purified via preparative LC/MS method D2 to separate both the isomers. The fractions containing the desired product were combined and dried via centrifugal evaporation.

Example 152 (Isomer 1): (9 mg, 6% yield) as a pale solid. LCMS retention time 1.45 min [E] MS m/z: 474.3 [M+H]$^+$; $^1$H NMR (400 MHz, METHANOL-d$_4$) δ ppm 8.58 (s, 1H), 8.41 (s, 1H), 7.60 (s, 1H), 7.31 (d, J=8.3 Hz, 1H), 7.08 (d, J=8.3 Hz, 1H), 3.76 (t, J=4.8 Hz, 2H), 3.52-3.38 (m, 5H), 3.03-2.93 (m, 1H), 2.91 (s, 3H), 2.73 (br. s, 1H), 2.66 (s, 3H), 2.26 (s, 3H), 2.19 (br. s, 3H), 1.87-1.72 (m, 4H), 1.46-1.35 (m, 6H).

Example 153 (Isomer 2): (5 mg, 3% yield) as a pale solid. LCMS retention time 1.56 min [E] MS m/z: 474.3 [M+H]$^+$; $^1$H NMR (400 MHz, METHANOL-d$_4$) δ ppm 8.56 (s, 1H), 8.55 (s, 1H), 8.39 (s, 1H), 7.71 (s, 1H), 7.33 (d, J=8.5 Hz, 1H), 7.18 (dd, J=8.5, 1.5 Hz, 1H), 3.65 (t, J=5.3 Hz, 2H), 3.41-3.38 (m, 3H), 3.22 (d, J=7.0 Hz, 1H), 3.18-3.07 (m, 3H), 3.03-2.94 (m, 1H), 2.68 (s, 3H), 2.66-2.59 (m, 3H), 2.34 (br. s., 2H), 2.26 (s, 3H), 2.01-1.82 (m, 6H), 1.42-1.38 (m, 6H).

TABLE 8

| Ex. No. | Structure | Mol Wt. | LCMS MH$^+$ | Ret Time (min) | HPLC Method |
|---|---|---|---|---|---|
| 151 | 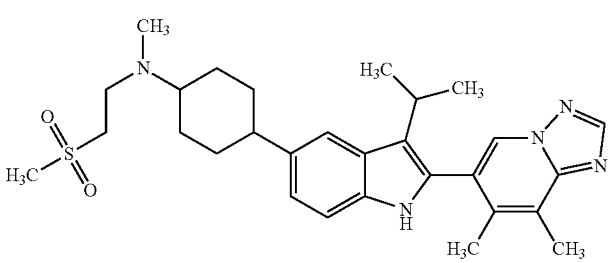 | 521.7 | 522.0 | 2.1 | P |

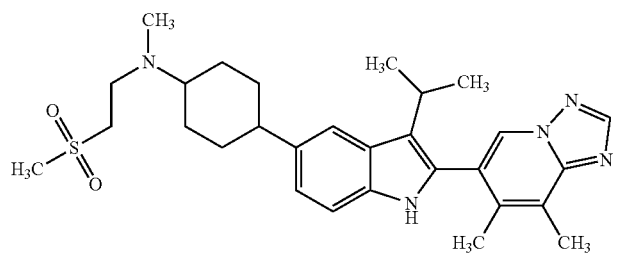 [SMILES: Cc1c(-c2[nH]c3ccc(C4CCC(N(C)CCS(C)(=O)=O)CC4)cc3c2C(C)C)cn2ncnc2c1C]

Example 154

2-(dimethylamino)-N-(4-(3-isopropyl-2-(8-methoxy-[1,2,4]triazolo[1,5-a]pyridin-6-yl)-1H-indol-5-yl)-1-methylcyclohexyl)acetamide

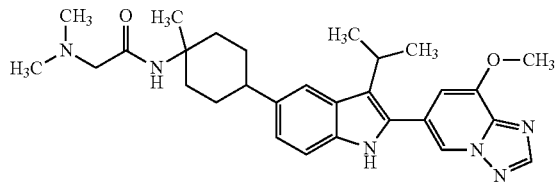

(154)

Intermediate 154A: N-(4-(2-(8-hydroxy-[1,2,4]triazolo[1,5-a]pyridin-6-yl)-3-isopropyl-1H-indol-5-yl)cyclohexylidene)-2-methylpropane-2-sulfinamide

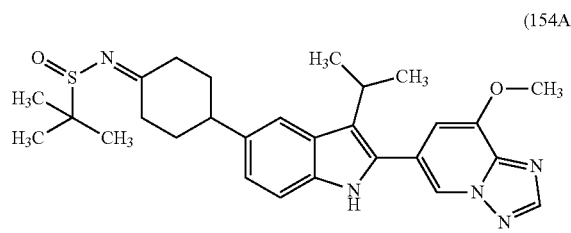

(154A)

To a solution of 4-(3-isopropyl-2-(8-methoxy-[1,2,4]triazolo[1,5-a]pyridin-6-yl)-1H-indol-5-yl)cyclohexanone (0.598 g, 1.485 mmol) and 2-methylpropane-2-sulfinamide (0.180 g, 1.485 mmol) in THF (15.0 mL) was added titanium ethoxide (2.97 mmol) at room temperature, then the mixture was stirred at same temperature for 4 h. The reaction mass was quenched with water, stirred for 10 min, filtered the solids, washed with excess DCM, the organic layer was washed with water, brine, dried over sodium sulphate and concentrated to afford N-(4-(3-isopropyl-2-(8-methoxy-[1,2,4]triazolo[1,5-a]pyridin-6-yl)-1H-indol-5-yl)cyclohexylidene)-2-methylpropane-2-sulfinamide (0.650 g, 1.285 mmol, 87% yield) as a light yellow semi solid compound. LCMS retention time 1.37 min. (L) MS (E+) m/z: 506.6 (M+H).

Intermediate 154B: N-(4-(3-isopropyl-2-(8-methoxy-[1,2,4]triazolo[1,5-a]pyridin-6-yl)-1H-indol-5-yl)-1-methylcyclohexyl)-2-methylpropane-2-sulfinamide

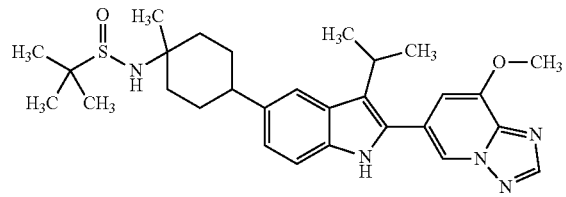

(154B)

To a solution of N-(4-(3-isopropyl-2-(8-methoxy-[1,2,4]triazolo[1,5-a]pyridin-6-yl)-1H-indol-5-yl)cyclohexylidene)-2-methylpropane-2-sulfinamide (0.550 g, 1.088 mmol) in THF (15 mL) was added methyl magnesium bromide (1.813 mL, 5.44 mmol) at −78° C., then slowly brought room temperature, stirred at room temperature for 16 h. The reaction was quenched with saturated $NH_4Cl$ solution, stirred for 10 min at room temperature, volatiles was evaporated, the residue was dissolved with excess DCM, washed with water, brine organic layer was dried over sodium sulphate and concentrated to afford N-(4-(3-isopropyl-2-(8-methoxy-[1,2,4]triazolo[1,5-a]pyridin-6-yl)-1H-indol-5-yl)-1-methylcyclohexyl)-2-methylpropane-2-sulfinamide (0.500 g, 0.958 mmol, 88% yield) as a gummy solid. LCMS retention time 1.37 min, MS m/z: 522.6 (M+H).

Intermediate 154C: 4-(3-isopropyl-2-(8-methoxy-[1,2,4]triazolo[1,5-a]pyridin-6-yl)-1H-indol-5-yl)-1-methylcyclohexanamine

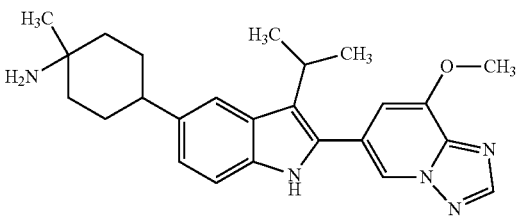

(154C)

To a solution of N-(4-(3-isopropyl-2-(8-methoxy-[1,2,4]triazolo[1,5-a]pyridin-6-yl)-1H-indol-5-yl)-1-methylcyclohexyl)-2-methylpropane-2-sulfinamide (0.550 g, 1.054 mmol) in dioxane (5.0 mL), was added 4M HCl in dioxane (5.27 mL, 21.08 mmol), the mixture was stirred at room temperature for 2 h. Volatiles was evaporated, the residue was triturated with diethyl ether, dried under vacuum to afford 4-(3-isopropyl-2-(8-methoxy-[1,2,4]triazolo[1,5-a]pyridin-6-yl)-1H-indol-5-yl)-1-methylcyclohexanamine (0.320 g, 0.766 mmol, 73% yield) as a light yellow solid. LCMS retention time 1.02 min. (L) MS m/z: 418.6 (M+H).

Example 154

To a solution of 4-(3-isopropyl-2-(8-methoxy-[1,2,4]triazolo[1,5-a]pyridin-6-yl)-1H-indol-5-yl)-1-methylcyclohexanamine (0.150 g, 0.359 mmol) in DMF (3.0 mL) and THF (1.0 mL) were added 2-(dimethylamino)acetic acid (0.074 g, 0.718 mmol), TEA (0.250 mL, 1.796 mmol) and HATU (0.137 g, 0.359 mmol) at room temperature, the mixture was stirred at same temperature for 16 h. The reaction mass was purified via preparative LC/MS using method D2, the fractions containing the desired product were combined and dried via centrifugal evaporation to afford 2-(dimethylamino)-N-(4-(3-isopropyl-2-(8-methoxy-[1,2,4]triazolo[1,5-a]pyridin-6-yl)-1H-indol-5-yl)-1-methylcyclohexyl)acetamide (4.0 mg, 2% yield). LCMS retention time 2.17 min [E] MS m/z: 503.2 (M+H); $^1$H NMR (400 MHz, METHANOL-$d_4$) δ ppm 8.45 (d, J=19.32 Hz, 2H) 7.62 (s, 1H) 7.34 (d, J=8.56 Hz, 1H) 7.24 (s, 1H) 7.06 (d, J=8.07 Hz, 1H) 4.59 (s, 1H) 4.11-4.20 (m, 3H) 3.82 (s, 1H) 3.37-3.47 (m, 2H) 3.07 (s, 2H) 2.67 (t, J=12.10 Hz, 1H) 2.39-2.53 (m, 8H) 1.64-1.93 (m, 5H) 1.50-1.60 (m, 8H) 1.45 (s, 3H).

Example 155

N-(4-(3-isopropyl-2-(8-methoxy-[1,2,4]triazolo[1,5-a]pyridin-6-yl)-1H-indol-5-yl)-1-methylcyclohexyl)-2-(methylamino)acetamide

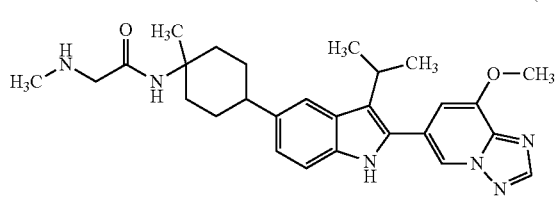
(155)

Intermediate 155A: tert-butyl (2-((4-(3-isopropyl-2-(8-methoxy-[1,2,4]triazolo[1,5-a]pyridin-6-yl)-1H-indol-5-yl)-1-methylcyclohexyl)amino)-2-oxoethyl)(methyl)carbamate

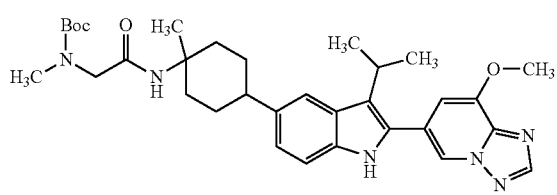
(155A)

tert-Butyl (2-((4-(3-isopropyl-2-(8-methoxy-[1,2,4]triazolo[1,5-a]pyridin-6-yl)-1H-indol-5-yl)-1-methylcyclohexyl)amino)-2-oxoethyl)(methyl)carbamate (0.150 g, 0.255 mmol, 71% yield) was prepared according to the general procedure described in Example 154 using 4-(3-isopropyl-2-(8-methoxy-[1,2,4]triazolo[1,5-a]pyridin-6-yl)-1H-indol-5-yl)-1-methylcyclohexanamine (0.150 g, 0.359 mmol) in DMF (3.0 mL) as the starting intermediate. LCMS retention time 1.49 min. (L) MS m/z: 589.6 (M+H).

Example 155

To a solution of tert-butyl (2-((4-(3-isopropyl-2-(8-methoxy-[1,2,4]triazolo[1,5-a]pyridin-6-yl)-1H-indol-5-yl)-1-methylcyclohexyl)amino)-2-oxoethyl)(methyl)carbamate (0.150 g, 0.255 mmol) in dioxane (2.0 mL) at 0° C., was added 4 M HCl in dioxane (1.274 mL, 5.10 mmol). The reaction mixture was stirred at room temperature for 2 h. The reaction mass was purified via preparative LC/MS with the following conditions: Column: Sunfire OBD-C18, 30×250 mm, 5 μm, particles; Mobile Phase A: 10 mM ammonium acetate pH 4.5 with $CH_3COOH$; Mobile Phase B: acetonitrile; Gradient: 20-70% B over 20 minutes, then a 0 minute hold at 0% B; Flow: 25 mL/min. The fractions containing the product were combined and dried via centrifugal evaporation to afford N-(4-(3-isopropyl-2-(8-methoxy-[1,2,4]triazolo[1,5-a]pyridin-6-yl)-1H-indol-5-yl)-1-methylcyclohexyl)-2-(methylamino)acetamide (12.0 mg, 10%). LCMS retention time 1.85 min [E], MS m/z: 489.1 (M+H); $^1$H NMR (400 MHz, DMSO-$d_6$) δ ppm 8.37-8.49 (m, 2H) 7.57-7.64 (m, 1H) 7.27-7.36 (m, 1H) 7.19-7.22 (m, 1H) 6.99-7.11 (m, 1H) 4.53-4.58 (m, 1H) 4.13 (s, 3H) 3.60-3.70 (m, 2H) 3.35-3.49 (m, 2H) 2.68 (s, 4H) 2.34-2.47 (m, 2H) 1.91-1.98 (m, 2H) 1.67-1.86 (m, 5H) 1.51 (d, J=6.85 Hz, 8H) 1.42 (s, 3H).

Examples 156 and 157

(4-(3-isopropyl-2-(8-methyl-[1,2,4]triazolo[1,5-a]pyridin-6-yl)-1H-indol-5-yl)cyclohexyl)(4-methylpiperazin-1-yl)methanone

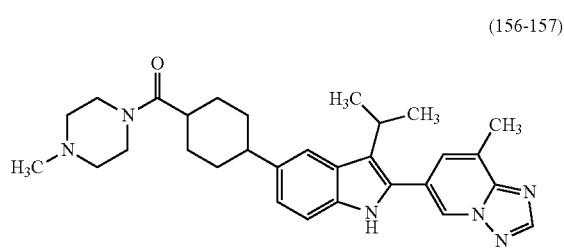 [SMILES: Cc1cc(-c2[nH]c3ccc(C4CCC(C(=O)N5CCN(C)CC5)CC4)cc3c2C(C)C)cn2ncnc12]
(156-157)

Intermediate 156A: tert-butyl 3-isopropyl-2-(8-methyl-[1,2,4]triazolo[1,5-a]pyridin-6-yl)-5-(4-oxocyclohexyl)-1H-indole-1-carboxylate

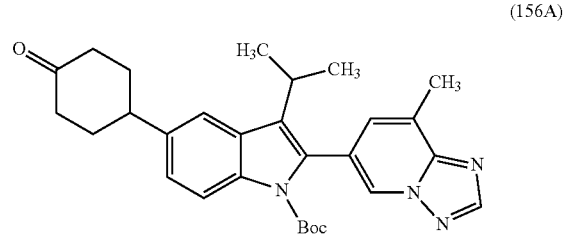 [SMILES: Cc1cc(-c2c(C(C)C)c3cc(C4CCC(=O)CC4)ccc3n2C(=O)OC(C)(C)C)cn2ncnc12]
(156A)

To a solution of 4-(3-isopropyl-2-(8-methyl-[1,2,4]triazolo[1,5-a]pyridin-6-yl)-1H-indol-5-yl)cyclohexanone (0.200 g, 0.517 mmol) in DCM (10.0 mL), were added TEA (0.289 mL, 2.070 mmol), $Boc_2O$ (0.180 mL, 0.776 mmol) and DMAP (0.063 g, 0.517 mmol) at room temperature. The reaction mixture was stirred at the same temperature for 16 h. The reaction was quenched with cold water. The reaction mixture was diluted with chloroform (100 mL), separated both the layers, the organic layer was dried over sodium sulphate and concentrated to get crude material. The crude material was purified by silica gel chromatography on an ISCO instrument using 24 g silica column, the compound was eluted with 55% ethyl acetate in petroleum ether, the fractions containing the product was collected and concentrated to afford tert-butyl 3-isopropyl-2-(8-methyl-[1,2,4]triazolo[1,5-a]pyridin-6-yl)-5-(4-oxocyclohexyl)-1H-indole-1-carboxylate (0.140 g, 0.288 mmol, 56% yield) as a brown solid. LCMS retention time 1.62 min [L]. MS m/z: 487.5 (M+H).

Intermediate 156B: tert-butyl 5-(4-cyanocyclohexyl)-3-isopropyl-2-(8-methyl-[1,2,4]triazolo[1,5-a]pyridin-6-yl)-1H-indole-1-carboxylate

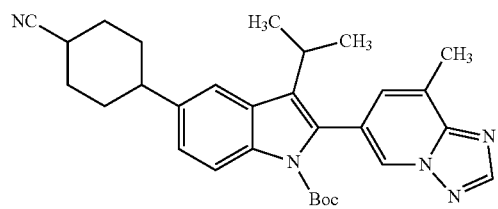

(156B)

To a solution of tert-butyl 3-isopropyl-2-(8-methyl-[1,2,4]triazolo[1,5-a]pyridin-6-yl)-5-(4-oxocyclohexyl)-1H-indole-1-carboxylate (0.200 g, 0.411 mmol) in DME (15.0 mL) and ethanol (0.5 mL) solvent mixture were added KOtBu (0.092 g, 0.822 mmol) and TosMIC (0.120 g, 0.617 mmol) at 0° C. The reaction mixture was stirred at 0° C. for 2 h and stirred at room temperature for 16 h. The reaction mixture was quenched with cold water, diluted with excess ethyl acetate, both the layers was separated, and the aqueous layer was extracted with ethyl acetate, combined organic layer was dried over sodium sulphate, and concentrated to afford crude compound. The crude material was purified by silica gel chromatography on an ISCO instrument using 24 g silica column, compound was eluted with 85% ethyl acetate in petroleum ether, the fractions containing the desired product was collected and concentrated to afford tert-butyl 5-(4-cyanocyclohexyl)-3-isopropyl-2-(8-methyl-[1,2,4]triazolo[1,5-a]pyridin-6-yl)-1H-indole-1-carboxylate (0.120 g, 0.241 mmol, 59% yield) as a light yellow solid. LCMS retention time 1.68 min [L]. MS m/z: 498.5 (M+H).

Intermediate 156C: 4-(3-isopropyl-2-(8-methyl-[1,2,4]triazolo[1,5-a]pyridin-6-yl)-1H-indol-5-yl)cyclohexanecarboxylic acid

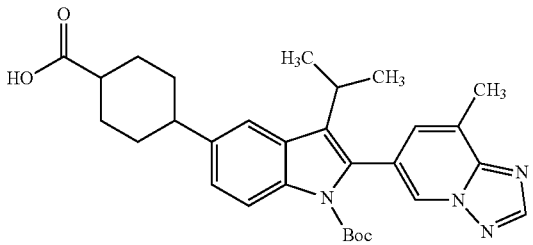

(156C)

A solution of tert-butyl 5-(4-cyanocyclohexyl)-3-isopropyl-2-(8-methyl-[1,2,4]triazolo[1,5-a]pyridin-6-yl)-1H-indole-1-carboxylate (0.100 g, 0.201 mmol) in hydrochloric acid, 37% (10.0 mL) was stirred at 100° C. for 16 h. Concentrated the reaction mass and azeotrope with toluene to afford 4-(3-isopropyl-2-(8-methyl-[1,2,4]triazolo[1,5-a]pyridin-6-yl)-1H-indol-5-yl)cyclohexanecarboxylic acid (0.070 g, 0.168 mmol, 84% yield) a light yellow solid. LCMS retention time 0.91 & 1.13 min. (L) MS m/z: 417.4 (M+H).

Examples 156 and 157

To a solution of 4-(3-isopropyl-2-(8-methyl-[1,2,4]triazolo[1,5-a]pyridin-6-yl)-1H-indol-5-yl)cyclohexanecarboxylic acid (0.070 g, 0.168 mmol) and 1-methylpiperazine (0.034 g, 0.336 mmol) in DMF (2.0 mL) were added TEA (0.070 mL, 0.504 mmol) and HATU (0.064 g, 0.168 mmol) at room temperature. The reaction mixture was stirred at same temperature for 16 h. The reaction mass was dissolved with excess DCM, washed with water, brine, dried over sodium sulphate and concentrated to afford crude compound. The crude material was purified via preparative LC/MS using method D2, to separate both die isomers. The fractions containing the desired product were combined and dried via centrifugal evaporation to afford:

Example 156 (isomer 1): (0.006 g, 6% yield). LCMS retention time 1.87 min (E). MS m/z: 499.3 [M+H]+.

Example 157 (isomer 2): (0.004 g, 4.5% yield). LCMS retention time 2.02 min. (E). MS m/z: 499.3 [M+H]+.

The following Examples were prepared according to the general procedure used to prepare Examples 156-157.

TABLE 9

| Ex. No. | Structure | Mol Wt. | LCMS MH+ | Ret Time (min) | HPLC Method |
|---|---|---|---|---|---|
| 158 | ![structure] | 540.8 | 541.2 | 1.58 | E |

TABLE 9-continued

| Ex. No. | Structure | Mol Wt. | LCMS MH+ | Ret Time (min) | HPLC Method |
|---|---|---|---|---|---|
| 159 | 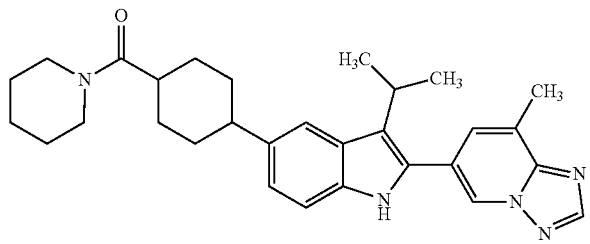 [SMILES: Cc1cc(-c2[nH]c3ccc(C4CCC(C(=O)N5CCCCC5)CC4)cc3c2C(C)C)cn2ncnc12] | 483.7 | 484.2 | 2.58 | E |
| 160 | 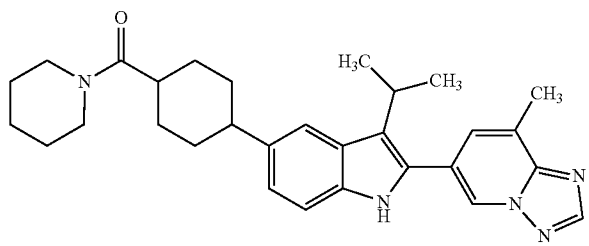 [SMILES: Cc1cc(-c2[nH]c3ccc(C4CCC(C(=O)N5CCCCC5)CC4)cc3c2C(C)C)cn2ncnc12] | 483.7 | 484.2 | 2.53 | E |
| 161 | 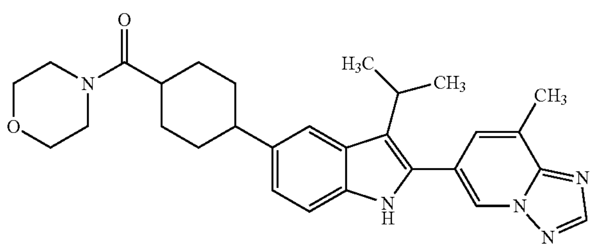 [SMILES: Cc1cc(-c2[nH]c3ccc(C4CCC(C(=O)N5CCOCC5)CC4)cc3c2C(C)C)cn2ncnc12] | 485.6 | 486.1 | 1.96 | E |

Examples 162 and 163

2-((4-(3-isopropyl-2-(8-methyl-[1,2,4]triazolo[1,5-a]pyridin-6-yl)-1H-indol-5-yl)cyclohexyl)amino)-N-methylacetamide (162-163)

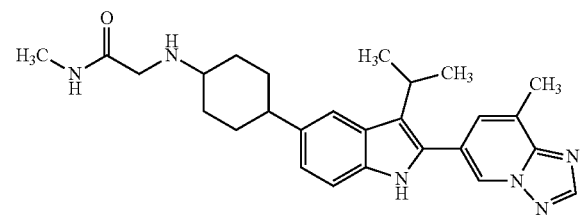

Intermediate 162A: Methyl 2-((4-(3-isopropyl-2-(8-methyl-[1,2,4]triazolo[1,5-a]pyridin-6-yl)-1H-indol-5-yl)cyclohexyl)amino)acetate (162A)

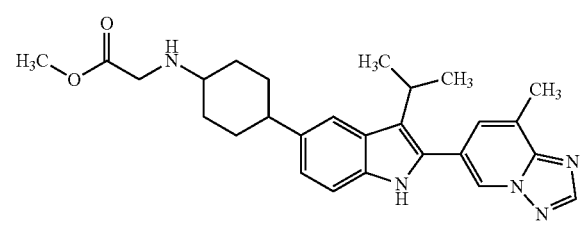

To a mixture of 4-(3-isopropyl-2-(8-methyl-[1,2,4]triazolo[1,5-a]pyridin-6-yl)-1H-indol-5-yl)cyclohexanone (0.200 g, 0.517 mmol) and methyl 2-aminoacetate hydrochloride (0.325 g, 2.59 mmol) in DMF (4.0 mL) and THF (4.0 mL) solvent mixture was added TEA (0.361 mL, 2.59 mmol) at room temperature, stirred for 2 h. then was added acetic acid (0.296 mL, 5.17 mmol) at 0° C., stirred at room temperature for 16 h. Concentrated the reaction mass, extracted with DCM, washed with water, brine, dried over sodium sulphate and concentrated to afford crude methyl 2-((4-(3-isopropyl-2-(8-methyl-[1,2,4]triazolo[1,5-a]pyridin-6-yl)-1H-indol-5-yl)cyclohexyl)amino) acetate (0.220 g, 0.479 mmol, 93% yield) as a gummy solid. LCMS retention time 1.22 & 1.42 min. (L) MS m/z: 460.6 (M+H).

Example 162 and 163

Mixture of methyl 2-((4-(3-isopropyl-2-(8-methyl-[1,2,4]triazolo[1,5-a]pyridin-6-yl)-1H-indol-5-yl)cyclohexyl)amino)acetate (0.150 g, 0.326 mmol) and methylamine (6.53 mL, 16.32 mmol, 2.5M in THF) in THF (2.0 mL) was stirred at 80° C. for 16 h. Concentrated the reaction mass, the residue was purified via preparative LC/MS using method D2 to separate both the isomers. The fractions containing the products were combined and dried via centrifugal evaporation to afford:

Example 162 (Isomer 1): (0.001 g, 1.5% yield), LCMS retention time 1.36 min. (E). MS m/z: 459.3 [M+H]+; $^1$H NMR (400 MHz, METHANOL-$d_4$) δ ppm 8.72 (s, 1H), 8.48 (s, 1H), 7.73-7.58 (m, 2H), 7.35 (d, J=8.3 Hz, 1H), 7.08 (d, J=9.5 Hz, 1H), 3.63 (s, 3H), 3.17 (br. s., 1H), 2.97 (br. s, 2H), 2.86 (s, 4H), 2.77-2.56 (m, 4H), 2.21 (d, J=11.5 Hz, 2H), 2.09 (d, J=11.7 Hz, 2H), 2.00 (s, 3H), 1.78-1.62 (m, 3H), 1.59-1.43 (m, 8H), 1.33 (br. s., 1H).

Example 163 (Isomer 2): (0.002 g, 3% yield). LCMS retention time 1.36 min (E). MS m/z: 459.3 [M+H]+, 1H NMR (400 MHz, METHANOL-d4) δ ppm 8.74 (s, 1H), 8.46 (s, 1H), 7.71-7.58 (m, 2H), 7.35 (d, J=8.3 Hz, 1H), 7.06 (d, J=9.5 Hz, 1H), 3.69 (s, 3H), 3.10 (br. s., 3H), 2.97 (br. s, 2H), 2.86 (s, 2H), 2.77-2.56 (m, 2H), 2.20 (d, J=11.5 Hz, 2H), 2.09 (d, J=11.7 Hz, 2H), 2.00 (s, 2H), 1.78-1.62 (m, 2H), 1.59-1.43 (m, 6H), 1.33 (br. s., 2H).

The following Examples were prepared according to the general procedure used to prepare Examples 162-163.

TABLE 10

| Ex. No. | Structure | Mol Wt. | LCMS MH+ | Ret Time (min) | HPLC Method |
|---------|-----------|---------|----------|----------------|-------------|
| 164 | 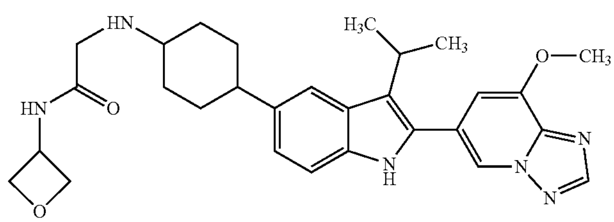 [SMILES: COc1cc(-c2[nH]c3ccc(C4CCC(NCC(=O)NC5COC5)CC4)cc3c2C(C)C)cn2ncnc12] | 516.6 | 517.2 | 1.51 | E |
| 165 | 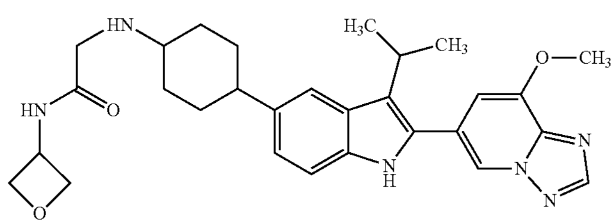 [SMILES: COc1cc(-c2[nH]c3ccc(C4CCC(NCC(=O)NC5COC5)CC4)cc3c2C(C)C)cn2ncnc12] | 516.6 | 517.2 | 1.75 | E |
| 166 | 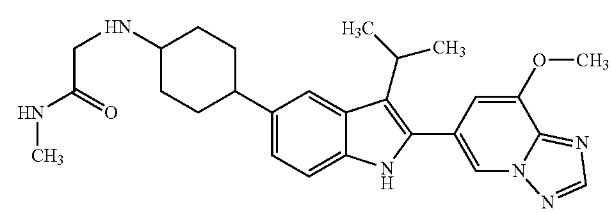 [SMILES: CNC(=O)CNC1CCC(c2ccc3[nH]c(-c4cc(OC)c5ncnn5c4)c(C(C)C)c3c2)CC1] | 474.6 | 475.2 | 1.41 | F |
| 167 | 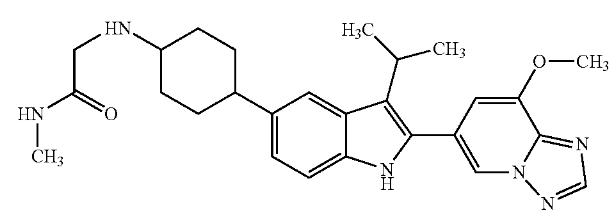 [SMILES: CNC(=O)CNC1CCC(c2ccc3[nH]c(-c4cc(OC)c5ncnn5c4)c(C(C)C)c3c2)CC1] | 474.6 | 475.1 | 1.53 | E |

Example 168

6-(3-isopropyl-5-(4-methoxycyclohexyl)-1H-indol-2-yl)-8-methyl-[1,2,4]triazolo[1,5-a]pyridine

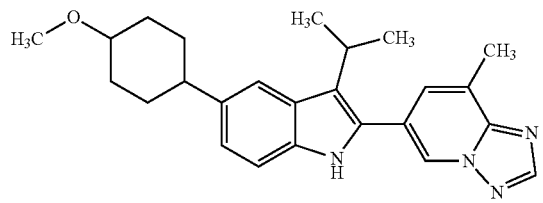
(168)

To a solution of 4-(3-isopropyl-2-(8-methyl-[1,2,4]triazolo[1,5-a]pyridin-6-yl)-1H-indol-5-yl)cyclohexanone (0.050 g, 0.129 mmol) in MeOH (5.0 mL) were added methylamine (0.517 mL, 1.294 mmol, 2.5M in THF) and acetic acid (0.741 µl, 0.013 mmol) at room temperature, stirred for 8 h, then was added sodium cyanoborohydride (0.012 g, 0.194 mmol) at 0° C., then stirred at room temperature for 16 h. Concentrated the reaction mass, extracted with DCM, washed with water, brine, dried over sodium sulphate and concentrated to afford crude. The crude material was purified via preparative LC/MS using method D2. The expected methylamino product was not isolated, however the fractions containing the methoxy product were combined and dried via centrifugal evaporation to afford 6-(3-isopropyl-5-(4-methoxy cyclohexyl)-1H-indol-2-yl)-8-methyl-[1,2,4]triazolo[1,5-a]pyridine (0.005 g, 10.5% yield). LCMS retention time 2.115 min. (E) MS m/z: 403.3 (M+H).

Example 169 and 170

4-(2-(2,6-dimethylpyridin-4-yl)-3-isopropyl-1H-indol-5-yl) cyclohexanone

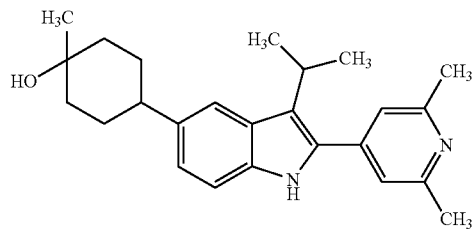
(169-170)

Intermediate 169A: 5-bromo-2-(2,6-dimethylpyridin-4-yl)-3-isopropyl-1H-indole

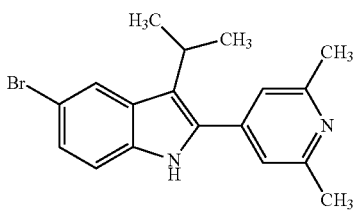
(169A)

To a degassed solution of 5-bromo-3-isopropyl-2-(4,4,5,5-tetramethyl-1,3,2-dioxaborolan-2-yl)-1H-indole (4.0 g, 10.99 mmol) and 4-bromo-2,6-dimethylpyridine (3.07 g, 16.48 mmol) in dioxane (80.00 mL) and water (10.0 mL) solvent mixture were added PdCl$_2$(dppf)-CH$_2$Cl$_2$ adduct (0.897 g, 1.099 mmol) and tripotassium phosphate (7.00 g, 33.0 mmol). The mixture was stirred at 95° C. for 1 h in a sealed tube. The reaction mixture was diluted with ethyl acetate, filtered and washed with excess ethyl acetate, combined organic layer was washed with water, brine, dried over sodium sulphate and concentrated to afford crude compound. The crude material was purified by silica gel chromatography on an ISCO instrument using 80 g silica column, compound was eluted with 85% ethyl acetate in petroleum ether, the fractions were collected and concentrated to afford 5-bromo-2-(2,6-dimethylpyridin-4-yl)-3-isopropyl-1H-indole (2.6 g, 7.57 mmol, 69% yield) as a light yellow solid. LCMS retention time 1.67 min. (L) MS (E345.4 (M+2H).

The following Intermediate was prepared according to the general procedure used to prepare Intermediate 169A.

TABLE 11

| Intermediate | Structure | Mol Wt. | LCMS MH+ | Ret Time (min) | HPLC Method |
|---|---|---|---|---|---|
| Int-169A2 | 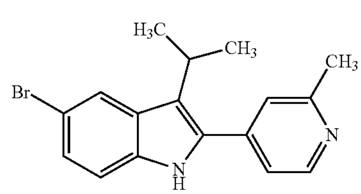 [SMILES: Cc1cc(-c2[nH]c3ccc(Br)cc3c2C(C)C)ccn1] | 329.2 | 331.1 | 1.38 | D |

Intermediate 169B: 2-(2,6-dimethylpyridin-4-yl)-3-isopropyl-5-(4,4,5,5-tetramethyl-1,3,2-dioxaborolan-2-yl)-1H-indole

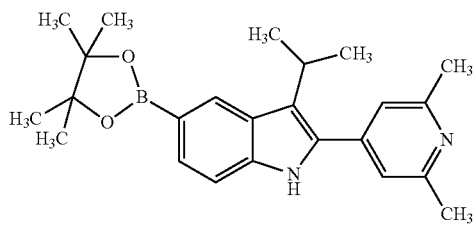

(169B)

To a degassed mixture of 5-bromo-2-(2,6-dimethylpyridin-4-yl)-3-isopropyl-1H-indole (2.6 g, 7.57 mmol) and bis(pinacolato)diboron (2.89 g, 11.36 mmol) in dioxane (40.00 mL) were added potassium acetate (2.230 g, 22.72 mmol) and PdCl$_2$(dppf)-CH$_2$Ch adduct (1.237 g, 1.515 mmol), the mixture was stirred at 95° C. for 14 h in a sealed tube. The reaction mixture was diluted with ethyl acetate, filtered and washed with excess ethyl acetate, combined organic layer was dried over sodium sulphate and concentrated to afford crude compound. The crude material was purified by silica gel chromatography on an ISCO instrument using 40 g silica column, compound was eluted with 30% ethyl acetate in petroleum ether, the fractions were collected and concentrated to afford 2-(2,6-dimethylpyridin-4-yl)-3-isopropyl-5-(4,4,5,5-tetramethyl-1,3,2-dioxaborolan-2-yl)-1H-indole (1.8 g, 4.61 mmol, 61% yield) as a light brown solid. LCMS retention time 3.41 min, (D) MS m/z: 391.4 (M+H).

Intermediate 169C: 2-(2,6-dimethylpyridin-4-yl)-3-isopropyl-5-(1,4-dioxaspiro[4.5]dec-7-en-8-yl)-1H-indole

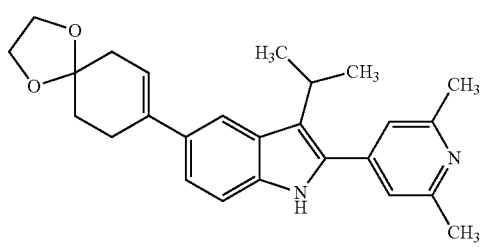

(169C)

To a degassed mixture of 2-(2,6-dimethylpyridin-4-yl)-3-isopropyl-5-(4,4,5,5-tetramethyl-1,3,2-dioxaborolan-2-yl)-1H-indole (2.5 g, 6.40 mmol) and 1,4-dioxaspiro[4.5]dec-7-en-8-yl trifluoromethanesulfonate (2.77 g, 9.61 mmol) in dioxane (40 mL) and water (5.0 mL) solvent mixture were added tripotassium phosphate (4.08 g, 19.21 mmol) and PdCl$_2$(dppf)-CH$_2$Ch adduct (1.046 g, 1.281 mmol), then the resulting mixture was stirred at 90° C. for 14 h. The reaction mixture was diluted with ethyl acetate, filtered and washed with excess ethyl acetate, combined organic layer was washed with water, brine, dried over sodium sulphate and concentrated to afford crude compound. The crude material was purified by silica gel chromatography on an ISCO instrument using 80 g silica column, compound was eluted in 45% ethyl acetate in petroleum ether, the fractions were collected and concentrated to afford 2-(2,6-dimethylpyridin-4-yl)-3-isopropyl-5-(1,4-dioxaspiro[4.5]dec-7-en-8-yl)-1H-indole (1.9 g, 4.72 mmol, 74% yield) as a light yellow solid. LCMS retention time 0.84 min. (G) MS m/z: 403.6 (M+H).

Intermediate 169D: 2-(2,6-dimethylpyridin-4-yl)-3-isopropyl-5-(1,4-dioxaspiro[4.5]decan-8-yl)-1H-indole

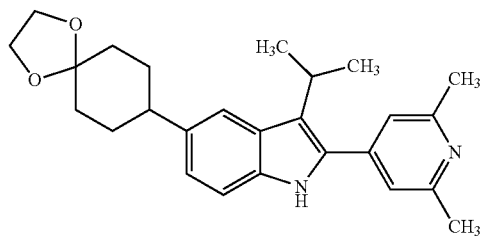

(169D)

To a solution of 2-(2,6-dimethylpyridin-4-yl)-3-isopropyl-5-(1,4-dioxaspiro(4.5 dec-7-en-8-yl)-1H-indole (1.6 g, 3.97 mmol) in mixture of ethyl acetate (50.0 mL) and MeOH (50.0 mL) solvent mixture was added Pd/C (0.846 g, 7.95 mmol), the resulting reaction mixture was stirred at room temperature for 16 h under hydrogen gas bladder pressure. The reaction mixture was filtered through celite bed, washed with ethyl acetate, the filtrate was collected and concentrated to afford 2-(2,6-dimethylpyridin-4-yl)-3-isopropyl-5-(1,4-dioxaspiro[4.5]decan-8-yl)-1H-indole (1.4 g, 3.46 mmol, 87% yield) as a light brown solid compound. LCMS retention time 3.31 min (D) MS m/z: 405.2 (M+H).

Intermediate 169E: 4-(2-(2,6-dimethylpyridin-4-yl)-3-isopropyl-1H-indol-5-yl) cyclohexanone

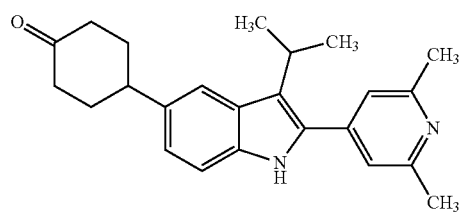

(169E)

To a solution of 2-(2,6-dimethylpyridin-4-yl)-3-isopropyl-5-(1,4-dioxaspiro[4.5]decan-8-yl)-1H-indole (1.5 g, 3.71 mmol) in DCM (15.0 mL) was added TFA (2.86 mL, 37.1 mmol) at 0° C., then was stirred at room temperature for 6 h. Concentrated the reaction mass, the residue was diluted with water, brought to basic with 10% aqueous NaHCO$_3$ solution, extracted with ethyl acetate (2×150 mL), the combined ethyl acetate layer was washed with water and brine. Organic layer was dried over sodium sulphate and concentrated to afford 4-(2-(2,6-dimethylpyridin-4-yl)-3-isopropyl-1H-indol-5-yl)cyclohexanone (1.1 g, 3.05 mmol, 82% yield) as a yellow solid. LCMS Retention time 1.30 min, (L) MS m/z: 361.5 (M+H).

Examples 169 and 170

To a solution of 4-(2-(2,6-dimethylpyridin-4-yl)-3-isopropyl-1H-indol-5-yl) cyclohexanone (0.100 g, 0.277 mmol) in THF (10.0 mL) was added methylmagnesium bromide (0.208 mL, 0.416 mmol, in THF) at −78° C., then slowly brought to 0° C. for 2 h. The reaction mixture was quenched with saturated NH$_4$Cl solution, extracted with DCM, washed with water, brine, dried over sodium sulphate and concentrated to afford crude. The crude material was purified via preparative LC/MS using method D2 to separate both the isomers, the fractions containing desired product was combined and dried using Genevac centrifugal evaporator to afford:

Example 169 (Isomer 1): (5.0 mg, 5.5% yield). LCMS retention time 2.108 min, (E) MS m/z: 377.3 (M+H); $^1$H NMR (400 MHz, DMSO-do) δ ppm 11.01 (s, 1H), 7.54 (s, 1H), 7.26 (d, J=8.6 Hz, 1H), 7.13 (s, 2H), 7.03 (d, J=8.3 Hz, 1H), 4.34 (s, 2H), 3.51 (br. s., 3H), 3.24-3.07 (m, 5H), 2.71-2.60 (m, 3H), 2.39-2.26 (m, 4H), 2.07 (s, 4H), 1.75 (br. s., 2H), 1.70-1.62 (m, 6H), 1.60-1.51 (m, 2H), 1.42 (d, J=7.1 Hz, 3H), 1.30-1.16 (m, 4H), 0.94 (d, J=6.6 Hz, 2H).

Example 170 (Isomer 2): (11 mg, 11.12% yield). LCMS retention time 2.26 min [L]. MS m/z: 377.2 (M+H); $^1$H NMR (400 MHz, METHANOL-d$_4$) δ ppm 7.67-7.60 (m, 1H), 7.33-7.25 (m, 1H), 7.24-7.21 (m, 2H), 7.13-7.03 (m, 1H), 4.65-4.52 (m, 2H), 3.50-3.36 (m, 1H), 3.17-3.09 (m, 1H), 2.56 (s, 6H), 2.05-1.88 (m, 3H), 1.86-1.76 (m, 2H), 1.74-1.66 (m, 2H), 1.64-1.54 (m, 2H), 1.50 (d, J=6.8 Hz, 6H), 1.26 (s, 3H).

Examples 171 and 172

4-(2-(2,6-dimethylpyridin-4-yl)-3-isopropyl-1H-indol-5-yl)cyclohexanol (171-172)

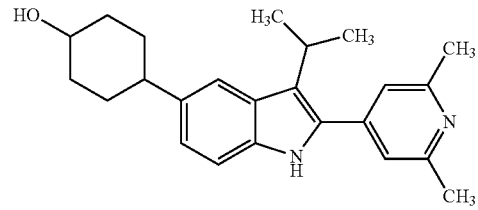

NaBH$_4$ (0.013 g, 0.333 mmol) was added to a solution of 4-(2-(2,6-dimethylpyridin-4-yl)-3-isopropyl-1H-indol-5-yl) cyclohexanone (0.060 g, 0.166 mmol) in MeOH (5.0 mL) at 10° C., then stirred at room temperature for 4 h. Quenched the reaction with cold water, evaporated the volatiles extracted with ethyl acetate, dried over sodium sulphate and concentrated to afford crude. The crude material was purified via preparative LC/MS using method D2 to separate both the isomers, the fractions containing the product was combined and dried using Genevac centrifugal evaporator to afford:

Example 171 (Isomer 1): (40.0 mg, 65% yield). LCMS retention time 1.92 min. (E) MS m/z: 363.2 (M+H); $^1$H NMR (400 MHz, METHANOL-d$_4$) δ ppm 7.77-7.63 (m, 3H), 7.38 (d, J=8.6 Hz, 1H), 7.19 (dd, J=8.6, 1.5 Hz, 1H), 3.75-3.61 (m, 1H), 3.60-3.43 (m, 1H), 2.78 (s, 6H), 2.68-2.56 (m, 1H), 2.11 (d, J=9.3 Hz, 2H), 1.97 (d, J=13.0 Hz, 2H), 1.77-1.61 (m, 2H), 1.59-1.53 (m, 6H), 1.51-1.39 (m, 2H).

Example 172 (Isomer 2): (5.0 mg, 8% yield), LCMS retention time 2.00 min. (E) MS m/z: 363.2 (M+H), $^1$H NMR (400 MHz, METHANOL-d$_4$) δ ppm 7.65 (s, 1H), 7.36 (d, J=8.1 Hz, 1H), 7.28 (s, 2H), 7.10 (d, J=9.5 Hz, 1H), 4.72-4.55 (m, 2H), 3.71 (d, J=11.0 Hz, 2H), 3.55 (br. s, 1H), 3.51-3.40 (m, 2H), 2.69-2.53 (m, 6H), 2.19-2.08 (m, 2H), 2.07-1.92 (m, 3H), 1.75-1.64 (m, 3H), 1.59-1.50 (m, 6H), 1.36 (s, 3H).

The following Examples were prepared according to the general procedure used to prepare Examples 171 and 172.

TABLE 12

| Ex. No. | Structure | Mol Wt. | LCMS MH$^+$ | Ret Time (min) | HPLC Method |
|---|---|---|---|---|---|
| 173 | ![structure] | 348.5 | 349.2 | 1.7 | E |
| 174 | ![structure] | 348.5 | 349.2 | 1.89 | E |

Example 175

4-(2-(2,6-dimethylpyridin-4-yl)-3-isopropyl-1H-indol-5-yl)-1-(trifluoro methyl)cyclohexanol

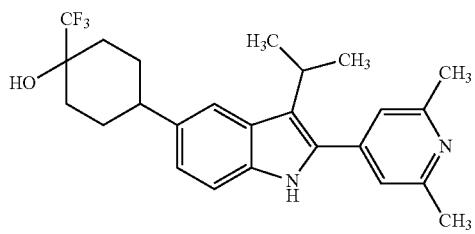

(175)

To a solution of 4-(2-(2,6-dimethylpyridin-4-yl)-3-isopropyl-1H-indol-5-yl)cyclohexanone (0.080 g, 0.222 mmol) and trifluoromethyl trimethylsilane (0.164 mL, 1.110 mmol) in THF (10.0 mL) was added TBAF (0.444 mL, 0.444 mmol in THF) at room temperature, then the mixture was stirred room temperature for 16 h. Quenched the reaction with saturated NH₄Cl solution. The reaction mixture was extracted with ethyl acetate, washed with brine, dried over sodium sulphate and concentrated to afford crude. The crude material was purified via preparative LC/MS using method D2, the fractions containing desired product was combined and dried using Genevac centrifugal evaporator to afford 4-(2-(2,6-dimethylpyridin-4-yl)-3-isopropyl-1H-indol-5-yl)-1-(trifluoromethyl)cyclohexanol (17 mg, 17% yield). LCMS retention time 2.23 min [E], MS m/z: 431.2 (M+H); $^1$H NMR (400 MHz, METHANOL-$d_4$) δ ppm 7.66 (s, 1H), 7.32 (d, J=8.5 Hz, 1H), 7.24 (s, 2H), 7.08 (dd, J=8.5, 1.5 Hz, 1H), 4.57 (s, 1H), 3.52-3.37 (m, 1H), 3.21 (br. s, 1H), 2.88 (dd, J=8.5, 3.5 Hz, 2H), 2.64-2.49 (m, 6H), 2.22-2.09 (m, 2H), 2.07-1.89 (m, 5H), 1.76-1.61 (m, 3H), 1.49 (d, J=7.0 Hz, 6H), 1.41-1.24 (m, 2H), 1.03 (t, J=7.3 Hz, 1H).

Example 176

1-(4-(2-(2,6-dimethylpyridin-4-yl)-3-isopropyl-1H-indol-5-yl)cyclohexyl)-N,N-dimethylmethanamine

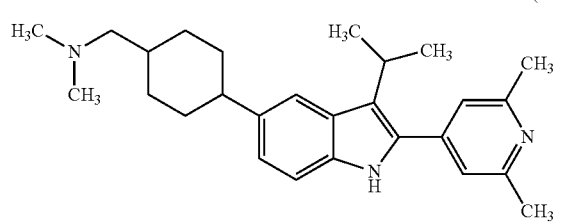

(176)

Intermediate 176A: tert-butyl 2-(2,6-dimethylpyridin-4-yl)-3-isopropyl-5-(4-oxocyclo hexyl)-1H-indole-1-carboxylate

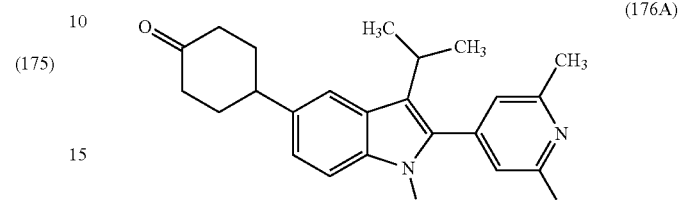

(176A)

tert-butyl 2-(2,6-dimethylpyridin-4-yl)-3-isopropyl-5-(4-oxocyclohexyl)-1H-indole-1-carboxylate (0.150 g, 0.326 mmol, 78% yield) was prepared according to the general procedure described in Examples 156 and 157 using 4-(2-(2,6-dimethylpyridin-4-yl)-3-isopropyl-1H-indol-5-yl)cyclohexanone (0.150 g, 0.416 mmol) as the starting intermediate. LCMS retention time 1.71 min [L], MS m/z: 461.6 (M+H).

Intermediate 176B: tert-butyl 5-(4-cyanocyclohexyl)-2-(2,6-dimethylpyridin-4-yl)-3-isopropyl-1H-indole-1-carboxylate

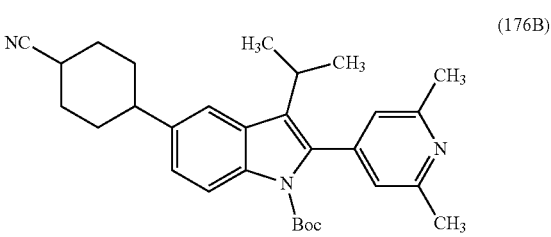 [SMILES: Cc1cc(-c2c(C(C)C)c3cc(C4CCC(C#N)CC4)ccc3n2C(=O)OC(C)(C)C)cc(C)n1]

(176B)

To a solution of tert-butyl 2-(2,6-dimethylpyridin-4-yl)-3-isopropyl-5-(4-oxocyclohexyl)-1H-indole-1-carboxylate (0.500 g, 1.086 mmol) in DME (15.0 mL) and ethanol (0.5 mL) solvent mixture were added KOtBu (0.244 g, 2.171 mmol) and TosMIC (0.318 g, 1.628 mmol) at 0° C. Then the mixture was stirred at 0° C. for 2 h and at room temperature for 14 h. Quenched the reaction with cool water. The reaction mixture was diluted with excess ethyl acetate, separated both the layers, the aqueous layer was extracted with ethyl acetate, combined organic layer was concentrated to afford crude compound. The crude material was purified by silica gel chromatography on an ISCO instrument using 24 g silica column, compound was eluted with 85% ethyl acetate in petroleum ether, the fraction was collected and concentrated to afford tert-butyl 5-(4-cyanocyclohexyl)-2-(2,6-dimethylpyridin-4-yl)-3-isopropyl-1H-indole-1-carboxylate (0.350 g, 0.742 mmol, 68% yield) as a light yellow solid. LCMS retention time 1.85 min [L] MS m/z: 472.6 (M+H).

Intermediate 176C: tert-butyl 5-(4-(aminomethyl)cyclohexyl)-2-(2,6-dimethylpyridin-4-yl)-3-isopropyl-1H-indole-1-carboxylate

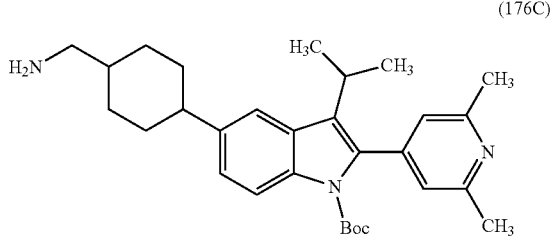 [SMILES: Cc1cc(-c2c(C(C)C)c3cc(C4CCC(CN)CC4)ccc3n2C(=O)OC(C)(C)C)cc(C)n1]

(176C)

To a solution of tert-butyl 5-(4-cyanocyclohexyl)-2-(2,6-dimethylpyridin-4-yl)-3-isopropyl-1H-indole-1-carboxylate (0.35 g, 0.742 mmol) in ethanol (100.0 mL) were added Raney®-Nickel (0.158 g, 1.484 mmol) and NH₄OH (0.973 mL, 14.84 mmol). The resulting reaction mixture was stirred at room temperature for 16 h under hydrogen gas pressure at 60 psi. The reaction mixture was diluted with ethyl acetate, filtered and washed with excess ethyl acetate. Combined organic layers was concentrated to afford tert-butyl 5-(4-(aminomethyl)cyclohexyl)-2-(2,6-dimethylpyridin-4-yl)-3-isopropyl-1H-indole-1-carboxylate (0.350 g, 0.736 mmol, 99% yield) as a light brown solid compound. LCMS retention time 1.47 min. (L) MS m/z: 476.6 (M+H).

Intermediate 176D: tert-butyl 5-(4-(((tert-butoxycarbonyl)amino)methyl)cyclohexyl)-2-(2,6-dimethylpyridin-4-yl)-3-isopropyl-1H-indole-1-carboxylate

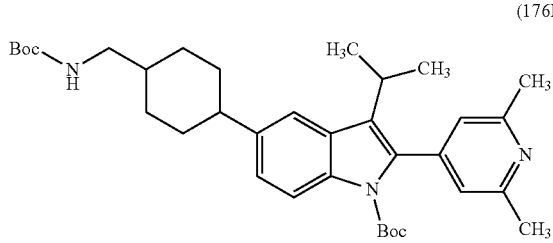

(176D)

To a solution of tert-butyl 5-(4-(aminomethyl)cyclohexyl)-2-(2,6-dimethylpyridin-4-yl)-3-isopropyl-1H-indole-1-carboxylate (0.080 g, 0.168 mmol) in DCM (10.0 mL) were added BOC₂O (0.059 mL, 0.252 mmol) and TEA (0.094 mL, 0.673 mmol) at room temperature, then stirred at room temperature for 16 h. The reaction mixture was quenched with cold water, diluted with CHCl₃ (100 mL), the organic layer was separated, dried over sodium sulphate and concentrated to afford crude. The crude material was purified by silica gel chromatography on an ISCO instrument using 24 g silica column, compound was eluted with 55% ethyl acetate in petroleum ether to afford tert-butyl 5-(4-(((tert-butoxycarbonyl)amino)methyl) cyclohexyl)-2-(2,6-dimethylpyridin-4-yl)-3-isopropyl-1H-indole-1-carboxylate (0.060 g, 0.104 mmol, 62% yield) as a brown solid. LCMS retention time 2.26 min (L) MS m/z: 576.6 (M+H).

Intermediate 176E: (4-(2-(2,6-dimethylpyridin-4-yl)-3-isopropyl-1H-indol-5-yl) cyclohexyl)methanamine

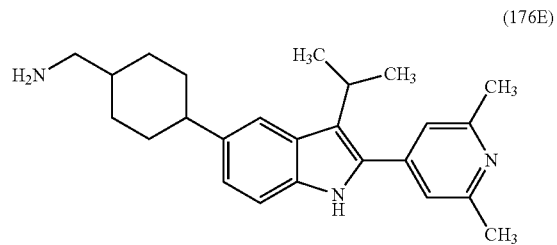 [SMILES: Cc1cc(-c2[nH]c3ccc(C4CCC(CN)CC4)cc3c2C(C)C)cc(C)n1]

(176E)

To a solution of tert-butyl 5-(4-(((tert-butoxycarbonyl)amino)methyl) cyclohexyl)-2-(2,6-dimethylpyridin-4-yl)-3-isopropyl-1H-indole-1-carboxylate (0.060 g, 0.104 mmol) in dioxane (2.0 mL) was added 4M HCl in dioxane (0.261 mL, 1.042 mmol) at room temperature, stirred at room temperature for 4 h. Concentrated the reaction mass to afford (4-(2-(2,6-dimethylpyridin-4-yl)-3-isopropyl-1H-indol-5-yl)cyclohexyl) methanamine (0.060 g) as a white solid. LCMS retention time 0.45 min [G], MS m/z: 376.2 (M+H).

Example 176

1-(4-(2-(2,6-dimethylpyridin-4-yl)-3-isopropyl-1H-indol-5-yl)cyclohexyl)-N,N-di methyl methanamine (1.0 mg, 1% yield) was prepared according to the general procedure described in Examples 6 and 7 using 4-(2-(2,6-dimethylpyridin-4-yl)-3-isopropyl-1H-indol-5-yl)cyclohexyl) methanamine (0.080 g, 0.213 mmol) as the starting intermediate. LCMS retention time 1.814 min [E]. MS m/z: 404.3 (M+H); ¹H NMR (400 MHz, METHANOL-d₄) δ ppm 7.67 (d, J=8.8 Hz, 3H), 7.38 (d, J=8.6 Hz, 1H), 7.18 (d, J=8.6 Hz, 1H), 3.60-3.46 (m, 2H), 3.08 (d, J=6.6 Hz, 2H), 2.94 (s, 6H), 2.75 (s, 6H), 2.65 (t, J=12.5 Hz, 1H), 2.09-1.92 (m, 5H), 1.76-1.61 (m, 3H), 1.55 (d, J=7.1 Hz, 6H), 1.41-1.24 (m, 4H).

Examples 177 and 178

2-((4-(3-isopropyl-2-(8-methyl-[1,2,4]triazolo[1,5-a]pyridin-6-yl)-1H-indol-5-yl)cyclohexyl)(methyl)amino)-N,N-dimethylacetamide

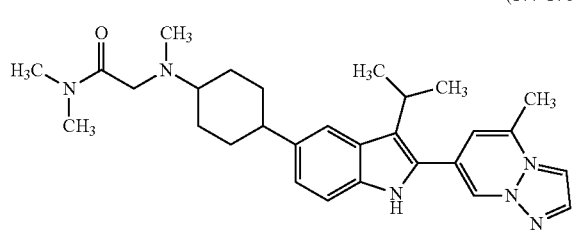

(177-178)

2-chloro-N,N-dimethylacetamide (0.091 g, 0.747 mmol) and TEA (0.260 mL, 1.868 mmol) were added to a solution of 4-(3-isopropyl-2-(8-methyl-[1,2,4]triazolo[1,5-a]pyridin-6-yl)-1H-indol-5-yl)-N-methylcyclohexanamine (0.150 g, 0.374 mmol) in DMF (1.0 mL) and THF (1.0 mL) at 0° C., then stirred at room temperature for 16 h. The reaction mass purified via preparative LC/MS using method D2 to separate both the isomers, the fractions containing the desired product were combined and dried via Genevac centrifugal evaporation to afford two isomers.

Example 177 (Isomer 1): (61.0 mg, 32% yield). LCMS retention time 1.38 min. MS m/z: 487.3 (M+H); $^1$H NMR (400 MHz, METHANOL-$d_4$) δ ppm 8.68 (s, 1H) 8.44 (s, 1H) 7.98 (s, 1H) 7.55-7.68 (m, 2H) 7.30 (d, J=8.53 Hz, 1H) 7.04 (d, J=8.53 Hz, 1H) 3.79 (d, J=1.00 Hz, 1H) 3.55 (br. s, 2H) 3.34-3.38 (m, 1H) 3.12 (s, 3H) 2.94-3.02 (m, 4H) 2.86 (s, 1H) 2.80 (br. s, 1H) 2.69 (s, 3H) 2.60 (t, J=11.80 Hz, 1H) 2.46 (br. s, 3H) 2.05 (d, J=12.05 Hz, 4H) 1.55-1.71 (m, 4H) 1.50 (d, J=7.03 Hz, 6H).

Example 178 (Isomer 2): (26.0 mg, 14% yield). LCMS retention time 1.57 min. MS m/z: 487.3 (M+H): $^1$H NMR (400 MHz, METHANOL-$d_4$) δ ppm 8.69 (s, 1H) 8.46 (s, 1H) 7.76 (s, 1H) 7.65 (s, 1H) 7.38 (d, J=8.31 Hz, 1H) 7.20 (d, J=8.31 Hz, 1H) 4.22-4.34 (m, 1H) 4.03-4.14 (m, 1H) 3.49 (d, J=10.27 Hz, 1H) 3.35-3.39 (m, 1H) 3.18 (br. s, 1H) 2.99 (d, J=10.52 Hz, 6H) 2.81-2.89 (m, 3H) 2.69 (s, 5H) 2.44 (br. s., 2H) 1.95-2.11 (m, 4H) 1.80-1.92 (m, 2H) 1.52 (d, J=7.09 Hz, 6H).

Examples 179 and 180

2-((4-(2-(2,6-dimethylpyridin-4-yl)-3-isopropyl-1H-indol-5-yl)cyclohexyl) amino)-N-methylacetamide

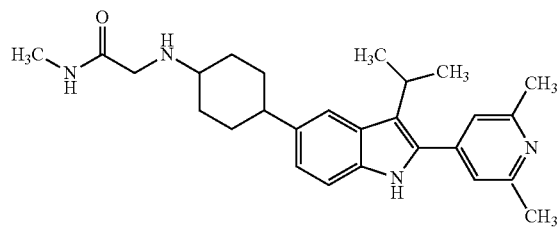

(179-180)

Isomer 1 (4.0 mg, 8.75% yield) and Isomer 2 (1.0 mg, 2.08% yield) were prepared as described in Examples 177-178 using 4-(2-(2,6-dimethylpyridin-4-yl)-3-isopropyl-1H-indol-5-yl)cyclohexanamine (0.040 g, 0.111 mmol) as the starting intermediate.

Example 179 (Isomer 1): LCMS retention time 1.68 min. (E) MS m/z: 433.3 (M+H); $^1$H NMR (400 MHz, DMSO-$d_6$) δ ppm 11.36 (br. s, 1H), 8.75 (br. s., 1H), 8.42-8.30 (m, 1H), 7.68-7.48 (m, 3H), 7.35 (d, J=8.6 Hz, 1H), 7.21 (d, J=9.8 Hz, 1H), 3.75 (br. s, 2H), 2.79-2.68 (m, 4H), 2.65 (s, 7H), 2.13-1.91 (m, 6H), 1.82 (d, J=13.0 Hz, 2H), 1.68 (d, J=12.2 Hz, 6H).

Example 180 (Isomer 2): LCMS retention time 1.98 min. (E) MS m/z: 433.3 (M+H); $^1$H NMR (400 MHz, METHANOL-$d_4$) δ ppm 7.77 (s, 1H), 7.63 (s, 2H), 7.40 (d, J=8.5 Hz, 1H), 7.25 (dd, J=8.5, 1.5 Hz, 1H), 3.84 (s, 2H), 3.59-3.43 (m, 2H), 2.88 (br. s, 1H), 2.83 (s, 3H), 2.74 (s, 6H), 2.12-1.87 (m, 8H), 1.57 (d, J=7.0 Hz, 6H).

Example 181

6-(3-isopropyl-5-(piperidin-3-yl)-1H-indol-2-yl)-8-methoxy-[1,2,4]triazolo[1,5-a]pyridine

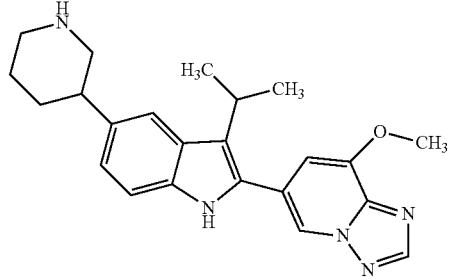

(181)

Intermediate 181A:
5-Bromo-2-iodo-3-isopropyl-1H-indole

(181A)

To a stirred solution of 5-bromo-3-isopropyl-1H-indole (30 g, 126 mmol) in THF (300 mL) was added silver trifluoromethanesulfonate (38.8 g, 151 mmol) was added $I_2$ (32.0 g, 126 mmol) in THF (300 mL) at room temperature, stirred at same temperature for 0.5 h. Quenched the reaction with aqueous $Na_2S_2O_3$ (50 ml). The reaction mixture was extracted with EtOAc (3×500 ml), dried over sodium sulphate and concentrated to afford crude product. The crude material was purified by silica gel chromatography on an ISCO instrument using 120 g silica column, the fractions containing the desired mass was collected and concentrated to afford 5-bromo-2-iodo-3-isopropyl-1H-indole (25 g, 68.7 mmol, 54.5% yield) as a brown liquid. LCMS retention time 1.72 min [D], MS m/z: 362.1 (M−H).

Intermediate 181B: 6-(5-bromo-3-isopropyl-1H-indol-2-yl)-8-methoxy-[1,2,4]triazolo[1,5-a]pyridine

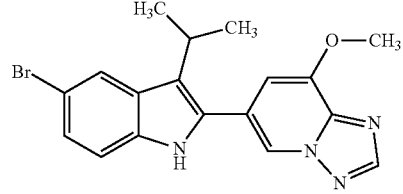

(181B)

6-(5-bromo-3-isopropyl-1H-indol-2-yl)-8-methoxy-[1,2,4]triazolo[1,5-a]pyridine (12.3 g, 31.9 mmol, 72.6% yield) was prepared according to the general procedure described in Intermediate 1G, using 5-bromo-2-iodo-3-isopropyl-1H-indole (16 g, 44.0 mmol) as the starting intermediate. LCMS retention time 1.46 min [D], MS m/z: 387.3 (M+H).

The following Intermediates were prepared according to the general procedure used to prepare Intermediate 181B.

TABLE 13

| Intermediate | Structure | Mol Wt. | LCMS [M + H] | Ret Time (min) | HPLC Method |
|---|---|---|---|---|---|
| 181B-2 | 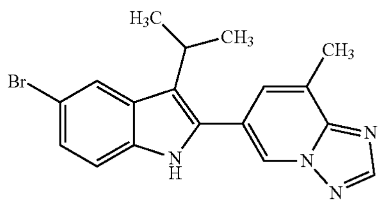 [SMILES: Cc1cc(-c2[nH]c3ccc(Br)cc3c2C(C)C)cn2ncnc12] | 368 | 370.2 | 3.24 | D |
| 181B-3 | 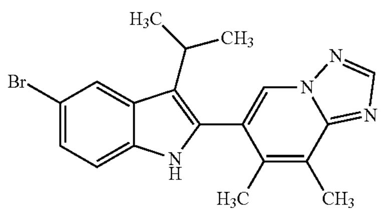 [SMILES: Cc1c(-c2[nH]c3ccc(Br)cc3c2C(C)C)cn2ncnc2c1C] | 383.3 | 385.4 | 1.54 | L |
| 181B-4 | 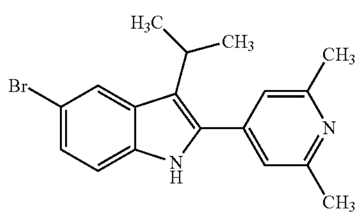 | 343.2 | 345.2 | 1.42 | W |
| 181B-5 | 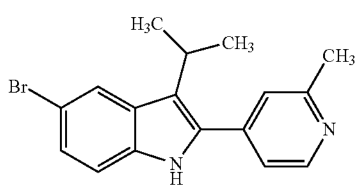 [SMILES: Cc1cc(-c2[nH]c3ccc(Br)cc3c2C(C)C)ccn1] | 329.2 | 331.2 | 1.47 | L |
| 181B-6 | 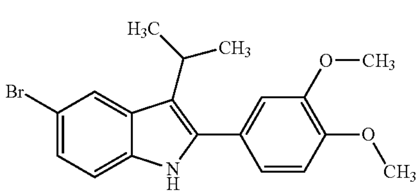 [SMILES: COc1ccc(-c2[nH]c3ccc(Br)cc3c2C(C)C)cc1OC] | 373 | 375.2 | 3.73 | E |
| 181B-7 | 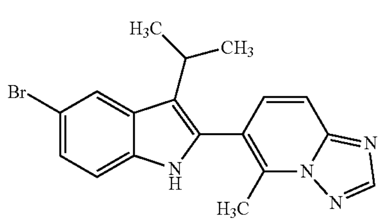 [SMILES: Cc1c(-c2[nH]c3ccc(Br)cc3c2C(C)C)ccc2ncnn12] | 369.1 | 371.1 | 1.49 | D |

Intermediate 181C: 6-(3-isopropyl-5-(4,4,5,5-tetramethyl-1,3,2-dioxaborolan-2-yl)-1H-indol-2-yl)-8-methoxy-[1,2,4]triazolo[1,5-a]pyridine

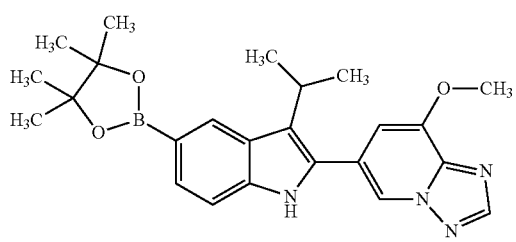

(181C)

To a stirred solution of 6-(5-bromo-3-isopropyl-1H-indol-2-yl)-8-methoxy-[1,2,4]triazolo[1,5-a]pyridine (9.5 g, 24.66 mmol) and bis(pinacolato)diboron (9.39 g, 37.0 mmol) in dioxane (10 mL) was added potassium acetate (7.26 g, 74.0 mmol), degassed the mixture with $N_2$ for 10 min, then was $PdCl_2(dppf)$ (1.804 g, 2.466 mmol) and again degassed for 10 min, then the mixture was stirred at 100° C. for 16 h. The reaction mass brought to room temperature, diluted with EtOAc, filtered the solids, concentrated the filtrate to afford crude compound. The crude mass was purified by silica gel chromatography on an ISCO instrument using 80 g silica column, the fraction containing the compound was collected and concentrated to afford 6-(3-isopropyl-5-(4,4,5,5-tetramethyl-1,3,2-dioxaborolan-2-yl)-1H-indol-2-yl)-8-methoxy-[1,2,4]triazolo[1,5-a]pyridine (5.2 g, 12.03 mmol, 49% yield) as a brown solid. LCMS retention time 1.55 min [D], MS m/z: 433.6 (M+H).

Intermediate 181D: 1-benzyl-1,2,5,6-tetrahydropyridin-3-yl trifluoromethanesulfonate

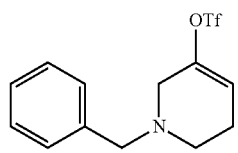

(181D)

To a stirred solution of 1-benzylpiperidin-3-one (4.2 g, 22.19 mmol) in THF (30 ml) was added drop wise lithium diisopropylamide (24.66 ml, 44.4 mmol) at −78° C., the reaction mixture was stirred at same temperature for 1 h, then was added N,N-bis(trifluoromethylsulfonyl)aniline (8.72 g, 24.41 mmol) in THF (35 ml) at same temperature, slowly brought to room temperature, stirring at room temperature for 16 h. The reaction mixture quenched with aqueous $NH_4Cl$ extracted with EtOAc, dried over sodium sulphate and concentrated to afford crude compound. The crude material was purified by silica gel chromatography on an ISCO instrument using a neutral alumina column, the fraction containing the desired compound w as collect and concentrated to afford 1-benzyl-1,2,5,6-tetrahydropyridin-3-yl trifluoromethanesulfonate (3.3 g, 10.27 mmol, 46% yield) as an oil. $^1$H NMR (400 MHz, DMSO-$d_6$) δ ppm 7.43-7.21 (m, 5H), 5.86 (d, J=8.5 Hz, 1H), 3.6 (d, J=7.0 Hz, 2H), 3.1 (d, J=7.0 Hz, 2H), 2.64-2.60 (m, 2H), 2.26-2.16 (m, 2H).

Intermediate 181E: 6-(5-(1-benzyl-1,2,5,6-tetrahydropyridin-3-yl)-3-isopropyl-1H-indol-2-yl)-8-methoxy-[1,2,4]triazolo[1,5-a]pyridine

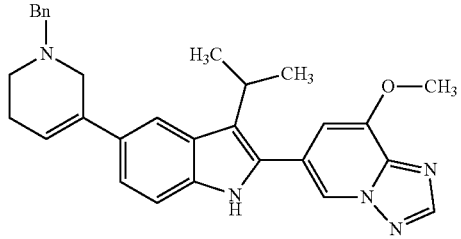

(181E)

To a stirred solution of 6-(3-isopropyl-5-(4,4,5,5-tetramethyl-1,3,2-dioxaborolan-2-yl)-1H-indol-2-yl)-8-methoxy-[1,2,4]triazolo[1,5-a]pyridine (4 g, 9.25 mmol), and 1-benzyl-1,2,5,6-tetrahydropyridin-3-yl trifluoromethanesulfonate (4.46 g, 13.88 mmol) in dioxane (50 mL), and water (0.5 mL) solvent mixture was added potassium phosphate tribasic (5.89 g, 27.8 mmol), degassed with $N_2$ gas for 10 min, then was added $PdCl_2(dppf)$ (0.677 g, 0.925 mmol) and again degassed for 10 min, then the mixture was stirred at 100° C. for 16 h. Quenched the reaction with water. The reaction mixture was extracted with EtOAc, the combined organic extracts was dried ($Na_2SO_4$) and concentrated to afford crude compound, the crude mass was purified by silica gel chromatography on an ISCO instrument using 40 g silica column, the fractions containing desired compound was collected and concentrated to afford 6-(5-(1-benzyl-1,2,5,6-tetrahydropyridin-3-yl)-3-isopropyl-1H-indol-2-yl)-8-methoxy-[1,2,4]triazolo[1,5-a]pyridine (3.5 g, 7.33 mmol, 79% yield) a white solid. LCMS retention time 1.65 min [D]. MS m/z: 478.6 (M+H).

Example 181

To a stirred solution of 6-(5-(1-benzyl-1,2,5,6-tetrahydropyridin-3-yl)-3-isopropyl-1H-indol-2-yl)-8-methoxy-[1,2,4]triazolo[1,5-a]pyridine (1 g, 2.094 mmol) in MeOH (25 mL) was added Pd/C (0.223 g, 2.094 mmol) the slurry was stirred room temperature under $H_2$ bladder for 16 h. Reaction mass was filtered through celite bed washed with MeOH, the filtrate was collected and concentrated to afford crude. The crude material was purified by preparative HPLC using method D2, fractions containing desired product was combined and dried using Genevac centrifugal evaporator to afford 6-(3-isopropyl-5-(piperidin-3-yl)-1H-indol-2-yl)-8-methoxy-[1,2,4]triazolo[1,5-a]pyridine (9.5 mg, 0.159 mmol, 26% yield). LCMS retention time 1.27 min [E]. MS m z: 390.1 (M+H); $^1$H NMR (400 MHz, DMSO-$d_6$) δ ppm 1.23 (s, 2H) 1.45 (d, J=6.85 Hz, 6H) 2.07 (s, 2H) 2.25-2.39 (m, 3H) 2.62-2.73 (m, 3H) 4.02-4.13 (m, 4H) 7.03 (d, J=8.07 Hz, 1H) 7.14 (s, 1H) 7.32 (d, J=8.56 Hz, 1H) 7.57 (s, 1H) 8.47-8.59 (m, 2H) 11.16 (s, 1H).

The following Examples were prepared according to the general procedure used to prepare Example 181.

TABLE 14

| Ex. No. | Structure | Mol Wt. | LCMS MH+ | Ret Time (min) | HPLC Method |
|---|---|---|---|---|---|
| 182 | 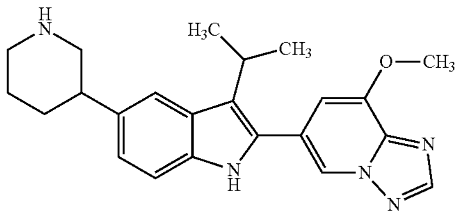 | 389.5 | 390.1 | 1.27 | E |
| 183 | 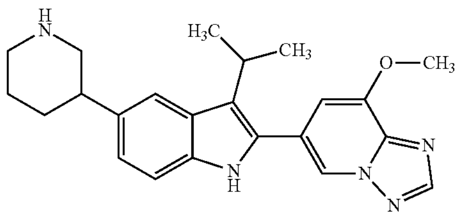 [SMILES: COc1cc(-c2[nH]c3ccc(C4CCCNC4)cc3c2C(C)C)cn2ncnc12] | 389.5 | 390.1 | 1.27 | E |
| 184 | 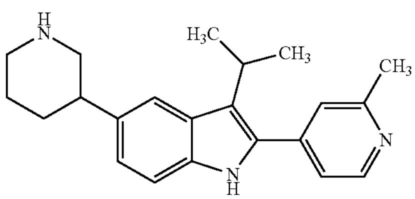 [SMILES: Cc1cc(-c2[nH]c3ccc(C4CCCNC4)cc3c2C(C)C)ccn1] | 333.5 | 334.2 | 1.94 | E |
| 185 | 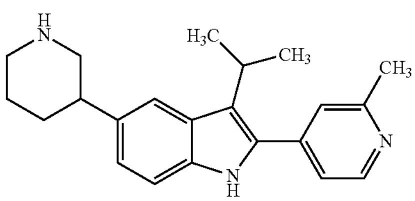 [SMILES: Cc1cc(-c2[nH]c3ccc(C4CCCNC4)cc3c2C(C)C)ccn1] | 333.5 | 334.2 | 1.94 | E |
| 186 | 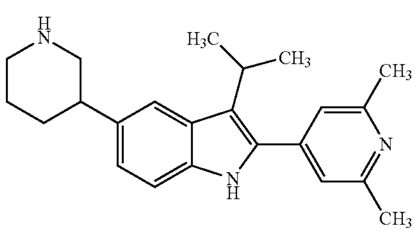 [SMILES: Cc1cc(-c2[nH]c3ccc(C4CCCNC4)cc3c2C(C)C)cc(C)n1] | 347.5 | 348.3 | 1.42 | D |
| 187 | 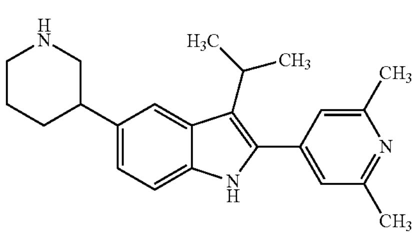 [SMILES: Cc1cc(-c2[nH]c3ccc(C4CCCNC4)cc3c2C(C)C)cc(C)n1] | 347.5 | 348.3 | 1.42 | D |

TABLE 14-continued

| Ex. No. | Structure | Mol Wt. | LCMS MH+ | Ret Time (min) | HPLC Method |
|---|---|---|---|---|---|
| 188 | 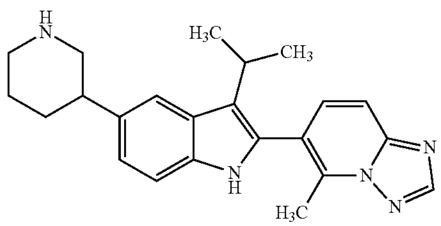 [SMILES: Cc1c(-c2[nH]c3ccc(C4CCCNC4)cc3c2C(C)C)ccc2ncnn12] | 373.5 | 374.2 | 1.33 | F |

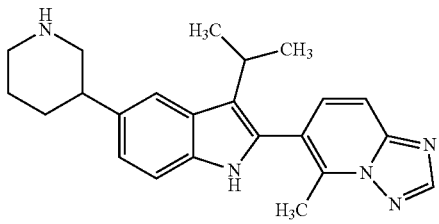

| 189 | | 387.5 | 388.2 | 1.15 | E |

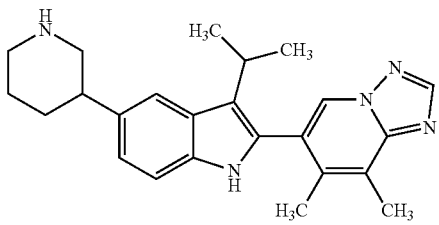 [SMILES: Cc1c(-c2[nH]c3ccc(C4CCCNC4)cc3c2C(C)C)cn2ncnc2c1C]

| 190 | | 387.5 | 388.3 | 1.14 | E |

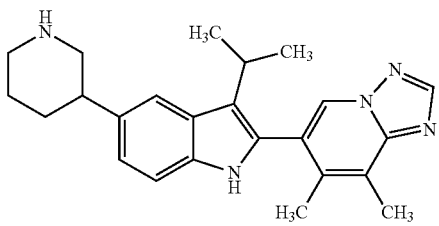

Example 191

2-(dimethylamino)-1-(3-(3-isopropyl-2-(8-methoxy-[1,2,4]triazolo[1,5-a]pyridin-6-yl)-1H-indol-5-yl)piperidin-1-ylethanone (191)

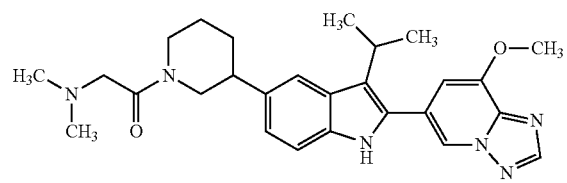

2-(dimethylamino)-1-(3-(3-isopropyl-2-(8-methoxy-[1,2,4]triazolo[1,5-a]pyridin-6-yl)-1H-indol-5-yl)piperidin-1-ylethanone (8.4 mg, 0.018 mmol, 23% yield) was prepared according to the general procedure described in Example 28 using 6-(3-isopropyl-5-(piperidin-3-yl)-1H-indol-2-yl)-8-methoxy-[1,2,4]triazolo[1,5-a]pyridine (30 mg, 0.077 mmol) as the starting intermediate. LCMS retention time 1.55 min [E]. MS m/z: 475.2 (M+H); $^1$H NMR (400 MHz, DMSO-Jo) δ ppm 1.18-1.30 (m, 1H) 1.39-1.53 (m, 6H) 1.73-1.86 (m, 2H) 2.02-2.08 (m, 4H) 2.20-2.35 (m, 6H) 3.05-3.21 (m, 4H) 3.99-4.13 (m, 4H) 7.01-7.18 (m, 2H) 7.31-7.37 (m, 1H) 7.55-7.69 (m, 1H) 8.43-8.62 (m, 2H) 11.02-11.20 (m, 1H).

The following Examples were prepared according to the general procedure used to prepare Example 191, TABLE 15
| Ex. No. | Structure | Mol Wt. | LCMS MH+ | Ret Time (min) | HPLC Method |
|---|---|---|---|---|---|
| 192 | 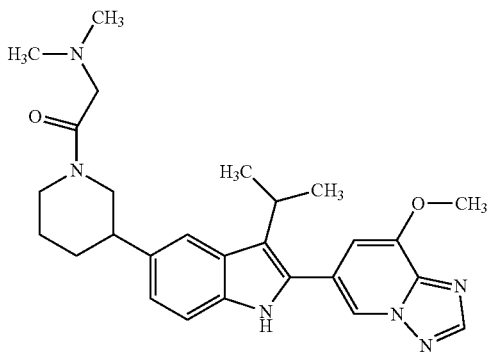 [SMILES: COc1cc(-c2[nH]c3ccc(C4CCCN(C(=O)CN(C)C)C4)cc3c2C(C)C)cn2ncnc12] | 474.6 | 475.1 | 1.55 | E |
| 193 | 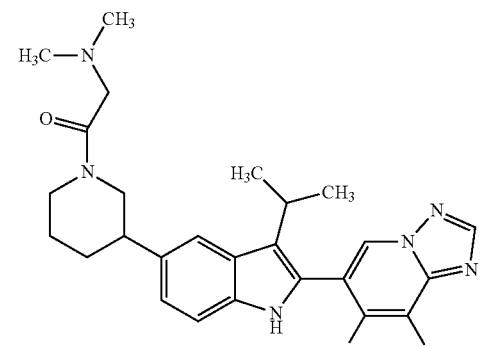 | 472.6 | 473.4 | 1.44 | E |
| 194 | 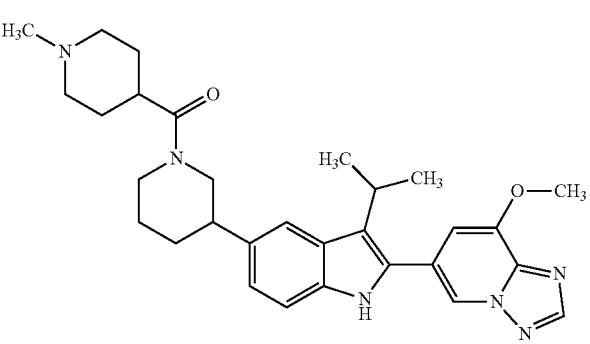 [SMILES: COc1cc(-c2[nH]c3ccc(C4CCCN(C(=O)C5CCN(C)CC5)C4)cc3c2C(C)C)cn2ncnc12] | 514.7 | 515.2 | 1.63 | E |
| 195 | 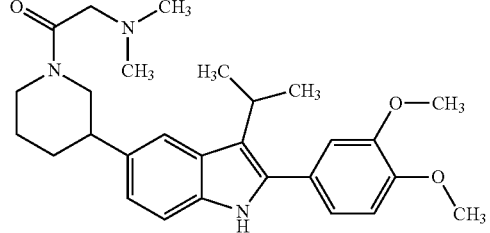 [SMILES: COc1ccc(-c2[nH]c3ccc(C4CCCN(C(=O)CN(C)C)C4)cc3c2C(C)C)cc1OC] | 463.6 | 464.0 | 1.73 | E |

TABLE 15-continued
| Ex. No. | Structure | Mol Wt. | LCMS MH+ | Ret Time (min) | HPLC Method |
|---|---|---|---|---|---|
| 196 | 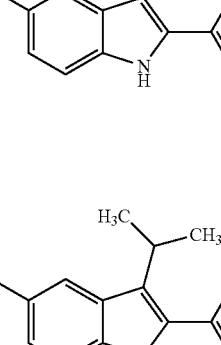 | 474.6 | 475.3 | 1.848 | E |
| 197 | 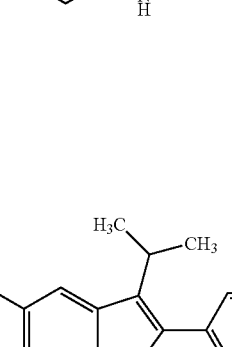 | 474.6 | 475.4 | 1.10 | E |
| 198 | 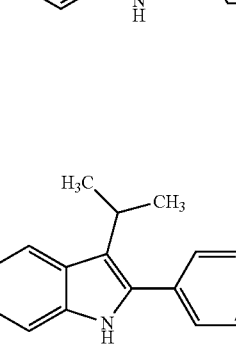 | 471.7 | 472.3 | 1.74 | F |
| 199 | 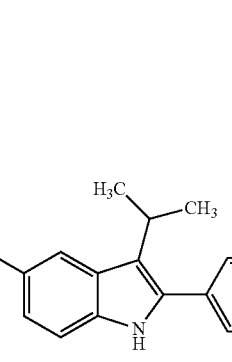 | 429.6 | 430.3 | 2.031 | E |
| 200 | 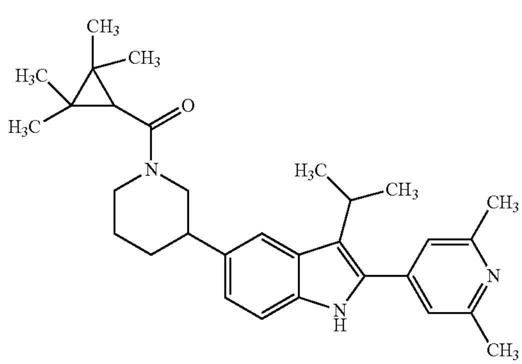 | 471.7 | 472.3 | 1.77 | E |

TABLE 15-continued

| Ex. No. | Structure | Mol Wt. | LCMS MH+ | Ret Time (min) | HPLC Method |
|---|---|---|---|---|---|
| 201 | 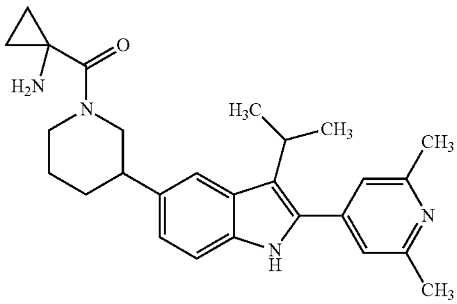 | 430.6 | 431.3 | 1.67 | E |
| 202 | 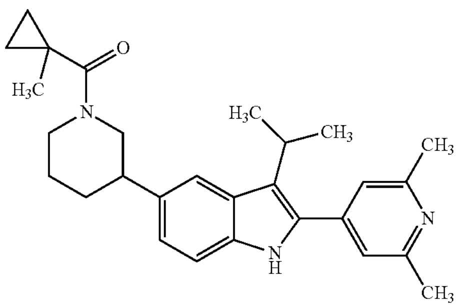 [SMILES: Cc1cc(-c2[nH]c3ccc(C4CCCN(C(=O)C5(C)CC5)C4)cc3c2C(C)C)cc(C)n1] | 429.6 | 430.3 | 2.04 | E |
| 203 | 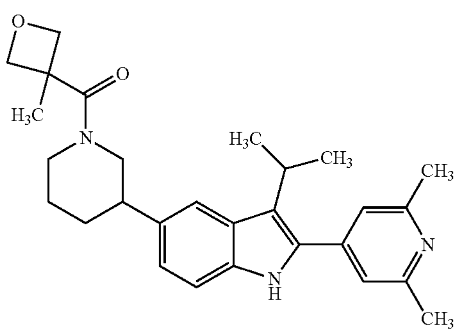 [SMILES: Cc1cc(-c2[nH]c3ccc(C4CCCN(C(=O)C5(C)COC5)C4)cc3c2C(C)C)cc(C)n1] | 445.6 | 446.3 | 1.358 | F |
| 204 | 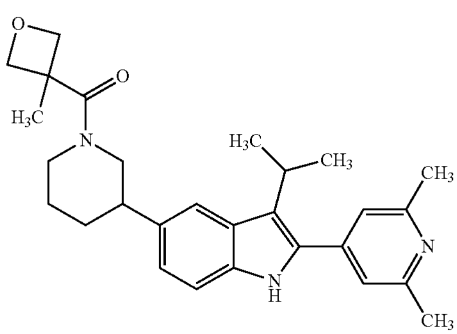 [SMILES: Cc1cc(-c2[nH]c3ccc(C4CCCN(C(=O)C5(C)COC5)C4)cc3c2C(C)C)cc(C)n1] | 445.6 | 446.3 | 1.87 | E |
| 205 | 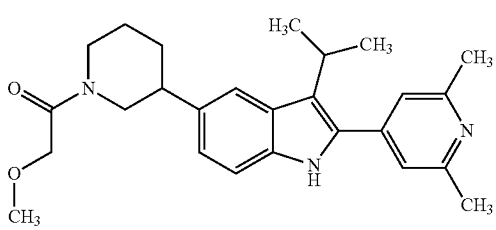 [SMILES: COCC(=O)N1CCCC(c2ccc3[nH]c(-c4cc(C)nc(C)c4)c(C(C)C)c3c2)C1] | 419.6 | 420.2 | 1.327 | F |

TABLE 15-continued

| Ex. No. | Structure | Mol Wt. | LCMS MH+ | Ret Time (min) | HPLC Method |
|---|---|---|---|---|---|
| 206 | 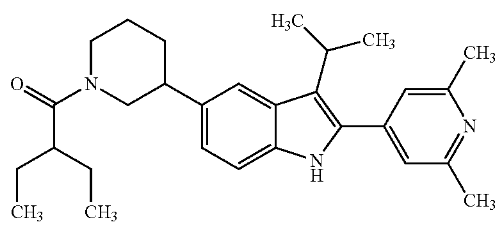 [SMILES: CCC(CC)C(=O)N1CCCC(c2ccc3[nH]c(-c4cc(C)nc(C)c4)c(C(C)C)c3c2)C1] | 445.7 | 446.3 | 2.25 | E |
| 207 | 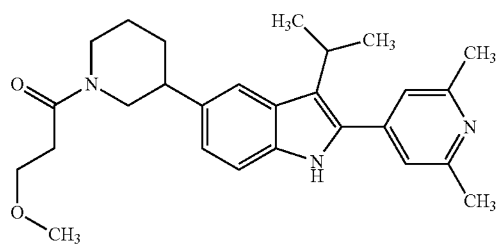 [SMILES: COCCC(=O)N1CCCC(c2ccc3[nH]c(-c4cc(C)nc(C)c4)c(C(C)C)c3c2)C1] | 433.6 | 434.3 | 1.371 | F |
| 208 | 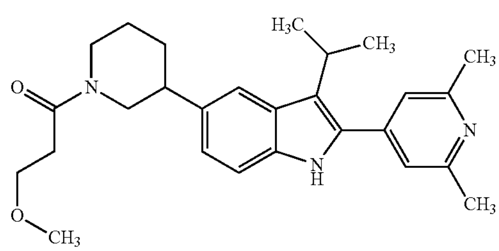 [SMILES: COCCC(=O)N1CCCC(c2ccc3[nH]c(-c4cc(C)nc(C)c4)c(C(C)C)c3c2)C1] | 433.6 | 434.3 | 1.89 | E |
| 209 | 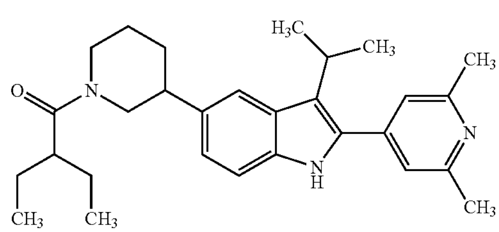 [SMILES: CCC(CC)C(=O)N1CCCC(c2ccc3[nH]c(-c4cc(C)nc(C)c4)c(C(C)C)c3c2)C1] | 445.7 | 446.3 | 2.26 | E |
| 210 | 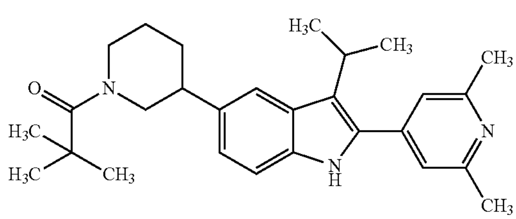 [SMILES: Cc1cc(-c2[nH]c3ccc(C4CCCN(C(=O)C(C)(C)C)C4)cc3c2C(C)C)cc(C)n1] | 431.6 | 432.3 | 1.594 | F |

Example 211

1-(3-(3-isopropyl-2-(8-methoxy-[1,2,4]triazolo[1,5-a]pyridin-6-yl)-1H-indol-5-yl) piperidin-1-yl)-2-(methylamino)ethan-1-one (211)

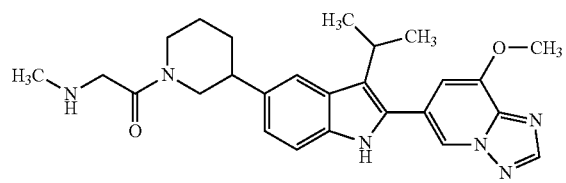

1-(3-(3-isopropyl-2-(8-methoxy-[1,2,4]triazolo[1,5-a]pyridin-6-yl)-1H-indol-5-yl)piperidin-1-yl)-2-(methylamino)ethan-1-one was prepared according to the general procedure described in Example 337 using 6-(3-isopropyl-5-(piperidin-3-yl)-1H-indol-2-yl)-8-methoxy-[1,2,4]triazolo[1,5-a]pyridine (30 mg, 0.077 mmol) as the starting intermediate. LCMS retention time 1.23 min [E], MS m/z: 461.3 (M+H); $^1$H NMR (400 MHz, DMSO-$d_6$) δ ppm 1.18-1.30 (m, 1H) 1.39-1.53 (m, 6H) 1.73-1.86 (m, 2H) 2.02-2.08 (m, 4H) 2.20-2.35 (m, 6H) 3.05-3.21 (m, 4H) 3.99-4.13 (m, 4H) 7.01-7.18 (m, 2H) 7.31-7.37 (m, 1H) 7.55-7.69 (m, 1H) 8.43-8.62 (m, 2H) 11.02-11.20 (m, 1H).

The following Examples were prepared according to the general procedure used to prepare Example 211.

TABLE 16

| Ex. No. | Structure | Mol Wt. | LCMS MH+ | Ret Time (min) | HPLC Method |
|---|---|---|---|---|---|
| 212 | 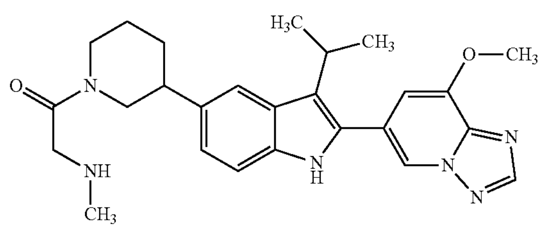 [SMILES: CNCC(=O)N1CCCC(c2ccc3[nH]c(-c4cc(OC)c5ncnn5c4)c(C(C)C)c3c2)C1] | 460.6 | 461.3 | 1.22 | E |
| 213 | 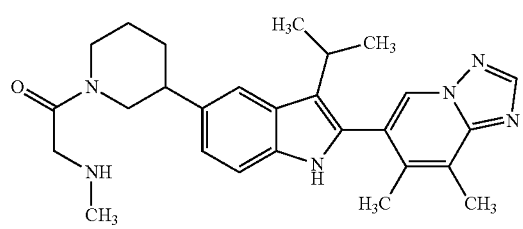 [SMILES: CNCC(=O)N1CCCC(c2ccc3[nH]c(-c4cn5ncnc5c(C)c4C)c(C(C)C)c3c2)C1] | 458.6 | 459.3 | 1.28 | E |
| 214 | 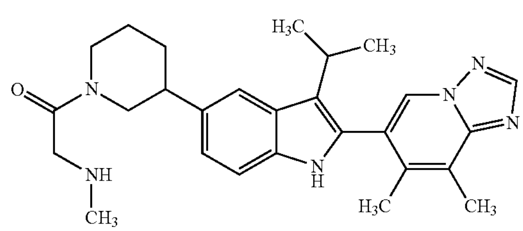 [SMILES: CNCC(=O)N1CCCC(c2ccc3[nH]c(-c4cn5ncnc5c(C)c4C)c(C(C)C)c3c2)C1] | 458.6 | 459.3 | 1.28 | E |
| 215 | 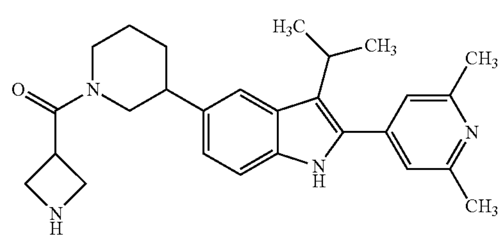 [SMILES: Cc1cc(-c2[nH]c3ccc(C4CCCN(C(=O)C5CNC5)C4)cc3c2C(C)C)cc(C)n1] | 430.6 | 431.3 | 1.546 | E |

| Ex. No. | Structure | Mol Wt. | LCMS MH+ | Ret Time (min) | HPLC Method |
|---|---|---|---|---|---|
| 216 | 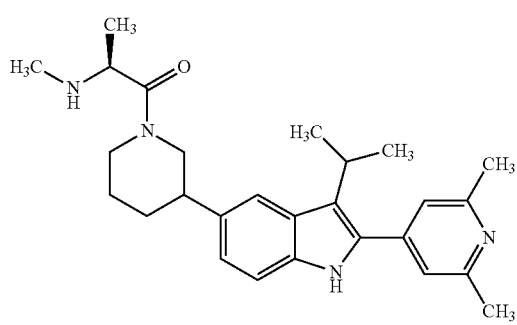 | 432.6 | 433.3 | 1.124 | F |
| 217 | 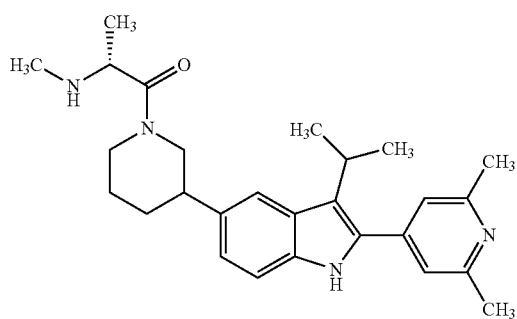 | 432.6 | 433.3 | 1.12 | F |
| 218 | 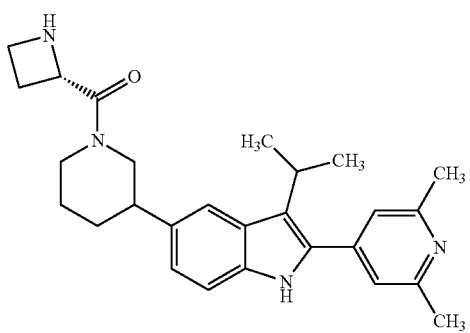 [SMILES: Cc1cc(-c2[nH]c3ccc(C4CCCN(C(=O)[C@@H]5CCN5)C4)cc3c2C(C)C)cc(C)n1] | 430.6 | 431.3 | 1.589 | E |
| 219 | 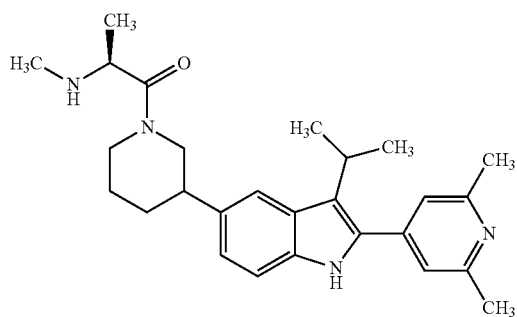 | 432.6 | 433.3 | 1.64 | E |

151 152

TABLE 16-continued

| Ex. No. | Structure | Mol Wt. | LCMS MH+ | Ret Time (min) | HPLC Method |
|---|---|---|---|---|---|
| 220 | 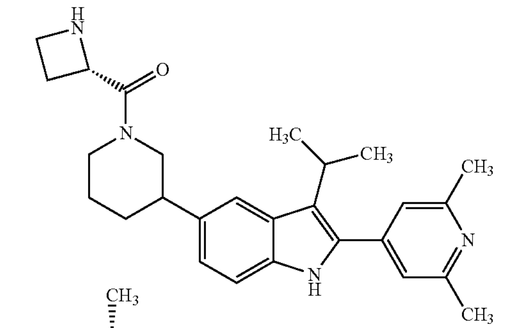 | 430.6 | 431.3 | 1.61 | E |
| 221 | 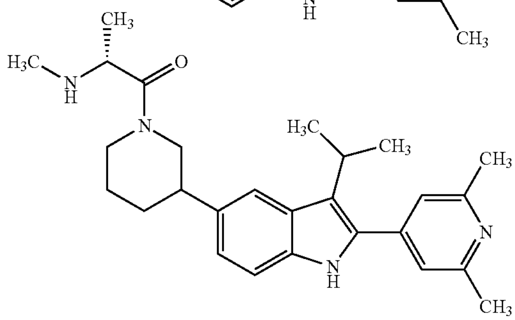 | 432.6 | 433.3 | 1.63 | E |

Example 222

2-(3-(3-isopropyl-2-(8-methoxy-[1,2,4]triazolo[1,5-a]pyridin-6-yl)-1H-indol-5-yl) piperidin-1-yl)-N,N-dimethylacetamide (222)

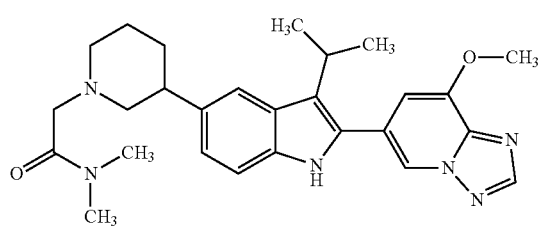

2-(3-(3-isopropyl-2-(8-methoxy-[1,2,4]triazolo[1,5-a]pyridin-6-yl)-1H-indol-5-yl) piperidin-1-yl)-N,N-dimethylacetamide (8.8 mg, 0.019 mmol, 24.07% yield) was prepared according to the general procedure described in Examples 177 and 178 using 6-(3-isopropyl-5-(piperidin-3-yl)-1H-indol-2-yl)-8-methoxy-[1,2,4]triazolo[1,5-a]pyridine (30 mg, 0.077 mmol) as the starting intermediate. LCMS retention time 1.63 min [E], MS m/z: 475.2 (M+H): $^1$H NMR (400 MHz, DMSO-$d_6$) δ ppm 1.16-1.31 (m, 2H) 1.35-1.53 (m, 6H) 1.90-2.06 (m, 2H) 2.29-2.38 (m, 4H) 2.79-2.89 (m, 3H) 2.93-3.08 (m, 4H) 3.10-3.22 (m, 2H) 3.98-4.17 (m, 4H) 6.97-7.06 (m, 1H) 7.11-7.20 (m, 1H) 7.27-7.42 (m, 1H) 7.52-7.68 (m, 1H) 8.40-8.61 (m, 2H) 11.06-11.22 (m, 1H).

The following Examples were prepared according to the general procedure used to prepare Example 222.

TABLE 17

| Ex. No | Structure | Mol Wt. | LCMS MH+ | Ret Time (min) | HPLC Method |
|---|---|---|---|---|---|
| 223 | 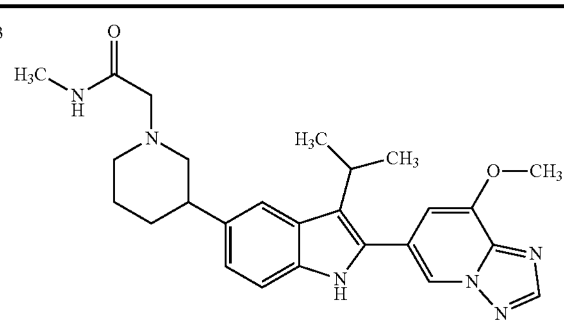 | 460.6 | 461.2 | 1.81 | E |

TABLE 17-continued

| Ex. No | Structure | Mol Wt. | LCMS MH+ | Ret Time (min) | HPLC Method |
|---|---|---|---|---|---|
| 224 | 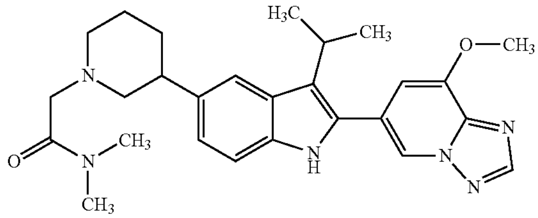 [SMILES: COc1cc(-c2[nH]c3ccc(C4CCCN(CC(=O)N(C)C)C4)cc3c2C(C)C)cn2ncnc12] | 474.6 | 475.1 | 1.61 | E |
| 225 | 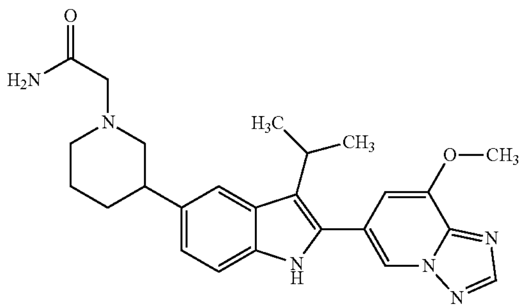 [SMILES: COc1cc(-c2[nH]c3ccc(C4CCCN(CC(N)=O)C4)cc3c2C(C)C)cn2ncnc12] | 446.6 | 447.3 | 1.45 | E |
| 226 | 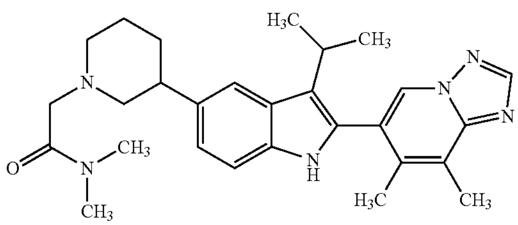 | 472.6 | 473.3 | 1.45 | E |
| 227 | 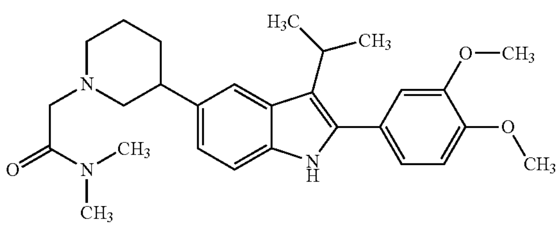 [SMILES: COc1ccc(-c2[nH]c3ccc(C4CCCN(CC(=O)N(C)C)C4)cc3c2C(C)C)cc1OC] | 463.6 | 464.0 | 1.77 | E |
| 228 | 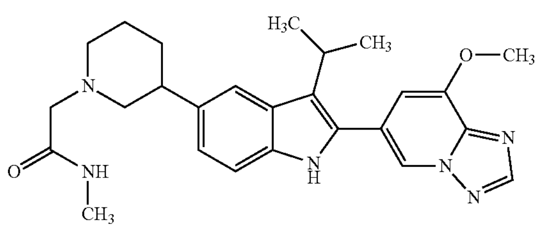 [SMILES: CNC(=O)CN1CCCC(c2ccc3[nH]c(-c4cc(OC)c5ncnn5c4)c(C(C)C)c3c2)C1] | 460.6 | 461.1 | 1.78 | E |
| 229 | 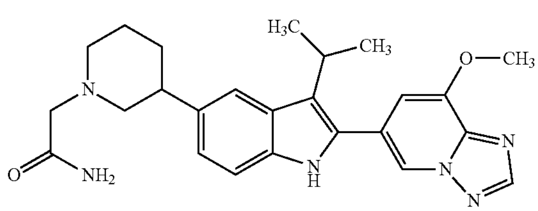 [SMILES: COc1cc(-c2[nH]c3ccc(C4CCCN(CC(N)=O)C4)cc3c2C(C)C)cn2ncnc12] | 446.6 | 447.1 | 1.77 | E |

TABLE 17-continued

| Ex. No | Structure | Mol Wt. | LCMS MH+ | Ret Time (min) | HPLC Method |
|---|---|---|---|---|---|
| 230 | 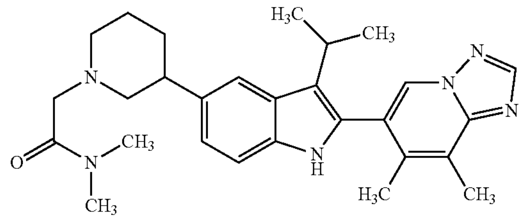 | 472.6 | 473.4 | 1.5 | E |
| 231 | 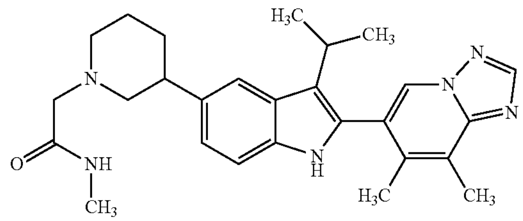 [SMILES: CNC(=O)CN1CCCC(c2ccc3[nH]c(-c4cn5ncnc5c(C)c4C)c(C(C)C)c3c2)C1] | 458.6 | 459.3 | 1.65 | E |
| 232 | 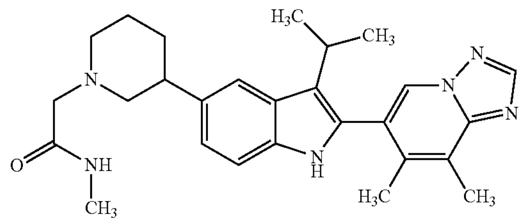 [SMILES: CNC(=O)CN1CCCC(c2ccc3[nH]c(-c4cn5ncnc5c(C)c4C)c(C(C)C)c3c2)C1] | 458.6 | 459.3 | 1.66 | E |
| 233 | 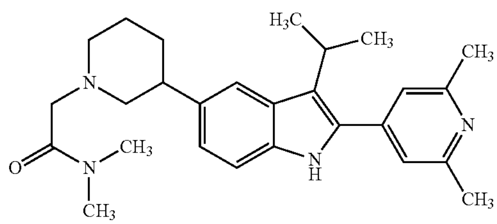 [SMILES: Cc1cc(-c2[nH]c3ccc(C4CCCN(CC(=O)N(C)C)C4)cc3c2C(C)C)cc(C)n1] | 432.6 | 433.3 | 1.83 | E |
| 234 | 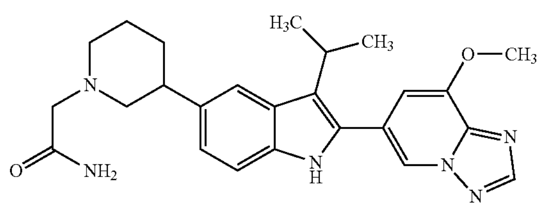 [SMILES: COc1cc(-c2[nH]c3ccc(C4CCCN(CC(N)=O)C4)cc3c2C(C)C)cn2ncnc12] | 446.6 | 447.1 | 1.77 | E |
| 235 | 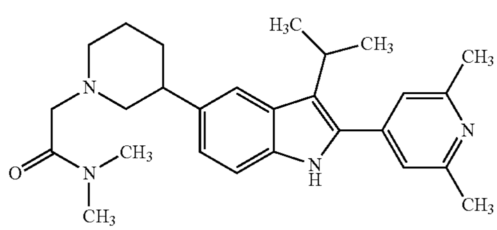 [SMILES: Cc1cc(-c2[nH]c3ccc(C4CCCN(CC(=O)N(C)C)C4)cc3c2C(C)C)cc(C)n1] | 432.6 | 433.3 | 1.84 | E |

Example 236

6-(3-isopropyl-5-(1-isopropylpiperidin-3-yl)-1H-indol-2-yl)-8-methoxy-[1,2,4]triazolo[1,5-a]pyridine

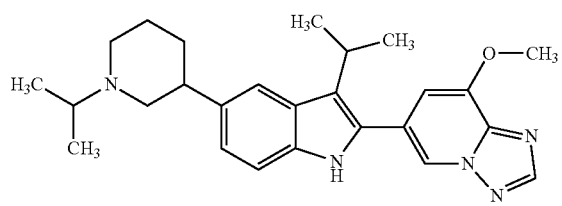

(236)

6-(3-isopropyl-5-(1-isopropylpiperidin-3-yl)-1H-indol-2-yl)-8-methoxy-[1,2,4]triazolo[1,5-a]pyridine (10.2 mg, 0.024 mmol, 31% yield) was prepared according to the general procedure described in Examples 152 and 153 using 6-(3-isopropyl-5-(piperidin-3-yl)-1H-indol-2-yl)-8-methoxy-[1,2,4]triazolo[1,5-a]pyridine (30 mg, 0.077 mmol) as the starting intermediate. LCMS retention time 1.44 min [E], MS m/z: 432.1 (M+H); $^1$H NMR (400 MHz, DMSO-$d_6$) δ ppm 1.45 (d, J=7.09 Hz, 6H) 1.84-1.98 (m, 3H) 2.23-2.37 (m, 3H) 2.64-2.75 (m, 6H) 3.17 (d, J=4.65 Hz, 3H) 4.07 (s, 4H) 7.05 (d, J=8.31 Hz, 1H) 7.15 (s, 1H) 7.31 (d, J=8.31 Hz, 1H) 7.61 (s, 1H) 8.44-8.60 (m, 2H) 11.13 (s, 1H).

The following Examples were prepared according to the general procedure used to prepare Example 236.

TABLE 18

| Ex. No. | Structure | Mol Wt. | LCMS MH+ | Ret Time (min) | HPLC Method |
|---|---|---|---|---|---|
| 237 | 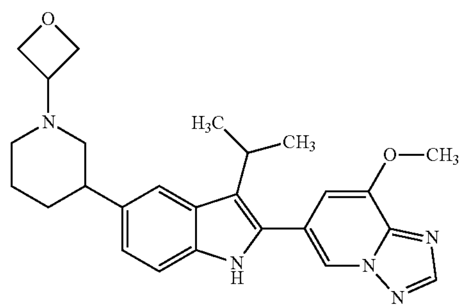 [SMILES: COc1cc(-c2[nH]c3ccc(C4CCCN(C5COC5)C4)cc3c2C(C)C)cn2ncnc12] | 445.6 | 446.2 | 1.92 | E |
| 238 | 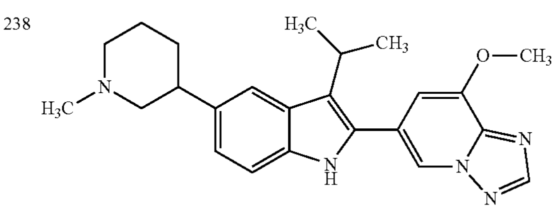 | 403.5 | 404.2 | 1.16 | E |
| 239 | 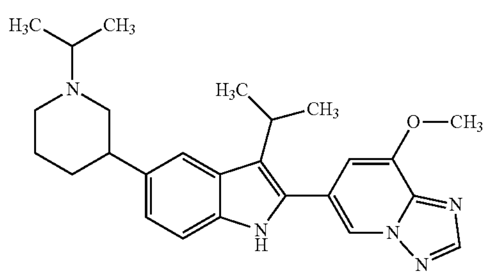 [SMILES: COc1cc(-c2[nH]c3ccc(C4CCCN(C(C)C)C4)cc3c2C(C)C)cn2ncnc12] | 431.6 | 432.2 | 1.43 | E |
| 240 | 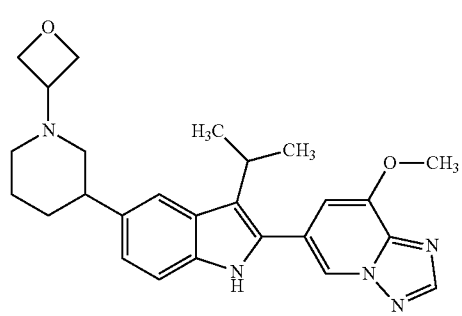 [SMILES: COc1cc(-c2[nH]c3ccc(C4CCCN(C5COC5)C4)cc3c2C(C)C)cn2ncnc12] | 445.6 | 446.1 | 1.84 | E |

TABLE 18-continued

| Ex. No. | Structure | Mol Wt. | LCMS MH+ | Ret Time (min) | HPLC Method |
|---|---|---|---|---|---|
| 241 | 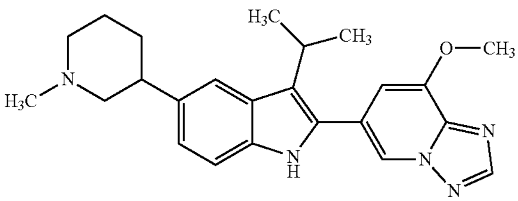 [SMILES: COc1cc(-c2[nH]c3ccc(C4CCCN(C)C4)cc3c2C(C)C)cn2ncnc12] | 403.5 | 404.3 | 1.17 | E |
| 242 | 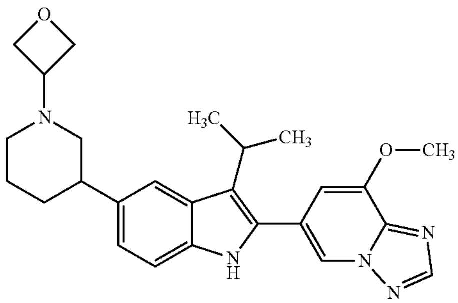 [SMILES: COc1cc(-c2[nH]c3ccc(C4CCCN(C5COC5)C4)cc3c2C(C)C)cn2ncnc12] | 445.6 | 446.2 | 1.6 | E |
| 243 | 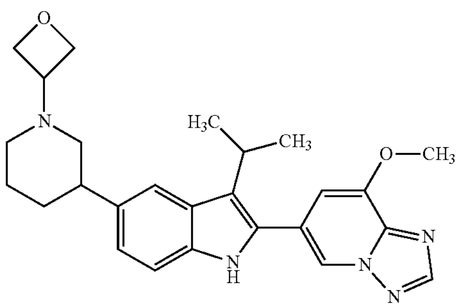 [SMILES: COc1cc(-c2[nH]c3ccc(C4CCCN(C5COC5)C4)cc3c2C(C)C)cn2ncnc12] | 445.6 | 446.3 | 1.16 | E |
| 244 | 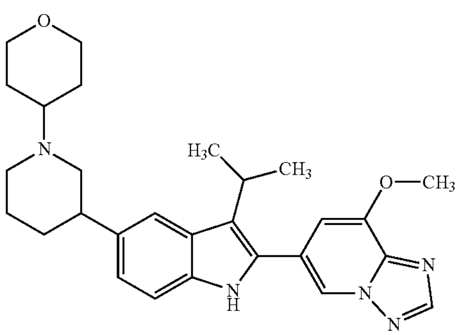 [SMILES: COc1cc(-c2[nH]c3ccc(C4CCCN(C5CCOCC5)C4)cc3c2C(C)C)cn2ncnc12] | 473.6 | 474.2 | 1.63 | E |
| 245 | 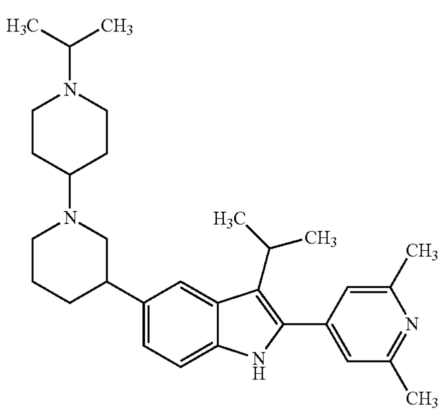 [SMILES: Cc1cc(-c2[nH]c3ccc(C4CCCN(C5CCN(C(C)C)CC5)C4)cc3c2C(C)C)cc(C)n1] | 472.7 | 473.0 | 1.61 | E |

TABLE 18-continued

| Ex. No. | Structure | Mol Wt. | LCMS MH+ | Ret Time (min) | HPLC Method |
|---|---|---|---|---|---|
| 246 | 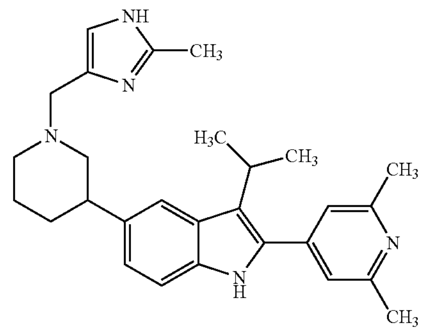 [SMILES: Cc1cc(-c2[nH]c3ccc(C4CCCN(Cc5c[nH]c(C)n5)C4)cc3c2C(C)C)cc(C)n1] | 441.6 | 442.3 | 1.52 | E |
| 247 | 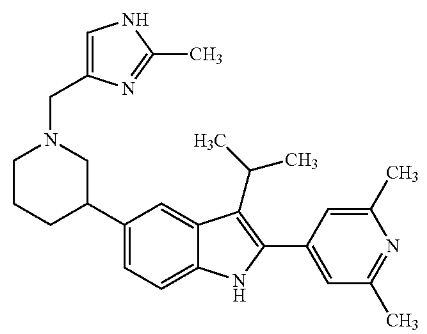 [SMILES: Cc1cc(-c2[nH]c3ccc(C4CCCN(Cc5c[nH]c(C)n5)C4)cc3c2C(C)C)cc(C)n1] | 441.6 | 442.3 | 1.52 | E |

Example 248

1-(3-(3-isopropyl-2-(8-methoxy-[1,2,4]triazolo[1,5-a]pyridin-6-yl)-1H-indol-5-yl)piperidin-1-yl)-2-methylpropan-2-ol

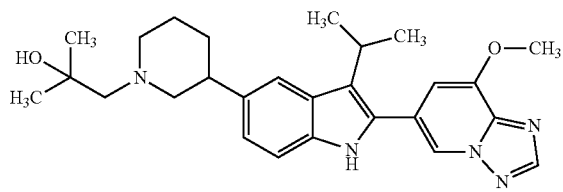

(248)

1-(3-(3-isopropyl-2-(8-methoxy-[1,2,4]triazolo[1,5-a]pyridin-6-yl)-1H-indol-5-yl)piperidin-1-yl)-2-methylpropan-2-ol (9.2 mg, 0.019 mmol, 24% yield) was prepared according to the procedure described in Examples 152 and 153 using 6-(3-isopropyl-5-(piperidin-3-yl)-1H-indol-2-yl)-8-methoxy-[1,2,4]triazolo[1,5-a]pyridine (70 mg, 0.180 mmol) as the starting intermediate. LCMS retention time 1.79 min [E], MS m/z: 462.2 (M+H); $^1$H NMR (400 MHz, DMSO-t/o) δ ppm 1.23 (s, 1H) 1.45 (d, J=7.09 Hz, 6H) 1.57-1.75 (m, 2H) 1.84 (d, J=10.52 Hz, 3H) 2.07-2.29 (m, 4H) 2.67 (d, J=1.96 Hz, 3H) 2.84 (br. s, 1H) 3.03 (d, J=9.54 Hz, 3H) 3.95-4.14 (m, 4H) 7.02 (d, J=8.31 Hz, 1H) 7.15 (s, 1H) 7.30 (d, J=8.31 Hz, 1H) 7.51-7.67 (m, 1H) 8.45-8.61 (m, 2H) 11.11 (s, 1H).

The following Examples were prepared according to the general procedure used to prepare Example 248.

TABLE 19

| Ex. No. | Structure | Mol Wt. | LCMS MH+ | Ret Time (min) | HPLC Method |
|---|---|---|---|---|---|
| 249 | 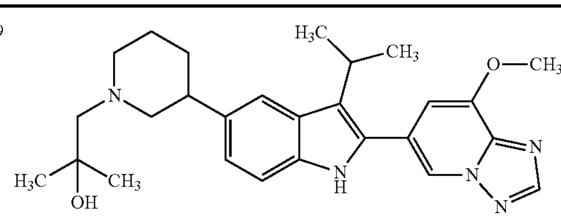 | 461.6 | 462.3 | 1.47 | E |

TABLE 19-continued

| Ex. No. | Structure | Mol Wt. | LCMS MH+ | Ret Time (min) | HPLC Method |
|---|---|---|---|---|---|
| 250 | 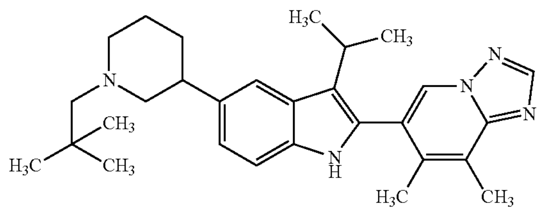 [SMILES: Cc1c(-c2[nH]c3ccc(C4CCCN(CC(C)(C)C)C4)cc3c2C(C)C)cn2ncnc2c1C] | 459.6 | 460.4 | 1.56 | E |

Example 251

6-(3-isopropyl-5-(1-(2-methoxyethyl)piperidin-3-yl)-1H-indol-2-yl)-8-methoxy-[1,2,4]triazolo[1,5-a]pyridine

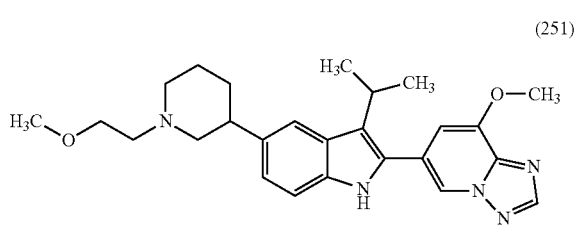 [SMILES: COCCN1CCCC(c2ccc3[nH]c(-c4cc(OC)c5ncnn5c4)c(C(C)C)c3c2)C1]

(251)

6-(3-isopropyl-5-(1-(2-methoxyethyl)piperidin-3-yl)-1H-indol-2-yl)-8-methoxy-[1,2,4]triazolo[1,5-a]pyridine was prepared according to the procedure described in Examples 152 and 153 using 6-(3-isopropyl-5-(piperidin-3-yl)-1H-indol-2-yl)-8-methoxy-[1,2,4]triazolo[1,5-a]pyridine as the starting intermediate. LCMS retention time 1.67 min [E], MS m/z: 448.3 (M+H); $^1$H NMR (400 MHz. DMSO-$d_6$) δ ppm 1.23 (s, 1H) 1.45 (d, >7.09 Hz, 6H) 1.57-1.75 (m, 2H) 1.84 (d, >10.52 Hz, 3H) 2.07-2.29 (m, 4H) 2.67 (d, J=1.96 Hz, 3H) 2.84 (br. s, 1H) 3.03 (d, >9.54 Hz, 3H) 3.95-4.14 (m, 4H) 7.02 (d, >8.31 Hz, 1H) 7.15 (s, 1H) 7.30 (d, J=8.31 Hz, 1H) 7.51-7.67 (m, 1H) 8.45-8.61 (m, 2H) 11.11 (s, 1H).

The following Examples were prepared according to the general procedure used to prepare Example 251.

TABLE 20

| Ex. No. | Structure | Mol Wt. | LCMS MH+ | Ret Time (min) | HPLC Method |
|---|---|---|---|---|---|
| 252 | 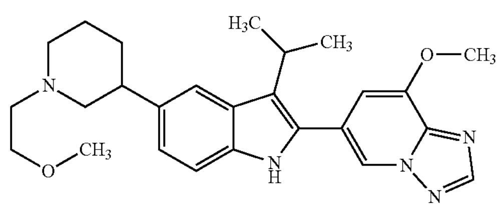 [SMILES: COCCN1CCCC(c2ccc3[nH]c(-c4cc(OC)c5ncnn5c4)c(C(C)C)c3c2)C1] | 447.6 | 448.3 | 1.35 | E |
| 253 | 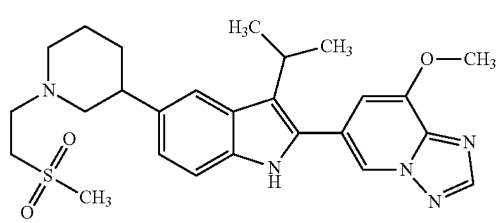 [SMILES: COc1cc(-c2[nH]c3ccc(C4CCCN(CCS(C)(=O)=O)C4)cc3c2C(C)C)cn2ncnc12] | 495.6 | 496.3 | 1.58 | E |

Example 254

2-(3-(2-(3,4-dimethoxyphenyl)-3-isopropyl-1H-indol-5-yl)piperidin-1-yl)-N-methylethanamine

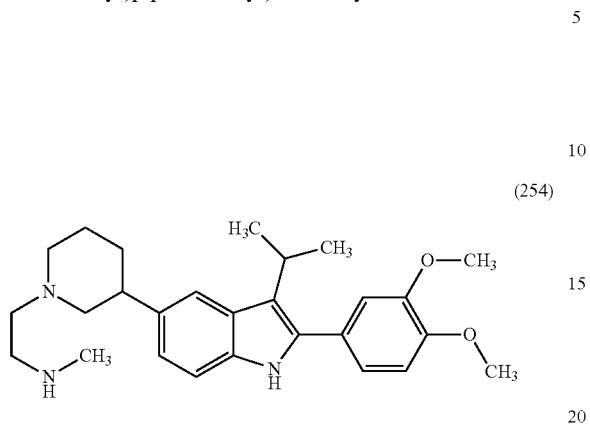

(254)

2-(3-(2-(3,4-dimethoxyphenyl)-3-isopropyl-1H-indol-5-yl)piperidin-1-yl)-N-methylethanamine (23 mg, 0.159 mmol, 26% yield) was prepared according to the general procedure described in Examples 152 and 153 using tert-butyl (2-(3-(2-(3,4-di methoxy phenyl)-3-isopropyl-1H-indol-5-yl)piperidin-1-yl)ethyl)(methyl)carbamate (150 mg, 0.280 mmol) as the starting intermediate. LCMS retention time 1.62 min [E], MS m/z: 436.0 (M+H); $^1$H NMR (400 MHz, DMSO-$d_6$) δ ppm 10.87-10.73 (m, 1H), 7.58-7.46 (s, 1H), 7.29-7.19 (m, 1H), 7.11-6.99 (m, 3H), 6.97-6.92 (m, 1H), 3.82 (d, J=7.5 Hz, 6H), 2.94-2.85 (m, 2H), 2.82-2.74 (m, 2H), 2.69-2.65 (m, 1H), 2.64-2.57 (m, 2H), 2.44-2.37 (m, 2H), 2.31 (m, 3H), 2.07-1.92 (m, 2H), 1.88 (s, 3H), 1.64-1.55 (m, 1H), 1.41 (d, J=7.0 Hz, 6H).

The following Examples were prepared according to the general procedure used to prepare Example 254.

Example 257

6-(5-(azetidin-3-yl)-3-isopropyl-1H-indol-2-yl)-8-methyl-[1,2,4]triazolo[1,5-a]pyridine

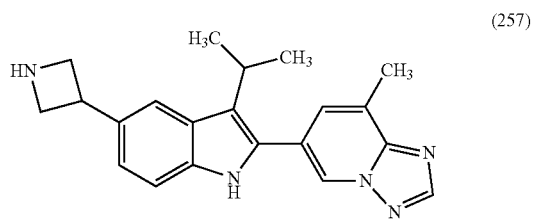

(257)

Intermediate 257A: 3-isopropyl-5-(4,4,5,5-tetramethyl-1,3,2-dioxaborolan-2-yl)-1H-indole

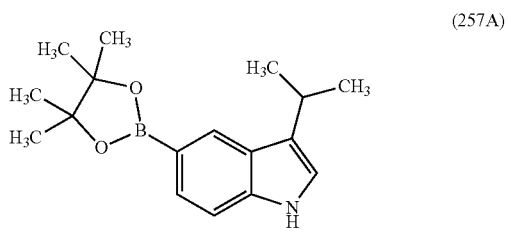

(257A)

To a solution of 5-bromo-3-isopropyl-1H-indole (5 g, 21.00 mmol) in dioxane (50 mL) were added bis(pinacolato)diboron (7.46 g, 29.4 mmol) and potassium acetate (6.18 g, 63.0 mmol), degassed the mixture with nitrogen for 5 min, then was added PdCl$_2$(dppf)-CH$_2$Cl$_2$ adduct (1.715 g, 2.100

TABLE 21

| Ex. No. | Structure | Mol Wt. | LCMS MH+ | Ret Time (min) | HPLC Method |
|---|---|---|---|---|---|
| 255 | 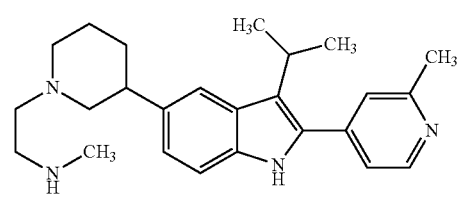 [SMILES: CNCCN1CCCC(c2ccc3[nH]c(-c4ccnc(C)c4)c(C(C)C)c3c2)C1] | 390.4 | 391.3 | 1.51 | E |
| 256 | 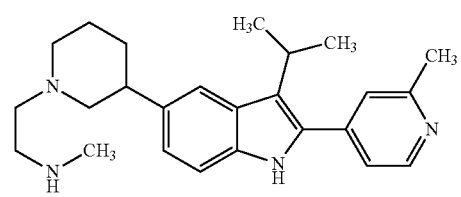 [SMILES: CNCCN1CCCC(c2ccc3[nH]c(-c4ccnc(C)c4)c(C(C)C)c3c2)C1] | 390.6 | 391.3 | 1.58 | E | mmol) and stirred in sealed tube at 90° C. for 16 h. Crude LCMS showed no starting material and formation of product. Concentrated the reaction mass, then the residue was dissolved in EtOAc (50 mL), the solid was filtered and washed with EtOAc (2×50 mL), the combined filtrates was collected and concentrated to afford crude compound. The crude material was purified by silica gel chromatography on an ISCO instrument using 120 g silica column, compound was eluted in 15% EA in hexanes, the fractions were collected and concentrated to afford 3-isopropyl-5-(4,4,5,5-tetramethyl-1,3,2-dioxaborolan-2-yl)-1H-indole (3.2 g, 11.22 mmol, 53.4% yield) white solid. LCMS retention time 3.525 min. MS m/z: 286.2 (M+H).

Intermediate 257B: tert-butyl 3-(3-isopropyl-1H-indol-5-yl)azetidine-1-carboxylate

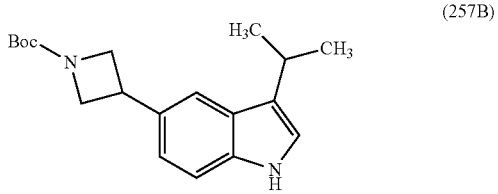 [SMILES: CC(C)c1c[nH]c2ccc(C3CN(C(=O)OC(C)(C)C)C3)cc12]

(257B)

To a solution of 3-isopropyl-5-(4,4,5,5-tetramethyl-1,3,2-dioxaborolan-2-yl)-1H-indole (1.5 g, 5.26 mmol) in dioxane (30 mL) and water (10.00 mL) solvent mixture were added tert-butyl 3-iodoazetidine-1-carboxylate (2.68 g, 9.47 mmol) and potassium phosphate tribasic (3.35 g, 15.78 mmol), degassed the mixture with nitrogen for 5 min, then was added $PdCl_2(dppf)$-$CH_2Cl_2$ adduct (0.430 g, 0.526 mmol) and stirred in sealed tube at 90° C. for 3 h. Crude LCMS showed no starting material and formation of product. Concentrated the reaction mass, then the residue was dissolved in EtOAc (50 mL), the solid was filtered and washed with EtOAc (2×30 mL), the combined filtrates was collected and concentrated to afford crude compound. The crude material was purified by silica gel chromatography on an ISCO instrument using 24 g silica column, compound was eluted in 15% EA in hexanes, the fractions were collected and concentrated to afford tert-butyl 3-(3-isopropyl-1H-indol-5-yl)azetidine-1-carboxylate (700 mg, 1.759 mmol, 33% yield) as an off-brown solid. LCMS retention time 3.439 min. MS m/z: 313.2 (M−H).

Intermediate 257C: tert-butyl 3-(2-bromo-3-isopropyl-1H-indol-5-yl)azetidine-1-carboxylate

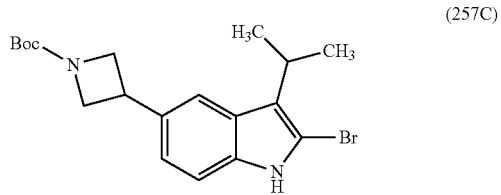 [SMILES: CC(C)c1c(Br)[nH]c2ccc(C3CN(C(=O)OC(C)(C)C)C3)cc12]

(257C)

To a solution of tert-butyl 3-(3-isopropyl-1H-indol-5-yl)azetidine-1-carboxylate (275 mg, 0.875 mmol in $CCl_4$ (10 mL) was cooled at 0° C., was added NBS (140 mg, 0.787 mmol), stirred at same temperature for 1 h. Crude LCMS showed no starting material and formation of product, filtered the reaction mass and concentrated to afford crude compound, the crude material was purified by silica gel chromatography on an ISCO instrument using 24 g silica column, compound was eluted in 10% EA in hexanes, the fractions were collected and concentrated to afford tert-butyl 3-(2-bromo-3-isopropyl-1H-indol-5-yl)azetidine-1-carboxylate (140 mg, 0.292 mmol, 33% yield) as an off-brown solid. LCMS retention time 3.105 min. MS m/z: 339.2 (M+H).

Intermediate 257D: tert-butyl-3-(3-isopropyl-2-(8-methyl-[1,2,4]triazolo[1,5-a]pyridin-6-yl)-1H-indol-5-yl)azetidine-1-carboxylate

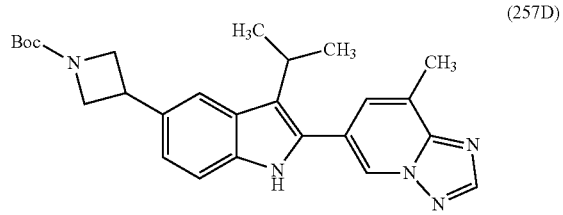 [SMILES: Cc1cc(-c2[nH]c3ccc(C4CN(C(=O)OC(C)(C)C)C4)cc3c2C(C)C)cn2ncnc12]

(257D)

tert-Butyl 3-(3-isopropyl-2-(8-methyl-[1,2,4]triazolo[1,5-a]pyridin-6-yl)-1H-indol-5-yl) azetidine-1-carboxylate (75 mg, 0.106 mmol, 27.8% yield) was prepared according to the general procedure described in Example 1 using tert-butyl 3-(2-bromo-3-isopropyl-1H-indol-5-yl)azetidine-1-carboxylate (150 mg, 0.381 mmol) as the starting intermediate. LCMS retention time 3.114 min. MS m/z: 446.4 (M+H).

The following Intermediates were prepared according to the general procedure used to prepare Intermediate 257D.

TABLE 22

| Intermediate | Structure | Mol Wt. | LCMS MH⁺ | Ret Time (min) | HPLC Method |
|---|---|---|---|---|---|
| INT-257D-2 | 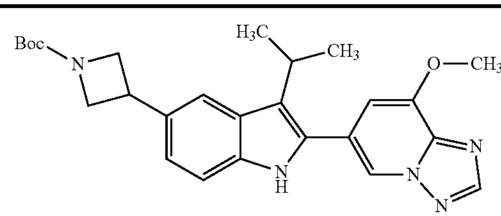 | 461.55 | 462.6 | 1.42 | L |

TABLE 22-continued

| Intermediate | Structure | Mol Wt. | LCMS MH+ | Ret Time (min) | HPLC Method |
|---|---|---|---|---|---|
| INT-257D-3 | 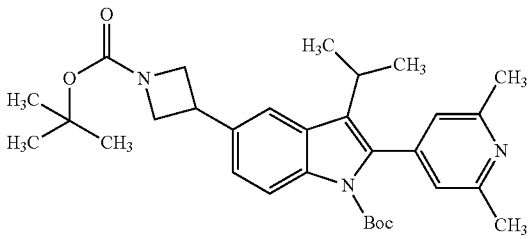 [SMILES: Cc1cc(-c2c(C(C)C)c3cc(C4CN(C(=O)OC(C)(C)C)C4)ccc3n2C(=O)OC(C)(C)C)cc(C)n1] | 519.7 | 520.4 | 1.13 | E |

Example 257

To a solution of tert-butyl 3-(3-isopropyl-2-(8-methyl-[1,2,4]triazolo[1,5-a]pyridin-6-yl)-1H-indol-5-yl)azetidine-1-carboxylate (190 mg, 0.426 mmol) in DCM (10 mL) were added 4 M dioxane in HCl (2 ml, 8.00 mmol), was stirred at room temperature for 3 h Concentrated the reaction mass, then the residue was washed with diethyl ether (20 mL) to afford 6-(5-(azetidin-3-yl)-3-isopropyl-1H-indol-2-yl)-8-methyl-[1,2,4]triazolo[1,5-a]pyridine (128 mg, 0.363 mmol, 85%). LCMS retention time 1.171 min. MS (E+) m/z: 346.2 (M+H).

The following Examples were prepared according to the general procedure used to prepare Example 257.

TABLE 23

| Ex. No. | Structure | Mol Wt. | LCMS MH+ | Ret Time (min) | HPLC Method |
|---|---|---|---|---|---|
| 258 | 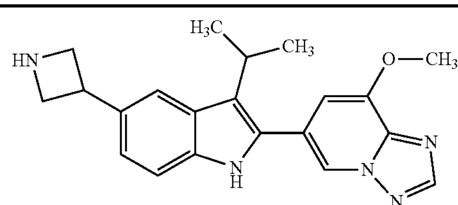 | 361.4 | 398.1 | 1.402 | E |
| 259 | 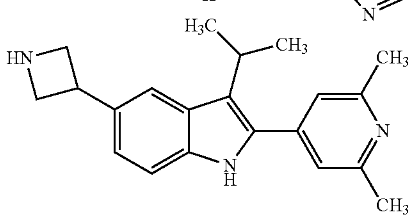 | 319.4 | 320.2 | 0.90 | E |

Example 260

2-(3-(3-isopropyl-2-(8-methyl-[1,2,4]triazolo[1,5-a]pyridin-6-yl)-1H-indol-5-yl)azetidin-1-yl)-N-methyl acetamide (260)

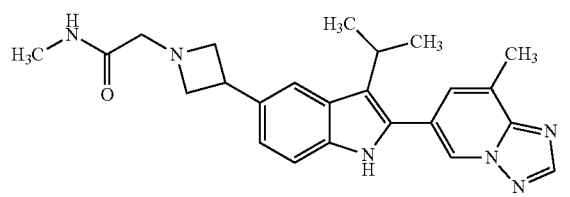

To a solution of 6-(5-(azetidin-3-yl)-3-isopropyl-1H-indol-2-yl)-8-methyl-[1,2,4]triazolo[1,5-a]pyridine (50 mg, 0.145 mmol) in THF (2.00 mL) and DMF (1.00 mL) were added DIPEA (0.126 mL, 0.724 mmol) and 2-chloro-N-methylacetamide (31.1 mg, 0.289 mmol) at room temperature, then the mixture was stirred at same temperature for 16 h. Crude LCMS showed no starting material and formation of product, concentrated the reaction mass to afford crude compound. The crude sample was purified by reverse phase prep HPLC using method D2. The fractions containing the compound was combined and evaporated to dryness using Genevac to afford 2-(3-(3-isopropyl-2-(8-methyl-[1,2,4]triazolo[1,5-a]pyridin-6-yl)-1H-indol-5-yl)azetidin-1-yl)-N-methylacetamide (5.1 mg, 0.012 mmol, 8.29%). LCMS retention time 1.536 min [H], MS m/z: 417.2 (M+H).

The following Examples were prepared according to the general procedure used to prepare Example 260.

TABLE 24

| Ex. No. | Structure | Mol Wt. | LCMS MH+ | Ret Time (min) | HPLC Method |
|---|---|---|---|---|---|
| 261 | 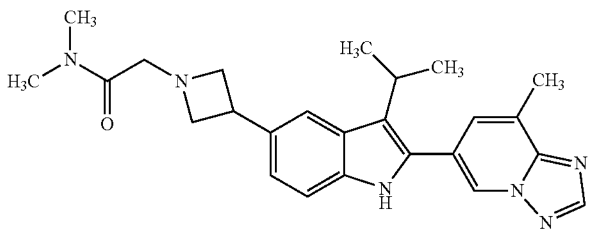 [SMILES: Cc1cc(-c2[nH]c3ccc(C4CN(CC(=O)N(C)C)C4)cc3c2C(C)C)cn2ncnc12] | 430.6 | 431.1 | 1.359 | D2 |
| 262 | 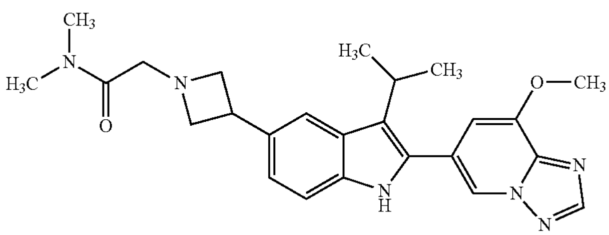 [SMILES: COc1cc(-c2[nH]c3ccc(C4CN(CC(=O)N(C)C)C4)cc3c2C(C)C)cn2ncnc12] | 446.6 | 447.3 | 1.873 | D2 |
| 263 | 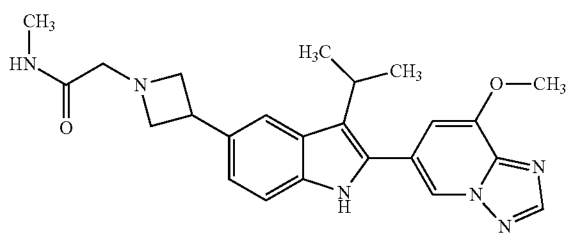 [SMILES: CNC(=O)CN1CC(c2ccc3[nH]c(-c4cc(OC)c5ncnn5c4)c(C(C)C)c3c2)C1] | 432.5 | 433.2 | 1.455 | D2 |
| 264 | 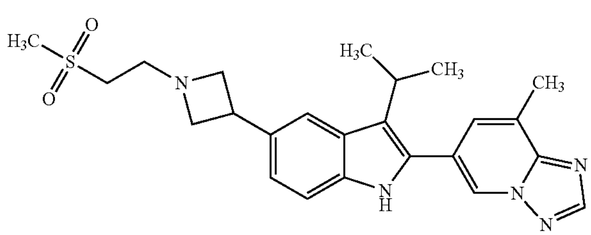 [SMILES: Cc1cc(-c2[nH]c3ccc(C4CN(CCS(C)(=O)=O)C4)cc3c2C(C)C)cn2ncnc12] | 451.6 | 452.2 | 1.398 | D2 |
| 265 | 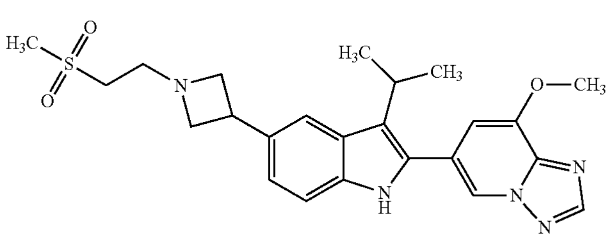 [SMILES: COc1cc(-c2[nH]c3ccc(C4CN(CCS(C)(=O)=O)C4)cc3c2C(C)C)cn2ncnc12] | 467.6 | 468.1 | 1.587 | D2 |

Example 266

2-(dimethylamino)-1-(3-(3-isopropyl-2-(8-methyl-[1,2,4]triazolo[1,5-a]pyridin-6-yl)-1H-indol-5-yl)azetidin-1-yl)ethan-1-one (266)

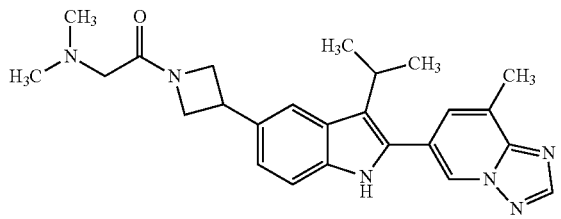

To a solution of 6-(5-(azetidin-3-yl)-3-isopropyl-1H-indol-2-yl)-8-methyl-[1,2,4]triazolo[1,5-a]pyridine (50 mg, 0.145 mmol) in DMF (1 mL) were added triethylamine (0.061 mL, 0.434 mmol), 2-(dimethylamino)acetic acid (29.9 mg, 0.289 mmol) and HATU (165 mg, 0.434 mmol) at 0° C., then stirred at room temperature for 3 h. Crude LCMS showed no starting material and formation of product. The crude material was purified by Preparative LCMS method D2, the fractions containing desired product was combined and dried using Genevac centrifugal evaporator to afford 2-(dimethylamino)-1-(3-(3-isopropyl-2-(8-methyl-[1,2,4]triazolo[1,5-a]pyridin-6-yl)-1H-indol-5-yl)azetidin-1-yl)ethanone (3.1 mg, 6.84 μmol, 5% yield). LCMS retention time 1.508 min. MS/n z: 431.2 (M+H).

Example 267

1-(3-(3-isopropyl-2-(8-methyl-[1,2,4]triazolo[1,5-a]pyridin-6-yl)-1H-indol-5-yl)azetidin-1-yl)-2-(methylamino)ethan-1-one (267)

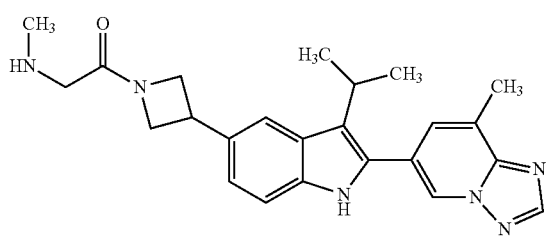

Intermediate 267A: tert-butyl (2-(3-(3-isopropyl-2-(8-methyl-[1,2,4]triazolo[1,5-a]pyridin-6-yl)-1H-indol-5-yl)azetidin-1-yl)-2-oxoethyl)(methyl)carbamate (267A)

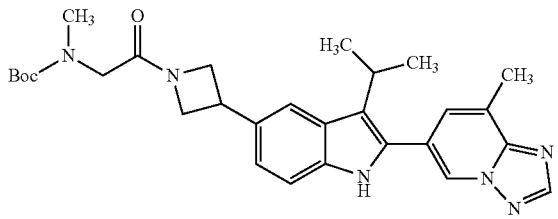

tert-butyl (2-(3-(3-isopropyl-2-(8-methyl-[1,2,4]triazolo[1,5-a]pyridin-6-yl)-1H-indol-5-yl) azetidin-1-yl)oxoethyl)(methyl)carbamate (40.6 mg, 0.079 mmol, 100%) was prepared according to the general procedure described in Example 266 using 6-(5-(azetidin-3-yl)-3-isopropyl-1H-indol-2-yl)-8-methyl-[1,2,4]triazolo[1,5-a]pyridine hydrochloride (30 mg, 0.079 mmol) as the starting intermediate. LCMS retention time 2.563 min. MS m/z: 517.0 (M+H).

Example 267

1-(3-(3-isopropyl-2-(8-methyl-[1,2,4]triazolo[1,5-a]pyridin-6-yl)-1H-indol-5-yl)azetidin-1-yl)-2-(methylamino)ethanone (7.6 mg, 0.018 mmol, 30%) was prepared according to the general procedure described in Example 128 using tert-butyl (2-(3-(3-isopropyl-2-(8-methyl-[1,2,4]triazolo[1,5-a]pyridin-6-yl)-1H-indol-5-yl)azetidin-1-yl)-2-oxoethyl)(methyl)carbamate (30 mg, 0.058 mmol) as the starting intermediate. LCMS retention time 1.118 min. MS (E$^+$) m z: 417.3 (M+H). $^1$H NMR (400 MHz, DMSO-d$_6$) δ ppm 11.23 (s, 1H), 8.82 (s, 1H), 8.65-8.36 (m, 1H), 7.85-7.51 (m, 2H), 7.39 (d, J=8.3 Hz, 1H), 7.23-6.97 (m, 1H), 4.71-4.04 (m, 5H), 2.75-2.57 (m, 4H), 2.41-2.23 (m, 4H), 1.41 (br. s., 6H).

The example in Table 25 were prepared according to the general procedure used to prepare Example 267.

TABLE 25

| Ex. No. | Structure | Mol Wt. | LCMS MH$^+$ | Ret Time (min) | HPLC Method |
|---|---|---|---|---|---|
| 268 | ![structure] | 432.5 | 433.1 | 1.307 | E |

Example 269

6-(5-(1-(2,2-dimethyltetrahydro-2H-pyran-4-yl)azetidin-3-yl)-3-isopropyl-1H-indol-2-yl)-8-methyl-[1,2,4]triazolo[1,5-a]pyridine (269)

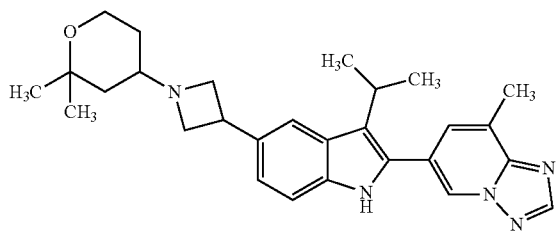

4-(3-(2-(2,6-dimethylpyridin-4-yl)-3-isopropyl-1H-indol-5-yl)azetidin-1-yl) tetrahydro-2H-thiopyran 1,1-dioxide (7.1 mg, 0.017 mmol, 11%) was prepared according to the general procedure described in Example 289 using 6-(5-(azetidin-3-yl)-3-isopropyl-1H-indol-2-yl)-8-methyl-[1,2,4]triazolo[1,5-a]pyridine hydrochloride (30 mg, 0.079 mmol) as the starting material. LCMS retention time 1.985 min. MS (E$^+$) m/z: 458.2 (M+H). $^1$H NMR (400 MHz, DMSO-d$_6$) δ ppm 8.81 (s, 1H), 8.53 (s, 1H), 7.61 (s, 2H), 7.34 (s, 1H), 7.17 (dd, J=8.4, 1.3 Hz, 1H), 3.90 (s, 2H), 3.70-3.61 (m, 7H), 3.10 (br. s., 5H), 2.67 (s, 4H), 1.69-1.54 (m, 2H), 1.43 (d, J=7.1 Hz, 6H), 1.23-1.09 (m, 7H), 1.06-0.91 (m, 2H).

The examples in Table 26 were prepared according to the general procedure used to prepare Example 269.

TABLE 26

| Ex. No. | Structure | Mol Wt. | LCMS MH$^+$ | Ret Time (min) | HPLC Method |
|---|---|---|---|---|---|
| 270 | 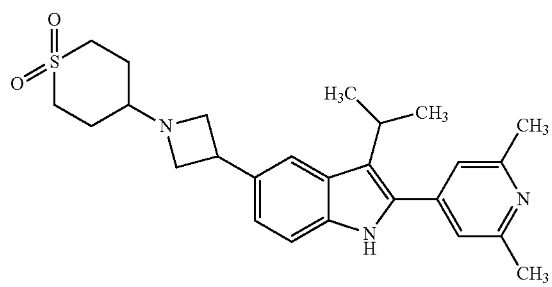 [SMILES: Cc1cc(-c2[nH]c3ccc(C4CN(C5CCS(=O)(=O)CC5)C4)cc3c2C(C)C)cc(C)n1] | 451.6 | 452.3 | 1.17 | E |
| 271 | 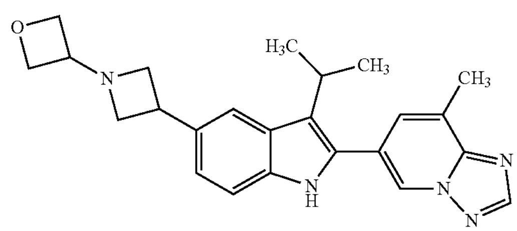 [SMILES: Cc1cc(-c2[nH]c3ccc(C4CN(C5COC5)C4)cc3c2C(C)C)cn2ncnc12] | 401.5 | 402.2 | 1.632 | E |
| 272 | 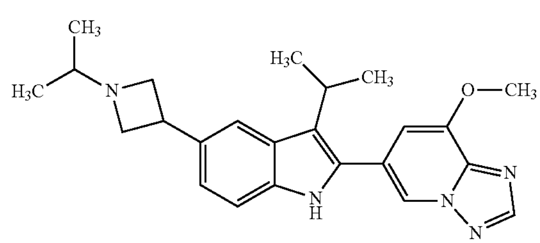 [SMILES: COc1cc(-c2[nH]c3ccc(C4CN(C(C)C)C4)cc3c2C(C)C)cn2ncnc12] | 403.5 | 404.1 | 1.388 | E |
| 273 | 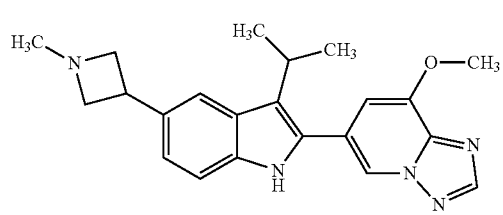 | 375.5 | 376.1 | 1.238 | E |

TABLE 26-continued

| Ex. No. | Structure | Mol Wt. | LCMS MH+ | Ret Time (min) | HPLC Method |
|---|---|---|---|---|---|
| 274 | 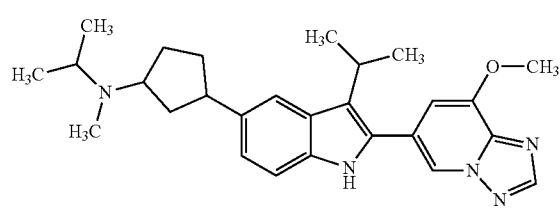 | 417.5 | 418.1 | 1.587 | E |

Examples 275 to 278

N-isopropyl-3-(3-isopropyl-2-(8-methoxy-[1,2,4]triazolo[1,5-a]pyridin-6-yl)-1H-indol-5-yl)-N-methylcyclopentan-1-amine (275 to 278)

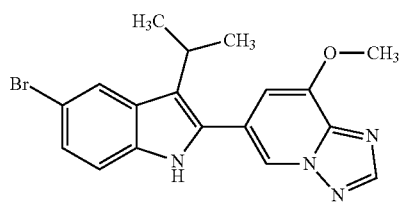

Intermediate 275A: 6-(5-bromo-3-isopropyl-1H-indol-2-yl)-8-methoxy-[1,2,4]triazolo[1,5-a]pyridine (275A)

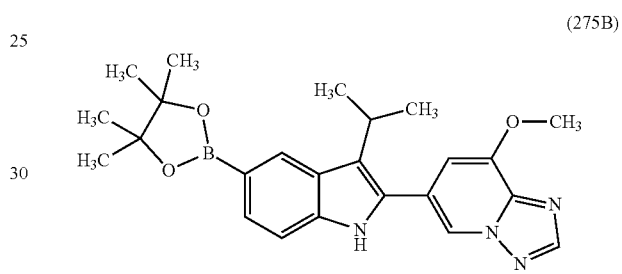

To a solution of 5-bromo-2-iodo-3-isopropyl-1H-indole (1.5 g, 4.12 mmol) and 8-methoxy-6-(4,4,5,5-tetramethyl-1,3,2-dioxaborolan-2-yl)-[1,2,4]triazolo[1,5-a]pyridine (1.700 g, 6.18 mmol) in dioxane (30 mL) and water (3.33 ml) was added potassium phosphate tribasic (2.153 g, 12.36 mmol) at ambient temperature. The mixture was degassed for 10 min with nitrogen, and was added PdCl$_2$(dppf)-CH$_2$Ch adduct (0.168 g, 0.206 mmol) and further degassed for 5 min. The resulting mixture was stirred at 80° C. for 3 h. The reaction mixture was diluted with ethyl acetate (200 mL), washed with water (2×100 mL), brine (50 mL), dried over sodium sulphate, and concentrated to afford crude product. The crude material w as purified by silica gel chromatography using 40 g silica column, compound was eluted with 45% ethyl acetate in petroleum ether, the fractions were collected, concentrated to afford 6-(5-bromo-3-isopropyl-1H-indol-2-yl)-8-methoxy-[1,2,4]triazolo[1,5-a]pyridine (1.0 g, 2.206 mmol, 53% yield) as a yellow solid. LCMS retention time 3.18 min (D). MS m/z: 385.4 (M+H).

Intermediate 275B: 6-(3-isopropyl-5-(4,4,5,5-tetramethyl-1,3,2-dioxaborolan-2-yl)-1H-indol-2-yl)-8-methoxy-[1,2,4]triazolo[1,5-a]pyridine (275B)

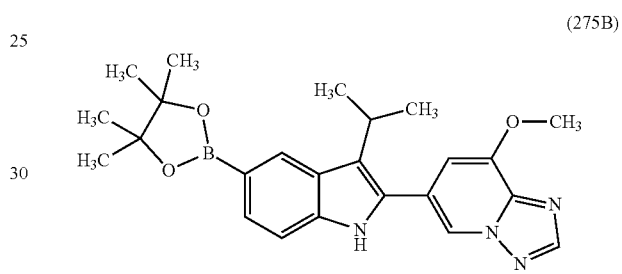

To a solution of 6-(5-bromo-3-isopropyl-1H-indol-2-yl)-8-methoxy-[1,2,4]triazolo[1,5-a]pyridine (0.95 g, 2.466 mmol) and bis(pinacolato)diboron (0.751 g, 2.96 mmol) in dioxane (40 mL) was added potassium acetate (0.726 g, 7.40 mmol) at ambient temperature. The mixture was degassed for 10 min with nitrogen, and was added PdCl$_2$(dppf)-CH$_2$Cl$_2$ adduct (0.201 g, 0.247 mmol) and further degassed for 5 min. The resulting mixture was stirred at 90° C. for 12 h. The reaction mass was filtered through celite bed to remove inorganics, washed with DCM (100 mL) and filtrate was concentrated to afford 6-(3-isopropyl-5-(4,4,5,5-tetramethyl-1,3,2-dioxaborolan-2-yl)-1H-indol-2-yl)-8-methoxy-[1,2,4]triazolo[1,5-a]pyridine (1.2 g, 2.276 mmol, 92% yield) as a brown solid. LCMS retention time 3.08 min [D], MS m/z: 433.4 (M+H).

Intermediate 275C: 3-(3-isopropyl-2-(8-methoxy-[1,2,4]triazolo[1,5-a]pyridin-6-yl)-1H-indol-5-yl)cyclopentanone (275C)

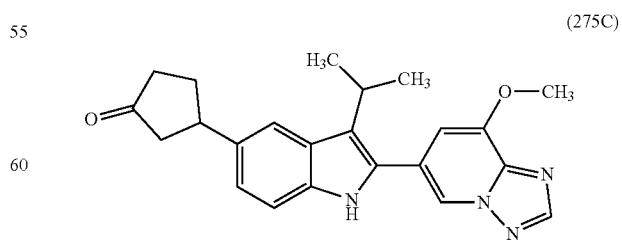

To a solution of 6-(3-isopropyl-5-(4,4,5,5-tetramethyl-1,3,2-dioxaborolan-2-yl)-1H-indol-2-yl)-8-methoxy-[1,2,4]triazolo[1,5-a]pyridine (1.0 g, 2.313 mmol) and cyclopent- 2-enone (0.752 mL, 9.25 mmol) in dioxane (30 mL)) and water (3.33 mL) was added potassium phosphate tribasic (1.473 g, 6.94 mmol) at ambient temperature. The mixture was degassed for 10 min with nitrogen, and was added chloro(1,5-cycloocatdiene)rhodium(I) dimer (0.114 g, 0.231 mmol) and further degassed for 5 min. The resulting mixture was stirred at 80° C. for 16 h. The reaction mixture was diluted with DCM (200 mL), washed with water (2×100 mL), brine (50 mL), dried over sodium sulphate, and concentrated to afford crude product. The crude material was purified by silica gel chromatography using 40 g silica column, compound was eluted with 78% ethyl acetate in petroleum ether, the fractions were collected and concentrated to afford 3-(3-isopropyl-2-(8-methoxy-[1,2,4]triazolo[1,5-a]pyridin-6-yl)-1H-indol-5-yl)cyclopentanone (0.7 g, 1.784 mmol, 77% yield) as an off-white solid. LCMS retention time 2.29 min [D], MS (ES): m/z 389.1 [M+H].

Examples 275 to 278

To a solution of 3-(3-isopropyl-2-(8-methoxy-[1,2,4]triazolo[1,5-a]pyridin-6-yl)-1H-indol-5-yl)cyclopentan-1-one (0.125 g, 0.322 mmol) and N-methylpropan-2-amine (0.024 g, 0.322 mmol) in methanol (5 mL) was added acetic acid (0.018 mL, 0.322 mmol) at 0° C., the resulting light yellow solution was stirred under nitrogen at room temperature for 12 h. Cooled the reaction mixture to 0° C. and was added sodium cyano borohydride (0.061 g, 0.965 mmol) and continued stirring at the same temperature for 6 h. The reaction mass was diluted with dichloromethane (10 mL), quenched with water. The organic layer was dried over sodium sulfate and concentrated. The crude material was purified by chiral SFC method. Column/dimensions: Chiralpak AD-H (250×21) mm, 5 μm, % CO$_2$: 75%,% Cosolvent: 25% of 0.2% DEA in ethanol, Total Flow: 70.0 g/min, Back Pressure: 100 bar, Temperature: 30° C. The fractions containing individual diastereomers were collected, concentrated and lyophilized to afford Examples 275 to 278.

Example 275: Diastereomer 1: (9 mg, 0.018 mmol, 6% yield). Chiral SFC RT: 3.79: LCMS retention time 1.81 min, [D], MS (ES): m/z=446.4 [M+H]; $^1$H NMR (400 MHz, DMSO-d$_6$) δ ppm 11.10 (s, 1H), 8.55 (d, J=1.2 Hz, 1H), 8.50 (s, 1H), 7.56 (s, 1H), 7.31 (d, J=7.8 Hz, 1H), 7.15 (s, 1H), 7.04 (d, J=8.1 Hz, 1H), 4.13-4.02 (m, 4H), 3.17 (d, J=5.4 Hz, 3H), 2.15 (br. s, 4H), 1.91 (s, 2H), 1.62 (s, 3H), 1.45 (d, J=7.1 Hz, 6H), 0.99 (d, J=6.8 Hz, 6H).

Example 276: Diastereomer 2: (11 mg, 0.021 mmol, 6% yield). Chiral SFC RT: 5.13; LCMS retention time 1.28 min, [E], MS (ES): m/z=446.4 [M+H]; $^1$H NMR (400 MHz, DMSO-d$_6$) δ ppm 11.10 (s, 1H), 8.55 (d, J=1.2 Hz, 1H), 8.50 (s, 1H), 7.56 (s, 1H), 7.31 (d, J=7.8 Hz, 1H), 7.15 (s, 1H), 7.04 (d, J=8.1 Hz, 1H), 4.13-4.02 (m, 4H), 3.17 (J=5.4 Hz, 3H), 2.15 (br. s., 4H), 1.91 (s, 2H), 1.62 (s, 3H), 1.45 (d, J=7.1 Hz, 6H), 0.99 (d, J=6.8 Hz, 6H).

Example 277: Diastereomer 3: (12 mg, 0.023 mmol, 7.00% yield). Chiral SFC RT: 6.87; LCMS retention time 1.28 min, [E], MS (ES): m/z=446.4 [M+H]; $^1$H NMR (400 MHz, DMSO-d$_6$) δ ppm 11.10 (s, 1H), 8.55 (d, J=1.5 Hz, 1H), 8.50 (s, 1H), 7.59 (s, 1H), 7.31 (d, J=8.3 Hz, 1H), 7.15 (d, J=1.0 Hz, 1H), 7.06 (d, J=8.6 Hz, 1H), 4.07 (s, 4H), 3.11 (dd, J=13.3, 7.0 Hz, 4H), 2.25-2.16 (m, 1H), 2.15-2.11 (m, 3H), 1.95-1.86 (m, 2H), 1.75-1.63 (m, 2H), 1.45 (d, J=7.1 Hz, 6H), 0.98 (d, J=6.6 Hz, 6H).

Example 278: Diastereomer 4: (21 mg, 0.044 mmol, 14% yield). Chiral SFC RT: 8.23; LCMS retention time 1.87 min, (D). MS (ES): m/z=446.4 [M+H]; $^1$H NMR (400 MHz, DMSO-d$_6$) δ ppm 11.10 (s, 1H), 8.55 (d, J=1.2 Hz, 1H), 8.50 (s, 1H), 7.56 (s, 1H), 7.31 (d, J=7.8 Hz, 1H), 7.15 (s, 1H), 7.04 (d, J=8.1 Hz, 1H), 4.13-4.02 (m, 4H), 3.17 (d/=5.4 Hz, 3H), 2.15 (br. s., 4H), 1.91 (s, 2H), 1.62 (s, 3H), 1.45 (d, J=7.1 Hz, 6H), 0.99 (d, J=6.8 Hz, 6H).

Example 279

1-(3-(2-(3,4-dimethoxyphenyl)-3-isopropyl-1H-indol-5-yl)-7-azabicyclo[4.1.1]octan-7-yl)-2-(dimethylamino)ethanone

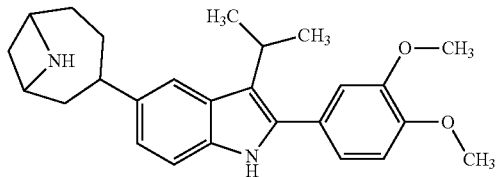

(279)

Intermediate 279A: Tert-butyl 3-(2-(3,4-dimethoxyphenyl)-3-isopropyl-1H-indol-5-yl)-7-azabicyclo[4.1.1]oct-3-ene-7-carboxylate

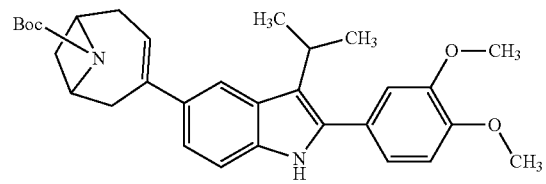

(279A)

To a solution of 5-chloro-2-(3,4-dimethoxyphenyl)-3-isopropyl-1H-indole (0.3 g, 0.910 mmol), tert-butyl 3-(4,4,5,5-tetramethyl-1,3,2-dioxaborolan-2-yl)-8-azabicyclo[3.2.1]Oct-3-ene-8-carboxylate (0.366 g, 1.092 mmol) in dioxane (10 mL) and water (2 ml) was added potassium carbonate (0.314 g, 2.274 mmol) at ambient temperature. The mixture was degassed for 10 minutes with nitrogen, and was added 1,1'-bis(di-tert-butylphosphino)ferrocene palladium dichloride (0.030 g, 0.045 mmol) and further degassed for 5 min. The resulting mixture was stirred at 100° C. for 6 h. The reaction mixture was diluted with ethyl acetate (200 mL), washed with water (2×100 mL), brine (50 mL), dried over sodium sulphate, and concentrated to afford crude product. The crude material was purified by silica gel chromatography using 40 g silica column, compound w as eluted with 20% ethyl acetate in petroleum ether, the fractions were collected, concentrated to afford tert-butyl 3-(2-(3,4-dimethoxyphenyl)-3-isopropyl-1H-indol-5-yl)-7-azabicyclo[4.1.1]oct-3-ene-7-carboxylate (0.15 g, 0.23 mmol, 25%) as an off-white solid. LCMS retention time 2.29 min [A], MS m/z: 503.2 (M+H).

Intermediate 279B: Tert-butyl 3-(2-(3,4-dimethoxyphenyl)-3-isopropyl-1H-indol-5-yl)-7-azabicyclo[4.1.1]octane-7-carboxylate

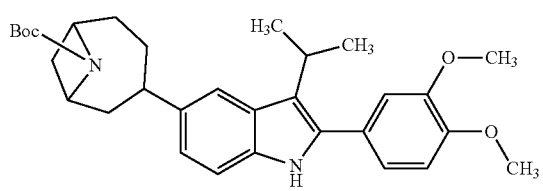

(279B)

To a solution of tert-butyl 3-(2-(3,4-dimethoxyphenyl)-3-isopropyl-1H-indol-5-yl)-7-azabicyclo[4.1.1]oct-3-ene-7-carboxylate (0.15 g, 0.298 mmol) in ethyl acetate (5 mL) was purged with nitrogen (N>), then was added Pd/C (7.94 mg, 7.46 µmol) and again purged with N$_2$, then the mixture was stirred at room temperature under a hydrogen balloon for 12 h. The suspension was filtered through celite bed, the filtrate was collected and concentrated to afford tert-butyl 3-(2-(3,4-dimethoxyphenyl)-3-isopropyl-1H-indol-5-yl)-7-azabicyclo[4.1.1]octane-7-carboxylate (0.15 g, 0.256 mmol, 86%) as a white solid. LCMS retention time 1.61 min [B], MS m/z: 505.2 (M+H).

Example 279

To a solution of tert-butyl 3-(2-(3,4-dimethoxyphenyl)-3-isopropyl-1H-indol-5-yl)-7-azabicyclo[4.1.1]octane-7-carboxylate (0.15 g, 0.297 mmol) in DCM (4 mL) was added TFA (0.092 mL, 1.189 mmol) at room temperature. The mixture was stirred at same temperature for 1 h. The solvent was removed under vacuum and the solid was washed with diethyl ether to remove nonpolar impurities to afford 3-(2-(3,4-dimethoxyphenyl)-3-isopropyl-1H-indol-5-yl)-7-azabicyclo[4.1.1]octane (0.16 g, 0.182 mmol, 62%) as a yellow solid. LCMS retention time 1.45 min [E]. MS m/z: 405.2 (M+H). $^1$H NMR (400 MHz, DMSO-d$_6$) δ ppm 10.80 (s, 1H), 7.51 (s, 1H), 7.23 (d, J=8.5 Hz, 1H), 7.11-7.04 (m, 2H), 7.03-6.99 (m, 1H), 6.96 (dd, J=8.3, 1.8 Hz, 1H), 3.82 (d, J=7.0 Hz, 4H), 3.31 (d, J=7.0 Hz, 2H), 3.02-2.93 (m, 2H), 2.26-2.16 (m, 2H), 1.74-1.64 (m, 4H), 1.56-1.50 (m, 2H), 1.46 (d, J=11.0 Hz, 2H), 1.41 (d, J=7.0 Hz, 6H).

Example 280

1-(3-(2-(3,4-dimethoxyphenyl)-3-isopropyl-1H-indol-5-yl)-7-azabicyclo[4.1.1]octan-7-yl)-2-(dimethylamino)ethanone

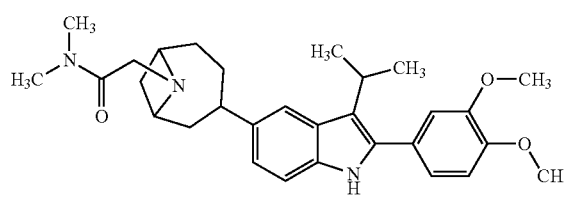

(280)

Intermediate 280A: 2-chloro-1-(3-(2-(3,4-dimethoxyphenyl)-3-isopropyl-1H-indol-5-yl)-7-azabicyclo[4.1.1]octan-7-yl)ethanone

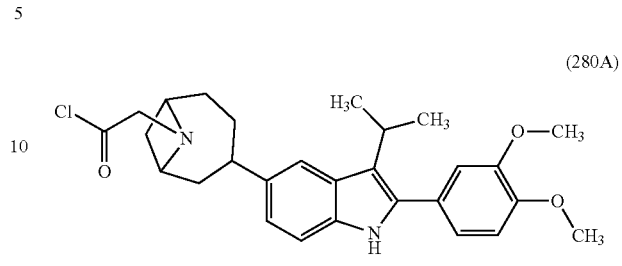

(280A)

To a solution of 3-(2-(3,4-dimethoxyphenyl)-3-isopropyl-1H-indol-5-yl)-7-azabicyclo [4.1.1]octane (0.16 g, 0.3% mmol) in THF (2 mL) was added DIPEA (0.104 mL, 0.593 mmol) followed by drop wise addition of chloroacetylchloride (0.032 mL, 0.396 mmol) at 0° C. The reaction mixture was allowed to stir at room temperature for 2 h. The reaction mixture was diluted with EtOAc (25 mL) and washed with water (2×50 mL), brine (50 mL), dried over sodium sulphate, and concentrated to afford 2-chloro-1-(3-(2-(3,4-dimethoxyphenyl)-3-isopropyl-1H-indol-5-yl)-7-azabicyclo [4.1.1]octan-7-yl)ethanone, (0.15 g, 0.184 mmol, 46.5%) as a yellow solid. LCMS retention time 1.11 min [B], MS m/z: 480.4 (M+H).

Example 280

To a solution of 2-chloro-1-(3-(2-(3,4-dimethoxyphenyl)-3-isopropyl-1H-indol-5-yl)-7-azabicyclo[4.1.1]octan-7-yl)ethanone (0.11 g, 0.229 mmol) in THF (2 mL) was added DIPEA (0.080 mL, 0.457 mmol) and dimethylamine (0.172 mL, 0.343 mmol) in THF. The reaction mixture was stirred at room temperature for 12 h. The reaction mixture was diluted with EtOAc (10 mL), washed with water (2×20 mL), dried over sodium sulphate, and concentrated to afford crude product. The crude material was purified by Preparative LCMS using method D2, the fractions containing the product was collected and concentrated to afford 1-(3-(2-(3,4-dimethoxyphenyl)-3-isopropyl-1H-indol-5-yl)-7-azabicyclo[4.1.1]octan-7-yl)-2-(dimethylamino)ethanone (1.5 mg, 1.34%). LCMS retention time 1.45 min (F). MS m/z: 490.4 (M+H). $^1$H NMR (400 MHz, DMSO-de) δ ppm 10.80 (s, 1H), 7.51 (s, 1H), 7.23 (d, J=8.5 Hz, 1H), 7.11-7.04 (m, 2H), 7.03-6.99 (m, 1H), 6.96 (dd, J=8.3, 1.8 Hz, 1H), 3.82 (d, J=7.0 Hz, 4H), 3.31 (d, J=7.0 Hz, 2H), 3.02-2.93 (m, 2H), 2.90 (s, 6H), 2.26-2.16 (m, 4H), 1.74-1.64 (m, 4H), 1.56-1.50 (m, 2H), 1.46 (d, J=11.0 Hz, 2H), 1.41 (d, J=7.0 Hz, 6H).

Example 281

2-(3-isopropyl-2-(8-methyl-[1,2,4]triazolo[1,5-a]pyridin-6-yl)-1H-indol-5-yl)morpholine

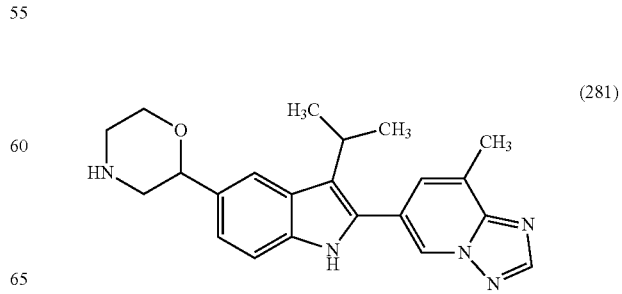

(281)

Intermediate 281A: 2-(4-nitrophenyl)oxirane

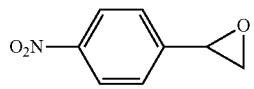
(281A)

To a solution of 2-bromo-1-(4-nitrophenyl)ethanone (10.503 g, 43.0 mmol) in MeOH (100 mL) (compound not dissolved completely) was added NaBH$_4$ (2.035 g, 53.8 mmol) portion wise at 0° C. (observed gas evolution and then it became clear solution), stirred at same temperature for 5 min, after stirring at room temperature for 2 h, K$_2$CO$_3$ (6.54 g, 47.3 mmol) was added portion wise, the suspension was stirred at room temperature for 6 h. Concentrated the reaction mass, the residue was diluted with water (100 mL), extracted with DCM (2×150 mL), the combined organic extracts was dried (Na$_2$SO$_4$) and concentrated to afford 2-(4-nitrophenyl)oxirane (6.63 g, 40.1 mmol, 93% yield) as a pale yellow solid. $^1$H NMR (300 MHz, CDCl$_3$) δ ppm 8.23 (d, J=9 Hz, 1H), 7.46 (d, J=9 Hz, 1H), 3.99-3.97 (m, 1H), 3.25-3.21 (m, 1H), 2.79-2.76 (m, 1H).

Intermediate 281B: 2-((2-hydroxyethyl)amino)-1-(4-nitrophenyl)ethanol

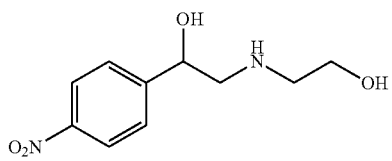
(281B)

2-(4-nitrophenyl)oxirane (6.256 g, 37.9 mmol) in ethanolamine (100.00 mL) was stirred at 40° C. for 2 h. TLC showed no starting material and formation of a new polar spot, diluted the reaction mixture with water (100 mL) and EtOAc (100 mL), separated both the layers, the aqueous layer was extracted with EtOAc (2×100 mL), the combined organic extracts was washed with water (100 mL), brine (20 mL), dried (Na$_2$SO$_4$) and concentrated to afford crude compound. The crude material was triturated with acetonitrile (3×20 mL) to afford 2-((2-hydroxyethyl)amino)-1-(4-nitrophenyl)ethanol (4.65 g, 20.55 mmol, 54.3% yield) as a white solid. LCMS retention time 0.48 min [G]. MS m/z: 227.3 [M+H]$^+$.

Intermediate 281C: tert-butyl (2-hydroxy-2-(4-nitrophenyl)ethyl)(2-hydroxyethyl) carbamate

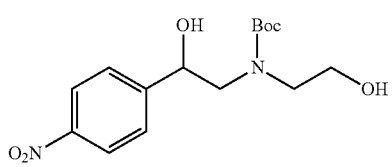
(281C)

To a solution of 2-((2-hydroxyethyl)amino)-1-(4-nitrophenyl)ethanol (4.62 g, 20.42 mmol) in DCM (60.00 mL) was added TEA (3.42 mL, 24.51 mmol), stirred for 5 min, then was added Boc$_2$O (5.22 mL, 22.46 mmol) dissolved in DCM (5 mL) drop wise at room temperature, then continued the stirring at same temperature, initially compound was not dissolved completely, after the addition of Boc$_2$O compound was dissolved completely, then stirred at room temperature for 2 h. Quenched the reaction with water, extracted with DCM, the organic layer was dried (Na$_2$SO$_4$) and concentrated to afford crude compound. The crude material was purified by silica gel chromatography on an ISCO instrument using 80 g silica column, compound was eluted in 4% MeOH in CHCl$_3$, the fractions were collected and concentrated to afford tert-butyl (2-hydroxy-2-(4-nitrophenyl)ethyl)(2-hydroxyethyl) carbamate (6.6 g, 20.22 mmol, 99% yield) as a white solid. LCMS retention time 1.00 min [G]. MS m/z: 327.3 [M+H]$^+$.

Intermediate 281D: tert-butyl 2-(4-nitrophenyl)morpholine-4-carboxylate

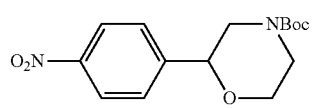
(281D)

To a solution of tert-butyl (2-hydroxy-2-(4-nitrophenyl)ethyl)(2-hydroxyethyl) carbamate (6.6 g, 20.22 mmol) and triphenylphosphine (6.37 g, 24.27 mmol) in toluene (120.00 mL) was added TEA (7.33 mL, 52.6 mmol) at 0° C., stirred for 5 min, and then was added drop wise di-tert-butyl azodicarboxylate (5.59 g, 24.27 mmol) dissolved in toluene (20 mL) at same temperature, then stirred at room temperature for 16 h. Quenched the reaction with water (50 mL), separated both the layers, the aqueous layer was extracted with EtOAc (2×50 mL), the combined organic extracts was dried (Na$_2$SO$_4$) and concentrated to afford crude compound. The crude material was purified by silica gel chromatography on an ISCO instrument using 80 g silica column, compound was 25% EA in hexane, the fraction was collected and concentrated to afford the compound as a gummy solid. The gummy solid compound was triturated with hexane (2×20 mL) and then the solid was dried under vacuum to afford tert-butyl 2-(4-nitrophenyl)morpholine-4-carboxylate (4.2 g, 13.62 mmol, 67% yield) as a white solid. (Product and reagent co-eluted in column purification and not able to remove from triturating with hexane either). LCMS retention time 2.804 min [G]. MS m/z: 253.2 [M+H-tBu]$^+$.

Intermediate 281E: tert-butyl 2-(4-aminophenyl)morpholine-4-carboxylate

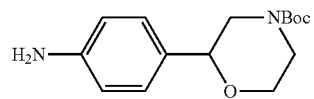
(281E)

To a solution of tert-butyl 2-(4-nitrophenyl)morpholine-4-carboxylate (4.2 g, 13.62 mmol) in MeOH (75 mL) was added Pd/C (1.450 g, 13.62 mmol), then the mixture was stirred at room temperature under H$_2$ bladder for 3 h.

Filtered the reaction mass through celite and concentrated to afford crude compound. The crude compound was purified by silica gel chromatography on an ISCO instrument using 80 g silica column, compound was eluted in 35% EA in hexanes, the fractions were collected and concentrated to afford tert-butyl 2-(4-aminophenyl) morpholine-4-carboxylate (2.25 g, 8.08 mmol, 59% yield) as a white solid. LCMS retention time 1.588 min [G], MS m/z: 223.0 [M+H-tBu]⁺.

Intermediate 281F: tert-butyl 2-(4-amino-3-iodophenyl)morpholine-4-carboxylate

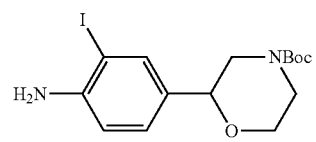

(281F)

To a solution of tert-butyl 2-(4-aminophenyl)morpholine-4-carboxylate (1.638 g, 5.88 mmol) in DCM (50.00 mL) and MeOH (25.00 mL) solvent mixture were added benzyltrimethylammonium dichloroiodate (2.048 g, 5.88 mmol) and calcium carbonate (1.885 g, 18.83 mmol) at room temperature, then the slurry was stirred at same temperature 2 h. Filtered the solids, concentrated the filtrate to afford crude compound. The crude material was purified by silica gel chromatography on an ISCO instrument using 40 g silica column, compound was eluted in 21% EA in hexane, the fractions were collected and concentrated to afford tert-butyl 2-(4-amino-3-iodophenyl)morpholine-4-carboxylate (2.17 g, 5.37 mmol, 91% yield) as an off white solid. LCMS retention time 1.34 min [G]. MS m/z: 349.2 M+H-tBu)⁺.

Intermediate 281G: 2-(3-iodo-4-((3-methylbut-2-en-1-yl)amino) phenyl)morpholine-4-carboxylate

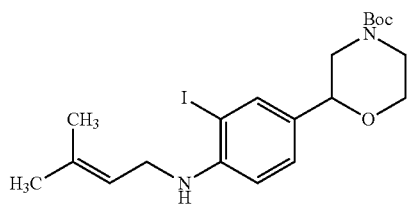

(281G)

To a solution of tert-butyl 2-(4-amino-3-iodophenyl)morpholine-4-carboxylate (2.170 g, 5.37 mmol) in THF (50 mL) was added LDA in THF (4.03 mL, 8.05 mmol) at −76° C., then brought to 10° C. in 30 min, again cooled to −76° C., and was added 1-bromo-3-methyl-2-butene (0.933 mL, 6.44 mmol), then brought to room temperature, stirred at same temperature for 3 h. Quenched the reaction with brine. The reaction mixture was extracted with EtOAc (2×30 ml), the combined organic extracts was, dried (Na₂SO₄) and concentrated to afford crude compound. The crude material was purified by silica gel chromatography on an ISCO instrument using 40 g silica column, compound was eluted in 15% EA in hexane, the fractions were collected and concentrated to afford tert-butyl 2-(3-iodo-4-((3-methylbut-2-en-1-yl)amino) phenyl) morpholine-4-carboxylate (2.16 g, 4.57 mmol, 85% yield) as an off-white solid. LCMS retention time 1.92 min [G]. MS m/z: 473.2 [M+H]⁺.

Intermediate 281H: tert-butyl 2-(3-isopropyl-1H-indol-5-yl)morpholine-4-carboxylate

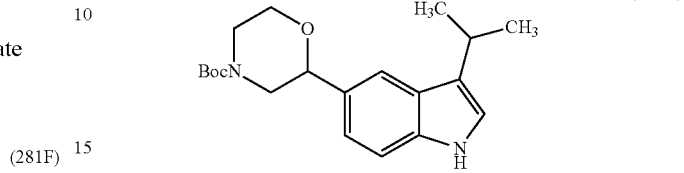

(281H)

Mixture of tert-butyl 2-(3-iodo-4-((3-methylbut-2-en-1-yl)amino)phenyl) morpholine-4-carboxylate (2.00 g, 4.23 mmol), Pd(OAc)₂ (0.095 g, 0.423 mmol) and TEA (1.770 mL, 12.70 mmol) in acetonitrile (60.00 mL) was degassed for 10 min, the mixture was stirred at 110° C. for 16 h. Crude LCMS showed 4:3 ratio starting material and formation of product. To the reaction mixture again was added TEA (1.770 mL, 12.70 mmol) and PdOAc₂ (0.095 g, 0.423 mmol), then degassed for 10 min and continued the reaction at 110° C. for 20 h. Crude LCMS showed 5:1 ratio starting material and formation of product. To the reaction mixture again was added TEA (1.770 mL, 12.70 mmol) and Pd(OAc)₂ (0.095 g, 0.423 mmol), then degassed for 10 min and continued the reaction at 110° C. for 20 h. Crude LCMS showed formation of product and traces starting material remains. Concentrated the reaction mass to afford crude compound, the crude material was purified by silica gel chromatography on an ISCO instrument using 40 g silica column, compound was eluted in 20% EA in hexanes, the fractions were collected and concentrated to afford tert-butyl 2-(3-isopropyl-1H-indol-5-yl)morpholine-4-carboxylate (0.810 g, 2.352 mmol, 55.5% yield) as a white solid. LCMS retention time 1.52 min [G], MS m/z: 343.5 [M+H]⁺.

Intermediate 281I: tert-butyl 2-(2-bromo-3-isopropyl-1H-indol-5-yl)morpholine-4-carboxylate

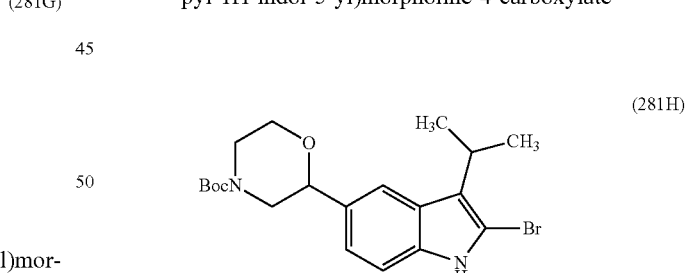

(281H)

To a solution of tert-butyl 2-(3-isopropyl-1H-indol-5-yl) morpholine-4-carboxylate (0.740 g, 2.148 mmol) in DCE (25.00 mL) was added drop wise NBS (0.382 g, 2.148 mmol) dissolved in DCE (10 mL) at 0° C., then the mixture was brought to room temperature in 15 min, stirred at room temperature for 5 min. Crude LCMS showed no starting material and formation of product. Quenched the reaction with water (20 mL). The reaction mixture was extracted with DCM (2×25 mL), combined organic extracts was concentrated and dried to afford crude compound. The crude compound was purified by silica gel chromatography on an ISCO instrument using 24 g silica column, compound was eluted in 22% EA in hexanes, the fractions were collected and concentrated to afford tert-butyl 2-(2-bromo-3-isopropyl-1H-indol-5-yl)morpholine-4-carboxylate (0.690 g, 1.630 mmol, 76% yield) as an off white solid. LCMS retention time 1.63 min [G]. MS m/z: 425.3 [M+2H]$^+$.

Intermediate 281J: tert-butyl 2-(3-isopropyl-2-(8-methyl-[1,2,4]triazolo[1,5-a]pyridin-6-yl)-1H-indol-5-yl)morpholine-4-carboxylate

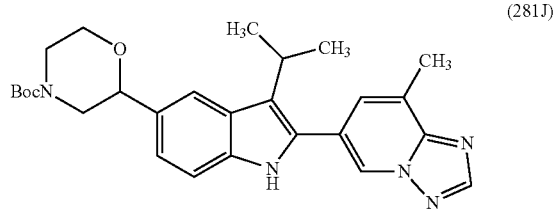 [SMILES: Cc1cc(-c2[nH]c3ccc(C4CN(C(=O)OC(C)(C)C)CCO4)cc3c2C(C)C)cn2ncnc12]

Mixture of tert-butyl 2-(2-bromo-3-isopropyl-1H-indol-5-yl)morpholine-4-carboxylate (0.666 g, 1.573 mmol), 8-methyl-6-(4,4,5,5-tetramethyl-1,3,2-dioxaborolan-2-yl)-[1,2,4]triazolo[1,5-a]pyridine (0.815 g, 3.15 mmol) and potassium phosphate tribasic (1.002 g, 4.72 mmol) in dioxane (18.0 mL) and water (6.00 mL) was degassed with nitrogen for 10 min. Next, PdCl$_2$(dppf)-CH$_2$Cl$_2$ adduct (0.128 g, 0.157 mmol) was added and the reaction mixture was stirred at 90° C. for 4 h. Crude LCMS showed no starting material and formation of product. Diluted the reaction with water (10 mL) and DCM (30 mL), separated both the layers, the aqueous layer was extracted with DCM (2×30 mL), combined organic extracts was concentrated and dried to afford crude compound. The crude compound was purified by silica gel chromatography on an ISCO instrument using 20 g silica column, compound was eluted in 60% EA in hexanes, the fractions were collected and concentrated to afford racemic tert-butyl 2-(3-isopropyl-2-(8-methyl-[1,2,4]triazolo[1,5-a]pyridin-6-yl)-1H-indol-5-yl)morpholine-4-carboxylate (660 mg) as an off-white solid. LCMS retention time 1.45 min [G]. MS m/z: 476.5 [M+H]$^+$.

The racemic compound was separated in the two enantiomer using chiral separation by Chiral SFC Method using column: Chiralcel OJH (250×4.6) mm, 5 µm, Run time: 25 min, Flow rate: 1.2 mL/min, mobile phase: 0.2% DEA in IPA, wave length: 220 nm racemic. After prep purification each of the pure enantiomers was collected separately, concentrated and lyophilized to afford enantiomer 1 (0.25 g, 0.524 mmol, 33% yield) as white solid; and enantiomer 2 (0.24 g, 0.505 mmol, 32% yield) as a white solid.

The following Intermediates were prepared according to the general procedure described in the preparation of Intermediate 281J.

TABLE XX

| Intermediate | Structure | Mol Wt. | LCMS MH$^+$ | Ret Time (min) | HPLC Method |
|---|---|---|---|---|---|
| 281J-2 | (structure) | 491.6 | 492.6 | 1.41 | D |
| 281J-3 | (structure) | 489.6 | 490.5 | 1.53 | D |
| 281J-4 | (structure) | 449.5 | 450.6 | 1.52 | L |

Example 281

To a solution of tert-butyl 2-(3-isopropyl-2-(8-methyl-[1,2,4]triazolo[1,5-a]pyridin-6-yl)-1H-indol-5-yl)morpholine-4-carboxylate (0.030 g, 0.063 mmol) in dioxane (1.00 mL) was added hydrochloric acid in dioxane (0.5 mL, 2.000 mmol) at room temperature, then the mixture was stirred at same temperature for 2 h. Crude LCMS showed no starting material and formation of product, concentrated the reaction mass to afford crude compound. The crude material was purified by Prep LCMS using method D2, fractions containing the product was combined and dried using Genevac centrifugal evaporator to afford 2-(3-isopropyl-2-(8-methyl-[1,2,4]triazolo[1,5-a]pyridin-6-yl)-1H-indol-5-yl)morpholine, HCl (0.011 g, 0.025 mmol, 40% yield) as a pale solid. LCMS retention time 1.039 min [E], MS m/z: 376.2 [M+H]$^+$; $^1$H NMR (400 MHz, CD$_3$OD) δ ppm 8.87 (s, 1H), 8.47 (s, 1H), 7.83 (s, 1H), 7.67 (s, 1H), 7.42 (d, J=8.4 Hz, 1H), 7.20 (d, J=8.4 Hz, 1H), 4.81-4.75 (m, 2H), 4.23-4.20 (m, 1H), 4.02-3.85 (m, 1H), 3.80 (d, J=0.8 Hz, 1H), 3.38-3.36 (m, 1H), 3.24-3.18 (m, 1H), 3.14-3.08 (m, 1H), 2.72 (s, 3H), 1.53 (d, J=7.2 Hz, 6H).

The following Examples were prepared according to the general procedure used to prepare Example 281.

TABLE 27

| Ex. No. | Structure | Mol Wt. | LCMS MH$^+$ | Ret Time (min) | HPLC Method |
|---|---|---|---|---|---|
| 282 | 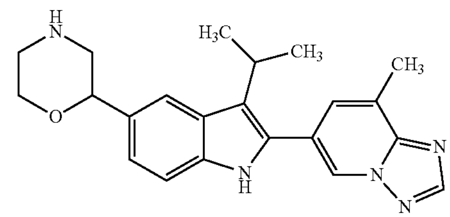 [SMILES: Cc1cc(-c2[nH]c3ccc(C4CNCCO4)cc3c2C(C)C)cn2ncnc12] | 375.5 | 376.1 | 1.248 | E |
| 283 | 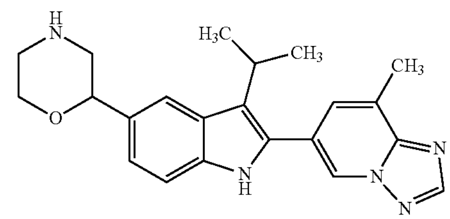 [SMILES: Cc1cc(-c2[nH]c3ccc(C4CNCCO4)cc3c2C(C)C)cn2ncnc12] | 375.5 | 376.1 | 1.248 | F |
| 284 | 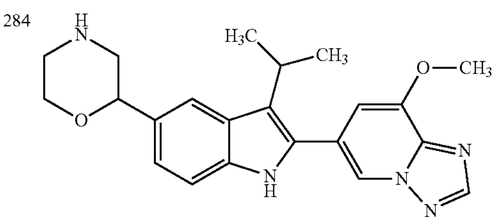 | 391.5 | 392 | 10.255 | I |
| 285 | 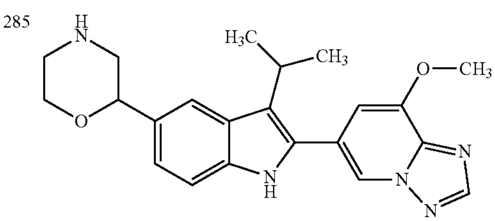 | 391.5 | 392.2 | 10.177 | I |
| 286 | 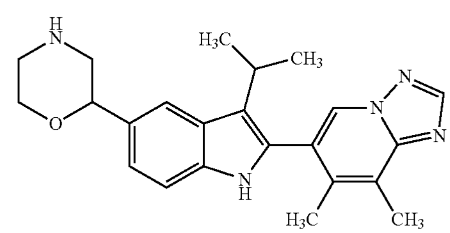 | 389.5 | 390.1 | 1.309 | E |
| 287 | 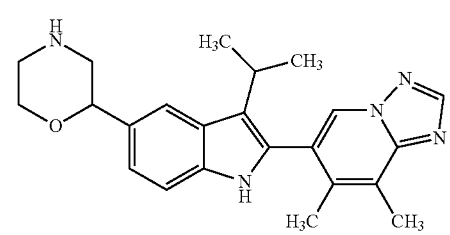 | 389.5 | 390.2 | 10.601 | I |

TABLE 27-continued

| Ex. No. | Structure | Mol Wt. | LCMS MH+ | Ret Time (min) | HPLC Method |
|---|---|---|---|---|---|
| 288 | 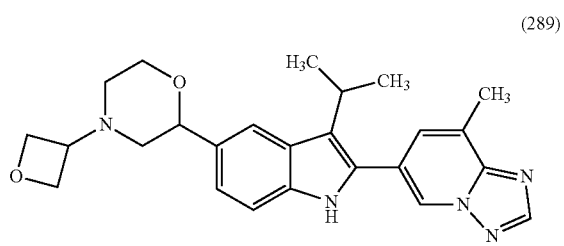 [SMILES: Cc1cc(-c2[nH]c3ccc(C4CN(C5COC5)CCO4)cc3c2C(C)C)cn2ncnc12] | 389.5 | 390.2 | 10.599 | I |

Example 289

2-(3-isopropyl-2-(8-methyl-[1,2,4]triazolo[1,5-a]pyridin-6-yl)-1H-indol-5-yl)-4-(oxetan-3-yl)morpholine (289)

To a solution of 2-(3-isopropyl-2-(8-methyl-[1,2,4]triazolo[1,5-a]pyridin-6-yl)-1H-indol-5-yl)morpholine, HCl (0.033 g, 0.080 mmol) in MeOH (3.00 mL) were added oxetan-3-one (0.017 g, 0.240 mmol) and acetic acid (0.3 mL, 5.24 mmol) at 0° C., stirred at same temperature for 1 h, then stirred at room temperature for 5 h. Again cooled the reaction mass and was added sodium cyanoborohydride (0.015 g, 0.240 mmol), then stirred at room temperature for 16 h. Crude LCMS showed no starting material and formation of product, concentrated the reaction mass to afford crude compound, the crude material was purified by Prep HPLC using method D2, the fractions containing the product was combined and dried using Genevac centrifugal evaporator to afford 2-(3-isopropyl-2-(8-methyl-[1,2,4]triazolo[1,5-a]pyridin-6-yl)-1H-indol-5-yl)-4-(oxetan-3-yl)morpholine (0.0134 g, 0.031 mmol, 39% yield) as a pale solid. LCMS retention time 1.653 min [E]. MS m/z: 432.1 [M+H]+; 1H NMR (400 MHz, DMSO-$d_6$) δ ppm 8.80 (s, 1H), 8.52 (s, 1H), 7.71 (s, 1H), 7.60 (s, 1H), 7.32 (d, J=8.4 Hz, 1H), 7.12 (d, J=8.4 Hz, 1H), 4.58-4.49 (m, 6H), 4.18-4.14 (m, 2H), 3.99-3.95 (m, 1H), 3.72-3.68 (m, 1H), 2.80-2.76 (m, 1H), 2.62 (s, 3H), 2.10-2.04 (m, 1H), 1.96-1.88 (m, 1H), 1.42 (d, J=6.8 Hz, 6H).

The following Examples were prepared according to the general procedure used to prepare Example 289.

TABLE 28

| Ex. No. | Structure | Mol Wt. | LCMS MH+ | Ret Time (min) | HPLC Method |
|---|---|---|---|---|---|
| 290 | 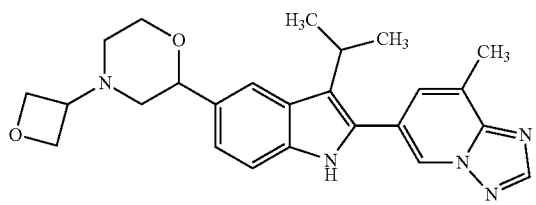 [SMILES: Cc1cc(-c2[nH]c3ccc(C4CN(C5COC5)CCO4)cc3c2C(C)C)cn2ncnc12] | 431.5 | 432.2 | 1.647 | E |
| 291 | 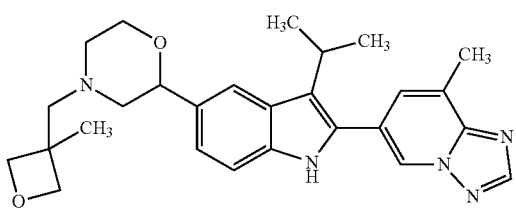 | 459.6 | 460.3 | 1.7 | P |

TABLE 28-continued

| Ex. No. | Structure | Mol Wt. | LCMS MH+ | Ret Time (min) | HPLC Method |
|---|---|---|---|---|---|
| 292 | 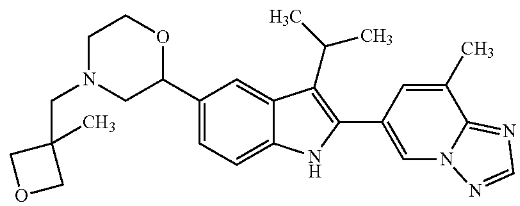 [SMILES: Cc1cc(-c2[nH]c3ccc(C4CN(CC5(C)COC5)CCO4)cc3c2C(C)C)cn2ncnc12] | 459.6 | 460.3 | 1.06 | Q |
| 293 | 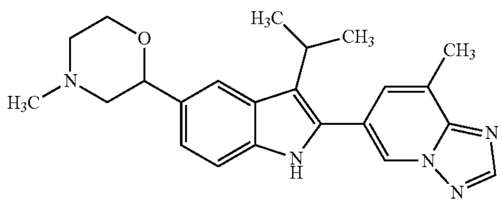 [SMILES: Cc1cc(-c2[nH]c3ccc(C4CN(C)CCO4)cc3c2C(C)C)cn2ncnc12] | 389.5 | 390.2 | 1.42 | P |
| 294 | 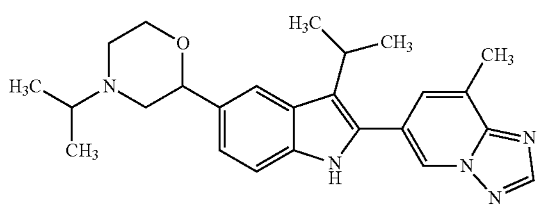 [SMILES: Cc1cc(-c2[nH]c3ccc(C4CN(C(C)C)CCO4)cc3c2C(C)C)cn2ncnc12] | 417.6 | 418.3 | 1.62 | P |
| 295 | 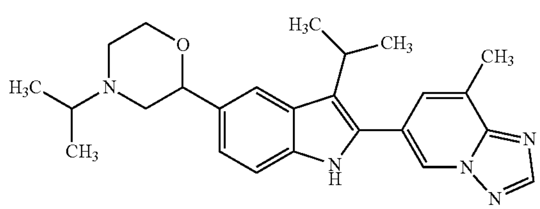 [SMILES: Cc1cc(-c2[nH]c3ccc(C4CN(C(C)C)CCO4)cc3c2C(C)C)cn2ncnc12] | 417.6 | 418.3 | 1.63 | P |
| 296 | 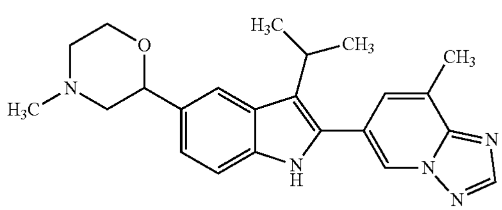 [SMILES: Cc1cc(-c2[nH]c3ccc(C4CN(C)CCO4)cc3c2C(C)C)cn2ncnc12] | 389.5 | 390.3 | 1.44 | P |
| 297 | 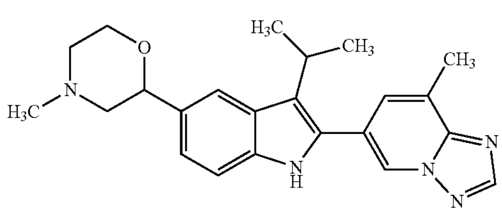 [SMILES: Cc1cc(-c2[nH]c3ccc(C4CN(C)CCO4)cc3c2C(C)C)cn2ncnc12] | 389.5 | 390.2 | 1.44 | P |
| 298 | 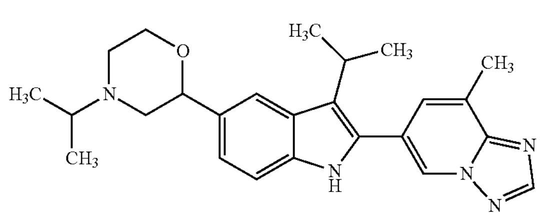 [SMILES: Cc1cc(-c2[nH]c3ccc(C4CN(C(C)C)CCO4)cc3c2C(C)C)cn2ncnc12] | 417.6 | 418.2 | 1.6 | P |

TABLE 28-continued
| Ex. No. | Structure | Mol Wt. | LCMS MH+ | Ret Time (min) | HPLC Method |
|---|---|---|---|---|---|
| 299 | 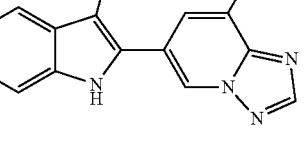 | 405.5 | 406.0 | 1.601 | E |
| 300 | 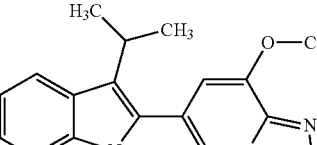 | 433.6 | 434.0 | 1.797 | E |
| 301 | 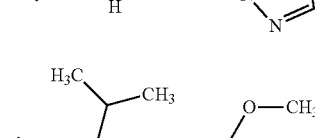 | 405.5 | 406.1 | 1.594 | E |
| 302 | 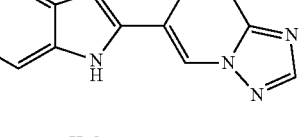 | 433.6 | 434.1 | 1.784 | E |
| 303 | 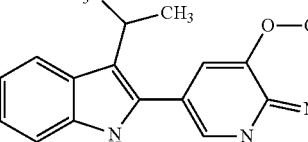 | 391.6 | 392.3 | 1.72 | P |
| 304 | 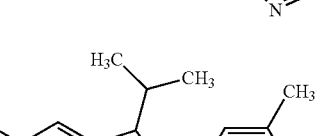 | 405.5 | 406.3 | 1.51 | P |
| 305 | 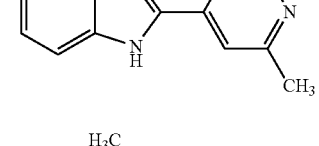 | 391.6 | 392.3 | 1.73 | P |

Example 306

2-(2-(3-isopropyl-2-(8-methyl-[1,2,4]triazolo[1,5-a]pyridin-6-yl)-1H-indol-5-yl)morpholino)-N,N-dimethylacetamide

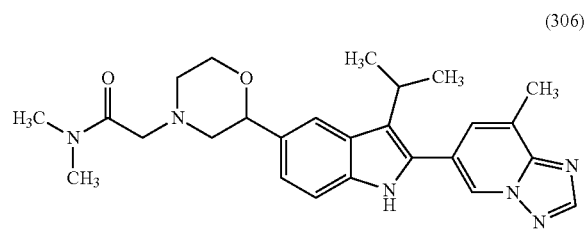 [SMILES: Cc1cc(-c2[nH]c3ccc(C4CN(CC(=O)N(C)C)CCO4)cc3c2C(C)C)cn2ncnc12]

(306)

To a solution of 2-(3-isopropyl-2-(8-methyl-[1,2,4]triazolo[1,5-a]pyridin-6-yl)-1H-indol-5-yl)morpholine (8.5 mg, 0.023 mmol) in THF (0.5 mL) and DMF (0.5 mL) solvent mixture were added TEA (0.1 mL, 0.717 mmol) and 2-chloro-N,N-dimethylacetamide (3.30 mg, 0.027 mmol) at room temperature, then the mixture was stirred at same temperature for 16 h. Crude LCMS showed no stating material and formation of product. The reaction mass was purified by Preparative LCMS purification using method D2, the fractions containing desired product was combined and dried using Genevac centrifugal evaporator to afford 2-(2-(3-isopropyl-2-(8-methyl-[1,2,4]triazolo[1,5-a]pyridin-6-yl)-1H-indol-5-yl)morpholino)-N,N-dimethylacetamide (0.002 mg, 0.0042 µmol, 0.018% yield) as a pale solid. LCMS retention time 1.634 min [E], MS m/z: 461.2 [M+H]$^+$; $^1$H NMR (400 MHz, CD$_3$OD) δ ppm 8.72 (s, 1H), 8.46 (s, 1H), 7.81 (s, 1H), 7.67 (s, 1H), 7.38 (d, J=8.4, 1H), 7.19 (d, J=8.4 Hz, 1H), 4.74-4.71 (m, 1H), 4.08-4.04 (m, 1H), 3.98-3.93 (m, 1H), 3.40-3.34 (m, 3H), 3.14 (s, 3H), 3.10-3.05 (m, 1H), 2.98 (s, 3H), 2.97-2.90 (m, 1H), 2.71 (s, 3H), 2.06-1.88 (m, 2H), 1.52 (dd, J=7.2, 1.2 Hz, 6H).

The following Examples were prepared according to the general procedure used to prepare Example 306.

TABLE 29

| Ex. No. | Structure | Mol Wt. | LCMS MH$^+$ | Ret Time (min) | HPLC Method |
|---|---|---|---|---|---|
| 307 | 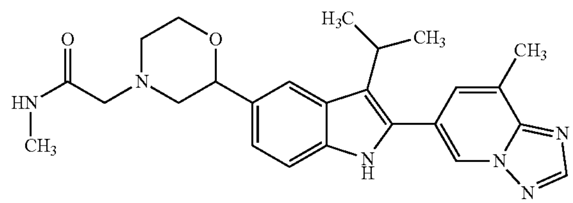 [SMILES: CNC(=O)CN1CCOC(c2ccc3[nH]c(-c4cc(C)c5ncnn5c4)c(C(C)C)c3c2)C1] | 446.6 | 447.2 | 1.579 | E |
| 308 | 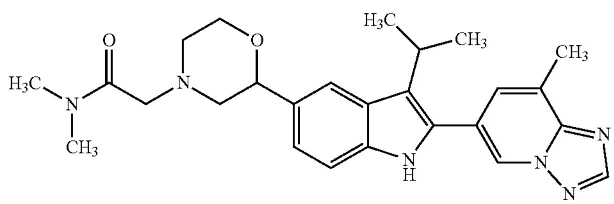 [SMILES: Cc1cc(-c2[nH]c3ccc(C4CN(CC(=O)N(C)C)CCO4)cc3c2C(C)C)cn2ncnc12] | 460.6 | 461.2 | 1.641 | E |
| 309 | 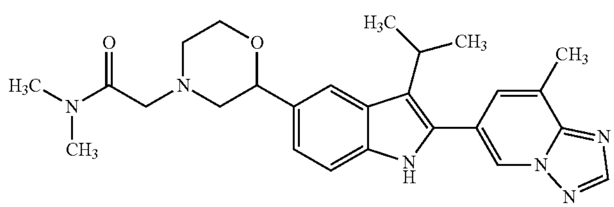 [SMILES: Cc1cc(-c2[nH]c3ccc(C4CN(CC(=O)N(C)C)CCO4)cc3c2C(C)C)cn2ncnc12] | 476.6 | 477.0 | 1.582 | E |
| 310 | 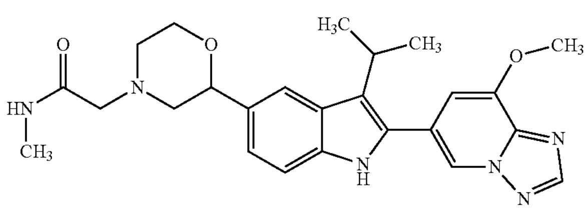 [SMILES: CNC(=O)CN1CCOC(c2ccc3[nH]c(-c4cc(OC)c5ncnn5c4)c(C(C)C)c3c2)C1] | 462.6 | 463.0 | 1.522 | E |

TABLE 29-continued

| Ex. No. | Structure | Mol Wt. | LCMS MH+ | Ret Time (min) | HPLC Method |
|---|---|---|---|---|---|
| 311 | 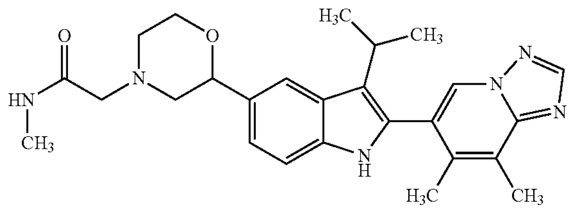 [SMILES: CNC(=O)CN1CCOC(c2ccc3[nH]c(-c4cn5ncnc5c(C)c4C)c(C(C)C)c3c2)C1] | 460.6 | 461.1 | 1.622 | E |
| 312 | 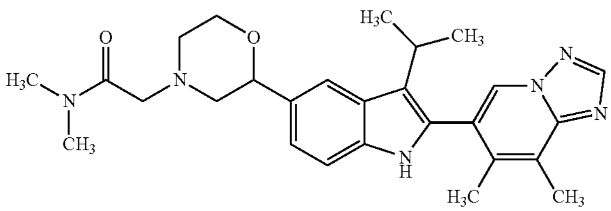 [SMILES: Cc1c(-c2[nH]c3ccc(C4CN(CC(=O)N(C)C)CCO4)cc3c2C(C)C)cn2ncnc2c1C] | 474.6 | 475.2 | 1.687 | E |
| 313 | 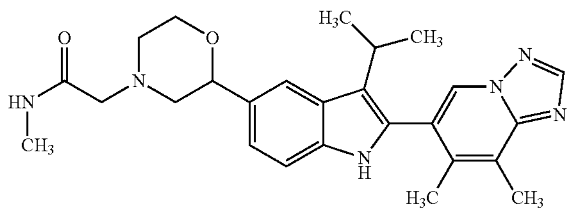 [SMILES: CNC(=O)CN1CCOC(c2ccc3[nH]c(-c4cn5ncnc5c(C)c4C)c(C(C)C)c3c2)C1] | 460.6 | 461.1 | 1.623 | E |
| 314 | 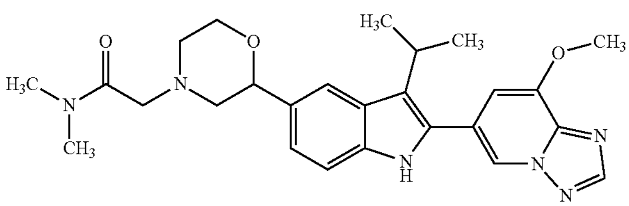 [SMILES: COc1cc(-c2[nH]c3ccc(C4CN(CC(=O)N(C)C)CCO4)cc3c2C(C)C)cn2ncnc12] | 476.6 | 477.1 | 1.577 | E |
| 315 | 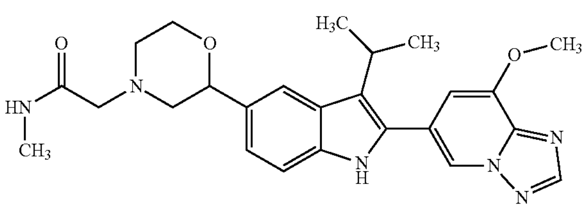 [SMILES: CNC(=O)CN1CCOC(c2ccc3[nH]c(-c4cc(OC)c5ncnn5c4)c(C(C)C)c3c2)C1] | 462.6 | 463.0 | 1.514 | E |
| 316 | 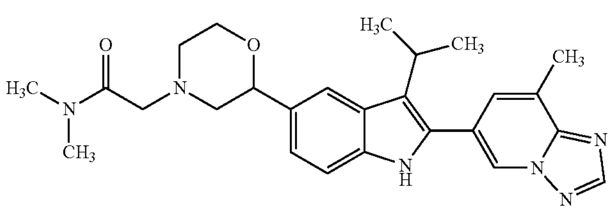 [SMILES: Cc1cc(-c2[nH]c3ccc(C4CN(CC(=O)N(C)C)CCO4)cc3c2C(C)C)cn2ncnc12] | 460.6 | 461.0 | 1.64 | E |
| 317 | 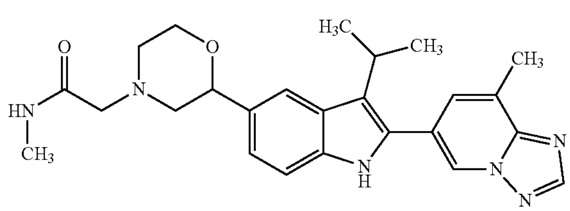 [SMILES: CNC(=O)CN1CCOC(c2ccc3[nH]c(-c4cc(C)c5ncnn5c4)c(C(C)C)c3c2)C1] | 446.6 | 447.0 | 1.577 | E |

TABLE 29-continued

| Ex. No. | Structure | Mol Wt. | LCMS MH+ | Ret Time (min) | HPLC Method |
|---|---|---|---|---|---|
| 318 | 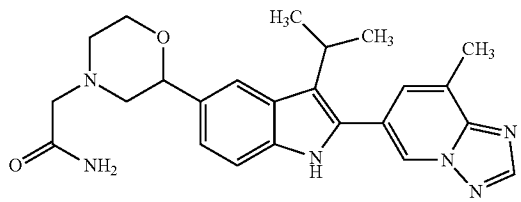 [SMILES: Cc1cc(-c2[nH]c3ccc(C4CN(CC(N)=O)CCO4)cc3c2C(C)C)cn2ncnc12] | 432.5 | 433.1 | 1.169 | F |
| 319 | 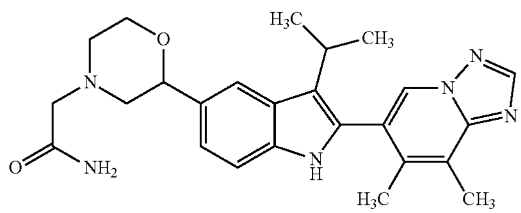 [SMILES: Cc1c(-c2[nH]c3ccc(C4CN(CC(N)=O)CCO4)cc3c2C(C)C)cn2ncnc2c1C] | 446.6 | 447.1 | 1.529 | E |
| 320 | 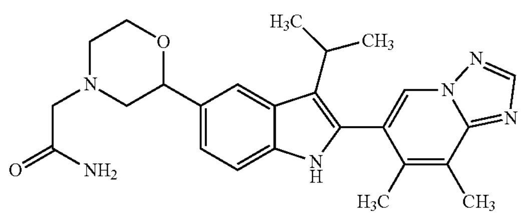 [SMILES: Cc1c(-c2[nH]c3ccc(C4CN(CC(N)=O)CCO4)cc3c2C(C)C)cn2ncnc2c1C] | 446.6 | 445.1 | 1.53 | E |
| 321 | 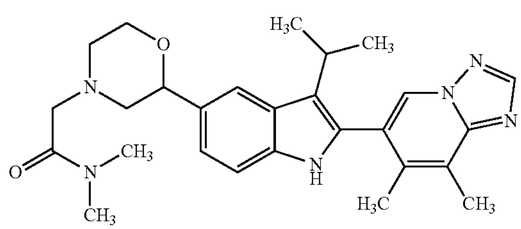 [SMILES: Cc1c(-c2[nH]c3ccc(C4CN(CC(=O)N(C)C)CCO4)cc3c2C(C)C)cn2ncnc2c1C] | 474.6 | 475.2 | 1.761 | E |
| 322 | 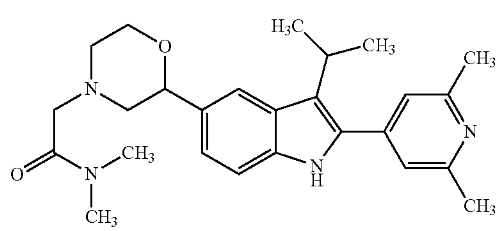 [SMILES: Cc1cc(-c2[nH]c3ccc(C4CN(CC(=O)N(C)C)CCO4)cc3c2C(C)C)cc(C)n1] | 434.6 | 435.3 | 1.5 | P |
| 323 | 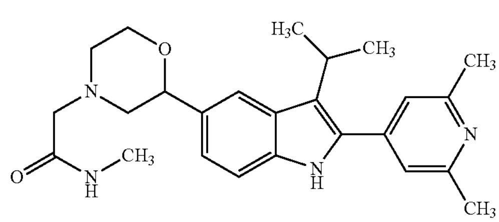 [SMILES: CNC(=O)CN1CCOC(c2ccc3[nH]c(-c4cc(C)nc(C)c4)c(C(C)C)c3c2)C1] | 420.6 | 421.1 | 1.44 | P |
| 324 | 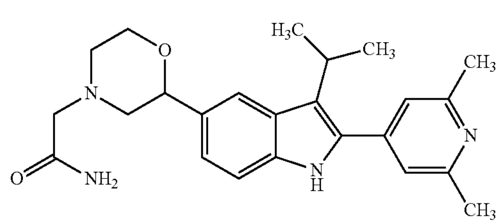 [SMILES: Cc1cc(-c2[nH]c3ccc(C4CN(CC(N)=O)CCO4)cc3c2C(C)C)cc(C)n1] | 406.5 | 407.3 | 1.34 | P |

TABLE 29-continued

| Ex. No. | Structure | Mol Wt. | LCMS MH+ | Ret Time (min) | HPLC Method |
|---|---|---|---|---|---|
| 325 | 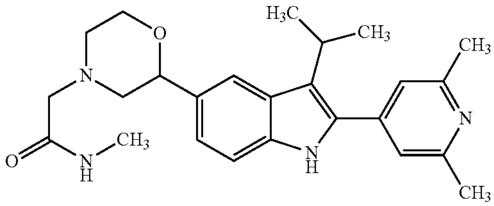 [SMILES: CNC(=O)CN1CCOC(c2ccc3[nH]c(-c4cc(C)nc(C)c4)c(C(C)C)c3c2)C1] | 420.6 | 421.3 | 1.44 | P |
| 326 | 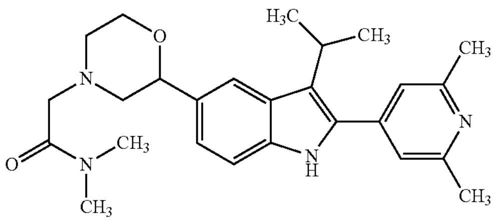 [SMILES: Cc1cc(-c2[nH]c3ccc(C4CN(CC(=O)N(C)C)CCO4)cc3c2C(C)C)cc(C)n1] | 434.6 | 435.3 | 1.5 | P |
| 327 | 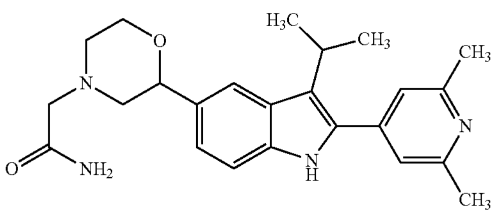 | 406.5 | 407.3 | 1.34 | P |

Example 328

2-(dimethylamino)-1-(2-(3-isopropyl-2-(8-methyl-[1,2,4]triazolo[1,5-a]pyridin-6-yl)-1H-indol-5-yl)morpholino)ethanone (328)

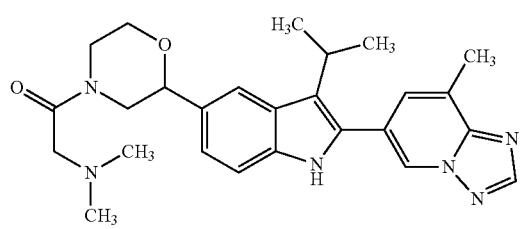

To a solution of 2-(3-isopropyl-2-(8-methyl-[1,2,4]triazolo[1,5-a]pyridin-6-yl)-1H-indol-5-yl)morpholine, HCl (0.022 g, 0.053 mmol) and 2-(dimethylamino)acetic acid (8.26 mg, 0.080 mmol) in DMF (1.00 mL) were added TEA (0.1 mL, 0.717 mmol) and HATU (0.041 g, 0.107 mmol) al room temperature, then stirred at same temperature for 2 h. Crude LCMS showed no starting material and formation of product. The reaction mass was purified by Preparative LCMS purification using method D2, the fractions containing the product was combined and dried using Genevac centrifugal evaporator to afford 2-(dimethylamino)-1-(2-<3-isopropyl-2-(8-methyl-[1,2,4]triazolo[1,5-a]pyridin-6-yl)-1H-indol-5-yl)morpholino)ethanone (0.011 g, 0.023 mmol, 43% yield) as a pale solid. LCMS retention time 1.441 min [E], MS m/z: 461.2 [M+H]+; $^1$H NMR (400 MHz, CD$_3$OD) δ ppm 8.73 (s, 1H), 8.47 (s, 1H), 7.85 (d, J=7.2 Hz, 1H), 7.67 (s, 1H), 7.42 (dd, J=8.4, 2.0 Hz, 1H), 7.24 (d, J=7.2 Hz, 1H), 4.56-4.50 (m, 1H), 4.18-4.08 (m, 2H), 3.98-3.91 (m, 1H), 3.80-3.71 (m, 1H), 3.63-3.52 (m, 2H), 3.44-3.38 (m, 1H), 3.07-3.00 (m, 1H), 2.92-2.86 (m, 1H), 2.71 (s, 3H), 2.46 (s, 6H), 1.53 (d, J=6.8 Hz, 6H).

The following Examples were prepared according to the general procedure used to prepare Example 328.

TABLE 30

| Ex. No. | Structure | Mol Wt. | LCMS MH+ | Ret Time (min) | HPLC Method |
|---|---|---|---|---|---|
| 329 | 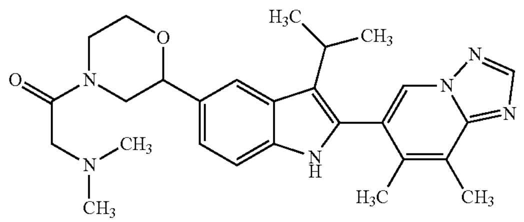 [SMILES: Cc1c(-c2[nH]c3ccc(C4CN(C(=O)CN(C)C)CCO4)cc3c2C(C)C)cn2ncnc2c1C] | 474.6 | 475.2 | 1.485 | E |
| 330 | 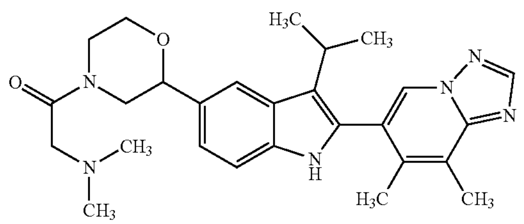 [SMILES: Cc1c(-c2[nH]c3ccc(C4CN(C(=O)CN(C)C)CCO4)cc3c2C(C)C)cn2ncnc2c1C] | 474.6 | 475.2 | 1.484 | E |
| 331 | 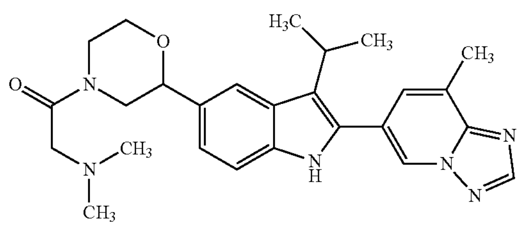 [SMILES: Cc1cc(-c2[nH]c3ccc(C4CN(C(=O)CN(C)C)CCO4)cc3c2C(C)C)cn2ncnc12] | 460.6 | 461.2 | 1.444 | E |
| 332 | 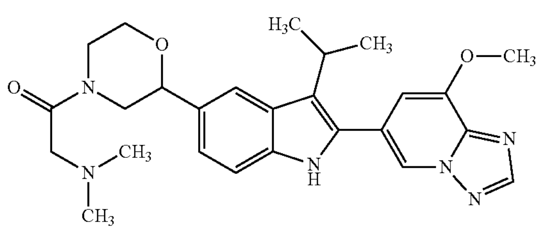 [SMILES: COc1cc(-c2[nH]c3ccc(C4CN(C(=O)CN(C)C)CCO4)cc3c2C(C)C)cn2ncnc12] | 476.6 | 477.2 | 1.386 | E |
| 333 | 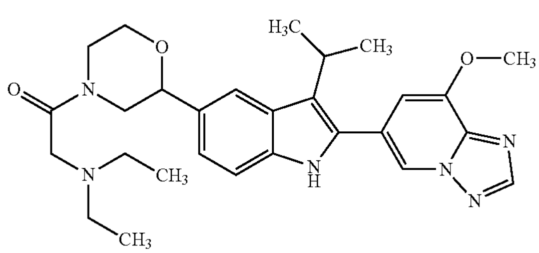 [SMILES: CCN(CC)CC(=O)N1CCOC(c2ccc3[nH]c(-c4cc(OC)c5ncnn5c4)c(C(C)C)c3c2)C1] | 504.6 | 505.2 | 1.305 | E |
| 334 | 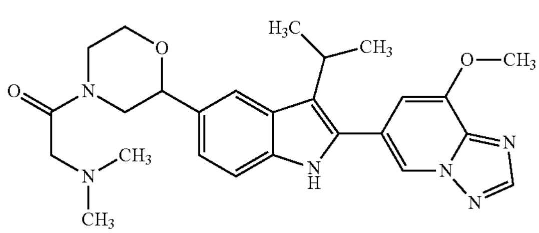 [SMILES: COc1cc(-c2[nH]c3ccc(C4CN(C(=O)CN(C)C)CCO4)cc3c2C(C)C)cn2ncnc12] | 476.6 | 477.3 | 1.216 | E |

TABLE 30-continued

| Ex. No. | Structure | Mol Wt. | LCMS MH+ | Ret Time (min) | HPLC Method |
|---|---|---|---|---|---|
| 335 | 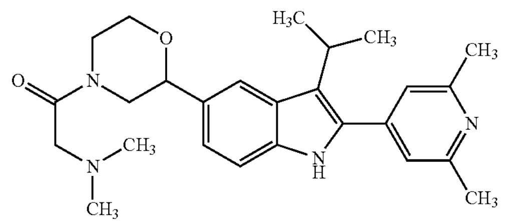 [SMILES: Cc1cc(-c2[nH]c3ccc(C4CN(C(=O)CN(C)C)CCO4)cc3c2C(C)C)cc(C)n1] | 434.6 | 435.2 | 1.44 | P |
| 336 | 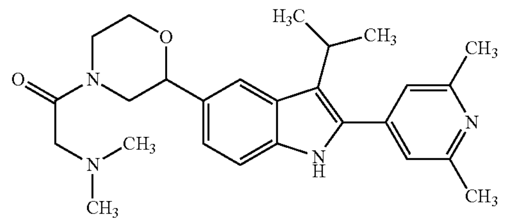 [SMILES: Cc1cc(-c2[nH]c3ccc(C4CN(C(=O)CN(C)C)CCO4)cc3c2C(C)C)cc(C)n1] | 434.6 | 435.3 | 1.33 | P |

Example 337

1-(2-(3-isopropyl-2-<8-methyl-[1,2,4]triazolo[1,5-a]pyridin-6-yl)-1H-indol-5-yl)morpholino)-2-(methylamino)ethanone (337)

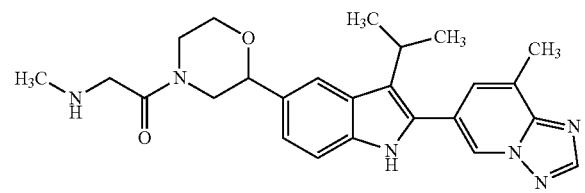

Intermediate 337A: tert-butyl (2-(2-(3-isopropyl-2-(8-methyl-[1,2,4]triazolo[1,5-a]pyridin-6-yl)-1H-indol-5-yl)morpholino)-2-oxoethyl)(methyl)carbamate (337A)

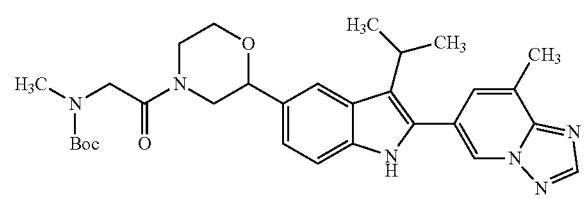

To a solution of crude 2-(3-isopropyl-2-(8-methyl-[1,2,4]triazolo[1,5-a]pyridin-6-yl)-1H-indol-5-yl)morpholine, HCl (0.021 g, 0.051 mmol) and 2-((tert-butoxycarbonyl)(methyl)amino)acetic acid (0.014 g, 0.076 mmol) in DMF (1.00 mL) were added TEA (0.1 mL, 0.717 mmol) and HATU (0.039 g, 0.102 mmol) at room temperature, then stirred at same temperature for 1 h. Crude LCMS showed no starting material and formation of product. Concentrated the reaction mass to afford crude compound. LCMS retention time 1.24 min [E], MS m/z: 547.6 [M+H]+.

Example 337

To a solution of tert-butyl (2-(2-(3-isopropyl-2-(8-methyl-[1,2,4]triazolo[1,5-a]pyridin-6-yl)-1H-indol-5-yl)morpholino)-2-oxoethyl)(methyl)carbamate (0.028 g, 0.051 mmol) in dioxane (1.00 mL) was added 4 M hydrochloric acid in dioxane (1.00 mL, 4.00 mmol) at room temperature, then the mixture was stirred at same temperature for 2 h. Crude LCMS showed no starting material and formation of product. Concentrated the reaction mass to afford crude compound, the crude material was purified by preparative LCMS purification using method D2, the fractions containing desired product was combined and dried using Genevac centrifugal evaporator to afford 1-(2-(3-isopropyl-2-(8-methyl-[1,2,4]triazolo[1,5-a]pyridin-6-yl)-1H-indol-5-yl)morpholino)-2-(methylamino)ethanone, HCl (0.0152 g, 0.030 mmol, 58% yield) as a pale solid. LCMS retention time 1.096 min [E], MS m/z: 447.3 [M+H]+; $^1$H NMR (400 MHz, CD$_3$OD) δ ppm 8.72 (s, 1H), 8.47 (s, 1H), 7.88 (bs, 1H), 7.84 (s, 1H), 7.67 (s, 1H), 7.42 (d, J=8.4 Hz, 1H), 7.27-7.22 (m, 1H), 4.62-4.51 (m, 4H), 4.16-4.10 (m, 1H), 4.05-3.95 (m, 1H), 3.86-3.71 (m, 3H), 3.49-3.43 (m, 1H), 3.08-2.92 (m, 1H), 2.71 (s, 3H), 2.65 (s, 3H), 1.53 (dd, J=6.8, 3.2 Hz, 6H).

The following Examples were prepared according to the general procedure used to prepare Example 337.

TABLE 31

| Ex. No. | Structure | Mol Wt. | LCMS MH+ | Ret Time (min) | HPLC Method |
|---|---|---|---|---|---|
| 338 | 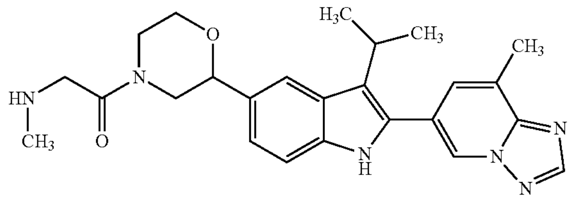 [SMILES: CNCC(=O)N1CCOC(c2ccc3[nH]c(-c4cc(C)c5ncnn5c4)c(C(C)C)c3c2)C1] | 446.6 | 447.1 | 1.273 | E |
| 339 | 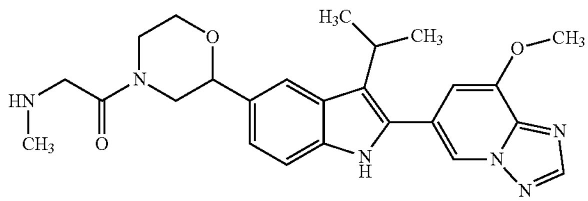 [SMILES: CNCC(=O)N1CCOC(c2ccc3[nH]c(-c4cc(OC)c5ncnn5c4)c(C(C)C)c3c2)C1] | 462.6 | 463.0 | 1.227 | E |
| 340 | 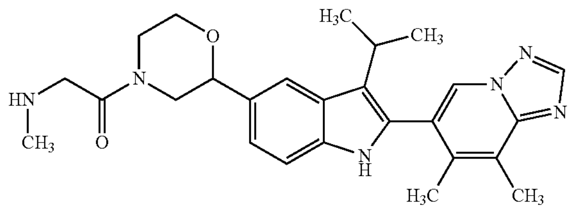 [SMILES: CNCC(=O)N1CCOC(c2ccc3[nH]c(-c4cn5ncnc5c(C)c4C)c(C(C)C)c3c2)C1] | 460.6 | 461.1 | 1.307 | E |
| 341 | 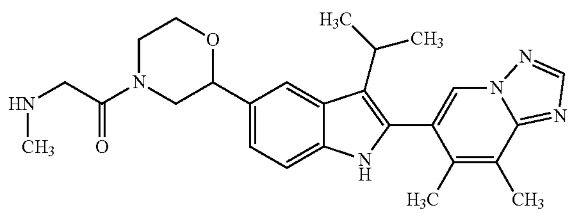 [SMILES: CNCC(=O)N1CCOC(c2ccc3[nH]c(-c4cn5ncnc5c(C)c4C)c(C(C)C)c3c2)C1] | 460.6 | 461.1 | 1.3 | E |
| 342 | 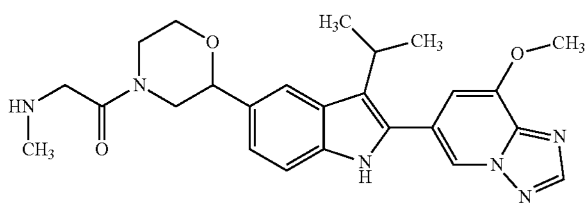 [SMILES: CNCC(=O)N1CCOC(c2ccc3[nH]c(-c4cc(OC)c5ncnn5c4)c(C(C)C)c3c2)C1] | 462.6 | 463.3 | 1.053 | E |

Example 343

2-(3-isopropyl-2-(8-methyl-[1,2,4]triazolo[1,5-a]pyridin-6-yl)-1H-indol-5-yl)-4-(2-(methylsulfonyl)ethyl)morpholine (343)

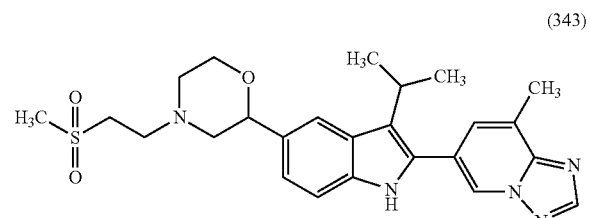

To a solution of 2-(3-isopropyl-2-(8-methyl-[1,2,4]triazolo[1,5-a]pyridin-6-yl)-1H-indol-5-yl)morpholine, HCl (0.026 g, 0.063 mmol) and 1-chloro-2-(methylsulfonyl) ethane (0.014 g, 0.095 mmol) in THF (2.00 mL) and DMF (1.00 mL) solvent mixture, was added DIPEA (0.1 mL, 0.573 mmol) at room temperature, then stirred at 90° C. for 5 h. Crude LCMS showed formation of product, concentrated the reaction mass to afford crude compound. The crude material was purified by Preparative LCMS purification using method D2, the fractions containing the product was combined and dried using Genevac centrifugal evaporator to afford 2-(3-isopropyl-2-(8-methyl-[1,2,4]triazolo[1,5-a]pyridin-6-yl)-1H-indol-5-yl)-4-(2-(methylsulfonyl)ethyl) morpholine (0.012 g, 0.025 mmol, 39% yield) as a pale solid. LCMS retention time 1.658 min [E], MS m/z: 482.2 [M+H]+; 1H NMR (400 MHz, CD3OD) δ ppm 8.72 (s, 1H), 8.47 (s, 1H), 7.82 (s, 1H), 7.67 (s, 1H), 7.39 (d, J=8.4 Hz, 1H), 7.20 (d, J=8.4 Hz, 1H), 4.67-4.64 (m, 1H), 4.11-4.06 (m, 1H), 3.91-3.84 (m, 1H), 3.40-3.32 (m, 3H), 3.13 (s, 3H), 3.10-3.04 (m, 1H), 2.97-2.91 (m, 3H), 2.71 (s, 3H), 2.44-2.28 (m, 2H), 1.52 (d, J=7.2 Hz, 6H).
The following Examples were prepared according to the general procedure used to prepare Example 343.
TABLE 32
| Ex. No. | Structure | Mol Wt. | LCMS MH+ | Ret Time (min) | HPLC Method |
|---|---|---|---|---|---|
| 344 | 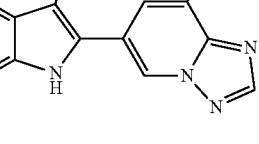 | 481.6 | 482.1 | 1.659 | E |
| 345 | 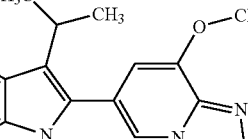 | 449.6 | 450.3 | 1.528 | E |
| 346 | 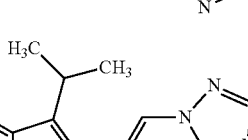 | 495.6 | 496.1 | 1.759 | E |
| 347 | 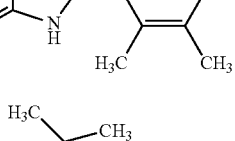 | 495.6 | 496.1 | 1.758 | E |
| 348 | 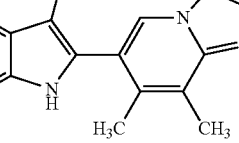 | 433.6 | 434.3 | 1.55 | P |
| 349 | 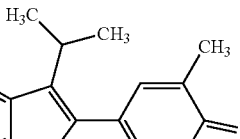 | 433.6 | 434.3 | 1.55 | P |
| 350 | 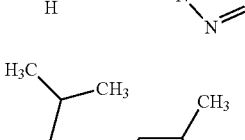 | 433.6 | 434.3 | 1.54 | P |

TABLE 32-continued

| Ex. No. | Structure | Mol Wt. | LCMS MH+ | Ret Time (min) | HPLC Method |
|---|---|---|---|---|---|
| 351 | 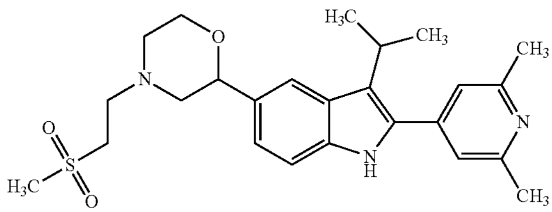 | 455.6 | 456.3 | 1.49 | P |
| 352 | 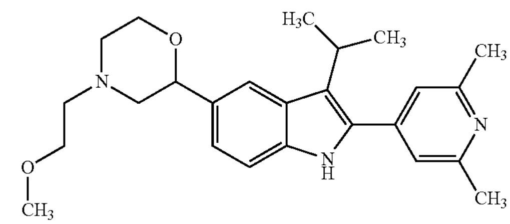 [SMILES: COCCN1CCOC(c2ccc3[nH]c(-c4cc(C)nc(C)c4)c(C(C)C)c3c2)C1] | 407.6 | 408.2 | 1.64 | P |
| 353 | 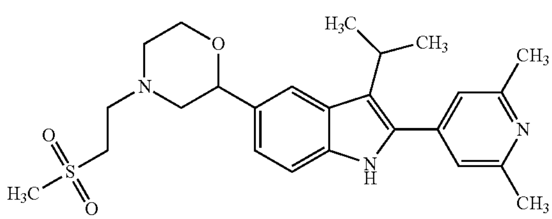 | 455.6 | 456.3 | 1.49 | P |

Example 355

1-(2-(3-isopropyl-2-(8-methyl-[1,2,4]triazolo[1,5-a]pyridin-6-yl)-1H-indol-5-yl)morpholino)-2-methylpropan-2-ol

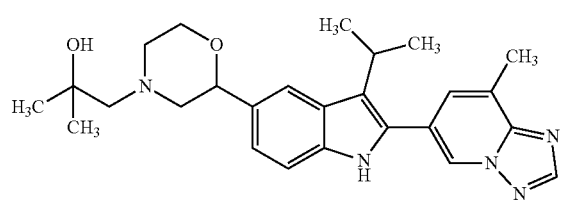

(355)

To a solution of 2-(3-isopropyl-2-(8-methyl-[1,2,4]triazolo[1,5-a]pyridin-6-yl)-1H-indol-5-yl)morpholine. HCl (0.026 g, 0.063 mmol) and 1-chloro-2-methylpropan-2-ol (10.28 mg, 0.095 mmol) in DMF (1.00 mL) was added $K_2CO_3$ (0.044 g, 0.316 mmol) at room temperature, then stirred at 90° C. for 16 h. Crude LCMS showed formation of product, filtered the reaction mass, concentrated the filtrate to afford crude compound, the crude material was purified by preparative LCMS purification using method D2, the fractions containing the product was combined and dried using Genevac centrifugal evaporator to afford 1-(2-(3-isopropyl-2-(8-methyl-[1,2,4]triazolo[1,5-a]pyridin-6-yl)-1H-indol-5-yl)morpholino)-2-methylpropan-2-ol (0.0076 g, 0.017 mmol, 27% yield) as a pale solid. LCMS retention time 1.923 min [E]. MS m/z: 448.2 [M+H]+; $^1$H NMR (400 MHz, CD$_3$OD) δ ppm 8.72 (s, 1H), 8.47 (s, 1H), 7.79 (s, 1H), 7.67 (s, 1H), 7.38 (d, J=8.4 Hz, 1H), 7.18 (d, J=8.4 Hz, 1H), 4.04-3.90 (m, 2H), 3.80 (s, 1H), 3.38-3.35 (m, 1H), 3.13-3.07 (m, 1H), 3.00-2.94 (m, 1H), 2.71 (s, 3H), 2.60-2.51 (m, 1H), 2.49-2.38 (m, 3H), 1.52 (dd, J=7.2, 1.2 Hz, 6H), 1.26 (s, 3H), 1.25 (s, 3H).

The following Examples were prepared according to the general procedure used to prepare Example 355.

TABLE 33

| Ex. No. | Structure | Mol Wt. | LCMS MH+ | Ret Time (min) | HPLC Method |
|---|---|---|---|---|---|
| 356 | 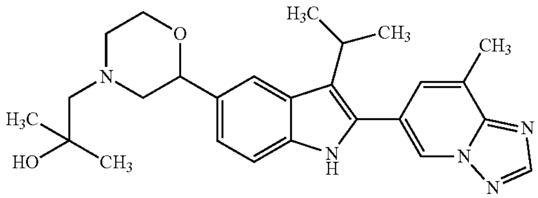 [SMILES: Cc1cc(-c2[nH]c3ccc(C4CN(CC(C)(C)O)CCO4)cc3c2C(C)C)cn2ncnc12] | 447.6 | 448.2 | 1.925 | E |
| 357 | 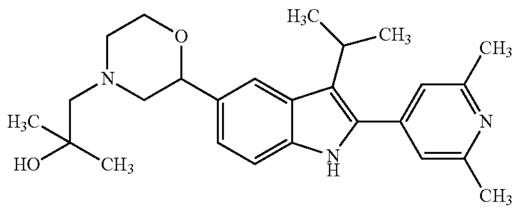 [SMILES: Cc1cc(-c2[nH]c3ccc(C4CN(CC(C)(C)O)CCO4)cc3c2C(C)C)cc(C)n1] | 421.6 | 422.3 | 1.77 | P |
| 358 | 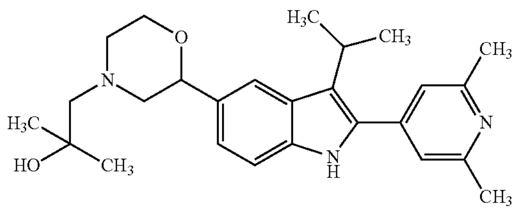 [SMILES: Cc1cc(-c2[nH]c3ccc(C4CN(CC(C)(C)O)CCO4)cc3c2C(C)C)cc(C)n1] | 421.6 | 422.3 | 1.77 | P |

Example 359

2-(ethyl(methyl)amino)-1-(2-(3-isopropyl-2-(8-methoxy-[1,2,4]triazolo[1,5-a]pyridin-6-yl)-1H-indol-5-yl)morpholino)ethanone (359)

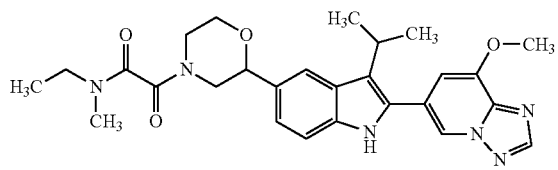

Example 359A: 2-chloro-1-(2-(3-isopropyl-2-(8-methoxy-[1,2,4]triazolo[1,5-a]pyridin-6-yl)-1H-indol-5-yl)morpholino)ethanone (359A)

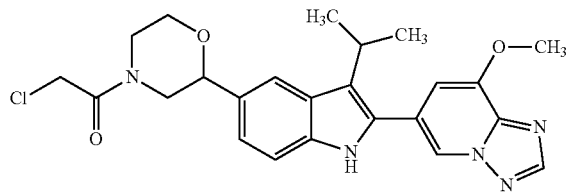

To a solution of 2-(3-isopropyl-2-(8-methoxy-[1,2,4]triazolo[1,5-a]pyridin-6-yl)-1H-indol-5-yl)morpholine (0.120 g, 0.307 mmol) in DCM (3.00 mL) were added TEA (0.214 mL, 1.533 mmol) and 2-chloroacetyl chloride (0.037 mL, 0.460 mmol) at 0° C., then stirred at same temperature for 4 h. Crude LCMS showed formation of product, quenched the reaction with water (5 mL), extracted with DCM (2×20 ML), the combined organic extracts was concentrated and dried under vacuum to afford crude compound. The crude material was purified by silica gel chromatography on an ISCO instrument using 12 g silica column, compound was eluted in 70% EA in Hexanes, the fraction was collected and concentrated to afford 2-chloro-1-(2-(3-isopropyl-2-(8-methoxy-[1,2,4]triazolo[1,5-a]pyridin-6-yl)-1H-indol-5-yl) morpholino)ethanone (0.042 g, 0.090 mmol, 29% yield) as a gummy solid. LCMS retention time 1.12 min E). MS m/z: 468.4 [M+H]+.

Example 359

To a solution of 2-chloro-1-(2-(3-isopropyl-2-(8-methoxy-[1,2,4]triazolo[1,5-a]pyridin-6-yl)-1H-indol-5-yl) morpholino)ethanone (0.012 g, 0.026 mmol) and N-methylethanamine (4.55 mg, 0.077 mmol) in THF (1.00 mL) and DMF (0.500 mL) solvent mixture was added TEA (0.2 mL, 1.435 mmol) at room temperature, then the mixture was stirred at same temperature for 16 h. Crude LCMS Showed no starting material and formation of product. The reaction mass purified by preparative LCMS purification using method D2, the fractions containing desired product was combined and dried using Genevac centrifugal evaporator to afford 2-(ethyl(methyl)amino)-1-(2-(3-isopropyl-2-(8-methoxy-[1,2,4]triazolo[1,5-a]pyridin-6-yl)-1H-indol-5-yl) morpholino) ethanone (0.006 g, 0.012 mmol, 47% yield) as a pale solid. LCMS retention time 1.467 min [E]. MS m/z: 491.1 M+H)+; 1H NMR (400 MHz, CD3OD) δ ppm 8.49 (s, 1H), 8.43 (s, 1H), 7.86 (d, J=11.2 Hz, 1H), 7.43 (d, J=8.4 Hz, 1H), 7.28-7.23 (m, 2H), 4.65-4.61 (m, 1H), 4.52-4.44 (m, 1H), 4.13 (s, 3H), 4.12-4.07 (m, 1H), 3.90-3.75 (m, 2H), 3.45-3.35 (m, 2H), 3.09-2.90 (m, 3H), 2.73-2.68 (m, 2H), 1.54 (d, J=6.8 Hz, 6H), 1.32-1.26 (m, 3H).

The following Examples were prepared according to the general procedure used to prepare Example 359.

TABLE 34

| Ex. No. | Structure | Mol Wt. | LCMS MH+ | Ret Time (min) | HPLC Method |
|---|---|---|---|---|---|
| 360 | 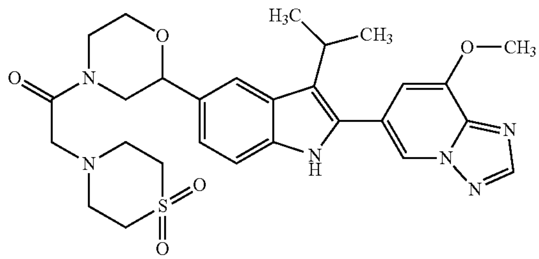 [SMILES: COc1cc(-c2[nH]c3ccc(C4CN(C(=O)CN5CCS(=O)(=O)CC5)CCO4)cc3c2C(C)C)cn2ncnc12] | 566.7 | 567.0 | 1.504 | E |
| 361 | 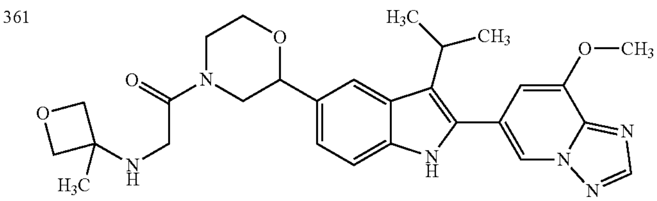 | 518.6 | 519.2 | 1.51 | E |

Examples 362 and 363

3-(2-(2,6-dimethylpyridin-4-yl)-3-isopropyl-1H-indol-5-yl)quinuclidine

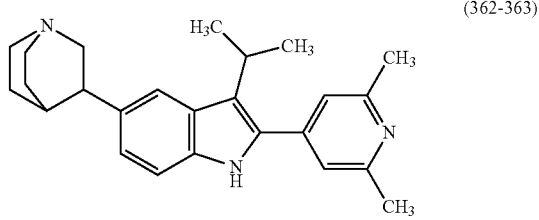 [SMILES: Cc1cc(-c2[nH]c3ccc(C4CN5CCC4CC5)cc3c2C(C)C)cc(C)n1]
(362-363)

Intermediate 362A: 3-(2-(2,6-dimethylpyridin-4-yl)-3-isopropyl-1H-indol-5-yl)-1-azabicyclo[2.2.2]oct-2-ene

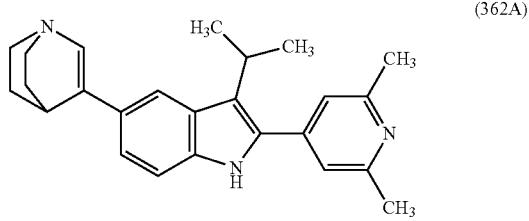 [SMILES: Cc1cc(-c2[nH]c3ccc(C4=CN5CCC4CC5)cc3c2C(C)C)cc(C)n1]
(362A)

To a solution of 2-(2,6-dimethylpyridin-4-yl)-3-isopropyl-5-(4,4,5,5-tetramethyl-1,3,2-dioxaborolan-2-yl)-1H-indole (300 mg, 0.769 mmol) and 1-azabicyclo[2.2.2]oct-2-en-3-yltrifluoromethanesulfonate (237 mg, 0.922 mmol) in a 100 ml round bottom flask was added THF (10 mL) followed by aqueous solution of tripotassium phosphate (245 mg, 1.153 mmol). The reaction mass was degassed with argon for 20 min prior to the addition of PdCl$_2$(dppf)-CH$_2$Cl$_2$ adduct (62.8 mg, 0.077 mmol). The system was evacuated under vacuum (via a needle from a nitrogen/vacuum manifold line) and backfilled with nitrogen gas. The reaction mass was heated at 75° C. for 12 h. The reaction mixture was diluted with EtOAc (100 mL), washed with water (2×50 mL) and brine (50 mL) dried (Na$_2$SO$_4$), filtered and the filtrate concentrated to give crude product. The crude product w as purified by silica gel chromatography on an ISCO instrument using 24 g silica gel column, compound was eluted over a 20 min gradient with 0%-50% EtOAc/hexanes, the fractions were collected and concentrated to afford 3-(2-(2,6-dimethylpyridin-4-yl)-3-isopropyl-1H-indol-5-yl)-1-azabicyclo[2.2.2]oct-2-ene (0.1 g. 0.387 mmol, 39% yield) as an white solid. LCMS retention time 2.51 min G). MS m/z: 258 [M+H]+.

Examples 362 and 363

To a solution of 3-(2-(2,6-dimethylpyridin-4-yl)-3-isopropyl-1H-indol-5-yl)-1-azabicyclo [2.2.2]oct-2-ene (60 mg, 0.161 mmol) in ethyl acetate (10 mL) was added Pd/C (17.19 mg, 0.161 mmol), then stirred at room temperature under H$_2$ gas bladder for 12 h., filtered the reaction mass and concentrated to afford crude compound. The crude material was purified by chiral HPLC to separate both the enantiomers. The fractions containing desired compound was combined and evaporated to dryness using Genevac to afford:

Example 362 (Enantiomer 1): (0.003 g, 5.4% yield) as a pale white solid. LCMS retention time 1.08 min [E], MS m/z: 374 (M+H); $^1$H NMR (400 MHz, DMSO-do) δ ppm 11.05 (s, 1H), 7.79 (s, 1H), 7.31 (d, J=8.40 Hz, 1H), 7.14 (s, 2H), 7.06 (d, J=7.60 Hz, 1H), 2.82-2.84 (m, 4H), 2.72-2.78 (m, 2H), 2.62-2.66 (m, 2H), 2.33-2.39 (m, 1H), 1.82 (s, 6H), 1.64-1.72 (m, 4H), 1.45 (d, J=4.00 Hz, 6H).

Example 363 (Enantiomer 2): (0.0025 g, 5.2% yield) as a pale white solid. LCMS retention time 1.08 min [E], MS m/z: 374 (M+H); $^1$H NMR (400 MHz, DMSO-d$_6$) δ ppm 11.05 (s, 1H), 7.79 (s, 1H), 7.31 (d, J=8.40 Hz, 1H), 7.14 (s, 2H), 7.06 (d, J=7.60 Hz, 1H), 2.82-2.84 (m, 4H), 2.72-2.78 (m, 2H), 2.62-2.66 (m, 2H), 2.33-2.39 (m, 1H), 1.82 (s, 6H), 1.64-1.72 (m, 4H), 1.45 (d, J=4.00 Hz, 6H).

The following Examples were prepared according to the general procedure used to prepare Examples 362 and 363.

TABLE 35

| Ex. No. | Structure | Mol Wt. | LCMS MH+ | Ret Time (min) | HPLC Method |
|---|---|---|---|---|---|
| 364 | 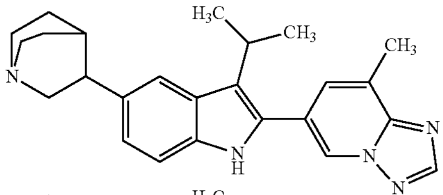 [SMILES: Cc1cc(-c2[nH]c3ccc(C4CN5CCC4CC5)cc3c2C(C)C)cn2ncnc12] | 399.5 | 400.3 | 4.77 | I |
| 365 | 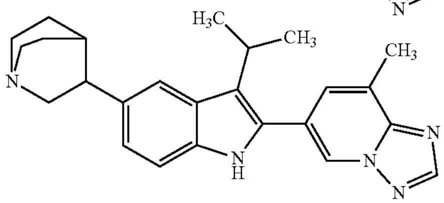 | 399.5 | 400.2 | 4.78 | I |

Example 366

8-(2-(2,6-dimethylpyridin-4-yl)-3-isopropyl-1H-indol-5-yl)-1,3-diazaspiro[4.5]decane-2,4-dione (366)

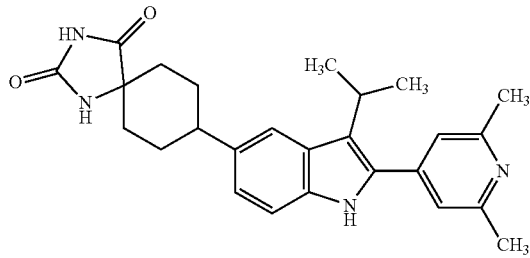

Intermediate 366A: tert-butyl 2-(2,6-dimethylpyridin-4-yl)-5-(2,4-dioxo-1,3-diazaspiro[4.5]decan-8-yl)-3-isopropyl-1H-indole-1-carboxylate (366A)

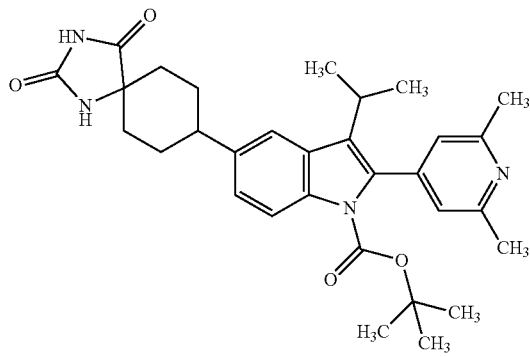

To a solution of tert-butyl 2-(2,6-dimethylpyridin-4-yl)-3-isopropyl-5-(4-oxocyclohexyl)-1H-indole-1-carboxylate (0.1 g, 0.217 mmol) in methanol (5 ml), were added ammonium carbonate (0.063 g, 0.651 mmol) and potassium cyanide (0.028 g, 0.434 mmol) at room temperature, then the reaction mixture was stirred at 70° C. for 12 h. The reaction mass was quenched with water, extracted with ethyl acetate. The organic layer was evaporated and purified by silica gel chromatography using tert-butyl 2-(2,6-dimethylpyridin-4-yl)-5-(2,4-dioxo-1,3-diazaspiro[4.5]decan-8-yl)-3-isopropyl-1H-indole-1-carboxylate (0.1 g, 0.187 mmol, 82% yield) as a pale white solid. LCMS retention time 2.94 min [E], MS m/z: 531 (M+H).

Example 366

A solution of tert-butyl 2-(2,6-dimethylpyridin-4-yl)-5-(2, 4-dioxo-1,3-diazaspiro[4.5]decan-8-yl)-3-isopropyl-1H-indole-1-carboxylate (0.1 g, 0.188 mmol) in dioxane-HCl (2 mL) was stirred for 5 h. The reaction mass was concentrated to afford crude product. The crude samples were purified by reverse phase prep HPLC using method D1. The fractions containing desired compound was combined and evaporated to dryness using Genevac to afford 8-(2-(2,6-dimethylpyridin-4-yl)-3-isopropyl-1H-indol-5-yl)-1,3-diazaspiro[4.5]decane-2,4-dione (0.002 g, 2.56% yield) as a pale white solid. LCMS retention time 1.3 min [E], MS m/z: 431 (M+H): $^1$H NMR (400 MHz, DMSO-d$_6$) δ ppm 11.10 (s, 1H), 10.80 (s, 1H), 8.79 (s, 1H), 7.63 (s, 1H), 7.26 (d, J=8.00 Hz, 1H), 7.14 (s, 1H), 7.09 (d, J=1.60 Hz, 2H), 4.10-4.21 (m, 2H), 3.32-3.38 (m, 4H), 1.82-1.84 (m, 8H), 1.45 (d, J=4.00 Hz, 6H).

Example 367

2-(3-isopropyl-2-(8-methyl-[1,2,4]triazolo[1,5-a] pyridin-6-yl)-1H-indol-5-yl)-5,5-dimethylmorpholine (367)

Intermediate 367A: 2-((2-hydroxy-2-(4-nitrophenyl)ethyl)amino)-2-methylpropan-1-ol

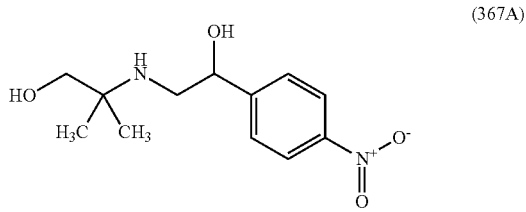 [SMILES: CC(C)(CO)NCC(O)c1ccc([N+](=O)[O-])cc1]
(367A)

To a solution of 2-(4-nitrophenyl)oxirane (8 g, 48.4 mmol) in methanol (160 mL) was added 2-amino-2-methylpropan-1-ol (11.99 mL, 121 mmol) and the mass was stirred at 70° C. for 4 h. The reaction mass was concentrated and the residue was quenched with cold water, and extracted with DCM (150 mL), dried over $Na_2SO_4$, and concentrated to afford the 2-((2-hydroxy-2-(4-nitrophenyl)ethyl)amino)-2-methylpropan-1-ol (9.2 g, 35.5 mmol, 73% yield) as viscous liquid. LCMS retention time 0.99 min [E], MS m/z: 255 (M+H).

Intermediate 367B: 5,5-dimethyl-2-(4-nitrophenyl)morpholine

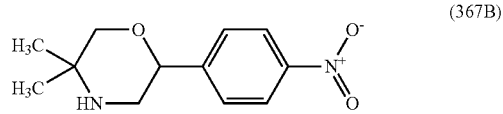
(367B)

To a solution of 2-((2-hydroxy-2-(4-nitrophenyl)ethyl)amino)-2-methylpropan-1-ol (30 g, 118 mmol)) in DCM (10 mL) was added $H_2SO_4$ (50 mL, 938 mmol) at 0° C., stirred for 5 min, then stirred at room temperature for 16 h. The reaction w as quenched in ice. The reaction mixture w as neutralized with 10% NaOH (500 mL), pH of the aqueous layer was brought to 8. The aqueous layer was extracted with DCM and the organic layer was dried over $Na_2SO_4$ and concentrated to afford 5,5-dimethyl-2-(4-nitrophenyl)morpholine (12 g, 35.6 mmol, 30% yield) as pale yellow solid. LCMS retention time 1.23 min [E], MS m/z: 237 (M+H).

Intermediate 367C: tert-butyl 5,5-dimethyl-2-(4-nitrophenyl)morpholine-4-carboxylate

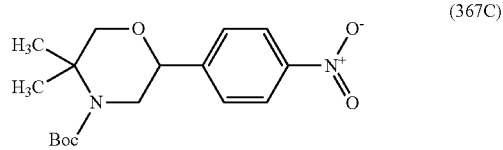 [SMILES: CC(C)(C)OC(=O)N1CC(c2ccc([N+](=O)[O-])cc2)OCC1(C)C]
(367C)

To a solution of 5,5-dimethyl-2-(4-nitrophenyl)morpholine (4 g, 16.93 mmol) in DCM (20 mL) w as added TEA (4.72 mL, 33.9 mmol) at 0° C., stirred for 5 min, and then was added drop wise BOC-anhydride (5.90 mL, 25.4 mmol), then stirred at ambient temperature for 16 h. The reaction mass was quenched with water (15 mL), separated both the layers, the aqueous layer was extracted with EtOAc (2×50 mL), the combined organic extracts was dried ($Na_2SO_4$) and concentrated to afford crude compound. This was further purified by silica gel chromatography using 80 g silica column, the compound was eluted in $CHCl_3$: MeOH (9:1), the fractions were collected and concentrated to afford tert-butyl 5,5-dimethyl-2-(4-nitrophenyl) morpholine-4-carboxylate (2.2 g, 6.47 mmol, 38% yield) as a white solid. LCMS retention time 3.62 min [E], MS m/z: 337 (M+H)

Intermediate 367D: tert-butyl 2-(4-aminophenyl)-5,5-dimethylmorpholine-4-carboxylate

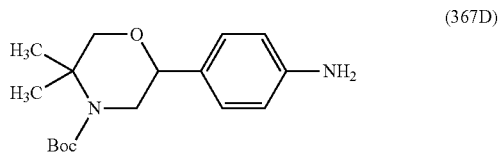
(367D)

To a solution of tert-butyl 5,5-dimethyl-2-(4-nitrophenyl) morpholine-4-carboxylate (2.3 g, 6.84 mmol) in methanol (80 mL) was added Pd/C (0.728 g, 6.84 mmol) and stirred at room temperature under hydrogen for 2 h. The reaction mixture was passed through the pad of celite and concentrated to afford tert-butyl 2-(4-aminophenyl)-5,5-dimethylmorpholine-4-carboxylate (1.8 g, 5.64 mmol, 82%) as white solid. LCMS retention time 2.65 min [E], MS m/z: 307 (M+H).

Intermediate 367E: tert-butyl 2-(4-amino-3-iodophenyl)-5,5-dimethylmorpholine-4-carboxylate

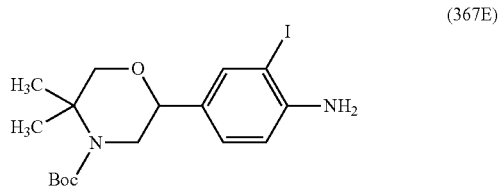 [SMILES: CC(C)(C)OC(=O)N1CC(c2ccc(N)c(I)c2)OCC1(C)C]
(367E)

To a solution of tert-butyl 2-(4-aminophenyl)-5,5-dimethylmorpholine-4-carboxylate (5 g, 16.32 mmol) in DCM (100 mL) and methanol (50.00 mL) solvent mixture were added calcium carbonate (5.23 g, 52.2 mmol) and benzyltrimethylaminoniumdichloroiodate (5.68 g, 16.32 mmol) at room temperature, then the slurry was stirred at same temperature 2 h. The reaction mass was diluted with water (20 mL), extracted with EtOAc, the combined organic extract was concentrated to afford crude product. The crude product was further purified by silica gel chromatography to afford tert-butyl 2-(4-amino-3-iodophenyl)-5,5-dimethylmorpholine-4-carboxylate (2.1 g, 4.76 mmol, 29%) as an off white solid. LCMS retention time 3.31 min [E], MS m/z: 433 (M+H).

Intermediate 367F: tert-butyl 2-(3-iodo-4-((3-methylbut-2-en-1-yl)amino)phenyl)-5,5-dimethylmorpholine-4-carboxylate

(367F)

To a solution of tert-butyl 2-(4-amino-3-iodophenyl)-5,5-dimethylmorpholine-4-carboxylate (2.1 g, 4.86 mmol) in THF (25 mL) was added LDA (3.64 mL, 7.29 mmol) at −10° C., then brought to 10° C. in 30 min, and stirred at same temperature for 30 min. Cooled to −76° C. and was added 1-bromo-3-methylbut-2-ene (0.673 mL, 5.83 mmol), then brought to ambient temperature and stirred at same temperature for 3 h. The reaction was quenched with brine. The reaction mixture was extracted with EtOAc (2×200 ml), the combined organic extracts was, dried ($Na_2SO_4$) and concentrated to afford crude compound. The crude product was further purified by silica gel chromatography using n-hexane:ethyl acetate to afford tert-butyl 2-(3-iodo-4-((3-methylbut-2-en-1-yl)amino) phenyl)-5,5-dimethylmorpholine-4-carboxylate (0.85 g, 1.7 mmol, 35%) as viscous liquid. LCMS retention time 4.38 min [E], MS m/z: 501 (M+H).

Intermediate 367G: tert-butyl 2-(3-isopropyl-1H-indol-5-yl)-5,5-dimethylmorpholine-4-carboxylate

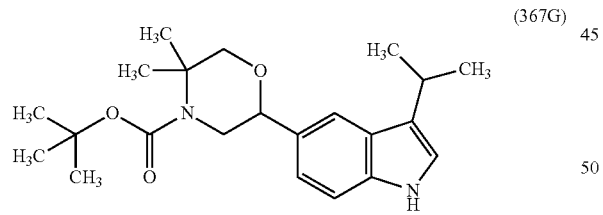

(367G)

To a solution of tert-butyl 2-(3-iodo-4-((3-methylbut-2-en-1-yl)amino)phenyl)-5,5-dimethylmorpholine-4-carboxylate (1 g, 1.998 mmol) in acetonitrile (10 mL) was degasified for 10 min with argon and added TEA (0.836 mL, 6.00 mmol) followed by $Pd(OAc)_2$ (0.045 g, 0.200 mmol), then heated to 110° C. for 12 h. The reaction was monitored by LCMS. LC/MS Showed formation of desired product along with starting material. Further TEA (0.836 mL, 6.00 mmol) was added and degasified for 2 min with argon and added $Pd(OAc)_2$ (0.045 g, 0.200 mmol) and continued the reaction for another 12 h. The reaction mass was concentrated to afford crude product. The crude mass was further purified by silica gel chromatography using 24 g silica column, to afford tert-butyl 2-(3-isopropyl-1H-indol-5-yl)-5,5-dimethylmorpholine-4-carboxylate (0.4 g, 1.052 mmol, 52%) as white solid. LCMS retention time 3.79 min [E], MS m/z: 373 (M+H).

Intermediate 367H: tert-butyl 2-(2-bromo-3-isopropyl-1H-indol-5-yl)-5,5-dimethyl morpholine-4-carboxylate

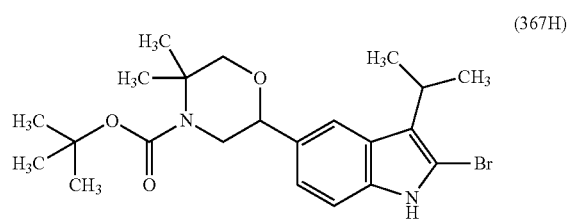 [SMILES: CC(C)c1c(Br)[nH]c2ccc(C3CN(C(=O)OC(C)(C)C)C(C)(C)CO3)cc12]

(367H)

To a solution of tert-butyl 2-(3-isopropyl-1H-indol-5-yl)-5,5-dimethylmorpholine-4-carboxylate (1.1 g, 2.95 mmol) in DCE (4 mL) was added NBS (0.526 g, 2.95 mmol) at −10° C., then brought to 10° C. in 30 min, and stirred at that temperature for 30 min. The reaction mass was quenched with brine, extracted with DCM (2×20 ml), the combined organic extracts was dried ($Na_2SO_4$) and concentrated to afford crude compound. This was further purified by silica gel chromatography using 40 g silica column, to afford tert-butyl 2-(2-bromo-3-isopropyl-1H-indol-5-yl)-5,5-dimethylmorpholine-4-carboxylate (0.8 g, 1.595 mmol, 54%). LCMS retention time 3.89 min [E], MS m/z: 451 (M+H).

Intermediate 367I: tert-butyl 2-(3-isopropyl-2-(8-methyl-[1,2,4]triazolo[1,5-a]pyridin-6-yl)-1H-indol-5-yl)-5,5-dimethylmorpholine-4-carboxylate

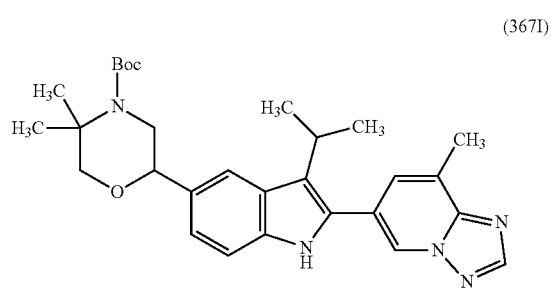 [SMILES: Cc1cc(-c2[nH]c3ccc(C4CN(C(=O)OC(C)(C)C)C(C)(C)CO4)cc3c2C(C)C)cn2ncnc12]

(367I)

tert-butyl 2-(3-isopropyl-2-(8-methyl-[1,2,4]triazolo[1,5-a]pyridin-6-yl)-1H-indol-5-yl)-5,5-dimethylmorpholine-4-carboxylate (0.5 g, 0.943 mmol, 53.2%) was prepared according to the general procedure described in intermediate 281J, using tert-butyl 2-(2-bromo-3-isopropyl-1H-indol-5-yl)-5,5-dimethyl morpholine-4-carboxylate (0.8 g, 1.772 mmol) as the starting intermediate. LCMS retention time 3.5 min (E), MS m/z: 504 (M+H).

The following Intermediates were prepared according to the general procedure used to prepare Intermediate 367I.

TABLE 36

| Intermediate | Structure | Mol Wt. | LCMS MH+ | Ret Time (min) | HPLC Method |
|---|---|---|---|---|---|
| INT-367I-2 | 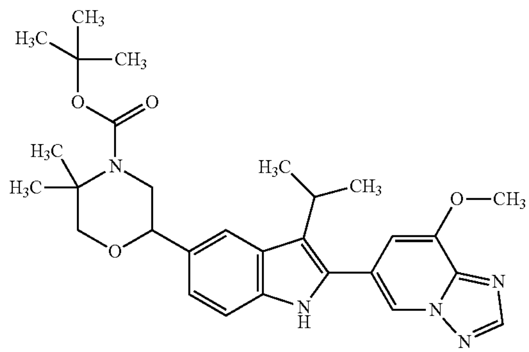 [SMILES: COc1cc(-c2[nH]c3ccc(C4CN(C(=O)OC(C)(C)C)C(C)(C)CO4)cc3c2C(C)C)cn2ncnc12] | 519.635 | 520 | 3.43 | D |
| INT-367I-3 | 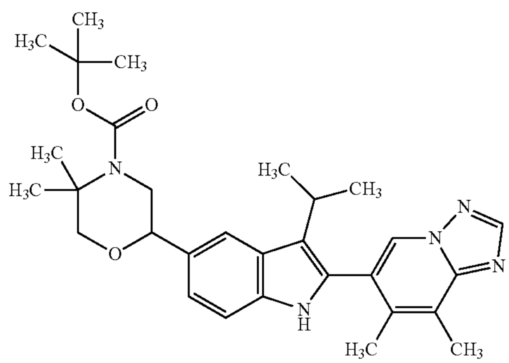 [SMILES: Cc1c(-c2[nH]c3ccc(C4CN(C(=O)OC(C)(C)C)C(C)(C)CO4)cc3c2C(C)C)cn2ncnc2c1C] | 517.6 | 518 | 3.62 | D |

Example 367

2-(3-isopropyl-2-(8-methyl-[1,2,4]triazolo[1,5-a]pyridin-6-yl)-1H-indol-5-yl)-5,5-dimethyl morpholine (0.15 g, 0.368 mmol, 95%) was prepared as described for Example 155, using tert-butyl 2-(3-isopropyl-2-(8-methyl-[1,2,4]triazolo[1,5-a]pyridin-6-yl)-1H-indol-5-yl)-5,5-dimethylmorpholine-4-carboxylate (0.195 g, 0.388 mmol) as the starting intermediate. LCMS retention time 1.38 min E, MS m/z: 404 (M+H); $^1$H NMR (400 MHz, DMSO-d$_6$) δ ppm 11.39 (s, 1H), 8.81 (s, 1H), 8.58 (s, 1H), 7.61 (d, J=8.00 Hz, 1H), 7.59 (s, 1H), 7.21 (d, J=4.00 Hz, 1H), 7.20 (d, J=0.80 Hz, 1H), 4.84-4.85 (m, 1H), 3.79-3.80 (m, 2H), 3.56 (s, 6H), 3.49 (d, J=6.80 Hz, 3H), 2.51 (d, J=1.60 Hz, 3H), 1.46 (d, J=6.40 Hz, 6H).

The following Examples were prepared according to the general procedure used to prepare in Example 367.

TABLE 37

| Ex. No. | Structure | Mol Wt. | LCMS MH+ | Ret Time (min) | HPLC Method |
|---|---|---|---|---|---|
| 368 | 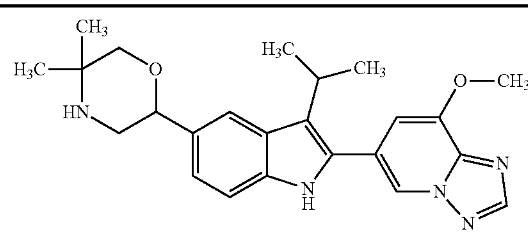 | 419.5 | 420.3 | 1.201 | E |
| 369 | 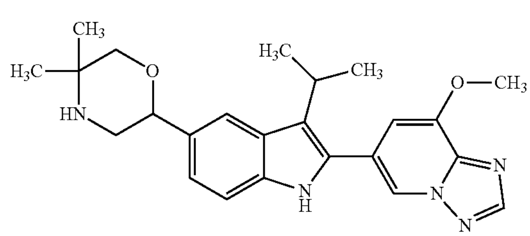 [SMILES: COc1cc(-c2[nH]c3ccc(C4CNC(C)(C)CO4)cc3c2C(C)C)cn2ncnc12] | 419.5 | 420.3 | 1.202 | E |

TABLE 37-continued

| Ex. No. | Structure | Mol Wt. | LCMS MH+ | Ret Time (min) | HPLC Method |
|---|---|---|---|---|---|
| 370 | 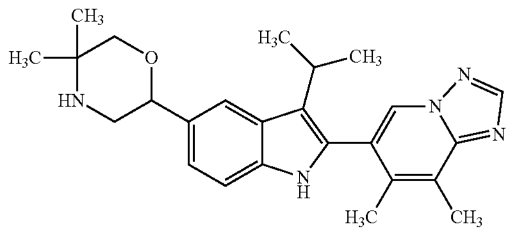 [SMILES: Cc1c(-c2[nH]c3ccc(C4CNC(C)(C)CO4)cc3c2C(C)C)cn2ncnc2c1C] | 417.6 | 418.0 | 1.29 | E |
| 371 | 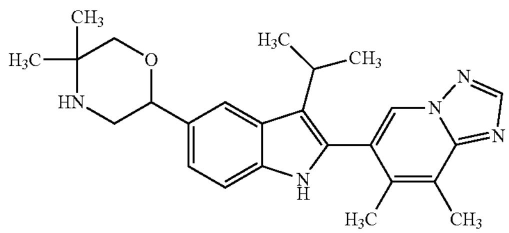 [SMILES: Cc1c(-c2[nH]c3ccc(C4CNC(C)(C)CO4)cc3c2C(C)C)cn2ncnc2c1C] | 417.6 | 418.3 | 1.297 | E |

Examples 372 and 373

2-(di methylamino)-1-(2-(3-isopropyl-2-(8-methyl-[1,2,4]triazolo[1,5-a]pyridin-6-yl)-1H-indol-5-yl)-5,5-dimethylmorpholino)ethanone

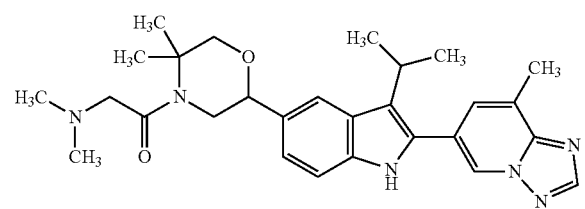

(372-373)

To a solution of 2-(3-isopropyl-2-(8-methyl-[1,2,4]triazolo[1,5-a]pyridin-6-yl)-1H-indol-5-yl)-5,5-dimethylmorpholine (0.1 g, 0.248 mmol) in DMF (1 mL) was added 2-(dimethylamino)acetic acid (0.051 g, 0.496 mmol)). TEA (0.104 mL, 0.743 mmol), and followed by the addition of HATU (0.141 g, 0.372 mmol) under an argon atmosphere and the reaction mixture was stirred at ambient temperature for 12 h. The reaction mass was then concentrated to remove the DMF to afford crude product. The crude samples were purified by reverse phase prep HPLC using method D1. The fractions containing desired compound was combined and evaporated to dryness using Genevac to afford racemate 2-(dimethylamino)-1-(2-(3-isopropyl-2-(8-methyl-[1,2,4]triazolo[1,5-a]pyridin-6-yl)-1H-indol-5-yl)-5,5-dimethylmorpholino)ethanone (0.001 g, 2% yield) as a pale white solid. LCMS retention time 1.96 min [E], MS m/z: 489 (M+H); $^1$H NMR (400 MHz, DMSO-d$_6$) δ ppm 11.23 (s, 1H), 8.82 (s, 1H), 8.53 (s, 1H), 7.71 (s, 1H), 7.61 (s, 1H), 7.34 (d, J=8.3 Hz, 1H), 7.17-7.09 (m, 1H), 4.57 (br. s, 1H), 3.90 (s, 2H), 3.69 (d, J=9.5 Hz, 1H), 3.58 (d, J=11.7 Hz, 1H), 3.27 (t, J=7.0 Hz, 1H), 3.10 (s, 3H), 2.81 (s, 3H), 2.73 (br. s., 1H), 2.67 (br. s, 1H), 2.63 (s, 3H), 1.42 (d, J=6.8 Hz, 3H), 1.44 (d, J=6.8 Hz, 3H), 1.19-1.09 (m, 3H), 1.05 (br. s, 3H).

The racemic 2-(dimethylamino)-1-(2-(3-isopropyl-2-(8-methyl-[1,2,4]triazolo[1,5-a]pyridin-6-yl)-1H-indol-5-yl)-5,5-dimethylmorpholino)ethanone was purified by Chiral HPLC using Column: Chiralcel OJ-H (250×4.6) mm, 5 μm, % CO$_2$: 70%, % Co solvent: 30% of (0.2% DEA in IP A), Total Flow: 80.0 g/min, Back Pressure: 100 bar, Temperature: 30° C., UV: 230 nm. The fractions were collected, concentrated and lyophilized to afford both enantiomers.

Example 372 (Enantiomer 1): (0.003 g, 2.02% yield) as a pale white solid. LCMS retention time 1.64 min [E], MS m/z: 489 (M+H): $^1$H NMR (400 MHz, DMSO-d$_6$) δ ppm 11.23 (s, 1H), 8.82 (s, 1H), 8.53 (s, 1H), 7.71 (s, 1H), 7.61 (s, 1H), 7.34 (d, J=8.3 Hz, 1H), 7.17-7.09 (m, 1H), 4.57 (br. s, 1H), 3.90 (s, 2H), 3.69 (d, J=9.5 Hz, 1H), 3.58 (d, J=11.7 Hz, 1H), 3.27 (t, J=7.0 Hz, 1H), 3.10 (s, 3H), 2.81 (s, 3H), 2.73 (br. s., 1H), 2.67 (br. s., 1H), 2.63 (s, 3H), 1.42 (d, J=6.8 Hz, 3H), 1.44 (d, J=6.8 Hz, 3H), 1.19-1.09 (m, 3H), 1.05 (br. s, 3H).

Example 373 (Enantiomer 2): (0.0029 g, 2.0% yield) as a pale white solid. LCMS retention time 1.66 min [E], MS m/z: 489 (M+H): $^1$H NMR (400 MHz, DMSO-d$_6$) δ ppm 11.22 (s, 1H), 8.82 (s, 1H), 8.53 (s, 1H), 7.71 (s, 1H), 7.61 (s, 1H), 7.34 (d, J=8.1 Hz, 1H), 7.13 (d, J=8.6 Hz, 1H), 4.56 (d, J=9.8 Hz, 1H), 3.90 (s, 2H), 3.69 (d, J=12.5 Hz, 1H), 3.58 (d, J=11.2 Hz, 1H), 3.29-3.23 (m, 1H), 3.10 (s, 3H), 2.81 (s, 3H), 2.73 (br. s., 1H), 2.63 (s, 3H), 1.42 (d, J=6.8 Hz, 3H), 1.44 (d, J=6.8 Hz, 3H), 1.11 (br. s, 3H), 1.05 (s, 3H).

The following Examples were prepared according to the general procedure used to prepare Examples 372 and 373.

TABLE 38

| Ex. No. | Structure | Mol Wt. | LCMS MH+ | Ret Time (min) | HPLC Method |
|---|---|---|---|---|---|
| 374 | 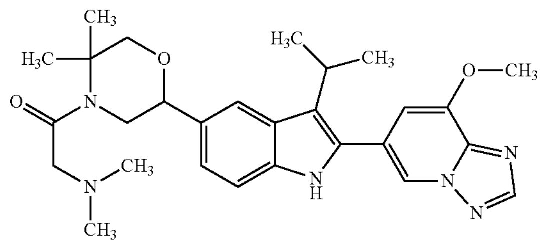 [SMILES: COc1cc(-c2[nH]c3ccc(C4CN(C(=O)CN(C)C)C(C)(C)CO4)cc3c2C(C)C)cn2ncnc12] | 504.6 | 505.4 | 1.39 | E |

Examples 375 and 376

2-(3-isopropyl-2-(8-methyl-[1,2,4]triazolo[1,5-a]pyridin-6-yl)-1H-indol-5-yl)-4,5,5-trimethylmorpholine (375-376)

2-(3-isopropyl-2-(8-methyl-[1,2,4]triazolo[1,5-a]pyridin-6-yl)-1H-indol-5-yl)-4,5,5-trimethylmorpholine (0.001 g, 1.02% yield) was prepared according to the general procedure described in Example 289 using 2-(3-isopropyl-2-(8-methyl-[1,2,4]triazolo[1,5-a]pyridin-6-yl)-1H-indol-5-yl)-5,5-dimethylmorpholine (50 mg, 0.124 mmol) as the starting intermediate. LCMS retention time 1.90 min [E], MS m/z: 418 (M+H); $^1$H NMR (400 MHz, DMSO-d$_6$) δ ppm 11.22 (s, 1H), 8.83 (s, 1H), 8.53 (s, 1H), 7.72 (s, 1H), 7.61 (s, 1H), 7.34 (d, J=8.6 Hz, 1H), 7.15 (d, J=8.3 Hz, 1H), 4.60 (d, J=9.5 Hz, 1H), 3.59 (d, J=10.0 Hz, 1H), 3.28-3.23 (m, 2H), 2.63 (s, 3H), 2.20 (br. s, 3H), 1.43 (d, >6.8 Hz, 3H), 1.44 (d, >6.8 Hz, 3H), 1.09 (br. s, 3H), 1.02 (br. s., 3H).

The racemic 2-(3-isopropyl-2-(8-methyl-[1,2,4]triazolo[1,5-a]pyridin-6-yl)-1H-indol-5-yl)-4,5,5-trimethylmorpholine was purified by Chiral HPLC using Column: Chiralcel OJ-H (250×4.6) mm, 5 nm, % CO$_2$: 70%, % Co solvent: 30% of (0.2% DEA in IPA), Total Flow: 80.0 g/min, Back Pressure: 100 bar, Temperature: 30° C., UV: 230 nm. The fractions were collected, concentrate and lyophilized to afford both the enantiomers.

Example 375 (Enantiomer 1): (1.2 mg, 2.52% yield) as a pale white solid. LCMS retention time 1.563 min [E], MS m/z: 418 (M+H); $^1$H NMR (400 MHz, DMSO-d$_6$) δ ppm 11.22 (s, 1H), 8.83 (s, 1H), 8.53 (s, 1H), 7.72 (s, 1H), 7.61 (s, 1H), 7.34 (d, J=8.6 Hz, 1H), 7.15 (d, J=8.3 Hz, 1H), 4.60 (d, J=9.5 Hz, 1H), 3.59 (d, J=10.0 Hz, 1H), 3.28-3.23 (m, 2H), 2.63 (s, 3H), 2.20 (br. s, 3H), 1.43 (d, J=6.8 Hz, 3H), 1.44 (d, J=6.8 Hz, 3H), 1.09 (br. s, 3H), 1.02 (br. s., 3H).

Example 376 (Enantiomer 2): (0.5 mg, 2.02% yield) as a pale white solid. LCMS retention time 1.56 min [E], MS m/z: 418 (M+H); $^1$H NMR (400 MHz, DMSO-d$_6$) δ ppm 11.22 (s, 1H), 8.83 (s, 1H), 8.53 (s, 1H), 7.72 (s, 1H), 7.61 (s, 1H), 7.34 (d, J=8.6 Hz, 1H), 7.15 (d, J=7.6 Hz, 1H), 4.60 (d, J=9.5 Hz, 1H), 3.58 (br. s., 1H), 3.27-3.18 (m, 2H), 2.64 (s, 3H), 2.20 (br. s, 3H), 1.43 (d, J=6.6 Hz, 3H), 1.44 (d, J=6.8 Hz, 3H), 1.15 (d, J=7.1 Hz, 1H), 1.12-0.88 (m, 6H).

The following Examples were prepared according to the general procedure used to prepare Examples 375 and 376.

TABLE 39

| Ex. No. | Structure | Mol Wt. | LCMS MH+ | Ret Time (min) | HPLC Method |
|---|---|---|---|---|---|
| 377 | 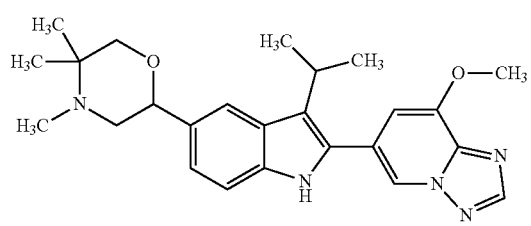 [SMILES: COc1cc(-c2[nH]c3ccc(C4CN(C)C(C)(C)CO4)cc3c2C(C)C)cn2ncnc12] | 433.6 | 434.3 | 1.52 | E |

TABLE 39-continued

| Ex. No. | Structure | Mol Wt. | LCMS MH+ | Ret Time (min) | HPLC Method |
|---|---|---|---|---|---|
| 378 | 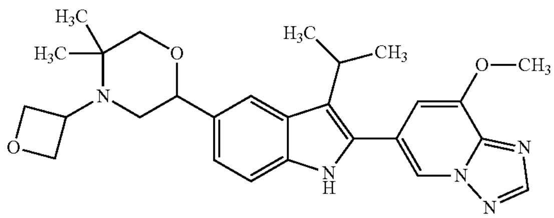 [SMILES: COc1cc(-c2[nH]c3ccc(C4CN(C5COC5)C(C)(C)CO4)cc3c2C(C)C)cn2ncnc12] | 475.6 | 476.3 | 1.59 | E |

Examples 379 and 380

2-(2-(3-isopropyl-2-(8-methyl-[1,2,4]triazolo[1,5-a]pyridin-6-yl)-1H-indol-5-yl)-5,5-dimethylmorpholino)-N,N-dimethylacetamide

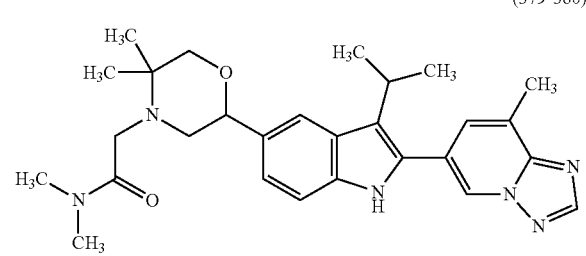

(379-380)

To a solution of 2-(3-isopropyl-2-(8-methyl-[1,2,4]triazolo[1,5-a]pyridin-6-yl)-1H-indol-5-yl)-5,5-dimethylmorpholine (75 mg, 0.186 mmol) in THF (1) and DMF (1 mL), were added TEA (0.078 mL, 0.558 mmol), 2-chloro-N,N-dimethylacetamide (45.2 mg, 0.372 mmol) at room temperature, the mixture was stirred at ambient temperature for 14 hours. The resulting black suspension was diluted with ethyl acetate, filtered and concentrated under vacuum to afford crude product. The crude samples were purified by reverse phase prep HPLC using method D1. The fractions containing the compound were combined and evaporated to dryness using Genevac to afford racemic 2-(2-(3-isopropyl-2-(8-methyl-[1,2,4]triazolo[1,5-a]pyridin-6-yl)-1H-indol-5-yl)-5,5-dimethylmorpholino)-N,N-dimethylacetamide (0.001 g, 1.02% yield) as a pale white solid. LCMS retention time 1.43 min (E), MS m/z: 489 (M+H); $^1$H NMR (400 MHz, DMSO-$d_6$) δ ppm 11.29 (s, 1H), 8.83 (s, 1H), 8.54 (s, 1H), 7.77 (s, 1H), 7.61 (s, 1H), 7.39 (d, J=8.3 Hz, 1H), 7.20 (d, J=7.1 Hz, 1H), 4.74 (dd, J=11.0, 3.2 Hz, 1H), 3.79 (d, J=1.5 Hz, 1H), 3.61 (br. s., 2H), 3.56-3.51 (m, 1H), 3.29-3.21 (m, 2H), 2.99-2.88 (m, 2H), 2.64 (s, 3H), 2.58 (br. s, 3H), 1.53 (s, 3H), 1.45 (dd, J=7.1, 2.2 Hz, 3H), 1.41 (s, 3H), 1.16 (d, J=7.3 Hz, 6H).

The racemic 2-(2-(3-isopropyl-2-(8-methyl-[1,2,4]triazolo[1,5-a]pyridin-6-yl)-1H-indol-5-yl)-5,5-dimethylmorpholino)-N,N-dimethylacetamide was purified by Chiral HPLC using Column: Chiralcel OJ-H (250×4.6) mm, 5 μm, % $CO_2$: 70%, % Co solvent: 30% of (0.2% DEA in IPA), Total Flow: 80.0 g/min, Back Pressure: 100 bar, Temperature: 30° C., UV: 230 nm. The fractions were collected, concentrate and lyophilized to afford both the enantiomers.

Example 379 (Enantiomer 1): (0.011 g, 0.023 mmol, 12% yield) as a pale white solid. LCMS retention time 1.43 min [E], MS m/z: 489 (M+H); $^1$H NMR (400 MHz, DMSO-$d_6$) δ ppm 11.29 (s, 1H), 8.83 (s, 1H), 8.54 (s, 1H), 7.77 (s, 1H), 7.61 (s, 1H), 7.39 (d, J=8.3 Hz, 1H), 7.20 (d, J=7.1 Hz, 1H), 4.74 (dd, J=11.0, 3.2 Hz, 1H), 3.79 (d, J=11.5 Hz, 1H), 3.61 (br. s, 2H), 3.56-3.51 (m, 1H), 3.29-3.21 (m, 2H), 2.99-2.88 (m, 2H), 2.64 (s, 3H), 2.58 (br. s, 3H), 1.53 (s, 3H), 1.45 (dd, J=7.1, 2.2 Hz, 3H), 1.41 (s, 3H), 1.16 (t, J=7.3 Hz, 6H).

Example 380 (Enantiomer 2): (0.08 g, 0.016 mmol, 8% yield) as a pale white solid. LCMS retention time 1.44 min [E], MS m/z: 489 (M+H): $^1$H NMR (400 MHz, DMSO-$d_6$) δ ppm 11.29 (s, 1H), 8.83 (s, 1H), 8.54 (s, 1H), 7.77 (s, 1H), 7.61 (s, 1H), 7.39 (d, J=8.3 Hz, 1H), 7.20 (d, J=7.1 Hz, 1H), 4.74 (dd, J=11.0, 3.2 Hz, 1H), 3.79 (d, J=11.5 Hz, 1H), 3.61 (br. s, 2H), 3.56-3.51 (m, 1H), 3.29-3.21 (m, 2H), 2.99-2.88 (m, 2H), 2.64 (s, 3H), 2.58 (br. s, 3H), 1.53 (s, 3H), 1.45 (dd, J=7.1, 2.2 Hz, 3H), 1.41 (s, 3H), 1.16 (d, J=7.3 Hz, 6H).

The following Examples were prepared according to the general procedure used to prepare Examples 379 and 380.

TABLE 40

| Ex. No. | Structure | Mol Wt. | LCMS MH+ | Ret Time (min) | HPLC Method |
|---|---|---|---|---|---|
| 381 | 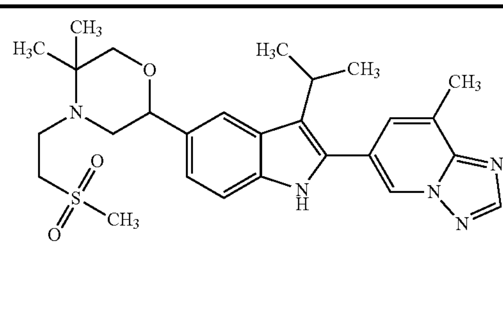 | 509.7 | 510.3 | 1.661 | E |

TABLE 40-continued

| Ex. No. | Structure | Mol Wt. | LCMS MH+ | Ret Time (min) | HPLC Method |
|---|---|---|---|---|---|
| 382 | 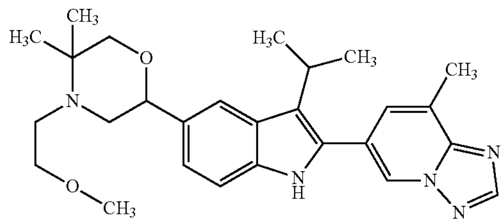 [SMILES: COCCN1CC(c2ccc3[nH]c(-c4cc(C)c5ncnn5c4)c(C(C)C)c3c2)OCC1(C)C] | 461.6 | 462.3 | 1.821 | E |
| 383 | 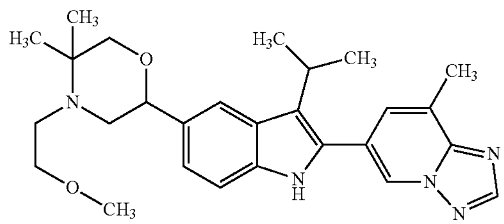 [SMILES: COCCN1CC(c2ccc3[nH]c(-c4cc(C)c5ncnn5c4)c(C(C)C)c3c2)OCC1(C)C] | 461.6 | 462.2 | 1.82 | E |
| 384 | 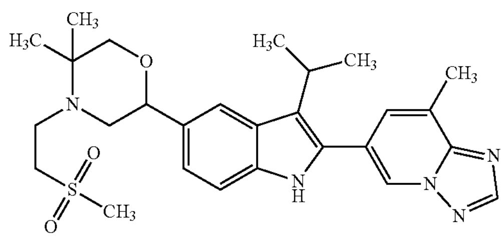 [SMILES: Cc1cc(-c2[nH]c3ccc(C4CN(CCS(C)(=O)=O)C(C)(C)CO4)cc3c2C(C)C)cn2ncnc12] | 509.7 | 510.3 | 1.662 | E |
| 385 | 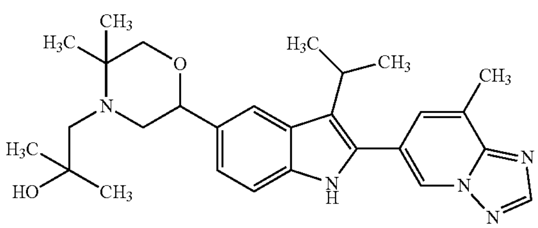 [SMILES: Cc1cc(-c2[nH]c3ccc(C4CN(CC(C)(C)O)C(C)(C)CO4)cc3c2C(C)C)cn2ncnc12] | 475.6 | 476.4 | 1.93 | E |
| 386 | 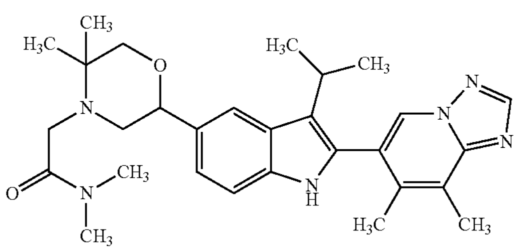 [SMILES: Cc1c(-c2[nH]c3ccc(C4CN(CC(=O)N(C)C)C(C)(C)CO4)cc3c2C(C)C)cn2ncnc2c1C] | 502.7 | 503.0 | 1.691 | E |
| 387 | 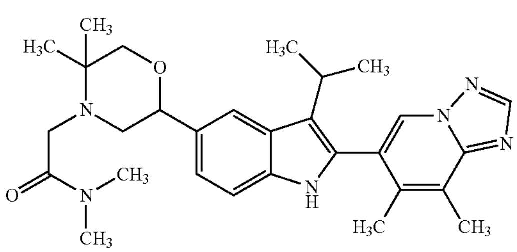 [SMILES: Cc1c(-c2[nH]c3ccc(C4CN(CC(=O)N(C)C)C(C)(C)CO4)cc3c2C(C)C)cn2ncnc2c1C] | 502.7 | 503.0 | 1.692 | E |

TABLE 40-continued

| Ex. No. | Structure | Mol Wt. | LCMS MH+ | Ret Time (min) | HPLC Method |
|---|---|---|---|---|---|
| 388 | 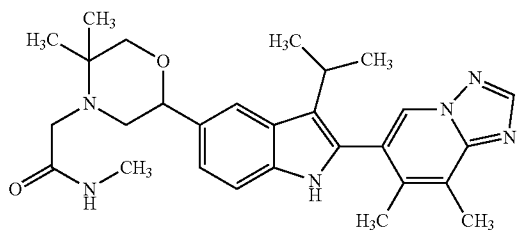 [SMILES: CNC(=O)CN1CC(c2ccc3[nH]c(-c4cn5ncnc5c(C)c4C)c(C(C)C)c3c2)OCC1(C)C] | 488.6 | 489.3 | 1.625 | E |
| 389 | 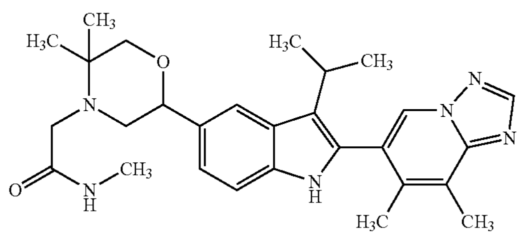 [SMILES: CNC(=O)CN1CC(c2ccc3[nH]c(-c4cn5ncnc5c(C)c4C)c(C(C)C)c3c2)OCC1(C)C] | 488.6 | 489.3 | 1.62 | E |

Example 390

2-(3,4-dimethoxyphenyl-3-ethyl-5-{[5-(propan-2-yl)-octahydropyrrolo[3,4-c]pyrrol-2-yl]methyl}-1H-indole (390)

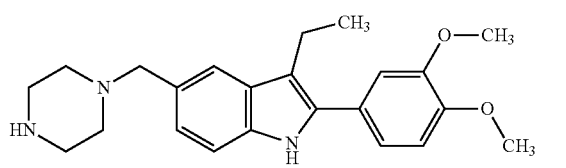

Intermediate 390A: 2-(3,4-dimethoxyphenyl)-3-ethyl-1H-indol-5-yl)methanol (390A)

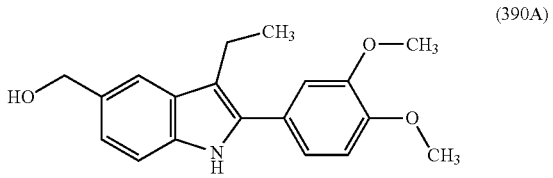 [SMILES: CCc1c(-c2ccc(OC)c(OC)c2)[nH]c2ccc(CO)cc12]

To a solution of methyl 2-(3,4-dimethoxyphenyl)-3-ethyl-1H-indole-5-carboxylate (1 g, 2.95 mmol), in THF (10 mL), was added LiAlH₄ (2.95 mL, 5.89 mmol) at −78° C., then the mixture was stirred at ambient temperature for 12 h. The reaction was quenched with cool water. The reaction mixture was diluted with ethyl acetate and passed through pad of celite, organic layer was separated and dried over sodium sulphate and concentrated to afford crude product, this was further purified by silica gel chromatography on an ISCO instrument using 40 g silica column, compound was eluted in 50% petroleum ether in ethyl acetate, tire fractions were collected and concentrated to afford 2-(3,4-dimethoxyphenyl)-3-ethyl-1H-indol-5-yl)methanol (0.7 g, 2.203 mmol, 75%) as white solid. LCMS retention time 2.06 min [G]. MS m/z: 312 [M+H]⁺.

Intermediate 390B 2-(3,4-dimethoxyphenyl)-3-ethyl-1H-indole-5-carbaldehyde (390B)

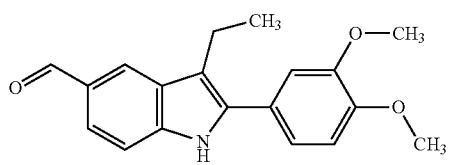

To a solution of (2-(3,4-dimethoxyphenyl)-3-ethyl-1H-indol-5-yl)methanol (250 mg, 0.803 mmol) in DCM (4 mL) was added manganese dioxide (698 mg, 8.03 mmol) at room temperature, the slurry was stirred at same temperature for 18 h. The reaction mass was diluted with DCM and passed through pad of celite. The organic layer was concentrated and dried under vacuum to afford 2-(3,4-di methoxy phenyl)-3-ethyl-1H-indole-5-carbaldehyde (0.2 g, 0.388 mmol, 80%) as pale yellow solid. LCMS retention time 2.35 min [G], MS m/z: 310 [M+H]⁺.

237

Intermediate 390C: tert-butyl 4-((2-(3,4-dimethoxy-phenyl)-3-ethyl-1H-indol-5-yl) methylpiperazine-1-carboxylate

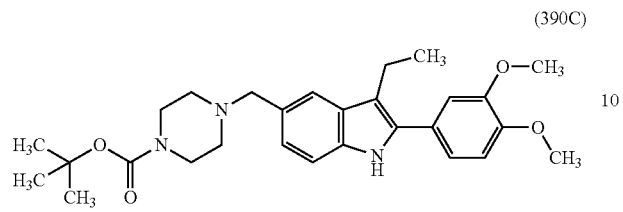

(390C)

To a solution of 2-(3,4-dimethoxyphenyl)-3-ethyl-1H-indole-5-carbaldehyde (70 mg, 0.226 mmol) in methanol (5 mL) were added tert-butyl piperazine-1-carboxylate (105 mg, 0.566 mmol), titanium(IV) isopropoxide (0.166 mL, 0.566 mmol) and heated the reaction mass for 12 h. The reaction mixture was cooled, was added sodium cyanoborohydride (35.5 mg, 0.566 mmol), and stirred the reaction mass for another 8 h. The reaction mass was diluted with ethyl acetate, solids was passed through celite, the filtrate was concentrated and purified by silica gel chromatography using 24 g silica column, $CHCl_3$: MeOH (9.1) as eluent, the fractions were collected and concentrated to afford tert-butyl 4-((2-(3,4-dimethoxyphenyl)-3-ethyl-1H-indol-5-yl) methyl)piperazine-1-carboxylate (0.050 g, 0.089 mmol, 40% yield). LCMS retention time 2.1 min [E], MS m/z 480 (M+H).

Example 390

To a solution of tert-butyl 4-((2-(3,4-dimethoxyphenyl)-3-ethyl-1H-indol-5-yl) methy 1 piperazine-1-carboxylate (30 mg, 0.063 mmol) in 4M dioxane-HCl (5 mL) was stirred at ambient temperature for 2 h. Concentrated the reaction mass to afford crude compound, the crude samples were purified by reverse phase prep HPLC using method D1. The fractions containing desired compound was combined and evaporated to dryness using Genevac to afford 2-(3,4-dimethoxyphenyl)-3-ethyl-5-(piperazin-1-ylmethyl)-1H-indole (0.005 g, 0.012 mmol, 19%, yield) as a white solid. LCMS retention time 1.91 min [E], MS m/z: 416 (M+H). $^1$H NMR (400 MHz, DMSO-$d_6$) δ ppm 10.94 (s, 1H), 7.39 (s, 1H), 7.27 (d, J=8.22 Hz, 1H), 7.12-7.18 (m, 2H), 7.07-7.11 (m, 1H), 7.03 (dd, J=8.25, 1.47 Hz, 1H), 3.83 (d, J=12.61 Hz, 6H), 3.50 (s, 2H), 2.84 (q, <J=7.61 Hz, 2H), 2.69-2.74 (m, 4H), 2.27-2.38 (m, 3H), 1.90 (s, 3H), 1.25 (t, J=9.60 Hz, 3H).

The following Example was prepared according to the general procedure described for Example 390.

Example 392

2-(3,4-dimethoxyphenyl)-3-ethyl-5-{[5-(propan-2-yl)-octahydropyrrolo[3,4-c]pyrrol-2-yl]methyl}-1H-indole

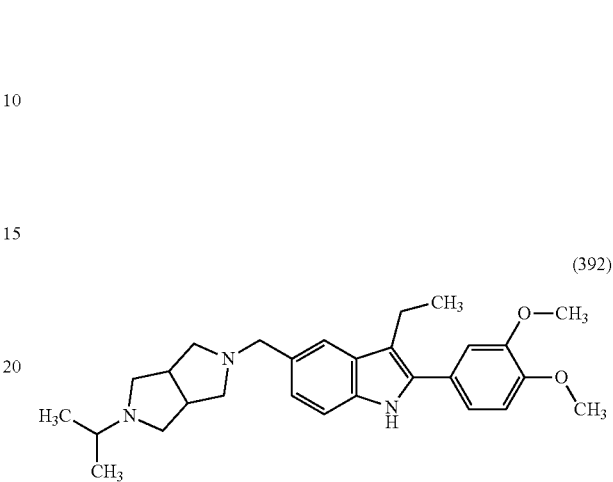

(392)

To a solution of 2-(3,4-dimethoxyphenyl)-3-ethyl-5-((hexahydropyrrolo[3,4-c]pyrrol-2(1H)-yl) methyl)-1H-indole (15 mg, 0.037 mmol) in methanol (5 mL) were added propan-2-one (5.37 mg, 0.092 mmol), titanium(IV) isopropoxide (0.027 mL, 0.092 mmol) and the reaction mass was heated to 60° C. for 8 h. The reaction mass and was added sodium cyanoborohydride (5.81 mg, 0.092 mmol), then stirred at room temperature for 4 h. The reaction mass was purified by reverse phase prep HPLC using method D1. The fractions containing desired compound was combined and evaporated to dry ness using Genevac to afford 2-(3,4-dimethoxyphenyl)-3-ethyl-5-((5-isopropylhexahydropyrrolo[3,4-c]pyrrol-2(1H)-yl)methyl)-1H-indole (0.003 g, 6.37 µmol, 17% yield) as a white solid. LCMS retention time 1.51 min [E], MS m/z: 448 (M+H); $^1$H NMR (400 MHz, DMSO-$d_6$) δ ppm 10.94 (s, 1H), 7.39 (s, 1H), 7.27 (d, J=8.22 Hz, 1H), 7.12-7.18 (m, 2H), 7.07-7.11 (m, 1H), 7.03 (dd, J=8.25, 1.47 Hz, 1H), 3.83 (d, J=12.61 Hz, 6H), 3.50 (s, 2H), 2.84 (q, J=7.61 Hz, 2H), 2.69-2.74 (m, 4H), 2.27-2.38 (m, 3H), 1.90 (s, 3H), 1.25 (t, J=7.2 Hz, 3H).

TABLE 41

| Ex. No. | Structure | Mol Wt. | LCMS MH+ | Ret Time (min) | HPLC Method |
|---|---|---|---|---|---|
| 391 | ![structure] | 405 | 406 | 1.29 | E |

Example 393

2-(2,6-dimethylpyridin-4-yl)-5-[2-(morpholin-4-yl)ethyl]-3-(propan-2-yl)-1H-indole

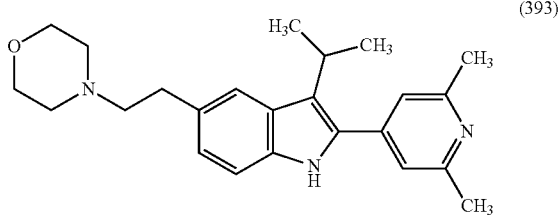 [SMILES: Cc1cc(-c2[nH]c3ccc(CCN4CCOCC4)cc3c2C(C)C)cc(C)n1]

Intermediate 393A: (Z)-tert-butyl 2-(2,6-dimethylpyridin-4-yl)-5-(2-ethoxyvinyl)-3-isopropyl-1H-indole-1-carboxylate

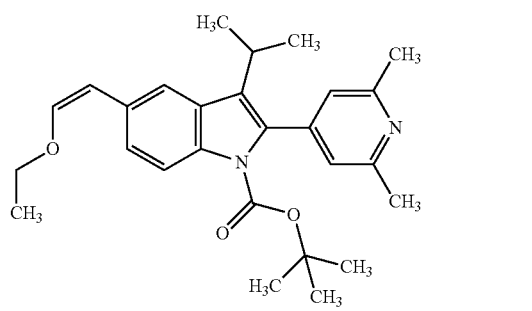

To a mixture containing tert-butyl 5-bromo-2-(2,6-dimethylpyridin-4-yl)-3-isopropyl-1H-indole-1-carboxylate (100 mg, 0.226 mmol), (Z)-1-ethoxy-2-(tributylstannyl)ethene (0.094 mL, 0.282 mmol), tetra-n-butylammonium chloride (69.0 mg, 0.248 mmol) and bis(triphenylphosphine)palladium(II) chloride (4.75 mg, 6.77 µmol) in a screw cap vial was added DMF (2 mL). The vial was fitted with a Teflon lined septum cap. The system was evacuated under vacuum (via a needle from a nitrogen/vacuum manifold line) and backfilled with nitrogen gas. The procedure was repeated three times. The needle was removed and the vial was heated at 80° C. for 18 h. The reaction mixture was cooled to room temperature, diluted with ethyl acetate (50 mL), poured into a separatory funnel and washed with aqueous 10% LiCl solution (3×10 mL) and saturated aqueous NaCl solution (10 mL), dried ($Na_2SO_4$), filtered and concentrated to give crude product. The crude product was dissolved in a small amount of DCM and charged to an ISCO silica gel 24 g ISCO Column which was eluted over a 15 min gradient with 0%-50% hexanes/ethylacetate to afford (Z)-tert-butyl 2-(2,6-dimethylpyridin-4-yl)-5-(2-ethoxyvinyl)-3-isopropyl-1H-indole-1-carboxylate.

Intermediate 393B: tert-butyl 2-(2,6-dimethylpyridin-4-yl)-3-isopropyl-5-(2-oxoethyl)-1H-indole-1-carboxylate

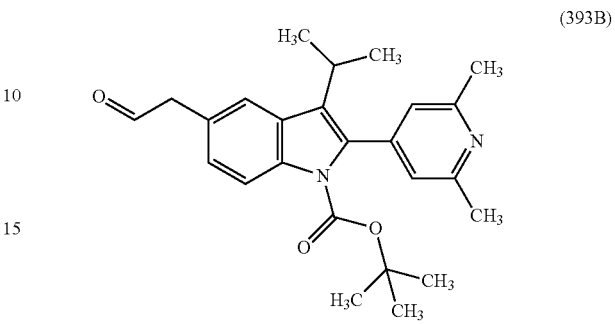

(Z)-tert-butyl 2-(2,6-dimethylpyridin-4-yl)-5-(2-ethoxyvinyl)-3-isopropyl-1H-indole-1-carboxylate was re-suspended in THF (1 mL) and 1 N HCl aq. (100 µL) and the mixture was heated at 50° C. for 1 h, cooled to room temperature, basified with aqueous $K_2HPO_4$ 1.5 M (5 mL) and extracted with ethylacetate to afford tert-butyl 2-(2,6-dimethylpyridin-4-yl)-3-isopropyl-5-(2-oxoethyl)-1H-indole-1-carboxylate (50 mg, 0.123 mmol, 54.5% yield), m/e (407, M+1). $^1$H NMR (400 MHz, CHLOROFORM-d) δ 9.84-9.82 (m, 1H), 8.29 (d, J=8.6 Hz, 1H), 7.60-7.58 (m, 1H), 7.21 (dd, J=8.5, 1.8 Hz, 1H), 6.96-6.91 (m, 2H), 3.84-3.81 (m, 2H), 2.98-2.89 (m, 1H), 2.61-2.59 (m, 6H), 1.36 (d, J=7.0 Hz, 6H), 1.27-1.24 (m, 9H).

Example 393

A mixture containing tert-butyl 2-(2,6-dimethylpyridin-4-yl)-3-isopropyl-5-(2-oxoethyl)-1H-indole-1-carboxylate (35 mg, 0.086 mmol), morpholine (15 mg, 0.17 mmol), and sodium triacetoxy borohydride (73.0 mg, 0.35 mmol) were suspended in THF (1 mL) and a drop of acetic acid was added. The reaction mixture was stirred for 20 h, diluted with ethylacetate (4 mL) and washed with 1N NaOH aqueous (2×1 mL) and the ethylacetate layer concentrated. The residue was treated with 50% TFA in DCM (1 mL) for 30 min and the reaction mixture was concentrated to dry ness and re-dissolved in mixture of HPLC solvents A and B (4/1.2 mL), mobile Phase A: 5:95 acetonitrile: water with 0.1% trifluoroacetic acid; Mobile Phase B: 95:5 acetonitrile: water with 0.1% trifluoroacetic acid). The sample was filtered through an Acrodisc, 13 mm, 0.45 micron nylon membrane syringe filter and submitted for HPLC purification. The crude material was purified via preparative LC/MS with the following conditions: Column: waters XBridge c-18, 19×200 mm, 5-Å¿m particles; Mobile Phase A: 5:95 acetonitrile: water with 10 mM ammonium acetate: Mobile Phase B: 95:5 acetonitrile: water with 10 mM ammonium acetate; Gradient: 5-45% B over 19 minutes, then a 5-minute hold at 100% B; Flow: 20 mL/min. Fractions containing the desired product were combined and dried via centrifugal evaporation to afford 4-(2-(2-(2,6-dimethylpyridin-4-yl)-3-isopropyl-1H-indol-5-yl)ethyl)morpholine (18.5 mg, 0.049 mmol, 57% yield. LCMS retention time 0.84 min [QC-ACN-TFA-XB], MS m/z: 378.3 (M+H). $^1$H NMR (500 MHz, DMSO-$d_6$) δ 11.09-11.04 (m, 1H), 7.59 (s, 1H), 7.27 (d, J=8.2 Hz, 1H), 7.14 (s, 2H), 7.01-6.94 (m, 1H), 3.63-3.57 (m, 1H), 3.48 (br d, J=7.5 Hz, 1H), 3.34 (quin. J=7.0 Hz, 1H), 3.19-3.15 (m, 1H), 2.81 (br t, J=7.7 Hz, 2H), 2.55 (m, 2H), 2.50-2.40 (br m, 10H), 1.45-1.43 (d, J=7.0 Hz, 6H).

Example 394

[3-ethyl-2-(2-methylpyridin-4-yl)-1H-indol-5-yl]methanamine

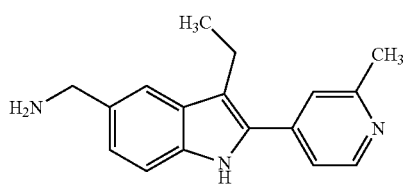
(394)

Intermediate 394A: 3-ethyl-2-(2-methylpyridin-4-yl)-1H-indole-5-carbonitrile

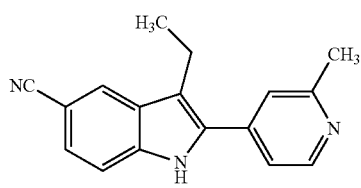
(394A)

To a 20 ml vial with pressure relief septum was added tert-butyl 5-chloro-3-ethyl-2-(2-methylpyridin-4-yl)-1H-indole-1-carboxylate (100 mg, 0.270 mmol), 2nd generation Xphos precatalyst (149 mg, 0.189 mmol), potassium ferrocyanide (49.7 mg, 0.135 mmol), and dioxane (4 mL). The vial was evacuated and purged with $N_2$ several times. Potassium acetate (3.31 mg, 0.034 mmol) in water (4 mL) was added to the vial. The vial was evacuated and purged with $N_2$ several times. The vial was heated to 100° C. for 1 hour. LCMS indicated that the reaction was complete. The reaction mixture was diluted with brine (25 ml) and EtOAc (25 ml). The layers were separated. The aqueous layer was extracted with EtOAc (2×20 ml). The organic layers were combined, dried over sodium sulfate, filtered, and concentrated under vacuum. The resulting foam was purified by silica gel chromatography on an ISCO instrument using (25 g Silica, dry load, 100% Hexanes to 100% EtOAc). Like fractions were combined and concentrated under vacuum to give a tan solid. Isolated 3-ethyl-2-(2-methylpyridin-4-yl)-1H-indole-5-carbonitrile (64 mg, 0.245 mmol, 91% yield). LCMS (Method A1) at t=0.66 min. (m+1=262) showed 1 major product with expected mass. $^1$H NMR (400 MHz, DMSO-do) δ 11.92 (s, 1H), 8.57 (d, J=5.1 Hz, 1H), 8.20 (d, J=0.6 Hz, 1H), 7.55-7.52 (m, 1H), 7.51-7.48 (m, 2H), 7.46-7.41 (m, 1H), 2.95 (q, J=7.5 Hz, 2H), 2.56 (s, 3H), 1.25 (t, J=7.5 Hz, 3H).

Example 394

To a dried, $N_2$ flushed 25 ml round bottom flask was added LAH (56 mg, 1.475 mmol) and THF (3 mL). The flask was cooled to 0° C. in an ice bath. 3-Ethyl-2-(2-methylpyridin-4-yl)-1H-indole-5-carbonitrile (64 mg, 0.245 mmol) was dissolved in THF (3 mL) and added over 10 minutes to the round bottom flask. Stirring was continued for 1 hour at 0° C. LCMS showed only starting material present. The reaction mixture was warmed to room temperature and additional LAH (56 mg, 1.475 mmol) was added. The reaction mixture was heated to 100° C. for 1 hour. LCMS indicated that the reaction was complete. The reaction mixture was cooled to room temperature, slowly added to ice, and the aqueous mixture was extracted with EtOAc (3×25 ml). The combined organic were dried over sodium sulfate, filtered, and dried under vacuum to give a brown oil (42 mg). The oil was diluted with DMF (2 ml) and 1 ml of the solution was submitted to SCP. The crude material was purified via preparative LC/MS with the following conditions: Column: XBridge C18, 19×200 mm, 5 angstrom particles; Mobile Phase A: 5:95 acetonitrile: water with 10 mM ammonium acetate; Mobile Phase B: 95:5 acetonitrile: water with 10 mM ammonium acetate; Gradient: 0-100% B over 15 minutes, then a 5-minute hold at 100% B; Flow: 20 mL/min. Fractions containing the product were combined and dried via centrifugal evaporation to afford (3-ethyl-2-(2-methylpyridin-4-yl)-1H-indol-5-yl)methanamine (9.8 mg, 0.037 mmol, 15% yield). LCMS retention time 0.78 min, M+H=266 [Method QC-ACN-TFA-XB], $^1$H NMR (500 MHz, DMSO-d$_6$) δ ppm 11.27 (br. s., 1H), 8.51 (d, J=5.1 Hz, 1H), 7.57 (s, 1H), 7.47 (s, 1H), 7.40 (d, J=4.5 Hz, 1H), 7.33 (d, J=8.3 Hz, 1H), 7.16 (d, J=8.3 Hz, 1H), 3.85 (s, 2H), 2.96-2.88 (m, 2H), 2.54 (s, 3H), 1.84 (s, 2H), 1.27 (t. J=7.3 Hz, 3H).

Example 395

3-(dimethylamino)-N-{[3-ethyl-2-(2-methylpyridin-4-yl)-1H-indol-5-yl]methyl}propanamide

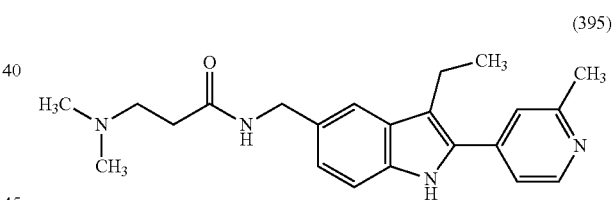
(395)

To a 1 dram vial were added 3-(dimethylamino)propanoic acid, HCl (17.37 mg, 0.113 mmol), EDC (21.67 mg, 0.113 mmol), HOBT (17.31 mg, 0.113 mmol), DMF (1 mL), and DIEA (0.026 mL, 0.151 mmol). The reaction mixture was stirred for 5 minutes. (3-ethyl-2-(2-methylpyridin-4-yl)-1H-indol-5-yl)methanamine (20 mg, 0.075 mmol) was added and the reaction mixture was stirred at 25° C. overnight. The reaction mixture was diluted with water (5 mL) and extracted with EtOAC (3×5 ml). The organic layers were combined, dried over sodium sulfate, filtered, and concentrated under vacuum. The aqueous layer was concentrated under a stream of $N_2$. Both fractions were dissolved in DMF (2 ml) and purified via preparative LC/MS with the following conditions: Column: Waters XBridge C18, 19×200 mm, 5 angstrom particles; Mobile Phase A: 5:95 acetonitrile: water with 10 mM ammonium acetate; Mobile Phase B: 95:5 acetonitrile: water with 10 mM ammonium acetate; Gradient: 5-100% B over 20 minutes, then a 5-minute hold at 100% B; Flow: 20 mL/min. Fractions containing the product were combined and dried via centrifugal evaporation to afford 3-(dimethylamino)-N-((3-ethyl-2-(2-methylpyridin-4-yl)-1H-indol-5-yl)methyl) propanamide (11.2 mg, 0.031 mmol, 41% yield). The estimated purity by LCMS analysis was 100%. LCMS retention time 0.637 min, M+H=365 [Method QC-ACN-TFA-XB], ¹H NMR (500 MHz, DMSO-d₆) δ 11.28 (s, 1H), 8.51 (d, J=5.1 Hz, 1H), 8.43 (br. s., 1H), 7.47 (d, J=4.8 Hz, 1H), 7.40 (d, J=4.5 Hz, 1H), 7.33 (d, J=8.2 Hz, 1H), 7.07 (d, J=8.2 Hz, 1H), 4.35 (d, J=5.6 Hz, 2H), 2.91 (q, J=7.5 Hz, 2H), 2.59-2.52 (m, 5H), 2.32 (t, J=7.0 Hz, 2H), 2.20 (s, 6H), 1.90 (s, 1H), 1.26 (t, J=7.4 Hz, 3H).

Examples 396 and 397

5-[(1-benzylpyrrolidin-2-yl)methyl]-2-{8-methyl-[1,2,4]triazolo[1,5-a]pyridin-6-yl}-3-(propan-2-yl)-1H-indole (396-397)

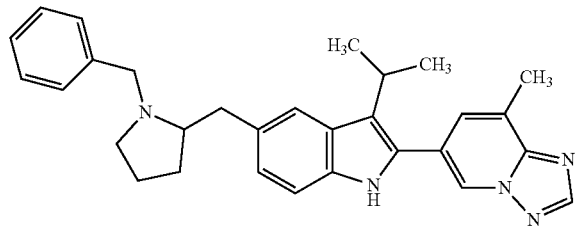

Intermediate 3% A: tert-butyl 5-bromo-3-isopropyl-2-(8-methyl-[1,2,4]triazolo[1,5-a]pyridin-6-yl)-1H-indole-1-carboxylate (396A)

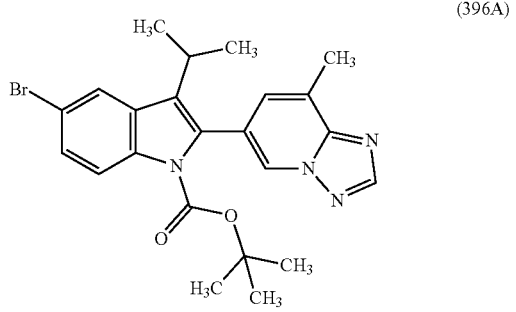 [SMILES: Cc1cc(-c2c(C(C)C)c3cc(Br)ccc3n2C(=O)OC(C)(C)C)cn2ncnc12]

To a solution of tert-butyl 5-bromo-2-iodo-3-isopropyl-1H-indole-1-carboxylate (0.456 g, 0.983 mmol), 8-methyl-6-(4,4,5,5-tetramethyl-1,3,2-dioxaborolan-2-yl)-[1,2,4]triazolo[1,5-a]pyridine (0.255 g, 0.983 mmol), and PdCl₂(dppf) (0.036 g, 0.049 mmol) in dioxane (6.55 mL) was added 3 M aqueous potassium phosphate tribasic (0.98 mL, 2.95 mmol) and the biphasic mixture was degassed with nitrogen for 10 min. The vial was sealed and stirred at 70° C. After stirring for 2 hours, the reaction mixture was cooled to room temperature. The reaction mixture was concentrated and some impurities were removed via flash column chromatography (silica gel, hexanes/EtOAc 0-100%) to obtain material in greater than quantitative yield (used as such in further reactions). Considered quantitative recovery for purpose of subsequent reaction of tert-butyl 5-bromo-3-isopropyl-2-(8-methyl-[1,2,4]triazolo[1,5-a]pyridin-6-yl)-1H-indole-1-carboxylate (0.461 g, 0.983 mmol, 100% yield). LCMS retention time 1.22 min [Method TS1]. MS (E⁺) m/z 469.1/471.1 (M+H/(M+2)+H).

Intermediate 396B: (E)-tert-butyl 5-(5-chloropent-1-en-1-yl)-3-isopropyl-2-(8-methyl-[1,2,4]triazolo[1,5-a]pyridin-6-yl)-1H-indole-1-carboxylate (396B)

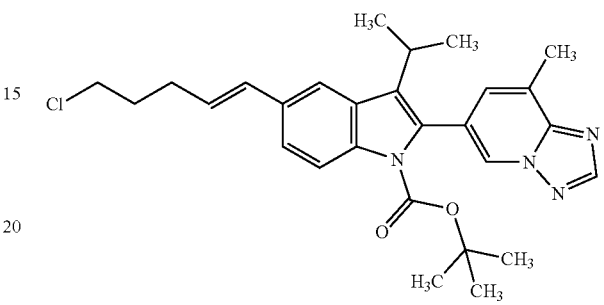

To a solution of tert-butyl 5-bromo-3-isopropyl-2-(8-methyl-[1,2,4]triazolo[1,5-a]pyridin-6-yl)-1H-indole-1-carboxylate (0.461 g, 0.983 mmol), (E)-2-(5-chloropent-1-en-1-yl)-4,4,5,5-tetramethyl-1,3,2-dioxaborolane (0.295 g, 1.278 mmol), and PdCl₂(dppf) (0.036 g, 0.049 mmol) in dioxane (6.55 mL) was added 3 M aqueous potassium phosphate tribasic (0.983 mL, 2.95 mmol). The biphasic mixture was degassed with nitrogen for 10 min. The vial was sealed and the reaction mixture was stirred at 90° C. After stirring for 3 hours, the reaction mixture was cooled to room temperature. Additional (E)-2-(5-chloropent-1-en-1-yl)-4,4,5,5-tetramethyl-1,3,2-dioxaborolane (0.100 g, 0.433 mmol) was added, the reaction mixture was degassed with nitrogen, heated to 90° C. for another hour, and then cooled to room temperature. The reaction mixture was concentrated and purified by flash column chromatography (silica gel, hexanes/EtOAc 0-60%) to afford (E)-tert-butyl 5-(5-chloropent-1-en-1-yl)-3-isopropyl-2-(8-methyl-[1,2,4]triazolo[1,5-a]pyridin-6-yl)-1H-indole-1-carboxylate. LCMS retention time 1.24 min [Method TS1], MS (E⁺) m/z 493.3 (M+H).

Intermediate 396C: (E)-tert-butyl 5-(5-(benzylamino)pent-1-en-1-yl)-3-isopropyl-2-(8-methyl-[1,2,4]triazolo[1,5-a]pyridin-6-yl)-1H-indole-1-carboxylate (396C)

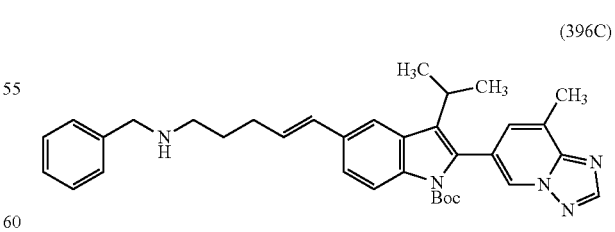

(E)-tert-butyl 5-(5-chloropent-1-en-1-yl)-3-isopropyl-2-(8-methyl-[1,2,4]triazolo[1,5-a]pyridin-6-yl)-1H-indole-1-carboxylate (107 mg, 0.217 mmol) was dissolved in DMSO (0.54 mL). TBAI (16 mg, 0.043 mmol) and benzylamine (95 μl, 0.868 mmol) were added. The vial was sealed and heated to 90° C. with stirring. After 5 hours, the reaction mixture was cooled to room temperature and diluted with DCM. The reaction mixture was washed with water twice and the organic layer was concentrated. The crude material was purified by flash column chromatography (silica gel, Hex/EtOAc 0-100%) to afford (E)-tert-butyl 5-(5-(benzylamino)pent-1-en-1-yl)-3-isopropyl-2-(8-methyl-[1,2,4]triazolo[1,5-a]pyridin-6-yl)-1H-indole-1-carboxylate (68 mg, 0.121 mmol, 55.6% yield). LCMS retention time 0.93 min [method TS1], MS (E$^+$) m/z 564.4 (M+H).

Intermediate 396D: 6-(5-((1-benzylpyrrolidin-2-yl)methyl)-3-isopropyl-7H-indol-2-yl)-8-methyl-[1,2,4]triazolo[1,5-a]pyridine, TFA

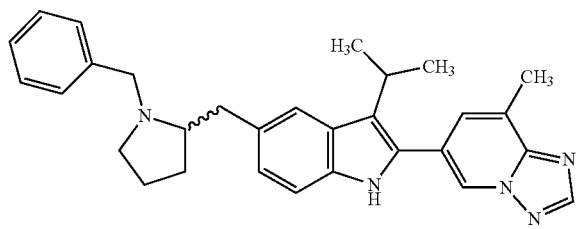

(396D)

A solution of (E)-tert-butyl 5-(5-(benzylamino)pent-1-en-1-yl)-3-isopropyl-2-(8-methyl-[1,2,4]triazolo[1,5-a]pyridin-6-yl)-1H-indole-1-carboxylate (68 mg, 0.121 mmol), TRIP thiophenol (28.5 mg, 0.121 mmol), and Ir(dF(CF$_3$)ppy)$_2$(bpy)PF$_6$ (2.4 mg, 2.4 µmol) in DCM w as evenly divided into four reaction vials and concentrated to dryness. To each vial was added 0.6 mL of dioxane, and then each vial was degassed by bubbling nitrogen through the solution for 10 minutes. Each vial was sealed and irradiated with Kessil brand 34 W Blue LED lamps. Two vials were stopped at 30 minutes, and the other two were stopped at 60 minutes. All 4 vials were combined, concentrated, and taken up in DCM (3 mL). TFA (3 mL) was added. After 1 hour, the solution was concentrated, taken up in DCM, and neutralized with 1.5 M K$_2$HPO$_4$ solution. The organic layer was separated, dried over sodium sulfate, filtered, and concentrated. This material w as taken up in DMF and purified via preparative LC/MS with the following conditions: Column: XBridge C18, 19×200 mm, 5 µm particles; Mobile Phase A: 5:95 acetonitrile: water with 10 mM ammonium acetate; Mobile Phase B: 95:5 acetonitrile: water with 10 mM ammonium acetate; Gradient: 20-60% B over 20 minutes, then a 5 minute hold at 100% B; Flow: 20 mL/min. Fractions containing the product were combined and dried via centrifugal evaporation. The material was further purified via preparative LC/MS with the following conditions: Column: Xbridge C18, 19×200 mm, 5-µm particles; Mobile Phase A: 5:95 acetonitrile: water with 0.1% trifluoroacetic acid; Mobile Phase B: 95:5 acetonitrile: water with 0.1% trifluoroacetic acid; Gradient: 15-55% B over 20 minutes, then a 5-minute hold at 100% B; Flow: 20 mL/min. Fractions containing the product were combined and dried via centrifugal evaporation to give 6-(5-((1-benzylpyrrolidin-2-yl)methyl)-3-isopropyl-1H-indol-2-yl)-8-methyl-[1,2,4]triazolo[1,5-a]pyridine, TFA (15.5 mg, 0.025 mmol, 21.13% yield). LCMS retention time 1.37 [QC-ACN-TFA-XB]. MS (E$^+$) m/z 464.4 (M+H). $^1$H NMR (600 MHz, DMSO-d$_6$) δ 11.25 (s, 1H), 8.80 (s, 1H), 8.53 (s, 1H), 8.40-8.17 (m, 1H), 7.62-7.52 (m, 4H), 7.52-7.46 (m, 3H), 7.34 (d, J=8.3 Hz, 1H), 6.98 (br d, J=8.3 Hz, 1H), 4.39 (br d, J=12.7 Hz, 1H), 4.27 (br d, J=12.5 Hz, 1H), 3.53-3.46 (m, 1H), 3.30-3.22 (m, 1H), 3.14-3.03 (m, 1H), 2.95-2.83 (m, 3H), 2.62 (s, 3H), 2.10-1.74 (m, 4H), 1.45 (dd, J=18.8, 6.9 Hz, 6H).

Examples 396 and 397

A portion of this material 6-(5-((1-benzylpyrrolidin-2-yl)methyl)-3-isopropyl-1H-indol-2-yl)-8-methyl-[1,2,4]triazolo[1,5-a]pyridine, TFA (14.1 mg, 0.024 mmol) was taken up in DCM and neutralized with aqueous 1.5 M K$_2$HPO$_4$ dibasic solution. The organic layer was dried over sodium sulfate, filtered, and concentrated to give 5.72 mg. The material was separated by chiral resolution on a Berger Prep SFC MGII with a chiral OD 25×3 cm, 5 µm column. Mobile phase 70/30 CO$_2$/MeOH w/0.1% DEA, flow rate 85.0 mL/min. Detection at 220 nm Injection volume 1 mL of 5.72 mg dissolved in 2.5 mL of MeOH. Concentration of the fractions afforded Examples 3% and 397.

Example 396 (Isomer 1): (1.35 mg, 2.65 µmol, 10.86% yield). LCMS retention time 0.76 min method TS1) MS (E$^+$) m/z 464.2

Example 397 (Isomer 2): (1.28 mg, 2.485 µmol, 10.18% yield). LCMS retention time 0.76 min [method TS1] MS (E$^+$) m/z 464.3 (M+H).

Example 398

2-{8-methyl-[1,2,4]triazolo[1,5-a]pyridin-6-yl}-3-(propan-2-yl)-5-[(pyrrolidin-2-yl) methyl]-1H-indole

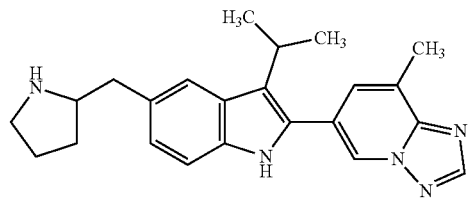

(398)

(E)-tert-butyl 5-(5-(benzylamino)pent-1-en-1-yl)-3-isopropyl-2-(8-methyl-[1,2,4]triazolo[1,5-a]pyridin-6-yl)-1H-indole-1-carboxylate (62 mg, 0110 mmol), TRIP thiophenol (26.0 mg, 0.110 mmol), and Ir(dF(CF$_3$)ppy)$_2$(bpy)PF$_6$ (2.2 mg, 2.2 µmol) were added to a reaction vial. The materials were dissolved in dioxane (2.2 mL) and the resulting solution was degassed by bubbling nitrogen through the solution for 10 minutes. The vial was sealed and irradiated with two Kessil brand 34 W Blue LED lamps for 22 hours. The reaction mixture was then concentrated, taken up in DCM (2.2 mL) and TFA (2 mL) was added. The mixture was stirred at room temperature for 1 hour and then concentrated, taken up in DCM and neutralized with 1.5 M K$_2$HPO$_4$ aqueous solution. The organic layer was separated, dried over sodium sulfate, filtered, and concentrated. The crude material was taken up in DMF and purified via preparative LCMS with the following conditions: Column: XBridge C18, 19×200 mm, 5 µm particles; Mobile Phase A: 5:95 acetonitrile: water with 10 mM ammonium acetate; Mobile Phase B: 95:5 acetonitrile: water with 10 mM ammonium acetate; Gradient: 10-70% B over 19 minutes, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×200 mm, 5-μm particles; Mobile Phase A: 5:95 acetonitrile: water with 10 mM ammonium acetate; Mobile Phase B: 95:5 acetonitrile: water with 10 mM ammonium acetate; Gradient: 0-60% B over 19 minutes, then a 5-minute hold at 100% B; Flow: 20 mL/min. Fractions containing the product were combined and dried via centrifugal evaporation to afford 6-(3-isopropyl-5-(pyrrolidin-2-ylmethyl)-1H-indol-2-yl)-8-methyl-[1,2,4]triazolo[1,5-a]pyridine (2.4 mg, 6.36 μmol, 5.78% yield). LCMS retention time 1.19 min [QC-ACN-TFA-XB] MS (E$^+$) m/z 374.1 (M+H). $^1$H NMR (500 MHz, DMSO-d$_6$) δ 11.20 (s, 1H), 8.78 (s, 1H), 8.52 (s, 1H), 7.62 (s, 1H), 7.59 (s, 1H), 7.31 (br d, J=8.2 Hz, 1H), 7.02 (br d, J=8.1 Hz, 1H), 3.24 (dt, J=13.9, 7.0 Hz, 1H), 3.09 (br s, 1H), 3.04-2.90 (m, 2H), 2.84 (br dd, J=13.3, 7.5 Hz, 1H), 2.62 (s, 3H), 1.92-1.68 (m, 4H), 1.54 (br d, J=9.3 Hz, 1H), 1.46-1.35 (m, 6H).

Example 399

5-[(azetidin-3-yl)methyl]-2-{7,8-dimethyl-[1,2,4]triazolo[1,5-a]pyridin-6-yl}-3-(propan-2-yl)-1H-indole

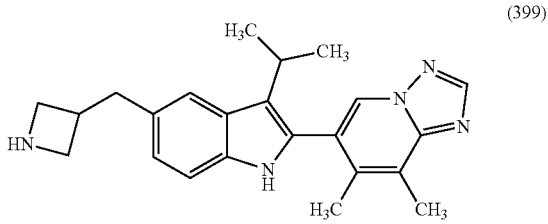 [SMILES: Cc1c(-c2[nH]c3ccc(CC4CNC4)cc3c2C(C)C)cn2ncnc2c1C]

(399)

Intermediate 399A: tert-butyl 5-((1-(tert-butoxycarbonyl)azetidin-3-yl)methyl)-3-isopropyl-1H-indole-1-carboxylate

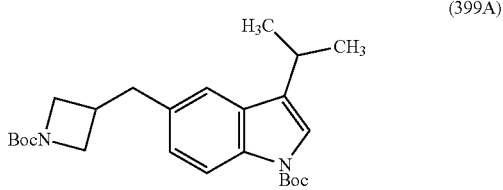 [SMILES: CC(C)c1cn(C(=O)OC(C)(C)C)c2ccc(CC3CN(C(=O)OC(C)(C)C)C3)cc12]

(399A)

tert-butyl 5-bromo-3-isopropyl-1H-indole-1-carboxylate (310 mg, 0.917 mmol), tert-butyl 3-(bromomethyl)azetidine-1-carboxylate (458 mg, 1.833 mmol), tris(trimethylsilyl)silane (342 mg, 1.375 mmol), Ir(dF(CF$_3$)ppy)$_2$(dtbbpy)PF$_6$ (10 mg, 9.2 μmol), and Na$_2$CO$_3$ (389 mg, 3.67 mmol) were placed in a Teflon screw cap vial with a stir bar. Dioxane (7.3 mL) was added, and the suspension was degassed with nitrogen for 5 minutes. To a separate vial were added nickel(II) chloride ethylene glycol dimethyl ether complex (10.1 mg, 0.046 mmol) and 4,4'-di-tert-butyl-2,2'-bipyridine (14.8 mg, 0.055 mmol), which was evacuated and backfilled with nitrogen gas followed by dioxane (1.8 mL). This solution was degassed with nitrogen gas for 10 minutes and stirred. The resulting solution was added to the reaction solution and then the reaction mixture was further degassed with nitrogen gas for another 10 minutes. The resulting suspension was placed in a block with stirring and irradiated with two Kessil brand 34 W Blue LED lamps for 17 hours. Upon completion, the reaction mixture was filtered through a large syringe filter and concentrated. Purification on flash column chromatography (Hex/DCM 0-100%) afforded tert-butyl 5-((1-(tert-butoxycarbonyl)azetidin-3-yl)methyl)-3-isopropyl-1H-indole-1-carboxylate contaminated with tert-butyl 3-methylazetidine-1-carboxylate, a byproduct from the reaction. LCMS retention time 1.20 min [method TS1] MS (E') m/z 429.1 (M+H). $^1$H NMR (499 MHz, CHLOROFORM-d) δ 8.06-7.95 (m, 1H), 7.34-7.29 (m, 2H), 7.09 (dd, J=8.4, 1.6 Hz, 1H), 4.00 (t, J=8.4 Hz, 2H), 3.69 (dd, J=8.5, 5.5 Hz, 2H), 3.16-3.05 (m, 1H), 3.00 (d, J=7.9 Hz, 2H), 2.93-2.81 (m, 1H), 1.67 (s, 9H), 1.45 (s, 9H), 1.35 (d, J=6.8 Hz, 6H).

Intermediate 399B: tert-butyl 5-((1-(tert-butoxycarbonyl)azetidin-3-yl)methyl)-3-isopropyl-2-(4,4,5,5-tetramethyl-1,3,2-dioxaborolan-2-yl)-1H-indole-1-carboxylate

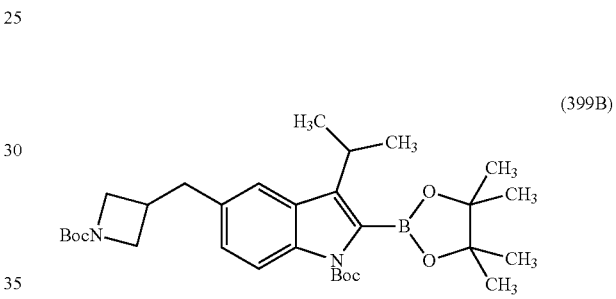

(399B)

A solution containing tert-butyl 5-((1-(tert-butoxycarbonyl)azetidin-3-yl)methyl)-3-isopropyl-1H-indole-1-carboxylate (1.45 mmol) and 2-isopropoxy-4,4,5,5-tetramethyl-1,3,2-dioxaborolane (0.59 mL, 2.90 mmol) in dry THF (7.25 mL), under a nitrogen atmosphere was cooled to −78° C. and treated with LDA (2M in THF) (3.63 mL, 7.26 mmol). The mixture was warmed to −30° C. over 30 min and stirred at −30° C. for 30 min. The reaction mixture was treated with saturated aqueous NH$_4$Cl solution, water, and DCM. The organic layer was dried over sodium sulfate, filtered and concentrated. The crude material was purified by flash column chromatography (silica gel, hexanes/EtOAc 0-40%). The fractions containing the product were collected and repurified by flash column chromatography (silica gel, hexanes/DCM 0-60%). The fractions containing the product were combined to afford tert-butyl 5-((1-(tert-butoxycarbonyl)azetidin-3-yl) methyl)-3-isopropyl-2-(4,4,5,5-tetramethyl-1,3,2-dioxaborolan-2-yl)-1H-indole-1-carboxylate contaminated with tert-butyl 3-methylazetidine-1-carboxylate, a byproduct from the previous reaction. LCMS retention time 1.27 min (method TS1) MS (E$^+$) m/z 555.1 (M+H). $^1$H NMR (499 MHz, CHLOROFORM-d) δ 7.76 (d, J=8.5 Hz, 1H), 7.35 (d, J=1.1 Hz, 1H), 7.01 (dd, J=8.4, 1.6 Hz, 1H), 4.02-3.98 (m, 2H), 3.68 (dd, J=8.7, 5.5 Hz, 2H), 3.18 (quin, J=7.1 Hz, 1H), 2.98 (d, J=7.9 Hz, 2H), 2.90-2.79 (m, 1H), 1.67 (s, 9H), 1.45 (s, 9H), 1.43 (s, 12H), 1.41 (d, J=7.0 Hz, 6H).

Intermediate 399C: tert-butyl 3-((3-isopropyl-2-(4,4,5,5-tetramethyl-1,3,2-dioxaborolan-2-yl)-7H-indol-5-yl)methyl)azetidine-1-carboxylate

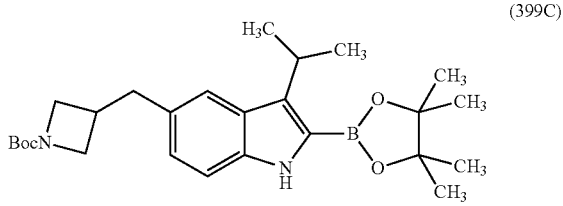 [SMILES: CC(C)c1c(B2OC(C)(C)C(C)(C)O2)[nH]c2ccc(CC3CN(C(=O)OC(C)(C)C)C3)cc12]

(399C)

tert-butyl 5-((1-(tert-butoxycarbonyl)azetidin-3-yl)methyl)-3-isopropyl-2-(4,4,5,5-tetramethyl-1,3,2-dioxaborolan-2-yl)-1H-indole-1-carboxylate (1.35 mmol) was placed in a Teflon screw cap vial with stirring under nitrogen atmosphere. The vial was placed in a heating block at 160° C. and the reaction mixture was stirred for 2.5 hours. Upon completion, the material w as cooled, taken up in DCM and concentrated to obtain an off-white foam, tert-butyl 3-((3-isopropyl-2-(4,4,5,5-tetramethyl-1,3,2-dioxaborolan-2-yl)-1H-indol-5-yl)methyl)azetidine-1-carboxylate contaminated with tert-butyl 3-methylazetidine-1-carboxylate, a byproduct from a previous step. LCMS retention time 1.17 min [method TS1] MS (E$^+$) m/z 455.1 (M+H).

Intermediate 399D: tert-butyl 3-((2-(7,8-dimethyl-[1,2,4]triazolo[1,5-a]pyridin-6-yl)-3-isopropyl-1H-indol-5-yl)methyl)azetidine-1-carboxylate

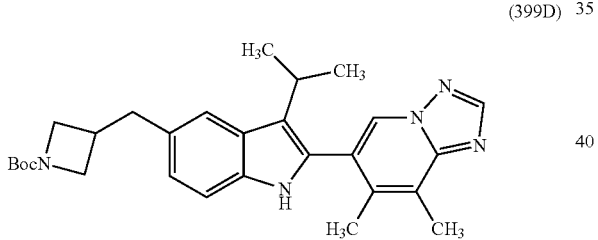

(399D)

To a solution of tert-butyl 3-((3-isopropyl-2-(4,4,5,5-tetramethyl-1,3,2-dioxaborolan-2-yl)-1H-indol-5-yl)methyl)azetidine-1-carboxylate (0.396 mmol), 6-bromo-7,8-dimethyl-[1,2,4]triazolo[1,5-a]pyridine (99 mg, 0.436 mmol), and XPhos 2$^{nd}$ generation precatalyst (15.6 mg, 0.020 mmol) in dioxane (2.64 mL) was added 3 M aqueous potassium phosphate tribasic (0.40 mL, 1.19 mmol). The biphasic mixture w as degassed with nitrogen for 10 min. The reaction vial was sealed and the reaction mixture was stirred at 65° C. After stirring for 1.5 hours, the reaction mixture was cooled to room temperature. The reaction mixture was concentrated and the crude material was purified by flash column chromatography (silica gel, hexanes/EtOAc 0-100%) to afford tert-butyl 3-((2-(7,8-dimethyl-[1,2,4]triazolo[1,5-a]pyridin-6-yl)-3-isopropyl-1H-indol-5-yl)methyl) azetidine-1-carboxylate (128 mg, 0.270 mmol, 68.2% yield). LCMS retention time 1.02 min [method TS1] MS (E$^+$) m/z 474.3 (M+H).

Example 399

To a solution of tert-butyl 3-((2-(7,8-dimethyl-[1,2,4]triazolo[1,5-a]pyridin-6-yl)-3-isopropyl-1H-indol-5-yl)methyl)azetidine-1-carboxylate (128 mg, 0.270 mmol) in DCM (5.4 mL) at room temperature was added HCl in dioxane, 4M (1.35 mL, 5.41 mmol). The reaction mixture was stirred at room temperature. After 30 minutes, the reaction mixture was concentrated to afford crude 6-(5-(azetidin-3-ylmethyl)-3-isopropyl-1H-indol-2-yl)-7,8-dimethyl-[1,2,4]triazolo[1,5-a]pyridine, HCl. LCMS retention time 0.73 min [method TS1] MS (E$^+$) m/z 374.3 (M+H). A portion (approximately one-ninth, 0.030 mmol) of this material was taken up in DMF with a few drops of Et$_3$N and purified by preparative LC/MS with the following conditions: Column: XBridge C18, 19×200 mm, 5 µm particles; Mobile Phase A: 5:95 acetonitrile: water with 10 mM ammonium acetate; Mobile Phase B: 95:5 acetonitrile: water with 10 mM ammonium acetate; Gradient: 10-50% B over 20 minutes, then a 4-minute hold at 100% B; Flow: 20 mL/min. Fractions containing the product were combined and dried via centrifugal evaporation to afford 6-(5-(azetidin-3-ylmethyl)-3-isopropyl-1H-indol-2-yl)-7,8-dimethyl-[1,2,4]triazolo[1,5-a]pyridine (4.0 mg, 10.28 µmol, 34% yield). LCMS retention time 1.18 min [QC-ACN-AA-XB] MS (E$^+$) m/z 373.9 (M+H). $^1$H NMR (500 MHz, DMSO-d$_6$) δ 10.98 (br s, 1H), 8.72 (s, 1H), 8.46 (s, 1H), 7.50 (s, 1H), 7.26 (br d, J=8.2 Hz, 1H), 6.94 (br d, J=8.1 Hz, 1H), 3.84-3.51 (m, 3H), 3.06-2.78 (m, 4H), 2.57 (s, 3H), 2.14 (s, 3H), 1.30 (br s, 6H).

Example 400

2-{3-(2-{7,8-dimethyl-[1,2,4]triazolo[1,5-a]pyridin-6-yl}-3-(propan-2-yl)-1H-indol-5-yl)methyl)azetidin-1-yl}-N,N-dimethylacetamide

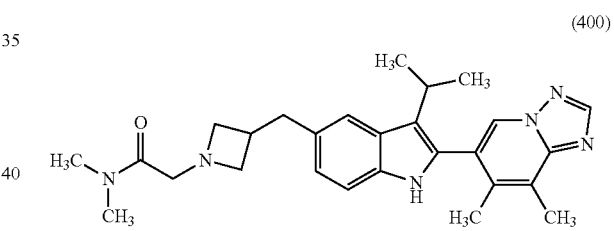

(400)

6-(5-(azetidin-3-ylmethyl)-3-isopropyl-1H-indol-2-yl)-7,8-dimethyl-[1,2,4]triazolo[1,5-a]pyridine. HCl (15.8 mg, 0.0384 mmol) was dissolved in DMF (1 mL). Et$_3$N (0.04 mL, 0.3 mmol) and 2-chloro-ACV-dimethylacetamide (9.34 mg, 0.077 mmol) were added sequentially, and the reaction mixture was stirred for 1 hour at room temperature. Upon completion, the reaction mixture w as diluted with a few drops of water and DMF, and purified via preparative LC/MS with the following conditions: Column: XBridge C18, 19×200 mm, 5 µm particles; Mobile Phase A: 5:95 acetonitrile: water with 10 mM ammonium acetate; Mobile Phase B: 95:5 acetonitrile: water with 10 mM ammonium acetate; Gradient: 10-50% B over 22 minutes, then a 4 minute hold at 100% B; Flow: 20 mL/min. Fractions containing the product were combined and dried via centrifugal evaporation to afford 2-(3-((2-(7,8-dimethyl-[1,2,4]triazolo[1,5-a]pyridin-6-yl)-3-isopropyl-1H-indol-5-yl)methyl)azetidin-1-yl)-N,N'-dimethylacetamide (3.1 mg, 6.42 µmol, 16.72% yield). LCMS retention time 1.25 QC-ACN-AA-XB) MS (E$^+$) m/z 459.1 (M+H) $^1$H NMR (500 MHz, DMSO-d$_6$) δ 10.94 (br s, 1H), 8.71 (s, 1H), 8.45 (s, 1H), 7.46 (s, 1H), 7.24 (d, J=8.2 Hz, 1H), 6.92 (br d. J=8.2 Hz, 1H), 2.90 (s, 3H), 2.76 (s, 3H), 2.57 (s, 3H), 2.14 (s, 3H), 1.29 (br s, 6H).

The following Examples were prepared according to the general procedure used to prepare the above examples.

TABLE 42

| Ex. No. | Structure | Mol Wt. | LCMS MH+ | Ret Time (min) | HPLC Method |
|---|---|---|---|---|---|
| 401 | 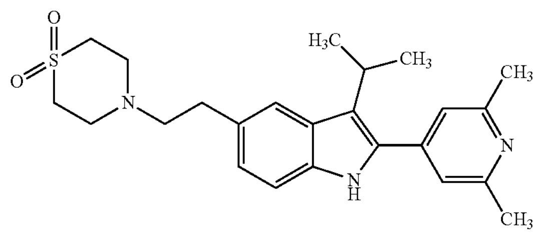 [SMILES: Cc1cc(-c2[nH]c3ccc(CCN4CCS(=O)(=O)CC4)cc3c2C(C)C)cc(C)n1] | 425.6 | 426.1 | 0.84 | QC-ACN-TFA-XB |
| 402 | 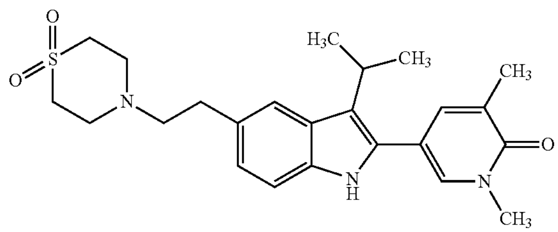 [SMILES: Cc1cc(-c2[nH]c3ccc(CCN4CCS(=O)(=O)CC4)cc3c2C(C)C)cn(C)c1=O] | 441.6 | 442.2 | 1.91 | QC-ACN-AA-XB |
| 403 | 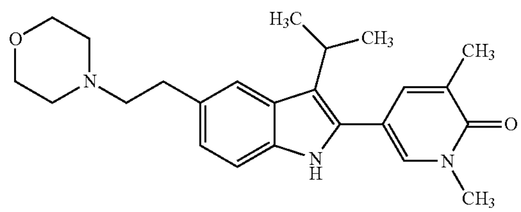 [SMILES: Cc1cc(-c2[nH]c3ccc(CCN4CCOCC4)cc3c2C(C)C)cn(C)c1=O] | 393.5 | 394.0 | 1.59 | QC-ACN-AA-XB |
| 404 | 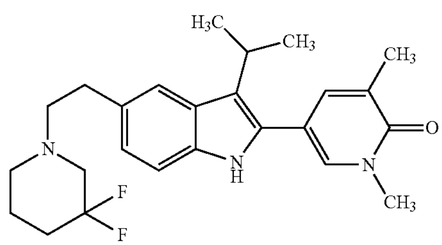 [SMILES: Cc1cc(-c2[nH]c3ccc(CCN4CCCC(F)(F)C4)cc3c2C(C)C)cn(C)c1=O] | 427.5 | 428.0 | 2.11 | QC-ACN-AA-XB |
| 405 | 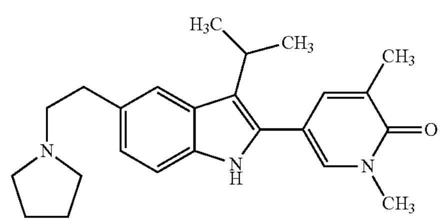 [SMILES: Cc1cc(-c2[nH]c3ccc(CCN4CCCC4)cc3c2C(C)C)cn(C)c1=O] | 377.5 | 378.1 | 1.28 | QC-ACN-AA-XB |
| 406 | 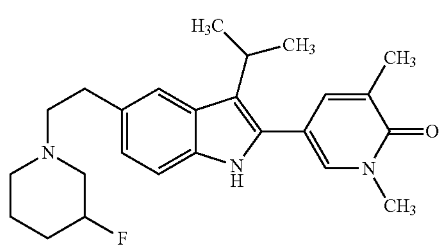 [SMILES: Cc1cc(-c2[nH]c3ccc(CCN4CCCC(F)C4)cc3c2C(C)C)cn(C)c1=O] | 409.5 | 410.1 | 1.25 | QC-ACN-TFA-XB |

TABLE 42-continued
| Ex. No. | Structure | Mol Wt. | LCMS MH+ | Ret Time (min) | HPLC Method |
|---|---|---|---|---|---|
| 407 | 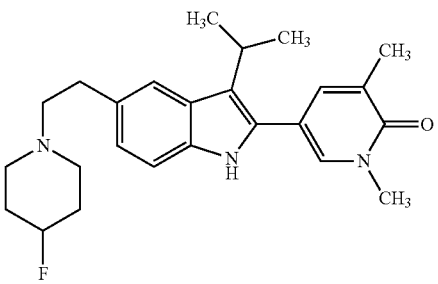 [SMILES: Cc1cc(-c2[nH]c3ccc(CCN4CCC(F)CC4)cc3c2C(C)C)cn(C)c1=O] | 409.5 | 410.4 | 1.46 | QC-ACN-AA-XB |
| 408 | 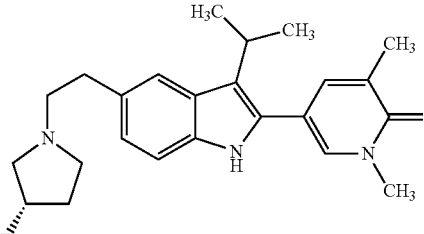 | 395.5 | 396.3 | 1.43 | QC-ACN-AA-XB |
| 409 | 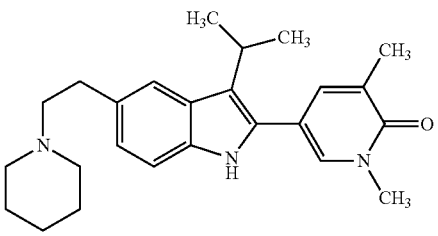 [SMILES: Cc1cc(-c2[nH]c3ccc(CCN4CCCCC4)cc3c2C(C)C)cn(C)c1=O] | 391.6 | 392.4 | 1.25 | QC-ACN-TFA-XB |
| 410 | 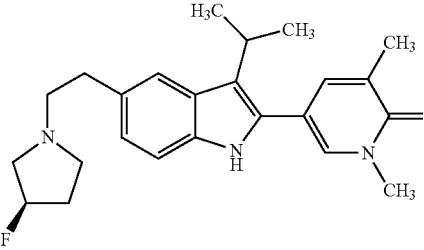 | 395.5 | 396.3 | 1.41 | QC-ACN-AA-XB |
| 411 | 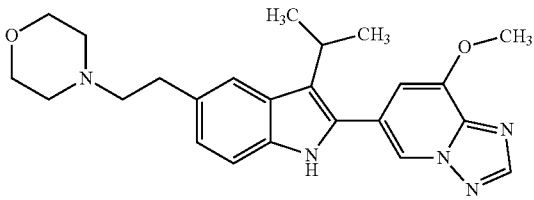 [SMILES: COc1cc(-c2[nH]c3ccc(CCN4CCOCC4)cc3c2C(C)C)cn2ncnc12] | 419.5 | 419.9 | 1.56 | QC-ACN-AA-XB |
| 412 | 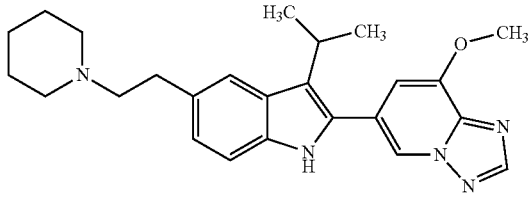 [SMILES: COc1cc(-c2[nH]c3ccc(CCN4CCCCC4)cc3c2C(C)C)cn2ncnc12] | 417.6 | 417.9 | 1.41 | QC-ACN-AA-XB |

TABLE 42-continued

| Ex. No. | Structure | Mol Wt. | LCMS MH+ | Ret Time (min) | HPLC Method |
|---|---|---|---|---|---|
| 413 | 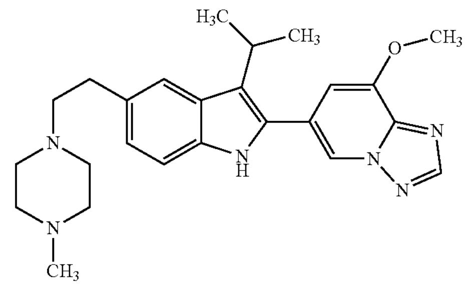 [SMILES: COc1cc(-c2[nH]c3ccc(CCN4CCN(C)CC4)cc3c2C(C)C)cn2ncnc12] | 432.6 | 433.2 | 1.3 | QC-ACN-AA-XB |
| 414 | 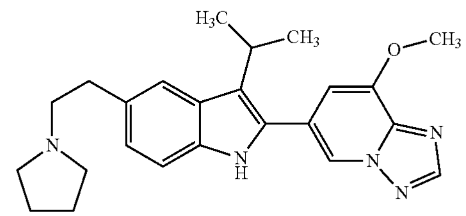 [SMILES: COc1cc(-c2[nH]c3ccc(CCN4CCCC4)cc3c2C(C)C)cn2ncnc12] | 403.5 | 404.0 | 1.17 | QC-ACN-AA-XB |
| 415 | 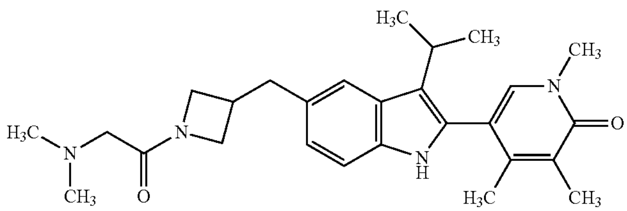 [SMILES: Cc1c(-c2[nH]c3ccc(CC4CN(C(=O)CN(C)C)C4)cc3c2C(C)C)cn(C)c(=O)c1C] | 448.6 | 449.1 | 1.26 | QC-ACN-AA-XB |
| 416 | 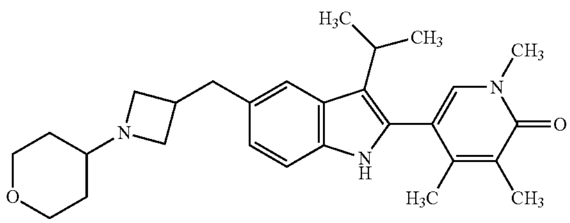 [SMILES: Cc1c(-c2[nH]c3ccc(CC4CN(C5CCOCC5)C4)cc3c2C(C)C)cn(C)c(=O)c1C] | 447.6 | 448.0 | 1.23 | QC-ACN-AA-XB |
| 417 | 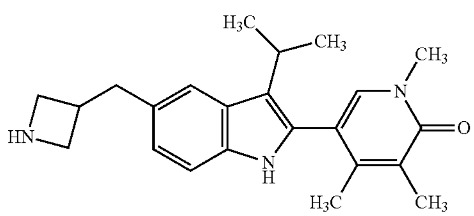 [SMILES: Cc1c(-c2[nH]c3ccc(CC4CNC4)cc3c2C(C)C)cn(C)c(=O)c1C] | 363.5 | 364.3 | 1.08 | QC-ACN-TFA-XB |
| 418 | 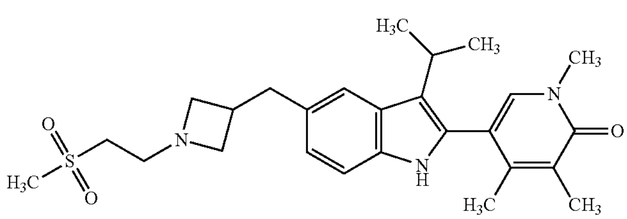 [SMILES: Cc1c(-c2[nH]c3ccc(CC4CN(CCS(C)(=O)=O)C4)cc3c2C(C)C)cn(C)c(=O)c1C] | 469.6 | 470.5 | 1.23 | QC-ACN-AA-XB |
| 419 | 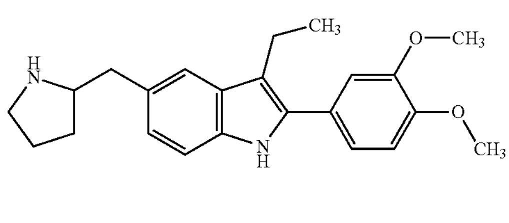 [SMILES: CCc1c(-c2ccc(OC)c(OC)c2)[nH]c2ccc(CC3CCCN3)cc12] | 364.5 | 365.4 | 1.25 | QC-ACN-AA-XB |

TABLE 42-continued

| Ex. No. | Structure | Mol Wt. | LCMS MH+ | Ret Time (min) | HPLC Method |
|---|---|---|---|---|---|
| 420 | 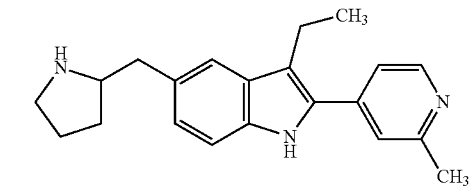 [SMILES: CCc1c(-c2ccnc(C)c2)[nH]c2ccc(CC3CCCN3)cc12] | 319.5 | 320.2 | 0.7 | QC-ACN-TFA-XB |
| 421 | 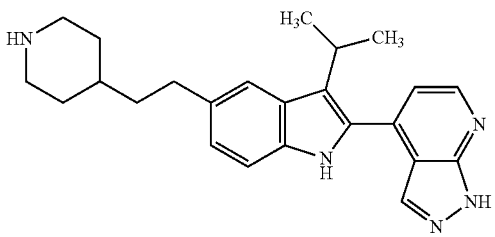 [SMILES: CC(C)c1c(-c2ccnc3[nH]ncc23)[nH]c2ccc(CCC3CCNCC3)cc12] | 387.5 | 388.1 | 1.17 | QC-ACN-AA-XB |
| 422 | 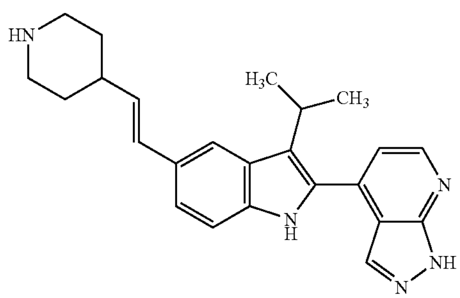 [SMILES: CC(C)c1c(-c2ccnc3[nH]ncc23)[nH]c2ccc(/C=C/C3CCNCC3)cc12] | 385.5 | 386.1 | 1.09 | QC-ACN-AA-XB |
| 423 | 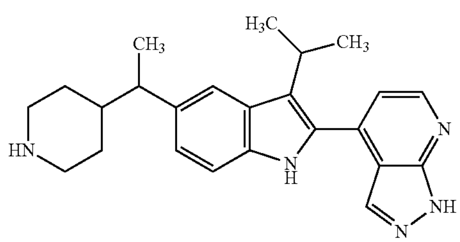 [SMILES: CC(C)c1c(-c2ccnc3[nH]ncc23)[nH]c2ccc(C(C)C3CCNCC3)cc12] | 387.5 | 388.3 | 1.14 | QC-ACN-TFA-XB |
| 424 | 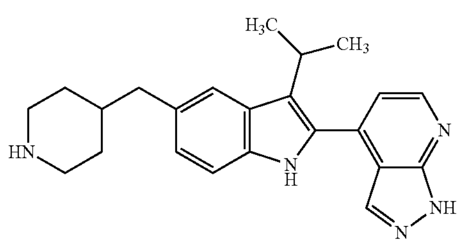 [SMILES: CC(C)c1c(-c2ccnc3[nH]ncc23)[nH]c2ccc(CC3CCNCC3)cc12] | 373.5 | 374.2 | 1.03 | QC-ACN-TFA-XB |
| 425 | 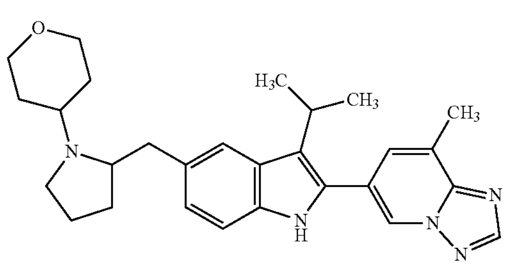 [SMILES: Cc1cc(-c2[nH]c3ccc(CC4CCCN4C4CCOCC4)cc3c2C(C)C)cn2ncnc12] | 457.6 | 458.4 | 1.29 | QC-ACN-AA-XB |

TABLE 42-continued

| Ex. No. | Structure | Mol Wt. | LCMS MH+ | Ret Time (min) | HPLC Method |
|---|---|---|---|---|---|
| 426 | 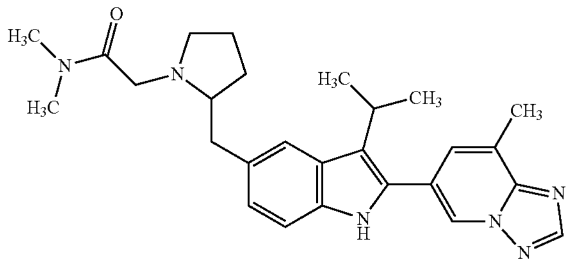 [SMILES: Cc1cc(-c2[nH]c3ccc(CC4CCCN4CC(=O)N(C)C)cc3c2C(C)C)cn2ncnc12] | 458.6 | 458,9 | 1.4 | QC-ACN-AA-XB |
| 427 | 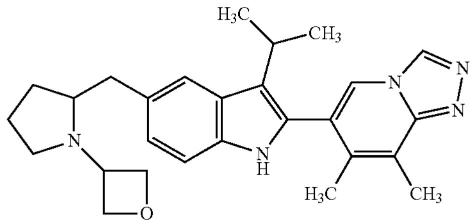 [SMILES: Cc1c(-c2[nH]c3ccc(CC4CCCN4C4COC4)cc3c2C(C)C)cn2cnnc2c1C] | 443.6 | 444.1 | 1.3 | QC-ACN-AA-XB |
| 428 | 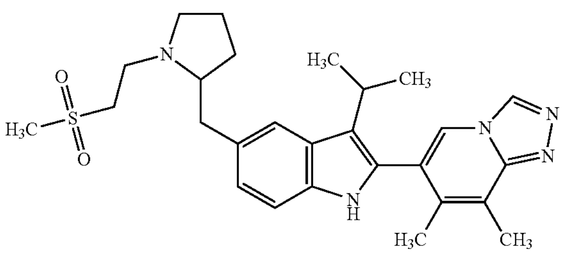 [SMILES: Cc1c(-c2[nH]c3ccc(CC4CCCN4CCS(C)(=O)=O)cc3c2C(C)C)cn2cnnc2c1C] | 493.7 | 494.3 | 1.12 | QC-ACN-TFA-XB |
| 429 | 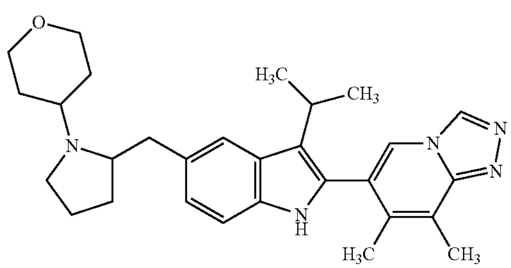 [SMILES: Cc1c(-c2[nH]c3ccc(CC4CCCN4C4CCOCC4)cc3c2C(C)C)cn2cnnc2c1C] | 471.6 | 472.5 | 0.94 | QC-ACN-TFA-XB |
| 430 | 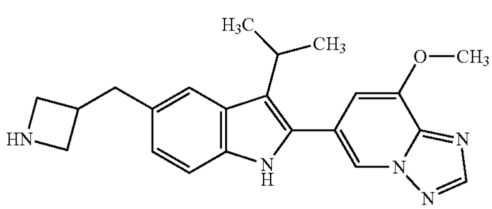 [SMILES: COc1cc(-c2[nH]c3ccc(CC4CNC4)cc3c2C(C)C)cn2ncnc12] | 375.5 | 376.3 | 1.05 | QC-ACN-AA-XB |
| 431 | 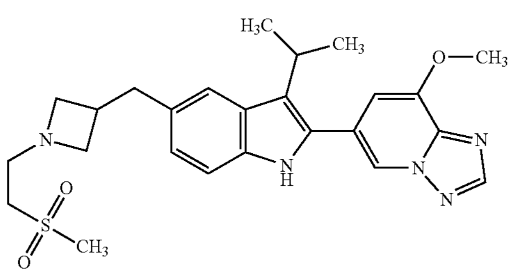 [SMILES: COc1cc(-c2[nH]c3ccc(CC4CN(CCS(C)(=O)=O)C4)cc3c2C(C)C)cn2ncnc12] | 481.6 | 482.4 | 1.13 | QC-ACN-TFA-XB |

TABLE 42-continued

| Ex. No. | Structure | Mol Wt. | LCMS MH+ | Ret Time (min) | HPLC Method |
|---|---|---|---|---|---|
| 432 | 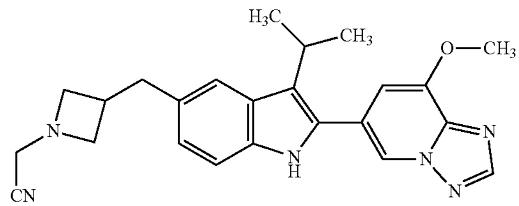 [SMILES: COc1cc(-c2[nH]c3ccc(CC4CN(CC#N)C4)cc3c2C(C)C)cn2ncnc12] | 414.5 | 414.9 | 1.68 | QC-ACN-AA-XB |
| 433 | 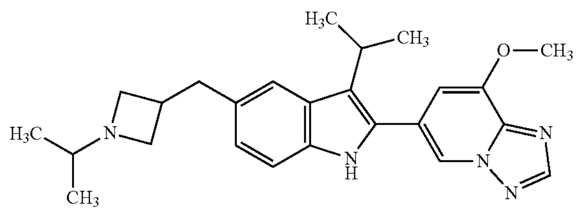 [SMILES: COc1cc(-c2[nH]c3ccc(CC4CN(C(C)C)C4)cc3c2C(C)C)cn2ncnc12] | 417.6 | 418.2 | 1.25 | QC-ACN-AA-XB |
| 434 | 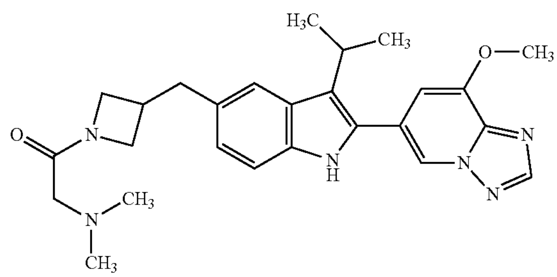 [SMILES: COc1cc(-c2[nH]c3ccc(CC4CN(C(=O)CN(C)C)C4)cc3c2C(C)C)cn2ncnc12] | 460.6 | 461.0 | 1.26 | QC-ACN-AA-XB |
| 435 | 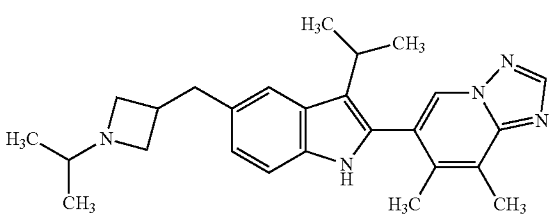 [SMILES: Cc1c(-c2[nH]c3ccc(CC4CN(C(C)C)C4)cc3c2C(C)C)cn2ncnc2c1C] | 415.6 | 416.4 | 1.28 | QC-ACN-AA-XB |
| 436 | 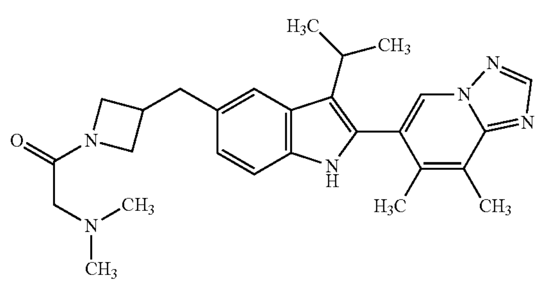 [SMILES: Cc1c(-c2[nH]c3ccc(CC4CN(C(=O)CN(C)C)C4)cc3c2C(C)C)cn2ncnc2c1C] | 458.6 | 459.1 | 1.22 | QC-ACN-TFA-XB |
| 437 | 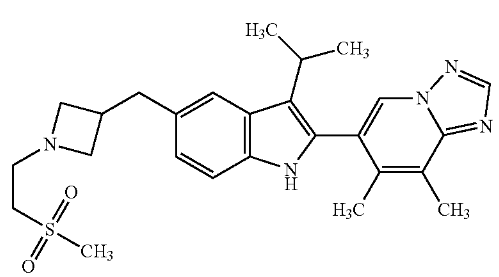 [SMILES: Cc1c(-c2[nH]c3ccc(CC4CN(CCS(C)(=O)=O)C4)cc3c2C(C)C)cn2ncnc2c1C] | 479.6 | 480.0 | 1.17 | QC-ACN-TFA-XB |

TABLE 42-continued

| Ex. No. | Structure | Mol Wt. | LCMS MH+ | Ret Time (min) | HPLC Method |
|---|---|---|---|---|---|
| 438 | 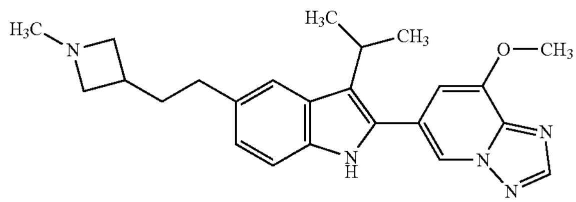 [SMILES: COc1cc(-c2[nH]c3ccc(CCC4CN(C)C4)cc3c2C(C)C)cn2ncnc12] | 403.5 | 404.1 | 1.31 | QC-ACN-TFA-XB |
| 439 | 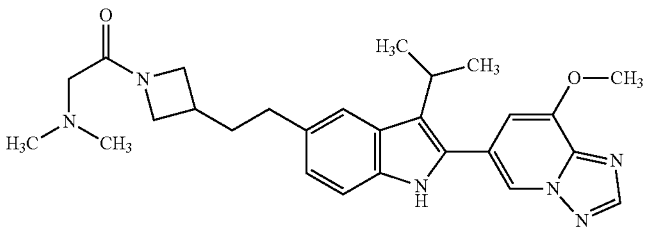 [SMILES: COc1cc(-c2[nH]c3ccc(CCC4CN(C(=O)CN(C)C)C4)cc3c2C(C)C)cn2ncnc12] | 474.6 | 475.4 | 1.31 | QC-ACN-TFA-XB |
| 440 | 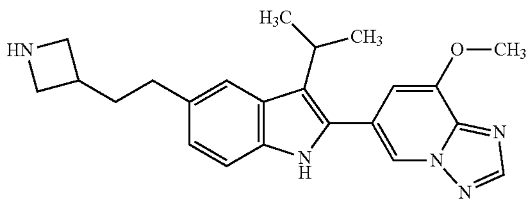 [SMILES: COc1cc(-c2[nH]c3ccc(CCC4CNC4)cc3c2C(C)C)cn2ncnc12] | 389.5 | 390.1 | 1.18 | QC-ACN-AA-XB |
| 441 | 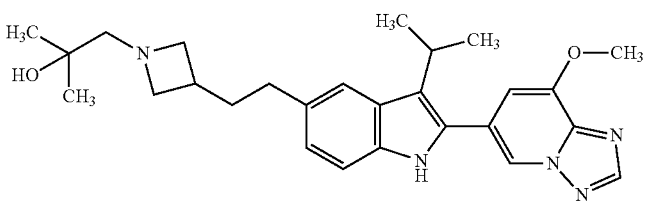 [SMILES: COc1cc(-c2[nH]c3ccc(CCC4CN(CC(C)(C)O)C4)cc3c2C(C)C)cn2ncnc12] | 461.6 | 462.2 | 1.38 | QC-ACN-AA-XB |
| 442 | 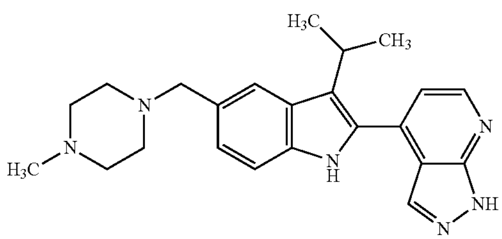 [SMILES: CC(C)c1c(-c2ccnc3[nH]ncc23)[nH]c2ccc(CN3CCN(C)CC3)cc12] | 388.5 | 389.1 | 1.09 | QC-ACN-AA-XB |
| 443 | 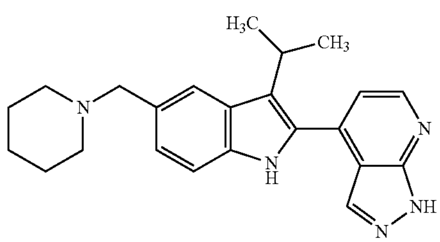 [SMILES: CC(C)c1c(-c2ccnc3[nH]ncc23)[nH]c2ccc(CN3CCCCC3)cc12] | 373.5 | 374.1 | 1.13 | QC-ACN-AA-XB |
| 444 | 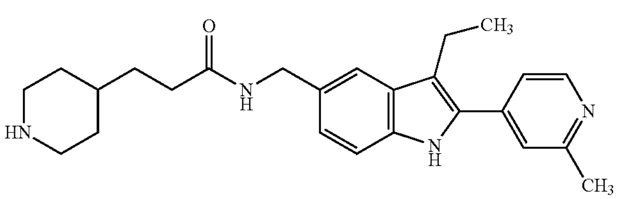 [SMILES: CCc1c(-c2ccnc(C)c2)[nH]c2ccc(CNC(=O)CCC3CCNCC3)cc12] | 404.6 | 405.3 | 0.96 | QC-ACN-AA-XB |

TABLE 42-continued

| Ex. No. | Structure | Mol Wt. | LCMS MH+ | Ret Time (min) | HPLC Method |
|---|---|---|---|---|---|
| 445 | 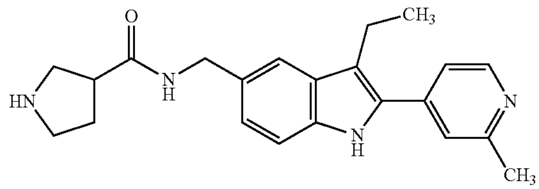 [SMILES: CCc1c(-c2ccnc(C)c2)[nH]c2ccc(CNC(=O)C3CCNC3)cc12] | 362.5 | 363.4 | 0.94 | QC-ACN-AA-XB |
| 446 | 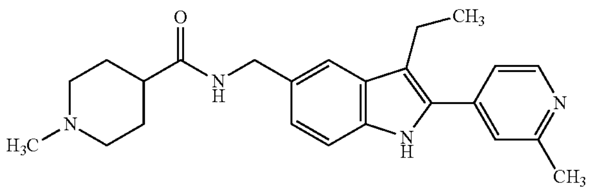 | 390.5 | 391.4 | 0.93 | QC-ACN-AA-XB |
| 447 | 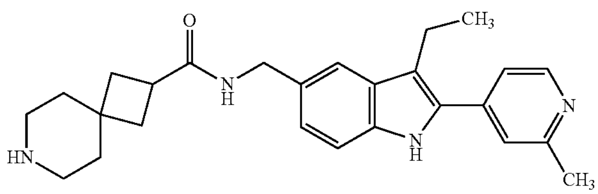 [SMILES: CCc1c(-c2ccnc(C)c2)[nH]c2ccc(CNC(=O)C3CC4(CCNCC4)C3)cc12] | 416.6 | 417.2 | 0.76 | QC-ACN-TFA-XB |
| 448 | 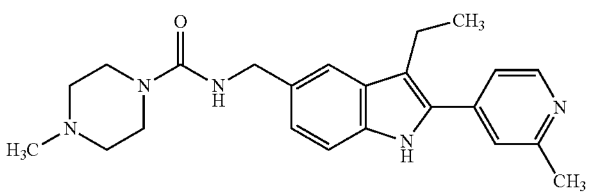 | 391.5 | 392.1 | 1.33 | QC-ACN-AA-XB |
| 449 | 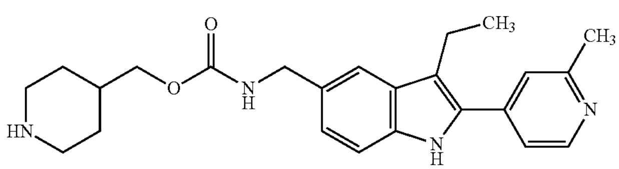 [SMILES: CCc1c(-c2ccnc(C)c2)[nH]c2ccc(CNC(=O)OCC3CCNCC3)cc12] | 406.5 | 407.4 | 0.78 | QC-ACN-TFA-XB |
| 450 | 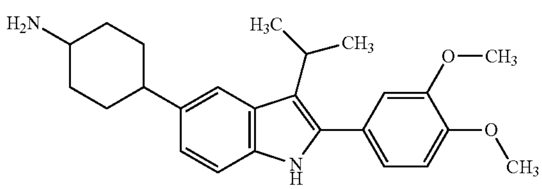 [SMILES: COc1ccc(-c2[nH]c3ccc(C4CCC(N)CC4)cc3c2C(C)C)cc1OC] | 392.5 | 393.1 | 1.5 | QC-ACN-AA-XB |
| 451 | 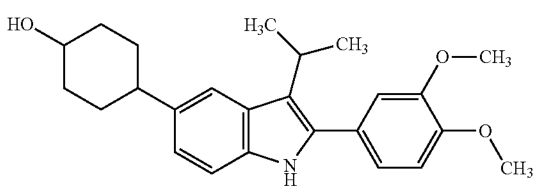 [SMILES: COc1ccc(-c2[nH]c3ccc(C4CCC(O)CC4)cc3c2C(C)C)cc1OC] | 393.5 | 394.3 | 1.87 | QC-ACN-AA-XB |
| 452 | 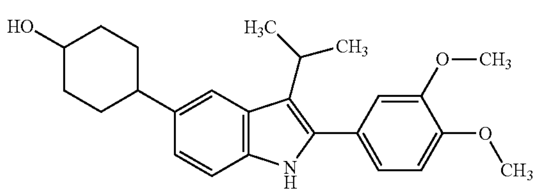 [SMILES: COc1ccc(-c2[nH]c3ccc(C4CCC(O)CC4)cc3c2C(C)C)cc1OC] | 393.5 | 394.1 | 2.01 | QC-ACN-TFA-XB |

TABLE 42-continued
| Ex. No. | Structure | Mol Wt. | LCMS MH+ | Ret Time (min) | HPLC Method |
|---|---|---|---|---|---|
| 453 | 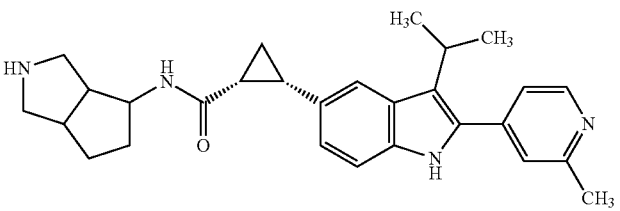 [SMILES: Cc1cc(-c2[nH]c3ccc([C@H]4C[C@H]4C(=O)NC4CCC5CNCC54)cc3c2C(C)C)ccn1] | 442.6 | 443.4 | 1.7 | QC-ACN-AA-XB |
| 454 | 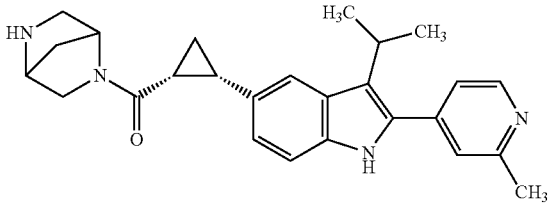 [SMILES: Cc1cc(-c2[nH]c3ccc([C@H]4C[C@H]4C(=O)N4CC5CC4CN5)cc3c2C(C)C)ccn1] | 414.6 | 415.0 | 1.17 | QC-ACN-AA-XB |
| 455 | 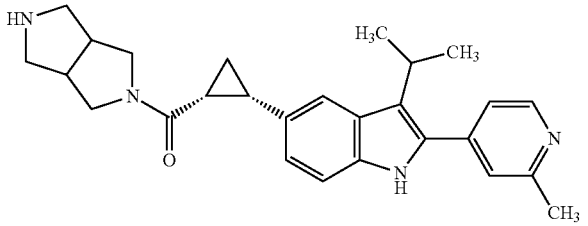 [SMILES: Cc1cc(-c2[nH]c3ccc([C@H]4C[C@H]4C(=O)N4CC5CNCC5C4)cc3c2C(C)C)ccn1] | 428.6 | 429.3 | 0.86 | QC-ACN-TFA-XB |
| 456 | 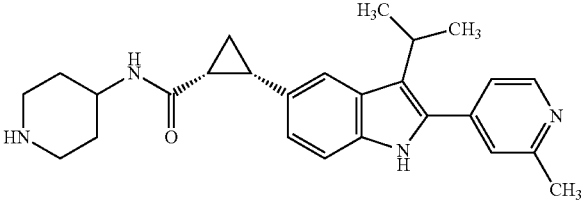 [SMILES: Cc1cc(-c2[nH]c3ccc([C@H]4C[C@H]4C(=O)NC4CCNCC4)cc3c2C(C)C)ccn1] | 416.6 | 417.3 | 0.88 | QC-ACN-TFA-XB |
| 457 | 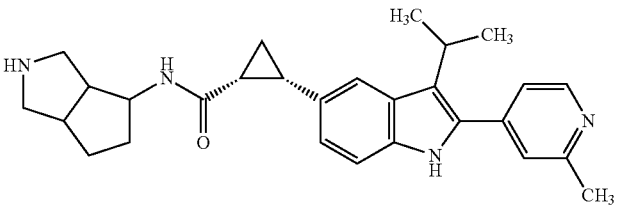 [SMILES: Cc1cc(-c2[nH]c3ccc([C@H]4C[C@H]4C(=O)NC4CCC5CNCC54)cc3c2C(C)C)ccn1] | 442.6 | 443.1 | 0.9 | QC-ACN-TFA-XB |
| 458 | 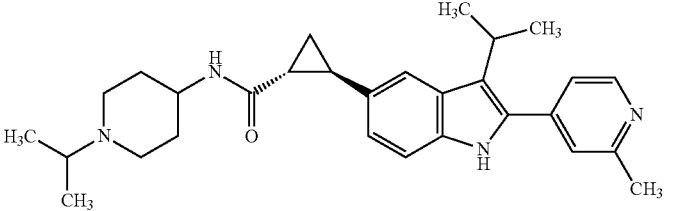 [SMILES: Cc1cc(-c2[nH]c3ccc([C@@H]4C[C@H]4C(=O)NC4CCN(C(C)C)CC4)cc3c2C(C)C)ccn1] | 458.7 | 459.2 | 0.98 | QC-ACN-TFA-XB |
| 459 | 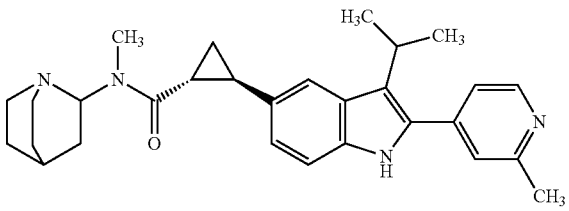 [SMILES: Cc1cc(-c2[nH]c3ccc([C@@H]4C[C@H]4C(=O)N(C)C4CC5CCN4CC5)cc3c2C(C)C)ccn1] | 456.6 | 457.4 | 0.96 | QC-ACN-TFA-XB |

TABLE 42-continued

| Ex. No. | Structure | Mol Wt. | LCMS MH+ | Ret Time (min) | HPLC Method |
|---|---|---|---|---|---|
| 460 | 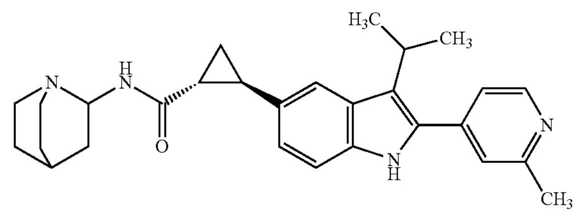 [SMILES: Cc1cc(-c2[nH]c3ccc([C@@H]4C[C@H]4C(=O)NC4CC5CCN4CC5)cc3c2C(C)C)ccn1] | 442.6 | 443.4 | 1.63 | QC-ACN-AA-XB |
| 461 | 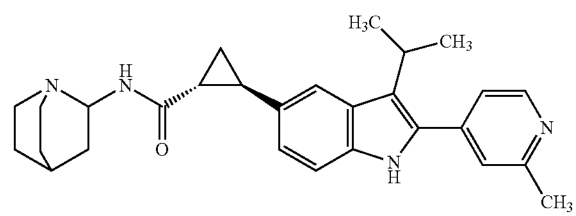 [SMILES: Cc1cc(-c2[nH]c3ccc([C@@H]4C[C@H]4C(=O)NC4CC5CCN4CC5)cc3c2C(C)C)ccn1] | 442.6 | 443.4 | 1.64 | QC-ACN-AA-XB |
| 462 | 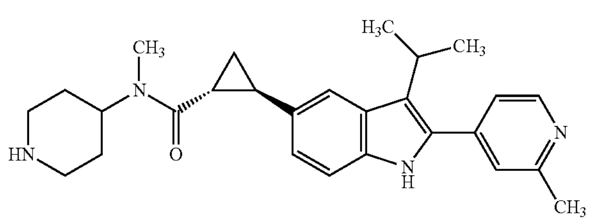 [SMILES: Cc1cc(-c2[nH]c3ccc([C@@H]4C[C@H]4C(=O)N(C)C4CCNCC4)cc3c2C(C)C)ccn1] | 430.6 | 431.4 | 1.59 | QC-ACN-AA-XB |
| 463 | 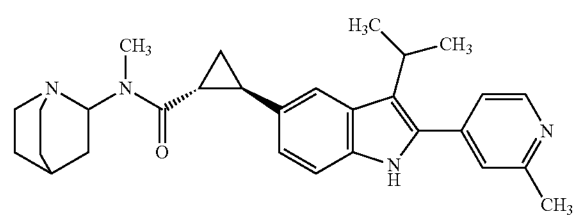 [SMILES: Cc1cc(-c2[nH]c3ccc([C@@H]4C[C@H]4C(=O)N(C)C4CC5CCN4CC5)cc3c2C(C)C)ccn1] | 456.6 | 457.1 | 1.28 | QC-ACN-AA-XB |
| 464 | 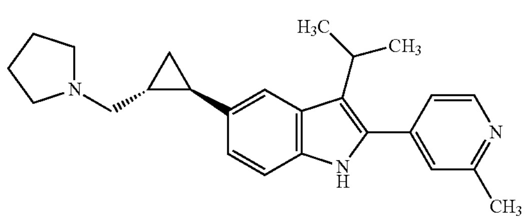 [SMILES: Cc1cc(-c2[nH]c3ccc([C@@H]4C[C@H]4CN4CCCC4)cc3c2C(C)C)ccn1] | 373.5 | 374.2 | 1.36 | QC-ACN-AA-XB |
| 465 | 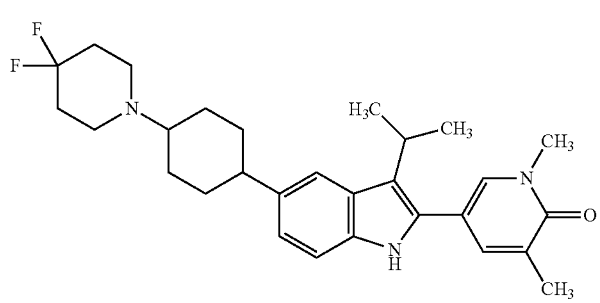 [SMILES: Cc1cc(-c2[nH]c3ccc(C4CCC(N5CCC(F)(F)CC5)CC4)cc3c2C(C)C)cn(C)c1=O] | 481.6 | 482.4 | 2.16 | QC-ACN-AA-XB |

TABLE 42-continued

| Ex. No. | Structure | Mol Wt. | LCMS MH+ | Ret Time (min) | HPLC Method |
|---|---|---|---|---|---|
| 466 | 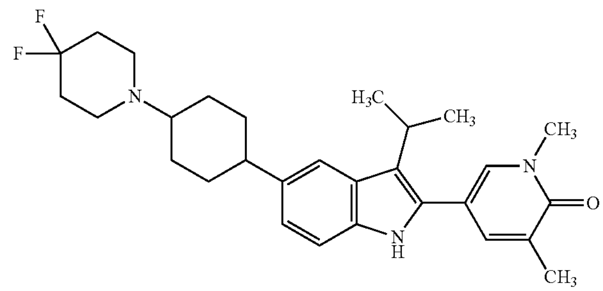 [SMILES: Cc1cc(-c2[nH]c3ccc(C4CCC(N5CCC(F)(F)CC5)CC4)cc3c2C(C)C)cn(C)c1=O] | 481.6 | 482.1 | 1.4 | QC-ACN-TFA-XB |
| 467 | 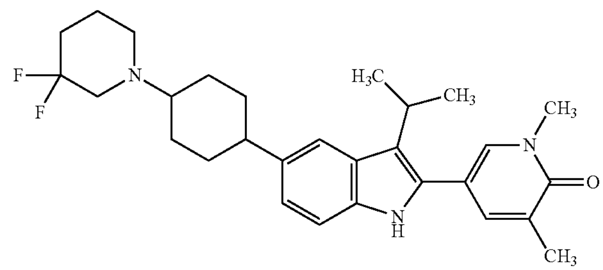 [SMILES: Cc1cc(-c2[nH]c3ccc(C4CCC(N5CCCC(F)(F)C5)CC4)cc3c2C(C)C)cn(C)c1=O] | 481.6 | 481.9 | 1.34 | QC-ACN-TFA-XB |
| 468 | 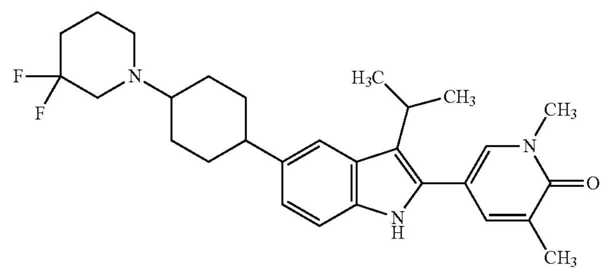 [SMILES: Cc1cc(-c2[nH]c3ccc(C4CCC(N5CCCC(F)(F)C5)CC4)cc3c2C(C)C)cn(C)c1=O] | 481.6 | 482.4 | 2.59 | QC-ACN-AA-XB |
| 469 | 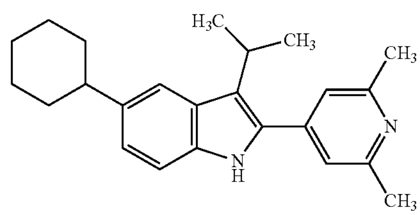 [SMILES: Cc1cc(-c2[nH]c3ccc(C4CCCCC4)cc3c2C(C)C)cc(C)n1] | 346.5 | 346.9 | 2.18 | QC-ACN-TFA-XB |
| 470 | 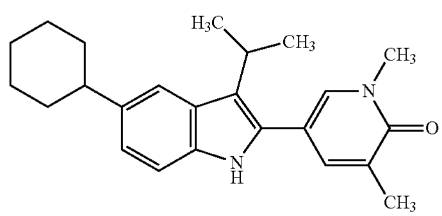 [SMILES: Cc1cc(-c2[nH]c3ccc(C4CCCCC4)cc3c2C(C)C)cn(C)c1=O] | 362.5 | 363.4 | 2.62 | QC-ACN-TFA-XB |
| 471 | 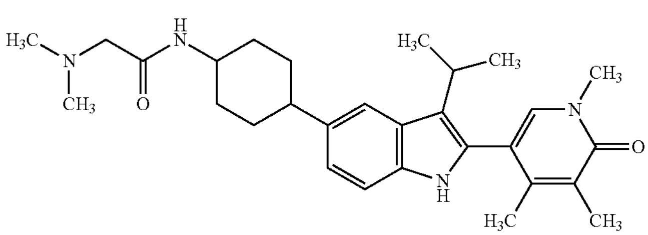 [SMILES: Cc1c(-c2[nH]c3ccc(C4CCC(NC(=O)CN(C)C)CC4)cc3c2C(C)C)cn(C)c(=O)c1C] | 476.7 | 477.2 | 1.51 | QC-ACN-AA-XB |

TABLE 42-continued

| Ex. No. | Structure | Mol Wt. | LCMS MH+ | Ret Time (min) | HPLC Method |
|---|---|---|---|---|---|
| 472 | 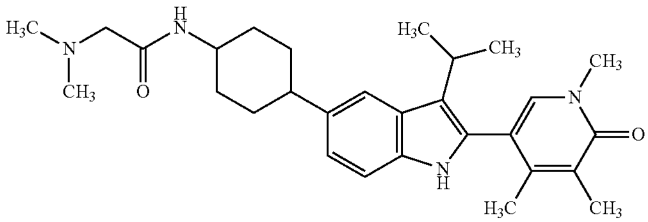 [SMILES: Cc1c(-c2[nH]c3ccc(C4CCC(NC(=O)CN(C)C)CC4)cc3c2C(C)C)cn(C)c(=O)c1C] | 476.7 | 477.2 | 1.36 | QC-ACN-AA-XB |
| 473 | 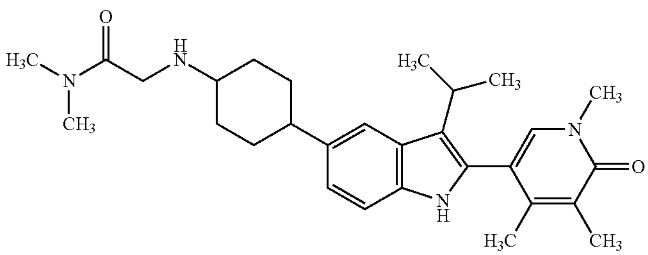 [SMILES: Cc1c(-c2[nH]c3ccc(C4CCC(NCC(=O)N(C)C)CC4)cc3c2C(C)C)cn(C)c(=O)c1C] | 476.7 | 477.5 | 1.47 | QC-ACN-AA-XB |
| 474 | 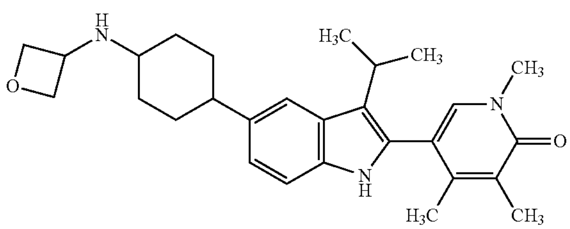 [SMILES: Cc1c(-c2[nH]c3ccc(C4CCC(NC5COC5)CC4)cc3c2C(C)C)cn(C)c(=O)c1C] | 447.6 | 447.9 | 1.49 | QC-ACN-AA-XB |
| 475 | 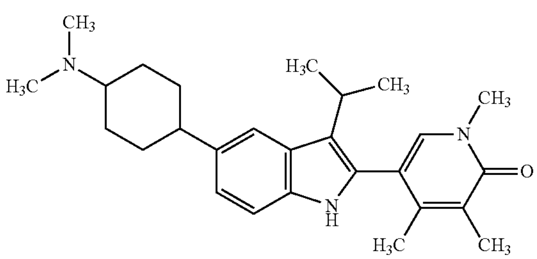 [SMILES: Cc1c(-c2[nH]c3ccc(C4CCC(N(C)C)CC4)cc3c2C(C)C)cn(C)c(=O)c1C] | 419.6 | 420.3 | 1.31 | QC-ACN-AA-XB |
| 476 | 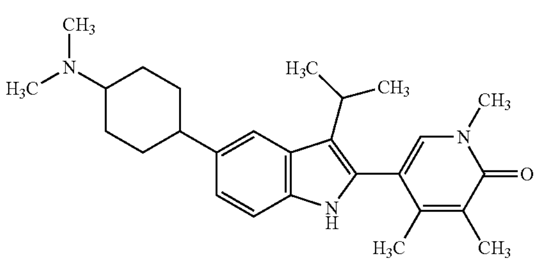 [SMILES: Cc1c(-c2[nH]c3ccc(C4CCC(N(C)C)CC4)cc3c2C(C)C)cn(C)c(=O)c1C] | 419.6 | 420.3 | 1.21 | QC-ACN-AA-XB |
| 477 | 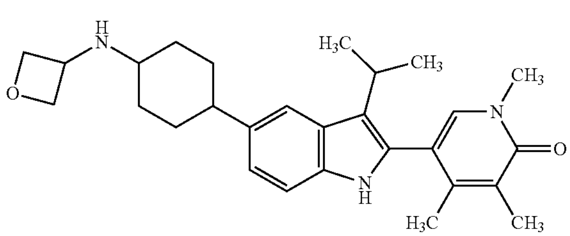 [SMILES: Cc1c(-c2[nH]c3ccc(C4CCC(NC5COC5)CC4)cc3c2C(C)C)cn(C)c(=O)c1C] | 447.6 | 448.1 | 1.34 | QC-ACN-AA-XB |

TABLE 42-continued

| Ex. No. | Structure | Mol Wt. | LCMS MH+ | Ret Time (min) | HPLC Method |
|---|---|---|---|---|---|
| 478 | 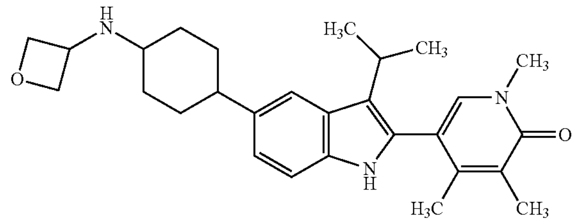 [SMILES: Cc1c(-c2[nH]c3ccc(C4CCC(NC5COC5)CC4)cc3c2C(C)C)cn(C)c(=O)c1C] | 447.6 | 448.0 | 1.37 | QC-ACN-TFA-XB |
| 479 | 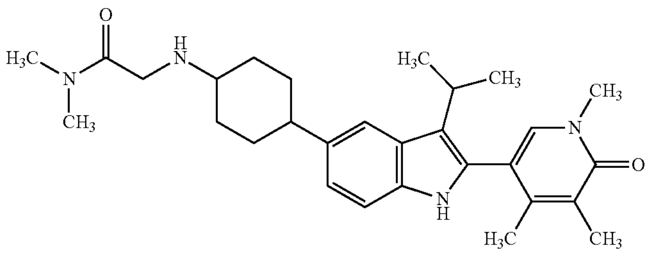 [SMILES: Cc1c(-c2[nH]c3ccc(C4CCC(NCC(=O)N(C)C)CC4)cc3c2C(C)C)cn(C)c(=O)c1C] | 476.7 | 477.5 | 1.21 | QC-ACN-AA-XB |
| 480 | 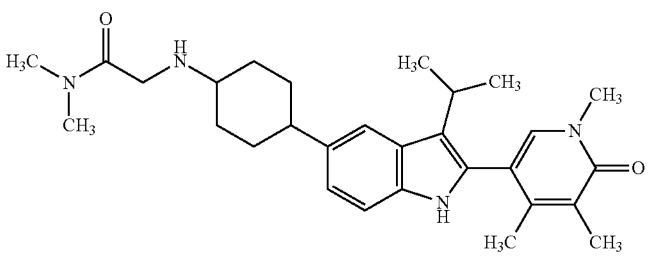 [SMILES: Cc1c(-c2[nH]c3ccc(C4CCC(NCC(=O)N(C)C)CC4)cc3c2C(C)C)cn(C)c(=O)c1C] | 476.7 | 477.4 | 1.4 | QC-ACN-AA-XB |
| 481 | 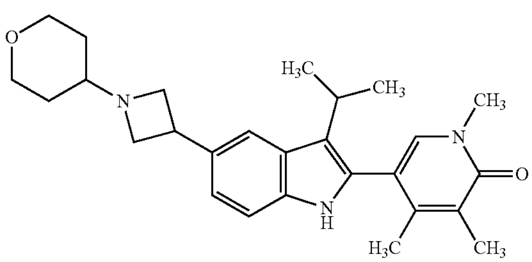 [SMILES: Cc1c(-c2[nH]c3ccc(C4CN(C5CCOCC5)C4)cc3c2C(C)C)cn(C)c(=O)c1C] | 433.6 | 434.2 | 1.23 | QC-ACN-TFA-XB |
| 482 | 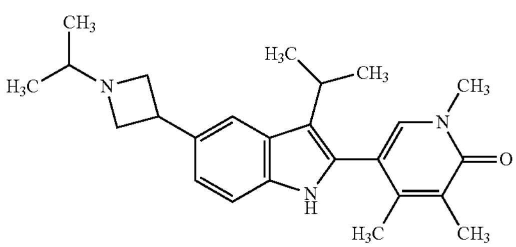 [SMILES: Cc1c(-c2[nH]c3ccc(C4CN(C(C)C)C4)cc3c2C(C)C)cn(C)c(=O)c1C] | 391.6 | 392.2 | 1.27 | QC-ACN-TFA-XB |
| 483 | 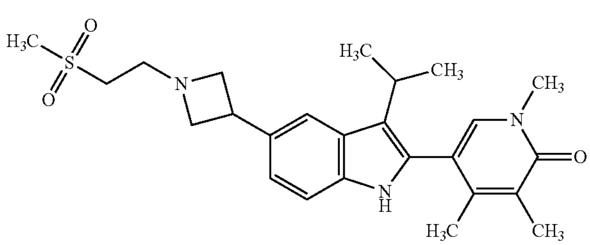 [SMILES: Cc1c(-c2[nH]c3ccc(C4CN(CCS(C)(=O)=O)C4)cc3c2C(C)C)cn(C)c(=O)c1C] | 455.6 | 455.9 | 1.28 | QC-ACN-AA-XB |

TABLE 42-continued

| Ex. No. | Structure | Mol Wt. | LCMS MH+ | Ret Time (min) | HPLC Method |
|---|---|---|---|---|---|
| 484 | 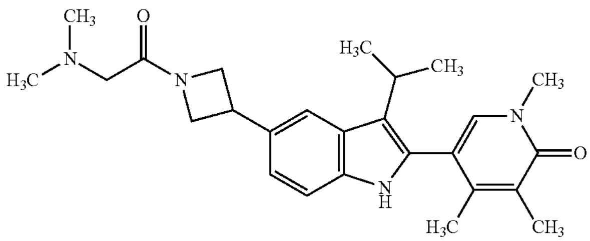 [SMILES: Cc1c(-c2[nH]c3ccc(C4CN(C(=O)CN(C)C)C4)cc3c2C(C)C)cn(C)c(=O)c1C] | 434.6 | 435.0 | 1.18 | QC-ACN-AA-XB |
| 485 | 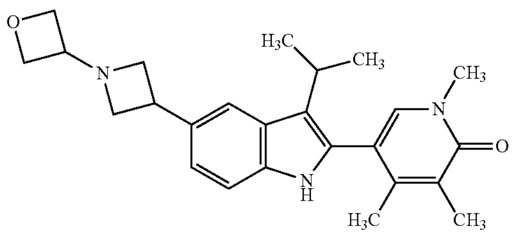 [SMILES: Cc1c(-c2[nH]c3ccc(C4CN(C5COC5)C4)cc3c2C(C)C)cn(C)c(=O)c1C] | 405.5 | 406.3 | 1.33 | QC-ACN-AA-XB |
| 486 | 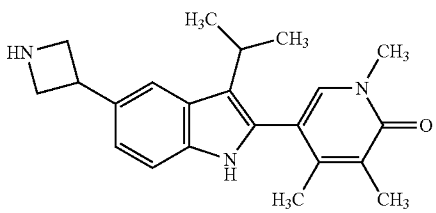 [SMILES: Cc1c(-c2[nH]c3ccc(C4CNC4)cc3c2C(C)C)cn(C)c(=O)c1C] | 349.5 | 350.3 | 0.95 | QC-ACN-AA-XB |
| 487 | 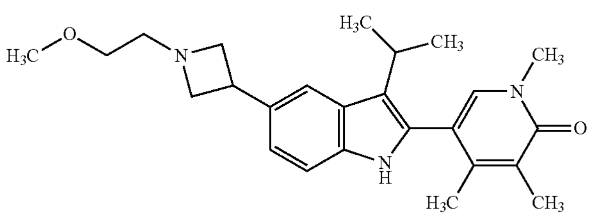 [SMILES: COCCN1CC(c2ccc3[nH]c(-c4cn(C)c(=O)c(C)c4C)c(C(C)C)c3c2)C1] | 407.6 | 408.5 | 1.2 | QC-ACN-AA-XB |
| 488 | 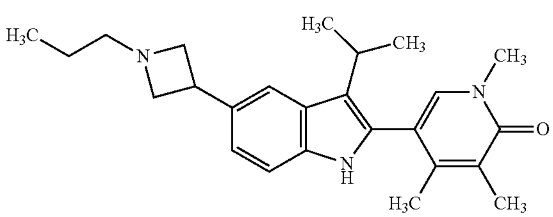 | 391.6 | 391.9 | 1.38 | QC-ACN-AA-XB |
| 489 | 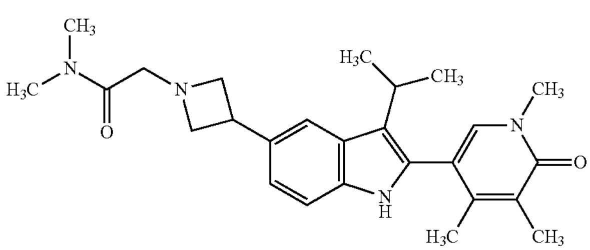 [SMILES: Cc1c(-c2[nH]c3ccc(C4CN(CC(=O)N(C)C)C4)cc3c2C(C)C)cn(C)c(=O)c1C] | 434.6 | 435.4 | 1.06 | QC-ACN-TFA-XB |

TABLE 42-continued

| Ex. No. | Structure | Mol Wt. | LCMS MH+ | Ret Time (min) | HPLC Method |
|---|---|---|---|---|---|
| 490 | 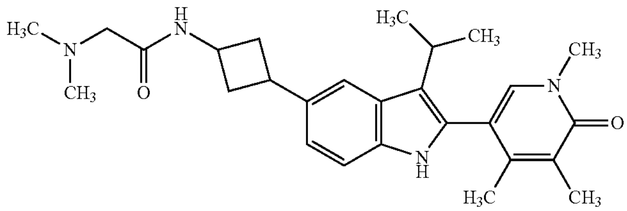 [SMILES: Cc1c(-c2[nH]c3ccc(C4CC(NC(=O)CN(C)C)C4)cc3c2C(C)C)cn(C)c(=O)c1C] | 448.6 | 449.6 | 1.48 | QC-ACN-AA-XB |
| 491 | 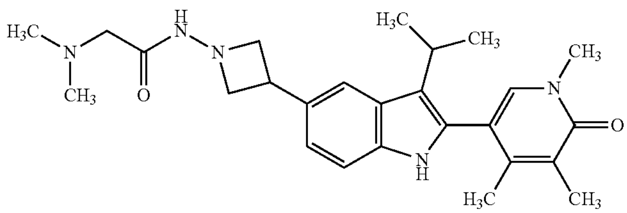 [SMILES: Cc1c(-c2[nH]c3ccc(C4CN(NC(=O)CN(C)C)C4)cc3c2C(C)C)cn(C)c(=O)c1C] | 448.6 | 449.2 | 1.46 | QC-ACN-AA-XB |
| 492 | 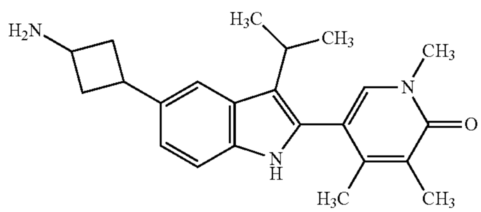 [SMILES: Cc1c(-c2[nH]c3ccc(C4CC(N)C4)cc3c2C(C)C)cn(C)c(=O)c1C] | 363.5 | 364.1 | 1.24 | QC-ACN-AA-XB |
| 493 | 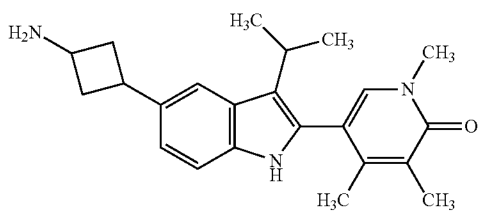 [SMILES: Cc1c(-c2[nH]c3ccc(C4CC(N)C4)cc3c2C(C)C)cn(C)c(=O)c1C] | 363.5 | 364.2 | 1.3 | QC-ACN-AA-XB |
| 494 | 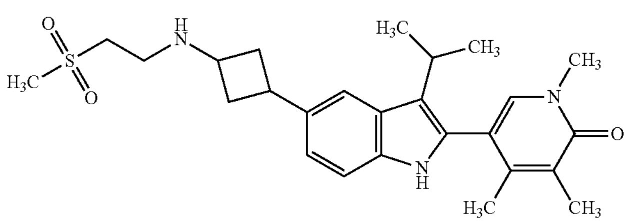 [SMILES: Cc1c(-c2[nH]c3ccc(C4CC(NCCS(C)(=O)=O)C4)cc3c2C(C)C)cn(C)c(=O)c1C] | 469.6 | 470.5 | 1.38 | QC-ACN-AA-XB |
| 495 | 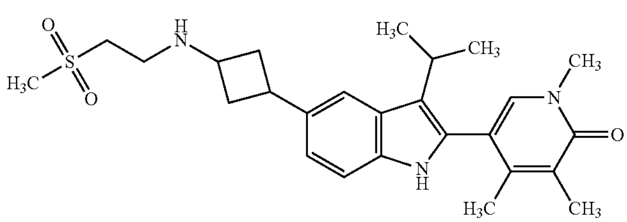 | 469.6 | 470.5 | 1.16 | QC-ACN-TFA-XB |
| 496 | 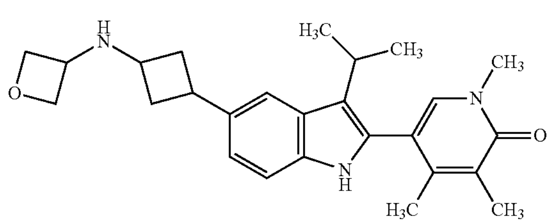 [SMILES: Cc1c(-c2[nH]c3ccc(C4CC(NC5COC5)C4)cc3c2C(C)C)cn(C)c(=O)c1C] | 419.6 | 420.4 | 1.38 | QC-ACN-AA-XB |

TABLE 42-continued

| Ex. No. | Structure | Mol Wt. | LCMS MH+ | Ret Time (min) | HPLC Method |
|---|---|---|---|---|---|
| 497 | 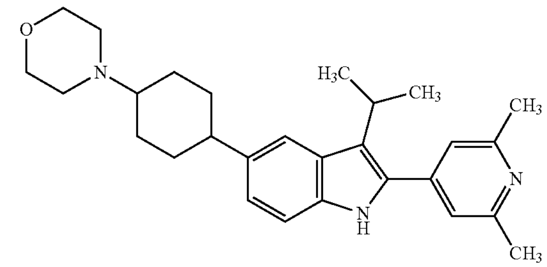 | 431.6 | 432.4 | 0.99 | QC-ACN-TFA-XB |
| 498 | 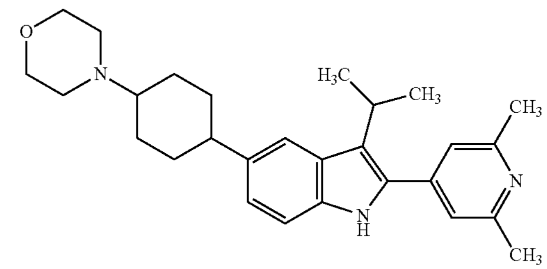 [SMILES: Cc1cc(-c2[nH]c3ccc(C4CCC(N5CCOCC5)CC4)cc3c2C(C)C)cc(C)n1] | 431.6 | 432.0 | 2.01 | QC-ACN-AA-XB |
| 499 | 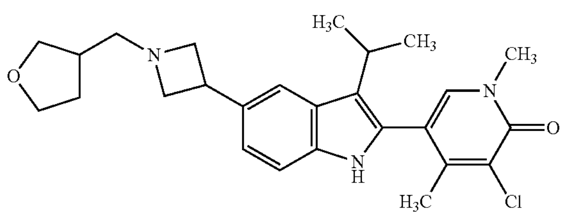 [SMILES: Cc1c(-c2[nH]c3ccc(C4CN(CC5CCOC5)C4)cc3c2C(C)C)cn(C)c(=O)c1Cl] | 454.0 | 453.9 | 1.41 | QC-ACN-AA-XB |
| 500 | 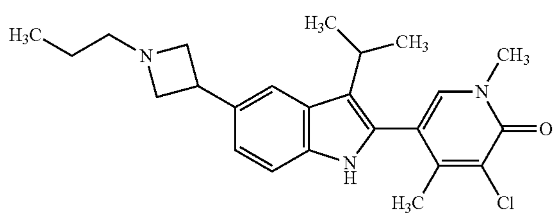 [SMILES: CCCN1CC(c2ccc3[nH]c(-c4cn(C)c(=O)c(Cl)c4C)c(C(C)C)c3c2)C1] | 412.0 | 412.1 | 1.38 | QC-ACN-AA-XB |
| 501 | 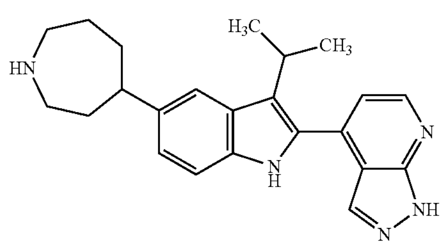 [SMILES: CC(C)c1c(-c2ccnc3[nH]ncc23)[nH]c2ccc(C3CCCNCC3)cc12] | 373.5 | 374.3 | 0.94 | QC-ACN-TFA-XB |
| 502 | 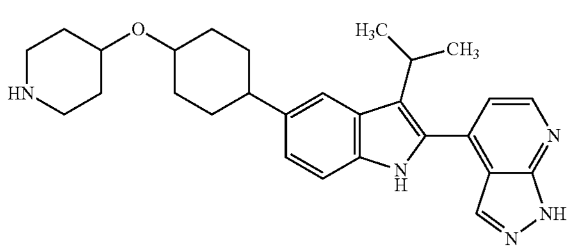 [SMILES: CC(C)c1c(-c2ccnc3[nH]ncc23)[nH]c2ccc(C3CCC(OC4CCNCC4)CC3)cc12] | 457.6 | 458.3 | 1.47 | QC-ACN-AA-XB |

TABLE 42-continued

| Ex. No. | Structure | Mol Wt. | LCMS MH+ | Ret Time (min) | HPLC Method |
|---|---|---|---|---|---|
| 503 | 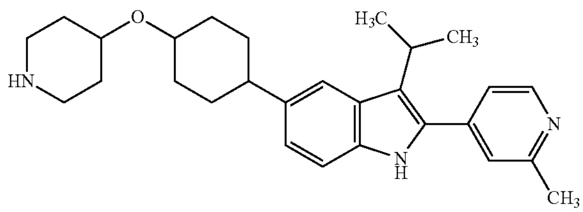 [SMILES: Cc1cc(-c2[nH]c3ccc(C4CCC(OC5CCNCC5)CC4)cc3c2C(C)C)ccn1] | 431.6 | 432.3 | 1.24 | QC-ACN-TFA-XB |
| 504 | 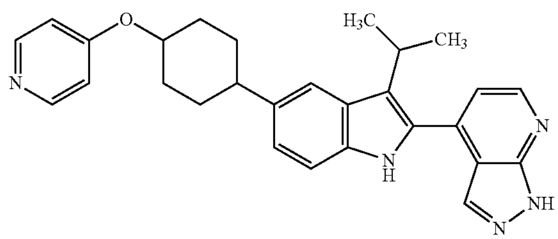 [SMILES: CC(C)c1c(-c2ccnc3[nH]ncc23)[nH]c2ccc(C3CCC(Oc4ccncc4)CC3)cc12] | 451.6 | 452.1 | 1.92 | QC-ACN-AA-XB |
| 505 | 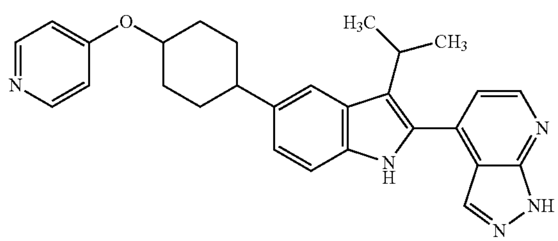 [SMILES: CC(C)c1c(-c2ccnc3[nH]ncc23)[nH]c2ccc(C3CCC(Oc4ccncc4)CC3)cc12] | 451.6 | 452.3 | 1.98 | QC-ACN-AA-XB |
| 506 | 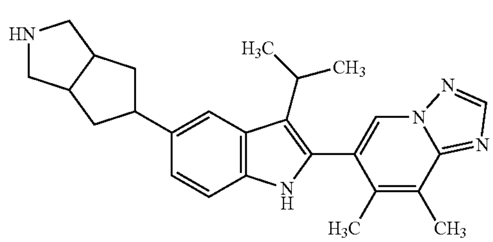 [SMILES: Cc1c(-c2[nH]c3ccc(C4CC5CNCC5C4)cc3c2C(C)C)cn2ncnc2c1C] | 413.6 | 414.4 | 1.36 | QC-ACN-AA-XB |
| 507 | 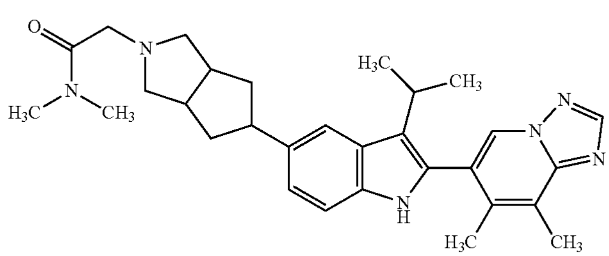 [SMILES: Cc1c(-c2[nH]c3ccc(C4CC5CN(CC(=O)N(C)C)CC5C4)cc3c2C(C)C)cn2ncnc2c1C] | 498.7 | 499.0 | 1.75 | QC-ACN-AA-XB |
| 508 | 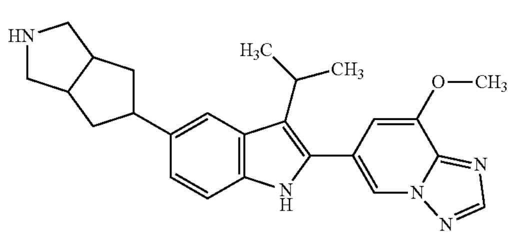 [SMILES: COc1cc(-c2[nH]c3ccc(C4CC5CNCC5C4)cc3c2C(C)C)cn2ncnc12] | 415.5 | 416.3 | 1.26 | QC-ACN-TFA-XB |

TABLE 42-continued
| Ex. No. | Structure | Mol Wt. | LCMS MH+ | Ret Time (min) | HPLC Method |
|---|---|---|---|---|---|
| 509 | 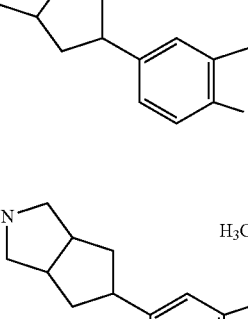 | 500.6 | 501.6 | 1.46 | QC-ACN-AA-XB |
| 510 | 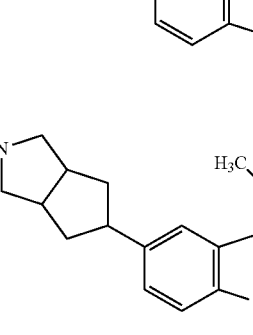 | 484.6 | 485.4 | 1.82 | QC-ACN-AA-XB |
| 511 | 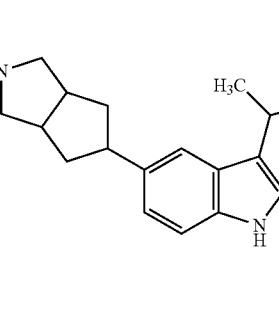 | 470.6 | 471.4 | 1.72 | QC-ACN-AA-XB |
| 512 | 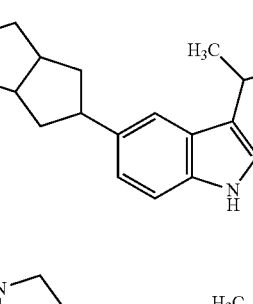 | 452.6 | 453.4 | 1.42 | QC-ACN-TFA-XB |
| 513 | 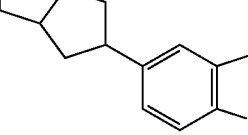 | 471.6 | 472.4 | 1.77 | QC-ACN-AA-XB |
| 514 | 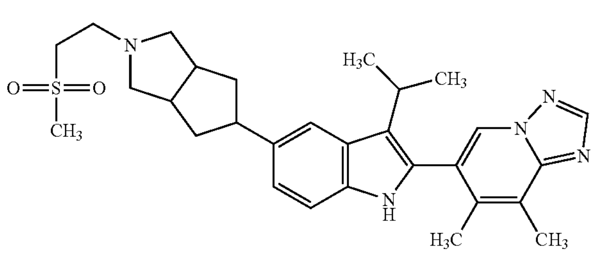 [SMILES: Cc1c(-c2[nH]c3ccc(C4CC5CN(CCS(C)(=O)=O)CC5C4)cc3c2C(C)C)cn2ncnc2c1C] | 519.7 | 520.2 | 2 | QC-ACN-AA-XB |

TABLE 42-continued

| Ex. No. | Structure | Mol Wt. | LCMS MH+ | Ret Time (min) | HPLC Method |
|---|---|---|---|---|---|
| 515 | 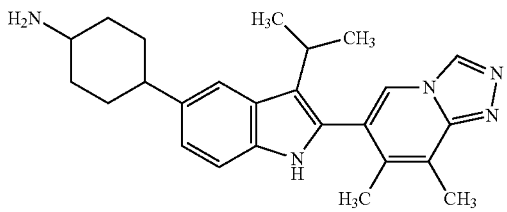 [SMILES: Cc1c(-c2[nH]c3ccc(C4CCC(N)CC4)cc3c2C(C)C)cn2cnnc2c1C] | 401.6 | 402.1 | 1.28 | QC-ACN-AA-XB |
| 516 | 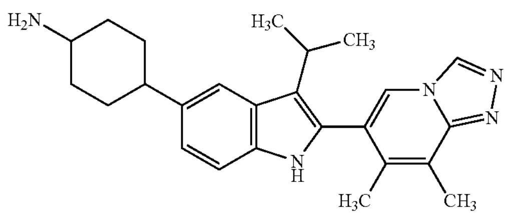 [SMILES: Cc1c(-c2[nH]c3ccc(C4CCC(N)CC4)cc3c2C(C)C)cn2cnnc2c1C] | 401.6 | 402.1 | 1.15 | QC-ACN-TFA-XB |
| 517 | 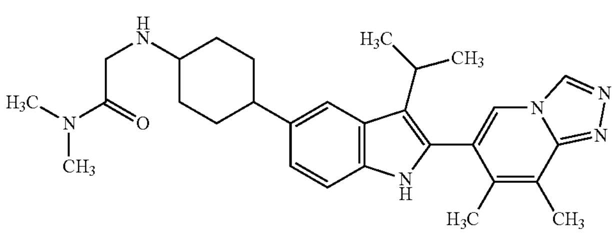 [SMILES: Cc1c(-c2[nH]c3ccc(C4CCC(NCC(=O)N(C)C)CC4)cc3c2C(C)C)cn2cnnc2c1C] | 486.7 | 487.3 | 1.12 | QC-ACN-TFA-XB |
| 518 | 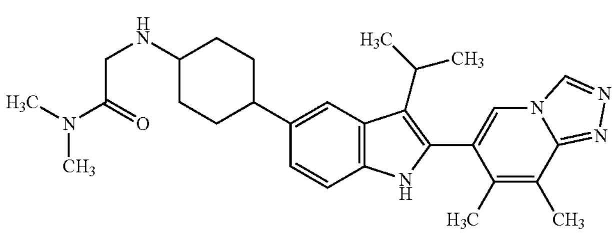 [SMILES: Cc1c(-c2[nH]c3ccc(C4CCC(NCC(=O)N(C)C)CC4)cc3c2C(C)C)cn2cnnc2c1C] | 486.7 | 487.2 | 1.29 | QC-ACN-AA-XB |
| 519 | 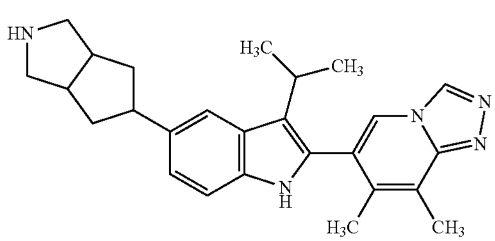 [SMILES: Cc1c(-c2[nH]c3ccc(C4CC5CNCC5C4)cc3c2C(C)C)cn2cnnc2c1C] | 413.6 | 413.9 | 1.16 | QC-ACN-AA-XB |
| 520 | 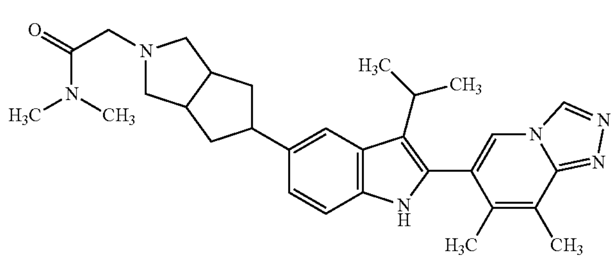 [SMILES: Cc1c(-c2[nH]c3ccc(C4CC5CN(CC(=O)N(C)C)CC5C4)cc3c2C(C)C)cn2cnnc2c1C] | 498.7 | 499.4 | 1.41 | QC-ACN-AA-XB |

| Ex. No. | Structure | Mol Wt. | LCMS MH+ | Ret Time (min) | HPLC Method |
|---|---|---|---|---|---|
| 521 | 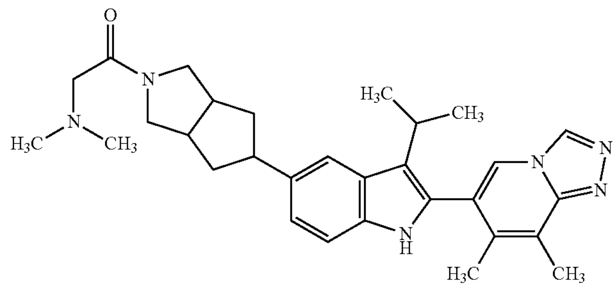 [SMILES: Cc1c(-c2[nH]c3ccc(C4CC5CN(C(=O)CN(C)C)CC5C4)cc3c2C(C)C)cn2cnnc2c1C] | 498.7 | 499.3 | 1.16 | QC-ACN-TFA-XB |
| 522 | 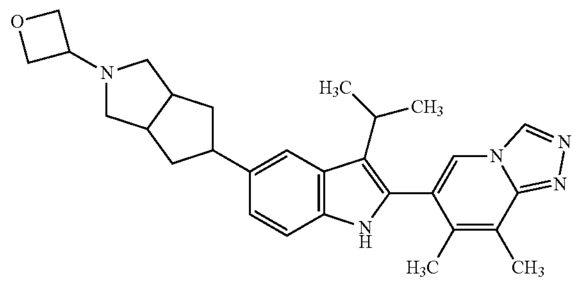 [SMILES: Cc1c(-c2[nH]c3ccc(C4CC5CN(C6COC6)CC5C4)cc3c2C(C)C)cn2cnnc2c1C] | 469.6 | 470.0 | 1.83 | QC-ACN-AA-XB |
| 523 | 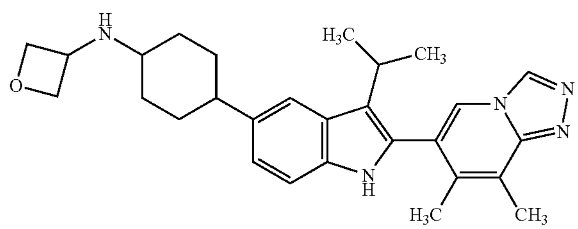 [SMILES: Cc1c(-c2[nH]c3ccc(C4CCC(NC5COC5)CC4)cc3c2C(C)C)cn2cnnc2c1C] | 457.6 | 458.4 | 1 | QC-ACN-TFA-XB |
| 524 | 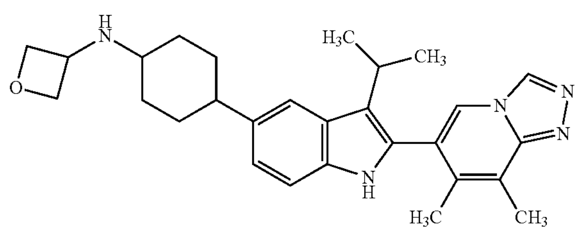 [SMILES: Cc1c(-c2[nH]c3ccc(C4CCC(NC5COC5)CC4)cc3c2C(C)C)cn2cnnc2c1C] | 457.6 | 458.4 | 1.59 | QC-ACN-AA-XB |
| 525 | 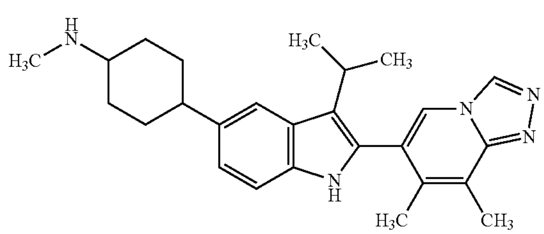 | 415.6 | 416.0 | 1.33 | QC-ACN-AA-XB |
| 526 | 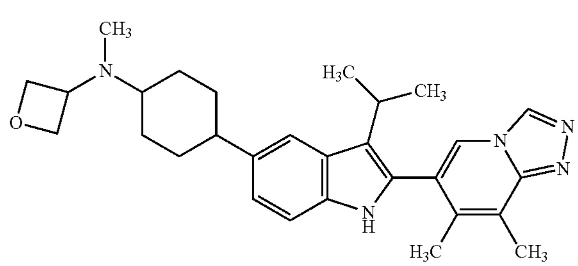 [SMILES: Cc1c(-c2[nH]c3ccc(C4CCC(N(C)C5COC5)CC4)cc3c2C(C)C)cn2cnnc2c1C] | 471.6 | 472.2 | 1.08 | QC-ACN-TFA-XB |

TABLE 42-continued

| Ex. No. | Structure | Mol Wt. | LCMS MH+ | Ret Time (min) | HPLC Method |
|---|---|---|---|---|---|
| 527 | 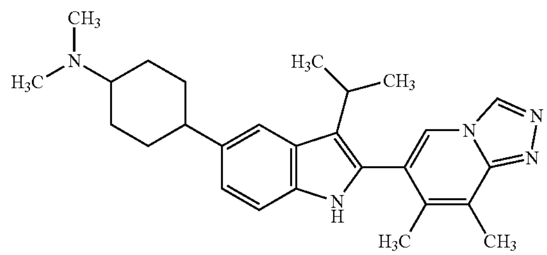 [SMILES: Cc1c(-c2[nH]c3ccc(C4CCC(N(C)C)CC4)cc3c2C(C)C)cn2cnnc2c1C] | 429.6 | 430.2 | 1.01 | QC-ACN-TFA-XB |
| 528 | 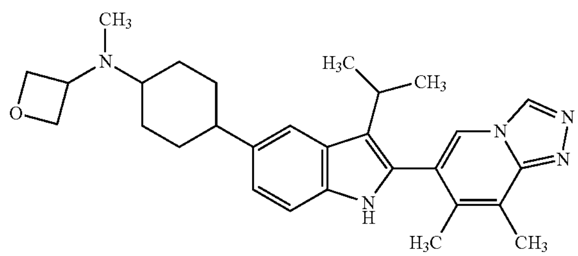 [SMILES: Cc1c(-c2[nH]c3ccc(C4CCC(N(C)C5COC5)CC4)cc3c2C(C)C)cn2cnnc2c1C] | 471.6 | 472.2 | 1.4 | QC-ACN-AA-XB |
| 529 | 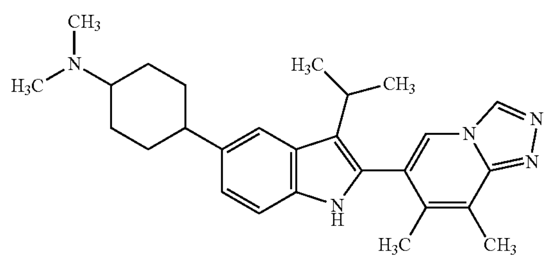 [SMILES: Cc1c(-c2[nH]c3ccc(C4CCC(N(C)C)CC4)cc3c2C(C)C)cn2cnnc2c1C] | 429.6 | 430.4 | 1.09 | QC-ACN-TFA-XB |
| 530 | 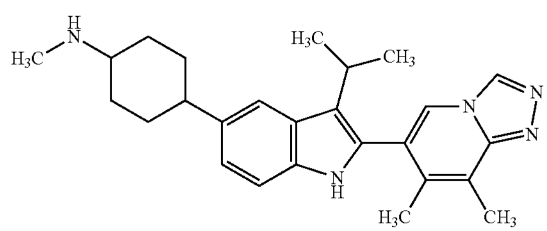 [SMILES: CNC1CCC(c2ccc3[nH]c(-c4cn5cnnc5c(C)c4C)c(C(C)C)c3c2)CC1] | 415.6 | 416.0 | 1.22 | QC-ACN-AA-XB |
| 531 | 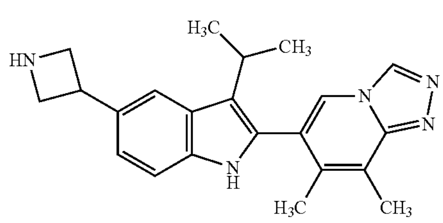 [SMILES: Cc1c(-c2[nH]c3ccc(C4CNC4)cc3c2C(C)C)cn2cnnc2c1C] | 359.5 | 360.2 | 1.02 | QC-ACN-TFA-XB |
| 532 | 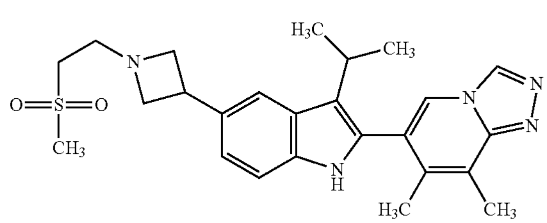 [SMILES: Cc1c(-c2[nH]c3ccc(C4CN(CCS(C)(=O)=O)C4)cc3c2C(C)C)cn2cnnc2c1C] | 465.6 | 465.9 | 1.39 | QC-ACN-AA-XB |

TABLE 42-continued

| Ex. No. | Structure | Mol Wt. | LCMS MH+ | Ret Time (min) | HPLC Method |
|---|---|---|---|---|---|
| 533 | 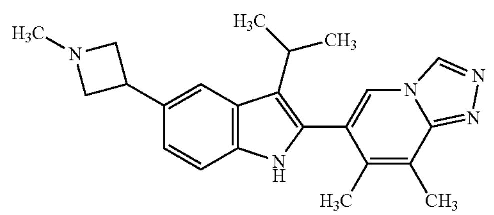 [SMILES: Cc1c(-c2[nH]c3ccc(C4CN(C)C4)cc3c2C(C)C)cn2cnnc2c1C] | 373.5 | 374.2 | 1.13 | QC-ACN-AA-XB |
| 534 | 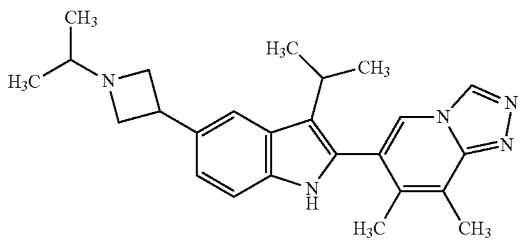 [SMILES: Cc1c(-c2[nH]c3ccc(C4CN(C(C)C)C4)cc3c2C(C)C)cn2cnnc2c1C] | 401.6 | 401.9 | 1.1 | QC-ACN-TFA-XB |
| 535 | 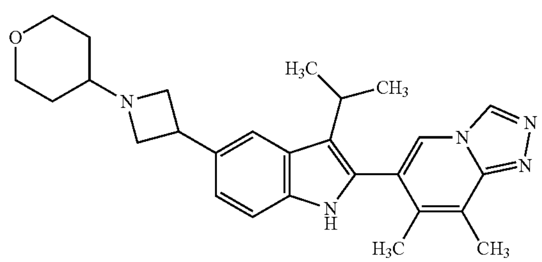 [SMILES: Cc1c(-c2[nH]c3ccc(C4CN(C5CCOCC5)C4)cc3c2C(C)C)cn2cnnc2c1C] | 443.6 | 444.0 | 1.31 | QC-ACN-AA-XB |
| 536 | 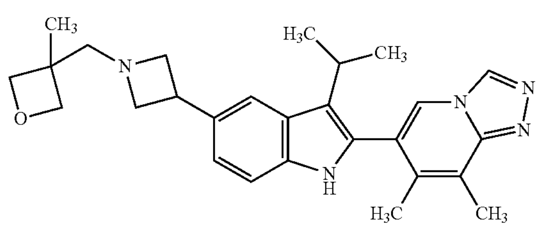 [SMILES: Cc1c(-c2[nH]c3ccc(C4CN(CC5(C)COC5)C4)cc3c2C(C)C)cn2cnnc2c1C] | 443.6 | 444.3 | 1.06 | QC-ACN-TFA-XB |
| 537 | 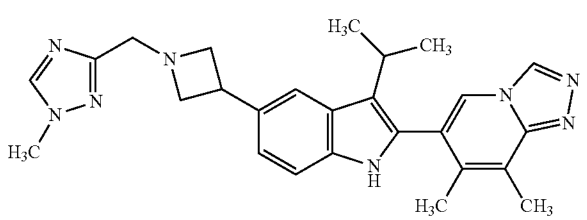 [SMILES: Cc1c(-c2[nH]c3ccc(C4CN(Cc5ncn(C)n5)C4)cc3c2C(C)C)cn2cnnc2c1C] | 454.6 | 455.0 | 0.83 | QC-ACN-TFA-XB |
| 538 | 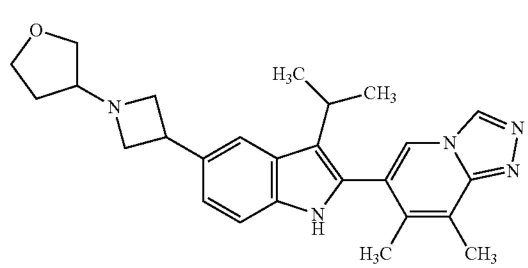 [SMILES: Cc1c(-c2[nH]c3ccc(C4CN(C5CCOC5)C4)cc3c2C(C)C)cn2cnnc2c1C] | 429.6 | 430.4 | 1.2 | QC-ACN-AA-XB |

TABLE 42-continued

| Ex. No. | Structure | Mol Wt. | LCMS MH+ | Ret Time (min) | HPLC Method |
|---|---|---|---|---|---|
| 539 | 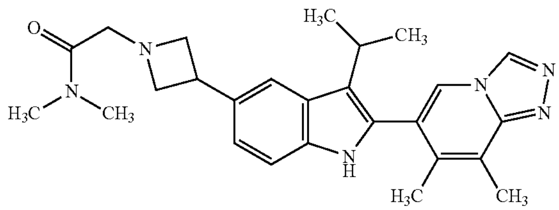 [SMILES: Cc1c(-c2[nH]c3ccc(C4CN(CC(=O)N(C)C)C4)cc3c2C(C)C)cn2cnnc2c1C] | 444.6 | 445.4 | 1.04 | QC-ACN-AA-XB |
| 540 | 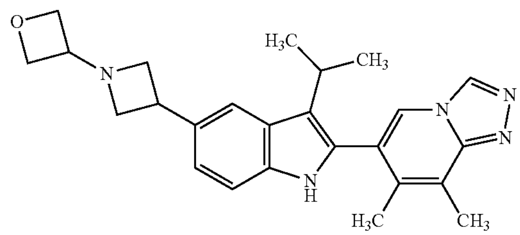 [SMILES: Cc1c(-c2[nH]c3ccc(C4CN(C5COC5)C4)cc3c2C(C)C)cn2cnnc2c1C] | 415.5 | 416.3 | 0.8 | QC-ACN-TFA-XB |
| 541 | 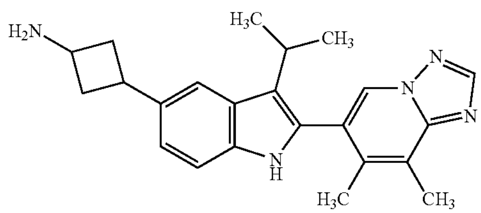 | 373.5 | 373.9 | 1.1 | QC-ACN-AA-XB |
| 542 | 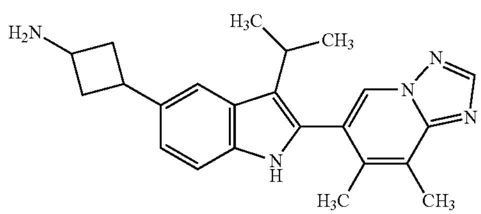 | 373.5 | 374.1 | 1.19 | QC-ACN-AA-XB |
| 543 | 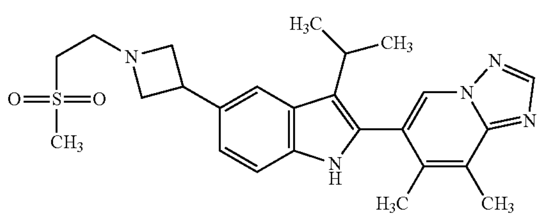 [SMILES: Cc1c(-c2[nH]c3ccc(C4CN(CCS(C)(=O)=O)C4)cc3c2C(C)C)cn2ncnc2c1C] | 465.6 | 466.4 | 1.08 | QC-ACN-TFA-XB |
| 544 | 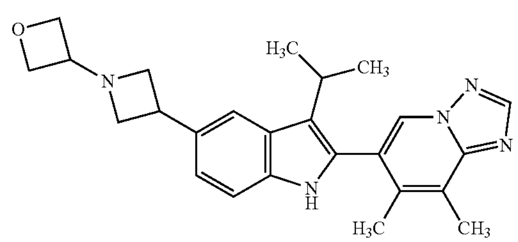 [SMILES: Cc1c(-c2[nH]c3ccc(C4CN(C5COC5)C4)cc3c2C(C)C)cn2ncnc2c1C] | 415.5 | 416.4 | 1.45 | QC-ACN-AA-XB |
| 545 | 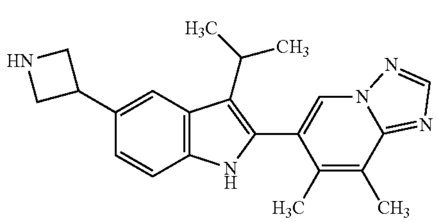 [SMILES: Cc1c(-c2[nH]c3ccc(C4CNC4)cc3c2C(C)C)cn2ncnc2c1C] | 359.5 | 360.2 | 1.08 | QC-ACN-AA-XB |

TABLE 42-continued
| Ex. No. | Structure | Mol Wt. | LCMS MH+ | Ret Time (min) | HPLC Method |
|---|---|---|---|---|---|
| 546 | 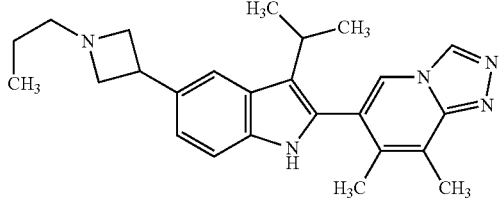 [SMILES: CCCN1CC(c2ccc3[nH]c(-c4cn5cnnc5c(C)c4C)c(C(C)C)c3c2)C1] | 401.6 | 402.0 | 1.12 | QC-ACN-AA-XB |
| 547 | 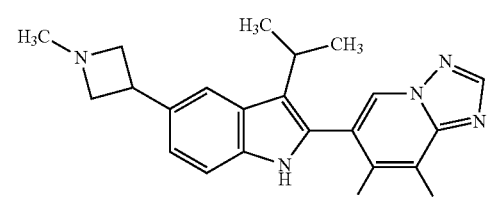 | 373.5 | 374.0 | 1.22 | QC-ACN-TFA-XB |
| 548 | 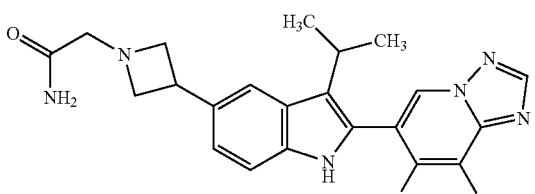 | 416.5 | 417.2 | 1.33 | QC-ACN-AA-XB |
| 549 | 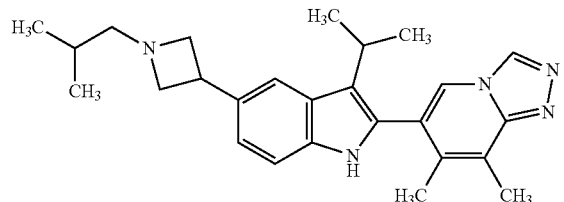 | 415.6 | 416.2 | 1.22 | QC-ACN-AA-XB |
| 550 | 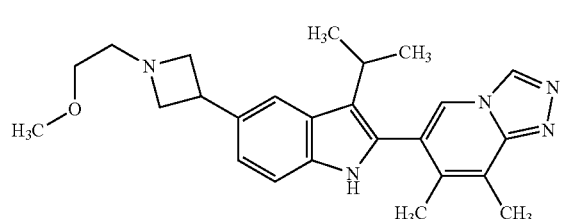 | 417.6 | 418.0 | 1.04 | QC-ACN-AA-XB |
| 551 | 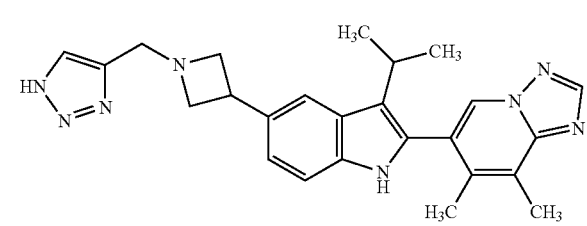 [SMILES: Cc1c(-c2[nH]c3ccc(C4CN(Cc5c[nH]nn5)C4)cc3c2C(C)C)cn2ncnc2c1C] | 440.6 | 441.2 | 1.2 | QC-ACN-TFA-XB |
| 552 | 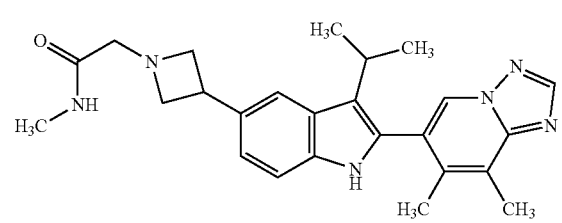 [SMILES: CNC(=O)CN1CC(c2ccc3[nH]c(-c4cn5ncnc5c(C)c4C)c(C(C)C)c3c2)C1] | 430.6 | 431.1 | 1.2 | QC-ACN-TFA-XB |

TABLE 42-continued

| Ex. No. | Structure | Mol Wt. | LCMS MH+ | Ret Time (min) | HPLC Method |
|---|---|---|---|---|---|
| 553 | 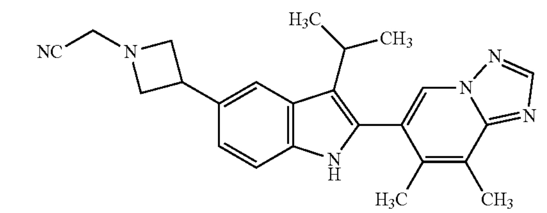 [SMILES: Cc1c(-c2[nH]c3ccc(C4CN(CC#N)C4)cc3c2C(C)C)cn2ncnc2c1C] | 398.5 | 399.2 | 1.73 | QC-ACN-AA-XB |
| 554 | 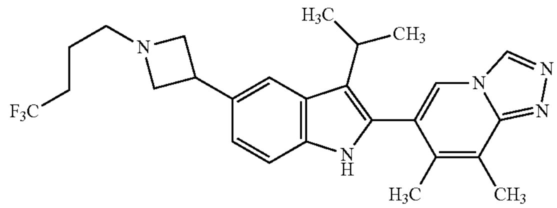 [SMILES: Cc1c(-c2[nH]c3ccc(C4CN(CCCC(F)(F)F)C4)cc3c2C(C)C)cn2cnnc2c1C] | 469.6 | 470.4 | 1.46 | QC-ACN-AA-XB |
| 555 | 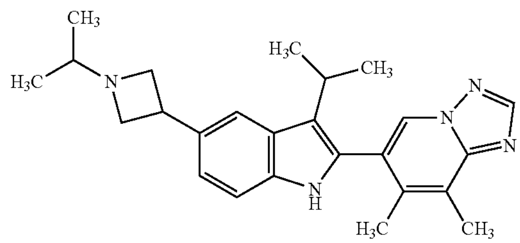 [SMILES: Cc1c(-c2[nH]c3ccc(C4CN(C(C)C)C4)cc3c2C(C)C)cn2ncnc2c1C] | 401.6 | 402.3 | 1.21 | QC-ACN-TFA-XB |
| 556 | 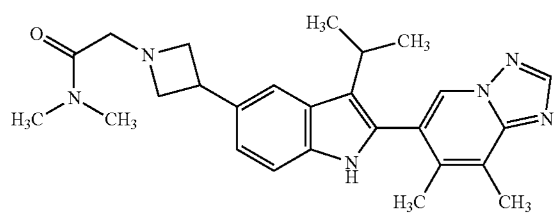 [SMILES: Cc1c(-c2[nH]c3ccc(C4CN(CC(=O)N(C)C)C4)cc3c2C(C)C)cn2ncnc2c1C] | 444.6 | 445.1 | 1.33 | QC-ACN-AA-XB |
| 557 | 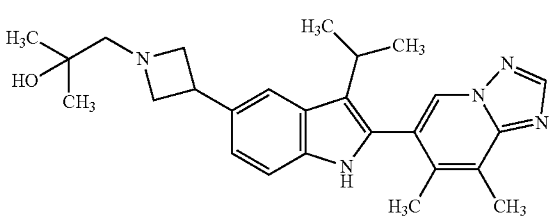 [SMILES: Cc1c(-c2[nH]c3ccc(C4CN(CC(C)(C)O)C4)cc3c2C(C)C)cn2ncnc2c1C] | 431.6 | 432.4 | 1.12 | QC-ACN-TFA-XB |
| 558 | 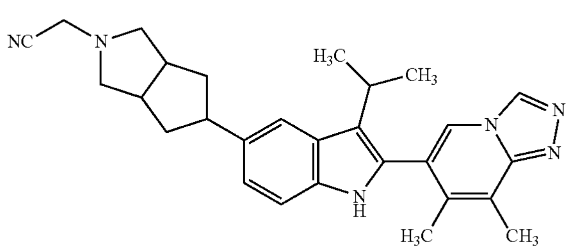 [SMILES: Cc1c(-c2[nH]c3ccc(C4CC5CN(CC#N)CC5C4)cc3c2C(C)C)cn2cnnc2c1C] | 452.6 | 453.4 | 1.18 | QC-ACN-TFA-XB |

TABLE 42-continued

| Ex. No. | Structure | Mol Wt. | LCMS MH+ | Ret Time (min) | HPLC Method |
|---|---|---|---|---|---|
| 559 | 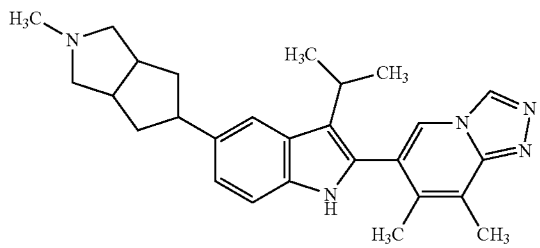 [SMILES: Cc1c(-c2[nH]c3ccc(C4CC5CN(C)CC5C4)cc3c2C(C)C)cn2cnnc2c1C] | 427.6 | 428.4 | 1.2 | QC-ACN-AA-XB |
| 560 | 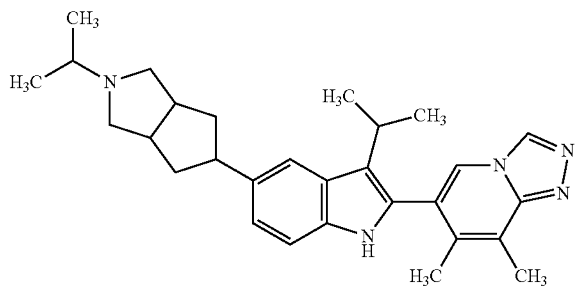 [SMILES: Cc1c(-c2[nH]c3ccc(C4CC5CN(C(C)C)CC5C4)cc3c2C(C)C)cn2cnnc2c1C] | 455.7 | 456.2 | 1.41 | QC-ACN-AA-XB |
| 561 | 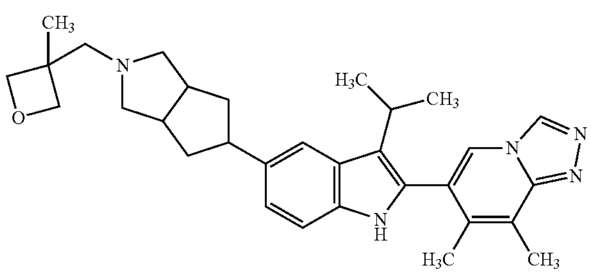 [SMILES: Cc1c(-c2[nH]c3ccc(C4CC5CN(CC6(C)COC6)CC5C4)cc3c2C(C)C)cn2cnnc2c1C] | 497.7 | 498.0 | 1.61 | QC-ACN-AA-XB |
| 562 | 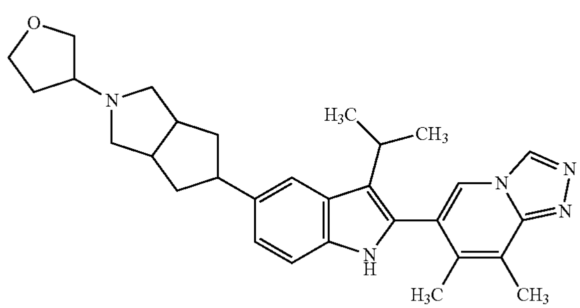 [SMILES: Cc1c(-c2[nH]c3ccc(C4CC5CN(C6CCOC6)CC5C4)cc3c2C(C)C)cn2cnnc2c1C] | 483.7 | 484.4 | 1.58 | QC-ACN-AA-XB |
| 563 | 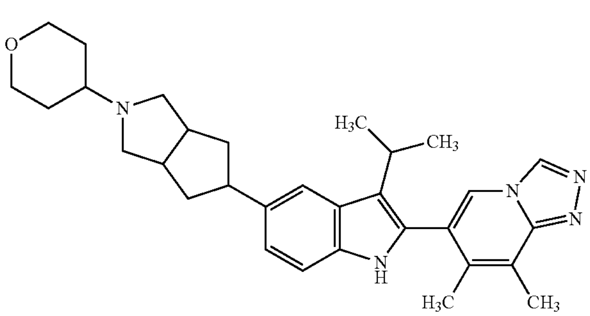 [SMILES: Cc1c(-c2[nH]c3ccc(C4CC5CN(C6CCOCC6)CC5C4)cc3c2C(C)C)cn2cnnc2c1C] | 497.7 | 498.2 | 1.48 | QC-ACN-AA-XB |

TABLE 42-continued

| Ex. No. | Structure | Mol Wt. | LCMS MH+ | Ret Time (min) | HPLC Method |
|---|---|---|---|---|---|
| 564 | 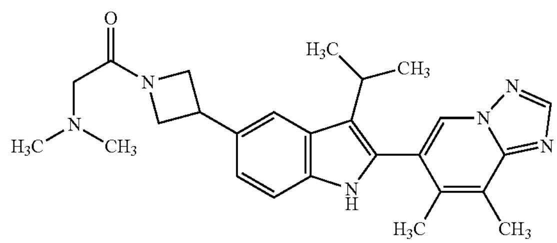 [SMILES: Cc1c(-c2[nH]c3ccc(C4CN(C(=O)CN(C)C)C4)cc3c2C(C)C)cn2ncnc2c1C] | 444.6 | 445.4 | 1.31 | QC-ACN-AA-XB |
| 565 | 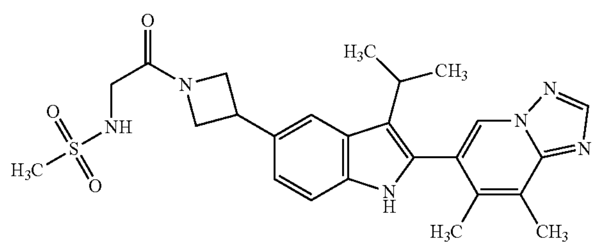 [SMILES: Cc1c(-c2[nH]c3ccc(C4CN(C(=O)CNS(C)(=O)=O)C4)cc3c2C(C)C)cn2ncnc2c1C] | 480.6 | 481.0 | 1.18 | QC-ACN-AA-XB |
| 566 | 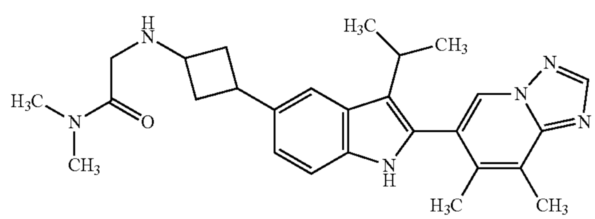 [SMILES: Cc1c(-c2[nH]c3ccc(C4CC(NCC(=O)N(C)C)C4)cc3c2C(C)C)cn2ncnc2c1C] | 458.6 | 459.2 | 1.37 | QC-ACN-AA-XB |
| 567 | 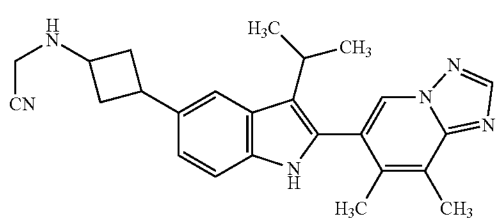 [SMILES: Cc1c(-c2[nH]c3ccc(C4CC(NCC#N)C4)cc3c2C(C)C)cn2ncnc2c1C] | 412.5 | 413.4 | 1.66 | QC-ACN-AA-XB |
| 568 | 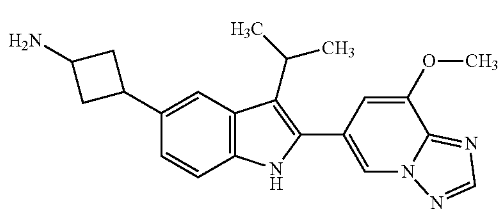 [SMILES: COc1cc(-c2[nH]c3ccc(C4CC(N)C4)cc3c2C(C)C)cn2ncnc12] | 375.5 | 376.1 | 1.2 | QC-ACN-TFA-XB |
| 569 | 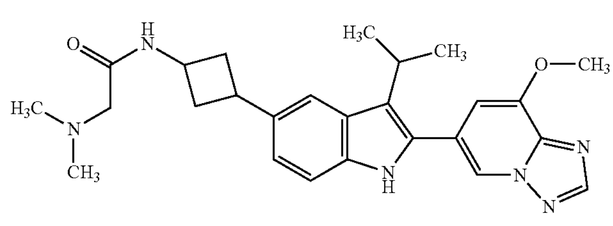 [SMILES: COc1cc(-c2[nH]c3ccc(C4CC(NC(=O)CN(C)C)C4)cc3c2C(C)C)cn2ncnc12] | 460.6 | 460.9 | 1.56 | QC-ACN-AA-XB |

TABLE 42-continued

| Ex. No. | Structure | Mol Wt. | LCMS MH+ | Ret Time (min) | HPLC Method |
|---|---|---|---|---|---|
| 570 | 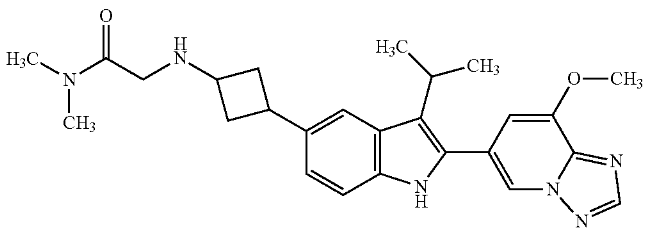 [SMILES: COc1cc(-c2[nH]c3ccc(C4CC(NCC(=O)N(C)C)C4)cc3c2C(C)C)cn2ncnc12] | 460.6 | 461.0 | 1.39 | QC-ACN-AA-XB |
| 571 | 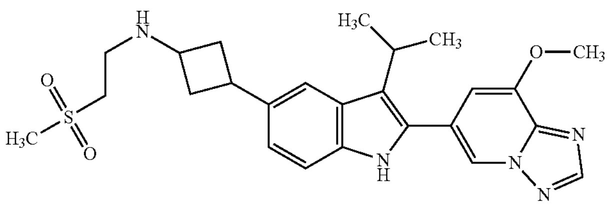 [SMILES: COc1cc(-c2[nH]c3ccc(C4CC(NCCS(C)(=O)=O)C4)cc3c2C(C)C)cn2ncnc12] | 481.6 | 482.2 | 1.48 | QC-ACN-AA-XB |
| 572 | 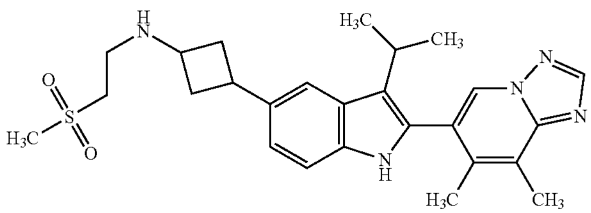 [SMILES: Cc1c(-c2[nH]c3ccc(C4CC(NCCS(C)(=O)=O)C4)cc3c2C(C)C)cn2ncnc2c1C] | 479.6 | 480.4 | 1.51 | QC-ACN-AA-XB |
| 573 | 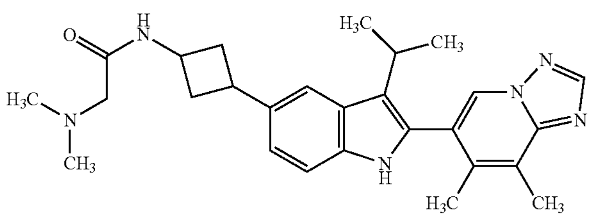 [SMILES: Cc1c(-c2[nH]c3ccc(C4CC(NC(=O)CN(C)C)C4)cc3c2C(C)C)cn2ncnc2c1C] | 458.6 | 459.5 | 1.51 | QC-ACN-AA-XB |
| 574 | 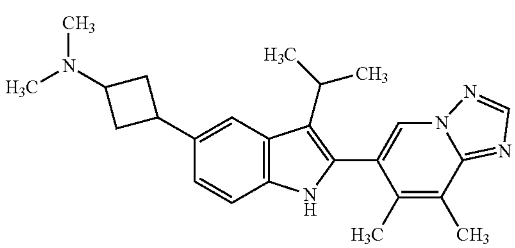 | 401.6 | 402.4 | 1.3 | QC-ACN-AA-XB |
| 575 | 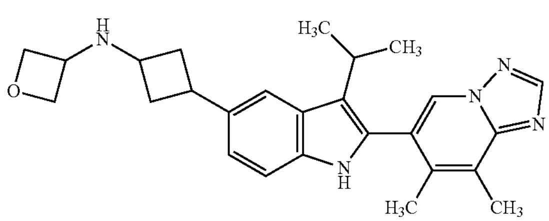 [SMILES: Cc1c(-c2[nH]c3ccc(C4CC(NC5COC5)C4)cc3c2C(C)C)cn2ncnc2c1C] | 429.6 | 430.4 | 1.49 | QC-ACN-AA-XB |
| 576 | 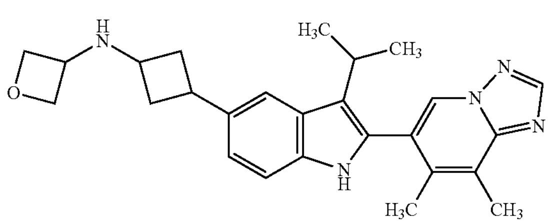 [SMILES: Cc1c(-c2[nH]c3ccc(C4CC(NC5COC5)C4)cc3c2C(C)C)cn2ncnc2c1C] | 429.6 | 430.1 | 1.6 | QC-ACN-AA-XB |

TABLE 42-continued
| Ex. No. | Structure | Mol Wt. | LCMS MH+ | Ret Time (min) | HPLC Method |
|---|---|---|---|---|---|
| 577 | 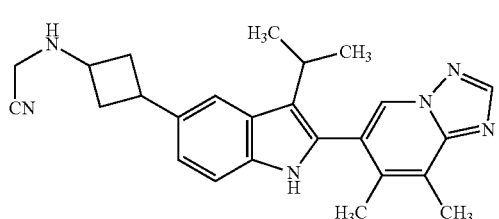 | 412.5 | 413.3 | 1.69 | QC-ACN-AA-XB |
| 578 | 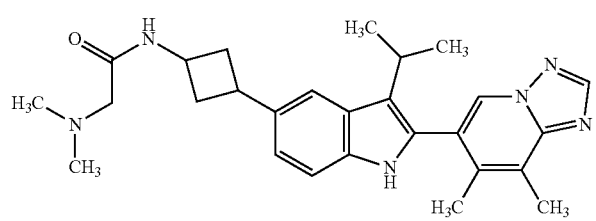 [SMILES: Cc1c(-c2[nH]c3ccc(C4CC(NC(=O)CN(C)C)C4)cc3c2C(C)C)cn2ncnc2c1C] | 458.6 | 459.2 | 1.37 | QC-ACN-AA-XB |
| 579 | 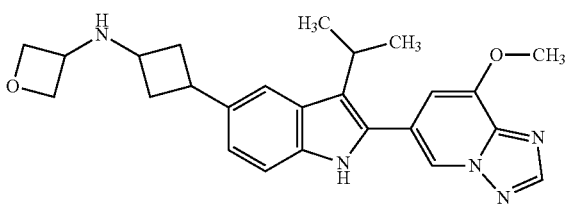 [SMILES: COc1cc(-c2[nH]c3ccc(C4CC(NC5COC5)C4)cc3c2C(C)C)cn2ncnc12] | 431.5 | 432.4 | 1.3 | QC-ACN-AA-XB |
| 580 | 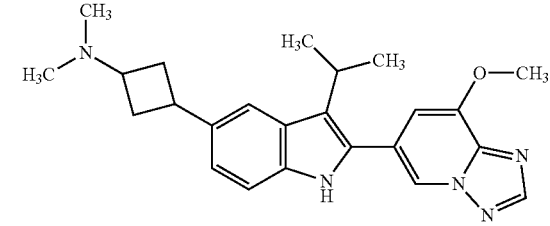 [SMILES: COc1cc(-c2[nH]c3ccc(C4CC(N(C)C)C4)cc3c2C(C)C)cn2ncnc12] | 403.5 | 404.4 | 1.15 | QC-ACN-TFA-XB |
| 581 | 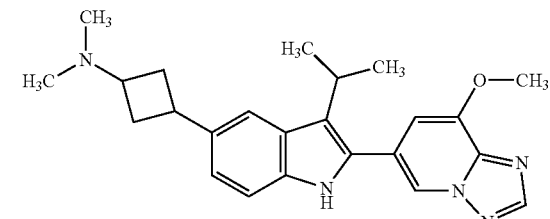 | 403.5 | 404.5 | 1.19 | QC-ACN-TFA-XB |
| 582 | 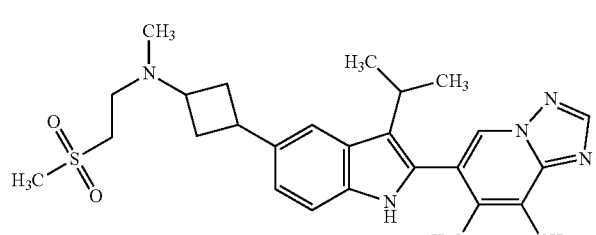 | 493.7 | 494.2 | 1.19 | QC-ACN-TFA-XB |

TABLE 42-continued

| Ex. No. | Structure | Mol Wt. | LCMS MH+ | Ret Time (min) | HPLC Method |
|---|---|---|---|---|---|
| 583 | 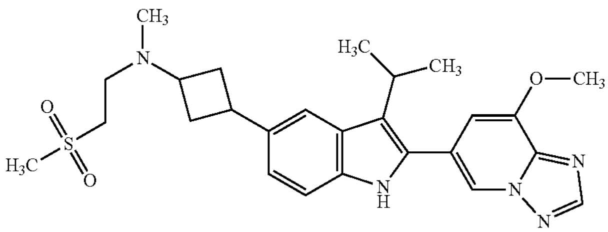 [SMILES: COc1cc(-c2[nH]c3ccc(C4CC(N(C)CCS(C)(=O)=O)C4)cc3c2C(C)C)cn2ncnc12] | 495.6 | 496.2 | 1.26 | QC-ACN-TFA-XB |
| 584 | 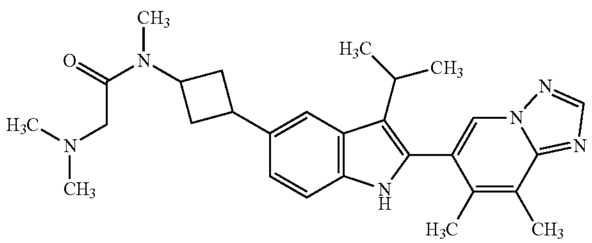 [SMILES: Cc1c(-c2[nH]c3ccc(C4CC(N(C)C(=O)CN(C)C)C4)cc3c2C(C)C)cn2ncnc2c1C] | 472.6 | 473.3 | 1.43 | QC-ACN-TFA-XB |
| 585 | 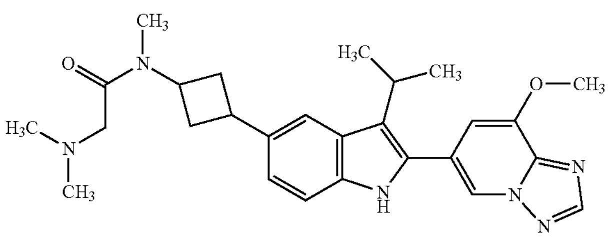 [SMILES: COc1cc(-c2[nH]c3ccc(C4CC(N(C)C(=O)CN(C)C)C4)cc3c2C(C)C)cn2ncnc12] | 474.6 | 475.3 | 1.27 | QC-ACN-AA-XB |
| 586 | 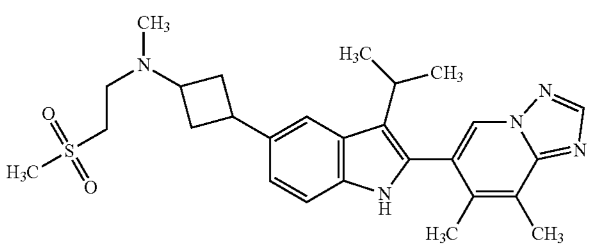 [SMILES: Cc1c(-c2[nH]c3ccc(C4CC(N(C)CCS(C)(=O)=O)C4)cc3c2C(C)C)cn2ncnc2c1C] | 493.7 | 494.2 | 1.77 | QC-ACN-AA-XB |
| 587 | 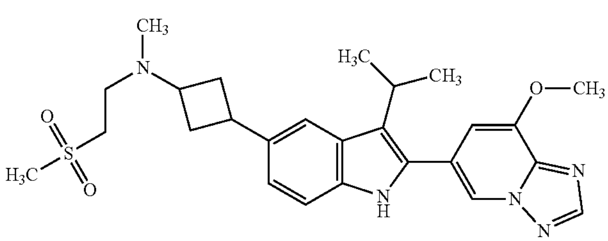 [SMILES: COc1cc(-c2[nH]c3ccc(C4CC(N(C)CCS(C)(=O)=O)C4)cc3c2C(C)C)cn2ncnc12] | 495.6 | 496.2 | 1.29 | QC-ACN-TFA-XB |
| 588 | 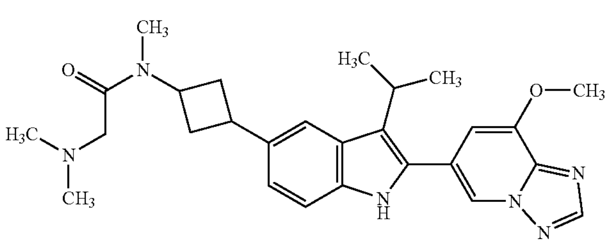 [SMILES: COc1cc(-c2[nH]c3ccc(C4CC(N(C)C(=O)CN(C)C)C4)cc3c2C(C)C)cn2ncnc12] | 474.6 | 475.1 | 1.34 | QC-ACN-TFA-XB |

TABLE 42-continued

| Ex. No. | Structure | Mol Wt. | LCMS MH+ | Ret Time (min) | HPLC Method |
|---|---|---|---|---|---|
| 589 | 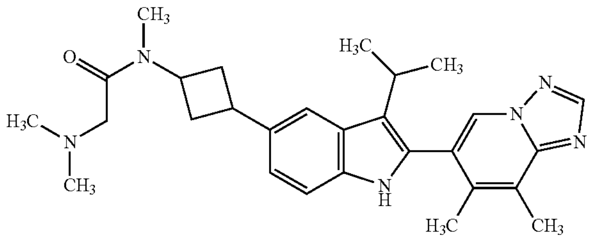 [SMILES: Cc1c(-c2[nH]c3ccc(C4CC(N(C)C(=O)CN(C)C)C4)cc3c2C(C)C)cn2ncnc2c1C] | 472.6 | 473.3 | 1.35 | QC-ACN-AA-XB |
| 590 | 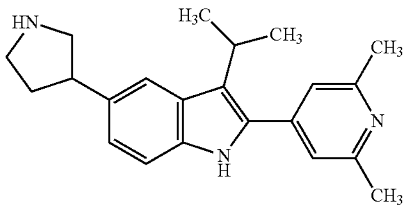 [SMILES: Cc1cc(-c2[nH]c3ccc(C4CCNC4)cc3c2C(C)C)cc(C)n1] | 333.5 | 334.3 | 0.8 | QC-ACN-TFA-XB |
| 591 | 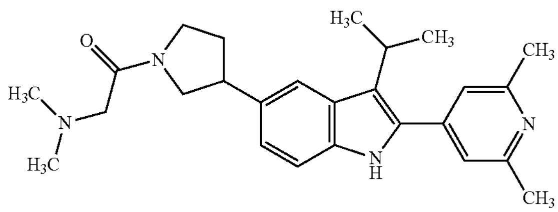 | 418.6 | 419.3 | 1.4 | QC-ACN-AA-XB |
| 592 | 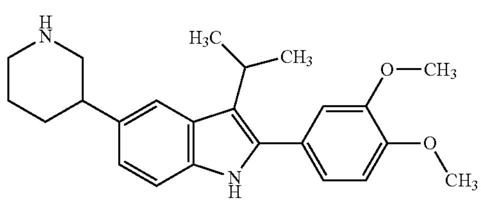 [SMILES: COc1ccc(-c2[nH]c3ccc(C4CCCNC4)cc3c2C(C)C)cc1OC] | 378.52 | 379 | 0.88 | L |

Biological Assays

The pharmacological properties of the compounds of this invention may be confirmed by a number of biological assays. The exemplified biological assays, which follow, have been carried out with compounds of the invention.

TLR7/8/9 Inhibition Reporter Assays

HEK-Blue™-cells (Invivogen) overexpressing human TLR7, TLR8 or TLR9 receptors were used for screening inhibitors of these receptors using an inducible SEAP (secreted embryonic alkaline phosphatase) reporter gene under the control of the IFN-β minimal promoter fused to five NF-κB and AP-1-binding sites. Briefly, cells are seeded into Greiner 384 well plates (15000 cells per well for TLR7, 20,000 for TLR8 and 25,000 for TLR9) and then treated with test compounds in DMSO to yield a final dose response concentration range of 0.05 nM-50 μM. After a 30 minute compound pre-treatment al room temperature, the cells are then stimulated with a TLR7 ligand (gardiquimod at a final concentration of 7.5 μM), TLR8 ligand (R848 at a final concentration of 15.9 μM) or TLR9 ligand (ODN2006 at a final concentration of 5 nM) to activate NF-κB and AP-1 which induce the production of SEAP. After a 22 hour incubation at 37° C., 5% $CO_2$, SEAP levels are determined with the addition of HEK-Blue™ Detection reagent (Invivogen), a cell culture medium that allows for detection of SEAP, according to manufacturer's specifications. The percent inhibition is determined as the % reduction in the HEK-Blue signal present in wells treated with agonist plus DMSO alone compared to wells treated with a known inhibitor.

TABLE 43

TLR7/8/9 Reporter Assay Data (NT = not tested)

| Ex. No. | TLR7 $IC_{50}$ (nM) | TLR8 $IC_{50}$ (nM) | TLR9 $IC_{50}$ (nM) |
|---|---|---|---|
| 1 | 0.49 | 1.3 | 793 |
| 2 | 0.37 | 1.1 | 3418 |
| 3 | 0.15 | 1 | 1288 |
| 4 | 6 | 45 | 3174 |
| 5 | 1 | 14 | 597 |
| 6 | 0.33 | 1 | 1208 |
| 7 | 1 | 4.4 | 2005 |
| 8 | 6 | 16 | 3689 |
| 9 | 0.36 | 1.8 | 1882 |
| 10 | 0.17 | 0.47 | 1263 |
| 11 | 2 | 3.7 | 2074 |
| 12 | 0.7 | 1.6 | 2129 |
| 13 | 1 | 4.8 | 2805 |
| 14 | 5 | 3.5 | 4085 |

TABLE 43-continued

TLR7/8/9 Reporter Assay Data (NT = not tested)

| Ex. No. | TLR7 IC$_{50}$ (nM) | TLR8 IC$_{50}$ (nM) | TLR9 IC$_{50}$ (nM) |
|---|---|---|---|
| 15 | 4 | 8.9 | 3593 |
| 16 | 0.15 | 0.47 | 661 |
| 17 | 0.73 | 0.7 | 3528 |
| 18 | 5 | 38 | 33590 |
| 19 | 26 | 218 | 29152 |
| 20 | 0.3 | 0.81 | 346 |
| 21 | 0.41 | 1.2 | 2380 |
| 22 | 0.85 | 3.9 | 1199 |
| 23 | 2 | 9.2 | 2838 |
| 24 | 7 | 21 | 24922 |
| 25 | 49 | 180 | >50000 |
| 26 | 0.92 | 0.84 | 260 |
| 27 | 2 | 2.8 | 1761 |
| 28 | 0.17 | 0.26 | 328 |
| 29 | 0.26 | 1.9 | 909 |
| 30 | 3 | 5 | 824 |
| 31 | 1 | 6.1 | 2113 |
| 32 | 0.14 | 0.16 | 170 |
| 33 | 2 | 3.4 | 491 |
| 34 | 5 | 23 | 20453 |
| 35 | 55 | 122 | 17958 |
| 36 | 2 | 3.9 | 417 |
| 37 | 29 | 56 | 583 |
| 38 | 1 | 2.1 | 2093 |
| 39 | 9 | 5.8 | 2231 |
| 40 | 0.75 | 1.2 | 2514 |
| 41 | 4 | 7.7 | 2280 |
| 42 | 0.2 | 1 | 2612 |
| 43 | 1 | 13 | 4373 |
| 44 | 0.21 | 0.76 | 1957 |
| 45 | 1 | 3.8 | 1987 |
| 46 | 0.1 | 0.84 | 1514 |
| 47 | 2 | 7.5 | 4652 |
| 48 | 0.55 | 0.4 | 1854 |
| 49 | 7 | 22 | 391 |
| 50 | 68 | 149 | 622 |
| 51 | 4 | 11 | 602 |
| 52 | 0.42 | 1.8 | 331 |
| 53 | 0.55 | 2.9 | 600 |
| 54 | 2 | 3.3 | 618 |
| 55 | 8 | 15 | 480 |
| 56 | 0.17 | 0.81 | 1368 |
| 57 | 1 | 8.2 | 6061 |
| 58 | 2 | 6.6 | 3100 |
| 59 | 0.14 | 0.88 | 3137 |
| 60 | 0.26 | 1.8 | 501 |
| 61 | 1 | 3.9 | 201 |
| 62 | 0.98 | 6.3 | 1835 |
| 63 | 0.81 | 5.9 | 5918 |
| 64 | 0.15 | 0.87 | 3027 |
| 65 | 0.23 | 1.3 | 1149 |
| 66 | 0.85 | 4.4 | 1175 |
| 67 | 0.17 | 1.3 | 5757 |
| 68 | 0.85 | 6.8 | 11631 |
| 69 | 0.22 | 0.59 | 1666 |
| 71 | 0.68 | 2.7 | 4411 |
| 72 | 0.3 | 1.2 | 1285 |
| 73 | 0.32 | 0.58 | 1585 |
| 74 | 3 | 13 | 24465 |
| 75 | 0.87 | 2 | 4764 |
| 76 | 1 | 5.7 | 2250 |
| 77 | 1 | 3.1 | 1916 |
| 78 | 3 | 32 | 16761 |
| 79 | 2 | 5.7 | 2575 |
| 80 | 0.85 | 2.1 | 1445 |
| 81 | 17 | 104 | 25514 |
| 82 | 7 | 23 | 5774 |
| 85 | 0.35 | 0.53 | 2885 |
| 86 | 2 | 2.6 | 5215 |
| 87 | 0.32 | 0.63 | 1911 |
| 88 | 2 | 4.7 | 1984 |
| 89 | 0.23 | 0.58 | 1325 |
| 90 | 0.48 | 1.7 | 1790 |
| 91 | 0.86 | 2.7 | 2704 |
| 92 | 0.39 | 0.33 | 2682 |
| 93 | 3 | 3.8 | 3795 |
| 95 | 2 | 3.6 | 1825 |
| 96 | 2 | 3.3 | 1744 |
| 99 | 7 | 53 | 15291 |
| 100 | 32 | 431 | 14603 |
| 101 | 0.18 | 0.36 | 1139 |
| 102 | 0.23 | 0.71 | 1889 |
| 103 | 2 | 7.4 | 4120 |
| 104 | 3 | 6.5 | 6412 |
| 105 | 0.75 | 1.8 | 2066 |
| 106 | 0.67 | 0.28 | 1393 |
| 107 | 0.22 | 1.5 | 1393 |
| 108 | 7 | 38 | 19828 |
| 109 | 0.83 | 4.1 | 1603 |
| 110 | 24 | 396 | 36978 |
| 111 | 1 | 2.6 | 4102 |
| 112 | 6 | 2 | 2323 |
| 113 | 1 | 0.79 | 3252 |
| 114 | 4 | 20 | 515 |
| 115 | 1 | 13 | 16132 |
| 116 | 9 | 61 | >50000 |
| 117 | 0.7 | 9.8 | 14055 |
| 118 | 2 | 22 | 15592 |
| 119 | 0.95 | 7.2 | 976 |
| 120 | 4 | 21 | 323 |
| 121 | 0.41 | 2.6 | 7149 |
| 122 | 0.24 | 2.4 | 8705 |
| 123 | 0.52 | 1 | >50000 |
| 124 | 9 | 12 | 8176 |
| 125 | 11 | 10 | 6978 |
| 126 | 0.51 | 2.3 | >50000 |
| 127 | 2 | 3.2 | 3160 |
| 128 | 0.37 | 1.4 | 2246 |
| 129 | 0.3 | 3.9 | 544 |
| 130 | 5 | 33 | 236 |
| 131 | 0.45 | 1 | 2991 |
| 132 | 0.44 | 1.5 | 6038 |
| 133 | 0.28 | 0.75 | 2024 |
| 134 | 1 | 2.5 | 4305 |
| 135 | 2 | 12 | 43812 |
| 136 | NT | 7.2 | 19207 |
| 137 | 2 | 4.9 | 26601 |
| 138 | 0.41 | 2.5 | 4441 |
| 139 | 18 | 40 | >50000 |
| 140 | 0.7 | 5.6 | 14159 |
| 141 | 2 | 18 | 4316 |
| 142 | 2 | 14 | 4415 |
| 143 | 2 | 8 | 27748 |
| 144 | 3 | 9.7 | 33285 |
| 145 | 0.22 | 0.73 | 569 |
| 146 | 0.79 | 3.7 | 1616 |
| 147 | 0.43 | 5.1 | 1488 |
| 148 | 1 | 7.7 | 2445 |
| 149 | 0.43 | 4.6 | 2299 |
| 150 | 0.35 | 0.44 | 1683 |
| 151 | 0.62 | 0.37 | 3341 |
| 152 | 4 | 3.4 | 2849 |
| 153 | 0.5 | 0.72 | 2142 |
| 154 | 4 | 12 | 5677 |
| 155 | 6 | 24 | 3697 |
| 156 | 0.82 | 6.7 | 3636 |
| 157 | 0.38 | 2.5 | 6253 |
| 158 | 0.47 | 3.2 | 2286 |
| 159 | 1691 | 1851 | 28625 |
| 160 | 9 | 154 | 30291 |
| 161 | 3 | 59 | 4797 |
| 162 | 0.56 | 1.2 | 2115 |
| 163 | 0.63 | 0.64 | 2239 |
| 164 | 1 | 7.1 | 1916 |
| 165 | 0.31 | 1.7 | 1994 |
| 166 | 4 | 18 | 16887 |
| 167 | 0.22 | 0.62 | 1295 |
| 168 | 15 | 265 | 34385 |

TABLE 43-continued

TLR7/8/9 Reporter Assay Data (NT = not tested)

| Ex. No. | TLR7 IC$_{50}$ (nM) | TLR8 IC$_{50}$ (nM) | TLR9 IC$_{50}$ (nM) |
|---|---|---|---|
| 169 | 29 | 293 | 41334 |
| 170 | 13 | 590 | NT |
| 171 | 27 | 212 | >50000 |
| 172 | 8 | 35 | 15822 |
| 173 | 46 | 56 | >50000 |
| 174 | 164 | 518 | >50000 |
| 175 | 37 | 119 | 2141 |
| 176 | 26 | 55 | 8886 |
| 177 | 5 | 24 | 7020 |
| 178 | 0.23 | 2.4 | 1784 |
| 179 | 2 | 3.5 | 767 |
| 180 | 2 | 4.5 | 277 |
| 181 | 0.4 | 2.8 | 1210 |
| 182 | 1 | 5.3 | 2370 |
| 183 | 2 | 7.9 | 4627 |
| 184 | 12 | 3.8 | 866 |
| 185 | 18 | 1.9 | 1237 |
| 186 | 4 | 3.6 | 280 |
| 187 | 2 | 3.9 | 274 |
| 188 | 161 | 66 | 7046 |
| 189 | 0.34 | 0.23 | 1027 |
| 190 | 0.43 | 0.35 | 851 |
| 191 | 0.34 | 2.6 | 1872 |
| 192 | 0.49 | 5.9 | 2826 |
| 193 | 1 | 2.9 | 6417 |
| 194 | 6 | 23 | 12006 |
| 195 | 20 | 43 | 2207 |
| 196 | 16 | 84 | 31641 |
| 197 | 2 | 16 | 44554 |
| 198 | 384 | 1099 | 23834 |
| 199 | 89 | 427 | 36908 |
| 200 | 40 | 244 | 26514 |
| 201 | 7 | 109 | 19253 |
| 202 | 4 | 35 | 12221 |
| 203 | 56 | 345 | 43927 |
| 204 | 4 | 55 | >50000 |
| 205 | 120 | 402 | >50000 |
| 206 | 428 | 717 | NT |
| 207 | 24 | 97 | 43536 |
| 208 | 6 | 43 | >50000 |
| 209 | 11 | 70 | >50000 |
| 210 | NT | NT | NT |
| 211 | 3 | 11 | 8005 |
| 212 | 3 | 13 | 8468 |
| 213 | 3 | 5 | 6521 |
| 214 | 2 | 2.9 | 5882 |
| 215 | 19 | 123 | 677 |
| 216 | 7 | 18 | 303 |
| 217 | 5 | 51 | 697 |
| 218 | 15 | 80 | 699 |
| 219 | 9 | 8.5 | 519 |
| 220 | 1 | 11 | 339 |
| 221 | NT | 4.4 | 357 |
| 222 | 2 | 9.2 | 3101 |
| 223 | 2 | 13 | 7498 |
| 224 | 2 | 16 | 1833 |
| 225 | 4 | 12 | 4728 |
| 226 | 17 | 7.4 | 9774 |
| 227 | 156 | 51 | 3767 |
| 228 | 2 | 10 | 4868 |
| 229 | 4 | 8.1 | 6381 |
| 230 | 13 | 13 | 5795 |
| 231 | 9 | 4.6 | 17305 |
| 232 | 9 | 8.1 | 16322 |
| 233 | 15 | 56 | 1348 |
| 234 | 3 | 5.7 | 7367 |
| 235 | 40 | 12 | 693 |
| 236 | 1 | 0.46 | 1247 |
| 237 | 15 | 38 | 21189 |
| 238 | 0.81 | 0.75 | 1245 |
| 239 | 2 | 3 | 1368 |
| 240 | 5 | 4.2 | 11604 |
| 241 | 0.53 | 1.9 | 1304 |
| 242 | 8 | 2.4 | 25432 |
| 243 | 10 | 16 | 12948 |
| 244 | 4 | 0.69 | 1191 |
| 245 | 104 | 19 | 419 |
| 246 | 10 | 16 | 56 |
| 247 | 8 | 6.9 | 116 |
| 248 | 0.76 | 2.1 | 2006 |
| 249 | 2 | 1.2 | 2333 |
| 250 | 19 | 5.1 | 5856 |
| 251 | 3 | 3.2 | 5264 |
| 252 | 2 | 1.6 | 1164 |
| 253 | 5 | 4.4 | 6219 |
| 254 | 107 | 16 | 742 |
| 255 | 19 | 5.2 | 157 |
| 256 | 226 | 3.2 | 611 |
| 257 | 0.44 | 1.9 | 760 |
| 258 | 2 | 9.5 | NT |
| 259 | 4 | 11 | 700 |
| 260 | 2 | 3.9 | 5254 |
| 261 | 4 | 11 | 3315 |
| 262 | 618 | 66 | 22904 |
| 263 | 2 | 4 | 3623 |
| 264 | 3 | 19 | 8173 |
| 265 | 1 | 2.9 | 3423 |
| 266 | 0.31 | 2.9 | 1446 |
| 267 | 0.96 | 5.5 | 2004 |
| 268 | 0.72 | 5.9 | 396 |
| 269 | 5 | 8.3 | 3668 |
| 270 | 14 | 20 | 888 |
| 271 | 5 | 22 | 29133 |
| 272 | 0.84 | 2.1 | 1308 |
| 273 | 28 | 97 | 5249 |
| 274 | 1 | 2.7 | 3876 |
| 275 | 0.86 | 0.23 | 1271 |
| 276 | 0.64 | 0.9 | 468 |
| 277 | 2 | 4.4 | 801 |
| 278 | 2 | 1.5 | 1415 |
| 279 | 37 | 73 | 3127 |
| 280 | 15 | 111 | 1163 |
| 281 | 0.38 | 1.1 | 4021 |
| 282 | 0.66 | 1 | 3804 |
| 283 | 0.95 | 1.3 | 2671 |
| 284 | 1 | 0.85 | 1821 |
| 285 | 0.43 | 0.56 | 959 |
| 286 | 1 | 0.73 | 5388 |
| 287 | 0.7 | 0.62 | 2547 |
| 288 | 0.61 | 0.52 | 3161 |
| 289 | 9 | 24 | >50000 |
| 290 | 36 | 177 | >50000 |
| 291 | 20 | 26 | >50000 |
| 292 | 22 | 2.8 | 34235 |
| 293 | 2 | 1.1 | 10053 |
| 294 | 4 | 12 | 3815 |
| 295 | 6 | 0.39 | 5950 |
| 296 | 3 | 6.3 | 8265 |
| 297 | 2 | 0.61 | 6630 |
| 299 | 2 | 3.3 | 5570 |
| 300 | 2 | 6.4 | 2497 |
| 301 | 7 | 0.56 | 6143 |
| 302 | 2 | 0.42 | 2597 |
| 303 | 15 | 12 | 699 |
| 304 | 89 | 108 | >50000 |
| 305 | 32 | 0.94 | 1013 |
| 306 | 8 | 39 | >50000 |
| 307 | 8 | 47 | >50000 |
| 308 | 8 | 18 | >50000 |
| 309 | 18 | 50 | >50000 |
| 310 | 15 | 57 | >50000 |
| 311 | 17 | 38 | >50000 |
| 312 | 46 | 21 | >50000 |
| 313 | 25 | 60 | >50000 |
| 314 | 24 | 13 | >50000 |
| 315 | 9 | 26 | >50000 |
| 316 | 9 | 55 | >50000 |

TABLE 43-continued

TLR7/8/9 Reporter Assay Data (NT = not tested)

| Ex. No. | TLR7 IC$_{50}$ (nM) | TLR8 IC$_{50}$ (nM) | TLR9 IC$_{50}$ (nM) |
|---|---|---|---|
| 317 | 12 | 90 | >50000 |
| 318 | 6 | 48 | >50000 |
| 319 | 14 | 24 | >50000 |
| 320 | 16 | 54 | >50000 |
| 321 | 15 | 25 | >50000 |
| 322 | 69 | 86 | 20281 |
| 323 | 35 | 54 | >50000 |
| 324 | 44 | 114 | 45045 |
| 325 | 29 | 21 | 36816 |
| 326 | 75 | 28 | 19392 |
| 327 | 54 | 48 | >50000 |
| 328 | 0.85 | 8.2 | 5490 |
| 329 | 1 | 3.4 | 4142 |
| 330 | 1 | 3.4 | 3326 |
| 331 | 1 | 4.6 | 3622 |
| 332 | 0.65 | 6.2 | 2803 |
| 333 | 0.71 | 4.7 | 4375 |
| 334 | 0.83 | 3.1 | 2747 |
| 335 | 5 | 12 | 729 |
| 336 | 10 | 10 | 530 |
| 337 | 1 | 7.1 | 3283 |
| 338 | 0.78 | 7.1 | 2052 |
| 339 | 1 | 6 | 863 |
| 340 | 2 | 5.1 | 4835 |
| 341 | 2 | 5 | 5967 |
| 342 | 3 | 16 | 1719 |
| 343 | 10 | 34 | >50000 |
| 344 | 7 | 14 | >50000 |
| 345 | 6 | 12 | 8612 |
| 346 | 25 | 24 | >50000 |
| 347 | 22 | 14 | >50000 |
| 348 | 66 | 61 | >50000 |
| 349 | 22 | 1.7 | >50000 |
| 350 | 40 | 5.8 | >50000 |
| 351 | 28 | 31 | 48269 |
| 352 | 42 | 15 | 3698 |
| 353 | 95 | 31 | >50000 |
| 354 | 49 | 2 | 3939 |
| 355 | 5 | 1.4 | 28883 |
| 356 | 6 | 4.6 | 6993 |
| 357 | 36 | 5.4 | 1973 |
| 358 | 91 | 1.9 | 4837 |
| 359 | 0.56 | 4.7 | 3627 |
| 360 | 11 | 68 | >50000 |
| 361 | 0.91 | 2.5 | 5321 |
| 362 | 6 | 14 | 432 |
| 363 | 2 | 5.3 | 438 |
| 364 | 0.64 | 3.8 | 1055 |
| 365 | 0.22 | 1.6 | 745 |
| 366 | 6 | 183 | 21677 |
| 368 | 0.45 | 1.6 | 2480 |
| 369 | 0.5 | 0.48 | 2616 |
| 370 | 2 | 0.35 | 14750 |
| 371 | 0.92 | 1.3 | 15510 |
| 372 | 8 | 11 | 26662 |
| 373 | 6 | 36 | >50000 |
| 374 | 20 | 110 | 5895 |
| 375 | 1 | 4.7 | 2063 |
| 376 | 2 | 2.1 | 2674 |
| 377 | 2 | 5.2 | 4724 |
| 378 | 50 | 176 | >50000 |
| 379 | 12 | 70 | 5370 |
| 382 | 15 | 3.4 | 7169 |
| 383 | 9 | 41 | 13681 |
| 384 | 13 | 11 | 30063 |
| 385 | 14 | 48 | 20445 |
| 386 | 34 | 49 | >50000 |
| 387 | 86 | 44 | >50000 |
| 388 | 37 | 41 | >50000 |
| 389 | 22 | 51 | >50000 |
| 390 | 138 | 73 | 5883 |
| 391 | 164 | 354 | 527 |
| 392 | 2386 | 553 | 1184 |
| 393 | 18 | 9.3 | 883 |
| 394 | 2556 | 1076 | 2589 |
| 395 | 966 | 182 | 823 |
| 396 | 2 | 2.8 | 2381 |
| 397 | 3 | 5.4 | 1597 |
| 398 | 1 | 3.5 | 1581 |
| 399 | 11 | 9.8 | 1963 |
| 400 | 18 | 5.1 | 2822 |
| 401 | 27 | 86 | 3427 |
| 402 | 108 | 74 | >50000 |
| 403 | 36 | 7.5 | 23010 |
| 404 | 50 | 31 | >50000 |
| 405 | 35 | 8.4 | 13745 |
| 406 | 14 | 3.2 | 8808 |
| 407 | 9 | 1.4 | 13623 |
| 408 | 15 | 2.3 | 13025 |
| 409 | 23 | 3 | 15629 |
| 410 | 13 | 0.72 | 15576 |
| 411 | 7 | 7.9 | 8958 |
| 412 | 5 | 2.9 | 5271 |
| 413 | 2 | 0.9 | 2748 |
| 414 | 3 | 4 | 4506 |
| 415 | 40 | 38 | 5023 |
| 416 | 115 | 6.4 | 4088 |
| 417 | 76 | 36 | 2108 |
| 418 | 77 | 7 | 9212 |
| 419 | 418 | 27 | 3756 |
| 420 | 306 | 38 | 1057 |
| 421 | 14 | 4 | 1095 |
| 422 | 13 | 2.1 | 457 |
| 423 | 34 | 16 | 2084 |
| 424 | 24 | 2.9 | 2098 |
| 425 | 0.72 | 1.4 | 2488 |
| 426 | 2 | 13 | 11162 |
| 427 | 12 | 19 | 17607 |
| 428 | 49 | 15 | 16221 |
| 429 | 11 | 17 | 6783 |
| 430 | 12 | 41 | 860 |
| 431 | 2 | 3.5 | 2775 |
| 432 | 8 | 49 | 5353 |
| 433 | 2 | 3 | 2193 |
| 434 | 1 | 7.4 | 7494 |
| 435 | 10 | 2.5 | 3408 |
| 436 | 3 | 11 | 10828 |
| 437 | 8 | 4.2 | 4716 |
| 438 | 5 | 37 | 2100 |
| 439 | 1 | 6.3 | 2237 |
| 440 | 4 | 16 | 1481 |
| 441 | 2 | 3.8 | 2573 |
| 442 | 26 | 4.6 | 7598 |
| 443 | 279 | 158 | 2851 |
| 444 | 3055 | 9240 | 4956 |
| 445 | 2684 | 3239 | 1625 |
| 446 | 541 | 70 | 406 |
| 447 | 4009 | 14 | 1137 |
| 448 | 1521 | 134 | 1250 |
| 449 | 1602 | 228 | 480 |
| 450 | 8 | 11 | 2199 |
| 451 | 139 | 238 | 19521 |
| 452 | 242 | 737 | 46478 |
| 453 | 77 | 66 | 191 |
| 454 | 96 | 5.5 | 363 |
| 455 | 188 | 16 | 326 |
| 456 | 124 | 56 | 224 |
| 457 | 189 | 50 | 646 |
| 458 | 57 | 21 | 2267 |
| 459 | 19 | 10 | 174 |
| 460 | 51 | 31 | 179 |
| 461 | 86 | 30 | 467 |
| 462 | 25 | 27 | 116 |
| 463 | 35 | 15 | 406 |
| 464 | 28 | 3.4 | 271 |
| 465 | 3 | 3.3 | >50000 |
| 466 | 32 | 26 | >50000 |
| 467 | 48 | 33 | 46970 |

TABLE 43-continued
TLR7/8/9 Reporter Assay Data (NT = not tested)
| Ex. No. | TLR7 IC$_{50}$ (nM) | TLR8 IC$_{50}$ (nM) | TLR9 IC$_{50}$ (nM) |
|---|---|---|---|
| 468 | 280 | 219 | >50000 |
| 469 | 1106 | 3125 | 9021 |
| 470 | 568 | 3125 | 18258 |
| 471 | 43 | 14 | 38309 |
| 472 | 3 | 4.6 | 23717 |
| 473 | 34 | 15 | 8968 |
| 474 | 45 | 19 | 28883 |
| 475 | 26 | 28 | 10573 |
| 476 | 3 | 2.6 | 4771 |
| 477 | 2 | 1.8 | 8206 |
| 478 | 20 | 7.6 | 10214 |
| 479 | 5 | 4.1 | 8614 |
| 480 | 20 | 6.3 | 6196 |
| 481 | 109 | 27 | 32810 |
| 482 | 34 | 9.2 | 10300 |
| 483 | 61 | 8.8 | 22748 |
| 484 | 41 | 9.5 | 16501 |
| 485 | 46 | 27 | 48026 |
| 486 | 19 | 13 | 5310 |
| 487 | 45 | 5.8 | 10510 |
| 488 | 22 | 6 | 4238 |
| 489 | 128 | 20 | 14931 |
| 490 | 2 | 1 | 13451 |
| 491 | 20 | 4.7 | >50000 |
| 492 | 4 | 1.6 | 6072 |
| 493 | 16 | 4.6 | 4200 |
| 494 | 5 | 0.48 | 12023 |
| 495 | 38 | 1.3 | 20695 |
| 496 | 57 | 4.3 | >50000 |
| 497 | 1 | 2.3 | 649 |
| 498 | 5 | 18 | 531 |
| 499 | 43 | 25 | 9974 |
| 500 | 16 | 13 | 5375 |
| 501 | 12 | 4.3 | 739 |
| 502 | 71 | 23 | 313 |
| 503 | 28 | 44 | 2863 |
| 504 | 98 | 162 | 5014 |
| 505 | 347 | 774 | 13851 |
| 506 | 1 | 21 | 6595 |
| 507 | 3 | 14 | 8180 |
| 508 | 0.43 | 11 | 1489 |
| 509 | 0.27 | 2.4 | 2343 |
| 510 | 2 | 12 | 20722 |
| 511 | 0.94 | 6.1 | 12307 |
| 512 | 3 | 15 | 16348 |
| 513 | 0.96 | 20 | 12455 |
| 514 | 1 | 18 | 15675 |
| 515 | 6 | 59 | 1229 |
| 516 | 3 | 13 | 707 |
| 517 | 5 | 42 | 2461 |
| 518 | 2 | 16 | 1308 |
| 519 | 6 | 127 | 2513 |
| 520 | 29 | 66 | 17718 |
| 521 | 4 | 37 | 7025 |
| 522 | 9 | 85 | 12720 |
| 523 | 0.48 | 5.1 | 2715 |
| 524 | 12 | 21 | 11085 |
| 525 | 7 | 50 | 4412 |
| 526 | 6 | 34 | 6967 |
| 527 | 0.52 | 4.5 | 765 |
| 528 | 2 | 16 | 5598 |
| 529 | 12 | 39 | 9127 |
| 530 | 2 | 12 | 696 |
| 531 | 57 | 137 | 10214 |
| 532 | 13 | 20 | 16898 |
| 533 | 8 | 42 | 2185 |
| 534 | 9 | 28 | 7168 |
| 536 | 26 | 21 | 11039 |
| 537 | 51 | 40 | 27812 |
| 538 | 33 | 45 | 16495 |
| 539 | 64 | 132 | 1888 |
| 540 | 19 | 36 | 18583 |
| 541 | 2 | 0.79 | 5737 |
| 542 | 3 | 1.2 | 5100 |
| 543 | 4 | 5.1 | 9488 |
| 544 | 5 | 12 | 21036 |
| 545 | 2 | 3.8 | 2042 |
| 546 | 4 | 5.8 | 3873 |
| 547 | 0.37 | 0.67 | 4551 |
| 548 | 4 | 5.1 | 8052 |
| 549 | 6 | 9.3 | 2188 |
| 550 | 17 | 13 | 13589 |
| 551 | 2 | 3.2 | 3354 |
| 552 | 4 | 3.4 | 5567 |
| 553 | 4 | 7.2 | 32335 |
| 554 | 18 | 15 | 5196 |
| 555 | 9 | 10 | 7726 |
| 556 | 6 | 4.9 | 5124 |
| 557 | 9 | 3.6 | 6752 |
| 558 | 6 | 117 | 3715 |
| 559 | 2 | 9.2 | 2116 |
| 560 | 1 | 27 | 2331 |
| 561 | 5 | 25 | 4679 |
| 562 | 4 | 28 | 3706 |
| 563 | 1268 | 3125 | 38208 |
| 564 | 3 | 7 | 7309 |
| 565 | 2 | 2.1 | 2553 |
| 566 | 1 | 0.6 | 4447 |
| 567 | 2 | 1.1 | 26696 |
| 568 | 0.53 | 0.76 | 980 |
| 569 | 0.32 | 0.62 | 4550 |
| 570 | 0.93 | 0.9 | 3447 |
| 571 | 0.53 | 0.33 | 2315 |
| 572 | 0.93 | 0.31 | 4958 |
| 573 | 3 | 2.3 | 12564 |
| 574 | 1 | 0.58 | 4253 |
| 575 | 4 | 1.1 | 22334 |
| 576 | 23 | 7.4 | NT |
| 577 | 4 | 4.5 | NT |
| 578 | 0.59 | 0.61 | 6445 |
| 579 | 1 | 0.73 | 7412 |
| 580 | 0.55 | 0.19 | 2172 |
| 581 | 1 | 9 | 1602 |
| 582 | 3 | 0.56 | 35651 |
| 583 | 0.99 | 0.32 | 31017 |
| 584 | 2 | 3.8 | 5653 |
| 585 | 0.55 | 2.9 | 2813 |
| 586 | 13 | 3.8 | 43974 |
| 587 | 5 | 5.7 | 21263 |
| 588 | 0.4 | 1.4 | 1866 |
| 589 | 2 | 2.8 | 5409 |
| 590 | 5 | 0.5 | 930 |
| 591 | 8 | 8.7 | 1011 |
| 592 | 31 | 10 | 1470 |
What is claimed is:
1. A compound of Formula (I)
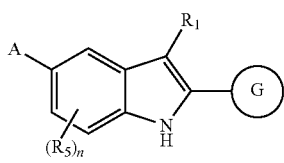
(I)

N-oxide, or a salt thereof, wherein:
G is:

(i)

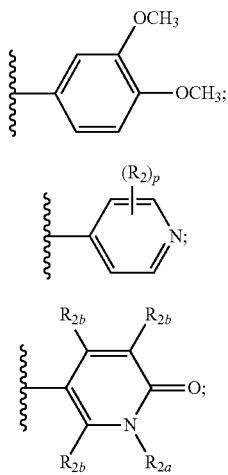

(ii)

(iii)

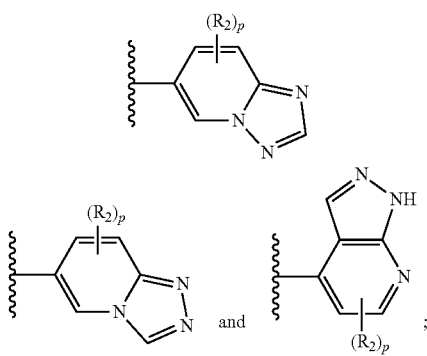

(iv) a 9-membered heterocyclic ring selected from:

A is: —CHR$_{12}$R$_{13}$, wherein R$_{12}$ and R$_{13}$ together with the carbon atom to which they are attached and the hydrogen atom attached to the carbon atom, form a cyclic group selected from azabicyclo[4.1.1]octanyl, azetidinyl, C$_{3-6}$ cycloalkyl, diazaspiro[4.5]decanonyl, morpholinyl, octahydrocyclopenta[c]pyrrolyl, or quinuclidinyl, each substituted with zero to 3 R$_{12a}$;
R$_1$ is —CH$_2$CH$_3$ or —CH(CH$_3$)$_2$;
each R$_2$ is independently —CH$_3$ or —OCH$_3$;
R$_{2a}$ is —CH$_3$;
each R$_{2b}$ is independently H or —CH$_3$;
each R$_{12a}$ is independently —OH, —CH$_3$, —CH$_2$CH$_2$CH$_3$, —CH(CH$_3$)$_2$, —CH$_2$CH(CH$_3$)$_2$, —CF$_3$, —CH$_2$CH$_2$CH$_2$CF$_3$, —CH$_2$CN, —CH$_2$C(CH$_3$)$_2$OH, —CH$_2$CH$_2$OCH$_3$, —CH$_2$C(O)NH(CH$_3$), —CH$_2$C(O)N(CH$_3$)$_2$, —CH$_2$C(O)NH$_2$, —CH$_2$CH$_2$S(O)$_2$CH$_3$, —CH$_2$CH$_2$NHS(O)$_2$CH$_3$, —OCH$_3$, —NR$_x$R$_x$, —N(CH$_3$)(CH$_2$CH$_3$), —N(CH$_3$)(CH(CH$_3$)$_2$), —NR$_x$(CH$_2$CHF$_2$)—NH(CH$_2$CF$_3$), —N(CH$_3$)(CH$_2$CH$_2$CF$_3$), —N(CH$_3$)(CH$_2$CH$_2$OCH$_3$), —NH(CH$_2$CN), —N(CH$_3$)CH$_2$N(CH$_3$)$_2$, —NH(CH$_2$C(CH$_3$)$_2$OH), —NH(CH$_2$C(O)NH$_2$), —N(CH$_3$)(OCH$_3$), —NR$_x$CH$_2$CH$_2$S(O)$_2$CH$_3$, —NHC(O)CH$_3$, —NHC(O)CH$_2$CF$_3$, —NHC(O)CHR$_x$NH(CH$_3$), —NR$_x$C(O)CH$_2$N(CH$_3$)$_2$, —NHC(O)CH$_2$N(CH$_3$)(CH$_2$CH$_3$), —NHC(O)CH$_2$N(CH$_2$CH$_3$)$_2$, —NHC(O)CH$_2$NH(CH$_2$C(CH$_3$)$_2$OH), —NHCH$_2$C(O)NR$_x$(CH$_3$), —NHS(O)$_2$CH$_3$, —C(O)C(CH$_3$)$_3$, —C(O)CH(CH$_2$CH$_3$)$_2$, —C(O)CH$_2$OCH$_3$, —C(O)CH$_2$CH$_2$OCH$_3$, —C(O)CH$_2$NH(CH$_3$), —C(O)CH$_2$N(CH$_3$)$_2$, —C(O)CH(CH$_3$)NH(CH$_3$), —C(O)CH$_2$N(CH$_3$)(CH$_2$CH$_3$), —C(O)CH$_2$N(CH$_2$CH$_3$)$_2$, R$_{12b}$, —CH$_2$R$_{12b}$, —C(O)R$_{12b}$, —C(O)CH$_2$R$_{12b}$, —C(O)CH$_2$NHR$_{12b}$, —C(O)NR$_x$R$_{12b}$, —NR$_x$C(O)CH$_2$R$_{12b}$, —NR$_x$R$_{12b}$, —NR$_x$CH$_2$R$_{12b}$, —NHC(O)CH$_2$NR$_x$R$_{12b}$, —NHC(O)CH$_2$NR$_x$CH$_2$R$_{12b}$, —NHCH$_2$C(O)NHR$_{12b}$, or —OR$_{12b}$;

R$_{12b}$ is azetidinyl, cyclopropyl, diazabicyclo[2.2.1]heptanyl, dioxolanyl, dioxidotetrahydrothiopyranyl, dioxidothiomorpholinyl, imidazolyl, morpholinyl, octahydrocyclopenta[c]pyrrolyl, octahydropyrrolo[3,4-c]pyrrolyl, oxaazaspiro[3.3]heptanyl, oxetanyl, phenyl, piperazinyl, piperazinonyl, piperidinyl, pyridinyl, pyrrolidinyl, quinuclidinyl, tetrahydrofuranyl, tetrahydropyranyl, or triazolyl, each substituted with zero to 4 substituents independently selected from F, —OH, —CH$_3$, —CH(CH$_3$)$_2$, —CH$_2$OH, —OCH$_3$, —CH$_2$CH$_2$OCH$_3$, —NR$_x$R$_x$, and —C(O)NH$_2$;
each R$_x$ is independently H or —CH$_3$;
n is zero; and
p is zero, 1, 2, or 3.

2. The compound according to claim 1, N-oxide, or a salt thereof, wherein A is azetidinyl, C$_{3-6}$ cycloalkyl, or morpholinyl, each substituted with zero to 3 R$_{12a}$.

3. The compound according to claim 2 or a salt thereof, wherein A is azetidinyl, cyclopropyl, cyclobutyl, cyclohexyl, or morpholinyl, each substituted with zero to 3 R$_{12a}$.

4. A pharmaceutical composition comprising a compound according to claim 1 or a pharmaceutically-acceptable salt thereof; and a pharmaceutically acceptable carrier.

5. The compound according to claim 1, N-oxide, or a salt thereof, wherein A is C$_{3-6}$ cycloalkyl, each substituted with zero to 3 R$_{12a}$.

6. A compound according to claim 5 or a salt thereof, wherein said compound is:
4-(3-isopropyl-2-(8-methoxy-[1,2,4]triazolo[1,5-a]pyridin-6-yl)-1H-indol-5-yl) cyclohexanamine (1-2);
4-(3-isopropyl-2-(8-methyl-[1,2,4]triazolo[1,5-a]pyridin-6-yl)-1H-indol-5-yl) cyclohexan-1-amine (3);
4-(3-isopropyl-2-(8-methyl-[1,2,4]triazolo[1,5-a]pyridin-6-yl)-1H-indol-5-yl) cyclohexan-1-amine (4);
4-(2-(2,6-dimethylpyridin-4-yl)-3-isopropyl-1H-indol-5-yl)cyclohexan-1-amine (5);
N-isopropyl-4-(3-isopropyl-2-(8-methoxy-[1,2,4]triazolo[1,5-a]pyridin-6-yl)-1H-indol-5-yl)-N-methylcyclohexanamine (6-7);
N-cyclopropyl-4-(3-isopropyl-2-(8-methyl-[1,2,4]triazolo[1,5-a]pyridin-6-yl)-1H-indol-5-yl)-N-methylcyclohexan-1-amine (8);
N-cyclopropyl-4-(3-isopropyl-2-(8-methyl-[1,2,4]triazolo[1,5-a]pyridin-6-yl)-1H-indol-5-yl)-N-methylcyclohexan-1-amine (9);
N-cyclopropyl-4-(3-isopropyl-2-(8-methoxy-[1,2,4]triazolo[1,5-a]pyridin-6-yl)-1H-indol-5-yl)cyclohexan-1-amine (10-11);
N-cyclopropyl-4-(3-isopropyl-2-(8-methoxy-[1,2,4]triazolo[1,5-a]pyridin-6-yl)-1H-indol-5-yl)-N-methylcyclohexan-1-amine (12-13);
N-cyclopropyl-4-(2-(7,8-dimethyl-[1,2,4]triazolo[1,5-a]pyridin-6-yl)-3-isopropyl-1H-indol-5-yl)cyclohexan-1-amine (14, 17);

N-cyclopropyl-4-(3-isopropyl-2-(8-methyl-[1,2,4]triazolo[1,5-a]pyridin-6-yl)-1H-indol-5-yl)cyclohexan-1-amine (15-16);

6-(5-(4-(3,3-difluoroazetidin-1-yl)cyclohexyl)-3-isopropyl-1H-indol-2-yl)-8-methoxy-[1,2,4]triazolo[1,5-a]pyridine (19-20);

1-(4-(3-isopropyl-2-(8-methoxy-[1,2,4]triazolo[1,5-a]pyridin-6-yl)-1H-indol-5-yl) cyclohexyl)azetidin-3-ol (20, 22);

6-(5-(4-(3-fluoroazetidin-1-yl)cyclohexyl)-3-isopropyl-1H-indol-2-yl)-8-methoxy-[1,2,4]triazolo[1,5-a]pyridine (21, 23);

6-(5-(4-(3,3-difluoroazetidin-1-yl)cyclohexyl)-3-isopropyl-1H-indol-2-yl)-7,8-dimethyl-[1,2,4]triazolo[1,5-a]pyridine (24-25);

(1-(4-(2-(7,8-dimethyl-[1,2,4]triazolo[1,5-a]pyridin-6-yl)-3-isopropyl-1H-indol-5-yl) cyclohexyl)azetidine-3,3-diyl)dimethanol (26-27);

(R)-1-(4-(3-isopropyl-2-(8-methoxy-[1,2,4]triazolo[1,5-a]pyridin-6-yl)-1H-indol-5-yl)cyclohexyl)-N,N-dimethylpyrrolidin-3-amine (28, 30);

(S)-1-(4-(3-isopropyl-2-(8-methoxy-[1,2,4]triazolo[1,5-a]pyridin-6-yl)-1H-indol-5-yl) cyclohexyl)pyrrolidine-2-carboxamide (29, 31);

(S)-1-(4-(3-isopropyl-2-(8-methoxy-[1,2,4]triazolo[1,5-a]pyridin-6-yl)-1H-indol-5-yl) cyclohexyl)-N,N-dimethylpyrrolidin-3-amine (32-33);

6-(5-(4-(3,3-difluoropiperidin-1-yl)cyclohexyl)-3-isopropyl-1H-indol-2-yl)-8-methoxy-[1,2,4]triazolo[1,5-a]pyridine (34-35);

2-(2,6-dimethylpyridin-4-yl)-3-isopropyl-5-(4-(4-methylpiperazin-1-yl)cyclohexyl)-1H-indole (36-37);

6-(3-isopropyl-5-(4-(4-(2-methoxyethyl)piperazin-1-yl)cyclohexyl)-1H-indol-2-yl)-8-methoxy-[1,2,4]triazolo[1,5-a]pyridine (38-39);

(2R,6S)-4-(4-(3-isopropyl-2-(8-methoxy-[1,2,4]triazolo[1,5-a]pyridin-6-yl)-1H-indol-5-yl)cyclohexyl)-2,6-dimethylmorpholine (40);

4-(4-(3-isopropyl-2-(8-methoxy-[1,2,4]triazolo[1,5-a]pyridin-6-yl)-1H-indol-5-yl) cyclohexyl)-2,6-dimethylmorpholine (41);

4-(3-isopropyl-2-(8-methoxy-[1,2,4]triazolo[1,5-a]pyridin-6-yl)-1H-indol-5-yl)-N-(1-methylcyclopropyl)cyclohexan-1-amine (42-43);

N-(4-(3-isopropyl-2-(8-methoxy-[1,2,4]triazolo[1,5-a]pyridin-6-yl)-1H-indol-5-yl) cyclohexyl)-3-methyloxetan-3-amine (44-45);

N-(4-(3-isopropyl-2-(8-methyl-[1,2,4]triazolo[1,5-a]pyridin-6-yl)-1H-indol-5-yl) cyclohexyl)-3-methyloxetan-3-amine (46-47);

N-(4-(2-(7,8-dimethyl-[1,2,4]triazolo[1,5-a]pyridin-6-yl)-3-isopropyl-1H-indol-5-yl) cyclohexyl)-3-methyloxetan-3-amine (48);

4-(2-(2,6-dimethylpyridin-4-yl)-3-isopropyl-1H-indol-5-yl)-N-(4-methoxybenzyl)cyclohexan-1-amine (49-50);

4-(2-(2,6-dimethylpyridin-4-yl)-3-isopropyl-1H-indol-5-yl)-N-methylcyclohexan-1-amine (51-52);

4-(2-(2,6-dimethylpyridin-4-yl)-3-isopropyl-1H-indol-5-yl)-N,N-dimethylcyclohexan-1-amine (53);

4-(4-(2-(2,6-dimethylpyridin-4-yl)-3-isopropyl-1H-indol-5-yl)cyclohexyl)morpholine (54-55);

4-(3-isopropyl-2-(8-methyl-[1,2,4]triazolo[1,5-a]pyridin-6-yl)-1H-indol-5-yl)-N-methylcyclohexan-1-amine (56, 58);

N-(4-(3-isopropyl-2-(8-methyl-[1,2,4]triazolo[1,5-a]pyridin-6-yl)-1H-indol-5-yl) cyclohexyl)oxetan-3-amine (57, 59);

N-(4-(2-(2,6-dimethylpyridin-4-yl)-3-isopropyl-1H-indol-5-yl)cyclohexyl)oxetan-3-amine (60-61);

N-ethyl-4-(3-isopropyl-2-(8-methyl-[1,2,4]triazolo[1,5-a]pyridin-6-yl)-1H-indol-5-yl)-N-methylcyclohexan-1-amine (62-63);

N-(4-(3-isopropyl-2-(8-methoxy-[1,2,4]triazolo[1,5-a]pyridin-6-yl)-1H-indol-5-yl) cyclohexyl)oxetan-3-amine (64, 90);

N-ethyl-4-(3-isopropyl-2-(8-methoxy-[1,2,4]triazolo[1,5-a]pyridin-6-yl)-1H-indol-5-yl)-N-methylcyclohexan-1-amine (65-66);

N-(2,2-difluoroethyl)-4-(3-isopropyl-2-(8-methoxy-[1,2,4]triazolo[1,5-a]pyridin-6-yl)-1H-indol-5-yl)cyclohexan-1-amine (67-68);

4-(4-(3-isopropyl-2-(8-methoxy-[1,2,4]triazolo[1,5-a]pyridin-6-yl)-1H-indol-5-yl) cyclohexyl)morpholine (69, 76);

6-(5-(4-(azetidin-1-yl)cyclohexyl)-3-isopropyl-1H-indol-2-yl)-8-methoxy-[1,2,4]triazolo[1,5-a]pyridine (70, 77);

4-(4-(3-isopropyl-2-(8-methoxy-[1,2,4]triazolo[1,5-a]pyridin-6-yl)-1H-indol-5-yl) cyclohexyl)piperazin-2-one (71, 78);

4-(3-isopropyl-2-(8-methoxy-[1,2,4]triazolo[1,5-a]pyridin-6-yl)-1H-indol-5-yl)-N-(2-methoxyethyl)-N-methylcyclohexan-1-amine (72, 79);

6-(4-(3-isopropyl-2-(8-methoxy-[1,2,4]triazolo[1,5-a]pyridin-6-yl)-1H-indol-5-yl) cyclohexyl)-2-oxa-6-azaspiro[3.3]heptane (73, 80);

N-(2,2-difluoroethyl)-4-(3-isopropyl-2-(8-methoxy-[1,2,4]triazolo[1,5-a]pyridin-6-yl)-1H-indol-5-yl)-N-methylcyclohexan-1-amine (74-75, 81);

4-(3-isopropyl-2-(8-methoxy-[1,2,4]triazolo[1,5-a]pyridin-6-yl)-1H-indol-5-yl)-N-methyl-N-(3,3,3-trifluoropropyl)cyclohexan-1-amine (82);

N-(4-(2-(7,8-dimethyl-[1,2,4]triazolo[1,5-a]pyridin-6-yl)-3-isopropyl-1H-indol-5-yl) cyclohexyl)oxetan-3-amine (85-86);

4-(2-(7,8-dimethyl-[1,2,4]triazolo[1,5-a]pyridin-6-yl)-3-isopropyl-1H-indol-5-yl)-N-ethyl-N-methylcyclohexan-1-amine (87-88);

4-(2-(7,8-dimethyl-[1,2,4]triazolo[1,5-a]pyridin-6-yl)-3-isopropyl-1H-indol-5-yl)-N-methylcyclohexan-1-amine (89, 91);

N-(4-(3-isopropyl-2-(8-methoxy-[1,2,4]triazolo[1,5-a]pyridin-6-yl)-1H-indol-5-yl)cyclohexyl)oxetan-3-amine (90);

4-(4-(2-(7,8-dimethyl-[1,2,4]triazolo[1,5-a]pyridin-6-yl)-3-isopropyl-1H-indol-5-yl) cyclohexyl)morpholine (92-93);

4-(2-(7,8-dimethyl-[1,2,4]triazolo[1,5-a]pyridin-6-yl)-3-isopropyl-1H-indol-5-yl)-N-(2-methoxyethyl)-N-methylcyclohexan-1-amine (94);

6-(4-(2-(7,8-dimethyl-[1,2,4]triazolo[1,5-a]pyridin-6-yl)-3-isopropyl-1H-indol-5-yl) cyclohexyl)-2-oxa-6-azaspiro[3.3]heptane (95);

6-(4-(3-isopropyl-2-(8-methoxy-[1,2,4]triazolo[1,5-a]pyridin-6-yl)-1H-indol-5-yl) cyclohexyl)-2-oxa-6-azaspiro[3.3]heptane (96);

N-(4-(3-isopropyl-2-(8-methoxy-[1,2,4]triazolo[1,5-a]pyridin-6-yl)-1H-indol-5-yl) cyclohexyl)-N,O-dimethylhydroxylamine (99-100);

1-((4-(3-isopropyl-2-(8-methoxy-[1,2,4]triazolo[1,5-a]pyridin-6-yl)-1H-indol-5-yl) cyclohexyl)amino)-2-methylpropan-2-ol (101);

4-(4-(3-isopropyl-2-(8-methyl-[1,2,4]triazolo[1,5-a]pyridin-6-yl)-1H-indol-5-yl) cyclohexyl)morpholine (102-103);

1-((4-(3-isopropyl-2-(8-methyl-[1,2,4]triazolo[1,5-a]pyridin-6-yl)-1H-indol-5-yl) cyclohexyl)amino)-2-methylpropan-2-ol (104);

4-(2-(7,8-dimethyl-[1,2,4]triazolo[1,5-a]pyridin-6-yl)-3-isopropyl-1H-indol-5-yl)-N,N-dimethylcyclohexan-1-amine (105, 111);

1-((4-(2-(7,8-dimethyl-[1,2,4]triazolo[1,5-a]pyridin-6-yl)-3-isopropyl-1H-indol-5-yl) cyclohexyl)amino)-2-methylpropan-2-ol (106, 112);

2-((4-(3-isopropyl-2-(8-methoxy-[1,2,4]triazolo[1,5-a]pyridin-6-yl)-1H-indol-5-yl) cyclohexyl)amino)acetamide (107, 109);

4-(3-isopropyl-2-(8-methoxy-[1,2,4]triazolo[1,5-a]pyridin-6-yl)-1H-indol-5-yl)-N-(2,2,2-trifluoroethyl)cyclohexan-1-amine (108, 110);

6-(4-(2-(7,8-dimethyl-[1,2,4]triazolo[1,5-a]pyridin-6-yl)-3-isopropyl-1H-indol-5-yl) cyclohexyl)-2-oxa-6-azaspiro[3.3]heptane (113);

4-(2-(2,6-dimethylpyridin-4-yl)-3-isopropyl-1H-indol-5-yl)-N,N-dimethylcyclohexan-1-amine (114);

N-(4-(3-isopropyl-2-(8-methoxy-[1,2,4]triazolo[1,5-a]pyridin-6-yl)-1H-indol-5-yl) cyclohexyl)acetamide (115-116);

N-(4-(3-isopropyl-2-(8-methoxy-[1,2,4]triazolo[1,5-a]pyridin-6-yl)-1H-indol-5-yl) cyclohexyl)methanesulfonamide (117);

3,3,3-trifluoro-N-(4-(3-isopropyl-2-(8-methoxy-[1,2,4]triazolo[1,5-a]pyridin-6-yl)-1H-indol-5-yl)cyclohexyl)propanamide (118);

2-(dimethylamino)-N-(4-(2-(2,6-dimethylpyridin-4-yl)-3-isopropyl-1H-indol-5-yl) cyclohexyl)acetamide (119-120);

2-(dimethylamino)-N-(4-(3-isopropyl-2-(8-methyl-[1,2,4]triazolo[1,5-a]pyridin-6-yl)-1H-indol-5-yl)cyclohexyl)acetamide (121-122);

N-(4-(2-(7,8-dimethyl-[1,2,4]triazolo[1,5-a]pyridin-6-yl)-3-isopropyl-1H-indol-5-yl) cyclohexyl)-2-(dimethylamino)acetamide (123-124);

2-(diethylamino)-N-(4-(2-(7,8-dimethyl-[1,2,4]triazolo[1,5-a]pyridin-6-yl)-3-isopropyl-1H-indol-5-yl)cyclohexyl)acetamide (125-126);

2-(dimethylamino)-N-(4-(3-isopropyl-2-(8-methoxy-[1,2,4]triazolo[1,5-a]pyridin-6-yl)-1H-indol-5-yl)cyclohexyl)acetamide (127);

N-(4-(2-(7,8-dimethyl-[1,2,4]triazolo[1,5-a]pyridin-6-yl)-3-isopropyl-1H-indol-5-yl) cyclohexyl)-2-(methylamino)acetamide (128);

N-(4-(2-(2,6-dimethylpyridin-4-yl)-3-isopropyl-1H-indol-5-yl)cyclohexyl)-2-(methylamino)acetamide (129-130);

(S)—N-(4-(2-(7,8-dimethyl-[1,2,4]triazolo[1,5-a]pyridin-6-yl)-3-isopropyl-1H-indol-5-yl)cyclohexyl)-2-(methylamino)propanamide (131);

2-(ethyl(methyl)amino)-N-(4-(3-isopropyl-2-(8-methoxy-[1,2,4]triazolo[1,5-a]pyridin-6-yl)-1H-indol-5-yl)cyclohexyl)acetamide (132);

N-(4-(3-isopropyl-2-(8-methoxy-[1,2,4]triazolo[1,5-a]pyridin-6-yl)-1H-indol-5-yl) cyclohexyl)-2-(pyrrolidin-1-yl)acetamide (133);

2-(3,3-bis(hydroxymethyl)azetidin-1-yl)-N-(4-(3-isopropyl-2-(8-methoxy-[1,2,4]triazolo[1,5-a]pyridin-6-yl)-1H-indol-5-yl)cyclohexyl)acetamide (134);

N-(4-(3-isopropyl-2-(8-methoxy-[1,2,4]triazolo[1,5-a]pyridin-6-yl)-1H-indol-5-yl) cyclohexyl)-2-((3-methyloxetan-3-yl)amino)acetamide (135);

2-(((2,2-dimethyl-1,3-dioxolan-4-yl)methyl)amino)-N-(4-(3-isopropyl-2-(8-methoxy-[1,2,4]triazolo[1,5-a]pyridin-6-yl)-1H-indol-5-yl)cyclohexyl)acetamide (136);

N-(4-(3-isopropyl-2-(8-methoxy-[1,2,4]triazolo[1,5-a]pyridin-6-yl)-1H-indol-5-yl) cyclohexyl)-2-(oxetan-3-ylamino)acetamide (137, 139);

N-(4-(3-isopropyl-2-(8-methoxy-[1,2,4]triazolo[1,5-a]pyridin-6-yl)-1H-indol-5-yl) cyclohexyl)-2-(2-oxa-6-azaspiro[3.3]heptan-6-yl)acetamide (138);

2-((2-hydroxy-2-methylpropyl)amino)-N-(4-(3-isopropyl-2-(8-methoxy-[1,2,4]triazolo[1,5-a]pyridin-6-yl)-1H-indol-5-yl)cyclohexyl)acetamide (140);

N-(4-(3-isopropyl-2-(8-methoxy-[1,2,4]triazolo[1,5-a]pyridin-6-yl)-1H-indol-5-yl) cyclohexyl)-2-morpholinoacetamide (141-142);

2-(cyclopropyl(methyl)amino)-N-(4-(3-isopropyl-2-(8-methoxy-[1,2,4]triazolo[1,5-a]pyridin-6-yl)-1H-indol-5-yl)cyclohexyl)acetamide (143);

2-(1,1-dioxidothiomorpholino)-N-(4-(3-isopropyl-2-(8-methoxy-[1,2,4]triazolo[1,5-a]pyridin-6-yl)-1H-indol-5-yl)cyclohexyl)acetamide (144);

4-(3-isopropyl-2-(8-methoxy-[1,2,4]triazolo[1,5-a]pyridin-6-yl)-1H-indol-5-yl)-N-methylcyclohexanamine (145-146);

2-(dimethylamino)-N-(4-(3-isopropyl-2-(8-methoxy-[1,2,4]triazolo[1,5-a]pyridin-6-yl)-1H-indol-5-yl)cyclohexyl)-N-methylacetamide (147);

2-(dimethylamino)-N-(4-(3-isopropyl-2-(8-methyl-[1,2,4]triazolo[1,5-a]pyridin-6-yl)-1H-indol-5-yl)cyclohexyl)-N-methylacetamide (148-149);

4-(3-isopropyl-2-(8-methoxy-[1,2,4]triazolo[1,5-a]pyridin-6-yl)-1H-indol-5-yl)-N-methyl-N-(2-(methylsulfonyl)ethyl)cyclohexanamine (150);

4-(2-(7,8-dimethyl-[1,2,4]triazolo[1,5-a]pyridin-6-yl)-3-isopropyl-1H-indol-5-yl)-N-methyl-N-(2-(methylsulfonyl)ethyl)cyclohexan-1-amine (151);

4-(2-(7,8-dimethyl-[1,2,4]triazolo[1,5-a]pyridin-6-yl)-3-isopropyl-1H-indol-5-yl)-N-(2-methoxyethyl)-N-methylcyclohexanamine (152-153);

2-(dimethylamino)-N-(4-(3-isopropyl-2-(8-methoxy-[1,2,4]triazolo[1,5-a] pyridin-6-yl)-1H-indol-5-yl)-1-methylcyclohexyl)acetamide (154);

N-(4-(3-isopropyl-2-(8-methoxy-[1,2,4]triazolo[1,5-a]pyridin-6-yl)-1H-indol-5-yl)-1-methylcyclohexyl)-2-(methylamino)acetamide (155);

(4-(3-isopropyl-2-(8-methyl-[1,2,4]triazolo[1,5-a]pyridin-6-yl)-1H-indol-5-yl) cyclohexyl)(4-methylpiperazin-1-yl)methanone (156-157);

4-(3-isopropyl-2-(8-methyl-[1,2,4]triazolo[1,5-a]pyridin-6-yl)-1H-indol-5-yl)-N-(1-isopropylpiperidin-4-yl)cyclohexane-1-carboxamide (158);

(4-(3-isopropyl-2-(8-methyl-[1,2,4]triazolo[1,5-a]pyridin-6-yl)-1H-indol-5-yl) cyclohexyl)(piperidin-1-yl)methanone (159-160);

(4-(3-isopropyl-2-(8-methyl-[1,2,4]triazolo[1,5-a]pyridin-6-yl)-1H-indol-5-yl) cyclohexyl)(morpholino)methanone (161);

2-((4-(3-isopropyl-2-(8-methyl-[1,2,4]triazolo[1,5-a]pyridin-6-yl)-1H-indol-5-yl) cyclohexyl)amino)-N-methylacetamide (162-163);

2-((4-(3-isopropyl-2-(8-methoxy-[1,2,4]triazolo[1,5-a]pyridin-6-yl)-1H-indol-5-yl) cyclohexyl)amino)-N-(oxetan-3-yl)acetamide (164-165);

2-((4-(3-isopropyl-2-(8-methoxy-[1,2,4]triazolo[1,5-a]
pyridin-6-yl)-1H-indol-5-yl) cyclohexyl)amino)-N-methylacetamide (166-167);

6-(3-isopropyl-5-(4-methoxycyclohexyl)-1H-indol-2-yl)-8-methyl-[1,2,4]triazolo[1,5-a]pyridine (168);

4-(2-(2,6-dimethylpyridin-4-yl)-3-isopropyl-1H-indol-5-yl) cyclohexanone (169-170);

4-(2-(2,6-dimethylpyridin-4-yl)-3-isopropyl-1H-indol-5-yl)cyclohexanol (171-172);

4-(3-isopropyl-2-(2-methylpyridin-4-yl)-1H-indol-5-yl) cyclohexan-1-ol (173-174);

4-(2-(2,6-dimethylpyridin-4-yl)-3-isopropyl-1H-indol-5-yl)-1-(trifluoro methyl)cyclohexanol (175);

1-(4-(2-(2,6-dimethylpyridin-4-yl)-3-isopropyl-1H-indol-5-yl)cyclohexyl)-N,N-dimethylmethanamine (176);

2-((4-(3-isopropyl-2-(8-methyl-[1,2,4]triazolo[1,5-a] pyridin-6-yl)-1H-indol-5-yl) cyclohexyl)(methyl) amino)-N,N-dimethylacetamide (177-178);

2-((4-(2-(2,6-dimethylpyridin-4-yl)-3-isopropyl-1H-indol-5-yl)cyclohexyl) amino)-N-methylacetamide (179-180);

4-(2-(3,4-dimethoxyphenyl)-3-isopropyl-1H-indol-5-yl) cyclohexan-1-amine (450);

4-(2-(3,4-dimethoxyphenyl)-3-isopropyl-1H-indol-5-yl) cyclohexan-1-ol (451-452);

5-(5-(4-(4,4-difluoropiperidin-1-yl)cyclohexyl)-3-isopropyl-1H-indol-2-yl)-1,3-dimethylpyridin-2(1H)-one (465-466);

5-(5-(4-(3,3-difluoropiperidin-1-yl)cyclohexyl)-3-isopropyl-1H-indol-2-yl)-1,3-dimethylpyridin-2(1H)-one (467-468);

5-cyclohexyl-2-(2,6-dimethylpyridin-4-yl)-3-isopropyl-1H-indole (469);

5-(5-cyclohexyl-3-isopropyl-1H-indol-2-yl)-1,3-dimethylpyridin-2(1H)-one (470);

2-(dimethylamino)-N-(4-(3-isopropyl-2-(1,4,5-trimethyl-6-oxo-1,6-dihydropyridin-3-yl)-1H-indol-5-yl)cyclohexyl)acetamide (471-472);

2-((4-(3-isopropyl-2-(1,4,5-trimethyl-6-oxo-1,6-dihydropyridin-3-yl)-1H-indol-5-yl) cyclohexyl)amino)-N,N-dimethylacetamide (473, 479-480);

5-(3-isopropyl-5-(4-(oxetan-3-ylamino)cyclohexyl)-1H-indol-2-yl)-1,3,4-trimethylpyridin-2(1H)-one (474, 477-478);

5-(5-(4-(dimethylamino)cyclohexyl)-3-isopropyl-1H-indol-2-yl)-1,3,4-trimethylpyridin-2(1H)-one (475-476);

4-(4-(2-(2,6-dimethylpyridin-4-yl)-3-isopropyl-1H-indol-5-yl)cyclohexyl)morpholine (497-498);

4-(3-isopropyl-5-(4-(piperidin-4-yloxy)cyclohexyl)-1H-indol-2-yl)-1H-pyrazolo[3,4-b]pyridine (502);

3-isopropyl-2-(2-methylpyridin-4-yl)-5-(4-(piperidin-4-yloxy)cyclohexyl)-1H-indole (503);

4-(3-isopropyl-5-(4-(pyridin-4-yloxy)cyclohexyl)-1H-indol-2-yl)-1H-pyrazolo[3,4-b]pyridine (504-505);

4-(2-(7,8-dimethyl-[1,2,4]triazolo[4,3-a]pyridin-6-yl)-3-isopropyl-1H-indol-5-yl)cyclohexan-1-amine (515-516);

2-((4-(2-(7,8-dimethyl-[1,2,4]triazolo[4,3-a]pyridin-6-yl)-3-isopropyl-1H-indol-5-yl) cyclohexyl)amino)-N,N-dimethylacetamide (517-518);

N-(4-(2-(7,8-dimethyl-[1,2,4]triazolo[4,3-a]pyridin-6-yl)-3-isopropyl-1H-indol-5-yl) cyclohexyl)oxetan-3-amine (523-524);

4-(2-(7,8-dimethyl-[1,2,4]triazolo[4,3-a]pyridin-6-yl)-3-isopropyl-1H-indol-5-yl)-N-methylcyclohexan-1-amine (525, 530);

N-(4-(2-(7,8-dimethyl-[1,2,4]triazolo[4,3-a]pyridin-6-yl)-3-isopropyl-1H-indol-5-yl) cyclohexyl)-N-methyloxetan-3-amine (526, 528); or 4-(2-(7,8-dimethyl-[1,2,4]triazolo[4,3-a]pyridin-6-yl)-3-isopropyl-1H-indol-5-yl)-N,N-dimethylcyclohexan-1-amine (527, 529).

7. A compound according to claim 5 or a salt thereof, wherein said compound is:

2-(dimethylamino)-N-(3-(3-isopropyl-2-(1,4,5-trimethyl-6-oxo-1,6-dihydropyridin-3-yl)-1H-indol-5-yl)cyclobutyl)acetamide (490-491);

5-(5-(3-aminocyclobutyl)-3-isopropyl-1H-indol-2-yl)-1,3,4-trimethylpyridin-2(1H)-one (492-493);

5-(3-isopropyl-5-(3-((2-(methylsulfonyl)ethyl)amino)cyclobutyl)-1H-indol-2-yl)-1,3,4-trimethylpyridin-2(1H)-one (494-495);

5-(3-isopropyl-5-(3-(oxetan-3-ylamino)cyclobutyl)-1H-indol-2-yl)-1,3,4-trimethylpyridin-2(1H)-one (496);

3-(2-(7,8-dimethyl-[1,2,4]triazolo[1,5-a]pyridin-6-yl)-3-isopropyl-1H-indol-5-yl) cyclobutan-1-amine (541);

2-((3-(2-(7,8-dimethyl-[1,2,4]triazolo[1,5-a]pyridin-6-yl)-3-isopropyl-1H-indol-5-yl) cyclobutyl)amino)-N,N-dimethylacetamide (566);

2-((3-(2-(7,8-dimethyl-[1,2,4]triazolo[1,5-a]pyridin-6-yl)-3-isopropyl-1H-indol-5-yl) cyclobutyl)amino)acetonitrile (567, 577);

3-(3-isopropyl-2-(8-methoxy-[1,2,4]triazolo[1,5-a]pyridin-6-yl)-1H-indol-5-yl) cyclobutan-1-amine (568);

2-((3-(3-isopropyl-2-(8-methoxy-[1,2,4]triazolo[1,5-a] pyridin-6-yl)-1H-indol-5-yl) cyclobutyl)amino)-N,N-dimethylacetamide (569-570);

3-(3-isopropyl-2-(8-methoxy-[1,2,4]triazolo[1,5-a]pyridin-6-yl)-1H-indol-5-yl)-N-(2-(methylsulfonyl)ethyl) cyclobutan-1-amine (571);

3-(2-(7,8-dimethyl-[1,2,4]triazolo[1,5-a]pyridin-6-yl)-3-isopropyl-1H-indol-5-yl)-N-(2-(methylsulfonyl)ethyl) cyclobutan-1-amine (572);

N-(3-(2-(7,8-dimethyl-[1,2,4]triazolo[1,5-a]pyridin-6-yl)-3-isopropyl-1H-indol-5-yl) cyclobutyl)-2-(dimethylamino)acetamide (573);

3-(2-(7,8-dimethyl-[1,2,4]triazolo[1,5-a]pyridin-6-yl)-3-isopropyl-1H-indol-5-yl)-N,N-dimethylcyclobutan-1-amine (574);

N-(3-(2-(7,8-dimethyl-[1,2,4]triazolo[1,5-a]pyridin-6-yl)-3-isopropyl-1H-indol-5-yl) cyclobutyl)oxetan-3-amine (575-576);

N-(3-(2-(7,8-dimethyl-[1,2,4]triazolo[1,5-a]pyridin-6-yl)-3-isopropyl-1H-indol-5-yl) cyclobutyl)-2-(dimethylamino)acetamide (578);

N-(3-(3-isopropyl-2-(8-methoxy-[1,2,4]triazolo[1,5-a] pyridin-6-yl)-1H-indol-5-yl) cyclobutyl)oxetan-3-amine (579);

3-(3-isopropyl-2-(8-methoxy-[1,2,4]triazolo[1,5-a]pyridin-6-yl)-1H-indol-5-yl)-N,N-dimethylcyclobutan-1-amine (580-581);

3-(2-(7,8-dimethyl-[1,2,4]triazolo[1,5-a]pyridin-6-yl)-3-isopropyl-1H-indol-5-yl)-N-methyl-N-(2-(methylsulfonyl)ethyl)cyclobutan-1-amine (582, 586);

3-(3-isopropyl-2-(8-methoxy-[1,2,4]triazolo[1,5-a]pyridin-6-yl)-1H-indol-5-yl)-N-methyl-N-(2-(methylsulfonyl)ethyl)cyclobutan-1-amine (583, 587);

N-(3-(2-(7,8-dimethyl-[1,2,4]triazolo[1,5-a]pyridin-6-yl)-3-isopropyl-1H-indol-5-yl) cyclobutyl)-2-(dimethylamino)-N-methylacetamide (584, 589); or 2-(dimethylamino)-N-(3-(3-isopropyl-2-(8-methoxy-[1,2,4]triazolo[1,5-a]pyridin-6-yl)-1H-indol-5-yl)cyclobutyl)-N-methylacetamide (585, 588).

8. A compound according to claim 5 or a salt thereof, wherein said compound is:

- (1R,2S)-2-(3-isopropyl-2-(2-methylpyridin-4-yl)-1H-indol-5-yl)-N-(octahydrocyclopenta[c]pyrrol-4-yl)cyclopropane-1-carboxamide (453, 457);
- (2,5-diazabicyclo[2.2.1]heptan-2-yl)((1R,2S)-2-(3-isopropyl-2-(2-methylpyridin-4-yl)-1H-indol-5-yl)cyclopropyl)methanone (454);
- (hexahydropyrrolo[3,4-c]pyrrol-2(1H)-yl)((1R,2S)-2-(3-isopropyl-2-(2-methylpyridin-4-yl)-1H-indol-5-yl)cyclopropyl)methanone (455);
- (1R,2S)-2-(3-isopropyl-2-(2-methylpyridin-4-yl)-1H-indol-5-yl)-N-(piperidin-4-yl) cyclopropane-1-carboxamide (456);
- (1R,2R)-2-(3-isopropyl-2-(2-methylpyridin-4-yl)-1H-indol-5-yl)-N-(1-isopropylpiperidin-4-yl)cyclopropane-1-carboxamide (458);
- (1R,2R)-2-(3-isopropyl-2-(2-methylpyridin-4-yl)-1H-indol-5-yl)-N-methyl-N-(quinuclidin-2-yl)cyclopropane-1-carboxamide (459, 463);
- (1R,2R)-2-(3-isopropyl-2-(2-methylpyridin-4-yl)-1H-indol-5-yl)-N-(quinuclidin-2-yl) cyclopropane-1-carboxamide (460-461);
- (1R,2R)-2-(3-isopropyl-2-(2-methylpyridin-4-yl)-1H-indol-5-yl)-N-methyl-N-(piperidin-4-yl)cyclopropane-1-carboxamide (462);
- 3-isopropyl-2-(2-methylpyridin-4-yl)-5-((1R,2R)-2-(pyrrolidin-1-ylmethyl) cyclopropyl)-1H-indole (464); or
- N-isopropyl-3-(3-isopropyl-2-(8-methoxy-[1,2,4]triazolo[1,5-a]pyridin-6-yl)-1H-indol-5-yl)-N-methylcyclopentan-1-amine (275 to 278).

9. The compound according to claim 1, N-oxide, or a salt thereof, wherein A is azetidinyl, each substituted with zero to 3 $R_{12a}$.

10. A compound according to claim 9 or a salt thereof, wherein said compound is:

- 6-(5-(azetidin-3-yl)-3-isopropyl-1H-indol-2-yl)-8-methyl-[1,2,4]triazolo [1,5-a]pyridine (257);
- 6-(5-(azetidin-3-yl)-3-isopropyl-1H-indol-2-yl)-8-methoxy-[1,2,4]triazolo[1,5-a]pyridine (258);
- 5-(azetidin-3-yl)-2-(2,6-dimethylpyridin-4-yl)-3-isopropyl-1H-indole (259);
- 2-(3-(3-isopropyl-2-(8-methyl-[1,2,4]triazolo[1,5-a]pyridin-6-yl)-1H-indol-5-yl) azetidin-1-yl)-N-methylacetamide (260);
- 2-(3-(3-isopropyl-2-(8-methyl-[1,2,4]triazolo[1,5-a]pyridin-6-yl)-1H-indol-5-yl) azetidin-1-yl)-N,N-dimethylacetamide (261);
- 2-(3-(3-isopropyl-2-(8-methoxy-[1,2,4]triazolo[1,5-a]pyridin-6-yl)-1H-indol-5-yl) azetidin-1-yl)-N,N-dimethylacetamide (262);
- 2-(3-(3-isopropyl-2-(8-methoxy-[1,2,4]triazolo[1,5-a]pyridin-6-yl)-1H-indol-5-yl) azetidin-1-yl)-N-methylacetamide (263);
- 6-(3-isopropyl-5-(1-(2-(methylsulfonyl)ethyl)azetidin-3-yl)-1H-indol-2-yl)-8-methyl-[1,2,4]triazolo[1,5-a]pyridine (264);
- 6-(3-isopropyl-5-(1-(2-(methylsulfonyl)ethyl)azetidin-3-yl)-1H-indol-2-yl)-8-methoxy-[1,2,4]triazolo[1,5-a]pyridine (265);
- 2-(dimethylamino)-1-(3-(3-isopropyl-2-(8-methyl-[1,2,4]triazolo[1,5-a] pyridin-6-yl)-1H-indol-5-yl)azetidin-1-yl)ethan-1-one (266);
- 1-(3-(3-isopropyl-2-(8-methyl-[1,2,4]triazolo[1,5-a]pyridin-6-yl)-1H-indol-5-yl) azetidin-1-yl)-2-(methylamino)ethan-1-one (267);
- 1-(3-(3-isopropyl-2-(8-methoxy-[1,2,4]triazolo[1,5-a]pyridin-6-yl)-1H-indol-5-yl) azetidin-1-yl)-2-(methylamino)ethan-1-one (268);
- 6-(5-(1-(2,2-dimethyltetrahydro-2H-pyran-4-yl)azetidin-3-yl)-3-isopropyl-1H-indol-2-yl)-8-methyl-[1,2,4]triazolo[1,5-a]pyridine (269);
- 4-(3-(2-(2,6-dimethylpyridin-4-yl)-3-isopropyl-1H-indol-5-yl)azetidin-1-yl) tetrahydro-2H-thiopyran 1,1-dioxide (270);
- 6-(3-isopropyl-5-(1-(oxetan-3-yl)azetidin-3-yl)-1H-indol-2-yl)-8-methyl-[1,2,4]triazolo[1,5-a]pyridine (271);
- 6-(3-isopropyl-5-(1-isopropylazetidin-3-yl)-1H-indol-2-yl)-8-methoxy-[1,2,4]triazolo[1,5-a]pyridine (272);
- 6-(3-isopropyl-5-(1-methylazetidin-3-yl)-1H-indol-2-yl)-8-methoxy-[1,2,4]triazolo[1,5-a]pyridine (273);
- 6-(3-isopropyl-5-(1-(oxetan-3-yl)azetidin-3-yl)-1H-indol-2-yl)-8-methoxy-[1,2,4]triazolo[1,5-a]pyridine (274);
- 5-(3-isopropyl-5-(1-(tetrahydro-2H-pyran-4-yl)azetidin-3-yl)-1H-indol-2-yl)-1,3,4-trimethylpyridin-2(1H)-one (481);
- 5-(3-isopropyl-5-(1-isopropylazetidin-3-yl)-1H-indol-2-yl)-1,3,4-trimethylpyridin-2(1H)-one (482);
- 5-(3-isopropyl-5-(1-(2-(methylsulfonyl)ethyl)azetidin-3-yl)-1H-indol-2-yl)-1,3,4-trimethylpyridin-2(1H)-one (483);
- 5-(5-(1-(dimethylglycyl)azetidin-3-yl)-3-isopropyl-1H-indol-2-yl)-1,3,4-trimethylpyridin-2(1H)-one (484);
- 5-(3-isopropyl-5-(1-(oxetan-3-yl)azetidin-3-yl)-1H-indol-2-yl)-1,3,4-trimethylpyridin-2(1H)-one (485);
- 5-(5-(azetidin-3-yl)-3-isopropyl-1H-indol-2-yl)-1,3,4-trimethylpyridin-2(1H)-one (486);
- 5-(3-isopropyl-5-(1-(2-methoxyethyl)azetidin-3-yl)-1H-indol-2-yl)-1,3,4-trimethylpyridin-2(1H)-one (487);
- 5-(3-isopropyl-5-(1-propylazetidin-3-yl)-1H-indol-2-yl)-1,3,4-trimethylpyridin-2(1H)-one (488);
- 2-(3-(3-isopropyl-2-(1,4,5-trimethyl-6-oxo-1,6-dihydropyridin-3-yl)-1H-indol-5-yl) azetidin-1-yl)-N,N-dimethylacetamide (489);
- 3-chloro-5-(3-isopropyl-5-(1-((tetrahydrofuran-3-yl)methyl)azetidin-3-yl)-1H-indol-2-yl)-1,4-dimethylpyridin-2(1H)-one (499);
- 3-chloro-5-(3-isopropyl-5-(1-propylazetidin-3-yl)-1H-indol-2-yl)-1,4-dimethylpyridin-2(1H)-one (500);
- 6-(5-(azetidin-3-yl)-3-isopropyl-1H-indol-2-yl)-7,8-dimethyl-[1,2,4]triazolo[4,3-a]pyridine (531);
- 6-(3-isopropyl-5-(1-(2-(methylsulfonyl)ethyl)azetidin-3-yl)-1H-indol-2-yl)-7,8-dimethyl-[1,2,4]triazolo[4,3-a]pyridine (532);
- 6-(3-isopropyl-5-(1-methylazetidin-3-yl)-1H-indol-2-yl)-7,8-dimethyl-[1,2,4]triazolo[4,3-a]pyridine (533);
- 6-(3-isopropyl-5-(1-isopropylazetidin-3-yl)-1H-indol-2-yl)-7,8-dimethyl-[1,2,4]triazolo[4,3-a]pyridine (534);
- 6-(3-isopropyl-5-(1-(tetrahydro-2H-pyran-4-yl)azetidin-3-yl)-1H-indol-2-yl)-7,8-dimethyl-[1,2,4]triazolo[4,3-a]pyridine (535);
- 6-(3-isopropyl-5-(1-((3-methyloxetan-3-yl)methyl)azetidin-3-yl)-1H-indol-2-yl)-7,8-dimethyl-[1,2,4]triazolo[4,3-a]pyridine (536);
- 6-(3-isopropyl-5-(1-((1-methyl-1H-1,2,4-triazol-3-yl)methyl)azetidin-3-yl)-1H-indol-2-yl)-7,8-dimethyl-[1,2,4]triazolo[4,3-a]pyridine (537);
- 6-(3-isopropyl-5-(1-(tetrahydrofuran-3-yl)azetidin-3-yl)-1H-indol-2-yl)-7,8-dimethyl-[1,2,4]triazolo[4,3-a]pyridine (538);

2-(3-(2-(7,8-dimethyl-[1,2,4]triazolo[4,3-a]pyridin-6-yl)-3-isopropyl-1H-indol-5-yl) azetidin-1-yl)-N,N-dimethylacetamide (539);

6-(3-isopropyl-5-(1-(oxetan-3-yl)azetidin-3-yl)-1H-indol-2-yl)-7,8-dimethyl-[1,2,4]triazolo[4,3-a]pyridine (540);

6-(3-isopropyl-5-(1-(2-(methylsulfonyl)ethyl)azetidin-3-yl)-1H-indol-2-yl)-7,8-dimethyl-[1,2,4]triazolo[1,5-a]pyridine (543);

6-(3-isopropyl-5-(1-(oxetan-3-yl)azetidin-3-yl)-1H-indol-2-yl)-7,8-dimethyl-[1,2,4]triazolo[1,5-a]pyridine (544);

6-(5-(azetidin-3-yl)-3-isopropyl-1H-indol-2-yl)-7,8-dimethyl-[1,2,4]triazolo[1,5-a]pyridine (545);

6-(3-isopropyl-5-(1-propylazetidin-3-yl)-1H-indol-2-yl)-7,8-dimethyl-[1,2,4]triazolo[4,3-a]pyridine (546);

6-(3-isopropyl-5-(1-methylazetidin-3-yl)-1H-indol-2-yl)-7,8-dimethyl-[1,2,4]triazolo[1,5-a]pyridine (547);

2-(3-(2-(7,8-dimethyl-[1,2,4]triazolo[1,5-a]pyridin-6-yl)-3-isopropyl-1H-indol-5-yl) azetidin-1-yl)acetamide (548);

6-(5-(1-isobutylazetidin-3-yl)-3-isopropyl-1H-indol-2-yl)-7,8-dimethyl-[1,2,4]triazolo[4,3-a]pyridine (549);

6-(3-isopropyl-5-(1-(2-methoxyethyl)azetidin-3-yl)-1H-indol-2-yl)-7,8-dimethyl-[1,2,4]triazolo[4,3-a]pyridine (550);

6-(5-(1-((1H-1,2,3-triazol-4-yl)methyl)azetidin-3-yl)-3-isopropyl-1H-indol-2-yl)-7,8-dimethyl-[1,2,4]triazolo[1,5-a]pyridine (551);

2-(3-(2-(7,8-dimethyl-[1,2,4]triazolo[1,5-a]pyridin-6-yl)-3-isopropyl-1H-indol-5-yl) azetidin-1-yl)-N-methylacetamide (552);

2-(3-(2-(7,8-dimethyl-[1,2,4]triazolo[1,5-a]pyridin-6-yl)-3-isopropyl-1H-indol-5-yl) azetidin-1-yl)acetonitrile (553);

6-(3-isopropyl-5-(1-(4,4,4-trifluorobutyl)azetidin-3-yl)-1H-indol-2-yl)-7,8-dimethyl-[1,2,4]triazolo[4,3-a]pyridine (554);

6-(3-isopropyl-5-(1-isopropylazetidin-3-yl)-1H-indol-2-yl)-7,8-dimethyl-[1,2,4]triazolo[1,5-a]pyridine (555);

2-(3-(2-(7,8-dimethyl-[1,2,4]triazolo[1,5-a]pyridin-6-yl)-3-isopropyl-1H-indol-5-yl) azetidin-1-yl)-N,N-dimethylacetamide (556);

1-(3-(2-(7,8-dimethyl-[1,2,4]triazolo[1,5-a]pyridin-6-yl)-3-isopropyl-1H-indol-5-yl) azetidin-1-yl)-2-methylpropan-2-ol (557);

1-(3-(2-(7,8-dimethyl-[1,2,4]triazolo[1,5-a]pyridin-6-yl)-3-isopropyl-1H-indol-5-yl) azetidin-1-yl)-2-(dimethylamino)ethan-1-one (564); or N-(2-(3-(2-(7,8-dimethyl-[1,2,4]triazolo[1,5-a]pyridin-6-yl)-3-isopropyl-1H-indol-5-yl)azetidin-1-yl)ethyl) methanesulfonamide (565).

11. The compound according to claim 1, N-oxide, or a salt thereof, wherein A is morpholinyl.

12. A compound according to claim 11 or a salt thereof, wherein said compound is:

2-(3-isopropyl-2-(8-methyl-[1,2,4]triazolo[1,5-a]pyridin-6-yl)-1H-indol-5-yl) morpholine (281);

2-(3-isopropyl-2-(8-methyl-[1,2,4]triazolo[1,5-a]pyridin-6-yl)-1H-indol-5-yl) morpholine (282-283);

2-(3-isopropyl-2-(8-methoxy-[1,2,4]triazolo[1,5-a]pyridin-6-yl)-1H-indol-5-yl) morpholine (284-285);

2-(2-(7,8-dimethyl-[1,2,4]triazolo[1,5-a]pyridin-6-yl)-3-isopropyl-1H-indol-5-yl) morpholine (286-288);

2-(3-isopropyl-2-(8-methyl-[1,2,4]triazolo[1,5-a]pyridin-6-yl)-1H-indol-5-yl)-4-(oxetan-3-yl)morpholine (289);

2-(3-isopropyl-2-(8-methyl-[1,2,4]triazolo[1,5-a]pyridin-6-yl)-1H-indol-5-yl)-4-(oxetan-3-yl)morpholine (290);

2-(3-isopropyl-2-(8-methyl-[1,2,4]triazolo[1,5-a]pyridin-6-yl)-1H-indol-5-yl)-4-((3-methyloxetan-3-yl)methyl) morpholine (291-292);

2-(3-isopropyl-2-(8-methyl-[1,2,4]triazolo[1,5-a]pyridin-6-yl)-1H-indol-5-yl)-4-methylmorpholine (293, 296-297);

4-isopropyl-2-(3-isopropyl-2-(8-methyl-[1,2,4]triazolo[1,5-a]pyridin-6-yl)-1H-indol-5-yl)morpholine (294-295, 298);

2-(3-isopropyl-2-(8-methyl-[1,2,4]triazolo[1,5-a]pyridin-6-yl)-1H-indol-5-yl)-4-methylmorpholine (297);

2-(3-isopropyl-2-(8-methoxy-[1,2,4]triazolo[1,5-a]pyridin-6-yl)-1H-indol-5-yl)-4-methylmorpholine (299, 301);

4-isopropyl-2-(3-isopropyl-2-(8-methoxy-[1,2,4]triazolo[1,5-a]pyridin-6-yl)-1H-indol-5-yl)morpholine (300, 302);

2-(2-(2,6-dimethylpyridin-4-yl)-3-isopropyl-1H-indol-5-yl)-4-isopropylmorpholine (303, 305);

2-(2-(2,6-dimethylpyridin-4-yl)-3-isopropyl-1H-indol-5-yl)-4-(oxetan-3-yl) morpholine (304);

2-(2-(3-isopropyl-2-(8-methyl-[1,2,4]triazolo[1,5-a]pyridin-6-yl)-1H-indol-5-yl) morpholino)-N,N-dimethylacetamide (306);

2-(2-(3-isopropyl-2-(8-methyl-[1,2,4]triazolo[1,5-a]pyridin-6-yl)-1H-indol-5-yl) morpholino)-N-methylacetamide (307, 317);

2-(2-(3-isopropyl-2-(8-methyl-[1,2,4]triazolo[1,5-a]pyridin-6-yl)-1H-indol-5-yl) morpholino)-N,N-dimethylacetamide (308, 316);

2-(2-(3-isopropyl-2-(8-methoxy-[1,2,4]triazolo[1,5-a]pyridin-6-yl)-1H-indol-5-yl) morpholino)-N,N-dimethylacetamide (309, 314);

2-(2-(3-isopropyl-2-(8-methoxy-[1,2,4]triazolo[1,5-a]pyridin-6-yl)-1H-indol-5-yl) morpholino)-N-methylacetamide (310, 315);

2-(2-(2-(7,8-dimethyl-[1,2,4]triazolo[1,5-a]pyridin-6-yl)-3-isopropyl-1H-indol-5-yl) morpholino)-N-methylacetamide (311, 313);

2-(2-(2-(7,8-dimethyl-[1,2,4]triazolo[1,5-a]pyridin-6-yl)-3-isopropyl-1H-indol-5-yl) morpholino)-N,N-dimethylacetamide (312, 321);

2-(2-(3-isopropyl-2-(8-methyl-[1,2,4]triazolo[1,5-a]pyridin-6-yl)-1H-indol-5-yl) morpholino)acetamide (318);

2-(2-(2-(7,8-dimethyl-[1,2,4]triazolo[1,5-a]pyridin-6-yl)-3-isopropyl-1H-indol-5-yl) morpholino)acetamide (319-320);

2-(2-(2-(2,6-dimethylpyridin-4-yl)-3-isopropyl-1H-indol-5-yl)morpholino)-N,N-dimethylacetamide (322, 326);

2-(2-(2-(2,6-dimethylpyridin-4-yl)-3-isopropyl-1H-indol-5-yl)morpholino)-N-methylacetamide (323, 325);

2-(2-(2-(2,6-dimethylpyridin-4-yl)-3-isopropyl-1H-indol-5-yl)morpholino)acetamide (324, 327);

2-(dimethylamino)-1-(2-(3-isopropyl-2-(8-methyl-[1,2,4]triazolo[1,5-a] pyridin-6-yl)-1H-indol-5-yl)morpholino)ethanone (328);

1-(2-(2-(7,8-dimethyl-[1,2,4]triazolo[1,5-a]pyridin-6-yl)-3-isopropyl-1H-indol-5-yl) morpholino)-2-(dimethylamino)ethan-1-one (329-330);

2-(dimethylamino)-1-(2-(3-isopropyl-2-(8-methyl-[1,2,4] triazolo[1,5-a]pyridin-6-yl)-1H-indol-5-yl)morpholino)ethan-1-one (331);

2-(dimethylamino)-1-(2-(3-isopropyl-2-(8-methoxy-[1,2,4]triazolo[1,5-a]pyridin-6-yl)-1H-indol-5-yl)morpholino)ethan-1-one (332, 334);
2-(diethylamino)-1-(2-(3-isopropyl-2-(8-methoxy-[1,2,4]triazolo[1,5-a]pyridin-6-yl)-1H-indol-5-yl)morpholino)ethan-1-one (333);
2-(dimethylamino)-1-(2-(2-(2,6-dimethylpyridin-4-yl)-3-isopropyl-1H-indol-5-yl) morpholino)ethan-1-one (335-336);
1-(2-(3-isopropyl-2-(8-methyl-[1,2,4]triazolo[1,5-a]pyridin-6-yl)-1H-indol-5-yl) morpholino)-2-(methylamino)ethanone (337);
1-(2-(3-isopropyl-2-(8-methyl-[1,2,4]triazolo[1,5-a]pyridin-6-yl)-1H-indol-5-yl) morpholino)-2-(methylamino)ethan-1-one (338);
1-(2-(3-isopropyl-2-(8-methoxy-[1,2,4]triazolo[1,5-a]pyridin-6-yl)-1H-indol-5-yl) morpholino)-2-(methylamino)ethan-1-one (339, 342);
1-(2-(2-(7,8-dimethyl-[1,2,4]triazolo[1,5-a]pyridin-6-yl)-3-isopropyl-1H-indol-5-yl) morpholino)-2-(methylamino)ethan-1-one (340-341);
2-(3-isopropyl-2-(8-methyl-[1,2,4]triazolo[1,5-a]pyridin-6-yl)-1H-indol-5-yl)-4-(2-(methylsulfonyl)ethyl)morpholine (343);
2-(3-isopropyl-2-(8-methyl-[1,2,4]triazolo[1,5-a]pyridin-6-yl)-1H-indol-5-yl)-4-(2-(methylsulfonyl)ethyl)morpholine (344);
2-(3-isopropyl-2-(8-methoxy-[1,2,4]triazolo[1,5-a]pyridin-6-yl)-1H-indol-5-yl)-4-(2-methoxyethyl)morpholine (345);
2-(2-(7,8-dimethyl-[1,2,4]triazolo[1,5-a]pyridin-6-yl)-3-isopropyl-1H-indol-5-yl)-4-(2-(methylsulfonyl)ethyl)morpholine (346-347);
2-(3-isopropyl-2-(8-methyl-[1,2,4]triazolo[1,5-a]pyridin-6-yl)-1H-indol-5-yl)-4-(2-methoxyethyl)morpholine (348-350);
2-(2-(2,6-dimethylpyridin-4-yl)-3-isopropyl-1H-indol-5-yl)-4-(2-(methylsulfonyl) ethyl)morpholine (351, 353);
2-(2-(2,6-dimethylpyridin-4-yl)-3-isopropyl-1H-indol-5-yl)-4-(2-methoxyethyl) morpholine (352);
1-(2-(3-isopropyl-2-(8-methyl-[1,2,4]triazolo[1,5-a]pyridin-6-yl)-1H-indol-5-yl) morpholino)-2-methylpropan-2-ol (355);
1-(2-(3-isopropyl-2-(8-methyl-[1,2,4]triazolo[1,5-a]pyridin-6-yl)-1H-indol-5-yl) morpholino)-2-methylpropan-2-ol (356);
1-(2-(2-(2,6-dimethylpyridin-4-yl)-3-isopropyl-1H-indol-5-yl)morpholino)-2-methylpropan-2-ol (357-358);
2-(ethyl(methyl)amino)-1-(2-(3-isopropyl-2-(8-methoxy-[1,2,4]triazolo[1,5-a]pyridin-6-yl)-1H-indol-5-yl)morpholino)ethanone (359);
2-(1,1-dioxidothiomorpholino)-1-(2-(3-isopropyl-2-(8-methoxy-[1,2,4]triazolo[1,5-a]pyridin-6-yl)-1H-indol-5-yl)morpholino)ethan-1-one (360);
1-(2-(3-isopropyl-2-(8-methoxy-[1,2,4]triazolo[1,5-a]pyridin-6-yl)-1H-indol-5-yl) morpholino)-2-((3-methyloxetan-3-yl)amino)ethan-1-one (361);
2-(3-isopropyl-2-(8-methyl-[1,2,4]triazolo[1,5-a]pyridin-6-yl)-1H-indol-5-yl)-5,5-dimethylmorpholine (367);
2-(3-isopropyl-2-(8-methoxy-[1,2,4]triazolo[1,5-a]pyridin-6-yl)-1H-indol-5-yl)-5,5-dimethylmorpholine (368-369);
2-(2-(7,8-dimethyl-[1,2,4]triazolo[1,5-a]pyridin-6-yl)-3-isopropyl-1H-indol-5-yl)-5,5-dimethylmorpholine (370-371);
2-(dimethylamino)-1-(2-(3-isopropyl-2-(8-methyl-[1,2,4]triazolo[1,5-a]pyridin-6-yl)-1H-indol-5-yl)-5,5-dimethylmorpholino)ethanone (372-373);
2-(dimethylamino)-1-(2-(3-isopropyl-2-(8-methoxy-[1,2,4]triazolo[1,5-a]pyridin-6-yl)-1H-indol-5-yl)-5,5-dimethylmorpholino)ethan-1-one (374);
2-(3-isopropyl-2-(8-methyl-[1,2,4]triazolo[1,5-a]pyridin-6-yl)-1H-indol-5-yl)-4,5,5-trimethylmorpholine (375-376);
2-(3-isopropyl-2-(8-methoxy-[1,2,4]triazolo[1,5-a]pyridin-6-yl)-1H-indol-5-yl)-4,5,5-trimethylmorpholine (377);
2-(3-isopropyl-2-(8-methoxy-[1,2,4]triazolo[1,5-a]pyridin-6-yl)-1H-indol-5-yl)-5,5-dimethyl-4-(oxetan-3-yl)morpholine (378);
2-(2-(3-isopropyl-2-(8-methyl-[1,2,4]triazolo[1,5-a]pyridin-6-yl)-1H-indol-5-yl)-5,5-dimethylmorpholino)-N,N-dimethylacetamide (379-380);
2-(3-isopropyl-2-(8-methyl-[1,2,4]triazolo[1,5-a]pyridin-6-yl)-1H-indol-5-yl)-5,5-dimethyl-4-(2-(methylsulfonyl)ethyl)morpholine (381, 384);
2-(3-isopropyl-2-(8-methyl-[1,2,4]triazolo[1,5-a]pyridin-6-yl)-1H-indol-5-yl)-4-(2-methoxyethyl)-5,5-dimethylmorpholine (382-383);
1-(2-(3-isopropyl-2-(8-methyl-[1,2,4]triazolo[1,5-a]pyridin-6-yl)-1H-indol-5-yl)-5,5-dimethylmorpholino)-2-methylpropan-2-ol (385);
2-(2-(2-(7,8-dimethyl-[1,2,4]triazolo[1,5-a]pyridin-6-yl)-3-isopropyl-1H-indol-5-yl)-5,5-dimethylmorpholino)-N,N-dimethylacetamide (386-387); or
2-(2-(2-(7,8-dimethyl-[1,2,4]triazolo[1,5-a]pyridin-6-yl)-3-isopropyl-1H-indol-5-yl)-5,5-dimethylmorpholino)-N-methylacetamide (388-389).

13. The compound according to claim 1, N-oxide, or a salt thereof, wherein A is azabicyclo[4.1.1]octanyl, diazaspiro[4.5]decanonyl, octahydrocyclopenta[c]pyrrolyl, or quinuclidinyl, each substituted with zero to 3 $R_{12a}$.

14. A compound according to claim 13 or a salt thereof, wherein said compound is:
1-(3-(2-(3,4-dimethoxyphenyl)-3-isopropyl-1H-indol-5-yl)-7-azabicyclo[4.1.1]octan-7-yl)-2-(dimethylamino)ethanone (279);
1-(3-(2-(3,4-dimethoxyphenyl)-3-isopropyl-1H-indol-5-yl)-7-azabicyclo[4.1.1]octan-7-yl)-2-(dimethylamino)ethanone (280);
3-(2-(2,6-dimethylpyridin-4-yl)-3-isopropyl-1H-indol-5-yl)quinuclidine (362-363);
3-(3-isopropyl-2-(8-methyl-[1,2,4]triazolo[1,5-a]pyridin-6-yl)-1H-indol-5-yl) quinuclidine (364-365);
8-(2-(2,6-dimethylpyridin-4-yl)-3-isopropyl-1H-indol-5-yl)-1,3-diazaspiro[4.5]decane-2,4-dione (366);
6-(3-isopropyl-5-(octahydrocyclopenta[c]pyrrol-5-yl)-1H-indol-2-yl)-7,8-dimethyl-[1,2,4]triazolo[1,5-a]pyridine (506);
2-(5-(2-(7,8-dimethyl-[1,2,4]triazolo[1,5-a]pyridin-6-yl)-3-isopropyl-1H-indol-5-yl) hexahydrocyclopenta[c]pyrrol-2(1H)-yl)-N,N-dimethylacetamide (507);
6-(3-isopropyl-5-(octahydrocyclopenta[c]pyrrol-5-yl)-1H-indol-2-yl)-8-methoxy-[1,2,4]triazolo[1,5-a]pyridine (508);
2-(5-(3-isopropyl-2-(8-methoxy-[1,2,4]triazolo[1,5-a]pyridin-6-yl)-1H-indol-5-yl) hexahydrocyclopenta[c]pyrrol-2(1H)-yl)-N,N-dimethylacetamide (509);
2-(5-(2-(7,8-dimethyl-[1,2,4]triazolo[1,5-a]pyridin-6-yl)-3-isopropyl-1H-indol-5-yl) hexahydrocyclopenta[c]pyrrol-2(1H)-yl)-N-methylacetamide (510);

2-(5-(2-(7,8-dimethyl-[1,2,4]triazolo[1,5-a]pyridin-6-yl)-3-isopropyl-1H-indol-5-yl) hexahydrocyclopenta[c]pyrrol-2(1H)-yl)acetamide (511);

2-(5-(2-(7,8-dimethyl-[1,2,4]triazolo[1,5-a]pyridin-6-yl)-3-isopropyl-1H-indol-5-yl) hexahydrocyclopenta[c]pyrrol-2(1H)-yl)acetonitrile (512);

6-(3-isopropyl-5-(2-(oxetan-3-yl)octahydrocyclopenta[c]pyrrol-5-yl)-1H-indol-2-yl)-8-methoxy-[1,2,4]triazolo[1,5-a]pyridine (513);

6-(3-isopropyl-5-(2-(2-(methylsulfonyl)ethyl)octahydrocyclopenta[c]pyrrol-5-yl)-1H-indol-2-yl)-7,8-dimethyl-[1,2,4]triazolo[1,5-a]pyridine (514);

6-(3-isopropyl-5-(octahydrocyclopenta[c]pyrrol-5-yl)-1H-indol-2-yl)-7,8-dimethyl-[1,2,4]triazolo[4,3-a]pyridine (519);

2-(5-(2-(7,8-dimethyl-[1,2,4]triazolo[4,3-a]pyridin-6-yl)-3-isopropyl-1H-indol-5-yl) hexahydrocyclopenta[c]pyrrol-2(1H)-yl)-N,N-dimethylacetamide (520);

1-(5-(2-(7,8-dimethyl-[1,2,4]triazolo[4,3-a]pyridin-6-yl)-3-isopropyl-1H-indol-5-yl) hexahydrocyclopenta[c]pyrrol-2(1H)-yl)-2-(dimethylamino)ethan-1-one (521);

6-(3-isopropyl-5-(2-(oxetan-3-yl)octahydrocyclopenta[c]pyrrol-5-yl)-1H-indol-2-yl)-7,8-dimethyl-[1,2,4]triazolo[4,3-a]pyridine (522);

2-(5-(2-(7,8-dimethyl-[1,2,4]triazolo[4,3-a]pyridin-6-yl)-3-isopropyl-1H-indol-5-yl) hexahydrocyclopenta[c]pyrrol-2(1H)-yl)acetonitrile (558);

6-(3-isopropyl-5-(2-methyloctahydrocyclopenta[c]pyrrol-5-yl)-1H-indol-2-yl)-7,8-dimethyl-[1,2,4]triazolo[4,3-a]pyridine (559);

6-(3-isopropyl-5-(2-isopropyloctahydrocyclopenta[c]pyrrol-5-yl)-1H-indol-2-yl)-7,8-dimethyl-[1,2,4]triazolo[4,3-a]pyridine (560);

6-(3-isopropyl-5-(2-((3-methyloxetan-3-yl)methyl)octahydrocyclopenta[c]pyrrol-5-yl)-1H-indol-2-yl)-7,8-dimethyl-[1,2,4]triazolo[4,3-a]pyridine (561);

6-(3-isopropyl-5-(2-(tetrahydrofuran-3-yl)octahydrocyclopenta[c]pyrrol-5-yl)-1H-indol-2-yl)-7,8-dimethyl-[1,2,4]triazolo[4,3-a]pyridine (562); or 6-(3-isopropyl-5-(2-(tetrahydro-2H-pyran-4-yl)octahydrocyclopenta[c]pyrrol-5-yl)-1H-indol-2-yl)-7,8-dimethyl-[1,2,4]triazolo[4,3-a]pyridine (563).

\* \* \* \* \*